US011761951B2

(12) United States Patent
Olson et al.

(10) Patent No.: US 11,761,951 B2
(45) Date of Patent: Sep. 19, 2023

(54) METHODS OF SELECTING THERAPEUTIC MOLECULES

(71) Applicants: Bristol-Myers Squibb Company, Princeton, NJ (US); Roche Innovation Center Copenhagen A/S, Horsholm (DK)

(72) Inventors: Richard E. Olson, Cambridge, MA (US); Angela M. Cacace, Haddam Neck, CT (US); Peter Hagedorn, Horsholm (DK); Anja Mølhart Høg, Hillerød (DK); Niels Fisker Nielsen, Kgs. Lyngby (DK); Dong LI, Cambridge, MA (US); Jeffrey M. Brown, Medway, MA (US); Stephen E. Mercer, Cambridge, MA (US); Marianne Lerbech Jensen, Køge (DK)

(73) Assignee: BRISTOL-MYERS SQUIBB COMPANY, Princeton, NJ (US)

( * ) Notice: Subject to any disclaimer, the term of this patent is extended or adjusted under 35 U.S.C. 154(b) by 840 days.

(21) Appl. No.: 15/548,390

(22) PCT Filed: Feb. 4, 2016

(86) PCT No.: PCT/US2016/016652
§ 371 (c)(1),
(2) Date: Dec. 18, 2017

(87) PCT Pub. No.: WO2016/127000
PCT Pub. Date: Aug. 11, 2016

(65) Prior Publication Data

US 2019/0383797 A1 Dec. 19, 2019

Related U.S. Application Data

(60) Provisional application No. 62/279,610, filed on Jan. 15, 2016, provisional application No. 62/156,684, filed on May 4, 2015, provisional application No. 62/112,058, filed on Feb. 4, 2015.

(51) Int. Cl.

| | |
|---|---|
| ***G01N 33/50*** | (2006.01) |
| ***A61K 49/00*** | (2006.01) |
| ***C12N 15/113*** | (2010.01) |
| ***G01N 33/53*** | (2006.01) |
| ***G01N 33/68*** | (2006.01) |

(52) U.S. Cl.
CPC ..... *G01N 33/5014* (2013.01); *A61K 49/0008* (2013.01); *C12N 15/113* (2013.01); *G01N 33/5058* (2013.01); *G01N 33/5308* (2013.01); *G01N 33/68* (2013.01); *C12N 2310/31* (2013.01); *C12N 2310/311* (2013.01); *C12N 2310/314* (2013.01); *C12N 2310/3125* (2013.01); *C12N 2310/3231* (2013.01); *C12N 2310/341* (2013.01)

(58) Field of Classification Search
CPC ........... G01N 33/5014; G01N 33/5058; G01N 33/5308; A61K 49/0008; C12Q 1/6811; C12Q 2310/10; C12Q 2600/142; C12N 15/113; C12N 2320/10
See application file for complete search history.

(56) References Cited

U.S. PATENT DOCUMENTS

| | | | |
|---|---|---|---|
| 4,683,195 | A | 7/1987 | Mullis et al. |
| 4,694,778 | A | 9/1987 | Learn et al. |
| 4,845,075 | A | 7/1989 | Murray et al. |
| 4,889,919 | A | 12/1989 | Murray et al. |
| 4,925,793 | A | 5/1990 | Goeddel et al. |
| 4,929,554 | A | 5/1990 | Goeddel et al. |
| 5,157,021 | A | 10/1992 | Balschmidt et al. |
| 5,166,195 | A | 11/1992 | Ecker |
| 5,194,596 | A | 3/1993 | Tischer et al. |
| 5,227,158 | A | 7/1993 | Jardieu |
| 5,248,670 | A | 9/1993 | Draper et al. |
| 5,264,423 | A | 11/1993 | Cohen et al. |
| 5,271,941 | A | 12/1993 | Cho-Chung |
| 5,453,491 | A | 9/1995 | Takatsu et al. |
| 5,599,905 | A | 2/1997 | Mosley et al. |
| 5,639,605 | A | 6/1997 | Kitamura et al. |
| 5,648,273 | A | 7/1997 | Bottaro et al. |
| 5,686,292 | A | 11/1997 | Schwall et al. |
| 5,834,598 | A | 11/1998 | Lowman et al. |

(Continued)

FOREIGN PATENT DOCUMENTS

| | | |
|---|---|---|
| CN | 1364812 A | 8/2002 |
| CN | 103797016 A | 5/2014 |

(Continued)

OTHER PUBLICATIONS

Barhoumi R et al. Image analysis of Ca2+ signals as a basis for neurotoxicity assays: promises and challenges. Neurotoxicol. Teratol. 2010, 32(1): 16. (Year: 2010).*

Hong SJ and Ghosh RN. Monitoring neurite morphology and synapse formation in primary neurons for neurotoxicity assessments and drug screening. Thermo Fisher Scientific, Application Notes C-AN_NT1112; www.thermofisher.com/content/dam/LifeTech/global/life; retrieved from internet Apr. 27, 2020. (Year: 2012).*

Kulig B et al. Animal behavioral methods in neurotoxicity assessment: SGOMSEC joint report. Enviorn. Health Perspect. 1996, 104(Suppl 2): 193-204. (Year: 1996).*

(Continued)

*Primary Examiner* — Kimberly Ballard
(74) *Attorney, Agent, or Firm* — STERNE, KESSLER, GOLDSTEIN & FOX P.L.L.C.

(57) ABSTRACT

The present disclosure provides methods of using a calcium oscillation assay and/or a sequence score calculation to identify a molecule that is safe for administration. The disclosure also includes a method of selecting or identifying a molecule having tolerable in vivo neurotoxicity using a calcium oscillation assay, a sequence score method, an in vivo tolerability assay, or any combination thereof.

19 Claims, 69 Drawing Sheets

Specification includes a Sequence Listing.

(56) References Cited

U.S. PATENT DOCUMENTS 5,877,016 A 3/1999 Presta et al.
5,910,574 A 6/1999 Presta et al.
6,099,841 A 8/2000 Hillan et al.
6,159,462 A 12/2000 Matthews et al.
6,403,764 B1 6/2002 Dubaquie et al.
6,506,874 B1 1/2003 Dubaquie et al.
6,576,608 B1 6/2003 Lee et al.
6,582,908 B2 6/2003 Fodor et al.
6,617,442 B1 9/2003 Crooke et al.
6,927,044 B2 8/2005 Stahl et al.
7,015,315 B1 3/2006 Cook et al.
7,038,106 B1 * 5/2006 Kaiser ................ G01N 33/5008 424/9.1
7,399,845 B2 7/2008 Swayze et al.
7,919,472 B2 4/2011 Monia et al.
8,580,756 B2 11/2013 Hansen et al.
8,703,728 B2 4/2014 Swayze et al.
9,243,291 B1 1/2016 Burel
10,799,523 B2 10/2020 Olson et al.
2010/0197762 A1 8/2010 Swayze
2011/0130441 A1 6/2011 Seth et al.
2012/0309687 A1 12/2012 Rossi
2012/0322851 A1 12/2012 Hardee et al.
2014/0107330 A1 4/2014 Freier et al.
2014/0249141 A1 9/2014 Mazurov et al.
2015/0275205 A1 10/2015 Miller et al.
2016/0032285 A1 2/2016 Rigo et al.
2016/0138014 A1 5/2016 Kordasiewicz et al.
2016/0145617 A1 5/2016 Kordasiewicz et al.
2016/0237427 A1 8/2016 Olson et al.

FOREIGN PATENT DOCUMENTS

EP 0240975 A2 10/1987
EP 0417014 A2 3/1991
EP 0455460 A2 11/1991
EP 0522530 A2 1/1993
EP 0417563 B1 7/2000
EP 2092065 B1 1/2012
EP 2410054 A1 1/2012
EP 1799859 B1 7/2014
EP 2410053 B1 10/2014
EP 1670896 B1 1/2015
WO WO-9014359 A1 11/1990
WO WO-9014425 A1 11/1990
WO WO-0040614 A2 7/2000
WO WO-200142266 A1 6/2001
WO WO-2004046160 A2 6/2004
WO WO-2004069992 A2 8/2004
WO WO-2004074301 A2 9/2004
WO WO-2006052712 A1 5/2006
WO WO-2007031091 A2 3/2007
WO WO-2007134181 A2 11/2007
WO WO-2007146511 A2 12/2007
WO WO-2008113832 A2 9/2008
WO WO-2008150729 A2 12/2008
WO WO-2008154401 A2 12/2008
WO WO-2009006478 A2 1/2009
WO WO-2009067647 A1 5/2009
WO WO-2009090182 A1 7/2009
WO WO-2009100320 A2 8/2009
WO WO-2009124295 A2 10/2009
WO WO-2010036698 A1 4/2010
WO WO-2010045624 A1 4/2010
WO WO-2010095042 A2 8/2010
WO WO-2011017521 A2 2/2011
WO WO-2011085102 A1 7/2011
WO WO-2011115818 A1 9/2011
WO WO-2012109395 A1 8/2012
WO WO-2013148260 A1 * 10/2013 ............ C07H 21/04
WO WO-2013148283 A1 10/2013
WO WO-2013159108 A2 10/2013
WO WO-2014059341 A2 4/2014
WO WO-2014153236 A1 9/2014
WO WO-2015006705 A2 1/2015
WO WO-2015010135 A2 1/2015
WO WO-2016019063 A1 2/2016

OTHER PUBLICATIONS

Bouchard P. Toxicological considerations for oligonucleotide therapeutics. Novartis slide presentation, Northern CA SOT, May 2010 ; www.toxicology.org/groups/rc/NorCal/docs/2010Spring/2010_3ToxConsider_OligonucleotideTherap.pdf. (Year: 2010).*

Lee JJA and Yokota T. Antisense therapy in neurology. J. Pers. Med. 2013, 3, 144-176. (Year: 2013).*

Magen I and Hornstein E. Oligonucleotide-based therapy for neurodegenerative diseases. Brain Research, Apr. 2014, 1584, 116-128. (Year: 2014).*

Smith RA et al. Antisense oligonucleotide therapy for neurodegenerative disease. J. Clin. Invest. 2006, 116(8), 2290-2296. (Year: 2006).*

Drygin D et al. Sequence-dependent cytotoxicity of second-generation oligonucleotides. Nucleic Acids Res. 32(22), 6585-6594. (Year: 2004).*

Hagedorn PH et al. Hepatoxic potential of therapeutic oligonucleotides can be predicted from their sequence and modification pattern. Nucleic Acid Therap. 23(5), 302-310. (Year: 2013).*

Sewing S et al. Establishment of a predictive in vitro assay for assessment of the hepatoxic potential of oligonucleotide drugs. PLoS One, 11(7):e0159431. (Year: 2016).*

Berman CL et al. Recommendations for safety pharmacology evaluations of oligonucleotide-based therapeutics. Nucleic Acid Therapeutics, 24(4), 2014, 291-301. (Year: 2014).*

Boudreau RL et al. Rational design of therapeutic siRNAs: Minimizing off-targeting potential to improved the safety of RNAi therapy for Huntington's disease. Mol. Therapy, 19(12), 2011, 2169-2177. (Year: 2011).*

McBride JL et al. Artificial miRNAs mitigate shRNA-mediated toxicity in the brain: Implications for the therapeutic development of RNAi. PNAS, 105(15), 2008, 5868-5873. (Year: 2008).*

Office Action (Non-Final) dated Feb. 12, 2018, in U.S. Appl. No. 15/016,169, Olson, R.E., et al., filed Feb. 4, 2016, 13 pages.

Office Action (Final) dated Oct. 25, 2018, in U.S. Appl. No. 15/016,169, Olson, R.E., et al., filed Feb. 4, 2016, 12 pages.

Cao, Z., et al., "Involvement of Caspase Activation in Azaspiracid-Induced Neurotoxicity in Neocortical Neurons," Toxicology Sciences 114(2):323-334, Oxford University Press, England (2010).

Takahashi, H., et al., "Neurotoxicity Test," Folia Pharmacologica Japonica 131:462-467, Pharmacological Society of Japan (2008).

Vito, S., et al., "Post-exposure administration of diazepam combined with soluble epoxide hydrolase inhibition stops seizures and modulates neuroinflammation in a murine model of acute TETS intoxication," Toxicology and Applied Pharmacology 281:185-194, Elsevier, Netherlands (Dec. 2014).

Office Action (Non-Final) dated Oct. 17, 2019, in U.S. Appl. No. 15/016,169, Olson, R.E. et al., filed Feb. 4, 2016, 10 pages.

Altschul, S.F. and Gish, W., "Local Alignment Statistics," *Methods in Enzymology* 266:460-480, Academic Press, United States (1996).

Altschul, S.F., et al., "Gapped BLAST and PSI-BLAST: A New Generation of Protein Database Search Programs," *Nucleic Acids Research* 25(17):3389-3402, Oxford University Press, England (1997).

Andorfer, C., et al., "Hyperphosphorylation and Aggregation of Tau in Mice Expressing Normal Human Tau Isoforms," *Journal of Neurochemistry* 86(3):582-590, Wiley on behalf of the International Society for Neurochemistry, England (2003).

Barciszewski, J., et al., "Locked Nucleic Acid Aptamers," in *Nucleic Acid and Peptide Aptamers; Methods and Protocols*, Chapter 10, vol. 535, Mayer, G., ed., pp. 165-186, Humana Press, United States (2009).

Barten, D.M., et al., "Tau Transgenic Mice as Models for Cerebrospinal Fluid Tau Biomarkers," *Journal of Alzheimer's Disease* 24(Suppl 2):127-141, IOS Press, Netherlands (2011).

Bird, R.E., et al., "Single-Chain Antigen-Binding Proteins," *Science* 242(4877):423-426, Association for the Advancement of Science, United States (1988).

(56) References Cited

OTHER PUBLICATIONS

Boehmerle, W., et al., "Paclitaxel induces calcium oscillations via an inositol 1,4,5-trisphosphate receptor and neuronal calcium sensor 1-dependent mechanism," *Proceedings of the National Academy of Sciences USA* 103(48):18356-18361, National Academy of Sciences, United States (2006).
Bojarski, L., et al., "Calcium dysregulation in Alzheimer's disease," *Neurochemistry International* 52(4-5):621-633, Elsevier Ltd., England (2008).
Cao, Z., et al., "Tetramethylenedisulfotetramine Alters $Ca^{2+}$ Dynamics in Cultured Hippocampal Neurons: Mitigation by NMDA Receptor Blockade and $GABA_A$ Receptor-Positive Modulation," *Toxicological Sciences* 130(2):362-372, Oxford University Press, England (2012).
Christensen, U.B. and Pedersen, E.B., "Intercalating Nucleic Acids Containing Insertions of 1-o-(1-pyrenylmethyl)glycerol: Stabilisation of dsDNA and Discrimination of DNA over RNA," *Nucleic Acids Research* 30(22):4918-4925, Oxford University Press, England (2002).
Co-pending U.S. Appl. No. 15/548,391, inventors Hagedorn, P., et al., I.A. filed Feb. 4, 2016, corresponding to International Publication No. WO 2016/127002 A1, Published as 2018/0023081 A1; Jan. 25, 2018.
Dass, C.R., "Vehicles for Oligonucleotide Delivery to Tumours," *The Journal of Pharmacy and Pharmacology* 54(1):3-27, Wiley, England (2002).
Dodart, J.C., et al., "Scopolamine-induced Deficits in a Two-trial Object Recognition Task in Mice," *NeuroReport* 8(5):1173-1178, Rapid Science Publishers, England (1997).
Dravid, S.M and Murray, T.F., "Spontaneous Synchronized Calcium Oscillations in Neocortical Neurons in the Presence of Physiological [$Mg^{2+}$]: Involvement of AMPA/kainate and Metabotropic Glutamate Receptors," *Brain Research* 1006(1):8-17, Elsevier B.V., Netherlands (2004).
Dyment, D.A., et al., "Homozygous nonsense mutation in SYNJ1 associated with intractable epilepsy and tau pathology," *Neurobiology of Aging* 36(2):1222.e.1-1222.e5, Elsevier Inc., United States (published online Sep. 6, 2014) (Feb. 2015).
Ennaceur, A. and Delacour, J., "A New One-trial Test for Neurobiological Studies of Memory in Rats. 1: Behavioral Data," *Behavioural Brain Research* 31(1):47-59, Elsevier/North-Holland Biomedical Press, Netherlands (1988).
Fluiter, K., et al., "Filling the Gap in LNA Antisense Oligo Gapmers: the Effects of Unlocked Nucleic Acid (UNA) and 4'-c-hydroxymethyl-DNA Modifications on Rnase H Recruitment and Efficacy of an LNA Gapmer," *Molecular BioSystems* 507:838-843, Royal Society of Chemistry, England (2009).
Freier, S.M. and Altmann, K.H., "The Ups and Downs of Nucleic Acid Duplex Stability: Structure-stability Studies on Chemically-modified DNA:RNA Duplexes," *Nucleic Acids Research* 25(22):4429-4443, Oxford University Press, England (1997).
Freshney, R.I., "Quantitation and Experimental Design," in *Culture of Animal Cells*, pp. 227-296, Alan R. Liss, Inc., United States (1987).
Frieden, M., et al., "Expanding the design horizon of antisense oligonucleotides with alpha-$_L$-LNA," *Nucleic Acids Research* 31(21):6365-6372, Oxford University Press, England (2003).
Frost, B., et al., "Connecting the dots between tau dysfunction and neurodegeneration," *Trends in Cell Biology* 25(1):46-53, Elsevier Ltd., England (Jan. 2015).
Frost, R.L., et al., "An SEM, EDS and Vibrational Spectroscopic Study of the Silicate Mineral Meliphanite $(Ca,Na)_2Be[(Si,Al)_2O_6(F,OH)]$," *Spectrochimica Acta Part A: Molecular and Biomolecular Spectroscopy* 136 Pt B:216-220, Elsevier B.V., England (Feb. 2015).
Genbank, "*Homo sapiens* Brain Abundant Membrane Attached Signal Protein 1 (BASP1), Transcript Variant 1, mRNA," Accession NM_006317.4, accessed at www.ncbi.nlm.nih.gov/nuccore/NM_006317.4, accessed on Oct. 12, 2017, 6 pages.
Genbank, "*Homo sapiens* chromosome 17, GRCh38.p2 Primary Assembly," Accession NC_000017.11, accessed at www.ncbi.nlm.nih.gov/nuccore/NC_000017, accessed on Apr. 18, 2016, 3 pages.
Genbank, "*Homo sapiens* microtubule associated protein tau (MAPT), RefSeqGene on chromosome 17," Accession NG_007398.1, accessed at www.ncbi.nlm.nih.gov/nuccore/NG_007398.1, accessed on Apr. 18, 2016, 37 pages.
Genbank, "*Homo sapiens* microtubule associated protein tau (MAPT), transcript variant 1, mRNA," Accession NM_016835.4, accessed at www.ncbi.nlm.nih.gov/nuccore/NM_016835, accessed on Apr. 18, 2016, 16 pages.
Genbank, "Human mRNA for amyloid A4 precursor of Alzheimer's disease," Accession Y00264, accessed at www.ncbi.nlm.nih.gov/nuccore/Y00264, accessed on Oct. 12, 2017, 4 pages.
Genbank, "Microtubule-associated protein tau," Accession Q6QT54, accessed at www.ncbi.nlm.nih.gov/protein/Q6QT54?report=genpept, accessed on Apr. 18, 2016, 2 pages.
Genbank, "Predicted: Macaca fascicularis microtubule associated protein tau (MAPT), transcript variant X13, mRNA," Accession XM_005584540.1, accessed at www.ncbi.nlm.nih.gov/nuccore/XM 005584540.1, accessed on Apr. 18, 2016, 4 pages.
Genbank, "Predicted: Macaca fascicularis microtubule-associated protein tau (MAPT), transcript variant X1, mRNA," Accession XM_005584529.1, accessed at www.ncbi.nlm.nih.gov/nuccore/XM_005584529.1?report=genbank, accessed on Apr. 18, 2016, 4 pages.
Genbank, "RecName: Full=Microtubule-associated protein tau; AltName: Full=Neurofibrillary tangle protein; AltName: Full=Paired helical filament-tau; Short-PHF-tau," Accession P10636.5, accessed at www.ncbi.nlm.nih.gov/protein/P10636, accessed on Apr. 18, 2016, 38 pages.
Genbank, "Microtubule-associated protein tau," Accession No. Q5CZI7, accessed at www.ncbi.nlm.nih.gov/protein/Q5CZI7?report=genpept, accessed on Apr. 18, 2016, 2 pages.
Genbank, "Microtubule-associated Protein Tau, Fetal," Accession No. P18518, accessed at www.ncbi.nlm.nih.gov/protein/P18518?report=genpept, accessed on Apr. 18, 2016, 2 pages.
Genbank, "Microtubule-associated protein tau (Microtubule-associated protein tau, isoform 4)," Accession No. Q53YB1, accessed at www.ncbi.nlm.nih.gov/protein/Q53YB1=report-genpept, accessed on Apr. 18, 2016, 2 pages.
Gheyara, A.L., et al., "Tau Reduction Prevents Disease in a Mouse Model of Dravet Syndrome," *Annals of Neurology* 76(3):443-456, Wiley-Liss, United States (2014).
Gordon, D., et al., "Antisense Suppression of Tau in Cultured Rat Oligodendrocytes Inhibits Process Formation," *Journal of Neuroscience Research* 86(12):2591-2601, Wiley-Liss, Inc., United States (2008).
He, S.J., et al., "Caffeine-dependent stimulus-triggered oscillations in the CA3 region of hippocampal slices from rats chronically exposed to lead," *Experimental Neurology* 190(2):525-534, Elsevier Inc., United States (2004).
Holm, S., "A Simple Sequentially Rejective Multiple Test Procedure," *Scandinavian Journal of Statistics* 6:65-70, John Wiley & Sons, Inc., United States (1979).
Hou, C.E., et al., "Non-alzheimer's Disease Dementias: Anatomic, Clinical, and Molecular Correlates," *Canadian Journal of Psychiatry* 49(3):164-171, Sage, United States (2004).
Huston, J.S., et al., "Protein engineering of antibody binding sites: recovery of specific activity in an anti-digoxin single-chain Fv analogue produced in *Escherichia coli*," *Proceedings of the National Academy of Sciences USA* 85(16):5879-5883, National Academy of Sciences, United States (1988).
Inoue, H., et al., "Elevation of Tau Protein Levels in the Cerebrospinal Fluid of Children with West Syndrome," *Epilepsy Research* 102(1-2):8-12, Elsevier B.V., Netherlands (2012).
International Preliminary Report on Patentability and Written Opinion for Application Serial No. PCT/US2016/016657, The International Bureau of WIPO, Geneva, Switzerland, dated Aug. 8, 2017, 7 pages.
International Preliminary Report on Patentability and Written Opinion for Application Serial No. PCT/US2016/016652, The International Bureau of WIPO, Geneva, Switzerland, dated Aug. 8, 2017, 9 pages.

(56) References Cited

OTHER PUBLICATIONS

International Search Report and Written Opinion for International Application No. PCT/US2016/016646, International Searching Authority, European Patent Office, Rijswijk, Netherlands, dated Jul. 8, 2016, 19 pages.

International Search Report and Written Opinion for International Application No. PCT/US2016/016652, International Searching Authority, European Patent Office, Rijswijk, Netherlands, dated Jul. 11, 2016, 17 pages.

International Search Report and Written Opinion for International Application No. PCT/US2016/016657, International Searching Authority, European Patent Office, Rijswijk, Netherlands, dated Apr. 28, 2016, 15 pages.

Jendreyko, N., et al., "Intradiabodies, Bispecific, Tetravalent Antibodies for the Simultaneous Functional Knockout of Two Cell Surface Receptors," *The Journal of Biological Chemistry* 278(48):47812-47819, The American Society for Biochemistry and Molecular Biology, Inc., United States (2003).

Jepsen, J.S., "Downregulation of p21$^{(WAF1/CIP1)}$and Estrogen Receptor α in MCF-7 Cells by Antisense Oligonucleotides Containing Locked Nucleic Acid (LNA)," *Oligonucleotides* 14(2):147-156, Mary Ann Liebert, Inc., United States (2004).

Karlin, S. and Altschul, S.E., "Methods for Assessing the Statistical Significance of Molecular Sequence Features by using General Scoring Schemes," *Proceedings of the National Academy of Sciences of the USA* 87(6):2264-2268, National Academy of Sciences, United States (1990).

Karlin, S, and Altschul, S.F., "Applications and Statistics for Multiple High-Scoring Segments in Molecular Sequences," *Proceedings of the National Academy of Sciences USA* 90(12):5873-5877, National Academy of Sciences, United States (1993).

Kurreck, J., et al., "Design of antisense oligonucleotides stabilized by locked nucleic acids," *Nucleic Acids Res.* 30(9):1911-1918, Oxford University Press, England (2002).

Laird, N.M. and Ware, J.H., "Random-effects Models for Longitudinal Data," *Biometrics* 38(4):963-974, Biometric Society, United States (1982).

Morris, R., "Developments of a Water-maze Procedure for Studying Spatial Learning in the Rat," *Journal of Neuroscience Methods* 11(1):47-60, Elsevier Science Publishers B.V., Netherlands (1984).

Moussaud, S., et al., "Alpha-synuclein and Tau: Teammates in Neurodegeneration?," *Molecular Neurodegeneration* 9:43, BioMed Central, England (2014).

Murphy, T.H., et al., "Spontaneous Synchronous Synaptic Calcium Transients in Cultured Cortical Neurons," *The Journal of Neuroscience* 12(12):4834-4845, Society for Neuroscience, United States (1992).

Myers, E.W. and Miller, W., "Optimal alignments in linear space," *Comput Appl Biosci.* 4(1):11-17, Oxford University Press, England (1988).

Needleman, S.B. and Wunsch, C.D., "A General Method Applicable To the Search for Similarities in the Amino Acid Sequence of Two Proteins," *Journal of Molecular Biology* 48(3):443-453, Academic Press, England (1970).

Oakley, J.C., et al., "Temperature- and Age-dependent Seizures in a Mouse Model of Severe Myoclonic Epilepsy in Infancy," *Proceedings of the National Academy of Sciences of the USA* 106(10):3994-3999, National Academy of Sciences, United States (2009).

Obika, S., et al., "Inhibition of ICAM-I gene expression by antisense 2',4'-BNA oligonucleotides," Nucleic Acids Symposium Series 1(1):145-146, Oxford University Press, England (2001).

Office Action (Final) dated Aug. 3, 2017, in U.S. Appl. No. 15/016,169, Olson, R.E., et al., filed Feb. 4, 2016, 17 pages.

Office Action (Non-Final) dated Feb. 28, 2017, in U.S. Appl. No. 15/016,169, Olson, R.E., et al., filed Feb. 4, 2016, 13 pages.

Partial International Search Report for International Application No. PCT/US2016/016646, International Searching Authority, European Patent Office, Rijswijk, Netherlands, dated May 2, 2016, 4 pages.

Pasti, L., et al., "Cytosolic Calcium Oscillations in Astrocytes May Regulate Exocytotic Release of Glutamate," *The Journal of Neuroscience* 21(2):477-484, Society for Neuroscience, United States (2001).

Polydoro, M., et al., "Age-dependent Impairment of Cognitive and Synaptic Function in the Htau Mouse Model of Tau Pathology," *The Journal of Neuroscience* 29(34):10747-10749, Society for Neuroscience, United States (2009).

Rose, C.R. and Konnerth, A., "Exciting Glial Oscillations," *Nature Neuroscience* 4(8):773-774, Nature America Inc., United States (2001).

Ross, W.T. and Olsen, M., "Care of the Adult Patient with Down Syndrome," *Southern Medical Journal* 107(11):715-721, Southern Medical Association, United States (2014).

Seth, P.P., et al., "Synthesis and Biophysical Evaluation of 2',4'-constrained 2'O-methoxyethyl and 2',4'-constrained 2'O-ethyl Nucleic Acid Analogues," *Journal of Organic Chemistry* 75(5):1569-1581, American Chemical Society, United States (2010).

Silahtaroglu, A.N., et al., "FISHing with locked nucleic acids (LNA): evaluation of different LNA/DNA mixmers," *Molecular and Cellular Probes* 17(4):165-169, Elsevier Ltd., England (2003).

Skerra, A. and Pluckthun, A., "Assembly of a Functional Immunoglobulin $F_v$ Fragment in *Escherichia coli*," *Science* 240(4855):1038-1041, Association for the Advancement of Science, United States (1988).

Stanton, R., et al., "Chemical Modification Study of Antisense Gapmers," *Nucleic Acid Therapeutics* 22(5):344-359, Mary Ann Liebert, Inc., United States (2012).

Stowe, R.P., et al., "Detection and Quantification of Epstein-Barr Virus EBER1 in EBV-infected Cells by Fluorescent in situ Hybridization and Flow Cytometry," *Journal of Virological Methods* 75(1):83-91, Elsevier Science B.V., Netherlands (1998).

Takagi-Sato, M., et al., "Design of ENA® gapmers as fine-tuning antisense oligonucleotides with sequence-specific inhibitory activity on mouse PADI4 mRNA expression," *Nucleic Acids Symposium Series* (*Oxford*) 50:319-320, Oxford University Press, England (2006).

Takagi-Sato, M., et al., "Fine-Tuning of ENA® Gapmers as Antisense Oligonucleotides for Sequence-Specific Inhibition," *Oligonucleotides* 17(3):291-301, Mary Ann Liebert, Inc., United States (2007).

Thom, M., et al., "Neurofibrillary Tangle Pathology and Braak Staging in Chronic Epilepsy in Relation to Traumatic Brain Injury and Hippocampal Sclerosis: a Post-mortem Study," *Brain : a Journal of Neurology* 134(Pt 10):2969-2981, Oxford University Press, England (2011).

Touboul, M., et al., "Early Detection of Chemoresistance In Vivo through the Use of a Radiolabeled Antisense Oligonucleotide," *Anticancer Research* 22(6A):3349-3356, International Institute of Anticancer Research, Greece (2002).

Uhlmann, E., "Recent Advances in the Medicinal Chemistry of Antisense Oligonucleotides," *Current Opinion in Drug Discovery and Development* 30:203-213, PharmaPress Ltd., England (2000).

Verjat, T., et al., "Detection of 8-oxoG DNA glycosylase activity and OGG1 transcripts in the rat CNS," *Mutation Research/DNA Repair* 460(2):127-138, Elsevier Science B.V., Netherlands (2000).

Vester, B., et al., "Chemically Modified Oligonucleotides with Efficient RNase H Response," *Bioorganic & Medicinal Chemistry Letters* 780:2296-2300, Elsevier Ltd., England (2008).

Vickers, T.A., et al., "Fully Modified 2' MOE Oligonucleotides Redirect Polyadenylation," *Nucleic Acids Research* 29(6):1293-1299, Oxford University Press, England (2001).

Ward, E.S., et al., "Binding Activities of a Repertoire of Single Immunoglobulin Variable Domains Secreted from *Escherichia coli*," *Nature* 341(6242):544-546, Nature Publishing Group, England (1989).

Xi, Z.Q., et al., "Is Intractable Epilepsy a Tauopathy?," *Medical Hypotheses* 76(6):897-900, Elsevier Ltd., England (2011).

Yaksh, T.L. and Rudy, T.A., "Chronic Catheterization of the Spinal Subarachnoid Space," *Physiology & Behavior* 17(6): 1031-1036, Pergamon Press and Brain Research Publ., United States (1976).

Yu, J.T., et al., "Calcium dysregulation in Alzheimer's disease: From mechanisms to therapeutic opportunities," *Progress in Neurobiology* 89(3):240-255, Elsevier Ltd., England (2009).

(56) References Cited

OTHER PUBLICATIONS

Zheng, P., et al., "Hyperphosphorylated Tau Is Implicated in Acquired Epilepsy and Neuropsychiatric Comorbidities," *Molecular Neurobiology* 49(3):1532-1539, Humana Press, United States (2014).

Zonta, M. and Carmignoto, G., "Calcium Oscillations Encoding Neuron-to-astrocyte Communication," *Journal of Physiology* 96(3-4):193-198, Elsevier Science Ltd., England (2002).

Zhen-Yu, R., et al., "Calcium Homeostasis in deregulation in glutamate-induced excitotoxicity and its role in neurodegenerative diseases," Chinese Pharmacological Bulletin 23 (3): 289-292, Institute of Clinical Pharmacology, China (2007).

* cited by examiner

Figure 4

| Oligomer Name | ASO Number | ASO Sequence | SEQ ID NO: | premRNA start NG_007398 | premRNA end NG_007398 | Oscillation data % control |
|---|---|---|---|---|---|---|
| ASO-001167 | ASO-001167 | AAAgatgaaatttgctcTTA | 4 | 134947 | 134966 | >100% |
| ASO-001168 | ASO-001168 | GAAagatgaaatttgctCTT | 5 | 134948 | 134967 | 100% |
| ASO-001169 | ASO-001169 | GGAaagatgaaatttgcTCT | 6 | 134949 | 134968 | 74% |
| ASO-000829 | ASO-000829 | AAGatgaaatttgCTC | 7 | 134950 | 134965 | >100% |
| ASO-001170 | ASO-001170 | TGGaaagatgaaatttgCTC | 8 | 134950 | 134969 | 6% |
| ASO-001171 | ASO-001171 | TTGgaaagatgaaatttGCT | 9 | 134951 | 134970 | 1% |
| ASO-001172 | ASO-001172 | TTTggaaagatgaaattTGC | 10 | 134952 | 134971 | 8% |
| ASO-001173 | ASO-001173 | ATTtggaaagatgaaatTTG | 11 | 134953 | 134972 | 0% |
| ASO-001174 | ASO-001174 | AATttggaaagatgaaaTTT | 12 | 134954 | 134973 | 0% |
| ASO-001175 | ASO-001175 | CAAtttggaaagatgaaATT | 13 | 134955 | 134974 | 4% |
| ASO-001176 | ASO-001176 | TCAatttggaaagatgaAAT | 14 | 134956 | 134975 | 0% |
| ASO-001177 | ASO-001177 | ATCaatttggaaagatgAAA | 15 | 134957 | 134976 | 10% |
| ASO-001178 | ASO-001178 | CATcaatttggaaagatGAA | 16 | 134958 | 134977 | 62% |
| ASO-001181 | ASO-001181 | ACCcatcaatttggaaaGAT | 17 | 134961 | 134980 | 73% |
| ASO-001179 | ASO-001179 | CCAtcaatttggaaagaTGA | 18 | 134959 | 134978 | 52% |
| ASO-001180 | ASO-001180 | CCCatcaatttggaaagATG | 19 | 134960 | 134979 | 58% |
| ASO-001182 | ASO-001182 | CACccatcaatttggaaAGA | 20 | 134962 | 134981 | 92% |
| ASO-001183 | ASO-001183 | CCAcccatcaatttggaAAG | 21 | 134963 | 134982 | 58% |
| ASO-001184 | ASO-001184 | CCCacccatcaatttggAAA | 22 | 134964 | 134983 | 12% |
| ASO-001062 | ASO-001062 | GCCcacccatcaatttgGAA | 23 | 134965 | 134984 | 1% |
| ASO-001063 | ASO-001063 | TAGcccacccatcaattTGG | 24 | 134967 | 134986 | 8% |
| ASO-001064 | ASO-001064 | CTAgcccacccatcaatTTG | 25 | 134968 | 134987 | 0% |
| ASO-001065 | ASO-001065 | ACTagcccacccatcaaTTT | 26 | 134969 | 134988 | 13% |
| ASO-001066 | ASO-001066 | TACtagcccacccatcaATT | 27 | 134970 | 134989 | 54% |
| ASO-000830 | ASO-000830 | TACtagcccacccATC | 28 | 134974 | 134989 | >100% |
| ASO-000260 | ASO-000260 | CCCtcttctacatGGA | 29 | 135077 | 135092 | |
| ASO-000305 | ASO-000305 | TGCctctgtgacaCCC | 30 | 135171 | 135186 | |
| ASO-000304 | ASO-000304 | TTCaaatcctttgTTG | 31 | 135194 | 135209 | |

Figure 4 cont.

| Oligomer Name | ASO Number | ASO Sequence | SEQ ID NO: | premRNA start NG_007398 | premRNA end NG_007398 | Oscillation data % control |
|---|---|---|---|---|---|---|
| ASO-000324 | ASO-000324 | CACacaaggttgaCAT | 32 | 135242 | 135257 | |
| ASO-000268 | ASO-000268 | CGTcacactcacaCAA | 33 | 135251 | 135266 | |
| ASO-000223 | ASO-000223 | GCCaccaaggacaGGC | 34 | 135441 | 135456 | |
| ASO-000224 | ASO-000224 | CAGcttgccttctCTT | 35 | 135533 | 135548 | |
| ASO-000319 | ASO-000319 | ATCaaggtcagtcTTT | 36 | 135585 | 135600 | |
| ASO-000208 | ASO-000208 | CCTtcagaactcaATA | 37 | 135690 | 135705 | |
| ASO-000689 | ASO-000689 | AAAgtcccaggtcTGC | 38 | 135737 | 135752 | |
| ASO-000434 | ASO-000434 | CTAaagtcccaggTCT | 39 | 135739 | 135754 | 59% |
| ASO-000409 | ASO-000409 | TAAagtcccaggTCT | 40 | 135739 | 135753 | >100% |
| ASO-000432 | ASO-000432 | CCTaaagtcccagGTC | 41 | 135740 | 135755 | 63% |
| ASO-000391 | ASO-000391 | TAAagtcccagGTC | 42 | 135740 | 135753 | 72% |
| ASO-001779 | ASO-001779 | TAGccctaaagtcccagGTC | 43 | 135740 | 135759 | 54% |
| ASO-000899 | ASO-000899 | CTAaagtcccagGTC | 44 | 135740 | 135754 | |
| ASO-000398 | ASO-000398 | CCCtaaagtcccaGGT | 45 | 135741 | 135756 | 76% |
| ASO-001778 | ASO-001778 | TTAgccctaaagtcccaGGT | 46 | 135741 | 135760 | 86% |
| ASO-000414 | ASO-000414 | GCCctaaagtcccAGG | 47 | 135742 | 135757 | 42% |
| ASO-000403 | ASO-000403 | CCCtaaagtcccAGG | 48 | 135742 | 135756 | 72% |
| ASO-001780 | ASO-001780 | GTTagccctaaagtcccAGG | 49 | 135742 | 135761 | 28% |
| ASO-000433 | ASO-000433 | GCCctaaagtccCAG | 50 | 135743 | 135757 | 34% |
| ASO-000411 | ASO-000411 | CCCtaaagtccCAG | 51 | 135743 | 135756 | 51% |
| ASO-001781 | ASO-001781 | GGTtagccctaaagtccCAG | 52 | 135743 | 135762 | 37% |
| ASO-000389 | ASO-000389 | TAGccctaaagtcCCA | 53 | 135744 | 135759 | 96% |
| ASO-001939 | ASO-001939 | TAGccctaaagtcCCA | 54 | 135744 | 135759 | >100% |
| ASO-001932 | ASO-001932 | TAGccctaaagtcCCA | 55 | 135744 | 135759 | 86% |
| ASO-001925 | ASO-001925 | TAGccctaaagtcCCA | 56 | 135744 | 135759 | >100% |
| ASO-001924 | ASO-001924 | TAGccctaaagtcCCA | 57 | 135744 | 135759 | 100% |
| ASO-001952 | ASO-001952 | TAGccctaaagtcCCA | 58 | 135744 | 135759 | 79% |
| ASO-001931 | ASO-001931 | TAGccctaaagtcCCA | 59 | 135744 | 135759 | 83% |
| ASO-001953 | ASO-001953 | TAGccctaaagtcCCA | 60 | 135744 | 135759 | 97% |

Figure 4 cont.

| Oligomer Name | ASO Number | ASO Sequence | SEQ ID NO: | premRNA start NG_007398 | premRNA end NG_007398 | Oscillation data % control |
|---|---|---|---|---|---|---|
| ASO-001945 | ASO-001945 | TAGccctaaagtcCCA | 61 | 135744 | 135759 | 68% |
| ASO-001946 | ASO-001946 | TAGccctaaagtcCCA | 62 | 135744 | 135759 | >100% |
| ASO-001971 | ASO-001971 | TAGccctaaagtcCCA | 63 | 135744 | 135759 | 81% |
| ASO-001938 | ASO-001938 | TAGccctaaagtcCCA | 64 | 135744 | 135759 | 87% |
| ASO-001959 | ASO-001959 | TAGccctaaagtcCCA | 65 | 135744 | 135759 | 83% |
| ASO-001965 | ASO-001965 | TAGccctaaagtcCCA | 66 | 135744 | 135759 | 83% |
| ASO-001782 | ASO-001782 | TGGttagccctaaagtcCCA | 67 | 135744 | 135763 | 75% |
| ASO-000900 | ASO-000900 | TAGccctaaagtcCCA | 68 | 135744 | 135759 | |
| ASO-000435 | ASO-000435 | TTAgccctaaagtCCC | 69 | 135745 | 135760 | 29% |
| ASO-000423 | ASO-000423 | GTTagccctaaagTCC | 70 | 135746 | 135761 | >100% |
| ASO-000442 | ASO-000442 | TAGccctaaagTCC | 71 | 135746 | 135759 | 88% |
| ASO-000416 | ASO-000416 | GGTtagccctaaaGTC | 72 | 135747 | 135762 | |
| ASO-000438 | ASO-000438 | GTTagccctaaAGT | 73 | 135748 | 135761 | 61% |
| ASO-000581 | ASO-000581 | ACTggttagccctAAA | 74 | 135750 | 135765 | 4% |
| ASO-000639 | ASO-000639 | AACtggttagcccTAA | 75 | 135751 | 135766 | 31% |
| ASO-000558 | ASO-000558 | GAActggttagccCTA | 76 | 135752 | 135767 | 80% |
| ASO-000597 | ASO-000597 | GAGaactggttagCCC | 77 | 135754 | 135769 | 2% |
| ASO-000245 | ASO-000245 | TACaaagagaactGGT | 78 | 135760 | 135775 | |
| ASO-000897 | ASO-000897 | CACaagtccttacAAA | 79 | 135770 | 135785 | |
| ASO-000185 | ASO-000185 | GGCacaagtccttACA | 80 | 135772 | 135787 | |
| ASO-000426 | ASO-000426 | AGGcacaagtccTTA | 81 | 135774 | 135788 | >100% |
| ASO-000417 | ASO-000417 | GAGgcacaagtccTTA | 82 | 135774 | 135789 | 76% |
| ASO-000393 | ASO-000393 | AGAggcacaagtcCTT | 83 | 135775 | 135790 | 78% |
| ASO-000449 | ASO-000449 | AAGaggcacaagtCCT | 84 | 135776 | 135791 | 82% |
| ASO-000406 | ASO-000406 | AGAggcacaagtCCT | 85 | 135776 | 135790 | 74% |
| ASO-000392 | ASO-000392 | CCAagaggcacaaGTC | 86 | 135778 | 135793 | 74% |
| ASO-000444 | ASO-000444 | CAAgaggcacaaGTC | 87 | 135778 | 135792 | >100% |
| ASO-000443 | ASO-000443 | CCCaagaggcacaAGT | 88 | 135779 | 135794 | 90% |
| ASO-000450 | ASO-000450 | CAAgaggcacaAGT | 89 | 135779 | 135792 | 36% |

Figure 4 cont.

| Oligomer Name | ASO Number | ASO Sequence | SEQ ID NO: | premRNA start NG_007398 | premRNA end NG_007398 | Oscillation data % control |
|---|---|---|---|---|---|---|
| ASO-000258 | ASO-000258 | CTCccaagaggcaCAA | 90 | 135781 | 135796 | |
| ASO-000205 | ASO-000205 | TGGccgtgggaagGAC | 91 | 135876 | 135891 | |
| ASO-000213 | ASO-000213 | GGTgaggctgggaATT | 92 | 135984 | 135999 | |
| ASO-000293 | ASO-000293 | GTGaggctgggaATT | 93 | 135984 | 135998 | |
| ASO-000321 | ASO-000321 | TGGtgaggctgggAAT | 94 | 135985 | 136000 | |
| ASO-000226 | ASO-000226 | CTCagtatggagtAGG | 95 | 136040 | 136055 | |
| ASO-000682 | ASO-000682 | AATttcaccctcaGTA | 96 | 136049 | 136064 | 73% |
| ASO-000673 | ASO-000673 | TTAatttcaccctCAG | 97 | 136051 | 136066 | 42% |
| ASO-000578 | ASO-000578 | CTTaatttcacccTCA | 98 | 136052 | 136067 | 40% |
| ASO-000540-21 | ASO-002180 | CCTTaatttcaccCTCA | 99 | 136052 | 136068 | |
| ASO-000540-22 | ASO-002192 | CCTTaatttcacCctCA | 100 | 136052 | 136068 | |
| ASO-000540-23 | ASO-002109 | CCTTAatttcacCctCA | 101 | 136052 | 136068 | |
| ASO-000540-24 | ASO-002121 | TcCCtTaatttcaccCT | 102 | 136054 | 136070 | |
| ASO-000540-25 | ASO-002133 | TcCCTtaatttcaccCT | 103 | 136054 | 136070 | |
| ASO-000540-26 | ASO-002145 | TcCCTtaatttcAccCT | 104 | 136054 | 136070 | |
| ASO-000540-27 | ASO-002157 | TcCCTTaatttcaccCT | 105 | 136054 | 136070 | |
| ASO-000540-28 | ASO-002169 | TCcCTTaatttcaccCT | 106 | 136054 | 136070 | |
| ASO-000540-29 | ASO-002181 | TCCcttaatttcacCCT | 107 | 136054 | 136070 | |
| ASO-000540-3 | ASO-002154 | CCCttaatttcacCcTC | 108 | 136053 | 136069 | |
| ASO-000540-42 | ASO-002147 | CCCTtaatttcacccTCA | 109 | 136052 | 136069 | |
| ASO-000540-43 | ASO-002159 | CCCTtaatttcaccCtCA | 110 | 136052 | 136069 | |
| ASO-000540-44 | ASO-002171 | CCCTtaatttcaccCTCA | 111 | 136052 | 136069 | |
| ASO-000540-45 | ASO-002183 | CCCTtaatttcacCctCA | 112 | 136052 | 136069 | |
| ASO-000540-46 | ASO-002195 | CCCTtaatttcacCcTCA | 113 | 136052 | 136069 | |

Figure 4 cont.

| Oligomer Name | ASO Number | ASO Sequence | SEQ ID NO: | premRNA start NG_007398 | premRNA end NG_007398 | Oscillation data % control |
|---|---|---|---|---|---|---|
| ASO-000540-47 | ASO-002196 | CCCTtaatttcaCcctCA | 114 | 136052 | 136069 | |
| ASO-000540-48 | ASO-002200 | CCCTtaatttcaCccTCA | 115 | 136052 | 136069 | |
| ASO-000540-49 | ASO-002204 | CCCTtaatttcaCcCtCA | 116 | 136052 | 136069 | |
| ASO-000540-5 | ASO-002178 | CCCttaatttcAcccTC | 117 | 136053 | 136069 | |
| ASO-000540-50 | ASO-002208 | CCCTtaatttcAccCtCA | 118 | 136052 | 136069 | |
| ASO-000540-51 | ASO-002212 | CCCTtaatttcAcCctCA | 119 | 136052 | 136069 | |
| ASO-000540-52 | ASO-002216 | TcCCTtaatttcacCcTC | 120 | 136053 | 136070 | |
| ASO-000540-53 | ASO-002220 | TCcCTtaatttcacccTC | 121 | 136053 | 136070 | |
| ASO-000540-54 | ASO-002224 | TCcCTTaatttcacCcTC | 122 | 136053 | 136070 | |
| ASO-000540-55 | ASO-002197 | TCCcttaatttcaccCTC | 123 | 136053 | 136070 | |
| ASO-000540-69 | ASO-002222 | TCCcTtaatttcacCctCA | 124 | 136052 | 136070 | |
| ASO-000540-70 | ASO-002226 | TCCCttaatttcaccCTCA | 125 | 136052 | 136070 | |
| ASO-000540-71 | ASO-002199 | TCCCttaatttcacCcTCA | 126 | 136052 | 136070 | |
| ASO-000540-72 | ASO-002203 | TCCCttaatttcacCCtCA | 127 | 136052 | 136070 | |
| ASO-000540-73 | ASO-002207 | TCCCttaatttcaCcCtCA | 128 | 136052 | 136070 | |
| ASO-000540-74 | ASO-002211 | TCCCttaatttcACcCtCA | 129 | 136052 | 136070 | |
| ASO-000540-75 | ASO-002215 | TCCCTtaatttcaccCTCA | 130 | 136052 | 136070 | |
| ASO-000540-76 | ASO-002219 | TCCCTtaatttcacCCtCA | 131 | 136052 | 136070 | |
| ASO-000540-77 | ASO-002223 | TCCCTtaatttcacCCTCA | 132 | 136052 | 136070 | |
| ASO-000540-8 | ASO-002119 | CCCtTaatttcaccCTC | 133 | 136053 | 136069 | |
| ASO-000540-9 | ASO-002131 | CCCtTaatttcacCcTC | 134 | 136053 | 136069 | |
| TBD-mm10 | ASO-002382 | CCttgATttcgccctCA | 135 | 136053 | 136069 | |

Figure 4 cont.

| Oligomer Name | ASO Number | ASO Sequence | SEQ ID NO: | premRNA start NG_007398 | premRNA end NG_007398 | Oscillation data % control |
|---|---|---|---|---|---|---|
| TBD-mm11 | ASO-002299 | CCttgATttcaccctCT | 136 | 136052 | 136068 | |
| TBD-mm12 | ASO-002311 | CCttaGTttcaccctCG | 137 | 136054 | 136070 | |
| TBD-mm19 | ASO-002300 | CCCttgatttcaccctCA | 138 | 136052 | 136069 | |
| TBD-mm20 | ASO-002312 | CCCttaatttcaccctCG | 139 | 136054 | 136071 | |
| TBD-mm21 | ASO-002324 | CCCttagtttcaccctCA | 140 | 136052 | 136069 | |
| TBD-mm22 | ASO-002336 | CCCttgatttcgccctCA | 141 | 136052 | 136069 | |
| TBD-mm23 | ASO-002348 | CCCttgatttcaccctCG | 142 | 136053 | 136070 | |
| TBD-mm24 | ASO-002360 | CCCttgatttcaccctCT | 143 | 136052 | 136069 | |
| TBD-mm31 | ASO-002349 | TCcCTtgatttcacCctCA | 144 | 136053 | 136071 | |
| TBD-mm32 | ASO-002361 | TCcCTtaatttcacCctCG | 145 | 136052 | 136070 | |
| TBD-mm33 | ASO-002373 | ACcCTtaatttcacCctCA | 146 | 136053 | 136071 | |
| TBD-mm34 | ASO-002385 | TCcCTtgatttcgcCctCA | 147 | 136052 | 136070 | |
| TBD-mm35 | ASO-002302 | TCcCTtagtttcacCctCG | 148 | 136054 | 136072 | |
| TBD-mm36 | ASO-002314 | ACcCTtgatttcacCctCA | 149 | 136054 | 136072 | |
| TBD-mm7 | ASO-002346 | CCttgATttcaccctCA | 150 | 136053 | 136069 | |
| TBD-mm8 | ASO-002358 | CCttaGTttcaccctCA | 151 | 136053 | 136069 | |
| TBD-mm9 | ASO-002370 | CCttaATttcaccctCG | 152 | 136052 | 136068 | |
| ASO-000540 | ASO-000540 | CCTtaatttcaccCTC | 153 | 136053 | 136068 | >100% |
| ASO-000555 | ASO-000555 | CTTaatttcaccCTC | 154 | 136053 | 136067 | >100% |
| ASO-000579 | ASO-000579 | TTAatttcaccCTC | 155 | 136053 | 136066 | 44% |
| ASO-000540-1 | ASO-002130 | CCCttaatttcacccTC | 156 | 136053 | 136069 | |
| ASO-000540-10 | ASO-002143 | CCCTtaatttcaccCTC | 157 | 136053 | 136069 | |
| ASO-000540-11 | ASO-002155 | CCCTtaatttcacCcTC | 158 | 136053 | 136069 | |

Figure 4 cont.

| Oligomer Name | ASO Number | ASO Sequence | SEQ ID NO: | premRNA start NG_007398 | premRNA end NG_007398 | Oscillation data % control |
|---|---|---|---|---|---|---|
| ASO-000540-12 | ASO-002167 | CCCTtaatttcacCCTC | 159 | 136053 | 136069 | |
| ASO-000540-13 | ASO-002179 | CCCTtaatttcaCccTC | 160 | 136053 | 136069 | |
| ASO-000540-14 | ASO-002191 | CCttaATttcaccctCA | 161 | 136052 | 136068 | |
| ASO-000540-15 | ASO-002108 | CCTtaatttcacccTCA | 162 | 136052 | 136068 | |
| ASO-000540-16 | ASO-002120 | CCTtaaTttcaccctCA | 163 | 136052 | 136068 | |
| ASO-000540-17 | ASO-002132 | CCTtaAtttcaccctCA | 164 | 136052 | 136068 | |
| ASO-000540-18 | ASO-002144 | CCTtaATttcaccctCA | 165 | 136052 | 136068 | |
| ASO-000540-19 | ASO-002156 | CCTtaATttcacccTCA | 166 | 136052 | 136068 | |
| ASO-000540-2 | ASO-002142 | CCCttaatttcaccCTC | 167 | 136053 | 136069 | |
| ASO-000540-20 | ASO-002168 | CCTTaatttcaccCtCA | 168 | 136052 | 136068 | |
| ASO-000540-56 | ASO-002201 | TCCcttaatttcacCcTC | 169 | 136053 | 136070 | |
| ASO-000540-57 | ASO-002205 | TCCcTtaatttcacccTC | 170 | 136053 | 136070 | |
| ASO-000540-58 | ASO-002209 | TCCcTtaatttcacCcTC | 171 | 136053 | 136070 | |
| ASO-000540-59 | ASO-002213 | TCCcTtaatttcaCccTC | 172 | 136053 | 136070 | |
| ASO-000540-6 | ASO-002190 | CCCttaatttcAcCcTC | 173 | 136053 | 136069 | |
| ASO-000540-60 | ASO-002217 | TCCcTtaatttcAcCcTC | 174 | 136053 | 136070 | |
| ASO-000540-61 | ASO-002221 | TCCCttaatttcacCCTC | 175 | 136053 | 136070 | |
| ASO-000540-62 | ASO-002225 | TCCCttaatttcaCcCTC | 176 | 136053 | 136070 | |
| ASO-000540-63 | ASO-002198 | TCCCttaatttcaCCcTC | 177 | 136053 | 136070 | |
| ASO-000540-64 | ASO-002202 | TCCCttaatttcAccCTC | 178 | 136053 | 136070 | |
| ASO-000540-65 | ASO-002206 | TCCCttaatttCaccCTC | 179 | 136053 | 136070 | |
| ASO-000540-66 | ASO-002210 | TCcCTtaatttcacCctCA | 180 | 136052 | 136070 | |

Figure 4 cont.

| Oligomer Name | ASO Number | ASO Sequence | SEQ ID NO: | premRNA start NG_007398 | premRNA end NG_007398 | Oscillation data % control |
|---|---|---|---|---|---|---|
| ASO-000540-67 | ASO-002214 | TCCcttaatttcacccTCA | 181 | 136052 | 136070 | |
| ASO-000540-68 | ASO-002218 | TCCcTtaatttcaccCtCA | 182 | 136052 | 136070 | |
| ASO-000540-mm1 | ASO-002297 | CCTtgatttcaccCTC | 183 | 136053 | 136068 | |
| ASO-000540-mm2 | ASO-002309 | CCTtaatttcgccCTC | 184 | 136053 | 136068 | |
| ASO-000540-mm3 | ASO-002321 | CCTtagtttcaccCTC | 185 | 136053 | 136068 | |
| ASO-000540-mm4 | ASO-002333 | CCTtgatttcgccCTC | 186 | 136053 | 136068 | |
| ASO-000540-mm5 | ASO-002345 | CCTtggtttcaccCTC | 187 | 136053 | 136068 | |
| ASO-000540-mm6 | ASO-002357 | CCTtagtttcgccCTC | 188 | 136053 | 136068 | |
| TBD-mm1 | ASO-002369 | CCCttgatttcacccTC | 189 | 136052 | 136068 | |
| TBD-mm2 | ASO-002381 | CCCttagtttcacccTC | 190 | 136053 | 136069 | |
| TBD-mm25 | ASO-002372 | TcCCTtgatttcacCcTC | 191 | 136052 | 136069 | |
| TBD-mm26 | ASO-002384 | TcCCTtaatttcgcCcTC | 192 | 136052 | 136069 | |
| TBD-mm27 | ASO-002301 | TcCCTtagtttcacCcTC | 193 | 136052 | 136069 | |
| TBD-mm28 | ASO-002313 | TcCCTtgatttcgcCcTC | 194 | 136054 | 136071 | |
| TBD-mm29 | ASO-002325 | TcCCTtagtttcgcCcTC | 195 | 136052 | 136069 | |
| TBD-mm3 | ASO-002298 | CCCttaatttcgcccTC | 196 | 136053 | 136069 | |
| TBD-mm30 | ASO-002337 | AcCCTtgatttcacCcTC | 197 | 136053 | 136070 | |
| TBD-mm4 | ASO-002310 | CCCttgatttcgcccTC | 198 | 136054 | 136070 | |
| TBD-mm5 | ASO-002322 | CCCttggtttcacccTC | 199 | 136052 | 136068 | |
| TBD-mm6 | ASO-002334 | CCCttagtttcgcccTC | 200 | 136052 | 136068 | |
| ASO-000662 | ASO-000662 | CCCttaatttcacCCT | 201 | 136054 | 136069 | 81% |

Figure 4 cont.

| Oligomer Name | ASO Number | ASO Sequence | SEQ ID NO: | premRNA start NG_007398 | premRNA end NG_007398 | Oscillation data % control |
|---|---|---|---|---|---|---|
| ASO-000566 | ASO-000566 | CCTtaatttcacCCT | 202 | 136054 | 136068 | >100% |
| ASO-000540-30 | ASO-002193 | TCCcTtaatttcaccCT | 203 | 136054 | 136070 | |
| ASO-000540-31 | ASO-002110 | TCCcTtaatttcAccCT | 204 | 136054 | 136070 | |
| ASO-000540-32 | ASO-002122 | TCCcTTaatttcaccCT | 205 | 136054 | 136070 | |
| ASO-000540-33 | ASO-002134 | TCCCttaatttcaccCT | 206 | 136054 | 136070 | |
| ASO-000540-34 | ASO-002146 | TCCCttaatttcaCcCT | 207 | 136054 | 136070 | |
| ASO-000540-35 | ASO-002158 | TCCCttaatttcaCCCT | 208 | 136054 | 136070 | |
| ASO-000540-36 | ASO-002170 | TCCCttaatttCaccCT | 209 | 136054 | 136070 | |
| ASO-000540-37 | ASO-002182 | CCCttaatttcaccctCA | 210 | 136052 | 136069 | |
| ASO-000540-38 | ASO-002194 | CCCttaatttcacccTCA | 211 | 136052 | 136069 | |
| ASO-000540-39 | ASO-002111 | CCCttaatttcacCctCA | 212 | 136052 | 136069 | |
| ASO-000540-4 | ASO-002166 | CCCttaatttcaCccTC | 213 | 136053 | 136069 | |
| ASO-000540-40 | ASO-002123 | CCCttaatttcaCcctCA | 214 | 136052 | 136069 | |
| ASO-000540-41 | ASO-002135 | CCCttaatttcAcCctCA | 215 | 136052 | 136069 | |
| TBD-mm13 | ASO-002323 | TcCCtT**g**atttcaccCT | 216 | 136053 | 136069 | |
| TBD-mm14 | ASO-002335 | TcCCtTaatttcaccC**A** | 217 | 136052 | 136068 | |
| TBD-mm15 | ASO-002347 | TcCCtTaatttc**g**ccCT | 218 | 136053 | 136069 | |
| TBD-mm16 | ASO-002359 | TcCCtT**g**atttcaccC**A** | 219 | 136053 | 136069 | |
| TBD-mm17 | ASO-002371 | TcCCtT**g**atttcaccC**G** | 220 | 136052 | 136068 | |
| TBD-mm18 | ASO-002383 | TcCCtTa**g**tttc**g**ccCT | 221 | 136052 | 136068 | |
| ASO-000628 | ASO-000628 | CCTtaatttcaCCC | 222 | 136055 | 136068 | 67% |
| ASO-000642 | ASO-000642 | CCCttaatttcaCCC | 223 | 136055 | 136069 | >100% |
| ASO-000274 | ASO-000274 | TCCcttaatttcaCCC | 224 | 136055 | 136070 | |

Figure 4 cont.

| Oligomer Name | ASO Number | ASO Sequence | SEQ ID NO: | premRNA start NG_007398 | premRNA end NG_007398 | Oscillation data % control |
|---|---|---|---|---|---|---|
| ASO-000339 | ASO-000339 | CCttaatttcaCCC | 225 | 136055 | 136068 | |
| ASO-000536 | ASO-000536 | TTCccttaatttcACC | 226 | 136056 | 136071 | >100% |
| ASO-000603 | ASO-000603 | TCCcttaatttcACC | 227 | 136056 | 136070 | 80% |
| ASO-000666 | ASO-000666 | TCCcttaatttCAC | 228 | 136057 | 136070 | >100% |
| ASO-000272 | ASO-000272 | AGAgtgagaggctGGG | 229 | 136099 | 136114 | |
| ASO-000255 | ASO-000255 | TGGatgagtggaaCTG | 230 | 136115 | 136130 | |
| ASO-000336 | ASO-000336 | GGAtgagtggaACT | 231 | 136116 | 136129 | |
| ASO-000206 | ASO-000206 | GTTggatgagtgGAA | 232 | 136118 | 136132 | |
| ASO-000271 | ASO-000271 | AGTtggatgagtGGA | 233 | 136119 | 136133 | |
| ASO-000340 | ASO-000340 | GTTggatgagtGGA | 234 | 136119 | 136132 | |
| ASO-000229 | ASO-000229 | CAGggaaccgaatCAG | 235 | 136160 | 136175 | |
| ASO-000273 | ASO-000273 | GCCctggctcacaTCT | 236 | 136193 | 136208 | |
| ASO-000264 | ASO-000264 | ACAaggcagaaacACC | 237 | 136229 | 136244 | |
| ASO-000341 | ASO-000341 | TGTcaacaaggCAG | 238 | 136236 | 136249 | |
| ASO-000198 | ASO-000198 | TGCcctgggtgccTTG | 239 | 136355 | 136370 | |
| ASO-000210 | ASO-000210 | AGCgggactgtggGCC | 240 | 136371 | 136386 | |
| ASO-000342 | ASO-000342 | GGgacagcgggACT | 241 | 136378 | 136391 | |
| ASO-000333 | ASO-000333 | GCGggctgggctgTCT | 242 | 136427 | 136442 | |
| ASO-000199 | ASO-000199 | CAGaacagacagcATG | 243 | 136541 | 136556 | |
| ASO-000280 | ASO-000280 | TCTatgtatatgtTCA | 244 | 136567 | 136582 | |
| ASO-000211 | ASO-000211 | ATCtatgtatatgTTC | 245 | 136568 | 136583 | |
| ASO-000347 | ASO-000347 | CATctatgtataTGT | 246 | 136570 | 136584 | |
| ASO-000352 | ASO-000352 | ACAtctatgtataTGT | 247 | 136570 | 136585 | |
| ASO-000232 | ASO-000232 | CAAcagggtgcagATG | 248 | 136600 | 136615 | |
| ASO-000257 | ASO-000257 | AGCataaacagacAAA | 249 | 136629 | 136644 | |
| ASO-000388 | ASO-000388 | ATAgtcactctggTGA | 250 | 136650 | 136665 | 86% |
| ASO-000390 | ASO-000390 | TAGtcactctggTGA | 251 | 136650 | 136664 | 78% |
| ASO-000413 | ASO-000413 | AGTcactctggTGA | 252 | 136650 | 136663 | 97% |
| ASO-000405 | ASO-000405 | CATagtcactctgGTG | 253 | 136651 | 136666 | 2% |

Figure 4 cont.

| Oligomer Name | ASO Number | ASO Sequence | SEQ ID NO: | premRNA start NG_007398 | premRNA end NG_007398 | Oscillation data % control |
|---|---|---|---|---|---|---|
| ASO-000430 | ASO-000430 | TAGtcactctgGTG | 254 | 136651 | 136664 | 82% |
| ASO-000447 | ASO-000447 | TCAtagtcactctGGT | 255 | 136652 | 136667 | 86% |
| ASO-000396 | ASO-000396 | TACatgcgtccTTT | 256 | 136693 | 136706 | 92% |
| ASO-000395 | ASO-000395 | GATacatgcgtccTTT | 257 | 136693 | 136708 | >100% |
| ASO-000394 | ASO-000394 | AAGatacatgcgtCCT | 258 | 136695 | 136710 | >100% |
| ASO-000421 | ASO-000421 | TTCaagatacatgCGT | 259 | 136698 | 136713 | |
| ASO-000400 | ASO-000400 | ATTtcaagatacaTGC | 260 | 136700 | 136715 | |
| ASO-000248 | ASO-000248 | GCAtttcaagataCAT | 261 | 136702 | 136717 | |
| ASO-000451 | ASO-000451 | AAGcatttcaagaTAC | 262 | 136704 | 136719 | 67% |
| ASO-000707 | ASO-000707 | ACAagcatttcaaGAT | 263 | 136706 | 136721 | |
| ASO-000619 | ASO-000619 | TTAcaagcatttcAAG | 264 | 136708 | 136723 | 37% |
| ASO-000671 | ASO-000671 | AACctctttacaaGCA | 265 | 136715 | 136730 | |
| ASO-000221 | ASO-000221 | GTTagaaacctctTTA | 266 | 136721 | 136736 | |
| ASO-000298 | ASO-000298 | CCAcacaggccacACG | 267 | 136776 | 136791 | |
| ASO-000311 | ASO-000311 | GTCtctgttgggtCCC | 268 | 136842 | 136857 | |
| ASO-000290 | ASO-000290 | TGAacggcctcctTAG | 269 | 136871 | 136886 | |
| ASO-000437 | ASO-000437 | CTGtgcttcaggcCTT | 270 | 136896 | 136911 | 51% |
| ASO-000446 | ASO-000446 | TCCtgtgcttcagGCC | 271 | 136898 | 136913 | 76% |
| ASO-000685 | ASO-000685 | AATcctgtgcttcAGG | 272 | 136900 | 136915 | 73% |
| ASO-000410 | ASO-000410 | TCCtgtgcttcAGG | 273 | 136900 | 136913 | >100% |
| ASO-000604 | ASO-000604 | AATcctgtgcttCAG | 274 | 136901 | 136915 | 57% |
| ASO-000490 | ASO-000490 | TAAtcctgtgcttCAG | 275 | 136901 | 136916 | 76% |
| ASO-000529 | ASO-000529 | AATcctgtgctTCA | 276 | 136902 | 136915 | 10% |
| ASO-000532 | ASO-000532 | CTAatcctgtgctTCA | 277 | 136902 | 136917 | 100% |
| ASO-000508 | ASO-000508 | TAAtcctgtgctTCA | 278 | 136902 | 136916 | 87% |
| ASO-000219 | ASO-000219 | CCTaatcctgtgcTTC | 279 | 136903 | 136918 | |
| ASO-000656 | ASO-000656 | TAAtcctgtgcTTC | 280 | 136903 | 136916 | 2% |
| ASO-000522 | ASO-000522 | CTAatcctgtgcTTC | 281 | 136903 | 136917 | 73% |
| ASO-000513 | ASO-000513 | CCTaatcctgtgCTT | 282 | 136904 | 136918 | 58% |

Figure 4 cont.

| Oligomer Name | ASO Number | ASO Sequence | SEQ ID NO: | premRNA start NG_007398 | premRNA end NG_007398 | Oscillation data % control |
|---|---|---|---|---|---|---|
| ASO-000640 | ASO-000640 | TCCtaatcctgtgCTT | 283 | 136904 | 136919 | 23% |
| ASO-000661 | ASO-000661 | CTAatcctgtgCTT | 284 | 136904 | 136917 | 26% |
| ASO-000478 | ASO-000478 | GTCctaatcctgtGCT | 285 | 136905 | 136920 | 88% |
| ASO-000500 | ASO-000500 | TCCtaatcctgtGCT | 286 | 136905 | 136919 | >100% |
| ASO-000601 | ASO-000601 | CCTaatcctgtGCT | 287 | 136905 | 136918 | 63% |
| ASO-000643 | ASO-000643 | AGTcctaatcctgTGC | 288 | 136906 | 136921 | 25% |
| ASO-000600 | ASO-000600 | GTCctaatcctgTGC | 289 | 136906 | 136920 | 37% |
| ASO-000525 | ASO-000525 | TCCtaatcctgTGC | 290 | 136906 | 136919 | 65% |
| ASO-000453 | ASO-000453 | TCAgtcctaatccTGT | 291 | 136908 | 136923 | 53% |
| ASO-000553 | ASO-000553 | CTTcagtcctaatCCT | 292 | 136910 | 136925 | 96% |
| ASO-000622 | ASO-000622 | GCTtcagtcctaATC | 293 | 136912 | 136926 | 11% |
| ASO-000325 | ASO-000325 | CTGacacagggagCCC | 294 | 136956 | 136971 | |
| ASO-000215 | ASO-000215 | GCCagaccagccaCAA | 295 | 136987 | 137002 | |
| ASO-000482 | ASO-000482 | CAGgagttgtaAGC | 296 | 137065 | 137078 | 78% |
| ASO-000337 | ASO-000337 | TGCaggagttgtaAGC | 297 | 137065 | 137080 | |
| ASO-000480 | ASO-000480 | ATGcaggagttgtAAG | 298 | 137066 | 137081 | 41% |
| ASO-000644 | ASO-000644 | GATgcaggagttgTAA | 299 | 137067 | 137082 | 0% |
| ASO-000695 | ASO-000695 | TGCaggagttgTAA | 300 | 137067 | 137080 | |
| ASO-000455 | ASO-000455 | TGAtgcaggagttGTA | 301 | 137068 | 137083 | 8% |
| ASO-000531 | ASO-000531 | GTGatgcaggagtTGT | 302 | 137069 | 137084 | 14% |
| ASO-000651 | ASO-000651 | TGTgatgcaggagTTG | 303 | 137070 | 137085 | 29% |
| ASO-000007 | ASO-000007 | TGTgatgcaggaGTT | 304 | 137071 | 137085 | |
| ASO-000419 | ASO-000419 | GTGatgcaggaGTT | 305 | 137071 | 137084 | 65% |
| ASO-000730 | ASO-000730 | TGTgatgcaggaGTT | 306 | 137071 | 137085 | |
| ASO-000728 | ASO-000728 | TGTgatgcaggaGTT | 307 | 137071 | 137085 | |
| ASO-000729 | ASO-000729 | TGTgatgcaggaGTT | 308 | 137071 | 137085 | |
| ASO-000727 | ASO-000727 | TGTgatgcaggaGTT | 309 | 137071 | 137085 | |
| ASO-000715 | ASO-000715 | TGtgatgcaggagTT | 310 | 137071 | 137085 | |
| ASO-000716 | ASO-000716 | GAtgcaggagTT | 311 | 137071 | 137082 | |

Figure 4 cont.

| Oligomer Name | ASO Number | ASO Sequence | SEQ ID NO: | premRNA start NG_007398 | premRNA end NG_007398 | Oscillation data % control |
|---|---|---|---|---|---|---|
| ASO-000721 | ASO-000721 | TGTgatgcaggaGTT | 312 | 137071 | 137085 | |
| ASO-000722 | ASO-000722 | TGTgatgcaggaGTT | 313 | 137071 | 137085 | |
| ASO-000723 | ASO-000723 | TGTgatgcaggaGTT | 314 | 137071 | 137085 | |
| ASO-000724 | ASO-000724 | TGTgatgcaggaGTT | 315 | 137071 | 137085 | |
| ASO-000725 | ASO-000725 | TGTgatgcaggaGTT | 316 | 137071 | 137085 | |
| ASO-000726 | ASO-000726 | TGTgatgcaggaGTT | 317 | 137071 | 137085 | |
| ASO-000731 | ASO-000731 | TGTgatgcaggaGTT | 318 | 137071 | 137085 | |
| ASO-000718 | ASO-000718 | TGatgcaggaGT | 319 | 137072 | 137083 | |
| ASO-000445 | ASO-000445 | TTGtgatgcagGAG | 320 | 137073 | 137086 | 0% |
| ASO-000436 | ASO-000436 | CTTgtgatgcagGAG | 321 | 137073 | 137087 | 88% |
| ASO-000717 | ASO-000717 | GTgatgcaggAG | 322 | 137073 | 137084 | |
| ASO-000570 | ASO-000570 | TTCttgtgatgcaGGA | 323 | 137074 | 137089 | 61% |
| ASO-000408 | ASO-000408 | TCTtgtgatgcaGGA | 324 | 137074 | 137088 | 92% |
| ASO-000401 | ASO-000401 | CTTgtgatgcaGGA | 325 | 137074 | 137087 | 70% |
| ASO-000719 | ASO-000719 | TGtgatgcagGA | 326 | 137074 | 137085 | |
| ASO-000313 | ASO-000313 | CAGagggcgagctTGG | 327 | 137173 | 137188 | |
| ASO-000331 | ASO-000331 | AATccctgctgtgGTC | 328 | 137223 | 137238 | |
| ASO-000251 | ASO-000251 | AGGcaattcatCCC | 329 | 137239 | 137252 | |
| ASO-000574 | ASO-000574 | TGGtcaaggctttGGG | 330 | 137326 | 137341 | 0% |
| ASO-000218 | ASO-000218 | TCTggtcaaggctTTG | 331 | 137328 | 137343 | |
| ASO-000634 | ASO-000634 | CTCtggtcaaggcTTT | 332 | 137329 | 137344 | 0% |
| ASO-000497 | ASO-000497 | GGTgctctggtcaAGG | 333 | 137333 | 137348 | 15% |
| ASO-000569 | ASO-000569 | GGTgctctggtCAA | 334 | 137335 | 137348 | >100% |
| ASO-000565 | ASO-000565 | GCTgaggtgctctGGT | 335 | 137338 | 137353 | 19% |
| ASO-000296 | ASO-000296 | AGTttgtgcaaggTCA | 336 | 137358 | 137373 | |
| ASO-000663 | ASO-000663 | GAGtttgtgcaagGTC | 337 | 137359 | 137374 | 0% |
| ASO-000670 | ASO-000670 | AGTttgtgcaagGTC | 338 | 137359 | 137373 | 0% |
| ASO-000261 | ASO-000261 | GGAgtttgtgcaaGGT | 339 | 137360 | 137375 | |
| ASO-000262 | ASO-000262 | GGAgtttgtgcaAGG | 340 | 137361 | 137375 | |

Figure 4 cont.

| Oligomer Name | ASO Number | ASO Sequence | SEQ ID NO: | premRNA start NG_007398 | premRNA end NG_007398 | Oscillation data % control |
|---|---|---|---|---|---|---|
| ASO-000275 | ASO-000275 | TGGagtttgtgcaAGG | 341 | 137361 | 137376 | |
| ASO-000247 | ASO-000247 | ATGgagtttgtgcAAG | 342 | 137362 | 137377 | |
| ASO-000303 | ASO-000303 | TGGagtttgtgcAAG | 343 | 137362 | 137376 | |
| ASO-000299 | ASO-000299 | ATGgagtttgtgCAA | 344 | 137363 | 137377 | |
| ASO-000270 | ASO-000270 | AGAtggagtttgtGCA | 345 | 137364 | 137379 | |
| ASO-000297 | ASO-000297 | AGCagatggagttTGT | 346 | 137367 | 137382 | |
| ASO-000259 | ASO-000259 | TTCtttaggcagcAAT | 347 | 137416 | 137431 | |
| ASO-000220 | ASO-000220 | TGTacccaaaccaGAA | 348 | 137462 | 137477 | |
| ASO-000278 | ASO-000278 | GTTgcctttaacTGT | 349 | 137475 | 137489 | |
| ASO-000334 | ASO-000334 | GCCctggatttctACT | 350 | 137505 | 137520 | |
| ASO-000241 | ASO-000241 | TGGtggagagttcTGG | 351 | 137583 | 137598 | |
| ASO-000289 | ASO-000289 | TTCtcagatccctTCA | 352 | 137643 | 137658 | |
| ASO-000233 | ASO-000233 | CTCtaaccaccacCAA | 353 | 137682 | 137697 | |
| ASO-000201 | ASO-000201 | AGGgcacaagaacTTC | 354 | 137765 | 137780 | |
| ASO-000645 | ASO-000645 | ATCttaggctggCCC | 355 | 137851 | 137865 | 51% |
| ASO-000546 | ASO-000546 | GATcttaggctggCCC | 356 | 137851 | 137866 | 91% |
| ASO-000692 | ASO-000692 | TGAtcttaggctgGCC | 357 | 137852 | 137867 | |
| ASO-000511 | ASO-000511 | GATcttaggctgGCC | 358 | 137852 | 137866 | 8% |
| ASO-000538 | ASO-000538 | TGAtcttaggctGGC | 359 | 137853 | 137867 | 44% |
| ASO-000214 | ASO-000214 | ATGatcttaggctGGC | 360 | 137853 | 137868 | |
| ASO-000653 | ASO-000653 | GATcttaggctGGC | 361 | 137853 | 137866 | 5% |
| ASO-000615 | ASO-000615 | CATgatcttaggcTGG | 362 | 137854 | 137869 | 8% |
| ASO-000524 | ASO-000524 | CCAtgatcttaggCTG | 363 | 137855 | 137870 | 18% |
| ASO-000492 | ASO-000492 | CATgatcttaggCTG | 364 | 137855 | 137869 | 46% |
| ASO-000468 | ASO-000468 | ACCatgatcttagGCT | 365 | 137856 | 137871 | 88% |
| ASO-000698 | ASO-000698 | CCAtgatcttagGCT | 366 | 137856 | 137870 | |
| ASO-000593 | ASO-000593 | CATgatcttagGCT | 367 | 137856 | 137869 | 25% |
| ASO-000519 | ASO-000519 | AAAccatgatcttAGG | 368 | 137858 | 137873 | 81% |
| ASO-000582 | ASO-000582 | CTAaaccatgatcTTA | 369 | 137860 | 137875 | 21% |

Figure 4 cont.

| Oligomer Name | ASO Number | ASO Sequence | SEQ ID NO: | premRNA start NG_007398 | premRNA end NG_007398 | Oscillation data % control |
|---|---|---|---|---|---|---|
| ASO-000635 | ASO-000635 | CCCtaaaccatgaTCT | 370 | 137862 | 137877 | 90% |
| ASO-000471 | ASO-000471 | CACcctaaaccatGAT | 371 | 137864 | 137879 | 71% |
| ASO-000701 | ASO-000701 | ATCaccctaaaccATG | 372 | 137866 | 137881 | |
| ASO-000533 | ASO-000533 | TGAtcaccctaaaCCA | 373 | 137868 | 137883 | >100% |
| ASO-000323 | ASO-000323 | GAGgagtgcccagCCC | 374 | 137947 | 137962 | |
| ASO-000329 | ASO-000329 | TGCaggtgggagaAGT | 375 | 137973 | 137988 | |
| ASO-000194 | ASO-000194 | TATctagcccaCCC | 376 | 138003 | 138016 | |
| ASO-000192 | ASO-000192 | CTAtctagcccaCCC | 377 | 138003 | 138017 | |
| ASO-000343 | ASO-000343 | TAtcctatctaGCC | 378 | 138008 | 138021 | |
| ASO-000212 | ASO-000212 | TTGataaagtgaGTC | 379 | 138050 | 138064 | |
| ASO-000230 | ASO-000230 | ATTgataaagtgAGT | 380 | 138051 | 138065 | |
| ASO-000188 | ASO-000188 | AACtattgataaAGT | 381 | 138055 | 138069 | |
| ASO-000415 | ASO-000415 | GAActattgatAAA | 382 | 138057 | 138070 | 86% |
| ASO-000448 | ASO-000448 | GGAactattgaTAA | 383 | 138058 | 138071 | 0% |
| ASO-000190 | ASO-000190 | AAAtggaactattGAT | 384 | 138060 | 138075 | |
| ASO-000191 | ASO-000191 | AATggaactatTGA | 385 | 138061 | 138074 | |
| ASO-000348 | ASO-000348 | TCAAtttaaatGGAA | 386 | 138068 | 138082 | |
| ASO-000349 | ASO-000349 | GTcaatttaaaTGGA | 387 | 138069 | 138083 | |
| ASO-000200 | ASO-000200 | GGAtacagtctcaCCA | 388 | 138089 | 138104 | |
| ASO-000630 | ASO-000630 | GCAaacaggatacAGT | 389 | 138096 | 138111 | 0% |
| ASO-000614 | ASO-000614 | CAAacaggatacAGT | 390 | 138096 | 138110 | 50% |
| ASO-000563 | ASO-000563 | AAAcaggatacAGT | 391 | 138096 | 138109 | >100% |
| ASO-000527 | ASO-000527 | TAGcaaacaggatACA | 392 | 138098 | 138113 | 50% |
| ASO-000617 | ASO-000617 | ATAgcaaacaggaTAC | 393 | 138099 | 138114 | 28% |
| ASO-000539 | ASO-000539 | AATagcaaacaggATA | 394 | 138100 | 138115 | 82% |
| ASO-000691 | ASO-000691 | CAAtagcaaacagGAT | 395 | 138101 | 138116 | |
| ASO-000589 | ASO-000589 | AATagcaaacagGAT | 396 | 138101 | 138115 | 4% |
| ASO-000509 | ASO-000509 | GCAatagcaaacaGGA | 397 | 138102 | 138117 | |
| ASO-000674 | ASO-000674 | CAAtagcaaacaGGA | 398 | 138102 | 138116 | |

Figure 4 cont.

| Oligomer Name | ASO Number | ASO Sequence | SEQ ID NO: | premRNA start NG_007398 | premRNA end NG_007398 | Oscillation data % control |
|---|---|---|---|---|---|---|
| ASO-000488 | ASO-000488 | GCAatagcaaacAGG | 399 | 138103 | 138117 | 41% |
| ASO-000507 | ASO-000507 | AGCaatagcaaacAGG | 400 | 138103 | 138118 | 49% |
| ASO-000521 | ASO-000521 | AGCaatagcaaaCAG | 401 | 138104 | 138118 | 53% |
| ASO-000288 | ASO-000288 | AAGcaatagcaaaCAG | 402 | 138104 | 138119 | |
| ASO-000552 | ASO-000552 | AAGcaatagcaaACA | 403 | 138105 | 138119 | >100% |
| ASO-000250 | ASO-000250 | CAAatgtggttgaAAT | 404 | 138223 | 138238 | |
| ASO-000294 | ASO-000294 | GCAaatgtggttgAAA | 405 | 138224 | 138239 | |
| ASO-000318 | ASO-000318 | TAGcaaatgtggtTGA | 406 | 138226 | 138241 | |
| ASO-000308 | ASO-000308 | CCCaagggcctctAAC | 407 | 138263 | 138278 | |
| ASO-000254 | ASO-000254 | AAAgcaaccagatGTC | 408 | 138361 | 138376 | |
| ASO-000545 | ASO-000545 | AAGagggcagcagGCC | 409 | 138377 | 138392 | 73% |
| ASO-000476 | ASO-000476 | GAAagagggcagcAGG | 410 | 138379 | 138394 | 0% |
| ASO-000620 | ASO-000620 | CTGaaagagggcaGCA | 411 | 138381 | 138396 | 37% |
| ASO-000477 | ASO-000477 | CCCtgaaagagggCAG | 412 | 138383 | 138398 | 18% |
| ASO-000562 | ASO-000562 | TGAttgtgggcttAGG | 413 | 138401 | 138416 | 3% |
| ASO-000547 | ASO-000547 | ATGattgtgggctTAG | 414 | 138402 | 138417 | 24% |
| ASO-000696 | ASO-000696 | TGAttgtgggctTAG | 415 | 138402 | 138416 | |
| ASO-000279 | ASO-000279 | GATtgtgggctTAG | 416 | 138402 | 138415 | |
| ASO-000543 | ASO-000543 | CATgattgtgggcTTA | 417 | 138403 | 138418 | 0% |
| ASO-000626 | ASO-000626 | TGAttgtgggcTTA | 418 | 138403 | 138416 | 29% |
| ASO-000650 | ASO-000650 | ATGattgtgggcTTA | 419 | 138403 | 138417 | 8% |
| ASO-000599 | ASO-000599 | CATgattgtgggCTT | 420 | 138404 | 138418 | 0% |
| ASO-000542 | ASO-000542 | GCAtgattgtgggCTT | 421 | 138404 | 138419 | 47% |
| ASO-000463 | ASO-000463 | GGCatgattgtggGCT | 422 | 138405 | 138420 | 6% |
| ASO-000605 | ASO-000605 | GCAtgattgtggGCT | 423 | 138405 | 138419 | 0% |
| ASO-000479 | ASO-000479 | CATgattgtggGCT | 424 | 138405 | 138418 | |
| ASO-000474 | ASO-000474 | GCAtgattgtgGGC | 425 | 138406 | 138419 | 86% |
| ASO-000675 | ASO-000675 | GGCatgattgtgGGC | 426 | 138406 | 138420 | 5% |
| ASO-000537 | ASO-000537 | AGGcatgattgtgGGC | 427 | 138406 | 138421 | 0% |

Figure 4 cont.

| Oligomer Name | ASO Number | ASO Sequence | SEQ ID NO: | premRNA start NG_007398 | premRNA end NG_007398 | Oscillation data % control |
|---|---|---|---|---|---|---|
| ASO-000287 | ASO-000287 | AGGgaggcatgatTGT | 428 | 138410 | 138425 | |
| ASO-000292 | ASO-000292 | GGGaggcatgatTGT | 429 | 138410 | 138424 | |
| ASO-000216 | ASO-000216 | TTAgggaggcatgATT | 430 | 138412 | 138427 | |
| ASO-000266 | ASO-000266 | TTAgggaggcatGAT | 431 | 138413 | 138427 | |
| ASO-000256 | ASO-000256 | TCTtagggaggcaTGA | 432 | 138414 | 138429 | |
| ASO-000269 | ASO-000269 | GAGgtggcacagaGGT | 433 | 138460 | 138475 | |
| ASO-000350 | ASO-000350 | CAGtgtgagaggtGG | 434 | 138469 | 138483 | |
| ASO-000353 | ASO-000353 | CAGtgtgagaggTG | 435 | 138470 | 138483 | |
| ASO-000310 | ASO-000310 | ACAaagatgaggaGGG | 436 | 138532 | 138547 | |
| ASO-000309 | ASO-000309 | AACaaagatgaggAGG | 437 | 138533 | 138548 | |
| ASO-000263 | ASO-000263 | GAAgagaaatcagAAG | 438 | 138631 | 138646 | |
| ASO-000197 | ASO-000197 | TCTaggccagtgcCCA | 439 | 138667 | 138682 | |
| ASO-000239 | ASO-000239 | AGTctattaggAGG | 440 | 138689 | 138702 | |
| ASO-000267 | ASO-000267 | GCTcaacatggcaAAC | 441 | 138714 | 138729 | |
| ASO-000306 | ASO-000306 | TGCaagtgccagAAA | 442 | 138737 | 138751 | |
| ASO-000345 | ASO-000345 | GCAagtgccagAAA | 443 | 138737 | 138750 | |
| ASO-000193 | ASO-000193 | AATcatgggacttGCA | 444 | 138748 | 138763 | |
| ASO-000284 | ASO-000284 | GATttcatgtcccTCC | 445 | 138788 | 138803 | |
| ASO-000209 | ASO-000209 | GCTaagctaagaTGA | 446 | 138802 | 138816 | |
| ASO-000207 | ASO-000207 | CTAagctaagaTGA | 447 | 138802 | 138815 | |
| ASO-000301 | ASO-000301 | TAGacattcacaGAC | 448 | 138822 | 138836 | |
| ASO-000234 | ASO-000234 | TATagacattcaCAG | 449 | 138824 | 138838 | |
| ASO-000332 | ASO-000332 | AAAcacacaatacACT | 450 | 138840 | 138855 | |
| SPC-15693-01 | ASO-002268 | CAgcaacagtcagtGT | 451 | 138869 | 138884 | |
| SPC-15692-01 | ASO-002268 | ACagcaacagtcagTG | 452 | 138870 | 138885 | |
| SPC-15691-01 | ASO-002260 | TAcagcaacagtcaGT | 453 | 138871 | 138886 | |
| SPC-15690-01 | ASO-002252 | TTAcagcaacagtcAG | 454 | 138872 | 138887 | |

Figure 4 cont.

| Oligomer Name | ASO Number | ASO Sequence | SEQ ID NO: | premRNA start NG_007398 | premRNA end NG_007398 | Oscillation data % control |
|---|---|---|---|---|---|---|
| SPC-15689-01 | ASO-002244 | TTTacagcaacagtCA | 455 | 138873 | 138888 | |
| SPC-15688-01 | ASO-002290 | TTttacagcaacaGTC | 456 | 138874 | 138889 | |
| SPC-15687-01 | ASO-002274 | CTtttacagcaacaGT | 457 | 138875 | 138890 | |
| SPC-15686-01 | ASO-002275 | ACttttacagcaaCAG | 458 | 138876 | 138891 | |
| SPC-15685-01 | ASO-002267 | CActtttacagcaaCA | 459 | 138877 | 138892 | |
| SPC-15684-01 | ASO-002259 | TCActtttacagcAAC | 460 | 138878 | 138893 | |
| SPC-15683-01 | ASO-002251 | TTCacttttacagCAA | 461 | 138879 | 138894 | |
| SPC-15682-01 | ASO-002243 | ATTcacttttacagCA | 462 | 138880 | 138895 | |
| SPC-15681-01 | ASO-002234 | AATtcacttttacaGC | 463 | 138881 | 138896 | |
| SPC-15680-01 | ASO-002289 | AAATtcacttttACAG | 464 | 138882 | 138897 | |
| SPC-15679-01 | ASO-002281 | CAAattcactttTACA | 465 | 138883 | 138898 | |
| ASO-002090 | ASO-002090 | ATTtcCaaattcactTtTAC | 466 | 138884 | 138903 | >100% |
| ASO-002043 | ASO-002043 | ATtTCcaaattcacttTTAC | 467 | 138884 | 138903 | >100% |
| ASO-002076 | ASO-002076 | ATtTCcaaattcacTTttAC | 468 | 138884 | 138903 | >100% |
| ASO-002062 | ASO-002062 | ATTtcCaaattcactTTtAC | 469 | 138884 | 138903 | >100% |
| ASO-002082 | ASO-002082 | ATtTcCaaattcactTtTAC | 470 | 138884 | 138903 | >100% |
| ASO-000753 | ASO-000753 | ATTTCcaaattcactTTTAC | 471 | 138884 | 138903 | >100% |
| ASO-001940 | ASO-001940 | ATtTCcaaattcactTTtAC | 472 | 138884 | 138903 | 85% |
| ASO-001933 | ASO-001933 | AtTTCcaaattcactTTtAC | 473 | 138884 | 138903 | >100% |
| ASO-001919 | ASO-001919 | ATTTccaaattcactTTTAC | 474 | 138884 | 138903 | >100% |
| ASO-002094 | ASO-002094 | ATtTCcaaattcacTtTtAC | 475 | 138884 | 138903 | 83% |
| ASO-002034 | ASO-002034 | ATTtCcaaattcactTtTAC | 476 | 138884 | 138903 | >100% |
| ASO-002036 | ASO-002036 | ATttCcAaattcacttTTAC | 477 | 138884 | 138903 | >100% |
| ASO-002084 | ASO-002084 | ATTtCcaaattcacTTttAC | 478 | 138884 | 138903 | >100% |
| ASO-002037 | ASO-002037 | ATTTccaaattcaCtTttAC | 479 | 138884 | 138903 | >100% |

Figure 4 cont.

| Oligomer Name | ASO Number | ASO Sequence | SEQ ID NO: | premRNA start NG_007398 | premRNA end NG_007398 | Oscillation data % control |
|---|---|---|---|---|---|---|
| ASO-002058 | ASO-002058 | ATTtCcaaattcacTttTAC | 480 | 138884 | 138903 | >100% |
| ASO-002057 | ASO-002057 | ATTTccaaattcaCttTtAC | 481 | 138884 | 138903 | >100% |
| ASO-001926 | ASO-001926 | ATTTCcaaattcacttTTAC | 482 | 138884 | 138903 | 79% |
| ASO-002092 | ASO-002092 | ATttCCaaattcactTtTAC | 483 | 138884 | 138903 | >100% |
| ASO-002023 | ASO-002023 | ATTTccaaattcacTTttAC | 484 | 138884 | 138903 | >100% |
| ASO-000758 | ASO-000758 | ATTtccaaattcactttTAC | 485 | 138884 | 138903 | >100% |
| ASO-002065 | ASO-002065 | ATttCCaaattcactTTtAC | 486 | 138884 | 138903 | >100% |
| ASO-002038 | ASO-002038 | ATTtCcaaattcacTtTtAC | 487 | 138884 | 138903 | >100% |
| ASO-002039 | ASO-002039 | ATtTCcaaattcacTttTAC | 488 | 138884 | 138903 | 35% |
| ASO-000763 | ASO-000763 | ATttccaaattcacttttAC | 489 | 138884 | 138903 | >100% |
| ASO-000768 | ASO-000768 | AtttccaaattcacttttAC | 490 | 138884 | 138903 | >100% |
| ASO-001933-mm1 | ASO-002291 | GtTTCcaaattcactTTtAC | 491 | 138884 | 138903 | |
| ASO-001933-mm2 | ASO-002303 | AtTTCcagattcactTTtAC | 492 | 138884 | 138903 | |
| ASO-001933-mm3 | ASO-002315 | TtTTCcaaattcactTTtAC | 493 | 138884 | 138903 | |
| ASO-001933-mm4 | ASO-002327 | GtTTCcagattcactTTtAC | 494 | 138884 | 138903 | |
| ASO-001933-mm5 | ASO-002339 | AtTTCcaagttcactTTtGC | 495 | 138884 | 138903 | |
| ASO-001933-mm6 | ASO-002351 | AtTTCcagattcgctTTtAC | 496 | 138884 | 138903 | |
| SPC-15678-01 | ASO-002274 | CCaaattcactttTAC | 497 | 138884 | 138899 | |
| SPC-15857-01 | ASO-002326 | ATtTcCaaattcacttTTAC | 498 | 138884 | 138903 | |
| SPC-15858-01 | ASO-002338 | ATTtcCaaattcacttTTAC | 499 | 138884 | 138903 | |
| SPC-15860-01 | ASO-002362 | ATTtCcaaattcacttTTAC | 500 | 138884 | 138903 | |
| SPC-15864-01 | ASO-002236 | ATTTccaaattcacTttTAC | 501 | 138884 | 138903 | |
| SPC-15868-01 | ASO-002269 | ATtTCcaaattcactTtTAC | 502 | 138884 | 138903 | |

Figure 4 cont.

| Oligomer Name | ASO Number | ASO Sequence | SEQ ID NO: | premRNA start NG_007398 | premRNA end NG_007398 | Oscillation data % control |
|---|---|---|---|---|---|---|
| SPC-15872-01 | ASO-002237 | ATttCCaaattcacttTTAC | 503 | 138884 | 138903 | |
| SPC-15873-01 | ASO-002246 | ATTtCcaaattcactTTtAC | 504 | 138884 | 138903 | |
| SPC-15874-01 | ASO-002254 | ATTTccaaattcacTtTtAC | 505 | 138884 | 138903 | |
| SPC-15878-01 | ASO-002284 | ATtTccAaattcacttTTAC | 506 | 138884 | 138903 | |
| SPC-15879-01 | ASO-002229 | ATTTccaaattcacttTTAC | 507 | 138884 | 138903 | |
| SPC-15880-01 | ASO-002238 | ATTTccaaattcactTtTAC | 508 | 138884 | 138903 | |
| SPC-15883-01 | ASO-002263 | ATtTcCaaattcactTTtAC | 509 | 138884 | 138903 | |
| SPC-15888-01 | ASO-002239 | ATTTccaaattcactTTtAC | 510 | 138884 | 138903 | |
| ASO-000754 | ASO-000754 | TATTTccaaattcacTTTTA | 511 | 138885 | 138904 | >100% |
| ASO-002055 | ASO-002055 | TAtTtCcaaattcacTTtTA | 512 | 138885 | 138904 | >100% |
| ASO-002035 | ASO-002035 | TAtTtcCaaattcactTTTA | 513 | 138885 | 138904 | >100% |
| ASO-002048 | ASO-002048 | TATtTccaaattcaCttTTA | 514 | 138885 | 138904 | >100% |
| ASO-002053 | ASO-002053 | TAtTtCcaaattcactTTTA | 515 | 138885 | 138904 | >100% |
| ASO-002067 | ASO-002067 | TAtTTccaaattcaCTttTA | 516 | 138885 | 138904 | >100% |
| ASO-001954 | ASO-001954 | TATTTccaaattcactTTTA | 517 | 138885 | 138904 | >100% |
| ASO-001947 | ASO-001947 | TATTtccaaattcacTTTTA | 518 | 138885 | 138904 | >100% |
| ASO-002081 | ASO-002081 | TATttCcaaattcacTtTTA | 519 | 138885 | 138904 | >100% |
| ASO-001966 | ASO-001966 | TAtTTccaaattcacTTtTA | 520 | 138885 | 138904 | >100% |
| ASO-002025 | ASO-002025 | TAttTcCaaattcactTTTA | 521 | 138885 | 138904 | >100% |
| ASO-002033 | ASO-002033 | TATtTccaaattcacTtTTA | 522 | 138885 | 138904 | >100% |
| ASO-001960 | ASO-001960 | TaTTTccaaattcacTTtTA | 523 | 138885 | 138904 | >100% |
| ASO-002056 | ASO-002056 | TAttTCcaaattcacTTtTA | 524 | 138885 | 138904 | >100% |
| ASO-002063 | ASO-002063 | TATttCcaaattcacTTtTA | 525 | 138885 | 138904 | >100% |
| ASO-002089 | ASO-002089 | TATTtccaaattcaCttTTA | 526 | 138885 | 138904 | >100% |
| ASO-002073 | ASO-002073 | TAtTtCcaaattcacTtTTA | 527 | 138885 | 138904 | >100% |
| ASO-002027 | ASO-002027 | TATtTccaaattcaCtTtTA | 528 | 138885 | 138904 | >100% |

Figure 4 cont.

| Oligomer Name | ASO Number | ASO Sequence | SEQ ID NO: | premRNA start NG_007398 | premRNA end NG_007398 | Oscillation data % control |
|---|---|---|---|---|---|---|
| ASO-002075 | ASO-002075 | TATtTccaaattcaCTttTA | 529 | 138885 | 138904 | >100% |
| ASO-002028 | ASO-002028 | TAtTTccaaattcaCttTTA | 530 | 138885 | 138904 | 77% |
| ASO-002085 | ASO-002085 | TAtTTccaaattcaCtTtTA | 531 | 138885 | 138904 | >100% |
| ASO-002083 | ASO-002083 | TAttTCcaaattcacTtTTA | 532 | 138885 | 138904 | >100% |
| ASO-000759 | ASO-000759 | TATttccaaattcacttTTA | 533 | 138885 | 138904 | >100% |
| ASO-000769 | ASO-000769 | TatttccaaattcactttTA | 534 | 138885 | 138904 | >100% |
| ASO-000764 | ASO-000764 | TAtttccaaattcactttTA | 535 | 138885 | 138904 | >100% |
| ASO-001954-mm1 | ASO-002340 | TATTTccagattcactTTTA | 536 | 138885 | 138904 | |
| ASO-001954-mm2 | ASO-002352 | TATTTccgaattcactTTTA | 537 | 138885 | 138904 | |
| ASO-001954-mm3 | ASO-002364 | GATTTccaaattcactTTTA | 538 | 138885 | 138904 | |
| ASO-001954-mm4 | ASO-002376 | GGTTTccaaattcactTTTA | 539 | 138885 | 138904 | |
| ASO-001954-mm5 | ASO-002293 | AATTTccagattcactTTTA | 540 | 138885 | 138904 | |
| ASO-001954-mm6 | ASO-002305 | TATTTccaagttcgctTTTA | 541 | 138885 | 138904 | |
| SPC-15677-01 | ASO-002266 | TCCaaattcactttTA | 542 | 138885 | 138900 | |
| SPC-15859-01 | ASO-002350 | TAtTTccaaattcactTTTA | 543 | 138885 | 138904 | |
| SPC-15861-01 | ASO-002374 | TAtTTccaaattcacTtTTA | 544 | 138885 | 138904 | |
| SPC-15862-01 | ASO-002386 | TATTtccaaattcaCTttTA | 545 | 138885 | 138904 | |
| SPC-15863-01 | ASO-002227 | TATtTccaaattcactTTTA | 546 | 138885 | 138904 | |
| SPC-15865-01 | ASO-002245 | TAttTCcaaattcactTTTA | 547 | 138885 | 138904 | |
| SPC-15867-01 | ASO-002261 | TATtTccaaattcacTTtTA | 548 | 138885 | 138904 | |
| SPC-15869-01 | ASO-002276 | TATttCcaaattcactTTTA | 549 | 138885 | 138904 | |
| SPC-15871-01 | ASO-002228 | TATTtccaaattcaCtTtTA | 550 | 138885 | 138904 | |

Figure 4 cont.

| Oligomer Name | ASO Number | ASO Sequence | SEQ ID NO: | premRNA start NG_007398 | premRNA end NG_007398 | Oscillation data % control |
|---|---|---|---|---|---|---|
| SPC-15882-01 | ASO-002255 | TATTtccaaattcactTTTA | 551 | 138885 | 138904 | |
| SPC-15886-01 | ASO-002285 | TATTtccaaattcacTTtTA | 552 | 138885 | 138904 | |
| SPC-15887-01 | ASO-002230 | TATTtccaaattcacTtTTA | 553 | 138885 | 138904 | |
| SPC-15890-01 | ASO-002256 | TATTtccaaattcAcTttTA | 554 | 138885 | 138904 | |
| SPC-15893-01 | ASO-002279 | TATTtccaaattcActTtTA | 555 | 138885 | 138904 | |
| ASO-002072 | ASO-002072 | TTAttTccaaattcaCTtTT | 556 | 138886 | 138905 | >100% |
| ASO-000755 | ASO-000755 | TTATTtccaaattcaCTTTT | 557 | 138886 | 138905 | >100% |
| ASO-002071 | ASO-002071 | TTaTtTccaaattcacTTTT | 558 | 138886 | 138905 | 89% |
| ASO-000760 | ASO-000760 | TTAtttccaaattcactTTT | 559 | 138886 | 138905 | >100% |
| ASO-001920 | ASO-001920 | TTATttccaaattcaCTTTT | 560 | 138886 | 138905 | >100% |
| ASO-002080 | ASO-002080 | TTatTTccaaattcacTTTT | 561 | 138886 | 138905 | >100% |
| ASO-001927 | ASO-001927 | TTATTtccaaattcacTTTT | 562 | 138886 | 138905 | >100% |
| ASO-001941 | ASO-001941 | TTaTTtccaaattcaCTtTT | 563 | 138886 | 138905 | >100% |
| ASO-002045 | ASO-002045 | TTaTttCcaaattcacTTTT | 564 | 138886 | 138905 | >100% |
| ASO-001934 | ASO-001934 | TtATTtccaaattcaCTtTT | 565 | 138886 | 138905 | 70% |
| ASO-002074 | ASO-002074 | TTatTTccaaattcaCTtTT | 566 | 138886 | 138905 | 89% |
| ASO-002093 | ASO-002093 | TTAtTtccaaattcACttTT | 567 | 138886 | 138905 | >100% |
| ASO-002054 | ASO-002054 | TTaTTtccaaattcaCtTTT | 568 | 138886 | 138905 | 81% |
| ASO-002091 | ASO-002091 | TTaTtTccaaattcaCtTTT | 569 | 138886 | 138905 | >100% |
| ASO-002064 | ASO-002064 | TTaTtTccaaattcaCTtTT | 570 | 138886 | 138905 | >100% |
| ASO-002066 | ASO-002066 | TTATttccaaattCacTtTT | 571 | 138886 | 138905 | 96% |
| ASO-002044 | ASO-002044 | TTAtTtccaaattcaCtTTT | 572 | 138886 | 138905 | >100% |
| ASO-002047 | ASO-002047 | TTATttccaaattCaCttTT | 573 | 138886 | 138905 | >100% |
| ASO-002046 | ASO-002046 | TTatTtCcaaattcacTTTT | 574 | 138886 | 138905 | >100% |
| ASO-000765 | ASO-000765 | TTatttccaaattcacttTT | 575 | 138886 | 138905 | >100% |
| ASO-000770 | ASO-000770 | TtatttccaaattcacttTT | 576 | 138886 | 138905 | >100% |
| ASO-001941-mm1 | ASO-002317 | ATaTTtccaaattcaCTtTT | 577 | 138886 | 138905 | |

Figure 4 cont.

| Oligomer Name | ASO Number | ASO Sequence | SEQ ID NO: | premRNA start NG_007398 | premRNA end NG_007398 | Oscillation data % control |
|---|---|---|---|---|---|---|
| ASO-001941-mm2 | ASO-002329 | TTaTTtccaaattcaCTtTA | 578 | 138886 | 138905 | |
| ASO-001941-mm3 | ASO-002341 | TTaTTtccaaattcaCTtTG | 579 | 138886 | 138905 | |
| ASO-001941-mm4 | ASO-002353 | ATaTTtccagattcaCTtTT | 580 | 138886 | 138905 | |
| ASO-001941-mm5 | ASO-002365 | TTaTTtccaagttcaCTtTC | 581 | 138886 | 138905 | |
| ASO-001941-mm6 | ASO-002377 | TTaTTtccagattcgCTtTT | 582 | 138886 | 138905 | |
| SPC-15676-01 | ASO-002258 | TTCcaaattcactTTT | 583 | 138886 | 138901 | |
| SPC-15866-01 | ASO-002253 | TTAtTtccaaattcaCTtTT | 584 | 138886 | 138905 | |
| SPC-15870-01 | ASO-002283 | TTAttTccaaattcacTTTT | 585 | 138886 | 138905 | |
| SPC-15875-01 | ASO-002262 | TTATttccaaattcacTTTT | 586 | 138886 | 138905 | |
| SPC-15876-01 | ASO-002270 | TTATttccaaattcaCtTTT | 587 | 138886 | 138905 | |
| SPC-15877-01 | ASO-002277 | TTATttccaaattcACttTT | 588 | 138886 | 138905 | |
| SPC-15881-01 | ASO-002247 | TTaTTtccaaattcacTTTT | 589 | 138886 | 138905 | |
| SPC-15884-01 | ASO-002271 | TTAtTtccaaattcacTTTT | 590 | 138886 | 138905 | |
| SPC-15885-01 | ASO-002278 | TTaTTtccaaattcACttTT | 591 | 138886 | 138905 | |
| SPC-15889-01 | ASO-002248 | TTaTTtccaaattcActTTT | 592 | 138886 | 138905 | |
| SPC-15891-01 | ASO-002264 | TTAtTtccaaattcActTTT | 593 | 138886 | 138905 | |
| SPC-15892-01 | ASO-002272 | TTaTTtccaaattcAcTtTT | 594 | 138886 | 138905 | |
| SPC-15894-01 | ASO-002286 | TTAtTtccaaattcAcTtTT | 595 | 138886 | 138905 | |
| SPC-15895-01 | ASO-002231 | TTATttccaaattcActTTT | 596 | 138886 | 138905 | |
| SPC-15896-01 | ASO-002240 | TTATttccaaattcAcTtTT | 597 | 138886 | 138905 | |

Figure 4 cont.

| Oligomer Name | ASO Number | ASO Sequence | SEQ ID NO: | premRNA start NG_007398 | premRNA end NG_007398 | Oscillation data % control |
|---|---|---|---|---|---|---|
| ASO-002020 | ASO-002020 | AcTTTatttccaaattcactTTtaC | 598 | 138884 | 138908 | 18% |
| ASO-000756 | ASO-000756 | TTTATttccaaattcACTTT | 599 | 138887 | 138906 | >100% |
| ASO-001967 | ASO-001967 | TTtATttccaaattcACtTT | 600 | 138887 | 138906 | >100% |
| ASO-001955 | ASO-001955 | TTTATttccaaattcaCTTT | 601 | 138887 | 138906 | >100% |
| ASO-001948 | ASO-001948 | TTTAtttccaaattcACTTT | 602 | 138887 | 138906 | >100% |
| ASO-002086 | ASO-002086 | AcTTtatttccaaattcactTTTaC | 603 | 138884 | 138908 | 77% |
| ASO-002029 | ASO-002029 | ACtTtatttccaaattcacttTTaC | 604 | 138884 | 138908 | 29% |
| ASO-001961 | ASO-001961 | TtTATttccaaattcACtTT | 605 | 138887 | 138906 | 83% |
| ASO-002095 | ASO-002095 | ACTttatttccaaattcactTtTaC | 606 | 138884 | 138908 | 18% |
| ASO-002059 | ASO-002059 | ACTttatttccaaattcacttTTAC | 607 | 138884 | 138908 | 35% |
| ASO-002077 | ASO-002077 | ActttatttccaaattcactTTTAC | 608 | 138884 | 138908 | 87% |
| ASO-002021 | ASO-002021 | AcTTtatttccaaattcactttTAC | 609 | 138884 | 138908 | 24% |
| ASO-000761 | ASO-000761 | TTTatttccaaattcacTTT | 610 | 138887 | 138906 | >100% |
| ASO-002068 | ASO-002068 | ACtTtatttccaaattcactTtTAC | 611 | 138884 | 138908 | 35% |
| ASO-000766 | ASO-000766 | TTtatttccaaattcactTT | 612 | 138887 | 138906 | >100% |
| ASO-000771 | ASO-000771 | TttatttccaaattcactTT | 613 | 138887 | 138906 | >100% |
| ASO-001967-mm1 | ASO-002294 | ATtATttccaaattcACtTT | 614 | 138887 | 138906 | |
| ASO-001967-mm2 | ASO-002306 | TTtATttccaagttcACtTT | 615 | 138887 | 138906 | |
| ASO-001967-mm3 | ASO-002318 | GTtATttccaaattcACtTT | 616 | 138887 | 138906 | |
| ASO-001967-mm4 | ASO-002330 | ATtATttccagattcACtTT | 617 | 138887 | 138906 | |
| ASO-001967-mm5 | ASO-002342 | TTtATttccaggttcACtTT | 618 | 138887 | 138906 | |
| ASO-001967-mm6 | ASO-002354 | CTtATttccaagttcACtTT | 619 | 138887 | 138906 | |
| SPC-15675-01 | ASO-002250 | TTTCcaaattcacTTT | 620 | 138887 | 138902 | |

Figure 4 cont.

| Oligomer Name | ASO Number | ASO Sequence | SEQ ID NO: | premRNA start NG_007398 | premRNA end NG_007398 | Oscillation data % control |
|---|---|---|---|---|---|---|
| ASO-002006 | ASO-002006 | CTtTAtttccaaattcACTT | 621 | 138888 | 138907 | 0% |
| ASO-000757 | ASO-000757 | CTTTAtttccaaattCACTT | 622 | 138888 | 138907 | >100% |
| ASO-002017 | ASO-002017 | CTtTAtttccaaattcaCTT | 623 | 138888 | 138907 | >100% |
| ASO-001928 | ASO-001928 | CTTTAtttccaaattcACTT | 624 | 138888 | 138907 | >100% |
| ASO-001968 | ASO-001968 | ACTTTatttccaaattCACTT | 625 | 138888 | 138908 | >100% |
| ASO-001921 | ASO-001921 | CTTTatttccaaattCACTT | 626 | 138888 | 138907 | >100% |
| ASO-001989 | ASO-001989 | CTTTatttccaaattcACTT | 627 | 138888 | 138907 | 0% |
| ASO-001942 | ASO-001942 | CTtTAtttccaaattCAcTT | 628 | 138888 | 138907 | >100% |
| ASO-000128 | ASO-000128 | TTTccaaattcaCTT | 629 | 138888 | 138902 | |
| ASO-001935 | ASO-001935 | CtTTAtttccaaattCAcTT | 630 | 138888 | 138907 | >100% |
| ASO-000013 | ASO-000013 | ATTtccaaattcaCTT | 631 | 138888 | 138903 | 91% |
| ASO-002002 | ASO-002002 | CTTtAtttccaaattcACTT | 632 | 138888 | 138907 | >100% |
| ASO-000762 | ASO-000762 | CTTtatttccaaattcaCTT | 633 | 138888 | 138907 | >100% |
| ASO-002010 | ASO-002010 | CTTtatttccaaatTcaCTT | 634 | 138888 | 138907 | >100% |
| ASO-002005 | ASO-002005 | CTtTatttccaaattcaCTT | 635 | 138888 | 138907 | >100% |
| ASO-001998 | ASO-001998 | CTttAtttccaaattcACTT | 636 | 138888 | 138907 | 75% |
| ASO-002001 | ASO-002001 | CTTTatttccaaattcaCTT | 637 | 138888 | 138907 | >100% |
| ASO-001994 | ASO-001994 | CTtTatttccaaattcACTT | 638 | 138888 | 138907 | 45% |
| ASO-002013 | ASO-002013 | CTTtAtttccaaattcaCTT | 639 | 138888 | 138907 | 30% |
| ASO-002009 | ASO-002009 | CTttAtttccaaattcaCTT | 640 | 138888 | 138907 | >100% |
| ASO-000767 | ASO-000767 | CTttatttccaaattcacTT | 641 | 138888 | 138907 | >100% |
| ASO-000772 | ASO-000772 | CtttatttccaaattcacTT | 642 | 138888 | 138907 | >100% |
| BMT-214296 | BMT-214296 | CTTTActtccaaattCACTT | 643 | 138888 | 138907 | |
| ASO-000013-mm1 | ASO-002366 | ***<u>G</u>***TTtccaaattcaCTT | 644 | 138888 | 138903 | |
| ASO-000013-mm2 | ASO-002378 | ATTtccaa***<u>g</u>***ttcaCTT | 645 | 138888 | 138903 | |
| ASO-000013-mm3 | ASO-002295 | ATTtcc***<u>g</u>***aattcaCTT | 646 | 138888 | 138903 | |

Figure 4 cont.

| Oligomer Name | ASO Number | ASO Sequence | SEQ ID NO: | premRNA start NG_007398 | premRNA end NG_007398 | Oscillation data % control |
|---|---|---|---|---|---|---|
| ASO-000013-mm4 | ASO-002307 | GTTtccagattcaCTT | 647 | 138888 | 138903 | |
| ASO-000013-mm5 | ASO-002319 | GTTtccaaattcaCTA | 648 | 138888 | 138903 | |
| ASO-000013-mm6 | ASO-002331 | ATTtccagattcaCTC | 649 | 138888 | 138903 | |
| ASO-000898 | ASO-000898 | ATTtccaaattcaCTT | 650 | 138888 | 138903 | |
| ASO-001942-mm1 | ASO-002363 | CTtTAtttccagattCAcTT | 651 | 138888 | 138907 | |
| ASO-001942-mm2 | ASO-002375 | CTtTAtttccaaattCAcTG | 652 | 138888 | 138907 | |
| ASO-001942-mm3 | ASO-002292 | CTtTAtttccaaattCGcTT | 653 | 138888 | 138907 | |
| ASO-001942-mm4 | ASO-002304 | CTtTAtttccagattCAcTA | 654 | 138888 | 138907 | |
| ASO-001942-mm5 | ASO-002316 | CTtTAtttccaggttCAcTT | 655 | 138888 | 138907 | |
| ASO-001942-mm6 | ASO-002328 | CTtTAtttccgagttCAcTT | 656 | 138888 | 138907 | |
| SPC-15674-01 | ASO-002242 | ATTtccaaattcACTT | 657 | 138888 | 138903 | |
| ASO-002004 | ASO-002004 | CTTTatttccaaatTcaCT | 658 | 138889 | 138907 | >100% |
| ASO-002012 | ASO-002012 | CTTtatttccaaatTcACT | 659 | 138889 | 138907 | >100% |
| ASO-001962 | ASO-001962 | ACTTTatttccaaattCACT | 660 | 138889 | 138908 | >100% |
| ASO-001956 | ASO-001956 | ACTTtatttccaaatTCACT | 661 | 138889 | 138908 | >100% |
| ASO-001949 | ASO-001949 | ACTTTatttccaaatTCACT | 662 | 138889 | 138908 | 98% |
| ASO-001987 | ASO-001987 | CTTTAtttccaaatTcACT | 663 | 138889 | 138907 | >100% |
| ASO-001991 | ASO-001991 | CTTTatttccaaatTCACT | 664 | 138889 | 138907 | >100% |
| ASO-001995 | ASO-001995 | CTTtatttccaaatTCACT | 665 | 138889 | 138907 | >100% |
| ASO-001992 | ASO-001992 | CTTTAtttccaaatTcaCT | 666 | 138889 | 138907 | >100% |
| ASO-002000 | ASO-002000 | CTTTatttccaaatTcACT | 667 | 138889 | 138907 | >100% |
| ASO-001996 | ASO-001996 | CTTTatttccaaatTCaCT | 668 | 138889 | 138907 | 93% |

Figure 4 cont.

| Oligomer Name | ASO Number | ASO Sequence | SEQ ID NO: | premRNA start NG_007398 | premRNA end NG_007398 | Oscillation data % control |
|---|---|---|---|---|---|---|
| ASO-002008 | ASO-002008 | CTTtatttccaaatTCaCT | 669 | 138889 | 138907 | >100% |
| ASO-002015 | ASO-002015 | CTTTAtttccaaatTCaCT | 670 | 138889 | 138907 | >100% |
| ASO-002016 | ASO-002016 | CTTtatttccaaatTcaCT | 671 | 138889 | 138907 | >100% |
| ASO-001986 | ASO-001986 | CTTTAtttccaaatTCACT | 672 | 138889 | 138907 | >100% |
| ASO-001995-mm1 | ASO-002343 | CTTtatttccagatTCACT | 673 | 138889 | 138907 | |
| ASO-001995-mm2 | ASO-002355 | CTTtgtttccaaatTCACT | 674 | 138889 | 138907 | |
| ASO-001995-mm3 | ASO-002367 | CTTtatttccaaatTCACG | 675 | 138889 | 138907 | |
| ASO-001995-mm4 | ASO-002379 | CTTtgtttccagatTCACT | 676 | 138889 | 138907 | |
| ASO-001995-mm5 | ASO-002296 | CTTtgtttccaagtTCACT | 677 | 138889 | 138907 | |
| ASO-001995-mm6 | ASO-002308 | CTTtatttccgagtTCACT | 678 | 138889 | 138907 | |
| SPC-15673-01 | ASO-002233 | TATttccaaattcACT | 679 | 138889 | 138904 | |
| ASO-002003 | ASO-002003 | CTTTatttccaaatTCAC | 680 | 138890 | 138907 | >100% |
| ASO-002007 | ASO-002007 | CTTtatttccaaatTCAC | 681 | 138890 | 138907 | >100% |
| ASO-002011 | ASO-002011 | CTtTatttccaaatTcAC | 682 | 138890 | 138907 | >100% |
| ASO-001988 | ASO-001988 | CTTTAtttccaaatTcAC | 683 | 138890 | 138907 | >100% |
| ASO-001999 | ASO-001999 | CTTTAtttccaaatTCAC | 684 | 138890 | 138907 | >100% |
| ASO-001993 | ASO-001993 | CTTTatttccaaatTcAC | 685 | 138890 | 138907 | 6% |
| ASO-001997 | ASO-001997 | CTTtatttccaaatTcAC | 686 | 138890 | 138907 | >100% |
| ASO-001997-mm1 | ASO-002320 | CTTtatttccagatTcAC | 687 | 138890 | 138907 | |
| ASO-001997-mm2 | ASO-002332 | CTTtatttccgaatTcAC | 688 | 138890 | 138907 | |
| ASO-001997-mm3 | ASO-002344 | CTTtgtttccaaatTcAC | 689 | 138890 | 138907 | |
| ASO-001997-mm4 | ASO-002356 | CTTtgtttccagatTcAC | 690 | 138890 | 138907 | |

Figure 4 cont.

| Oligomer Name | ASO Number | ASO Sequence | SEQ ID NO: | premRNA start NG_007398 | premRNA end NG_007398 | Oscillation data % control |
|---|---|---|---|---|---|---|
| ASO-001997-mm5 | ASO-002368 | CTTtatttcca***gg***tTcAC | 691 | 138890 | 138907 | |
| ASO-001997-mm6 | ASO-002380 | CTTt***g***tttccaa***g***tTcAC | 692 | 138890 | 138907 | |
| SPC-15672-01 | ASO-002288 | TTAtttccaaattCAC | 693 | 138890 | 138905 | |
| SPC-15671-01 | ASO-002280 | TTTatttccaaatTCA | 694 | 138891 | 138906 | |
| SPC-15670-01 | ASO-002273 | CTTtatttccaaATTC | 695 | 138892 | 138907 | |
| SPC-15669-01 | ASO-002265 | ACTTtatttccaAATT | 696 | 138893 | 138908 | |
| ASO-000139 | ASO-000139 | AACtttatttccaAAT | 697 | 138894 | 138909 | |
| SPC-15668-01 | ASO-002257 | AACTttatttccAAAT | 698 | 138894 | 138909 | |
| SPC-15667-01 | ASO-002249 | TAACtttatttcCAAA | 699 | 138895 | 138910 | |
| SPC-15666-01 | ASO-002241 | ATAActttatttcCAA | 700 | 138896 | 138911 | |
| ASO-000118 | ASO-000118 | AATaactttatttCCA | 701 | 138897 | 138912 | |
| SPC-15665-01 | ASO-002232 | AATaactttattTCCA | 702 | 138897 | 138912 | |
| ASO-000101 | ASO-000101 | TAAtaactttattTCC | 703 | 138898 | 138913 | |
| SPC-15664-01 | ASO-002287 | TAAtaactttatTTCC | 704 | 138898 | 138913 | |
| ASO-000148 | ASO-000148 | GTAataactttatTTC | 705 | 138899 | 138914 | |
| ASO-000184 | ASO-000184 | TAAtaactttatTTC | 706 | 138899 | 138913 | |
| ASO-000112 | ASO-000112 | GTAataactttaTTT | 707 | 138900 | 138914 | |
| ASO-000170 | ASO-000170 | AGTaataactttaTTT | 708 | 138900 | 138915 | |
| ASO-000154 | ASO-000154 | GAGtaataactttATT | 709 | 138901 | 138916 | |
| ASO-000125 | ASO-000125 | AGTaataactttATT | 710 | 138901 | 138915 | |
| ASO-000167 | ASO-000167 | GAGtaataacttTAT | 711 | 138902 | 138916 | |
| ASO-000134 | ASO-000134 | AGAgtaataacttTAT | 712 | 138902 | 138917 | |
| ASO-000175 | ASO-000175 | CAGagtaataactTTA | 713 | 138903 | 138918 | |
| ASO-000178 | ASO-000178 | AGAgtaataactTTA | 714 | 138903 | 138917 | |
| ASO-000138 | ASO-000138 | CAGagtaataacTTT | 715 | 138904 | 138918 | |

Figure 4 cont.

| Oligomer Name | ASO Number | ASO Sequence | SEQ ID NO: | premRNA start NG_007398 | premRNA end NG_007398 | Oscillation data % control |
|---|---|---|---|---|---|---|
| ASO-000171 | ASO-000171 | TCAgagtaataacTTT | 716 | 138904 | 138919 | |
| ASO-000236 | ASO-000236 | ATCagagtaataaCTT | 717 | 138905 | 138920 | |
| ASO-000127 | ASO-000127 | TCAgagtaataaCTT | 718 | 138905 | 138919 | |
| ASO-000177 | ASO-000177 | CAGagtaataaCTT | 719 | 138905 | 138918 | |
| ASO-000238 | ASO-000238 | AATcagagtaataACT | 720 | 138906 | 138921 | |
| ASO-000222 | ASO-000222 | TAAtcagagtaatAAC | 721 | 138907 | 138922 | |
| ASO-000307 | ASO-000307 | AATcagagtaatAAC | 722 | 138907 | 138921 | |
| ASO-000204 | ASO-000204 | TTAatcagagtaaTAA | 723 | 138908 | 138923 | |
| ASO-000330 | ASO-000330 | TAAtcagagtaaTAA | 724 | 138908 | 138922 | |
| ASO-000326 | ASO-000326 | TTTaatcagagtaATA | 725 | 138909 | 138924 | |
| ASO-000249 | ASO-000249 | TTTaatcagagtAAT | 726 | 138910 | 138924 | |
| ASO-002022 | ASO-002022 | TTATttccaaattcaCTtTT | 727 | 138886 | 138905 | >100% |
| ASO-002026 | ASO-002026 | TTatTTccaaattcaCtTTT | 728 | 138886 | 138905 | >100% |
| ASO-002024 | ASO-002024 | TTAttTccaaattcaCtTTT | 729 | 138886 | 138905 | >100% |
| ASO-002049 | ASO-002049 | ACTTtatttccaaattcactTTtAC | 730 | 138884 | 138908 | 29% |
| ASO-002019 | ASO-002019 | ActtTatttccaaattcactTTtaC | 731 | 138884 | 138908 | 18% |

"mm" indicates mismatches. The mismatched bases are underlined, bolded, italicized, and highlighted.

Figure 5

| ASO Number | ASO Sequence | SEQ ID NO: | premRNA start NG_007398 | premRNA end NG_007398 | *In vivo* acute tolerability score | brain tau mRNA % remaining |
|---|---|---|---|---|---|---|
| ASO-000013 | ATTtccaaattcaCTT | 686 | 138888 | 138903 | 0 | 29 |
| ASO-000118 | AATaactttatttCCA | 773 | 138897 | 138912 | 0.17 | 59 |
| ASO-000125 | AGTaataactttATT | 782 | 138901 | 138915 | | |
| ASO-000128 | TTTccaaattcaCTT | 684 | 138888 | 138902 | | |
| ASO-000134 | AGAgtaataacttTAT | 784 | 138902 | 138917 | | |
| ASO-000170 | AGTaataactttaTTT | 780 | 138900 | 138915 | | |
| ASO-000178 | AGAgtaataactTTA | 786 | 138903 | 138917 | | |
| ASO-000204 | TTAatcagagtaaTAA | 795 | 138908 | 138923 | | |
| ASO-000249 | TTTaatcagagtAAT | 798 | 138910 | 138924 | | |
| ASO-000307 | AATcagagtaatAAC | 794 | 138907 | 138921 | | |
| ASO-000326 | TTTaatcagagtaATA | 797 | 138909 | 138924 | | |
| ASO-000330 | TAAtcagagtaaTAA | 796 | 138908 | 138922 | | |
| ASO-000388 | ATAgtcactctggTGA | 250 | 136650 | 136665 | 20 | |
| ASO-000389 | TAGccctaaagtcCCA | 53 | 135744 | 135759 | 3.83 | 32 |
| ASO-000390 | TAGtcactctggTGA | 251 | 136650 | 136664 | 16.67 | |
| ASO-000394 | AAGatacatgcgtCCT | 258 | 136695 | 136710 | 11.67 | |
| ASO-000396 | TACatgcgtccTTT | 256 | 136693 | 136706 | 20 | |
| ASO-000411 | CCCtaaagtccCAG | 51 | 135743 | 135756 | 13.33 | |
| ASO-000435 | TTAgccctaaagtCCC | 69 | 135745 | 135760 | 7.17 | |
| ASO-000442 | TAGccctaaagTCC | 71 | 135746 | 135759 | 10 | |
| ASO-000447 | TCAtagtcactctGGT | 255 | 136652 | 136667 | 13.67 | |
| ASO-000449 | AAGaggcacaagtCCT | 84 | 135776 | 135791 | 3.83 | |
| ASO-000451 | AAGcatttcaagaTAC | 262 | 136704 | 136719 | 7.33 | |
| ASO-000468 | ACCatgatcttagGCT | 365 | 137856 | 137871 | 18 | |
| ASO-000478 | GTCctaatcctgtGCT | 285 | 136905 | 136920 | 16 | |
| ASO-000527 | TAGcaaacaggatACA | 392 | 138098 | 138113 | 8.33 | |
| ASO-000540 | CCTtaatttcaccCTC | 153 | 136053 | 136068 | 0.33 | 29 |

Figure 5 cont.

| ASO Number | ASO Sequence | SEQ ID NO: | premRNA start NG_007398 | premRNA end NG_007398 | *In vivo* acute tolerability score | brain tau mRNA % remaining |
|---|---|---|---|---|---|---|
| ASO-000543 | CATgattgtgggcTTA | 417 | 138403 | 138418 | 20 | |
| ASO-000555 | CTTaatttcaccCTC | 154 | 136053 | 136067 | 4.17 | 38 |
| ASO-000558 | GAActggttagccCTA | 76 | 135752 | 135767 | 17.67 | |
| ASO-000566 | CCTtaatttcacCCT | 202 | 136054 | 136068 | 0 | 42 |
| ASO-000581 | ACTggttagccctAAA | 74 | 135750 | 135765 | 20 | |
| ASO-000603 | TCCcttaatttcACC | 227 | 136056 | 136070 | 0 | 48 |
| ASO-000614 | CAAacaggatacAGT | 390 | 138096 | 138110 | 10.67 | |
| ASO-000635 | CCCtaaaccatgaTCT | 370 | 137862 | 137877 | 2.33 | 71 |
| ASO-000642 | CCCttaatttcaCCC | 223 | 136055 | 136069 | 0.7 | 30 |
| ASO-000662 | CCCttaatttcacCCT | 201 | 136054 | 136069 | 0.5 | 20 |
| ASO-000753 | ATTTCcaaattcactTTTAC | 471 | 138884 | 138903 | 2.33 | 29 |
| ASO-000755 | TTATTtccaaattcaCTTTT | 587 | 138886 | 138905 | 1.67 | 18 |
| ASO-000756 | TTTATttccaaattcACTTT | 644 | 138887 | 138906 | 0.83 | 10 |
| ASO-000757 | CTTTAtttccaaattCACTT | 677 | 138888 | 138907 | 0.17 | 6 |
| ASO-000758 | ATTtccaaattcactttTAC | 485 | 138884 | 138903 | 0.17 | 49 |
| ASO-000759 | TATttccaaattcacttTTA | 548 | 138885 | 138904 | 0.33 | 77 |
| ASO-000760 | TTAtttccaaattcactTTT | 589 | 138886 | 138905 | 0 | 63 |
| ASO-000761 | TTTatttccaaattcacTTT | 655 | 138887 | 138906 | 0.33 | 44 |
| ASO-000762 | CTTtatttccaaattcaCTT | 688 | 138888 | 138907 | 0 | 30 |
| ASO-000829 | AAGatgaaatttgCTC | 7 | 134950 | 134965 | 4.67 | 28 |
| ASO-000830 | TACtagcccacccATC | 28 | 134974 | 134989 | 6.67 | |
| ASO-000898 | ATTtccaaattcaCTT | 705 | 138888 | 138903 | | |
| ASO-001778 | TTAgccctaaagtcccaGGT | 46 | 135741 | 135760 | 20 | |
| ASO-001779 | TAGccctaaagtcccagGTC | 43 | 135740 | 135759 | 20 | |
| ASO-001780 | GTTagccctaaagtcccAGG | 49 | 135742 | 135761 | 20 | |
| ASO-001781 | GGTtagccctaaagtccCAG | 52 | 135743 | 135762 | 20 | |
| ASO-001782 | TGGttagccctaaagtcCCA | 67 | 135744 | 135763 | 12.33 | |
| ASO-001919 | ATTTccaaattcactTTTAC | 474 | 138884 | 138903 | 4.33 | 16 |

Figure 5 cont.

| ASO Number | ASO Sequence | SEQ ID NO: | premRNA start NG_007398 | premRNA end NG_007398 | *In vivo* acute tolerability score | brain tau mRNA % remaining |
|---|---|---|---|---|---|---|
| ASO-001920 | TTATttccaaattcaCTTTT | 590 | 138886 | 138905 | 1.5 | 27 |
| ASO-001921 | CTTTatttccaaattCACTT | 681 | 138888 | 138907 | 1 | 10 |
| ASO-001925 | TAGccctaaagtcCCA | 56 | 135744 | 135759 | 11 | |
| ASO-001926 | ATTTCcaaattcacttTTAC | 482 | 138884 | 138903 | 0.67 | 46 |
| ASO-001927 | TTATTtccaaattcacTTTT | 592 | 138886 | 138905 | 1.17 | 44 |
| ASO-001928 | CTTTAtttccaaattcACTT | 679 | 138888 | 138907 | 1.33 | 6 |
| ASO-001933 | AtTTCcaaattcactTTtAC | 473 | 138884 | 138903 | 0.83 | 20 |
| ASO-001934 | TtATTtccaaattcaCTtTT | 595 | 138886 | 138905 | 0.67 | 43 |
| ASO-001935 | CtTTAtttccaaattCAcTT | 685 | 138888 | 138907 | 1.33 | 19 |
| ASO-001940 | ATtTCcaaattcactTTtAC | 472 | 138884 | 138903 | 0.29 | 22 |
| ASO-001941 | TTaTTtccaaattcaCTtTT | 593 | 138886 | 138905 | 2 | 14 |
| ASO-001942 | CTtTAtttccaaattCAcTT | 683 | 138888 | 138907 | 2 | 16 |
| ASO-001947 | TATTtccaaattcacTTTTA | 533 | 138885 | 138904 | 3.83 | 26 |
| ASO-001948 | TTTAtttccaaattcACTTT | 647 | 138887 | 138906 | 0.33 | 11 |
| ASO-001953 | TAGccctaaagtcCCA | 60 | 135744 | 135759 | 4 | |
| ASO-001954 | TATTTccaaattcactTTTA | 532 | 138885 | 138904 | 1.17 | 23 |
| ASO-001955 | TTTATttccaaattcaCTTT | 646 | 138887 | 138906 | 0.5 | 19 |
| ASO-001956 | ACTTtatttccaaatTCACT | 716 | 138889 | 138908 | 0 | 15 |
| ASO-001960 | TaTTTccaaattcacTTtTA | 538 | 138885 | 138904 | 5 | 23 |
| ASO-001961 | TtTATttccaaattcACtTT | 650 | 138887 | 138906 | 2.17 | 25 |
| ASO-001962 | ACTTTatttccaaattCACT | 715 | 138889 | 138908 | 2 | 9 |
| ASO-001966 | TAtTTccaaattcacTTtTA | 535 | 138885 | 138904 | 4.33 | 23 |
| ASO-001967 | TTtATttccaaattcACtTT | 645 | 138887 | 138906 | 1 | 22 |
| ASO-001968 | ACTTTatttccaaattCACTT | 680 | 138888 | 138908 | 0.67 | 19 |
| ASO-001995 | CTTtatttccaaatTCACT | 720 | 138889 | 138907 | 0.17 | 57 |
| ASO-001997 | CTTtatttccaaatTcAC | 745 | 138890 | 138907 | | |
| ASO-001998 | CTttAtttccaaattcACTT | 691 | 138888 | 138907 | | |
| ASO-002002 | CTTtAtttccaaattcACTT | 687 | 138888 | 138907 | | |

Figure 5 cont.

| ASO Number | ASO Sequence | SEQ ID NO: | premRNA start NG_007398 | premRNA end NG_007398 | *In vivo* acute tolerability score | brain tau mRNA % remaining |
|---|---|---|---|---|---|---|
| ASO-002005 | CTtTatttccaaattcaCTT | 690 | 138888 | 138907 | | |
| ASO-002007 | CTTtatttccaaatTCAC | 740 | 138890 | 138907 | 0.13 | 26 |
| ASO-002008 | CTTtatttccaaatTCaCT | 724 | 138889 | 138907 | 0.67 | 34 |
| ASO-002009 | CTttAtttccaaattcaCTT | 695 | 138888 | 138907 | | |
| ASO-002010 | CTTtatttccaaatTcaCTT | 689 | 138888 | 138907 | | |
| ASO-002011 | CTtTatttccaaatTcAC | 741 | 138890 | 138907 | | |
| ASO-002012 | CTTtatttccaaatTcACT | 714 | 138889 | 138907 | 0 | 36 |
| ASO-002016 | CTTtatttccaaatTcaCT | 726 | 138889 | 138907 | | |
| ASO-002022 | TTATttccaaattcaCTtTT | 799 | 138886 | 138905 | | |
| ASO-002023 | ATTTccaaattcacTTttAC | 484 | 138884 | 138903 | | |
| ASO-002024 | TTAttTccaaattcaCtTTT | 801 | 138886 | 138905 | | |
| ASO-002025 | TAttTcCaaattcactTTTA | 536 | 138885 | 138904 | | |
| ASO-002026 | TTatTTccaaattcaCtTTT | 800 | 138886 | 138905 | | |
| ASO-002027 | TATtTccaaattcaCtTtTA | 543 | 138885 | 138904 | | |
| ASO-002028 | TAtTTccaaattcaCttTTA | 545 | 138885 | 138904 | | |
| ASO-002033 | TATtTccaaattcacTtTTA | 537 | 138885 | 138904 | | |
| ASO-002034 | ATTtCcaaattcactTtTAC | 476 | 138884 | 138903 | 0.83 | 34 |
| ASO-002035 | TAtTtcCaaattcactTTTA | 528 | 138885 | 138904 | 0.5 | 42 |
| ASO-002036 | ATttCcAaattcacttTTAC | 477 | 138884 | 138903 | 0.33 | 34 |
| ASO-002037 | ATTTccaaattcaCtTttAC | 479 | 138884 | 138903 | | |
| ASO-002038 | ATTtCcaaattcacTtTtAC | 487 | 138884 | 138903 | 0 | 42 |
| ASO-002043 | ATtTCcaaattcacttTTAC | 467 | 138884 | 138903 | 0.83 | 48 |
| ASO-002044 | TTAtTtccaaattcaCtTTT | 602 | 138886 | 138905 | | |
| ASO-002045 | TTaTttCcaaattcacTTTT | 594 | 138886 | 138905 | | |
| ASO-002046 | TTatTtCcaaattcacTTTT | 604 | 138886 | 138905 | | |
| ASO-002047 | TTATttccaaattCaCttTT | 603 | 138886 | 138905 | | |
| ASO-002048 | TATtTccaaattcaCttTTA | 529 | 138885 | 138904 | 1.17 | 59 |
| ASO-002053 | TAtTtCcaaattcactTTTA | 530 | 138885 | 138904 | 1 | 47 |

Figure 5 cont.

| ASO Number | ASO Sequence | SEQ ID NO: | premRNA start NG_007398 | premRNA end NG_007398 | *In vivo* acute tolerability score | brain tau mRNA % remaining |
|---|---|---|---|---|---|---|
| ASO-002054 | TTaTTtccaaattcaCtTTT | 598 | 138886 | 138905 | | |
| ASO-002055 | TAtTtCcaaattcacTTtTA | 527 | 138885 | 138904 | | |
| ASO-002056 | TAttTCcaaattcacTTtTA | 539 | 138885 | 138904 | | |
| ASO-002057 | ATTTccaaattcaCttTtAC | 481 | 138884 | 138903 | | |
| ASO-002058 | ATTtCcaaattcacTttTAC | 480 | 138884 | 138903 | 0.83 | 39 |
| ASO-002062 | ATTtcCaaattcactTTtAC | 469 | 138884 | 138903 | | |
| ASO-002063 | TATttCcaaattcacTTtTA | 540 | 138885 | 138904 | | |
| ASO-002064 | TTaTtTccaaattcaCTtTT | 600 | 138886 | 138905 | | |
| ASO-002065 | ATttCCaaattcactTTtAC | 486 | 138884 | 138903 | 0 | 36 |
| ASO-002066 | TTATttccaaattCacTtTT | 601 | 138886 | 138905 | | |
| ASO-002067 | TAtTTccaaattcaCTttTA | 531 | 138885 | 138904 | | |
| ASO-002071 | TTaTtTccaaattcacTTTT | 588 | 138886 | 138905 | 1 | 33 |
| ASO-002072 | TTAttTccaaattcaCTtTT | 586 | 138886 | 138905 | | |
| ASO-002073 | TAtTtCcaaattcacTtTTA | 542 | 138885 | 138904 | | |
| ASO-002074 | TTatTTccaaattcaCTtTT | 596 | 138886 | 138905 | | |
| ASO-002075 | TATtTccaaattcaCTttTA | 544 | 138885 | 138904 | | |
| ASO-002076 | ATtTCcaaattcacTTttAC | 468 | 138884 | 138903 | 0.33 | 60 |
| ASO-002077 | ActttatttccaaattcactTTTAC | 653 | 138884 | 138908 | | |
| ASO-002080 | TTatTTccaaattcacTTTT | 591 | 138886 | 138905 | 0 | 36 |
| ASO-002081 | TATttCcaaattcacTtTTA | 534 | 138885 | 138904 | | |
| ASO-002082 | ATtTcCaaattcactTtTAC | 470 | 138884 | 138903 | 0.13 | 31 |
| ASO-002083 | TAttTCcaaattcacTtTTA | 547 | 138885 | 138904 | 0.83 | 54 |
| ASO-002084 | ATTtCcaaattcacTTttAC | 478 | 138884 | 138903 | 0.33 | 52 |
| ASO-002085 | TAtTTccaaattcaCtTtTA | 546 | 138885 | 138904 | | |
| ASO-002086 | AcTTtatttccaaattcactTTTaC | 648 | 138884 | 138908 | | |
| ASO-002089 | TATTtccaaattcaCttTTA | 541 | 138885 | 138904 | | |
| ASO-002090 | ATTtcCaaattcactTtTAC | 466 | 138884 | 138903 | | |
| ASO-002091 | TTaTtTccaaattcaCtTTT | 599 | 138886 | 138905 | | |

Figure 5 cont.

| ASO Number | ASO Sequence | SEQ ID NO: | premRNA start NG_007398 | premRNA end NG_007398 | *In vivo* acute tolerability score | brain tau mRNA % remaining |
|---|---|---|---|---|---|---|
| ASO-002092 | ATttCCaaattcactTtTAC | 483 | 138884 | 138903 | 0.48 | 14 |
| ASO-002093 | TTAtTtccaaattcACttTT | 597 | 138886 | 138905 | | |
| ASO-002094 | ATtTCcaaattcacTtTtAC | 475 | 138884 | 138903 | 0.5 | 61 |

Figure 6.

| SEQ ID NO: | Oligomer Name | ASO Number | ASO Sequence | premRNA start NG_0073 98 | premRN A end NG_0073 98 | mRNA start NM_016 835 | Tau/Tubu lin % inhibition |
|---|---|---|---|---|---|---|---|
| 4 | ASO-001167 | ASO-001167 | AAAgatgaaatttgctcTTA | 134947 | 134966 | 2787 | 77 |
| 5 | ASO-001168 | ASO-001168 | GAAagatgaaatttgctCTT | 134948 | 134967 | 2788 | 89 |
| 6 | ASO-001169 | ASO-001169 | GGAaagatgaaatttgcTCT | 134949 | 134968 | 2789 | 99 |
| 7 | ASO-000829 | ASO-000829 | AAGatgaaatttgCTC | 134950 | 134965 | 2790 | 99 |
| 8 | ASO-001170 | ASO-001170 | TGGaaagatgaaatttgCTC | 134950 | 134969 | 2790 | 100 |
| 9 | ASO-001171 | ASO-001171 | TTGgaaagatgaaatttGCT | 134951 | 134970 | 2791 | 97 |
| 10 | ASO-001172 | ASO-001172 | TTTggaaagatgaaattTGC | 134952 | 134971 | 2792 | 96 |
| 11 | ASO-001173 | ASO-001173 | ATTtggaaagatgaaatTTG | 134953 | 134972 | 2793 | 43 |
| 12 | ASO-001174 | ASO-001174 | AATttggaaagatgaaaTTT | 134954 | 134973 | 2794 | 0 |
| 13 | ASO-001175 | ASO-001175 | CAAtttggaaagatgaaATT | 134955 | 134974 | 2795 | 3 |
| 14 | ASO-001176 | ASO-001176 | TCAatttggaaagatgaAAT | 134956 | 134975 | 2796 | 36 |
| 15 | ASO-001177 | ASO-001177 | ATCaatttggaaagatgAAA | 134957 | 134976 | 2797 | 45 |
| 16 | ASO-001178 | ASO-001178 | CATcaatttggaaagatGAA | 134958 | 134977 | 2798 | 26 |
| 17 | ASO-001179 | ASO-001179 | CCAtcaatttggaaagaTGA | 134959 | 134978 | 2799 | 79 |
| 18 | ASO-001180 | ASO-001180 | CCCatcaatttggaaagATG | 134960 | 134979 | 2800 | 77 |
| 19 | ASO-001181 | ASO-001181 | ACCcatcaatttggaaaGAT | 134961 | 134980 | 2801 | 82 |
| 20 | ASO-001182 | ASO-001182 | CACccatcaatttggaaAGA | 134962 | 134981 | 2802 | 85 |

Figure 6 cont.

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 21 | ASO-001183 | ASO-001183 | CCAcccatcaatttggaAAG | 134963 | 134982 | 2803 | 97 |
| 22 | ASO-001184 | ASO-001184 | CCCacccatcaatttggAAA | 134964 | 134983 | 2804 | 89 |
| 23 | ASO-001062 | ASO-001062 | GCCcacccatcaatttgGAA | 134965 | 134984 | 2805 | 79 |
| 24 | ASO-001063 | ASO-001063 | TAGcccacccatcaattTGG | 134967 | 134986 | 2807 | 98 |
| 25 | ASO-001064 | ASO-001064 | CTAgcccacccatcaatTTG | 134968 | 134987 | 2808 | 99 |
| 26 | ASO-001065 | ASO-001065 | ACTagcccacccatcaaTTT | 134969 | 134988 | 2809 | 100 |
| 27 | ASO-001066 | ASO-001066 | TACtagcccacccatcaATT | 134970 | 134989 | 2810 | 94 |
| 28 | ASO-000830 | ASO-000830 | TACtagcccacccATC | 134974 | 134989 | 2814 | 99 |
| 29 | ASO-000260 | ASO-000260 | CCCtcttctacatGGA | 135077 | 135092 | 2917 | 99 |
| 30 | ASO-000305 | ASO-000305 | TGCctctgtgacaCCC | 135171 | 135186 | 3011 | 99 |
| 31 | ASO-000304 | ASO-000304 | TTCaaatcctttgTTG | 135194 | 135209 | 3034 | 96 |
| 32 | ASO-000324 | ASO-000324 | CACacaaggttgaCAT | 135242 | 135257 | 3082 | 99 |
| 33 | ASO-000268 | ASO-000268 | CGTcacactcacaCAA | 135251 | 135266 | 3091 | 99 |
| 34 | ASO-000223 | ASO-000223 | GCCaccaaggacaGGC | 135441 | 135456 | 3281 | 8 |
| 35 | ASO-000224 | ASO-000224 | CAGcttgccttctCTT | 135533 | 135548 | 3373 | 99 |
| 36 | ASO-000319 | ASO-000319 | ATCaaggtcagtcTTT | 135585 | 135600 | 3425 | 99 |
| 37 | ASO-000208 | ASO-000208 | CCTtcagaactcaATA | 135690 | 135705 | 3530 | 97 |
| 38 | ASO-000689 | ASO-000689 | AAAgtcccaggtcTGC | 135737 | 135752 | 3577 | 99 |
| 39 | ASO-000434 | ASO-000434 | CTAaagtcccaggTCT | 135739 | 135754 | 3579 | 99 |
| 40 | ASO-000409 | ASO-000409 | TAAagtcccaggTCT | 135739 | 135753 | 3579 | 98 |
| 41 | ASO-000432 | ASO-000432 | CCTaaagtcccagGTC | 135740 | 135755 | 3580 | 98 |
| 42 | ASO-000391 | ASO-000391 | TAAagtcccagGTC | 135740 | 135753 | 3580 | 98 |
| 43 | ASO-001779 | ASO-001779 | TAGccctaaagtcccagGTC | 135740 | 135759 | 3580 | 100 |
| 44 | ASO-000899 | ASO-000899 | CTAaagtcccagGTC | 135740 | 135754 | 3580 | 6 |

Figure 6 cont.

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 45 | ASO-000398 | ASO-000398 | CCCtaaagtcccaGGT | 135741 | 135756 | 3581 | 85 |
| 46 | ASO-001778 | ASO-001778 | TTAgccctaaagtcccaGGT | 135741 | 135760 | 3581 | 100 |
| 47 | ASO-000414 | ASO-000414 | GCCctaaagtcccAGG | 135742 | 135757 | 3582 | 58 |
| 48 | ASO-000403 | ASO-000403 | CCCtaaagtcccAGG | 135742 | 135756 | 3582 | 45 |
| 49 | ASO-001780 | ASO-001780 | GTTagccctaaagtcccAGG | 135742 | 135761 | 3582 | 100 |
| 50 | ASO-000433 | ASO-000433 | GCCctaaagtccCAG | 135743 | 135757 | 3583 | 99 |
| 51 | ASO-000411 | ASO-000411 | CCCtaaagtccCAG | 135743 | 135756 | 3583 | 99 |
| 52 | ASO-001781 | ASO-001781 | GGTtagccctaaagtccCAG | 135743 | 135762 | 3583 | 100 |
| 53 | ASO-000389 | ASO-000389 | TAGccctaaagtcCCA | 135744 | 135759 | 3584 | 100 |
| 54 | ASO-001939 | ASO-001939 | TAGccctaaagtcCCA | 135744 | 135759 | 3584 | 100 |
| 55 | ASO-001932 | ASO-001932 | TAGccctaaagtcCCA | 135744 | 135759 | 3584 | 100 |
| 56 | ASO-001925 | ASO-001925 | TAGccctaaagtcCCA | 135744 | 135759 | 3584 | 100 |
| 57 | ASO-001924 | ASO-001924 | TAGccctaaagtcCCA | 135744 | 135759 | 3584 | 100 |
| 58 | ASO-001952 | ASO-001952 | TAGccctaaagtcCCA | 135744 | 135759 | 3584 | 100 |
| 59 | ASO-001931 | ASO-001931 | TAGccctaaagtcCCA | 135744 | 135759 | 3584 | 100 |
| 60 | ASO-001953 | ASO-001953 | TAGccctaaagtcCCA | 135744 | 135759 | 3584 | 100 |
| 61 | ASO-001945 | ASO-001945 | TAGccctaaagtcCCA | 135744 | 135759 | 3584 | 100 |
| 62 | ASO-001946 | ASO-001946 | TAGccctaaagtcCCA | 135744 | 135759 | 3584 | 99 |
| 63 | ASO-001971 | ASO-001971 | TAGccctaaagtcCCA | 135744 | 135759 | 3584 | 100 |
| 64 | ASO-001938 | ASO-001938 | TAGccctaaagtcCCA | 135744 | 135759 | 3584 | 100 |
| 65 | ASO-001959 | ASO-001959 | TAGccctaaagtcCCA | 135744 | 135759 | 3584 | 100 |
| 66 | ASO-001965 | ASO-001965 | TAGccctaaagtcCCA | 135744 | 135759 | 3584 | 99 |
| 67 | ASO-001782 | ASO-001782 | TGGttagccctaaagtcCCA | 135744 | 135763 | 3584 | 99 |
| 68 | ASO-000900 | ASO-000900 | TAGccctaaagtcCCA | 135744 | 135759 | 3584 | 0 |
| 69 | ASO-000435 | ASO-000435 | TTAgccctaaagtCCC | 135745 | 135760 | 3585 | 98 |
| 70 | ASO-000423 | ASO-000423 | GTTagccctaaagTCC | 135746 | 135761 | 3586 | 99 |

Figure 6 cont.

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 71 | ASO-000442 | ASO-000442 | TAGccctaaagTCC | 135746 | 135759 | 3586 | 91 |
| 72 | ASO-000416 | ASO-000416 | GGTtagccctaaaGTC | 135747 | 135762 | 3587 | 100 |
| 73 | ASO-000438 | ASO-000438 | GTTagccctaaAGT | 135748 | 135761 | 3588 | 98 |
| 74 | ASO-000581 | ASO-000581 | ACTggttagccctAAA | 135750 | 135765 | 3590 | 100 |
| 75 | ASO-000639 | ASO-000639 | AACtggttagcccTAA | 135751 | 135766 | 3591 | 100 |
| 76 | ASO-000558 | ASO-000558 | GAActggttagccCTA | 135752 | 135767 | 3592 | 100 |
| 77 | ASO-000597 | ASO-000597 | GAGaactggttagCCC | 135754 | 135769 | 3594 | 100 |
| 78 | ASO-000245 | ASO-000245 | TACaaagagaactGGT | 135760 | 135775 | 3600 | 100 |
| 79 | ASO-000897 | ASO-000897 | CACaagtccttacAAA | 135770 | 135785 | 3610 | 4 |
| 80 | ASO-000185 | ASO-000185 | GGCacaagtccttACA | 135772 | 135787 | 3612 | 99 |
| 81 | ASO-000426 | ASO-000426 | AGGcacaagtccTTA | 135774 | 135788 | 3614 | 52 |
| 82 | ASO-000417 | ASO-000417 | GAGgcacaagtccTTA | 135774 | 135789 | 3614 | 39 |
| 83 | ASO-000393 | ASO-000393 | AGAggcacaagtcCTT | 135775 | 135790 | 3615 | 75 |
| 84 | ASO-000449 | ASO-000449 | AAGaggcacaagtCCT | 135776 | 135791 | 3616 | 95 |
| 85 | ASO-000406 | ASO-000406 | AGAggcacaagtCCT | 135776 | 135790 | 3616 | 78 |
| 86 | ASO-000392 | ASO-000392 | CCAagaggcacaaGTC | 135778 | 135793 | 3618 | 99 |
| 87 | ASO-000444 | ASO-000444 | CAAgaggcacaaGTC | 135778 | 135792 | 3618 | 99 |
| 88 | ASO-000443 | ASO-000443 | CCCaagaggcacaAGT | 135779 | 135794 | 3619 | 100 |
| 89 | ASO-000450 | ASO-000450 | CAAgaggcacaAGT | 135779 | 135792 | 3619 | 99 |
| 90 | ASO-000258 | ASO-000258 | CTCccaagaggcaCAA | 135781 | 135796 | 3621 | 97 |
| 91 | ASO-000205 | ASO-000205 | TGGccgtgggaagGAC | 135876 | 135891 | 3716 | 90 |
| 92 | ASO-000213 | ASO-000213 | GGTgaggctgggaATT | 135984 | 135999 | 3823 | 100 |
| 93 | ASO-000293 | ASO-000293 | GTGaggctgggaATT | 135984 | 135998 | 3823 | 100 |
| 94 | ASO-000321 | ASO-000321 | TGGtgaggctgggAAT | 135985 | 136000 | 3824 | 99 |
| 95 | ASO-000226 | ASO-000226 | CTCagtatggagtAGG | 136040 | 136055 | 3879 | 90 |
| 96 | ASO-000682 | ASO-000682 | AATttcaccctcaGTA | 136049 | 136064 | 3888 | 79 |
| 97 | ASO-000673 | ASO-000673 | TTAatttcaccctCAG | 136051 | 136066 | 3890 | 84 |
| 98 | ASO-000578 | ASO-000578 | CTTaatttcacccTCA | 136052 | 136067 | 3891 | 99 |

Figure 6 cont.

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 99 | ASO-000540-21 | ASO-002180 | CCTTaatttcaccCTCA | 136052 | 136068 | 3891 | 98 |
| 100 | ASO-000540-22 | ASO-002192 | CCTTaatttcacCctCA | 136052 | 136068 | 3891 | 99 |
| 101 | ASO-000540-23 | ASO-002109 | CCTTAatttcacCctCA | 136052 | 136068 | 3891 | 97 |
| 102 | ASO-000540-24 | ASO-002121 | TcCCtTaatttcaccCT | 136054 | 136070 | 3893 | 98 |
| 103 | ASO-000540-25 | ASO-002133 | TcCCTtaatttcaccCT | 136054 | 136070 | 3893 | 97 |
| 104 | ASO-000540-26 | ASO-002145 | TcCCTtaatttcAccCT | 136054 | 136070 | 3893 | 90 |
| 105 | ASO-000540-27 | ASO-002157 | TcCCTTaatttcaccCT | 136054 | 136070 | 3893 | 95 |
| 106 | ASO-000540-28 | ASO-002169 | TCcCTTaatttcaccCT | 136054 | 136070 | 3893 | 91 |
| 107 | ASO-000540-29 | ASO-002181 | TCCcttaatttcacCCT | 136054 | 136070 | 3893 | 92 |
| 108 | ASO-000540-3 | ASO-002154 | CCCttaatttcacCcTC | 136053 | 136069 | 3892 | 97 |
| 109 | ASO-000540-42 | ASO-002147 | CCCTtaatttcacccTCA | 136052 | 136069 | 3891 | 99 |
| 110 | ASO-000540-43 | ASO-002159 | CCCTtaatttcaccCtCA | 136052 | 136069 | 3891 | 97 |
| 111 | ASO-000540-44 | ASO-002171 | CCCTtaatttcaccCTCA | 136052 | 136069 | 3891 | 96 |
| 112 | ASO-000540-45 | ASO-002183 | CCCTtaatttcacCctCA | 136052 | 136069 | 3891 | 98 |
| 113 | ASO-000540-46 | ASO-002195 | CCCTtaatttcacCcTCA | 136052 | 136069 | 3891 | 91 |
| 114 | ASO-000540-47 | ASO-002196 | CCCTtaatttcaCcctCA | 136052 | 136069 | 3891 | 100 |
| 115 | ASO-000540-48 | ASO-002200 | CCCTtaatttcaCccTCA | 136052 | 136069 | 3891 | 95 |

Figure 6 cont.

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 116 | ASO-000540-49 | ASO-002204 | CCCTtaatttcaCcCtCA | 136052 | 136069 | 3891 | 82 |
| 117 | ASO-000540-5 | ASO-002178 | CCCttaatttcAcccTC | 136053 | 136069 | 3892 | 97 |
| 118 | ASO-000540-50 | ASO-002208 | CCCTtaatttcAccCtCA | 136052 | 136069 | 3891 | 93 |
| 119 | ASO-000540-51 | ASO-002212 | CCCTtaatttcAcCctCA | 136052 | 136069 | 3891 | 87 |
| 120 | ASO-000540-52 | ASO-002216 | TcCCTtaatttcacCcTC | 136053 | 136070 | 3892 | 97 |
| 121 | ASO-000540-53 | ASO-002220 | TCcCTtaatttcacccTC | 136053 | 136070 | 3892 | 99 |
| 122 | ASO-000540-54 | ASO-002224 | TCcCTTaatttcacCcTC | 136053 | 136070 | 3892 | 85 |
| 123 | ASO-000540-55 | ASO-002197 | TCCcttaatttcaccCTC | 136053 | 136070 | 3892 | 99 |
| 124 | ASO-000540-69 | ASO-002222 | TCCcTtaatttcacCctCA | 136052 | 136070 | 3891 | 97 |
| 125 | ASO-000540-70 | ASO-002226 | TCCCttaatttcaccCTCA | 136052 | 136070 | 3891 | 93 |
| 126 | ASO-000540-71 | ASO-002199 | TCCCttaatttcacCcTCA | 136052 | 136070 | 3891 | 83 |
| 127 | ASO-000540-72 | ASO-002203 | TCCCttaatttcacCCtCA | 136052 | 136070 | 3891 | 78 |
| 128 | ASO-000540-73 | ASO-002207 | TCCCttaatttcaCcCtCA | 136052 | 136070 | 3891 | 58 |
| 129 | ASO-000540-74 | ASO-002211 | TCCCttaatttcACcCtCA | 136052 | 136070 | 3891 | 26 |
| 130 | ASO-000540-75 | ASO-002215 | TCCCTtaatttcaccCTCA | 136052 | 136070 | 3891 | 84 |
| 131 | ASO-000540-76 | ASO-002219 | TCCCTtaatttcacCCtCA | 136052 | 136070 | 3891 | 44 |
| 132 | ASO-000540-77 | ASO-002223 | TCCCTtaatttcacCCTCA | 136052 | 136070 | 3891 | 30 |

Figure 6 cont.

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 133 | ASO-000540-8 | ASO-002119 | CCCtTaatttcaccCTC | 136053 | 136069 | 3892 | 98 |
| 134 | ASO-000540-9 | ASO-002131 | CCCtTaatttcacCcTC | 136053 | 136069 | 3892 | 96 |
| 135 | TBD-mm10 | ASO-002382 | CCttgATttcgccctCA | 136053 | 136069 | 3891 | 84 |
| 136 | TBD-mm11 | ASO-002299 | CCttgATttcaccctCT | 136052 | 136068 | 3891 | 98 |
| 137 | TBD-mm12 | ASO-002311 | CCttaGTttcaccctCG | 136054 | 136070 | 3891 | 98 |
| 138 | TBD-mm19 | ASO-002300 | CCCttgatttcaccctCA | 136052 | 136068 | 3891 | 50 |
| 139 | TBD-mm20 | ASO-002312 | CCCttaatttcaccctCG | 136054 | 136070 | 3891 | 50 |
| 140 | TBD-mm21 | ASO-002324 | CCCttagtttcaccctCA | 136052 | 136069 | 3891 | 50 |
| 141 | TBD-mm22 | ASO-002336 | CCCttgatttcgccctCA | 136052 | 136069 | 3891 | 57 |
| 142 | TBD-mm23 | ASO-002348 | CCCttgatttcaccctCG | 136053 | 136070 | 3891 | 52 |
| 143 | TBD-mm24 | ASO-002360 | CCCttgatttcaccctCT | 136052 | 136070 | 3891 | 52 |
| 144 | TBD-mm31 | ASO-002349 | TCcCTtgatttcacCctCA | 136053 | 136070 | 3891 | 97 |
| 145 | TBD-mm32 | ASO-002361 | TCcCTtaatttcacCctCG | 136052 | 136070 | 3891 | 98 |
| 146 | TBD-mm33 | ASO-002373 | ACcCTtaatttcacCctCA | 136053 | 136069 | 3891 | 100 |
| 147 | TBD-mm34 | ASO-002385 | TCcCTtgatttcgcCctCA | 136052 | 136068 | 3891 | 92 |
| 148 | TBD-mm35 | ASO-002302 | TCcCTtagtttcacCctCG | 136054 | 136070 | 3891 | 50 |
| 149 | TBD-mm36 | ASO-002314 | ACcCTtgatttcacCctCA | 136054 | 136070 | 3891 | 95 |
| 150 | TBD-mm7 | ASO-002346 | CCttgATttcaccctCA | 136053 | 136070 | 3891 | 98 |
| 151 | TBD-mm8 | ASO-002358 | CCttaGTttcaccctCA | 136053 | 136069 | 3891 | 99 |
| 152 | TBD-mm9 | ASO-002370 | CCttaATttcaccctCG | 136052 | 136070 | 3891 | 100 |
| 153 | ASO-000540 | ASO-000540 | CCTtaatttcaccCTC | 136053 | 136068 | 3892 | 99 |
| 154 | ASO-000555 | ASO-000555 | CTTaatttcaccCTC | 136053 | 136067 | 3892 | 98 |

Figure 6 cont.

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 155 | ASO-000579 | ASO-000579 | TTAatttcaccCTC | 136053 | 136066 | 3892 | 94 |
| 156 | ASO-000540-1 | ASO-002130 | CCCttaatttcacccTC | 136053 | 136069 | 3892 | 97 |
| 157 | ASO-000540-10 | ASO-002143 | CCCTtaatttcaccCTC | 136053 | 136069 | 3892 | 98 |
| 158 | ASO-000540-11 | ASO-002155 | CCCTtaatttcacCcTC | 136053 | 136069 | 3892 | 96 |
| 159 | ASO-000540-12 | ASO-002167 | CCCTtaatttcacCCTC | 136053 | 136069 | 3892 | 88 |
| 160 | ASO-000540-13 | ASO-002179 | CCCTtaatttcaCccTC | 136053 | 136069 | 3892 | 95 |
| 161 | ASO-000540-14 | ASO-002191 | CCttaATttcaccctCA | 136052 | 136068 | 3891 | 99 |
| 162 | ASO-000540-15 | ASO-002108 | CCTtaatttcacccTCA | 136052 | 136068 | 3891 | 98 |
| 163 | ASO-000540-16 | ASO-002120 | CCTtaaTttcaccctCA | 136052 | 136068 | 3891 | 98 |
| 164 | ASO-000540-17 | ASO-002132 | CCTtaAtttcaccctCA | 136052 | 136068 | 3891 | 98 |
| 165 | ASO-000540-18 | ASO-002144 | CCTtaATttcaccctCA | 136052 | 136068 | 3891 | 99 |
| 166 | ASO-000540-19 | ASO-002156 | CCTtaATttcacccTCA | 136052 | 136068 | 3891 | 99 |
| 167 | ASO-000540-2 | ASO-002142 | CCCttaatttcaccCTC | 136053 | 136069 | 3892 | 98 |
| 168 | ASO-000540-20 | ASO-002168 | CCTTaatttcaccCtCA | 136052 | 136068 | 3891 | 99 |
| 169 | ASO-000540-56 | ASO-002201 | TCCcttaatttcacCcTC | 136053 | 136070 | 3892 | 98 |
| 170 | ASO-000540-57 | ASO-002205 | TCCcTtaatttcacccTC | 136053 | 136070 | 3892 | 98 |
| 171 | ASO-000540-58 | ASO-002209 | TCCcTtaatttcacCcTC | 136053 | 136070 | 3892 | 93 |
| 172 | ASO-000540-59 | ASO-002213 | TCCcTtaatttcaCccTC | 136053 | 136070 | 3892 | 84 |

Figure 6 cont.

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 173 | ASO-000540-6 | ASO-002190 | CCCttaatttcAcCcTC | 136053 | 136069 | 3892 | 80 |
| 174 | ASO-000540-60 | ASO-002217 | TCCcTtaatttcAcCcTC | 136053 | 136070 | 3892 | 3 |
| 175 | ASO-000540-61 | ASO-002221 | TCCCttaatttcacCCTC | 136053 | 136070 | 3892 | 69 |
| 176 | ASO-000540-62 | ASO-002225 | TCCCttaatttcaCcCTC | 136053 | 136070 | 3892 | 36 |
| 177 | ASO-000540-63 | ASO-002198 | TCCCttaatttcaCCcTC | 136053 | 136070 | 3892 | 48 |
| 178 | ASO-000540-64 | ASO-002202 | TCCCttaatttcAccCTC | 136053 | 136070 | 3892 | 61 |
| 179 | ASO-000540-65 | ASO-002206 | TCCCttaatttCaccCTC | 136053 | 136070 | 3892 | 69 |
| 180 | ASO-000540-66 | ASO-002210 | TCcCTtaatttcacCctCA | 136052 | 136070 | 3891 | 99 |
| 181 | ASO-000540-67 | ASO-002214 | TCCcttaatttcacccTCA | 136052 | 136070 | 3891 | 99 |
| 182 | ASO-000540-68 | ASO-002218 | TCCcTtaatttcaccCtCA | 136052 | 136070 | 3891 | 99 |
| 183 | ASO-000540-mm1 | ASO-002297 | CCTtgatttcaccCTC | 136053 | 136068 | 3892 | 97 |
| 184 | ASO-000540-mm2 | ASO-002309 | CCTtaatttcgccCTC | 136053 | 136068 | 3892 | 87 |
| 185 | ASO-000540-mm3 | ASO-002321 | CCTtagtttcaccCTC | 136053 | 136068 | 3892 | 91 |
| 186 | ASO-000540-mm4 | ASO-002333 | CCTtgatttcgccCTC | 136053 | 136068 | 3892 | 89 |
| 187 | ASO-000540-mm5 | ASO-002345 | CCTtggtttcaccCTC | 136053 | 136068 | 3892 | 96 |
| 188 | ASO-000540-mm6 | ASO-002357 | CCTtagtttcgccCTC | 136053 | 136068 | 3892 | 13 |
| 189 | TBD-mm1 | ASO-002369 | CCCttgatttcacccTC | 136052 | 136070 | 3892 | 95 |
| 190 | TBD-mm2 | ASO-002381 | CCCttagtttcacccTC | 136053 | 136069 | 3892 | 98 |

Figure 6 cont.

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 191 | TBD-mm25 | ASO-002372 | TcCCTtgatttcacCcTC | 136052 | 136070 | 3892 | 51 |
| 192 | TBD-mm26 | ASO-002384 | TcCCTtaatttcgcCcTC | 136052 | 136068 | 3892 | 61 |
| 193 | TBD-mm27 | ASO-002301 | TcCCTtagtttcacCcTC | 136052 | 136068 | 3892 | 52 |
| 194 | TBD-mm28 | ASO-002313 | TcCCTtgatttcgcCcTC | 136054 | 136070 | 3892 | 51 |
| 195 | TBD-mm29 | ASO-002325 | TcCCTtagtttcgcCcTC | 136052 | 136069 | 3892 | 23 |
| 196 | TBD-mm3 | ASO-002298 | CCCttaatttcgcccTC | 136053 | 136069 | 3892 | 97 |
| 197 | TBD-mm30 | ASO-002337 | AcCCTtgatttcacCcTC | 136053 | 136070 | 3892 | 100 |
| 198 | TBD-mm4 | ASO-002310 | CCCttgatttcgcccTC | 136054 | 136070 | 3892 | 71 |
| 199 | TBD-mm5 | ASO-002322 | CCCttggtttcacccTC | 136052 | 136069 | 3892 | 91 |
| 200 | TBD-mm6 | ASO-002334 | CCCttagtttcgcccTC | 136052 | 136069 | 3892 | 51 |
| 201 | ASO-000662 | ASO-000662 | CCCttaatttcacCCT | 136054 | 136069 | 3893 | 96 |
| 202 | ASO-000566 | ASO-000566 | CCTtaatttcacCCT | 136054 | 136068 | 3893 | 94 |
| 203 | ASO-000540-30 | ASO-002193 | TCCcTtaatttcaccCT | 136054 | 136070 | 3893 | 89 |
| 204 | ASO-000540-31 | ASO-002110 | TCCcTtaatttcAccCT | 136054 | 136070 | 3893 | 74 |
| 205 | ASO-000540-32 | ASO-002384 | TCCcTTaatttcaccCT | 136054 | 136070 | 3893 | 84 |
| 206 | ASO-000540-33 | ASO-002301 | TCCCttaatttcacCCT | 136054 | 136070 | 3893 | 75 |
| 207 | ASO-000540-34 | ASO-002313 | TCCCttaatttcaCcCT | 136054 | 136070 | 3893 | 60 |
| 208 | ASO-000540-35 | ASO-002325 | TCCCttaatttcaCCCT | 136054 | 136070 | 3893 | 33 |
| 209 | ASO-000540-36 | ASO-002298 | TCCCttaatttCaccCT | 136054 | 136070 | 3893 | 66 |
| 210 | ASO-000540-37 | ASO-002337 | CCCttaatttcaccctCA | 136052 | 136069 | 3891 | 98 |

Figure 6 cont.

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 211 | ASO-000540-38 | ASO-002310 | CCCttaatttcacccTCA | 136052 | 136069 | 3891 | 98 |
| 212 | ASO-000540-39 | ASO-002322 | CCCttaatttcacCctCA | 136052 | 136069 | 3891 | 98 |
| 213 | ASO-000540-4 | ASO-002334 | CCCttaatttcaCccTC | 136053 | 136069 | 3892 | 96 |
| 214 | ASO-000540-40 | ASO-000662 | CCCttaatttcaCcctCA | 136052 | 136069 | 3891 | 99 |
| 215 | ASO-000540-41 | ASO-000566 | CCCttaatttcAcCctCA | 136052 | 136069 | 3891 | 96 |
| 216 | TBD-mm13 | ASO-002193 | TcCCtTgatttcaccCT | 136053 | 136069 | 3893 | 95 |
| 217 | TBD-mm14 | ASO-002110 | TcCCtTaatttcaccCA | 136052 | 136069 | 3893 | 99 |
| 218 | TBD-mm15 | ASO-002347 | TcCCtTaatttcgccCT | 136053 | 136070 | 3893 | 91 |
| 219 | TBD-mm16 | ASO-002359 | TcCCtTgatttcaccCA | 136053 | 136070 | 3893 | 97 |
| 220 | TBD-mm17 | ASO-002371 | TcCCtTgatttcaccCG | 136052 | 136070 | 3893 | 95 |
| 221 | TBD-mm18 | ASO-002383 | TcCCtTagtttcgccCT | 136052 | 136068 | 3893 | 65 |
| 222 | ASO-000628 | ASO-000628 | CCTtaatttcaCCC | 136055 | 136068 | 3894 | 98 |
| 223 | ASO-000642 | ASO-000642 | CCCttaatttcaCCC | 136055 | 136069 | 3894 | 98 |
| 224 | ASO-000274 | ASO-000274 | TCCcttaatttcaCCC | 136055 | 136070 | 3894 | 99 |
| 225 | ASO-000339 | ASO-000339 | CCttaatttcaCCC | 136055 | 136068 | 3894 | 100 |
| 226 | ASO-000536 | ASO-000536 | TTCccttaatttcACC | 136056 | 136071 | 3895 | 91 |
| 227 | ASO-000603 | ASO-000603 | TCCcttaatttcACC | 136056 | 136070 | 3895 | 87 |
| 228 | ASO-000666 | ASO-000666 | TCCcttaatttCAC | 136057 | 136070 | 3896 | 63 |
| 229 | ASO-000272 | ASO-000272 | AGAgtgagaggctGGG | 136099 | 136114 | 3938 | 100 |
| 230 | ASO-000255 | ASO-000255 | TGGatgagtggaaCTG | 136115 | 136130 | 3954 | 99 |
| 231 | ASO-000336 | ASO-000336 | GGAtgagtggaACT | 136116 | 136129 | 3955 | 98 |
| 232 | ASO-000206 | ASO-000206 | GTTggatgagtgGAA | 136118 | 136132 | 3957 | 99 |
| 233 | ASO-000271 | ASO-000271 | AGTtggatgagtGGA | 136119 | 136133 | 3958 | 100 |
| 234 | ASO-000340 | ASO-000340 | GTTggatgagtGGA | 136119 | 136132 | 3958 | 100 |

Figure 6 cont.

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 235 | ASO-000229 | ASO-000229 | CAGggaaccgaatCAG | 136160 | 136175 | 3999 | 100 |
| 236 | ASO-000273 | ASO-000273 | GCCctggctcacaTCT | 136193 | 136208 | 4032 | 95 |
| 237 | ASO-000264 | ASO-000264 | ACAaggcagaaacACC | 136229 | 136244 | 4068 | 100 |
| 238 | ASO-000341 | ASO-000341 | TGTcaacaaggCAG | 136236 | 136249 | 4075 | 56 |
| 239 | ASO-000198 | ASO-000198 | TGCcctgggtgccTTG | 136355 | 136370 | 4194 | 97 |
| 240 | ASO-000210 | ASO-000210 | AGCgggactgtggGCC | 136371 | 136386 | 4210 | 92 |
| 241 | ASO-000342 | ASO-000342 | GGgacagcgggACT | 136378 | 136391 | 4217 | |
| 242 | ASO-000333 | ASO-000333 | GCGggctgggctgTCT | 136427 | 136442 | 4266 | 99 |
| 243 | ASO-000199 | ASO-000199 | CAGaacagacagcATG | 136541 | 136556 | 4380 | 99 |
| 244 | ASO-000280 | ASO-000280 | TCTatgtatatgtTCA | 136567 | 136582 | 4406 | 100 |
| 245 | ASO-000211 | ASO-000211 | ATCtatgtatatgTTC | 136568 | 136583 | 4407 | 99 |
| 246 | ASO-000347 | ASO-000347 | CATctatgtataTGT | 136570 | 136584 | 4409 | 42 |
| 247 | ASO-000352 | ASO-000352 | ACAtctatgtataTGT | 136570 | 136585 | 4409 | 4 |
| 248 | ASO-000232 | ASO-000232 | CAAcagggtgcagATG | 136600 | 136615 | 4439 | 98 |
| 249 | ASO-000257 | ASO-000257 | AGCataaacagacAAA | 136629 | 136644 | 4468 | 99 |
| 250 | ASO-000388 | ASO-000388 | ATAgtcactctggTGA | 136650 | 136665 | 4489 | 99 |
| 251 | ASO-000390 | ASO-000390 | TAGtcactctggTGA | 136650 | 136664 | 4489 | 97 |
| 252 | ASO-000413 | ASO-000413 | AGTcactctggTGA | 136650 | 136663 | 4489 | 37 |
| 253 | ASO-000405 | ASO-000405 | CATagtcactctgGTG | 136651 | 136666 | 4490 | 100 |
| 254 | ASO-000430 | ASO-000430 | TAGtcactctgGTG | 136651 | 136664 | 4490 | 100 |
| 255 | ASO-000447 | ASO-000447 | TCAtagtcactctGGT | 136652 | 136667 | 4491 | 100 |
| 256 | ASO-000396 | ASO-000396 | TACatgcgtccTTT | 136693 | 136706 | 4532 | 100 |
| 257 | ASO-000395 | ASO-000395 | GATacatgcgtccTTT | 136693 | 136708 | 4532 | 99 |
| 258 | ASO-000394 | ASO-000394 | AAGatacatgcgtCCT | 136695 | 136710 | 4534 | 100 |
| 259 | ASO-000421 | ASO-000421 | TTCaagatacatgCGT | 136698 | 136713 | 4537 | 100 |
| 260 | ASO-000400 | ASO-000400 | ATTtcaagatacaTGC | 136700 | 136715 | 4539 | 99 |
| 261 | ASO-000248 | ASO-000248 | GCAtttcaagataCAT | 136702 | 136717 | 4541 | 100 |
| 262 | ASO-000451 | ASO-000451 | AAGcatttcaagaTAC | 136704 | 136719 | 4543 | 99 |
| 263 | ASO-000707 | ASO-000707 | ACAagcatttcaaGAT | 136706 | 136721 | 4545 | 100 |

Figure 6 cont.

| SEQ ID NO: | Oligomer Name | ASO Number | ASO Sequence | premRNA start NG_0073 98 | premRN A end NG_0073 98 | mRNA start NM_016 835 | Tau/Tubu lin % inhibition |
|---|---|---|---|---|---|---|---|
| 264 | ASO-000619 | ASO-000619 | TTAcaagcatttcAAG | 136708 | 136723 | 4547 | 88 |
| 265 | ASO-000671 | ASO-000671 | AACctctttacaaGCA | 136715 | 136730 | 4554 | |
| 266 | ASO-000221 | ASO-000221 | GTTagaaacctctTTA | 136721 | 136736 | 4560 | 100 |
| 267 | ASO-000298 | ASO-000298 | CCAcacaggccacACG | 136776 | 136791 | 4615 | 98 |
| 268 | ASO-000311 | ASO-000311 | GTCtctgttgggtCCC | 136842 | 136857 | 4681 | 97 |
| 269 | ASO-000290 | ASO-000290 | TGAacggcctcctTAG | 136871 | 136886 | 4710 | 99 |
| 270 | ASO-000437 | ASO-000437 | CTGtgcttcaggcCTT | 136896 | 136911 | 4735 | 100 |
| 271 | ASO-000446 | ASO-000446 | TCCtgtgcttcagGCC | 136898 | 136913 | 4737 | 98 |
| 272 | ASO-000685 | ASO-000685 | AATcctgtgcttcAGG | 136900 | 136915 | 4739 | 65 |
| 273 | ASO-000410 | ASO-000410 | TCCtgtgcttcAGG | 136900 | 136913 | 4739 | 23 |
| 274 | ASO-000604 | ASO-000604 | AATcctgtgcttCAG | 136901 | 136915 | 4740 | 94 |
| 275 | ASO-000490 | ASO-000490 | TAAtcctgtgcttCAG | 136901 | 136916 | 4740 | 89 |
| 276 | ASO-000529 | ASO-000529 | AATcctgtgctTCA | 136902 | 136915 | 4741 | 100 |
| 277 | ASO-000532 | ASO-000532 | CTAatcctgtgctTCA | 136902 | 136917 | 4741 | 99 |
| 278 | ASO-000508 | ASO-000508 | TAAtcctgtgctTCA | 136902 | 136916 | 4741 | 95 |
| 279 | ASO-000219 | ASO-000219 | CCTaatcctgtgcTTC | 136903 | 136918 | 4742 | 100 |
| 280 | ASO-000656 | ASO-000656 | TAAtcctgtgcTTC | 136903 | 136916 | 4742 | 99 |
| 281 | ASO-000522 | ASO-000522 | CTAatcctgtgcTTC | 136903 | 136917 | 4742 | 98 |
| 282 | ASO-000513 | ASO-000513 | CCTaatcctgtgCTT | 136904 | 136918 | 4743 | 97 |
| 283 | ASO-000640 | ASO-000640 | TCCtaatcctgtgCTT | 136904 | 136919 | 4743 | 93 |
| 284 | ASO-000661 | ASO-000661 | CTAatcctgtgCTT | 136904 | 136917 | 4743 | 85 |
| 285 | ASO-000478 | ASO-000478 | GTCctaatcctgtGCT | 136905 | 136920 | 4744 | 96 |
| 286 | ASO-000500 | ASO-000500 | TCCtaatcctgtGCT | 136905 | 136919 | 4744 | 94 |
| 287 | ASO-000601 | ASO-000601 | CCTaatcctgtGCT | 136905 | 136918 | 4744 | 93 |
| 288 | ASO-000643 | ASO-000643 | AGTcctaatcctgTGC | 136906 | 136921 | 4745 | 99 |
| 289 | ASO-000600 | ASO-000600 | GTCctaatcctgTGC | 136906 | 136920 | 4745 | 98 |
| 290 | ASO-000525 | ASO-000525 | TCCtaatcctgTGC | 136906 | 136919 | 4745 | 90 |
| 291 | ASO-000453 | ASO-000453 | TCAgtcctaatccTGT | 136908 | 136923 | 4747 | 60 |
| 292 | ASO-000553 | ASO-000553 | CTTcagtcctaatCCT | 136910 | 136925 | 4749 | 95 |

Figure 6 cont.

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 293 | ASO-000622 | ASO-000622 | GCTtcagtcctaATC | 136912 | 136926 | 4751 | 100 |
| 294 | ASO-000325 | ASO-000325 | CTGacacagggagCCC | 136956 | 136971 | 4795 | 99 |
| 295 | ASO-000215 | ASO-000215 | GCCagaccagccaCAA | 136987 | 137002 | 4826 | 97 |
| 296 | ASO-000482 | ASO-000482 | CAGgagttgtaAGC | 137065 | 137078 | 4904 | 60 |
| 297 | ASO-000337 | ASO-000337 | TGCaggagttgtaAGC | 137065 | 137080 | 4904 | 88 |
| 298 | ASO-000480 | ASO-000480 | ATGcaggagttgtAAG | 137066 | 137081 | 4905 | 57 |
| 299 | ASO-000644 | ASO-000644 | GATgcaggagttgTAA | 137067 | 137082 | 4906 | 97 |
| 300 | ASO-000695 | ASO-000695 | TGCaggagttgTAA | 137067 | 137080 | 4906 | 41 |
| 301 | ASO-000455 | ASO-000455 | TGAtgcaggagttGTA | 137068 | 137083 | 4907 | 94 |
| 302 | ASO-000531 | ASO-000531 | GTGatgcaggagtTGT | 137069 | 137084 | 4908 | 100 |
| 303 | ASO-000651 | ASO-000651 | TGTgatgcaggagTTG | 137070 | 137085 | 4909 | 96 |
| 304 | ASO-000007 | ASO-000007 | TGTgatgcaggaGTT | 137071 | 137085 | 4910 | 92 |
| 305 | ASO-000419 | ASO-000419 | GTGatgcaggaGTT | 137071 | 137084 | 4910 | 100 |
| 306 | ASO-000730 | ASO-000730 | TGTgatgcaggaGTT | 137071 | 137085 | 4910 | 92 |
| 307 | ASO-000728 | ASO-000728 | TGTgatgcaggaGTT | 137071 | 137085 | 4910 | 91 |
| 308 | ASO-000729 | ASO-000729 | TGTgatgcaggaGTT | 137071 | 137085 | 4910 | 12 |
| 309 | ASO-000727 | ASO-000727 | TGTgatgcaggaGTT | 137071 | 137085 | 4910 | 1 |
| 310 | ASO-000715 | ASO-000715 | TGtgatgcaggagTT | 137071 | 137085 | 4910 | 2 |
| 311 | ASO-000716 | ASO-000716 | GAtgcaggagTT | 137071 | 137082 | 4910 | 97 |
| 312 | ASO-000721 | ASO-000721 | TGTgatgcaggaGTT | 137071 | 137085 | 4910 | 99 |
| 313 | ASO-000722 | ASO-000722 | TGTgatgcaggaGTT | 137071 | 137085 | 4910 | 99 |
| 314 | ASO-000723 | ASO-000723 | TGTgatgcaggaGTT | 137071 | 137085 | 4910 | |
| 315 | ASO-000724 | ASO-000724 | TGTgatgcaggaGTT | 137071 | 137085 | 4910 | 99 |
| 316 | ASO-000725 | ASO-000725 | TGTgatgcaggaGTT | 137071 | 137085 | 4910 | 100 |
| 317 | ASO-000726 | ASO-000726 | TGTgatgcaggaGTT | 137071 | 137085 | 4910 | 12 |
| 318 | ASO-000731 | ASO-000731 | TGTgatgcaggaGTT | 137071 | 137085 | 4910 | |
| 319 | ASO-000718 | ASO-000718 | TGatgcaggaGT | 137072 | 137083 | 4911 | 100 |
| 320 | ASO-000445 | ASO-000445 | TTGtgatgcagGAG | 137073 | 137086 | 4912 | 100 |
| 321 | ASO-000436 | ASO-000436 | CTTgtgatgcagGAG | 137073 | 137087 | 4912 | 98 |

Figure 6 cont.

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 322 | ASO-000717 | ASO-000717 | GTgatgcaggAG | 137073 | 137084 | 4912 | 99 |
| 323 | ASO-000570 | ASO-000570 | TTCttgtgatgcaGGA | 137074 | 137089 | 4913 | 91 |
| 324 | ASO-000408 | ASO-000408 | TCTtgtgatgcaGGA | 137074 | 137088 | 4913 | 90 |
| 325 | ASO-000401 | ASO-000401 | CTTgtgatgcaGGA | 137074 | 137087 | 4913 | 88 |
| 326 | ASO-000719 | ASO-000719 | TGtgatgcagGA | 137074 | 137085 | 4913 | 100 |
| 327 | ASO-000313 | ASO-000313 | CAGagggcgagctTGG | 137173 | 137188 | 5012 | 100 |
| 328 | ASO-000331 | ASO-000331 | AATccctgctgtgGTC | 137223 | 137238 | 5062 | 100 |
| 329 | ASO-000251 | ASO-000251 | AGGcaattcatCCC | 137239 | 137252 | 5078 | 97 |
| 330 | ASO-000574 | ASO-000574 | TGGtcaaggctttGGG | 137326 | 137341 | 5165 | 99 |
| 331 | ASO-000218 | ASO-000218 | TCTggtcaaggctTTG | 137328 | 137343 | 5167 | 99 |
| 332 | ASO-000634 | ASO-000634 | CTCtggtcaaggcTTT | 137329 | 137344 | 5168 | 99 |
| 333 | ASO-000497 | ASO-000497 | GGTgctctggtcaAGG | 137333 | 137348 | 5172 | 99 |
| 334 | ASO-000569 | ASO-000569 | GGTgctctggtCAA | 137335 | 137348 | 5174 | 100 |
| 335 | ASO-000565 | ASO-000565 | GCTgaggtgctctGGT | 137338 | 137353 | 5177 | 99 |
| 336 | ASO-000296 | ASO-000296 | AGTttgtgcaaggTCA | 137358 | 137373 | 5197 | 98 |
| 337 | ASO-000663 | ASO-000663 | GAGtttgtgcaagGTC | 137359 | 137374 | 5198 | 100 |
| 338 | ASO-000670 | ASO-000670 | AGTttgtgcaagGTC | 137359 | 137373 | 5198 | 100 |
| 339 | ASO-000261 | ASO-000261 | GGAgtttgtgcaaGGT | 137360 | 137375 | 5199 | 100 |
| 340 | ASO-000262 | ASO-000262 | GGAgtttgtgcaAGG | 137361 | 137375 | 5200 | 99 |
| 341 | ASO-000275 | ASO-000275 | TGGagtttgtgcaAGG | 137361 | 137376 | 5200 | 7 |
| 342 | ASO-000247 | ASO-000247 | ATGgagtttgtgcAAG | 137362 | 137377 | 5201 | 98 |
| 343 | ASO-000303 | ASO-000303 | TGGagtttgtgcAAG | 137362 | 137376 | 5201 | 99 |
| 344 | ASO-000299 | ASO-000299 | ATGgagtttgtgCAA | 137363 | 137377 | 5202 | 96 |
| 345 | ASO-000270 | ASO-000270 | AGAtggagtttgtGCA | 137364 | 137379 | 5203 | 100 |
| 346 | ASO-000297 | ASO-000297 | AGCagatggagttTGT | 137367 | 137382 | 5206 | 96 |
| 347 | ASO-000259 | ASO-000259 | TTCtttaggcagcAAT | 137416 | 137431 | 5255 | |
| 348 | ASO-000220 | ASO-000220 | TGTacccaaaccaGAA | 137462 | 137477 | 5301 | 98 |
| 349 | ASO-000278 | ASO-000278 | GTTgcctttaacTGT | 137475 | 137489 | 5314 | 99 |
| 350 | ASO-000334 | ASO-000334 | GCCctggatttctACT | 137505 | 137520 | 5344 | 61 |

Figure 6 cont.

| SEQ ID NO: | Oligomer Name | ASO Number | ASO Sequence | premRNA start NG_0073 98 | premRN A end NG_0073 98 | mRNA start NM_016 835 | Tau/Tubu lin % inhibition |
|---|---|---|---|---|---|---|---|
| 351 | ASO-000241 | ASO-000241 | TGGtggagagttcTGG | 137583 | 137598 | 5422 | 99 |
| 352 | ASO-000289 | ASO-000289 | TTCtcagatccctTCA | 137643 | 137658 | 5482 | 99 |
| 353 | ASO-000233 | ASO-000233 | CTCtaaccaccacCAA | 137682 | 137697 | 5521 | 100 |
| 354 | ASO-000201 | ASO-000201 | AGGgcacaagaacTTC | 137765 | 137780 | 5604 | 90 |
| 355 | ASO-000645 | ASO-000645 | ATCttaggctggCCC | 137851 | 137865 | 5689 | 94 |
| 356 | ASO-000546 | ASO-000546 | GATcttaggctggCCC | 137851 | 137866 | 5689 | 92 |
| 357 | ASO-000692 | ASO-000692 | TGAtcttaggctgGCC | 137852 | 137867 | 5690 | 99 |
| 358 | ASO-000511 | ASO-000511 | GATcttaggctgGCC | 137852 | 137866 | 5690 | 76 |
| 359 | ASO-000538 | ASO-000538 | TGAtcttaggctGGC | 137853 | 137867 | 5691 | 99 |
| 360 | ASO-000214 | ASO-000214 | ATGatcttaggctGGC | 137853 | 137868 | 5691 | 99 |
| 361 | ASO-000653 | ASO-000653 | GATcttaggctGGC | 137853 | 137866 | 5691 | 98 |
| 362 | ASO-000615 | ASO-000615 | CATgatcttaggcTGG | 137854 | 137869 | 5692 | 89 |
| 363 | ASO-000524 | ASO-000524 | CCAtgatcttaggCTG | 137855 | 137870 | 5693 | 98 |
| 364 | ASO-000492 | ASO-000492 | CATgatcttaggCTG | 137855 | 137869 | 5693 | 95 |
| 365 | ASO-000468 | ASO-000468 | ACCatgatcttagGCT | 137856 | 137871 | 5694 | 99 |
| 366 | ASO-000698 | ASO-000698 | CCAtgatcttagGCT | 137856 | 137870 | 5694 | 100 |
| 367 | ASO-000593 | ASO-000593 | CATgatcttagGCT | 137856 | 137869 | 5694 | 55 |
| 368 | ASO-000519 | ASO-000519 | AAAccatgatcttAGG | 137858 | 137873 | 5696 | 96 |
| 369 | ASO-000582 | ASO-000582 | CTAaaccatgatcTTA | 137860 | 137875 | 5698 | 74 |
| 370 | ASO-000635 | ASO-000635 | CCCtaaaccatgaTCT | 137862 | 137877 | 5700 | 98 |
| 371 | ASO-000471 | ASO-000471 | CACcctaaaccatGAT | 137864 | 137879 | 5702 | 96 |
| 372 | ASO-000701 | ASO-000701 | ATCaccctaaaccATG | 137866 | 137881 | 5704 | 100 |
| 373 | ASO-000533 | ASO-000533 | TGAtcaccctaaaCCA | 137868 | 137883 | 5706 | 96 |
| 374 | ASO-000323 | ASO-000323 | GAGgagtgcccagCCC | 137947 | 137962 | 5785 | |
| 375 | ASO-000329 | ASO-000329 | TGCaggtgggagaAGT | 137973 | 137988 | 5811 | |
| 376 | ASO-000194 | ASO-000194 | TATctagcccaCCC | 138003 | 138016 | 5841 | 100 |
| 377 | ASO-000192 | ASO-000192 | CTAtctagcccaCCC | 138003 | 138017 | 5841 | 99 |
| 378 | ASO-000343 | ASO-000343 | TAtcctatctaGCC | 138008 | 138021 | 5846 | |
| 379 | ASO-000212 | ASO-000212 | TTGataaagtgaGTC | 138050 | 138064 | 5888 | |

Figure 6 cont.

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 380 | ASO-000230 | ASO-000230 | ATTgataaagtgAGT | 138051 | 138065 | 5889 | 99 |
| 381 | ASO-000188 | ASO-000188 | AACtattgataaAGT | 138055 | 138069 | 5893 | 4 |
| 382 | ASO-000415 | ASO-000415 | GAActattgatAAA | 138057 | 138070 | 5895 | 21 |
| 383 | ASO-000448 | ASO-000448 | GGAactattgaTAA | 138058 | 138071 | 5896 | 100 |
| 384 | ASO-000190 | ASO-000190 | AAAtggaactattGAT | 138060 | 138075 | 5898 | |
| 385 | ASO-000191 | ASO-000191 | AATggaactatTGA | 138061 | 138074 | 5899 | 97 |
| 386 | ASO-000348 | ASO-000348 | TCAAtttaaatGGAA | 138068 | 138082 | 5906 | |
| 387 | ASO-000349 | ASO-000349 | GTcaatttaaaTGGA | 138069 | 138083 | 5907 | |
| 388 | ASO-000200 | ASO-000200 | GGAtacagtctcaCCA | 138089 | 138104 | 5927 | 100 |
| 389 | ASO-000630 | ASO-000630 | GCAaacaggatacAGT | 138096 | 138111 | 5934 | 100 |
| 390 | ASO-000614 | ASO-000614 | CAAacaggatacAGT | 138096 | 138110 | 5934 | 99 |
| 391 | ASO-000563 | ASO-000563 | AAAcaggatacAGT | 138096 | 138109 | 5934 | 90 |
| 392 | ASO-000527 | ASO-000527 | TAGcaaacaggatACA | 138098 | 138113 | 5936 | 99 |
| 393 | ASO-000617 | ASO-000617 | ATAgcaaacaggaTAC | 138099 | 138114 | 5937 | 99 |
| 394 | ASO-000539 | ASO-000539 | AATagcaaacaggATA | 138100 | 138115 | 5938 | 99 |
| 395 | ASO-000691 | ASO-000691 | CAAtagcaaacagGAT | 138101 | 138116 | 5939 | 99 |
| 396 | ASO-000589 | ASO-000589 | AATagcaaacagGAT | 138101 | 138115 | 5939 | 99 |
| 397 | ASO-000509 | ASO-000509 | GCAatagcaaacaGGA | 138102 | 138117 | 5940 | |
| 398 | ASO-000674 | ASO-000674 | CAAtagcaaacaGGA | 138102 | 138116 | 5940 | |
| 399 | ASO-000488 | ASO-000488 | GCAatagcaaacAGG | 138103 | 138117 | 5941 | 100 |
| 400 | ASO-000507 | ASO-000507 | AGCaatagcaaacAGG | 138103 | 138118 | 5941 | 99 |
| 401 | ASO-000521 | ASO-000521 | AGCaatagcaaaCAG | 138104 | 138118 | 5942 | 99 |
| 402 | ASO-000288 | ASO-000288 | AAGcaatagcaaaCAG | 138104 | 138119 | 5942 | |
| 403 | ASO-000552 | ASO-000552 | AAGcaatagcaaACA | 138105 | 138119 | 5943 | 98 |
| 404 | ASO-000250 | ASO-000250 | CAAatgtggttgaAAT | 138223 | 138238 | 6061 | |
| 405 | ASO-000294 | ASO-000294 | GCAaatgtggttgAAA | 138224 | 138239 | 6062 | |
| 406 | ASO-000318 | ASO-000318 | TAGcaaatgtggtTGA | 138226 | 138241 | 6064 | |
| 407 | ASO-000308 | ASO-000308 | CCCaagggcctctAAC | 138263 | 138278 | 6101 | |
| 408 | ASO-000254 | ASO-000254 | AAAgcaaccagatGTC | 138361 | 138376 | 6199 | |

Figure 6 cont.

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 409 | ASO-000545 | ASO-000545 | AAGagggcagcagGCC | 138377 | 138392 | 6215 | 92 |
| 410 | ASO-000476 | ASO-000476 | GAAagagggcagcAGG | 138379 | 138394 | 6217 | 100 |
| 411 | ASO-000620 | ASO-000620 | CTGaaagagggcaGCA | 138381 | 138396 | 6219 | 63 |
| 412 | ASO-000477 | ASO-000477 | CCCtgaaagagggCAG | 138383 | 138398 | 6221 | 39 |
| 413 | ASO-000562 | ASO-000562 | TGAttgtgggcttAGG | 138401 | 138416 | 6239 | 100 |
| 414 | ASO-000547 | ASO-000547 | ATGattgtgggctTAG | 138402 | 138417 | 6240 | 100 |
| 415 | ASO-000696 | ASO-000696 | TGAttgtgggctTAG | 138402 | 138416 | 6240 | 99 |
| 416 | ASO-000279 | ASO-000279 | GATtgtgggctTAG | 138402 | 138415 | 6240 | |
| 417 | ASO-000543 | ASO-000543 | CATgattgtgggcTTA | 138403 | 138418 | 6241 | 100 |
| 418 | ASO-000626 | ASO-000626 | TGAttgtgggcTTA | 138403 | 138416 | 6241 | 100 |
| 419 | ASO-000650 | ASO-000650 | ATGattgtgggcTTA | 138403 | 138417 | 6241 | 100 |
| 420 | ASO-000599 | ASO-000599 | CATgattgtgggCTT | 138404 | 138418 | 6242 | 98 |
| 421 | ASO-000542 | ASO-000542 | GCAtgattgtgggCTT | 138404 | 138419 | 6242 | 96 |
| 422 | ASO-000463 | ASO-000463 | GGCatgattgtggGCT | 138405 | 138420 | 6243 | 79 |
| 423 | ASO-000605 | ASO-000605 | GCAtgattgtggGCT | 138405 | 138419 | 6243 | 61 |
| 424 | ASO-000479 | ASO-000479 | CATgattgtggGCT | 138405 | 138418 | 6243 | |
| 425 | ASO-000474 | ASO-000474 | GCAtgattgtgGGC | 138406 | 138419 | 6244 | 99 |
| 426 | ASO-000675 | ASO-000675 | GGCatgattgtgGGC | 138406 | 138420 | 6244 | 95 |
| 427 | ASO-000537 | ASO-000537 | AGGcatgattgtgGGC | 138406 | 138421 | 6244 | 89 |
| 428 | ASO-000287 | ASO-000287 | AGGgaggcatgatTGT | 138410 | 138425 | 6248 | |
| 429 | ASO-000292 | ASO-000292 | GGGaggcatgatTGT | 138410 | 138424 | 6248 | |
| 430 | ASO-000216 | ASO-000216 | TTAgggaggcatgATT | 138412 | 138427 | 6250 | 96 |
| 431 | ASO-000266 | ASO-000266 | TTAgggaggcatGAT | 138413 | 138427 | 6251 | |
| 432 | ASO-000256 | ASO-000256 | TCTtagggaggcaTGA | 138414 | 138429 | 6252 | |
| 433 | ASO-000269 | ASO-000269 | GAGgtggcacagaGGT | 138460 | 138475 | 6298 | |
| 434 | ASO-000350 | ASO-000350 | CAGtgtgagaggtGG | 138469 | 138483 | 6307 | |
| 435 | ASO-000353 | ASO-000353 | CAGtgtgagaggTG | 138470 | 138483 | 6308 | |
| 436 | ASO-000310 | ASO-000310 | ACAaagatgaggaGGG | 138532 | 138547 | 6370 | |
| 437 | ASO-000309 | ASO-000309 | AACaaagatgaggAGG | 138533 | 138548 | 6371 | |

Figure 6 cont.

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 438 | ASO-000263 | ASO-000263 | GAAgagaaatcagAAG | 138631 | 138646 | 6469 | |
| 439 | ASO-000197 | ASO-000197 | TCTaggccagtgcCCA | 138667 | 138682 | 6505 | 99 |
| 440 | ASO-000239 | ASO-000239 | AGTctattaggAGG | 138689 | 138702 | 6527 | 100 |
| 441 | ASO-000267 | ASO-000267 | GCTcaacatggcaAAC | 138714 | 138729 | 6552 | |
| 442 | ASO-000306 | ASO-000306 | TGCaagtgccagAAA | 138737 | 138751 | 6575 | |
| 443 | ASO-000345 | ASO-000345 | GCAagtgccagAAA | 138737 | 138750 | 6575 | |
| 444 | ASO-000193 | ASO-000193 | AATcatgggacttGCA | 138748 | 138763 | 6586 | 100 |
| 445 | ASO-000284 | ASO-000284 | GATttcatgtcccTCC | 138788 | 138803 | 6626 | |
| 446 | ASO-000209 | ASO-000209 | GCTaagctaagaTGA | 138802 | 138816 | 6640 | 99 |
| 447 | ASO-000207 | ASO-000207 | CTAagctaagaTGA | 138802 | 138815 | 6640 | 97 |
| 448 | ASO-000301 | ASO-000301 | TAGacattcacaGAC | 138822 | 138836 | 6660 | |
| 449 | ASO-000234 | ASO-000234 | TATagacattcaCAG | 138824 | 138838 | 6662 | 100 |
| 450 | ASO-000332 | ASO-000332 | AAAcacacaatacACT | 138840 | 138855 | 6678 | |
| 451 | SPC-15693-01 | ASO-002268 | CAgcaacagtcagtGT | 138869 | 138884 | 6707 | 100 |
| 452 | SPC-15692-01 | ASO-002268 | ACagcaacagtcagTG | 138870 | 138885 | 6708 | 100 |
| 453 | SPC-15691-01 | ASO-002260 | TAcagcaacagtcaGT | 138871 | 138886 | 6709 | 99 |
| 454 | SPC-15690-01 | ASO-002252 | TTAcagcaacagtcAG | 138872 | 138887 | 6710 | 100 |
| 455 | SPC-15689-01 | ASO-002244 | TTTacagcaacagtCA | 138873 | 138888 | 6711 | 100 |
| 456 | SPC-15688-01 | ASO-002290 | TTttacagcaacaGTC | 138874 | 138889 | 6712 | 100 |
| 457 | SPC-15687-01 | ASO-002274 | CTtttacagcaacaGT | 138875 | 138890 | 6713 | 86 |
| 458 | SPC-15686-01 | ASO-002275 | ACttttacagcaaCAG | 138876 | 138891 | 6714 | 100 |
| 459 | SPC-15685-01 | ASO-002267 | CActtttacagcaaCA | 138877 | 138892 | 6715 | 93 |
| 460 | SPC-15684-01 | ASO-002259 | TCActtttacagcAAC | 138878 | 138893 | 6716 | 99 |
| 461 | SPC-15683-01 | ASO-002251 | TTCacttttacagCAA | 138879 | 138894 | 6717 | 100 |
| 462 | SPC-15682-01 | ASO-002243 | ATTcacttttacagCA | 138880 | 138895 | 6718 | 98 |
| 463 | SPC-15681-01 | ASO-002234 | AATtcacttttacaGC | 138881 | 138896 | 6719 | 77 |

Figure 6 cont.

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 464 | SPC-15680-01 | ASO-002289 | AAATtcacttttACAG | 138882 | 138897 | 6720 | 96 |
| 465 | SPC-15679-01 | ASO-002281 | CAAattcactttTACA | 138883 | 138898 | 6721 | 99 |
| 466 | ASO-002090 | ASO-002090 | ATTtcCaaattcactTtTAC | 138884 | 138903 | 6722 | 99 |
| 467 | ASO-002043 | ASO-002043 | ATtTCcaaattcacttTTAC | 138884 | 138903 | 6722 | 99 |
| 468 | ASO-002076 | ASO-002076 | ATtTCcaaattcacTTttAC | 138884 | 138903 | 6722 | 99 |
| 469 | ASO-002062 | ASO-002062 | ATTtcCaaattcactTTtAC | 138884 | 138903 | 6722 | 100 |
| 470 | ASO-002082 | ASO-002082 | ATtTcCaaattcactTtTAC | 138884 | 138903 | 6722 | 100 |
| 471 | ASO-000753 | ASO-000753 | ATTTCcaaattcactTTTAC | 138884 | 138903 | 6722 | 96 |
| 472 | ASO-001940 | ASO-001940 | ATtTCcaaattcactTTtAC | 138884 | 138903 | 6722 | 99 |
| 473 | ASO-001933 | ASO-001933 | AtTTCcaaattcactTTtAC | 138884 | 138903 | 6722 | 99 |
| 474 | ASO-001919 | ASO-001919 | ATTTccaaattcactTTTAC | 138884 | 138903 | 6722 | 99 |
| 475 | ASO-002094 | ASO-002094 | ATtTCcaaattcacTtTtAC | 138884 | 138903 | 6722 | 98 |
| 476 | ASO-002034 | ASO-002034 | ATTtCcaaattcactTtTAC | 138884 | 138903 | 6722 | 100 |
| 477 | ASO-002036 | ASO-002036 | ATttCcAaattcacttTTAC | 138884 | 138903 | 6722 | 100 |
| 478 | ASO-002084 | ASO-002084 | ATTtCcaaattcacTTttAC | 138884 | 138903 | 6722 | 99 |
| 479 | ASO-002037 | ASO-002037 | ATTTccaaattcaCtTttAC | 138884 | 138903 | 6722 | 99 |
| 480 | ASO-002058 | ASO-002058 | ATTtCcaaattcacTttTAC | 138884 | 138903 | 6722 | 99 |
| 481 | ASO-002057 | ASO-002057 | ATTTccaaattcaCttTtAC | 138884 | 138903 | 6722 | 99 |
| 482 | ASO-001926 | ASO-001926 | ATTTCcaaattcacttTTAC | 138884 | 138903 | 6722 | 99 |
| 483 | ASO-002092 | ASO-002092 | ATttCCaaattcactTtTAC | 138884 | 138903 | 6722 | 99 |
| 484 | ASO-002023 | ASO-002023 | ATTTccaaattcacTTttAC | 138884 | 138903 | 6722 | 100 |
| 485 | ASO-000758 | ASO-000758 | ATTtccaaattcactttTAC | 138884 | 138903 | 6722 | 97 |
| 486 | ASO-002065 | ASO-002065 | ATttCCaaattcactTTtAC | 138884 | 138903 | 6722 | 99 |
| 487 | ASO-002038 | ASO-002038 | ATTtCcaaattcacTtTtAC | 138884 | 138903 | 6722 | 99 |
| 488 | ASO-002039 | ASO-002039 | ATtTCcaaattcacTttTAC | 138884 | 138903 | 6722 | 98 |
| 489 | ASO-000763 | ASO-000763 | ATttccaaattcacttttAC | 138884 | 138903 | 6722 | 14 |
| 490 | ASO-000768 | ASO-000768 | AtttccaaattcacttttAC | 138884 | 138903 | 6722 | 0 |

Figure 6 cont.

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 491 | ASO-001933-mm1 | ASO-002291 | GtTTCcaaattcactTTtAC | 138884 | 138903 | 6722 | 50 |
| 492 | ASO-001933-mm2 | ASO-002303 | AtTTCcagattcactTTtAC | 138884 | 138903 | 6722 | 50 |
| 493 | ASO-001933-mm3 | ASO-002315 | TtTTCcaaattcactTTtAC | 138884 | 138903 | 6722 | 50 |
| 494 | ASO-001933-mm4 | ASO-002327 | GtTTCcagattcactTTtAC | 138884 | 138903 | 6722 | 83 |
| 495 | ASO-001933-mm5 | ASO-002339 | AtTTCcaagttcactTTtGC | 138884 | 138903 | 6722 | 69 |
| 496 | ASO-001933-mm6 | ASO-002351 | AtTTCcagattcgctTTtAC | 138884 | 138903 | 6722 | 75 |
| 497 | SPC-15678-01 | ASO-002274 | CCaaattcactttTAC | 138884 | 138899 | 6722 | 79 |
| 498 | SPC-15857-01 | ASO-002326 | ATtTcCaaattcacttTTAC | 138884 | 138903 | 6722 | 99 |
| 499 | SPC-15858-01 | ASO-002338 | ATTtcCaaattcacttTTAC | 138884 | 138903 | 6722 | 99 |
| 500 | SPC-15860-01 | ASO-002362 | ATTtCcaaattcacttTTAC | 138884 | 138903 | 6722 | 99 |
| 501 | SPC-15864-01 | ASO-002236 | ATTTccaaattcacTttTAC | 138884 | 138903 | 6722 | 100 |
| 502 | SPC-15868-01 | ASO-002269 | ATtTCcaaattcactTtTAC | 138884 | 138903 | 6722 | 100 |
| 503 | SPC-15872-01 | ASO-002237 | ATttCCaaattcacttTTAC | 138884 | 138903 | 6722 | 100 |
| 504 | SPC-15873-01 | ASO-002246 | ATTtCcaaattcactTTtAC | 138884 | 138903 | 6722 | 99 |
| 505 | SPC-15874-01 | ASO-002254 | ATTTccaaattcacTtTtAC | 138884 | 138903 | 6722 | 11 |
| 506 | SPC-15878-01 | ASO-002284 | ATtTccAaattcacttTTAC | 138884 | 138903 | 6722 | 100 |
| 507 | SPC-15879-01 | ASO-002229 | ATTTccaaattcacttTTAC | 138884 | 138903 | 6722 | 99 |
| 508 | SPC-15880-01 | ASO-002238 | ATTTccaaattcactTtTAC | 138884 | 138903 | 6722 | 100 |
| 509 | SPC-15883-01 | ASO-002263 | ATtTcCaaattcactTTtAC | 138884 | 138903 | 6722 | |
| 510 | SPC-15888-01 | ASO-002239 | ATTTccaaattcactTTtAC | 138884 | 138903 | 6722 | 100 |

Figure 6 cont.

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 511 | ASO-000754 | ASO-000754 | TATTTccaaattcacTTTTA | 138885 | 138904 | 6723 | 100 |
| 512 | ASO-002055 | ASO-002055 | TAtTtCcaaattcacTTtTA | 138885 | 138904 | 6723 | 99 |
| 513 | ASO-002035 | ASO-002035 | TAtTtcCaaattcactTTTA | 138885 | 138904 | 6723 | 100 |
| 514 | ASO-002048 | ASO-002048 | TATtTccaaattcaCttTTA | 138885 | 138904 | 6723 | 100 |
| 515 | ASO-002053 | ASO-002053 | TAtTtCcaaattcactTTTA | 138885 | 138904 | 6723 | 100 |
| 516 | ASO-002067 | ASO-002067 | TAtTTccaaattcaCTttTA | 138885 | 138904 | 6723 | 99 |
| 517 | ASO-001954 | ASO-001954 | TATTTccaaattcactTTTA | 138885 | 138904 | 6723 | 99 |
| 518 | ASO-001947 | ASO-001947 | TATTtccaaattcacTTTTA | 138885 | 138904 | 6723 | 99 |
| 519 | ASO-002081 | ASO-002081 | TATttCcaaattcacTtTTA | 138885 | 138904 | 6723 | 100 |
| 520 | ASO-001966 | ASO-001966 | TAtTTccaaattcacTTtTA | 138885 | 138904 | 6723 | 99 |
| 521 | ASO-002025 | ASO-002025 | TAttTcCaaattcactTTTA | 138885 | 138904 | 6723 | 100 |
| 522 | ASO-002033 | ASO-002033 | TATtTccaaattcacTtTTA | 138885 | 138904 | 6723 | 99 |
| 523 | ASO-001960 | ASO-001960 | TaTTTccaaattcacTTtTA | 138885 | 138904 | 6723 | 99 |
| 524 | ASO-002056 | ASO-002056 | TAttTCcaaattcacTTtTA | 138885 | 138904 | 6723 | 100 |
| 525 | ASO-002063 | ASO-002063 | TATttCcaaattcacTTtTA | 138885 | 138904 | 6723 | 99 |
| 526 | ASO-002089 | ASO-002089 | TATTtccaaattcaCttTTA | 138885 | 138904 | 6723 | 100 |
| 527 | ASO-002073 | ASO-002073 | TAtTtCcaaattcacTtTTA | 138885 | 138904 | 6723 | 99 |
| 528 | ASO-002027 | ASO-002027 | TATtTccaaattcaCtTtTA | 138885 | 138904 | 6723 | 99 |
| 529 | ASO-002075 | ASO-002075 | TATtTccaaattcaCTttTA | 138885 | 138904 | 6723 | 99 |
| 530 | ASO-002028 | ASO-002028 | TAtTTccaaattcaCttTTA | 138885 | 138904 | 6723 | 99 |
| 531 | ASO-002085 | ASO-002085 | TAtTTccaaattcaCtTtTA | 138885 | 138904 | 6723 | 99 |
| 532 | ASO-002083 | ASO-002083 | TAttTCcaaattcacTtTTA | 138885 | 138904 | 6723 | 99 |
| 533 | ASO-000759 | ASO-000759 | TATttccaaattcacttTTA | 138885 | 138904 | 6723 | 93 |
| 534 | ASO-000769 | ASO-000769 | TatttccaaattcactttTA | 138885 | 138904 | 6723 | 0 |
| 535 | ASO-000764 | ASO-000764 | TAtttccaaattcactttTA | 138885 | 138904 | 6723 | 0 |
| 536 | ASO-001954-mm1 | ASO-002340 | TATTTccagattcactTTTA | 138885 | 138904 | 6723 | 98 |

Figure 6 cont.

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 537 | ASO-001954-mm2 | ASO-002352 | TATTTccgaattcactTTTA | 138885 | 138904 | 6723 | 99 |
| 538 | ASO-001954-mm3 | ASO-002364 | GATTTccaaattcactTTTA | 138885 | 138904 | 6723 | 97 |
| 539 | ASO-001954-mm4 | ASO-002376 | GGTTTccaaattcactTTTA | 138885 | 138904 | 6723 | 38 |
| 540 | ASO-001954-mm5 | ASO-002293 | AATTTccagattcactTTTA | 138885 | 138904 | 6723 | 96 |
| 541 | ASO-001954-mm6 | ASO-002305 | TATTTccaagttcgctTTTA | 138885 | 138904 | 6723 | 52 |
| 542 | SPC-15677-01 | ASO-002266 | TCCaaattcactttTA | 138885 | 138900 | 6723 | 99 |
| 543 | SPC-15859-01 | ASO-002350 | TAtTTccaaattcactTTTA | 138885 | 138904 | 6723 | 99 |
| 544 | SPC-15861-01 | ASO-002374 | TAtTTccaaattcacTtTTA | 138885 | 138904 | 6723 | 100 |
| 545 | SPC-15862-01 | ASO-002386 | TATTtccaaattcaCTttTA | 138885 | 138904 | 6723 | 99 |
| 546 | SPC-15863-01 | ASO-002227 | TATtTccaaattcactTTTA | 138885 | 138904 | 6723 | 99 |
| 547 | SPC-15865-01 | ASO-002245 | TAttTCcaaattcactTTTA | 138885 | 138904 | 6723 | 100 |
| 548 | SPC-15867-01 | ASO-002261 | TATtTccaaattcacTTtTA | 138885 | 138904 | 6723 | 99 |
| 549 | SPC-15869-01 | ASO-002276 | TATttCcaaattcactTTTA | 138885 | 138904 | 6723 | 100 |
| 550 | SPC-15871-01 | ASO-002228 | TATTtccaaattcaCtTtTA | 138885 | 138904 | 6723 | 97 |
| 551 | SPC-15882-01 | ASO-002255 | TATTtccaaattcactTTTA | 138885 | 138904 | 6723 | 98 |
| 552 | SPC-15886-01 | ASO-002285 | TATTtccaaattcacTTtTA | 138885 | 138904 | 6723 | 83 |
| 553 | SPC-15887-01 | ASO-002230 | TATTtccaaattcacTtTTA | 138885 | 138904 | 6723 | 100 |
| 554 | SPC-15890-01 | ASO-002256 | TATTtccaaattcAcTttTA | 138885 | 138904 | 6723 | 99 |
| 555 | SPC-15893-01 | ASO-002279 | TATTtccaaattcActTtTA | 138885 | 138904 | 6723 | 100 |
| 556 | ASO-002072 | ASO-002072 | TTAttTccaaattcaCTtTT | 138886 | 138905 | 6724 | 99 |
| 557 | ASO-000755 | ASO-000755 | TTATTtccaaattcaCTTTT | 138886 | 138905 | 6724 | 99 |

Figure 6 cont.

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 558 | ASO-002071 | ASO-002071 | TTaTtTccaaattcacTTTT | 138886 | 138905 | 6724 | 100 |
| 559 | ASO-000760 | ASO-000760 | TTAtttccaaattcactTTT | 138886 | 138905 | 6724 | 96 |
| 560 | ASO-001920 | ASO-001920 | TTATttccaaattcaCTTTT | 138886 | 138905 | 6724 | 99 |
| 561 | ASO-002080 | ASO-002080 | TTatTTccaaattcacTTTT | 138886 | 138905 | 6724 | 100 |
| 562 | ASO-001927 | ASO-001927 | TTATTtccaaattcacTTTT | 138886 | 138905 | 6724 | 99 |
| 563 | ASO-001941 | ASO-001941 | TTaTTtccaaattcaCTtTT | 138886 | 138905 | 6724 | 99 |
| 564 | ASO-002045 | ASO-002045 | TTaTttCcaaattcacTTTT | 138886 | 138905 | 6724 | 100 |
| 565 | ASO-001934 | ASO-001934 | TtATTtccaaattcaCTtTT | 138886 | 138905 | 6724 | 98 |
| 566 | ASO-002074 | ASO-002074 | TTatTTccaaattcacTtTT | 138886 | 138905 | 6724 | 100 |
| 567 | ASO-002093 | ASO-002093 | TTAtTtccaaattcACttTT | 138886 | 138905 | 6724 | 100 |
| 568 | ASO-002054 | ASO-002054 | TTaTTtccaaattcaCtTTT | 138886 | 138905 | 6724 | 100 |
| 569 | ASO-002091 | ASO-002091 | TTaTtTccaaattcaCtTTT | 138886 | 138905 | 6724 | 99 |
| 570 | ASO-002064 | ASO-002064 | TTaTtTccaaattcaCTtTT | 138886 | 138905 | 6724 | 99 |
| 571 | ASO-002066 | ASO-002066 | TTATttccaaattCacTtTT | 138886 | 138905 | 6724 | 99 |
| 572 | ASO-002044 | ASO-002044 | TTAtTtccaaattcaCtTTT | 138886 | 138905 | 6724 | 99 |
| 573 | ASO-002047 | ASO-002047 | TTATttccaaattCaCttTT | 138886 | 138905 | 6724 | 99 |
| 574 | ASO-002046 | ASO-002046 | TTatTtCcaaattcacTTTT | 138886 | 138905 | 6724 | 96 |
| 575 | ASO-000765 | ASO-000765 | TTatttccaaattcacttTT | 138886 | 138905 | 6724 | 39 |
| 576 | ASO-000770 | ASO-000770 | TtatttccaaattcacttTT | 138886 | 138905 | 6724 | 0 |
| 577 | ASO-001941-mm1 | ASO-002317 | **A**TaTTtccaaattcaCTtTT | 138886 | 138905 | 6724 | 50 |
| 578 | ASO-001941-mm2 | ASO-002329 | TTaTTtccaaattcaCTtT**A** | 138886 | 138905 | 6724 | 99 |
| 579 | ASO-001941-mm3 | ASO-002341 | TTaTTtccaaattcaCTtT**G** | 138886 | 138905 | 6724 | 99 |
| 580 | ASO-001941-mm4 | ASO-002353 | **A**TaTTtcca**g**attcaCTtTT | 138886 | 138905 | 6724 | 76 |
| 581 | ASO-001941-mm5 | ASO-002365 | TTaTTtccaa**g**ttcaCTtT**C** | 138886 | 138905 | 6724 | 87 |
| 582 | ASO-001941-mm6 | ASO-002377 | TTaTTtcca**g**attc**g**CTtTT | 138886 | 138905 | 6724 | 79 |

Figure 6 cont.

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 583 | SPC-15676-01 | ASO-002258 | TTCcaaattcactTTT | 138886 | 138901 | 6724 | 100 |
| 584 | SPC-15866-01 | ASO-002253 | TTAtTtccaaattcaCTtTT | 138886 | 138905 | 6724 | 97 |
| 585 | SPC-15870-01 | ASO-002283 | TTAttTccaaattcacTTTT | 138886 | 138905 | 6724 | 99 |
| 586 | SPC-15875-01 | ASO-002262 | TTATttccaaattcacTTTT | 138886 | 138905 | 6724 | 100 |
| 587 | SPC-15876-01 | ASO-002270 | TTATttccaaattcaCtTTT | 138886 | 138905 | 6724 | 100 |
| 588 | SPC-15877-01 | ASO-002277 | TTATttccaaattcACttTT | 138886 | 138905 | 6724 | 100 |
| 589 | SPC-15881-01 | ASO-002247 | TTaTTtccaaattcacTTTT | 138886 | 138905 | 6724 | 100 |
| 590 | SPC-15884-01 | ASO-002271 | TTAtTtccaaattcacTTTT | 138886 | 138905 | 6724 | 100 |
| 591 | SPC-15885-01 | ASO-002278 | TTaTTtccaaattcACttTT | 138886 | 138905 | 6724 | 100 |
| 592 | SPC-15889-01 | ASO-002248 | TTaTTtccaaattcActTTT | 138886 | 138905 | 6724 | 100 |
| 593 | SPC-15891-01 | ASO-002264 | TTAtTtccaaattcActTTT | 138886 | 138905 | 6724 | 100 |
| 594 | SPC-15892-01 | ASO-002272 | TTaTTtccaaattcAcTtTT | 138886 | 138905 | 6724 | 100 |
| 595 | SPC-15894-01 | ASO-002286 | TTAtTtccaaattcAcTtTT | 138886 | 138905 | 6724 | 99 |
| 596 | SPC-15895-01 | ASO-002231 | TTATttccaaattcActTTT | 138886 | 138905 | 6724 | 100 |
| 597 | SPC-15896-01 | ASO-002240 | TTATttccaaattcAcTtTT | 138886 | 138905 | 6724 | 100 |
| 598 | ASO-002020 | ASO-002020 | ACttTatttccaaattcactTTtaC | 138884 | 138909 | 6722 | 99 |
| 599 | ASO-000756 | ASO-000756 | TTTATttccaaattcACTTT | 138887 | 138906 | 6725 | 100 |
| 600 | ASO-001967 | ASO-001967 | TTtATttccaaattcACtTT | 138887 | 138906 | 6725 | 99 |
| 601 | ASO-001955 | ASO-001955 | TTTATttccaaattcaCTTT | 138887 | 138906 | 6725 | 99 |
| 602 | ASO-001948 | ASO-001948 | TTTAtttccaaattcACTTT | 138887 | 138906 | 6725 | 100 |
| 603 | ASO-002086 | ASO-002086 | AcTTtatttccaaattcactTTTaC | 138884 | 138908 | 6722 | 98 |
| 604 | ASO-002029 | ASO-002029 | ACtTtatttccaaattcacttTTaC | 138884 | 138908 | 6722 | 98 |

Figure 6 cont.

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 605 | ASO-001961 | ASO-001961 | TtTATttccaaattcACtTT | 138887 | 138906 | 6725 | 99 |
| 606 | ASO-002095 | ASO-002095 | ACTttatttccaaattcactTtTaC | 138884 | 138908 | 6722 | 94 |
| 607 | ASO-002059 | ASO-002059 | ACTttatttccaaattcacttTTAC | 138884 | 138908 | 6722 | 93 |
| 608 | ASO-002077 | ASO-002077 | ActttatttccaaattcactTTTAC | 138884 | 138908 | 6722 | 91 |
| 609 | ASO-002021 | ASO-002021 | AcTTtatttccaaattcactttTAC | 138884 | 138908 | 6722 | 91 |
| 610 | ASO-000761 | ASO-000761 | TTTatttccaaattcacTTT | 138887 | 138906 | 6725 | 93 |
| 611 | ASO-002068 | ASO-002068 | ACtTtatttccaaattcactTtTAC | 138884 | 138908 | 6722 | 86 |
| 612 | ASO-000766 | ASO-000766 | TTtatttccaaattcactTT | 138887 | 138906 | 6725 | 3 |
| 613 | ASO-000771 | ASO-000771 | TttatttccaaattcactTT | 138887 | 138906 | 6725 | 0 |
| 614 | 17-18-19mer-19 | ASO-002416 | TATttccaaattcaCTTT | 138887 | 138904 | 6725 | 100 |
| 615 | ASO-001967-mm2 | ASO-002306 | TTtATttccaagttcACtTT | 138887 | 138906 | 6725 | 50 |
| 616 | ASO-001967-mm3 | ASO-002318 | GTtATttccaaattcACtTT | 138887 | 138906 | 6725 | 99 |
| 617 | ASO-001967-mm4 | ASO-002330 | ATtATttccagattcACtTT | 138887 | 138906 | 6725 | 83 |
| 618 | ASO-001967-mm5 | ASO-002342 | TTtATttccaggttcACtTT | 138887 | 138906 | 6725 | 48 |
| 619 | ASO-001967-mm6 | ASO-002354 | CTtATttccaagttcACtTT | 138887 | 138906 | 6725 | 87 |
| 620 | SPC-15675-01 | ASO-002250 | TTTCcaaattcacTTT | 138887 | 138902 | 6725 | 99 |
| 621 | ASO-002006 | ASO-002006 | CTtTAtttccaaattcACTT | 138888 | 138907 | 6726 | 99 |
| 622 | ASO-000757 | ASO-000757 | CTTTAtttccaaattCACTT | 138888 | 138907 | 6726 | 100 |
| 623 | ASO-002017 | ASO-002017 | CTtTAtttccaaattcaCTT | 138888 | 138907 | 6726 | 99 |
| 624 | ASO-001928 | ASO-001928 | CTTTAtttccaaattcACTT | 138888 | 138907 | 6726 | 100 |

Figure 6 cont.

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 625 | ASO-001968 | ASO-001968 | ACTTTatttccaaattCACTT | 138888 | 138908 | 6726 | 100 |
| 626 | ASO-001921 | ASO-001921 | CTTTatttccaaattCACTT | 138888 | 138907 | 6726 | 100 |
| 627 | ASO-001989 | ASO-001989 | CTTTatttccaaattcACTT | 138888 | 138907 | 6726 | 100 |
| 628 | ASO-001942 | ASO-001942 | CTtTAtttccaaattCAcTT | 138888 | 138907 | 6726 | 99 |
| 629 | ASO-000128 | ASO-000128 | TTTccaaattcaCTT | 138888 | 138902 | 6726 | 100 |
| 630 | ASO-001935 | ASO-001935 | CtTTAtttccaaattCAcTT | 138888 | 138907 | 6726 | 100 |
| 631 | ASO-000013 | ASO-000013 | ATTtccaaattcaCTT | 138888 | 138903 | 6726 | 95 |
| 632 | ASO-002002 | ASO-002002 | CTTtAtttccaaattcACTT | 138888 | 138907 | 6726 | 100 |
| 633 | ASO-000762 | ASO-000762 | CTTtatttccaaattcaCTT | 138888 | 138907 | 6726 | 97 |
| 634 | ASO-002010 | ASO-002010 | CTTtatttccaaatTcaCTT | 138888 | 138907 | 6726 | 98 |
| 635 | ASO-002005 | ASO-002005 | CTtTatttccaaattcaCTT | 138888 | 138907 | 6726 | 98 |
| 636 | ASO-001998 | ASO-001998 | CTttAtttccaaattcACTT | 138888 | 138907 | 6726 | 99 |
| 637 | ASO-002001 | ASO-002001 | CTTTatttccaaattcaCTT | 138888 | 138907 | 6726 | 97 |
| 638 | ASO-001994 | ASO-001994 | CTtTatttccaaattcACTT | 138888 | 138907 | 6726 | 95 |
| 639 | ASO-002013 | ASO-002013 | CTTtAtttccaaattcaCTT | 138888 | 138907 | 6726 | 98 |
| 640 | ASO-002009 | ASO-002009 | CTttAtttccaaattcaCTT | 138888 | 138907 | 6726 | 94 |
| 641 | ASO-000767 | ASO-000767 | CTttatttccaaattcacTT | 138888 | 138907 | 6726 | 32 |
| 642 | ASO-000772 | ASO-000772 | CtttatttccaaattcacTT | 138888 | 138907 | 6726 | 0 |
| 643 | BMT-214296 | ASO-214296 | CTTTActtccaaattCACTT | 138888 | 138907 | 6726 | |
| 644 | ASO-000013-mm1 | ASO-002366 | ***G***TTtccaaattcaCTT | 138888 | 138903 | 6726 | 97 |
| 645 | ASO-000013-mm2 | ASO-002378 | ATTtccaa***g***ttcaCTT | 138888 | 138903 | 6726 | 55 |
| 646 | ASO-000013-mm3 | ASO-002295 | ATTtcc***g***aattcaCTT | 138888 | 138903 | 6726 | 60 |
| 647 | ASO-000013-mm4 | ASO-002307 | ***G***TTtcca***g***attcaCTT | 138888 | 138903 | 6726 | 52 |
| 648 | ASO-000013-mm5 | ASO-002319 | ***G***TTtccaaattcaCT***A*** | 138888 | 138903 | 6726 | 98 |

Figure 6 cont.

| SEQ ID NO: | Oligomer Name | ASO Number | ASO Sequence | premRNA start NG_0073 98 | premRNA end NG_0073 98 | mRNA start NM_016 835 | Tau/Tubulin % inhibition |
|---|---|---|---|---|---|---|---|
| 649 | ASO-000013-mm6 | ASO-002331 | ATTtccagattcaCTC | 138888 | 138903 | 6726 | 46 |
| 650 | ASO-000898 | ASO-000898 | ATTtccaaattcaCTT | 138888 | 138903 | 6726 | |
| 651 | ASO-001942-mm1 | ASO-002363 | CTtTAtttccagattCAcTT | 138888 | 138907 | 6726 | 98 |
| 652 | ASO-001942-mm2 | ASO-002375 | CTtTAtttccaaattCAcTG | 138888 | 138907 | 6726 | 99 |
| 653 | ASO-001942-mm3 | ASO-002292 | CTtTAtttccaaattCGcTT | 138888 | 138907 | 6726 | 50 |
| 654 | ASO-001942-mm4 | ASO-002304 | CTtTAtttccagattCAcTA | 138888 | 138907 | 6726 | 50 |
| 655 | ASO-001942-mm5 | ASO-002316 | CTtTAtttccaggttCAcTT | 138888 | 138907 | 6726 | 52 |
| 656 | ASO-001942-mm6 | ASO-002328 | CTtTAtttccgagttCAcTT | 138888 | 138907 | 6726 | 96 |
| 657 | SPC-15674-01 | ASO-002242 | ATTtccaaattcACTT | 138888 | 138903 | 6726 | 100 |
| 658 | ASO-002004 | ASO-002366 | CTTTatttccaaatTcaCT | 138889 | 138907 | 6727 | 98 |
| 659 | ASO-002012 | ASO-002378 | CTTtatttccaaatTcACT | 138889 | 138907 | 6727 | 100 |
| 660 | ASO-001962 | ASO-002295 | ACTTTatttccaaattCACT | 138889 | 138908 | 6727 | 100 |
| 661 | ASO-001956 | ASO-002307 | ACTTtatttccaaatTCACT | 138889 | 138908 | 6727 | 99 |
| 662 | ASO-001949 | ASO-002319 | ACTTTatttccaaatTCACT | 138889 | 138908 | 6727 | 100 |
| 663 | ASO-001987 | ASO-002331 | CTTTAtttccaaatTcACT | 138889 | 138907 | 6727 | 99 |
| 664 | ASO-001991 | ASO-000898 | CTTTatttccaaatTCACT | 138889 | 138907 | 6727 | 100 |
| 665 | ASO-001995 | ASO-002363 | CTTtatttccaaatTCACT | 138889 | 138907 | 6727 | 99 |
| 666 | ASO-001992 | ASO-002375 | CTTTAtttccaaatTcaCT | 138889 | 138907 | 6727 | 100 |
| 667 | ASO-002000 | ASO-002292 | CTTTatttccaaatTcACT | 138889 | 138907 | 6727 | 100 |
| 668 | ASO-001996 | ASO-001996 | CTTTatttccaaatTCaCT | 138889 | 138907 | 6727 | 99 |

Figure 6 cont.

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 669 | ASO-002008 | ASO-002008 | CTTtatttccaaatTCaCT | 138889 | 138907 | 6727 | 99 |
| 670 | ASO-002015 | ASO-002015 | CTTTAtttccaaatTCaCT | 138889 | 138907 | 6727 | 98 |
| 671 | ASO-002016 | ASO-002016 | CTTtatttccaaatTcaCT | 138889 | 138907 | 6727 | 98 |
| 672 | ASO-001986 | ASO-001986 | CTTTAtttccaaatTCACT | 138889 | 138907 | 6727 | 95 |
| 673 | ASO-001995-mm1 | ASO-002343 | CTTtatttccagatTCACT | 138889 | 138907 | 6727 | 97 |
| 674 | ASO-001995-mm2 | ASO-002355 | CTTtgtttccaaatTCACT | 138889 | 138907 | 6727 | 98 |
| 675 | ASO-001995-mm3 | ASO-002367 | CTTtatttccaaatTCACG | 138889 | 138907 | 6727 | 100 |
| 676 | ASO-001995-mm4 | ASO-002379 | CTTtgtttccagatTCACT | 138889 | 138907 | 6727 | 86 |
| 677 | ASO-001995-mm5 | ASO-002296 | CTTtgtttccaagtTCACT | 138889 | 138907 | 6727 | 52 |
| 678 | ASO-001995-mm6 | ASO-002308 | CTTtatttccgagtTCACT | 138889 | 138907 | 6727 | 51 |
| 679 | SPC-15673-01 | ASO-002233 | TATttccaaattcACT | 138889 | 138904 | 6727 | 99 |
| 680 | ASO-002003 | ASO-002003 | CTTTatttccaaatTCAC | 138890 | 138907 | 6728 | 99 |
| 681 | ASO-002007 | ASO-002007 | CTTtatttccaaatTCAC | 138890 | 138907 | 6728 | 99 |
| 682 | ASO-002011 | ASO-002011 | CTtTatttccaaatTcAC | 138890 | 138907 | 6728 | 100 |
| 683 | ASO-001988 | ASO-001988 | CTTTAtttccaaatTcAC | 138890 | 138907 | 6728 | 99 |
| 684 | ASO-001999 | ASO-001999 | CTTTAtttccaaatTCAC | 138890 | 138907 | 6728 | 100 |
| 685 | ASO-001993 | ASO-001993 | CTTTatttccaaatTcAC | 138890 | 138907 | 6728 | 99 |
| 686 | ASO-001997 | ASO-001997 | CTTtatttccaaatTcAC | 138890 | 138907 | 6728 | 99 |
| 687 | ASO-001997-mm1 | ASO-002320 | CTTtatttccagatTcAC | 138890 | 138907 | 6728 | 83 |
| 688 | ASO-001997-mm2 | ASO-002332 | CTTtatttccgaatTcAC | 138890 | 138907 | 6728 | 85 |
| 689 | ASO-001997-mm3 | ASO-002344 | CTTtgtttccaaatTcAC | 138890 | 138907 | 6728 | 83 |
| 690 | ASO-001997-mm4 | ASO-002356 | CTTtgtttccagatTcAC | 138890 | 138907 | 6728 | 33 |

Figure 6 cont.

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 691 | ASO-001997-mm5 | ASO-002368 | CTTtatttccaggtTcAC | 138890 | 138907 | 6728 | 6 |
| 692 | ASO-001997-mm6 | ASO-002380 | CTTtgtttccaagtTcAC | 138890 | 138907 | 6728 | 50 |
| 693 | SPC-15672-01 | ASO-002288 | TTAtttccaaattCAC | 138890 | 138905 | 6728 | 93 |
| 694 | SPC-15671-01 | ASO-002280 | TTTatttccaaatTCA | 138891 | 138906 | 6729 | 100 |
| 695 | SPC-15670-01 | ASO-002273 | CTTtatttccaaATTC | 138892 | 138907 | 6730 | 99 |
| 696 | SPC-15669-01 | ASO-002265 | ACTTtatttccaAATT | 138893 | 138908 | 6731 | 84 |
| 697 | ASO-000139 | ASO-000139 | AACtttatttccaAAT | 138894 | 138909 | 6732 | 23 |
| 698 | SPC-15668-01 | ASO-002257 | AACTttatttccAAAT | 138894 | 138909 | 6732 | 93 |
| 699 | SPC-15667-01 | ASO-002249 | TAACtttatttcCAAA | 138895 | 138910 | 6733 | 97 |
| 700 | SPC-15666-01 | ASO-002241 | ATAActttatttcCAA | 138896 | 138911 | 6734 | 97 |
| 701 | ASO-000118 | ASO-000118 | AATaactttatttCCA | 138897 | 138912 | 6735 | 92 |
| 702 | SPC-15665-01 | ASO-002232 | AATaactttattTCCA | 138897 | 138912 | 6735 | 99 |
| 703 | ASO-000101 | ASO-000101 | TAAtaactttattTCC | 138898 | 138913 | 6736 | 60 |
| 704 | SPC-15664-01 | ASO-002287 | TAAtaactttatTTCC | 138898 | 138913 | 6736 | 76 |
| 705 | ASO-000148 | ASO-000148 | GTAataactttatTTC | 138899 | 138914 | 6737 | 41 |
| 706 | ASO-000184 | ASO-000184 | TAAtaactttatTTC | 138899 | 138913 | 6737 | 7 |
| 707 | ASO-000112 | ASO-000112 | GTAataactttaTTT | 138900 | 138914 | 6738 | 1 |
| 708 | ASO-000170 | ASO-000170 | AGTaataactttaTTT | 138900 | 138915 | 6738 | 1 |
| 709 | ASO-000154 | ASO-000154 | GAGtaataactttATT | 138901 | 138916 | 6739 | 0 |
| 710 | ASO-000125 | ASO-000125 | AGTaataactttATT | 138901 | 138915 | 6739 | 1 |
| 711 | ASO-000167 | ASO-000167 | GAGtaataacttTAT | 138902 | 138916 | 6740 | 5 |
| 712 | ASO-000134 | ASO-000134 | AGAgtaataacttTAT | 138902 | 138917 | 6740 | 12 |
| 713 | ASO-000175 | ASO-000175 | CAGagtaataactTTA | 138903 | 138918 | 6741 | 43 |
| 714 | ASO-000178 | ASO-000178 | AGAgtaataactTTA | 138903 | 138917 | 6741 | 2 |
| 715 | ASO-000138 | ASO-000138 | CAGagtaataacTTT | 138904 | 138918 | 6742 | 43 |

Figure 6 cont.

| SEQ ID NO: | Oligomer Name | ASO Number | ASO Sequence | premRNA start NG_007398 | premRNA end NG_007398 | mRNA start NM_016835 | Tau/Tubulin % inhibition |
|---|---|---|---|---|---|---|---|
| 716 | ASO-000171 | ASO-000171 | TCAgagtaataacTTT | 138904 | 138919 | 6742 | 39 |
| 717 | ASO-000236 | ASO-000236 | ATCagagtaataaCTT | 138905 | 138920 | 6743 | 65 |
| 718 | ASO-000127 | ASO-000127 | TCAgagtaataaCTT | 138905 | 138919 | 6743 | 29 |
| 719 | ASO-000177 | ASO-000177 | CAGagtaataaCTT | 138905 | 138918 | 6743 | 28 |
| 720 | ASO-000238 | ASO-000238 | AATcagagtaataACT | 138906 | 138921 | 6744 | 21 |
| 721 | ASO-000222 | ASO-000222 | TAAtcagagtaatAAC | 138907 | 138922 | 6745 | 15 |
| 722 | ASO-000307 | ASO-000307 | AATcagagtaatAAC | 138907 | 138921 | 6745 | 3 |
| 723 | ASO-000204 | ASO-000204 | TTAatcagagtaaTAA | 138908 | 138923 | 6746 | 1 |
| 724 | ASO-000330 | ASO-000330 | TAAtcagagtaaTAA | 138908 | 138922 | 6746 | 2 |
| 725 | ASO-000326 | ASO-000326 | TTTaatcagagtaATA | 138909 | 138924 | 6747 | 9 |
| 726 | ASO-000249 | ASO-000249 | TTTaatcagagtAAT | 138910 | 138924 | 6748 | 0 |
| 727 | ASO-002022 | ASO-002022 | TTATttccaaattcaCTtTT | 138886 | 138905 | 6724 | 99 |
| 728 | ASO-002026 | ASO-002026 | TTatTTccaaattcaCtTTT | 138886 | 138905 | 6724 | 100 |
| 729 | ASO-002024 | ASO-002024 | TTAttTccaaattcaCtTTT | 138886 | 138905 | 6724 | 99 |
| 730 | ASO-002049 | ASO-002049 | ACTTtatttccaaattcactTTtAC | 138884 | 138908 | 6722 | 99 |
| 731 | ASO-002019 | ASO-002019 | ACttTatttccaaattcactTTtaC | 138884 | 138908 | 6722 | 98 |

SEQUENCE LISTING

<160> NUMBER OF SEQ ID NOS: 805

<210> SEQ ID NO 1
<211> LENGTH: 758
<212> TYPE: PRT
<213> ORGANISM: Artificial Sequence
<220> FEATURE:
<223> OTHER INFORMATION: Microtubule-associated protein tau (Tau) protein sequence

<400> SEQUENCE: 1

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Glu Pro Glu Ser
        115                 120                 125

Gly Lys Val Val Gln Glu Gly Phe Leu Arg Glu Pro Gly Pro Pro Gly
    130                 135                 140

Leu Ser His Gln Leu Met Ser Gly Met Pro Gly Ala Pro Leu Leu Pro
145                 150                 155                 160

Glu Gly Pro Arg Glu Ala Thr Arg Gln Pro Ser Gly Thr Gly Pro Glu
                165                 170                 175

Asp Thr Glu Gly Gly Arg His Ala Pro Glu Leu Leu Lys His Gln Leu
            180                 185                 190

Leu Gly Asp Leu His Gln Glu Gly Pro Pro Leu Lys Gly Ala Gly Gly
        195                 200                 205

Lys Glu Arg Pro Gly Ser Lys Glu Glu Val Asp Glu Asp Arg Asp Val
    210                 215                 220

Asp Glu Ser Ser Pro Gln Asp Ser Pro Pro Ser Lys Ala Ser Pro Ala
225                 230                 235                 240

Gln Asp Gly Arg Pro Pro Gln Thr Ala Ala Arg Glu Ala Thr Ser Ile
                245                 250                 255

Pro Gly Phe Pro Ala Glu Gly Ala Ile Pro Leu Pro Val Asp Phe Leu
            260                 265                 270

Ser Lys Val Ser Thr Glu Ile Pro Ala Ser Glu Pro Asp Gly Pro Ser
        275                 280                 285

Val Gly Arg Ala Lys Gly Gln Asp Ala Pro Leu Glu Phe Thr Phe His
    290                 295                 300

Val Glu Ile Thr Pro Asn Val Gln Lys Glu Gln Ala His Ser Glu Glu
305                 310                 315                 320

His Leu Gly Arg Ala Ala Phe Pro Gly Ala Pro Gly Glu Gly Pro Glu
                325                 330                 335

Ala Arg Gly Pro Ser Leu Gly Glu Asp Thr Lys Glu Ala Asp Leu Pro
            340                 345                 350
```

```
Glu Pro Ser Glu Lys Gln Pro Ala Ala Ala Pro Arg Gly Lys Pro Val
        355                 360                 365

Ser Arg Val Pro Gln Leu Lys Ala Arg Met Val Ser Lys Ser Lys Asp
    370                 375                 380

Gly Thr Gly Ser Asp Asp Lys Lys Ala Lys Thr Ser Thr Arg Ser Ser
385                 390                 395                 400

Ala Lys Thr Leu Lys Asn Arg Pro Cys Leu Ser Pro Lys His Pro Thr
                405                 410                 415

Pro Gly Ser Ser Asp Pro Leu Ile Gln Pro Ser Ser Pro Ala Val Cys
            420                 425                 430

Pro Glu Pro Pro Ser Ser Pro Lys His Val Ser Ser Val Thr Ser Arg
        435                 440                 445

Thr Gly Ser Ser Gly Ala Lys Glu Met Lys Leu Lys Gly Ala Asp Gly
    450                 455                 460

Lys Thr Lys Ile Ala Thr Pro Arg Gly Ala Ala Pro Pro Gly Gln Lys
465                 470                 475                 480

Gly Gln Ala Asn Ala Thr Arg Ile Pro Ala Lys Thr Pro Pro Ala Pro
                485                 490                 495

Lys Thr Pro Pro Ser Ser Gly Glu Pro Pro Lys Ser Gly Asp Arg Ser
            500                 505                 510

Gly Tyr Ser Ser Pro Gly Ser Pro Gly Thr Pro Gly Ser Arg Ser Arg
        515                 520                 525

Thr Pro Ser Leu Pro Thr Pro Pro Thr Arg Glu Pro Lys Lys Val Ala
    530                 535                 540

Val Val Arg Thr Pro Pro Lys Ser Pro Ser Ser Ala Lys Ser Arg Leu
545                 550                 555                 560

Gln Thr Ala Pro Val Pro Met Pro Asp Leu Lys Asn Val Lys Ser Lys
                565                 570                 575

Ile Gly Ser Thr Glu Asn Leu Lys His Gln Pro Gly Gly Gly Lys Val
            580                 585                 590

Gln Ile Ile Asn Lys Lys Leu Asp Leu Ser Asn Val Gln Ser Lys Cys
        595                 600                 605

Gly Ser Lys Asp Asn Ile Lys His Val Pro Gly Gly Gly Ser Val Gln
    610                 615                 620

Ile Val Tyr Lys Pro Val Asp Leu Ser Lys Val Thr Ser Lys Cys Gly
625                 630                 635                 640

Ser Leu Gly Asn Ile His His Lys Pro Gly Gly Gly Gln Val Glu Val
                645                 650                 655

Lys Ser Glu Lys Leu Asp Phe Lys Asp Arg Val Gln Ser Lys Ile Gly
            660                 665                 670

Ser Leu Asp Asn Ile Thr His Val Pro Gly Gly Gly Asn Lys Lys Ile
        675                 680                 685

Glu Thr His Lys Leu Thr Phe Arg Glu Asn Ala Lys Ala Lys Thr Asp
    690                 695                 700

His Gly Ala Glu Ile Val Tyr Lys Ser Pro Val Val Ser Gly Asp Thr
705                 710                 715                 720

Ser Pro Arg His Leu Ser Asn Val Ser Ser Thr Gly Ser Ile Asp Met
                725                 730                 735

Val Asp Ser Pro Gln Leu Ala Thr Leu Ala Asp Glu Val Ser Ala Ser
            740                 745                 750

Leu Ala Lys Gln Gly Leu
        755
```

```
<210> SEQ ID NO 2
<211> LENGTH: 140924
<212> TYPE: DNA
<213> ORGANISM: Homo Sapiens

<400> SEQUENCE: 2

gggattacag gcgtgagcca ccacacccag cccagaatgt ttattagaat gcacaattaa     60

taccagaggc agtggggaag gaaggactga gcagaggagg aagttgagtt gtgattcaac    120

ccaacaactg cctggctggc atggggagct ctggagttaa atagggccat cagactttcc    180

cagtgtgggg ccaacatgac tgggtcttta taccccccacc tctgtcagtc actcaacgtg    240

gtctccctgc aacaaggtga ctcttgcagc cgagacaatc cctgaaggga cagaggctga    300

agcctgtctg ccaacagcac tcccagtggc tggaacaagt ccttccctat aggggaatct    360

gggcggcaca cctccatctc catgtccatc acatacgata tcacagacat ttaaatattt    420

tgataactgt acataagagt ttcctttata atcttataga tcttatttta tgcatttgaa    480

aatattcttc tgagacaggg cttttatcat attgccatag ggtgccacga tataaaaaag    540

gttaaatact ctctgattca gaagtatcca atgatgactt ctctctcatg catttaattg    600

aaaatctggt tttctcctt ctctgctagt tctctacctc tctccccacc tcccacatca    660

tagcctattc acatatgtct gaatctcatg atagacaagt tcaggttctt ttcccaggtt    720

ctttttacca catcccccca cccccacata aaaagtatat atggcacagc ctaggttcca    780

cccaaatcct ttctcctctt cttcctgggc ccacaactct cctacataca ttggtatacc    840

ttgcgcttag ggatggccat gtgactaagt tctaacagtg gaacatgatc agatgccact    900

tccagcctct aagacagcca gtgtgtttcc tccataagct ccttctcttc ctcccaactg    960

gagactctaa atgatgaccc tgcctcaagc aagcaaacaa caagtccctc aggggtggtg   1020

taggctgcaa atggaaggag cttgagtccc aaaccttcca cggagaaggc tggctaccaa   1080

cctggatcac tcacccaaga ctgctcgaag agttggtttg aaccattgtg ttttggggtc   1140

tatttattac aacagtttag cttgctttgt gaatagattt agtggcagag cctccaaatt   1200

ctatagatac attgatctca gtcctaaccg catctggaac accattaaat aaaggaattg   1260

caaacccaga gaaggtaatg aatttgtcta aggtcataca agatggctag gatcaggacc   1320

caactctcca gttttctttc ttctctgcta ttctgccttc tgtgatccta cataagtggg   1380

catgattgta taacatatgc ggccatgaga tttctctttc agcaagagaa agggacagga   1440

agaaagagag ggaatgcatt ttcttggcct gaattagtgt gagccattag ttacctacat   1500

tgactaaatt atctggaatg aacattcaac tctacatcac atatagttaa aatgacagat   1560

ctgcttaaga ttgtttctag catacgttat ttcaatttag gcaaatgtga ccattcagtg   1620

tgaggggacc atactgtcat taggtccctg tcagttctca attatactgt tatcttagag   1680

ggggaaaaat gtgaaatttg aatgtagacg agtgttgatt tgactgctac agtttatttt   1740

acgtatagaa ataaaataat gtgtagcaaa agcattatta caaagatgat aatgaaataa   1800

ctagtattta taatagtata atagtatagt atttataata gtatgatagt ttaatgacta   1860

tttgtcagat gttgtgtaag aaactttata cacacacaca cacacacctc atttaattcc   1920

tgtatcaatc aggatacagg acgctgtggt aacaactcct caaatctcgg tggcttgcac   1980

aacaaatgct tatttctttt ttttttttga caccaagtct tgctctgtaa caggctggag   2040

tgcaatggtg caatctcggc tcactgcagc ctctgcctcc tgggttcaag cgattctcct   2100

gcctcagtct ctcgagtagc tgggaacaca ggcacgcgcc accacatctg gctaattttt   2160
```

```
gtgattttag tagagatggg atttcaccat gttgctcagg ctggccttga actcctgacc   2220
tcaagcgatc cacccacctc agcctcccaa agtgctggga ttacaggcat gagccactgc   2280
gcccagcccc aaatgtttat ttcttgctca tgtgacatgt acttcctcga gtttttcctt   2340
cctgagatct aagctgaagg aacagctctc tggagccacg ccattctggt ggcggaaagg   2400
aagagtaaaa gtggtagaac cttgcaatgc tcttgaagcg cctatttgga atgtctacat   2460
catgtaaatg gtaatggaca agtatgtata atccccacac caaaaaaagg ggacactatt   2520
ggggacaata accacatttc aatgctgcaa gacggatatt gactgcaccc ccttccccact   2580
ttcagaaaga agaagagtaa ttttgctgaa ctccttctag agactggaaa tgtcccttcc   2640
agttggggtg attagggaag gctttggtaa aatttgagct agagtttgaa ggttaggtag   2700
actactggtg ggtgaagaaa gaacaaggac ctttgtaggc aaaggaaaac ctcagaatta   2760
cagaggtgga aaaagagttc tagtcaagcc acttcagctg gctacagagt aggtgggaaa   2820
gaaaatggga ggacaagggc tcagatgatg gggggttggg gcattggggg gacacttgaa   2880
agctaaacta aggggttgaa cttaatttag gaggcagtta gaagctttta catatttttg   2940
agcaagagag tgacataatt aaaatgatct gggccaggtg tggtggctca cacctgtaat   3000
cccagcactt tgggaggctg aggagcttgg gtcacctgag gtcaggagat cgagaccagc   3060
ctggccaaca tggtgaaatc ccgtcctact aaaaatacaa aaattagccg ggagtggtgg   3120
catatgcctg taatcccagt agctgggagg ctgagacagg aaaatcgctt gaacccggga   3180
aacaggttgc agtgagccga gatcgtgcca ctgcactcca gcctgggcaa cagagcgaga   3240
ctccatctca aaaaaacaaa acaaacacac acaaaaaacc aaaaataaat aaataaaatg   3300
atcacttctg aatactgatc taactagggg ttgcagggtg ggctgatata gggagaaact   3360
ggagagcaag gagatcacta aggtccctac atgtccagaa ccaagataga ggtcttgaac   3420
taggatggtg gcagttagaa caacaacaac aaaaagtcaa ttccaggctg agtgcagtgg   3480
ctcatgcttg taatcccaac gctttgggag gctgaggtgg gagttagaaa gcagcctggg   3540
caacactgca agacctcctc tctaaaaaaa aaaaaaaaaa aaagttagcc aggtgtggtg   3600
gtgcccacct gtagtcccag caactcagaa ggctgaggtg ggaagattgc ttgagcccca   3660
ggagttcaag cttgccgtga gctacgattg tgccactgca ctccagcctg agcaagacct   3720
tgtctccaaa aaaaggtcaa ttccactgac ttttctaagg tgtacaccat caaggggcag   3780
ctccatctcc aggccattgg ctcatgagac attctgtagt cagaaggcta gggcagattg   3840
ctttgagcaa gcccccatgg tggttctcac tcctacttct ttgggtatat gcccctctgt   3900
ttaaaaataa agttaatatg catttaaaaa aaaaaaggag aaaaaggtca gttccagaaa   3960
ctgtgtgaat aaagcatttt acttgctttt tctattaatc tataacatat gttgattttt   4020
taaaaagaat ataagagcta tgcaaattgg agcttcaaga caacttccca tctccctagg   4080
aggagatggc tgccctaaac cccctacat agaaatcatc ccactgcttg ggcttaaact   4140
tgatgttggg gaaatgaaaa atccaagcta aggccgaagc ctggggcctg ggcgaccagc   4200
agaatgagga ccactggtca gtttcaggct gaggtgcgtc ttccagggga caatctctag   4260
ctggccctta aacattcaga cttcaagctc tatttacagc ataaaggtgt ttcaaaagac   4320
gtgatacaaa taactgcaaa tgctctgcga tgtgttaagc actgtttgaa attcgtctaa   4380
tttaagattt ttttttctga cgtaacggtt agattcacgt ttcttttttt ttaagtacag   4440
ttctactgta ttgtaactga gttagcttgc tttaagccga tttgttaagg aaaggattca   4500
ccttggtcag taacaaaaaa ggtgggaaaa aagcaaggag aaaggaagca gcctggggga   4560
```

```
aagagacctt agccaggggg gcggtttcgg gactacgaag ggtcggggcg gacggactcg   4620
agggccggcc acgtggaagg ccgctcagga cttctgtagg agaggacacc gccccaggct   4680
gactgaaagt aaagggcagc ggacccagcg gcggagccac tggccttgcc ccgaccccgc   4740
atggcccgaa ggaggacacc cacccccaca acgacacaaa gactccaact acaggaggtg   4800
gagaaagcgc gtgcgccacg gaacgcgcgt gcgcgctgcg gtcagcgccg cggcctgagg   4860
cgtagcggga gggggaccgc gaaagggcag cgccgagagg aacgagccgg gagacgccgg   4920
acggccgagc ggcagggcgc tcgcgcgcgc ccactagtgg ccggaggaga aggctcccgc   4980
ggaggccgcg ctgcccgccc cctcccctgg ggaggctcgc gttcccgctg ctcgcgcctg   5040
cgccgcccgc cggcctcagg aacgcgccct cttcgccggc gcgcgccctc gcagtcaccg   5100
ccacccacca gctccggcac caacagcagc gccgctgcca ccgcccacct tctgccgccg   5160
ccaccacagc caccttctcc tcctccgctg tcctctcccg tcctcgcctc tgtcgactat   5220
caggtaagcg ccgcggctcc gaaatctgcc tcgccgtccg cctctgtgca cccctgcgcc   5280
gccgcccctc gccctccctc tccgcagact ggggcttcgt gcgccgggca tcggtcgggg   5340
ccaccgcagg gcccctccct gcctcccctg ctcgggggct ggggccaggg cggcctggaa   5400
agggacctga gcaagggatg cacgcacgcg tgagtgcgcg cgtgtgtgtg tgctggaggg   5460
tcttcaccac cagattcgcg cagaccccag gtggaggctg tgccggcagg gtggggcgcg   5520
gcggcggtga cttgggggag ggggctgccc ttcactctcg actgcagcct tttgccgcaa   5580
tgggcgtgtg tgtgtgtgtg tgtgtgtgtg tgtgtgtgtg tgtgtgtgtg gaggggtccg   5640
ataacgaccc ccgaaaccga atctgaaatc cgctgtccct gccgctgttc gccatcagct   5700
ctaagaaaga cgtggatcgg gttctagaaa agatgactcc ctgcacgccc ctccctgcac   5760
ctcccgagca gtgattccga cagggccttc actgcccctg attttaggcg ggggccggcc   5820
ccctcccctt ttcctccttc agaaacccgt aggggacatt tgggggctgg gagaaatcga   5880
ggagatgggg aggggtccac gcgctgtcac tttagttgcc cttccccctg cgcacgcctg   5940
gcacagagac gcgagcagcg ccgtgcctga gaacagtgcg cggatcccac tgtgcacgct   6000
cgcaaaggca gggttcacct ggcctggcga tgtggacgga ctcggcggcc gctggtcccc   6060
gttcgcgggc acgcacagcc gcagccacgc acggatgggc gcggggctgc aggtgcatct   6120
cggggcggat ttctttctca gcgctcggag cgcagggcgc ccggcgtgtg cgctccctgc   6180
cggaggcgcg gggctggcgc gcagggctcg cccctcactg cggcagtggg tgtggaccct   6240
ggtgggcgag gaagggggag gataggctgt gcctcctccc actcccgccc ccagcccccc   6300
tttttttccc cctcggaacg cgaggtgcca tctttttttcg gcgtgtcacg tctttacggt   6360
gccatgccaa accgggtggc cggcttcat aggacagggc ggggcctggc attaaaggga   6420
gggggacaat cagcgctgaa atcttggcgt tttgctgctg cgggcgtgag cactgggggc   6480
gttcgcccag caccttcttc gggggctctt tgctttgtct gtagaggtta cgtgatctgc   6540
gctcccagcc ctggtttctg gcttttattc tgagggtgtt cagtcaacct ccccccctacg   6600
cccatgcgcc tctctttcct ttttcgctcc tcatttccga gcccattgtt ggatctcgag   6660
gcttgctggg ttcgatgaac tcgagtcaac cccccgaccc ccggcacgca tggaacgggc   6720
gtgaccgcgc gcagcctcgt ctcggagtct gccggcgccg ggaagcttct gaagggatgg   6780
gattcgagtc tccgtgcgcg ctgcgggcgg cggcagaggg atctcgcccc tccctacacc   6840
ccaagtgtcc tgagggccac gccacaccag gttgcccagc gagggacgct ggctacccat   6900
```

-continued

```
ccggggatgg gtggggagcc ctggcggggc ctctccggct ttacgccctg ttgcttcgcc   6960

tggccggaga atgtgaggaa ggggcataag gttactggtg cttcggccac acccatcttt   7020

ctgagcccac tggactgggc gcagaggggg gattgccatg gaaaccacag gtgtccggag   7080

aggggatctt ggggctggcc tcacccctc cctgcggaga ttggggaccc tggggtaggg   7140

ggagccgcgc ccagtcggcc tcctggagga cacgggagga agccccgaac ccccgcgcct   7200

gaggctgttt ctgattggcc cctggaggcc gcagacacgc agataggcgg ccctgggtgt   7260

atttttatta atattatgtc cgtactgatt aatattattt atcttaaata aatttcaccc   7320

gtgtccaagt tcaccgcgcc cccaaaaccg agtctggggc ggcaggggga actcctggcc   7380

aacgaatcca tgcctcgccc tcctgtgatg aacctggtac gcacggtttt ctggttaatt   7440

ctatcgctga aaactggtgc ggggggcgca cttctgagac ggaagagcat ctaggagctg   7500

aatcctccac gcgggtcgcc caggttgatc tgaatttctg ggaatggctt tggctgcccg   7560

cccgggacca ggccgaccct ccttgacggt ggcgtagagg gctggagcct gggtactgcg   7620

aggctcctcg catggctggg cccgccgcga ggggttgcag agcggctcag ggatcgattc   7680

aagcatcgtc tctcctccct cgcccccaga cagagctggg cgcggggttc cccttccaga   7740

tggagcgagg gtctcggggt ggccccggaa aaggggagcc cgcggccacg gctacgtatt   7800

gccatctcgc gagcagagat gtcacctcct gcctttggag gaaagggagc ccggtgggga   7860

tgagcgcatt tagcccaatg ctgggaacaa agcgcactcc gcgcttctgc gatttcgctc   7920

cattttgaaa tgtgttggcg ctttggtggg gccgctgcgg tgggcaaggc cgggggcgct   7980

gttaatggag gaacctcagg gggacggtcc ttcgtaggaa actctatcct ggctctgcgc   8040

gcgctttaag gaaatggctt ccctccagga cctcgaggga tgcagctttt gcgcggatga   8100

cggtggggtg ctgaaccagc cggtgcgcct ctggaaatgt ctgggcacgg atcctggggc   8160

catcgacgac tcctccccat tcccagcagg cgggagctct tacattccga gcgagtgacc   8220

cctctcaccc tctggcgctc acacacctgt aactccaaac ctccgtctca gaatggtcca   8280

ggctggaagg gatgatgggg gctccgacag cgactgccta gctcacccct ctgcgtgctc   8340

aggctccagg ctcagcagga ccaatttgag ttctatctga tccccctcgg ccccttaact   8400

gacccatcct acaggagaca gggaaatgtc tttcctaccg cggttgattc tggggtgtca   8460

ttttgtgttt tgtgatggct gcttatattt actgtataag cattgtattt actgtataag   8520

cattgtatta taattactgt ataagctgct tatatttact gtataagcat ctccaaatcc   8580

tccctctacg taaacaaatt aatggataaa cagataagtg tatcccctgc ccccacccct   8640

gctacgcagg tccggagtga ctcttgaagc tcatacattc cttggccaag tttgcttctc   8700

taacagatgt ttatatagca ataacctggc ttggctcttg ggttcacctt tggacgattt   8760

ggggaagggg cttgttggct ttgctgggtt ttggatgagt gacagtccat gactgttcct   8820

gctggaaggg cgtgactttt aagtggtttc taatatcagg cattgctcct ccgacaggaa   8880

caaaagaaat ggatactgcc cataaattgt tagaaaactt agaatcgctt tgattgagga   8940

aaggttagat ttattccggt tggaaaaagt ggcctttcta ttaaacgtgc cctttgaccc   9000

tcatgccctt ggaggtcggt gccagcctgg agatgggata agattgtggt tttccttctg   9060

cctttttaac atctgttgtt acagtccatt tgttgaaaat ttaaagaaac tgttttattc   9120

cactttccct cagcatttat gtgtgtggtt tcagtagctc tgtggctata tgtacgaaca   9180

cgtgttattt ttccaattgg acatgtgata attttccaac tggaccttgc cttctattga   9240

tgtatttatt tagcatcttc cttactccct ccttgaaaaa gaatcactca aaaacaaata   9300
```

```
aaaacagccg taggggccta atacagtgct agacatacaa gaggtattcg gtccatacca   9360
aatggatttt atccatgaag gataaatggg gaaatacagt gggaagcagg tgggaaactg   9420
cgtttgactc tgctctttcc tccaccacca ctttcctcat caccgtgttc agagaccccc   9480
aaagccccct cacactccca gaaacacccc cctggccact cctaacttgc catgcccagg   9540
agttaggtgc ttccactagt gacatggagc tggcgtttgg ggggcacctc agcaggtgac   9600
gggaagagaa gaccccagcc tcaccagctg ggctgcagca gggagaggag tcctcatgtt   9660
ccagcaggga ctctcagctg ttttcctgta aaaccatggt tctcaactgg gggccactga   9720
gatgtctaga gagatgtttt tgttttcaca actcggggag ggtgctactg acatcttgtg   9780
ggtagaggcc aggaatgctg ttaaacatcc tacaaggaag gcacaggaca gtctcctaca   9840
tcaaaatatg acccagtccc aatgtcacca ctgctggggt tgacactggc actgctatct   9900
taattacatt cattgagtgt cttttaggag gccctattct aagtgcttgc taagattatc   9960
tcatttaatc ctcacaacac ttccgctatg tagcaggtgc tgttattatc tccgtgatgg  10020
ggaaactgaa gcacagagag ggttagtaac ttgctaaagg tcacagagcc agtgggtggt  10080
ggagctggtt gcctgacact agttccctcc cctctcagcc acatgtgggt ttacttggcc  10140
attgtggact agtctgggaa cccagatatg atctataaca ttgacccagt agaatattga  10200
ttccaaaacc actgtctcac aaatgaattt ttacaagagt ctgtaatcgg agcatgaccc  10260
agaataaggt tagggagatg tggagttaaa gctctcaatt tcttatctgg ccccgacaca  10320
gagagcaagg catttcactc tacattggtg ctctgtttat aaaacaaaga gcaaatatct  10380
cttcctaagg tccttaaacc tcttccccca atccagggtt tctggactgc tctgccatat  10440
gacggggcag ctggtttgat tgacccaggg aaggctggaa atcaagactg gggatcaag   10500
acgtagattc agtgtggcca aggtcaagtc tctgaggttt agggacatca gatccccagc  10560
ttaggttctg tacctcggca aggtgaaagc gttggcgccc actgatgagg cctgctctga  10620
gattgtgggt gtgggttgag ttgggtgggc ataggcaagt cctcttgtaa gaatcttttg  10680
gcaaagatgg gcctgggagg cttttctcac ttcctggggc ccaggctttg caataagtat  10740
tccattatac tgtggtacct tggggctacc tgagaatcct ctgtctcgcc cctgttgcct  10800
tgccaaagag tttgctgtcc aagaattcct ttcctgtctc caggtgccat gctcctgcca  10860
cctctgccag gttccctgcc tgcccagatg gctcccaact gagtgtgagg aggaatttga  10920
gacaggtttt gagctttctg ggttctccag ttaggaaact ttctgtaagc atgcagatag  10980
aatgggcttc agcaaaatac aaactcgaac aacttccatg tatagtccct taattttctt  11040
tgcttttttc atatttcatc aggctccatg ctgagcccaa tcagggaccc gatagaaatc  11100
caaacaccat gtcagcgagt ccccaagaaa tgcattttgt gccaaggcta ttcaaggaag  11160
gtttgggagc agctcaaggg cagacactgt taccctcccc caggtcccca gtgcagggca  11220
gtgttctgca tgtggaggca gtttggccta atggttaagg aggtaggctc tgatcgggcc  11280
tcctgggcac aaatcccagc tccctgctca ctgtgagacc taagccatat tgtttagctg  11340
cttggagagt tttttgtcat ccacaacttg gagtatgatg gtacctgtct cacgggttgc  11400
catggggttc acacaagcta acccggtact cactagggcc aagcacatag taactgctca  11460
gtaaatggca tcatcggcgg tgtcctgtgg atgagtgctt gtgattggct gaatgaccag  11520
aggggtctaa agatcctggt gatggaatca gttgtacaga taaattgtta cactgagtag  11580
ggatcaagat aggaaaagtc ggcaactacc cagctcccct gcaccaaact gggcagaagt  11640
```

```
ggatcctctg aaaattgcac acacccatgt ttaaatgtac acacagaact cttgccacag  11700
gcaagcggag atttgtcatc tgctgtccct gcctcatctt cttcctgaaa tccactccat  11760
gccaggaata aactgcatgc tctccaccag cccaaactga cctgccttcc cgccagccat  11820
cccgggcagg gtgacctggc ttagtacatc gggttcagag atctttccag tttactcgtt  11880
gaataaaaag tgagggctga tcgagaaagt aatggcagtc agggaaggcg aaggaggtaa  11940
agaagagatt ttacaaatga agtaattcaa cagagtgctg acattggtaa actggcaaac  12000
agatttcagg gtggttggtt gagagtagag tagaaaagga ttaaataaag caaacttgtg  12060
gtgtactgaa tcttaggaat tccatgtatc caataagtat agtcatttat gaattaataa  12120
attcggccta agaagccttc ttatcgctta aatcaagact aagtaacaat atatcagttt  12180
taaaaagtca ttatatcaga aaatcattta aatgatacac atagatttcc aagattttac  12240
tttaaccgaa actatataaa tgtgaatttg ttcacccatc ttttgacaca gggctcaggt  12300
cttctcttgg tgtctggatc agccagttga aatttcttgt ctgttttgcc tatgccacat  12360
taataatgca ctgtctgggt cctccgattt cagtttggat tttgggttta cattgtggag  12420
tcatctgaat gcagaatcct tcagggattt tacttttttt tttttttttc atggtcttta  12480
ccatcccatt tgatagtaaa tattactcac ctttatgaag tctttccaaa acattcaact  12540
aaattttctt aaaatcattg aatgatttga agagcttatt cctcagcact tttactccat  12600
cagcttgcac cttatttttt aatctttttt tgagacggag tctcgctcta tcgcccaggc  12660
ttaagtgcaa tggcgcgatc ttggctcact gcgacctcca cctcctgggt tcaagcaatt  12720
ccgcctcagc ctccgccgta gccgggacta caggtacaca ccataatgct cggctgattt  12780
ttgtattttt gtagggatgg ggtatcgcca tgttggccag gctggtcccg aacttctgac  12840
ccaagtgatc cacccacctc ggcctcccaa agtgctggga ttacaggtgt gagccaccgc  12900
gcccggccag cttgcacctt atttaggata tgtgattatt atagcaagtc tggtgtacat  12960
acaagatttt gaatgggcac agatgacctt tagtaagtgc ttggctgtga taagaggcag  13020
tcctgactgc agatcaggct gtgtggaccc cagccttgca tgtttacaga ccttcatgtc  13080
ttattcttac agggtatcag aagaacacct actggggaaa cttataaatt agtaaaaggt  13140
gggcattctc cccgcccatc ttctgtctgt ctgccaggac tagcacagca ctttgaagtc  13200
attcacatag aatcccaact taagagggta aaatcctcct caacagactg aaaataagtt  13260
taaattccct ttgctatatt aactcccctg aggaaagagt cttagatcaa tgtccaacac  13320
taaaaacagt tttaaatcag caagtgagaa ttaaatctga agcaattgat aataatgttt  13380
cattcattcc tctcctttgg ccccgtccac cctactgcta aatccaggca tcaaagagaa  13440
gagggacata attatctcta gtcccagctg ctggttttcc ttccagccta tggcccagtt  13500
ttctgtttta ctgagaaggc tggtgatgtt atcttgggat ctaagtctgc agtttcacca  13560
caaaaagtcc agggatgcac tttcatgctt gtgtcctcct ccctgggata gcaaggatat  13620
tagaagaccc ctggctctgt aattgcttgt catgtgctct acagacgcca cagaatgcca  13680
agaacgaagt gctgggaagg acaaattcat ggaaccgtgg gacggtgctc ctcccccagc  13740
gtaaaggaca gctcctcctc ctgaattgga gccagcgttc taaatcatgt gtcaacagag  13800
ttgtcctgga tcggatccag ttctgccatt gatttgcagg tcatttcagt ggtacctgtt  13860
tccagttgtt cttaattgaa cagtggcacc aaactattgt cttgcctcat ccccctccca  13920
tggcctgtcc cccaaaaaga gacttcttgg gtaattaatc agggcaacat caggcagtct  13980
gggcgcggtg gctcacgcct gtaatcccag cactttggga ggccgaggcg ggcagatcat  14040
```

```
gaggttagga gattgagacc atcctggctt tgtgaaaccc cgtctctact aaaaatacaa  14100
aaaattagcc gggcgtggtg gcgggcgcct gtagtcccag ctactcgaga ggctgaggca  14160
ggggaatggc gtgaacccgg gaggtggagg ttgcagtgag ccgagatcgc accactgcac  14220
tctagcctgg gcgacagagc tagacttctt ctcaaaaaaa aaaaaaaaaa ggaatctctt  14280
tggttttata tatttttttt tatatatata atatatatta aaatataata tatatattta  14340
tataatataa tatataaata tattatatat tatatatttt tatatattat atattatata  14400
tattatatat tatatattta tatatttata tattatatat atttatatat tatatattta  14460
tatatattat atatttatat ataatatata ttatatatta tatattatat attatatatt  14520
atatatttat atatattata tattatatat attatatatt atatatttat atattatata  14580
tttatatata ttatatatta tatattatat atttatatat tatatattta tatattatat  14640
atatttatat atattatata ttatatatta tatatgtata tattatatat gttatatatt  14700
atatatattt atatatataa tatattgtat atattatata tctaatatat tatatatatt  14760
atatatatta tatattataa tatatattat atattatata tatttttata tatataatat  14820
gtataatata taatatatat aaaaacatat ataatatata ttatatatta tatatatatt  14880
atatatatta tatatattaa atatatttta tatatattat atatattata tatattaaat  14940
atattttata tatattatat atatatacac atatatatat ataaatgagg ccaggctcgg  15000
tggctcacac ttgtaatccc agcactgtgg gaggatcact tgaagccagg agtctgagac  15060
tagcctgggc aacaaaacaa gatcctgtct ctacaaaagg aaactgtaaa aattagctgg  15120
gcatgatggc atgtgtctgt agccctagct acttgggagg ccgaagcagg aggatcgctt  15180
gagcccagga gttcaaggct acagtgagct atgattgtcc catagcactc cagcctgggt  15240
aacacagcaa ggccctgtct ctaaactttt ttttttaat tctatttata tttacatgta  15300
tttaaatgtg aatattcact acctatttgt tgcatgcctg catttttat actgggcttg  15360
ccaaaaaccc gaacagcttt ctactttgac aatgtatcag aatttaaatc agcaatatgt  15420
taataagcca agcaaaggtt atatatgcaa ataaaactgt tgtctataac ctcctgttac  15480
actggggcac agcaaaagtc atggtgtagt cgcatgtgaa cctgtccctt tcatagctgc  15540
tcattgccag gaaacatcag gaatagccat ttggaagagt catcagccct cccaccatcc  15600
gttttctgtc ttgtcttttc cctatgagca ggggaaattc cacgctggcc ccaatcccca  15660
gtgcagcggc tcagcctctg cctctgctgc tggtccccat gaggccagct tagaaacgga  15720
ggattttgca gaacatccct aaatccgctt gaataatgaa gtgatcattc ataaactcac  15780
ctgaacctta ttaaaaccta tttaatattt ttcctggata atcctatagg gataacttgc  15840
ctcctgggct tctctccacc gggttcagtt cttcctttag tggtgaagtt cctcccttct  15900
tagcatctca actgtgcctg agaaaaggcc agtggcggct gcactctgtt ccctgtggag  15960
tgttaataaa gactgaataa attgaaataa atccctttca atgtcattaa gtgctataaa  16020
taatcatgaa ccaatgttcg atggctgatg agaaatgcaa gaaaaaattt ttaatcagta  16080
ggattcataa gttgacaatc tgggccaagt taaaaaaaat aaaaataaaa agacttttaa  16140
aaagatctta tcgtttgtta ccagtaagac tgaattccag aagcaagcta ctccctcatt  16200
tgtgggcccc tgttatcact ggctgcttag ggttgccaag ccctgaattc atttgtcaac  16260
taagagattt ttggccaaga ttaagatttc ccatgcctcc atatttccat ctgagaaatg  16320
gagattatac tgtcttcccc ctcagaatgg atgataatgt ggtctctctt ctgttcgcat  16380
```

```
agtcatagaa ctgaaataaa acaacttaag agaattcctt tgagcttctc agaagtgctg  16440
cagggctggg ggatgcctcc caggagccgc agtcaggtgc tgatctgaag tctttggtgg  16500
gctgacttta gcctgacctg aaatagtata gctgctgcca cctggctccc ttagcgtcag  16560
tcagacggtg cagctggttc ctaggggtga gggctgagcc agcagggtcc gtgcccagga  16620
gggatgcatg ggtggccaca gcccagcctg cactgatctt gtctgtcccc ttctttggaa  16680
ggaaggagcc ccaaaccagg gtgcaagaca gtgggtgggg gtgccttgag catgacctca  16740
agtgatttcc agcccctgcc agtgctgact tctctgggga agggctggga cttccttctg  16800
ggctcaagtc acgacccttg gatggaattt cctgggagct tttctgtttt ttctggagtt  16860
ttcagttttt tcctaaccag acagggactt ggtacagaat ctcatattct aattatgcct  16920
aggagcagcc tctccccacc actcacagtg tttagcatgt gacaggaatc gattaaggca  16980
tgagtgatta aattaaagcc aggcattgac ttggatggtg taatattctg acatctgttt  17040
ggtgtcaaag gcacggggca ggcgcgttaa ttgaactgct tgcacctggc atttgaattg  17100
agccagagcg gggctaaagt cagtttgcct tcaccctgta aatggagggt ttctccggag  17160
cgtggatggt gggaggtatt tcagggtgta tgcataaccc ccaccctgac aatggcccat  17220
ctcttctcca gcgtggccag gtttgagtgc cagtcctggg tgtccagtgg ccccatagcc  17280
ttgcgtttta gtaaaatgct gcccccatta ccacctggtc tgtgcacttc ggtcactgga  17340
atttgccatc ttccagtccc gaatgtggca agccatggag ccttaagctc ttctccctcc  17400
acatcctgga acagacccgc cagtttcttc caggcattgc ctcagtttgc ccctctgttt  17460
ccagtcacac tctcaccagc gataaaatga ttttagacct tatcatctca ccctcggatc  17520
cttatggaaa caataatgag ttgttccctg tttcaattcc aaaattcata tccaatccgt  17580
tttgcatgcc attgccaaat tcctcccaga gcaaccccgt cacctgccct ggccctctcc  17640
aagtgtggtc ctgccatggg catcgcctgc taagccaagc tggcctcgag ctgcctgccc  17700
gggtccccac accttggctc acctccctgc ccagtcccgc ctcctgccag cctgccctgt  17760
ggctccttca tagatgccgt gctctttctg ccccttgctc acccatggca gccttgcccc  17820
tctctccctg ccccaccccc tatttaaatt gacctgacct tcctcagtgt ccatcttccc  17880
cgaagctttc cccagccttg gcactcaagg tccagaggct acgcgtttcc tctcacctgt  17940
ggcagcgccg tgctccccag tgcctcacag tttccttctt gcccccgctt cctgtgtagg  18000
actcatctgc ccacaggttg cacgtcctgt gagggcaagg actgtgtctt atgtgacttt  18060
ccttctccag tcacagagct gggcacatag atagctcaaa accctcttta ttaacacagt  18120
tggatgttga gaaatcaaac aggccaatgt caaatgagct ctccttattt aaatcaagtc  18180
agttctccac ctcctagcac tcagttccag tactctatat acatggaaat aataaaaaac  18240
acatttcctt tgaaacattc tataatcgtt cctttgccct acttcagacc aacttaacgc  18300
actccccatt ggtccaaatg agttttgcta tacgaagatg ctgataataa tagcagcagt  18360
ggattattct gctaaaacca ttgcctcgtt aatcctcagt cccgaggtgg ggattattat  18420
cctcattttg cagagaagca aactgagact cagagatttc acagctgggg agggagccag  18480
ctcatccctc tgtccaggcc caagctctct cccgcttgcc ttcctgcctc tgcaacctca  18540
gagcatcccc catctggttc tactgcctgt gctagtcgtg caggagccaa aagacacgtc  18600
tttagtgcta aggactggag aagccatgcc ctccagcctc tgtgaatggg tcatatgtaa  18660
catgagcctg gagaaattat ttgaaaccaa aggcaagcct ctaaaccagg ctgctgcttc  18720
atggcgccgg tgacggcaga accaaattta gtgctgtggg caggtccaca cttatcaaat  18780
```

```
agagaagctc atttttcttc cggctcacat caagcatgaa aaatgttcac acatacccccc  18840
cacacacaca tgctttccgg aggggtccat gtggctagag gctggaagat gtggatgaga  18900
ggagcctggc aggtaagccc agggaagatg acattcagct tcccagacag catctacagg  18960
gagaaattta attaaaagtg ggcggtttc cctgagcaag gcagacaaag tcagccctct  19020
actgttaaga aaaagggtca cagtgagagg ggaggtgagg agactgagtc tgtatttttct  19080
agtctgttgg gctacactac ctgatccccc ttcctcaaaa atccacttta ctttccccat  19140
gtctacacca atgtggttca cactctggga ccaggaaaag ggggagtgat ggggaacaga  19200
gaagggagga gctcacacag ctgaggctgg ggttatgcat atcgaattac ttagaatttg  19260
caacctcaca gggtactttc atggcgttga aatacacttc ccacagccac cctccctcta  19320
actaaaagca agagtcattt ctcagttctg gtcttgcctc ccacgttctc ctccacattt  19380
aagaaaatcc accagctaca aagtgaagat accatatgtg atatcccacc ctagtttctg  19440
ttttatcagg gtttggagca ggtggagcag gcagagggat catttcagcc tataaattgt  19500
attaagggtg agtactgagt cattcttcaa gaaaagtttt agaagcatcc aaaactgaag  19560
ggtggagcca cctggagaca gtatcatcag tcctggcccc gagcatggcc tgcataggcc  19620
cccatggatc ccagcgggag ctgcagagtg cgggcacctt ggcacacagc cctgagtgca  19680
aaattaggag ctgggcagag ggcatctctc tgtcgccatt gggcagccca gggcacactg  19740
gtcatagcct tagaccacga acaccctgtg cccgggggac agatgcaacc agtgtgccct  19800
gggctgccca atggcaacag agagatcgac acctggaccc catgtcacgg ggactccact  19860
actaaggctc ctaagactgc caccttccag tgggataagc cctgcctcct actgggccca  19920
caatgtgcag agaacacttg ggactacctg gctttctgga tacacaaata ttgatccaat  19980
ctggactaat tagaaggtca gtcccaataa caaatcgaag tcagctgggc gtgatggctc  20040
actcctataa tcccagcact ttgggaggct gaggtgggca gatcatttga agccagaagt  20100
tcaagaccag cctgggcaac atagcaaaac cctgtctcta ctaaaaatac aaataattag  20160
gctgggtgtg gtggctcatg cctgtaatcc caacagtttg ggaggctgag gcaggtggtc  20220
acctgaggtc aggagtttga gaccagcctg gccaacaggg tgaaaccccg tgtctactaa  20280
aaacataaaa attagccaag catgatggca tgtgcctata atcctggcta ctagggaggc  20340
tgagacagga gagaatcgct tgaatccagg aggtggttgc agtgagctga gatggtgcca  20400
ctgcactcca gcctggttga cagagcaaga ctctgtctca aaaaaaaaaa aaaaaaaaaa  20460
aaaagccatg cctggtggag cactacgtgt aatctcagct atttgggagg ctgaggcacg  20520
agaatcactt gaacctggga ggcagtggtt gcagtgagct gagatcgcgc cactgcactc  20580
cagcctgggc gacagagtga gtgagactcc atttcaaaaa aataataaat ctgagtcact  20640
ttaatattgt tatttggatg tcaacctcta ggtgtttgag acaggagagt gatatggggg  20700
cactggaaac acacaggcac ggggtgtcct cacacttggg tagcccacac gatgtgattt  20760
cagggtgctg ggaggtcccc ccactcccca aattactaac aagtggatag tactttacag  20820
tttatatgat ctcatttgat tcttaacatg agcctgtgag tgaaaaattc cttcccctct  20880
tctacagatt aggacgttga gattcaggga ggttcagagg gattcaggga agtcaagtgg  20940
cacctggagt cccgtggcta atttgaggcc ggtaggggat tcgaacccag gatttgtgct  21000
tcttatgcct gggcttctgc tccctggggc atggtcttcc ccctagcttt cccattcact  21060
gctttagcct aggggtccta ccctttatta aactgccagt gcctcactgc ttttctcccc  21120
```

caaagacaaa aaaaaagtgt ttttgctttt gttttgtttt tcatgggcag agacctggaa 21180
tttcagcttg agaatttgtg ccatatgata aataaatcaa cagatggctt tttccttaaa 21240
aaaaaaaaaa aaaaaaacta agatgtattt gcagtgaggc ataatttgta ccaaaaagtg 21300
ctcaccacac tgtagtcatg ggggcaggag gcagccgcgg gtgaagggag aaatcttgga 21360
gtccaggcag ccccttctg ggctgaactg gggagctggg ggtgctgcca gccctgccag 21420
gttctcctag gaggcggcag ctcatatggc tgtgggagga ggcagaggga gcctcatatg 21480
cacccacatt tccagggatc tagaagacag aaggaggaaa accaccatca tgttaaagca 21540
gacagttagg taacacatcc tgtaatacaa gttatttttt ccacatctaa aggctaaaaa 21600
tagttgttag aatttaaaga taattggtaa atgagtttct atccttctag tttcacatca 21660
aatggaatca tgctgccttc acatcactag tgcccgttat ttgtgtttaa tttccacaat 21720
gttgtctaat tccactcttt gggcttcccc agggatccag cctccctcac tcgcccatcg 21780
cagggagatg ctttattcat ctttgtgtct tctgtgccgg gcatagcgca tggcacagaa 21840
taagcactca gtaattgatt cacgagtgaa taaatggatg agtgggtgag ttcaatattg 21900
actacaaaaa ccctaaggcc acactggtga gtggctgcgc ctgtagtccc agctgctggg 21960
gaatctgagg caggaggatc tcttgagccc aggagtttga aactagcctg ggcgatatag 22020
cgagaacctg tctcaaatga caaaaacagg gccaggtgca gtggctcacg cctggaatcc 22080
cagcacttta ggaggccaag atgggaggat cacttgaggc caggagtccg agaccagcct 22140
gggcaacata gggagaccct gtctctacaa aaaatttttt aaaaattagc tgggcatggc 22200
ggtgtgcgct tgtagtccca gctactcagg aggctgaggc aggaggatca cttgagccca 22260
ggaaattgag gctgcagcga gccatgatgg caccactgca ctgcagcctg ggcgtcagaa 22320
cgagacctgc tctcaaaaaa acaaacaaac aacaaaaaaa aaggctttct taaagagact 22380
tgagaacaga aaggggaaca gatacataac ttatatattt atttgttcat ctttccacct 22440
tcctggaggg tggaggggaa caggtctgta tttggagttt tgaatgctaa aagtgggaat 22500
acatgtactg tttgccatga tctgttcaaa agttaagcca aatgccttag attctcctga 22560
aaactggaat gccactgtaa actataagcc ccacttcaaa gataaaagat cttgatgaac 22620
agggctgggt ctgtggactg ggcctctccc caccacacaa ggaagggtgg tgccagttga 22680
aggaaaatca cttaaatcct tgctgtctcc taataaggtg tggtcccagg tagggctgtc 22740
agaattagca aattaaaaca cagggcatct gtgaaaatta gaatttcaga taacaacaaa 22800
taattggcat aggctgcata atgtccctca aagatatcag gtcctaatct ccagaacctg 22860
taaatgtgat cttatttgga aaaggggtct ttgtagatgt ggttaaatta aggattttga 22920
gatgggggga ttatcctgta ttatctaggt aggtcctaaa tgcagtcaca ctcatccttg 22980
taagaggaag gaagagagag atggaaaaca cagaagagaa gacaatgtgg tgatggaggc 23040
agagattgga gtgaggtggc cacaagccaa ggactgctgg cagctaccag cagccagaaa 23100
agtccaggaa ccaattctct cttggagctc cagagggagt gtggccctgc tgacacctta 23160
gcttcaacct agtgatcctg attttggact ttggccttca gaagtgtgag ggaatgaata 23220
tctgttgttt taagccacca agtttatggt catttcctac agcagccaca ggaatcaaaa 23280
acagtaagta tgtcccatgc aatgtttgtg acacacacca aaaatattac ttgttgttca 23340
cctgaaattc aaatttaact gggtctcctg tattttattt ggccaaccta gttcccaggc 23400
ccaaagaaag aggcttttga aatttgcaag aaagctggtt ggagctgtca gaaagtggac 23460
tttgtaaaca cagtaccacc gaaccaattt gaactgtact acctctagac aaaagagagg 23520

```
gcagtcagac agttgttcgt gatttcttct ttcaacagtc atttgagcac ttactacaaa  23580
acagaagcta tgtgtaaggg tggaggcgtt agctgttaat caggacctcc aggctaagtt  23640
tctgtattag tccgttttca cgctgctgat aaagacatac ccgagactgg ggaatttaca  23700
aaagaaagag gtttaattgg acttacagtt ccaagtggct ggggaagcct cacaatcatg  23760
gcagaaggca aggaggagca agccacatct tacatggatg gcagcagaca gacagggaga  23820
gagagcttgt gcaggggaac tcctcttttt aaaaccatca gatctcgtta gacttattca  23880
ctatcaagag aacagcacag aaaagacctg cccccatgat tcagttactt cccaccagat  23940
ccctcccaca acatgtggga attcaagatg agatttgtta ccatatcagt taccaaccct  24000
tccagataaa tcacgtgaaa tatcgccatt aacagagtga gctcaggtgg ttcttcagtg  24060
catttctgat acctgaacct tccctgggaa tttcacagac catcaggctc tccacccttt  24120
gatagcagga tagcagggcc caggttctgc aggaggagat gttaccacag gcctgaaagg  24180
gagggagggg cagatgctac aggaagatgc tggctctgga ttcgctggag gagctttcaa  24240
gggaagtaga tacacactgt ctccatcatt tcatgtccat cacactctaa aatgctttgg  24300
acaagaagca aatgttaaag acaaatgtgg cccattttcc tgtacaaaga gggctgctcc  24360
catgccaggc tattggcact ggtgggcatg aggcttctct gctgccctgg ccggggggtt  24420
ctctcactca ccattggctc tctgacacct ggagagacca ccacccttgg gctttcatga  24480
tgctcacaga atccacactg ttggagcttt aaggagcctg gatcaactgg aacaggcagg  24540
gagtactagg acagcccagc attgccccaa aatatccagg cctgataaaa gagaaaaaca  24600
ggtagctcac aggaaaagga taaaaaaagg aggagggatt taacatgaaa aggtgcttga  24660
tctccctcat aataaaaaga ctgctgattc catccaggca agtgacagaa aaaaaaaatt  24720
taatttaaaa agactgctga taaaaccaca gcgagacact gctgctcagg gatctgaggg  24780
tgtgggcagc caggctgcca cgcatcatgg gtcggagagg aagaccacac ccctggagca  24840
gagggcggct gatctgtcag atgccctttg acagcacctc agcttccaag aattaaccct  24900
ttctatgtga gcagaggcat ccatgggggg acacactggt gaatcatctg ttatgtagaa  24960
gtctggaaaa catcaggatg gaactggtga aataagtgtg gcctctgacg gaatggagcg  25020
gtccgtctgc actgctgcgg gtgcccctca gatcctgtgg gtcagtgaga aaagcagtga  25080
ggaacaaggc aggtactgtg tactgtcctc tgcgtgcaag gaaggccagc gcatgcaaca  25140
gagtccacac agacatagcc taactctgga aggaagaatg agaatgcagt ttcagtggtg  25200
gcctctggtg gggagaaact gggtgaaggg agatgtcatt tccatttctc tactattaat  25260
tttgtattac catgcttaaa tgttactttt taccttttttt ttttttttg agacagggtc  25320
tctctctgtt gcccaggcag gagtgcagtg gtacaatcat ggttcactgc agcctgaacc  25380
tcccaggctc aagcaatcct cccacctcag cctcctgagt agctgggact ataggcacgc  25440
ataccaccgt gcccagctat tttttttaat caagatggag tttttctatg ttgcccaggc  25500
tggtctcaag ctcctggact caagcaatcc tcctgcctca gcctcccaaa gggctgagat  25560
taaaacgtga gtcaccctgc ccagccaatt gctttttaaa aaagattaaa tgcatgtata  25620
cgctcaggca tcagcacact tggaaaggat gaaaatatcc ggaagaaggg ttcttttaaa  25680
aggctcctca agtgatgctg gcaggcatga cgaatgtccc tggtcacaaa agctctgatc  25740
tggcctaacc ctgtcatgtt agagactgga gtgcgtgtgt gtgcgcgcaa agtgtggggg  25800
gatgggggtg agtgtgtgtg gtgtgtaagc atgagtgtgt atgtgtgtgg tgtgggggtg  25860
```

```
tgtgctgtgt gagcgtgtgt gagtctgtgt gtgtagtgtg tgtgtgaagt atgtggtgtg  25920
tatgtgtgac gtgaggtgtg tgtggtgtgt gagttgtgta tggtgtgtgc atgagcatgt  25980
gtgtgggcat gtgatgtgtg tgtggtgtgt aagcatgtgt gagtgtgtat gtttgagcat  26040
gtgtggtgtg ttgtgatatg tgtgtggtgt gtgagcatgt gtgtgtgatg tgtctgtgtg  26100
tggtgtgtgt gagcatgtgt gtttgtgtgtg tggtgcatgt gtgtggcgtg tgagcgtgtg  26160
tgtgcattgt gtctgtgagc atgtgtgagt gtgtgtgtgt tcagcatata taaggcatgt  26220
aactgaacac agcactttag agggctctcc tggagtcaga gggggtgggt aggaggagaa  26280
gggaggtggg ctagtgtgct gaagtatcta ctccttgtca tagtctgtga caacccagac  26340
tagcccatga gccaccctgt tccctgcatt tccaatgaga cctcggtgga catgttccct  26400
gaggtgaggc tgactgatgt catttgacga tcttgatgcc aaatcctttt atatcaaaaa  26460
caaccagaac actctctttt ctcttagtgc tttcacccag atgaccacat ttcatcctcc  26520
cagccactct gggccaggtg gcactgctgg tttgaaaggg aggtctcccc tggagtaact  26580
tccgtgggcg gattcacacc ctgcccacag tcctgtccca gtcagcccac catggtggtc  26640
tccggttcct ccagaattcc cgcttttcag ctcatcccca cattcccgga gggactgaga  26700
gcgcagcccc agggccctgc tctttggggg ccgtctctac acccagagaa gcagcaaggc  26760
attcctaggt ttctctttca gatgcagaac ttcagtgttc agagatgttc ccactggtcc  26820
tgagagggct cagttcagct ttaatgactg cgctgttgcg tgtgctctgc agagggcggg  26880
tggcccagcg tggctgactg cagttttcct gacgtggagc ccgagcctgc cccgctgttt  26940
attaattaag gatcactctg cttgcagaac cctgaactcc ccagaactgt gaggtgggag  27000
aaccccgaga ggccacctgg ccccacttcc cacctgctgc ccaaaccccc tctctgcctt  27060
cctgacagtc accccaactc ccagtgatcc ccatcaacca tctgacaagg ggactgagag  27120
ggaagagaaa ggaggggccc aaagaggaag gtaaaactgt cgggaacagc ccccaaatgt  27180
gtgacagcct tcagtggagt tgcccacttt cccttttctc ctccctgcag gacctccctt  27240
ctccccagtc ctccccaact tctgaggtta cattgagaaa agtctgcaga gaggtgccag  27300
catcacaagg tgttaaggac cacgagtttg gcattttaac agatgccaga gccacttgag  27360
aaatgtggta actaagccca gagaggtaca gttaacctcc ccagagtcac acagcaggtt  27420
catggcaaag ctggactagc acaggtgtcc ttcccctgca gatccccttc tgtgccccac  27480
atcacctccc tccagtgtct gggccacctg gagatgggcc ctcagactca cccggccaga  27540
ggtgccatct catgggagag gtctggccag gaagcatcga tatttgagat cccaagaaat  27600
gaagacttgg cctgtcagat gacagacttc ggtcatggga acacgtgatc tgttttacac  27660
atgcgtcccc tcagcagcag ctttccagaa cattcccact ttcttctgta gtgagaagaa  27720
ctctttccct gcagcctcct gcccaactcc tccttcagtg tctttgcttc agtgtctttg  27780
ataaaccatt ctgctttgca gagtgcgagc tctgccttgc agggttcgca tctgcctgtg  27840
ctgagtaacc aacgctaagg tcgagtggtc ggtcacctct cataagagct agggttgtct  27900
catgctgatg actaggactt gccctcaagg agaaaaataa atcaaaacaa aagcaaaaac  27960
agcaaacatg catctcttaa agaaggctct gagtccaggt aaatttcctt ccactgaagc  28020
agccaggctg aattcgaatt atctttgccc ctgcttaaaa actaatgcaa attttcctag  28080
agaatatcca ctaattcctg gagggggcat gggcattcct gatgcccatg agaggaccat  28140
ttgctcttcc ctcagtatgc taaataacag aagcgacatt tgttgctgga aagtatcagt  28200
gaagttaata aggtttttct tgcccagggt gagggaacag ttcccaatga caaatgctgt  28260
```

```
atgggaaggg gctgtagaac tgccagcccc tttggtccat ccgtaaagtg aactctgtgg  28320
atcctggagg attccagcgt cttttttttt ttttcttttt ttttaagaca gagccttgct  28380
gtcacccagg ctggagtgca gtggcacgat ctcagttcac tgcaacctcc gcctcccggg  28440
ttcaagcgat tctcatgtct cggcctcccg agcagcaaga ctacaggtgc gcaccaccat  28500
gcccgactaa tttttgtatt attagtagag acggggtttt cactctgttg gccaggctgg  28560
tctcaaactc ctgacctcag gtgatccacc cgcctcagcc tcccaaagtg ctgggattac  28620
aggcatgagc caccatgccc agccagcatc tttcattttt ctgtctgctt tggccctttc  28680
ctctctcact gtcttccttt tccatttcca aagtcagtcc atctcactat tagcacaaaa  28740
actgctagag cgcttgtcat tggtcatctc tccctgcacc tggctggtct gttcttggcc  28800
actgaagcgt ttcccccagc tgttgcttta atcattttat tgttattatg ccttacttaa  28860
gaaatggata tgagatgcat ttacctgtct cttcctgcca ctctgcagag ccagtaagat  28920
gtggtggaaa gggcccaggc tttggaggag ggctggctgg ggttggatct tggctgcccc  28980
ctactagctg tgtgaccttg ggtaagtagc tggacctctc tgagcctggt tcggaatcat  29040
agcacctctc tttcagggct gctgtaagga atagcagtgg tgtgtataaa gcagagcgca  29100
cagccagcaa ctggccccta gccacactgc tgagcaccta ctgtgataag ctgccattgt  29160
ggtgtgtgaa gcaaagggga aacatgcctg ctgtagtgag cttcctgtag ggcaggttgt  29220
agaaccagag gtgggttcca aggttacaaa gggactctta gtgtattagt ctgttctcac  29280
attactataa agacctacct gagactggat catttataaa gaaaagaggt ttaattggct  29340
cacattggct gggtgcggtg gctcacgcct gtaatcccag cattttggga ggccaaggcc  29400
ggcggatcac ttgaggtcag gaatttgaga ccagcctggc caacatggtg aaaccctgtc  29460
tcttctaaaa taaaatacaa aaattagctg gccatggtgg tgtgcgcctg gaatcccagc  29520
tactcaggag gctgaggtgg aagaattgct tgagcccggg aggtggaggt tgcagtgagc  29580
caagatcgcc ccactgcact ctagcctggg cagcagactg agactctgtc tcaataaaaa  29640
aaaaaaaaaa gaaaagaaaa agaattgcaa gaaataaatt attgtttatg agctatatgg  29700
tctgtggtac cttgttgtgg gactgggagt cttggcgtct ccctgaccct gcctgttgct  29760
gcagcaccgc tcagccctgc ctgctcccta cctgcctccc ctcggcctct cctgcctcca  29820
ccgggcccct ggtgcctcct ctagagacag tcctcctggg accgattgtg ttctcactta  29880
cacgaggcat ccaggactac agataaccag aggaaggggc gcccccccccg cctgccctcc  29940
tccctggcat cctcacgctg cagaggtcag agcctcatcc cagcccctta cctgccccta  30000
ctctgtggag aaccgtggtc agttcgccag gccggatcca cgaacggcct tgtggaagat  30060
ggtgagctca cacccagagc tggctccgat gaccctgtct cctttacatg tttctacctt  30120
cccctcccta ccttccccca ctgctgggcg cagagtggag gcagatgagg tttaaagctc  30180
agaagggctt aaacgggttg gggcgcagtg gctcatgcct gtaatcccgg cactttggga  30240
ggccaaggca gaggatcact tgagcccagg agttcgagac caacctgagc aacatagtga  30300
gaccgcgtct ctacaaaaaa taaaataaat aaaattagct ttgcagggtg gcatgcacct  30360
gcagtccctg ctactcagaa ggctgaggtg ggaggatcgc ttgtgcccag gagtttgagg  30420
ctgcagtgag ctatgctggc accacagcac tccagcctga gtaacagaat gagatcctgt  30480
ctcaaaacaa acaaacaaac aaacaaaaga aggcttaaag gggggctccag gtgggcttgg  30540
cagcacaaag ctatgaagtt ctatcttaga cacaagttct gttactgggc ctttgcaggc  30600
```

```
tggcctgggt acctggctgc catagacagg gaaccttcca gatgagctgc aggcgtggag  30660
cacaggagcc agggtgctct tcctgggctc tgtccacagg cagaacgtac acagtctttg  30720
tacacgtccg gcggctctgg tgcctatttt tgtttgtgtt tttcttttgt ttggggggat  30780
ggatttggtt tcccccgagc cctctgtcct cctgtcacct ggctggtgct cggcaatgtt  30840
gaccagctgc ctggctggag ttggcagtgg ctaaggctgt gacagctaac atgttcctga  30900
gtcctctcat ttcttcacca taatgccctg ttgagtttgc agatactgtc tctgttttta  30960
tctcccgggg aaactgaggc tcagagtggc taggccacct tcccatggtc cctcagctca  31020
tgagggccac acagggcatt gcggtggcct tctcctcagc cttgaccctc cggccccagc  31080
attgctgcct caaggggtct cctctgctga gccgtgcacc ttctgcctgg cagctccaac  31140
tctgtggctg tgttcagtgg ctcagcactg ccccttgacc ctccctggcc ttctgcggat  31200
gccagactgg agcactctga caaggtctgg ggtggttgta tgggtcctgt gacctctata  31260
cacctcccag tgcctgggaa tcctgcagat acaccctcct tagccgtccc taaccataga  31320
ggacatttct gaggtccccg agagagtggg gcacccctgc aggatccaac tgctgggccc  31380
aggaaggata gcagcagcat gaggggttcc attagccaca aactcacggc atggaacctt  31440
cacccacctc gcccctcatc tgctgtttag cacctggcac gccgtgtata cttactgatt  31500
attacatttt aatggcaaat tatagtggca aacgtatgca tctttgcaca attgttgtac  31560
agcatgatga acaagtcatt aatagtaaag aataaatgtg aaagtgagaa aaatctgact  31620
gccaaagttt ttactccttc cttccctccc cagactttta aatgaaagtt tagggataat  31680
cccttagttg tcctgctagt aggacttgca attaaaagaa ttgggccaag aacacttcta  31740
cgcttctcct tttaggtttg ggtgtaaatt cggggtattt ctcactgatg aaagcctggt  31800
gcagggcaga ccgtgggaag ctttcatttc cggaatggac catcaacatc ccttggagaa  31860
gaattctctt ctccagaccc agacctggtg tcctggcacc cattgggcaa gtgggtccta  31920
gaagacaaac ctggtcagag cctggaggct gcttagcatt ccccacgcac attagcagct  31980
cggagagctc aggaagccgc agcccctcct tgcctcacca gcctggatca ggacagcatc  32040
ccctggaaga cacacagggc ctggcctctg attacccagc ctggagggaa agctcaatcg  32100
agcatcatgt cacccggtgc ccccatgcag ggtggcactg gtgagacccc caagccaatg  32160
ataccacctc acaggagtgc aggcccattg tggccagatc atcttgactt ttcaagataa  32220
atcagaaatc gtatttccat gagatatccc tatttgcaag tgatggtgac taaattagaa  32280
gtttttgaat attgtaacat gttcgtaggc tgtttgtctg gtttaaactc tatctggagg  32340
aattcaagct agacttcagg aataacttct tgaggcaagg attttgagac cttagggaaa  32400
gaaggacgtc ttgggggtat tctgactgtt gtcctcctgg aagggaagaa cagagaacta  32460
gaagactgcc cttagcgaag ttcaaagcac ctaagcccgg gaccctcagc aagtgttctt  32520
gagtcacaga ttctccctga ggcgcctctt tctggctcca tagaatggct gattctgtaa  32580
ctcggtgagt ttgctttttt tttttcctcc atcacccagg ctggagtgca gtgaagctgg  32640
agtgccgtgg agcgatcact gcaacctctg tctcccaggt tcaagcaatt ctccttcctc  32700
agcctcccaa gtagctggga ttacaagcat gcagcaccac acctggctaa tttttgtgtt  32760
tttaatagag acggcccgaa gtgctaggat tacaggcatg agccaccgcg gccagccata  32820
actctgtgac tcttgttaca aaggccttat attttgctct ttgagggtgg ttttggtttg  32880
atgcctgttg gttgccatct tttaactagg gatgttttat caaaatgccc agccaaagtg  32940
tccaaacaaa ttataccta aagtttgaaa atgtctggca cttctaattc aatgcctgtt  33000
```

```
gtgccaggca ctgggctgct gaggaactga gtcccgtccc tgcaggctag ctagagaaca  33060
cacacacaca cacacacaca cacacacaca gagtggtctt acaagtcagt tttatattct  33120
acctatatgc aataaaggta ttattatgtt gaggtgcctt gatataaaaa tttttcttaa  33180
aggagaggat gcctaaaaca ggcattacct gaaacctcct ctctccagca ttggttgtct  33240
tctgtcatga ctcagggttt tcactgagaa tgggatggaa atgtggtcta aagatagggc  33300
caatgttggg actggatccc ctctgggaag tcagaccagg ctagggcagg tccttgaagc  33360
catcaggaaa agcctctgga gccagaaaca aaacaaaaaa aaaatggtgt taactaaact  33420
cagtctcaaa tcctgaatag gactcaagtc aagcaaaata attaaaggag ttagcaaagg  33480
gcaagtcaga gagaccgagc aacaccaatg tcttccggga gccctgtggc gagtgacaga  33540
gcctggactc tggagtagaa ctcatcttgt gtcttcttct gccactcgtt agctgggtga  33600
ccttgagcca agccccttaa cctcttggac cctatgttct tatctctaag taggggctgg  33660
taatatcttc ccctttgagg aatgccctct aaggggtgtt gtgaagattc ggtaaggtgg  33720
caggggtagg actcctggcc agaaacaggc acataataaa tgctaagtct ctccttctct  33780
ccacctgctg gatgctgtag atactaagga tttcgatgtg aatgagacaa aacccctgcc  33840
ttccaggagc ctttgagaat cagagaacta gacccatttc cagaacaagg ggatgcaggg  33900
tctggataaa gttttgggga tcaatagagc agagggctcc cagaggatcc catagggttg  33960
actcctaact caagggcatg agacaacccc caggaagggc accctggaag ggtccggct  34020
gtccctgatt tacttgtggg cactggggga atgcccggag ccatccagcc ctcagggctc  34080
tgtgtgattc tgggttcctc ccataaaaga taatcagatt ctttcacgtt aatgtctttc  34140
tccacctcat tgcacatcat gcagctattc attgactcag caagtatcag ctttgcatgc  34200
gaccttggcc tacccacttt agcttttagt aatagctccc ttcttgaata atacaaccag  34260
tggggaaaca gaacctaact cttacctctg ggaggcttat ttgctttgag aacatatgtc  34320
ctgcagtttt gttcatatgg cagtgaagtt tcgtgcacac actctagagc caggcagcct  34380
gggttcaaag cgcagctctg ccaggtccta actgcatgaa tttgggcaag tcgctcaacc  34440
tctccatgcc tgagtttcct catctgtaag attggagcaa tggtaatacc tgctttttag  34500
ggttgagaag agaattaaat gaattaagat gggtaaagtg cttagagtgg agctttgcaa  34560
gtagtaagtg ctatgtaagt gttcgattta aaatgaaaga cccttaaata cattctttgt  34620
tcatttcaca agcccttcat ttcacaacct tacatttcac aaccaagctc tgtctcccct  34680
ggaatccagc cataactctg ctcacaagtg tgagacaggc cccagcagag ctgcacgaag  34740
aggagagaag gcagcccccc agactcccaa ccccctgtcc aagatggcaa aaccagaaca  34800
cagcctctgt accaccccag caggtattca gaatctgcaa tctccaaagc ccacttcaat  34860
tgtaaatgta gagccacgtg cgctttaagt cacctgtcac tctggaggct cttttgctca  34920
gttcctcacc attagcaggg atgacaggga gtgcaggagt gcggtcgact cccagatatt  34980
ggagagcgct gggctagctg cccattctcc cggcctccac tcctctttgc tgtccagcca  35040
tcacttgctc tttgaaggca aacaaaacag aaaacagtgc caaaagtatg ggaagaaagc  35100
cagcttctcc cctggggtgc ctgtgatgcc atgcccaccc tccctgacca cgcagcccct  35160
gtggaccctc agggccccaa gcccccattt ccatcacatg cgtacaccca tgtgtgtcca  35220
tagccgccca tctcagtcaa taaggctgct cctgcccact tggaatagtg gtgacaacca  35280
ggagtggctt atgggaacta tcccaatggc ctgacagcat gtccgctgca aaccgctgag  35340
```

```
gtaggacact gccctcatgt ctagctgatc agcaagaggc gcagttgctt tcttaggtaa  35400
cattgctgct gtgtcctggc cattgctggg gggtggcact taatctacac cagatttttc  35460
cctcctgtat cttccaagct gcttggatct tggtgctgaa ttaggttgga ctttgtcttg  35520
tggggaaggg aggactatag accctcaacg taagcaatgg tcagactatt ctaagaaaac  35580
tcgccgaatt aaagcatgag gtaaatttag ttctgacttc tgtccacccc actgccactg  35640
tccccttta tcccatgatc ccttgctttt cttttcctcc tctctcccta tctcttgtgt  35700
ttgacgcatg ataggaattc agaaatatat gtttgtggat ttgtttattc acgtagcaaa  35760
ccatttcttg agtgcctacc atgggccagg tagaatgggc ggccccgggc tgcagtggtt  35820
tcttcagccc ctctccaggg tttacactgt gcaagacggt ttgtgatggg tcctcccatc  35880
gaggaccaca ctcttctttc tctgtgcccc ttggtcctca gtctctgacc ccacttcaaa  35940
ggcagcattc actcagggaa gctcccatac aatgctagtc agagtaaaag tttggacaaa  36000
ttgccaggaa gcagcttgtc agtatgcata aacagccttt aaaatattac tactctttga  36060
cccagaattt cacttctagg aatctgtcct aaggaagtag tcacatgcaa aagatttatg  36120
taccaagatg ttcatcaaag tgttgtttta taacaggaag tctcagaagc tggataaata  36180
tccaacctct ggaaatggtt agatagaata gtatgtagcc attagaaaat tatgtctatg  36240
gggtttaaaa tgtcatggga aaacacttct gacataaaag agcatgagaa ctgtatattt  36300
agcataatct taactatgtt ttagaatgca caggaaaaaa atgtacaaac atattcatag  36360
tgatgtctct ggtggtagga ttatgatcag taagtacttc tgtctcttca tattttcctg  36420
tatttgataa tacatgcata tgttgttttt aaaataagaa aaattttaag tttaaaattg  36480
gagctgaaaa gtgtttttag gtcaggcgag gtggctcaca cctgtaatag caccactttg  36540
ggaggctgag gcagtcagat cacttgagcc caggagttcg agaccagcct ggccaacatg  36600
gtgaaacccc atctctacta aaaataaaaa aattagccat gtgtggtggc acacatctgt  36660
aatcccagct acttgggagg ctgaggcatg agaattgctt gaacccagga ggtggaggtt  36720
gcagtgagcc aagatcgtgc cactgcactc tagtctgggc aacagagtaa gactctatgt  36780
caaagaaaaa aaaaaaagaa aagccttttt aaacagtagc agacataact atataatcct  36840
tactaagctg tcggtcaaat ttttatttat atatttattt tattcattta ttatttttag  36900
acagggtctc actctgttgc ccaggctgga gtacagtggc gtgatcatgg ctctcttcaa  36960
acttgacctc ccgggctcaa gtgatcctcc catcttagcc tcccaagtag atgggaccac  37020
aggtgcatac caccacacct ggctaatttt ttttattttt tatttttaga gatggtgttt  37080
actatgttgc ccaggctagt ctcaaactcc tgggctcaag ctatcctccc acctcggcct  37140
cccgaagtgc tggggttacc agcatgagcc actgtaccca gccctcaaat ttttaaaaat  37200
ctataagaga cattattgga caattagaga aattcacata tggacttata atagtatcag  37260
agtgtgtggt gtgatggttc tggagggaat ggactttttc tttggagaca ggcttttcta  37320
tgcccaccct tttatcttgc taacttatca tcatccaggt tccagcagaa acattacttc  37380
ccccaggaaa tttcttaagg gtgcagtatc atgatgtctg cagcaaattc tcaaatagct  37440
caggaaaaaa gtacgtgtgt ggtatgagtg tgtgtatgta tgtgtgtata tatatacaca  37500
tatatacaca tatatataca tatatgtgta tatatataca tatatgtgta tatatataca  37560
cacacataca catatatata cacacacaca tacatacatg tatttttata taattatata  37620
tgcagagagt gcaaatgttg ccaagttaaa gattggtgag tctaggtgaa gggaatatgg  37680
tatttattgt attatttgtg caacttttct taagtttgaa aattttcaaa acaaaaaatt  37740
```

```
ggaggaagaa ggcatgccag tctaccccaa gccctccatt ggaatgctga aaatctaaac  37800
aatgtgattt ggcaatttca tttcttttct gttgtgggcc agtagtcctt agatgttggg  37860
gaagggggta gtcgctgagg tgtggttgac ttaggatgga agaagcagaa gtcaagactc  37920
ccagggtcaa agtggtttgc tctgctgacc caagtgtggg aggcccagag tcagcgtttc  37980
aggtgtgcta attcagcatg gttctattca cggccaaagt ccaccctggg cacctctctg  38040
gcagcaatct tgggtgactc tactaaggcc aggcctccat gaccctatgt ctggatccca  38100
tatctccacc tctcccactg tctcaggaac ggtgcttagc tttttctttt ccctctcctg  38160
tcttctttgc cagcatgtag aaagtttaaa taattcccct ctttacaaca aaacaaaaca  38220
taccccttc agtcaaccac cctagctctc ttctcctttt cccagccaga tttttttaaa  38280
agcatcctag gccaggcgcg gtgactcacg cctgtaattc cagcactttg ggaggccaag  38340
gtgggtggat cacaaggtca ggagatcgag accatcctgg ctaacatggt gaaaccccat  38400
ctctactaaa aatacaaaaa agtagccggg agtggtggca ggtgcctgta gtcccagcta  38460
ctcgggaggc tgaggcagga gaatggcgtg aacctggtag gcggaggttg cagtgagccg  38520
agatggcgcc actgcactcc agcctgggtg acagagtgag actccgtctc aggaaaaaaa  38580
aaaaaaaaaa aaaaaaaagc atcctcagca ctttggcaac tccatctcct cccaacatgt  38640
ccctgttact ggaatccagc caggactcag ccccgatctt tctactctaa ccagttgtct  38700
cagttaacaa ggacaggttt atgctgcagt gacaaacaag atcccaaatt cttgtggctt  38760
cacacatctg gcaccacctc atcttccagc cttaggagtc atcttttagt tccttgaaaa  38820
ctctttacag ttttctgttg gggccttgtc atatactatt cccctggaat gttctttcct  38880
atcccctccc tttcaccttg ctaacttgtg cccatccttc aggtctcagc agaaacatca  38940
cttccttggg gaagttttct ccaacaccca cactacacag gtgtcccatc tacactccta  39000
tgactttgtg gtacttgtct cacttcattt tccactgcct tccccacaag gcacctgcac  39060
aagggcaagg accgtaccac tgtacctatg tcactcattg ctgtggtcac ctgcactctg  39120
gctgcctacc ttaactacac attagaatca cctgaggagc ttttaaagcc acaatgcaag  39180
actccaccct aggccaattg gatccaaatc cctggggtag ggccagacat cagtggagtt  39240
atatatacat atatatattt tgtttgtttg tttgtttgtt ttttgagaca gagttttgct  39300
ctgtcaccca ggctggagtg cagtggcgcg atcttggctc actgcaagct ccgcctctcg  39360
ggttcacacc attctcctgc ctcagcctcc tgagtggctg gaactacaag tgctcgccac  39420
cacgcccagc taattttttt gtgtttttag tagagatggg gtttcaccgt gttagccagg  39480
atggtctcga tctcctgacc tcatgatctg cctgcctcat cagcctccca gagtgctggg  39540
attacaggca tgagccactg cacccggcca tcagtggata tatttttaaa gcactgcaga  39600
gaattctgtt gcatcagctt gagaaccact gatctgcctt gtgcttcaca tttaaaactt  39660
ttttttaatg aataaataaa ccccaaaaaa ttaatctccc taagcctccc tagaagatag  39720
gatggtaagg atattttcct aggtaaaaat atgttaattt catatttcat gaaatttcat  39780
gtttcatttc aatcaagctc tgtcatacac cttacatggg gcaagcccag tgcctgggca  39840
gggtgtaatt atactcatta cacaggcaag gaaaagtcac attaggtgat ggagcacaaa  39900
taggcagtta atggtttcag ggctagttag gatatgtttg tctttcaatt gcaagtaata  39960
gaagcccaaa gaaattggtt atttatataa tataattgat tggttcccaa atttgaaaaa  40020
ttcaggaata gacccagctt aggtacagct ggatccagtc actcaaacaa tgtcacaaag  40080
```

```
aacccctttga caggaatgta tcctgtgttg actctacttt gctctgagta gtctttcccc  40140
aggtgatgat aaaaatggtc atcatcgcca ggcttgtgtc ctgtttagta ggaatataca  40200
agaagagctc agtaaatgct ggccccacca ctaagcaaaa acaaaacttt tgttgttgtt  40260
attgttgttt taaataacag cttagacctt tcttctttcc ttgttattct ctttcatctg  40320
taatccagtt ttctacttct gaagtataga atgttctgat gatttattct tcattaccca  40380
caacttgcac atgtttattt aaaaatgcca ggattgcctg gccgttgtgt gctgttaacc  40440
tttgtttgct gttagtggat ccctgaagtt caggctccca ggggagcaga taatgggtat  40500
ccagttcctg caatatccac cctctggcaa gccaagttcc ttcctgggta aggttttgcc  40560
tacctgcatt cctagggaag tttctgggcc tgaccaccaa gccagctctg agaaggggtg  40620
cataagcccc accatgcttt ggctctgtcc ctatagaata ttttatgttg ttactgaaaa  40680
ctaaaggaag atgggtgcgg tggctcatgc ctgtaatccc agcactttgg gaggccaaga  40740
cagattgatc actcgatgcc aggagttcaa gaccagcctg gccaacatgg tgaaaccttg  40800
tctctacaaa aacaaaacaa aacaaaaatt agccgggtat ggtggcatgc acctgtggta  40860
ccagctactc aagaggctga ggcacaagaa tctcttgaac ctgggaggta gaggttgcag  40920
tgagccgaga tcgcactact gcattccagc ctgggtgaca gagcaagatt ctgtctccaa  40980
aaaaaaaaaa aaaaagaaaa ggaaagctaa aggagagaga ctaaaatgat atcaggttcc  41040
tggagaacaa acagacatga ttttgcttca tggcaggaca gccggaagaa gtgggattat  41100
atcctcacat tacaaataag aaaactgaga ctcagaatgg ttaagtcact tgtcccaggc  41160
cacacagcca gtaaattaca gaaacagaat ttgaacccaa atcttccagc tccaaagctt  41220
gtgttctttt cactacctcc tgcttaattt tttaatttct aagattagac ccttcatcta  41280
tccatgacac ctgcctgtca tcccctgaaa aaaggtgaac gccgttcaga aatttttcta  41340
gcctgagctc actcccagtt cacttatttt tgctttgtca tggctgccca gtccccactt  41400
gtagaccagg aataggtcat ggctgcgggg actacacgct gtcgctgctg caagggccgg  41460
cctctgtttc cggggctgag tgggggccag acctgccagg agcaccatct tctgtgggtc  41520
ctgcctggat gtcacatccc ggccccaaga agtcactgca aaccttcgta ttattgagct  41580
tcacatccta gaatttgctg tcactgtggc tgctgcatga agttgtcctg agagaaacgg  41640
gcattgtcat taacagggaa attgatggtc tgggggaaaa gtcatcctca ttctcttgca  41700
gatctatggg tgattgagac tggctgatgt tgaaggggtt tctcagccat cgtgtgccat  41760
gttatggaac agtggtgtag ccagccattt gacacccagc gctgaccttt gtttaacaac  41820
ctcacctata tatgacaaaa tgattgtcag aaataatcgt gtaatgaaat gactgtaata  41880
atggccagaa aagaaacgca gatagtaaaa tgtttctctt gttgaactct gtacatataa  41940
ttgcaccagg atttttttca aataaaaagt aaatattata ctacaaaaaa gggaaaaagc  42000
acaagcattt attaaatagc tttctatatc tttctgagtt ttgatccttt gattgcagac  42060
tgatgtaata ttttatgtaa atcattgctt ggttactaag tgaactttaa gaaaagtgag  42120
acgtctgcag aagttgccca taatttagca gctactgtat tgtaccattg atgtacggct  42180
ttattttctt gattaattat ttaaacaata taattcacaa ttttaaaata ataaatttcc  42240
acttaaaatg gtatttaaac tcagcaaaat atatcatcta tgagtaaaat ttgtatttac  42300
caagcaaaaa tattacagtt tgtggttcac atgctgtctc actgttttaa attttaaata  42360
caaaaactcc aagtaggctg ggtgtggtgg ctcacacctg taatcccagt actttgggag  42420
gctgaggcag gcatatcgct tgagttcagg agttcaagat ttgcctgggc aacatagtga  42480
```

```
gatcctgtct ctactgaaaa caattagctg ggtgtggtgg cacatgcctg cggtcccagc  42540
tactcaggag gctgagatag gaggatcact tgaaccctgg gggacagagg ttgcagtgag  42600
gcaagattgc accactgcac tccagcctgg gtgacagatt gagaccctgt ctcaaaaaaa  42660
gaaaaaaaaa aaagaaacac aaaaactcca ggtggtcgca cagaatgaca ggactgaagt  42720
aacttagctc caatttctgt cttcataatc actgtcctac cattgtctgt gcttagaatc  42780
tacttgctta atgcaggaac atgtgttctc acagagatgg aaaatgcaaa tggcgccaga  42840
agcaagctgg aaattctgaa ccattaagaa tttactctct gccaggcacg gtggctcacg  42900
cctgtaatcc caggactttg ggaggctgag gcaggcagat catctgaggt caggagttca  42960
agaccagcct ggccaacatg gtgaaacttc atctctacaa aaatacaaaa attagccagg  43020
catgatggtg ggtgcctgta atcccagcta ctcgggaggc tgaggcagga gaatcgcttg  43080
cacctgagag gtggaggttg cagtgagccg agatctatct gcaccattgc acttcagcct  43140
gggagacaga gtaagactcc atctcaaaaa aaaaaaaaaa aaaaaagaac ttactctcaa  43200
aataaatacg tgtggctgac tccacatatg gtagggccaa ctgtataact agaagttctc  43260
caaataactt ctgtggagaa aaaaaagttt attaaaggtt aacttttttta aagtgctaac  43320
tagaacctta ctaacactga gatcgcacca attgtttata acttagacag ggccgggtgc  43380
agtggctcat gcctataatc ccaacacttt gggaggccga ggcaggtgga tcacttgatg  43440
tcaggagttc gagaccagcc taaccaacat gatgaaaccc catctctact aaaaatacaa  43500
aaattagcca ggcacggtgg tacacgcctg taatcccagc tactggggag ggtgaggcag  43560
gagaatctct tgaacccagg aggcggagat tgcagtgggc caagatcgca ccattgcact  43620
ctagccccag caacaagagt gaaactctgt ttcaaacaaa caaacaaaaa aaaaaacctc  43680
ttggaccagg aaaatatttt ttaagggagg agtattttat cactggcatt gtttaggatt  43740
gcaggcacat gatgctaatg aaaagcagac taactattag ttggttttat tactgttttt  43800
gaactctctc tctccctttt tttttttttt gagacagagt ctctctctct gtcacccagg  43860
ctggaatgca gtgactgcag tctcagctca ctacatcctc tgcctcctca gttcaagtga  43920
ttctcgtgcc tcagcctccc gagtagctgg gattacaggg caccacacca ggctaagttt  43980
ttgtattttt agtagaggca gggtttcacc atgttgccca ggctggtctc aaactcctgg  44040
cctcaagcga tctgcccatc ttgacctccc aaagtgttgg gattacaggc gtgagccacc  44100
gtgcctagcc ctgtttttga actctctaga gacagtccag cccccttatta cttgtcctga  44160
ggcagctgct cccttcacct ggcccccccgc attgtgttcc ggacccttgt cctggtggtg  44220
ctaaagaata tctctgtcga tcctttgggg actggggaaa ctgaggccca gtgccacgcg  44280
atgccatttg ttcagggaag attaggtcat ctgctaggtc cccagtcact tgaccttctt  44340
cccagacagg aagaagctgc tctgggtctc tcagtgctcc acgtgtcttt gcacattgaa  44400
atgttttctg attttttttt tttttttttt gctgttacat ttacttttaa aaaataacaa  44460
gcaataaaat gttacatttg agaaggttga aatgagaatt gatttgagtt aaattctagc  44520
agatttttct tagaagaatg atatcatcat ctccagctac ctgcaattga tctactctga  44580
attaagaaag agacttccat ttgttgttta tattttgcac tcttgatgtg tttctttaaa  44640
ttatggtcat gggccaggtg taggagctca cacctgtaat cccagcacct tgggactctg  44700
aggagggagg atcactggag gccaggagtt caagacctcg tctgtacagt aaattttaaa  44760
aattagccag gcatggtagc attcacctgt agtcttagct acttgggagg ctgagatggg  44820
```

aggattgctt gagccagaac tttgaggcta cagtgagtta ttttcacgcc actgccctct 44880
agcctggctg acagagcaag acctgcctca aaaaaataag taaaaaataa attaaatttc 44940
aatcattagc agtcattagg atatttaaat acagtatgtt gaatcaaagt tacgcatgtg 45000
tgtatttttt tttccagaga gttgtttatc atgtgggttt taatttaact ttaaaaaaat 45060
gttggctgga cagttgccca aatggtatca tcagccattt ggttgagaac gtatgtcctg 45120
cgggctcctc tgtcactgga gttttgctag ctgacagcca ctggctagtt agagactgca 45180
gtcagcacag atgcaggcgt ggacttgcgc acgtaaccat gtcaatgcaa agccatcact 45240
tcttaaaaat tctgaaccct gctgtctgag atggtggtgc agcggataga actctgctct 45300
aagaggcagt agctaattcc atgtcttctt tgcccttgac tagctgagtg actttgcaca 45360
tggggcttgc ctctctgttg ccttgtctgc aaagtggaat catcttttcc ttgctagaca 45420
gaaggtggac cctggaccta tggccttttt gagtttcccc cccgcttctt agaaggacct 45480
ctgatcctac tgagtttaat acccacgggt taataattgg gaaaagcaaa ggaagcgctt 45540
ctgtttaggt aattatatgc atgtttttgt ctttttctgg ctggaaagat atccaagcca 45600
ctgggaaggt ccgtggctac ccagggtagc cctctctggg gagggctgct atatccaaga 45660
gcccctcatg agaatttgaa aatcgaccat ggtagggcct gctgactttt gacagctaat 45720
ggtgtgctga gaattgtccc tccaaagatg cctttccatt ccctcgggag agtctgggca 45780
gcccctactg gggctggga tgctggctct tccctcagcc tccaccccaa ctgctctctt 45840
ccctcctccc ctccccagcc ccctaatttc tctcacaagg ctttgttctg cagcaacctt 45900
tcctaatgca gtcctggcct cttcgcagct tcattacata accttccgtg gactcctggt 45960
ccaaggatca ccccagaaag ccagtcagag gtaggcacgc agctggggtc catttactta 46020
ccttccccac cccctcggaa ctcagaggtg gtgcaggaat ttggactcca agaattaaca 46080
gctccaccac catcaccaga gccaaaactc aggatgcatg tgcttcatct gctgcttatt 46140
tccagctgag agccagtggt gccatggttc cttagggagc cggtcccctg atgccggctc 46200
ctggccccaa atctctctga tccgggctct tccagaatgt cttgtctcca ccatcgcctt 46260
tgaccaatgg tgtccctttg cctggtaatg tccccttttgc ctgatgatgg ccctgtcact 46320
cctctcttta gcacagagga ggctgtttca tcccttcaag cctgccctcc cttcaagtct 46380
tagctcaagt tcaccttctc cgcagagcct tctccaatct tcttgactac gtctcctctc 46440
agctccagca acctctgtct ctggcactga ttccttactt agctaagaga atcacagaca 46500
cttggggctc aggacaatct gctttctctc ttcttaccca tggccttgga ctgtgtgtac 46560
ctctttgtct ccactcccaa acccaacccc cagagggcag agagcatgtt gtctgtccct 46620
ttgctcagca tgaagccatg cgtgtggtag atcggcagag ttccataact tgtgttgacc 46680
gaggggtcac tttgctctga aattacccct gtgtccttca gtatttgcac agatagcttc 46740
ctggccagac cgaatatatc caagggcatg gcccacctct gctcctgttt ccaggtccct 46800
ggtgggggtt agttcatgcc ttcctcataa tctgcccact ggcctggtcc tcaaggtctt 46860
cccaactgct cagccagagt tgagaaaatg ggtcgctcca tcctgtttgt gtcgttctct 46920
ccttcctggc ccactctcct gcccacaggt atccaggggc tgcctgtagc attagaggac 46980
atacatgcac atgcgtgggc atgggacact cacgtagcct ccaagcacag catcaataat 47040
gcattctgtg ctttatagca tggaaagctg ctctaaactt tattacacag tggacatgtc 47100
tgaagcagct cccaaatcca cccctgagtg tgttggaatt ggcaagccta tcacttggga 47160
gtctagtttt tttgttcgtt aataatagat gcttcctgtg gccccagctt ggcaattttg 47220
atttaaagtg atcttaactg aagagactaa tggacgggtc tgaatttgtg ccttttaagc 47280
acaaagtatt gctcttaatt aactggattc tatcctttga gcaggcagag gccttccccc 47340
aagggcgtca ttaacgatcc acatctggac atcttccaaa gccttcttct gtttcaggcc 47400
aaccgcaggt gtgttcctga acacccagga ggctatgaga gccacatatg cctcccaaat 47460
acacacagtg tgcatgccca gggacataga gcagtgtgca aagtcccatt ccatctctct 47520
ccacctggga gaggatggct cttctgtctg attcatggct caaagtggta aaggagctcc 47580
ccactccccg tcccacgcct actcagagtc tgcaaatatg tatgcgatat gagagctcgt 47640
cagttagctg tcttcagtgt ggcgcacatt tgaggagtct gactcccctc cagcacaggc 47700
caatgtgcac tgctctccta tctttgtacc cccactgttg cactgtgcag aggttggagc 47760
catagaagta ccagagctgt gaaaggagag gccccctctc acctctgccc tggtctccat 47820
ccccactttc tctaggaagc tagtaggtgc tgacagggga gagaagggag gggaggggtc 47880
cagaaacagt ggctcatgcc tgcaatccta gcactttggg aggctgaggc aggaggatca 47940
tttgaggtca ggagtttgag accagcctgg gcaatgtagc aagaccctat ctctacaaaa 48000
agaaaaaatg taattagctg ggtgtggtgg tgggcacctg tagtcctagc tacttgggag 48060
gatgaggtgg gaggattgct tgagcccaag agtttgaggt tacagtaagc tgtgattgca 48120
ccactgcact ccagcctggg caacagagct gagaccctat ctcaaaaaaa gaaaaaaaaa 48180
aagaaaggag agagagagaa agaaaagaaa agaaaaaaaa aaaagaaggg aagggaaagc 48240
ccagaagagt gtggggagag gaggcggccg tcattctggg gccctcagtg tgcacaacca 48300
gataacacat gctctgtggg cttttgtacc attttgcttg agcataaaga aaggaaggct 48360
gcccctaaat agaaagcact ctggaggcaa acaaatctga ctccaatcct ggccctgcca 48420
ctttcccagc tgaggactta gacaagcacc ctagcctctt ggacattctc agagccatct 48480
gctgcaagtg ggtgctgcca tacccacctt actgggcagg cttgggggac caagggtggt 48540
aaatggctca gtctttcatg atgcggccac acagcaggtg cgccatccag gtccatttct 48600
ttccttcctt tcccccaaat caagttgtca ttaaagtact agtccacatt aatgaaatca 48660
actgtattaa ttttctattt gctgctataa taaatcatca gaaatttagt ggcttaaacc 48720
aacacaaatg tattacctta cagttctgga ggccagaagc cctccatagg tgtcactggg 48780
ctgaaatcaa ggttttggca aggttgcggt cctttctgga gggtccaggg gagaatccat 48840
tttcttcctt tttccagctt ctaaaggttt catgcattcc ttggctcatg atcttctata 48900
gctatagtca gaaaaatttt ccatcaatca tcttcaaagc cagcaatggc aggatgagtc 48960
ctcacatcac cttgctctga caccagttct ctgcctccct cttccacatg tcaggaccct 49020
catgattact ttgggctcac tctgataatc tgggatgatc tctctatttt agagtcagct 49080
gactgggaac cttaattcca tctacaaccc caattcctct ttgccatgta cagtgacata 49140
ttcacaggtt ctggggatta ggacgagcct gtctctgaaa ggctacttta catgaaaatt 49200
catttttta attaagattt ttttttcctc ttgagacaag gtctcactct atggttcagg 49260
ctggagtgca gtggtatgat cacagctcac tgcagcctcg acgtctctgg gctcaggtga 49320
tcctcccacc tcagcttccc tagtagctgg aactacaggg gtgagccccc atgcccagct 49380
aatttttttt ttttttttt tttgagacag agtctcactc agtcacccag gctggtgtgc 49440
agtggtgcaa tctcagctca cagcaacctc cgcctcctgg gttcaagtga ttcttgtgcc 49500
tcagcctccc aaggagctgg gactacaggt gtgcaccacc acgcccgact aatttttgta 49560

```
tttttagtaa agatggggtt tcaccatgtt ggccaggctg gtctcaaact cctgatctca  49620
agtgatccac caacctcagc ctctcaaagt gctgggatta caggtgtaag ccaacatgcc  49680
cggccccagc taatttttaa atattttttt tgtagagatg gggttttacc attttgtcta  49740
ggctggtctt gaactcctgg gctcaagcaa acctcccacc ttggtctccc aaagtgctgg  49800
gattacagca tgagccactg cactcggcct taagagaaga tttaataatt aatactttac  49860
aacaagatct ggaagaggtg ggatgagtaa ctaaatgagg atacaagtaa cccgggtcat  49920
atttgctaat acccttggtc acattgaact tgatatctta tcagattttc ctaatcagct  49980
cctttagcag cagtgttgca gcatcttatc tcattttgtt ttttgttttt ttgcctagca  50040
catgcctgta aatcactgga ttgaggtgtt tagatgtttg ttgtcctttg gatgcttctt  50100
ataaatccat atttcatggc tccctggaaa gtgctatgca aatgataagc tgcaaggatg  50160
gaaaggaaat tgcagtgctc ctgaattgta aatgggcttt tacgaggagg tttctaatta  50220
ctcgctcttt ctcttgaact gaggagttga agtgtaggtg gcagatccat aacagataat  50280
catgtgtgtg atgtgacttc agcctgagcg tcgaggacca agtcacagag caggaacagc  50340
cactctccag tgtccttggg gctacgtctg aggagaacct gggatttcat atatgacctg  50400
cactggctgg ggggctctct tgacgtaacg tgttccctct gagcatgtta cagattctga  50460
cattcttatg ttccttctgt ggagagacat gtacttagtg acctaactca ctttagcata  50520
tttttgctca tcgtttgtgt agcttaaagg aatcagataa ttacccccctc cccactactt  50580
tcggaagcac aaatgcaatg ccctagaatt gtactgggga ctcaaaaaga aaagagagta  50640
gtaaaatcta ttaaagggga caaagacagc ctatatacta caagctttct atttttatgg  50700
cagagaatgc catttctaa gtaaacagag aactgcattt gacctgcaat atcaaatgca  50760
tggatttgat gctttggaaa gcaactgttt tctgcgttaa tctgggtgtc ttccgtgaaa  50820
tgtcctcctg cctttggctt aaacactagc tttgtctaca gccattccat cctgaacctg  50880
cccaatcttg tctgaatcct ggtttcacca ctgacaagct gtgtgtcctt gggcaagtta  50940
cttcacctgt ctgtgcttca gagtcctcat ctgtgagttg gggaatctgg acagaatcta  51000
ccccataggg cgtagtgagg atgtgttgaa ttatcccaag tggctacaca gagtaagcac  51060
tcaaatgatg tcatcgttgt catgattgct gttaccagag cctagagttc attctgatac  51120
tcgagtctgt ggcccatcca gcccaggtaa ggaatagttg gaggagttgg gcatgttcag  51180
cttgaagagg agacgacagg ggatatggga tagttgaatc tgtgaagggc cccctgggat  51240
gaagaactgg catgttctgt gtggctccag ggcactgagc aggacccatt tgccaaagtc  51300
tcagggacac agtttctagc tatagacaga aaaattttct gtcactcaga ggatgaaaat  51360
agaatgagcc cccttaagag gtaatgagct ccctgtcatt ggaaggattc cagaagagct  51420
aggtaaccac tttaggtgct atcaaggggc ttttttcttt aaagtccttt ccaaaagctt  51480
ctgagattgc ataaacaata ggaagccatc ttggtgcttt aacacaaact ctccccagtg  51540
atgagggttg agccaaagcc agattggcaa gcagagagga gacttgtgta caaggagttc  51600
ctcgagtcaa ttgctttttc cttgttctag ccagccagag ggctcctgtt ggaaaacagg  51660
agaccggaga ggctgaggcc tgaccaaacc agcttctgca ggccagctgg gaggccacaa  51720
ctcctaccta cgggaaaact gaagggcatc tctattttta gattagcaaa agaaaataaa  51780
tttaagtttg agtctccttt gcaactttta aaagacatct ttattgagat gatcattcac  51840
attctataaa attcccccac tttgagttac aattcagtgg ttttagtctt ccttgatgat  51900
tttgatggtc ttttcttaag gctcttggaa gacccagaag cctctcagac acaggtgggt  51960
```

```
gtggagggcg tagcacagag gcagacttct catttcctgg gtctcccctt taatgactct  52020
cagagacccc tccttccccc tgcccctggc ttctacccca ggggtgtaga gttttgccat  52080
tttccaagca gaacttcatt tcctcttctg tgtctacact ctttgtgctt ctttcttgcc  52140
agctttttct cctttgcccg cccttccttc cttccttccc tccctccctc cttccctcct  52200
tccctctttc cctccttccc cccttccacc cttcccccct tccccccttc cctccttcct  52260
tccttccctc cttccttcct tccttcctgc cttccttcct tcctgccttc cttccttcct  52320
gccttccttc cttccttcct tccttccttc cttccttcct ggtatgtgac taatttctgt  52380
ttcaggacat aaatgttgtc caggctgttc tttggtcttt ctgttggata atggacattt  52440
ggcattgaga gaggctgctt tttctgaaat catgttcttg gggcccagaa cctaggtgtg  52500
tgcttctgac tttgttttct tcctgatcca aattctgata tgtccattta aattgatcta  52560
gacccacagg gcactgtggg acagatcctc agtggaacat gactctgtaa cgagagcatt  52620
ttgttttgtc aaaatgagaa catattattg cctttcatct gattgtaaac ataatacatg  52680
tttataaaac agtataatga gacaaaaatg tagacactaa taagggaaaa tctccctaat  52740
tgtatttctc ttcacagaga aagcccctgt tgggcatata tactctagtt tgtttatttg  52800
tttgactaca catatatgta ttcttttctt atgtataaaa attctgaaca tgcacatttc  52860
tgcaactact gttttcactt gatgatgcat ggacctctct agagtgtacg tttcttcttc  52920
cttacaaagc agttggcttc gcccagggta caccaggaca cggttttggc tctgtcccca  52980
gggtgtcacg ggaccagggg atgatctcac agggtctgcc atctgccctg cctggccgga  53040
ggctgcatcg agagggccaa ggggcaccac gtgtcgtggg tactgtcaaa caagagcctt  53100
cagagccttc cacagtcttt cttttgcttc ccagcattgc ttccccgctg gtggactctg  53160
aatctagaac tagctccagg cgcctctcca aattcagacg ggagctgggg cactattata  53220
atgcaaatct aggcaaagcc ctcccaatac caggatccag aatggggtgg ggcccctttgc  53280
cctgaaaagc tgtttagttt gaaaatacaa acaggagaca gaaaagtttg gctaaattaa  53340
tggataaagt tttaacgatg gtaaccatag tagggttcat cgacagccag cgatggttct  53400
gaacacttga catgtattaa ctcacctaat ccccacattt tacagacaat gcaaaggagg  53460
ctctgggagg ttgagtgact tgccccaaag tcgcacagct cctaagtgaa ggattcggag  53520
tggactccag gcagcctggt ctgactccct gcactgcgct gtgcttatct ctggccccaa  53580
tgccgccatg cagaagtgtc tgggggcact ttgtctctgt cagacagaat tcggagatgt  53640
gtatgcttgc cctggtatgg cacttctctt tttttgagac agaatctcac tctgtcaccc  53700
tggctggagt gcagtggcat gatctcagct cactgcaacc tccgcctccc aggttcaagc  53760
aattcttgtg cctcagcctc ccaagtagct gggattatag atgtgcacca tcgtgcctag  53820
ctaaattttt gtacttttag taaagatgtt gttttgctgt gttggccaag ctgatctcga  53880
acttttggcc tcaagtgatc tgcctacctc agcctcccaa agtgctggga ttacaggcat  53940
gagccaccat gcctggcagt gtggcacttc ttacgtgtgt tcagcggaca ctgtttatct  54000
tctgtccctc caagacggtg ctgagctcag gtcgttcatt actggcagac aactgctgat  54060
ttccaacaga attgccatcc tcttctcccc tgcgactttc agagtgtgac ctcagactca  54120
aaaattagaa gtgaaaacat cttaaaaact atcacctttt cttcctaatc ctcctctccc  54180
ctccctgtct tccttgttgt ccccatctaa tgaactatca tggcaaaaag agcccatttc  54240
tggtcatttt ctgtggcctt tcaaactccc acctacccca ctgctcctgg gtgcattacc  54300
```

```
cgaaagctga gacttcagtg cagaaagtgc caggccctct gtccccccag atcgccttcc  54360
ttgtcttccc tgtgcttgcc tgtcacattg tgtgggttcc agcgctggaa ggaatgagga  54420
acagattctc tggttctcct tttgaagttt accttcgctc caccacttct gagaccttcc  54480
cggaagttgc cccttgtttc tctcctctcc agggctgccc cagagctgcc tctcacctct  54540
tcctgctgtc accccaccac catcagggca gaagttggga caaagcctct cctactggct  54600
cctgcttttc tcccttaggt ccagcctcct cttctccatc ttcaggagtc tccttctcca  54660
ctcacacgtc atgacttcag cacctcgcat cagtccagaa tatgactgct tgttcaagtg  54720
ccacctttct catgcatttt tttctagtga caatcacagc caccctgtgg ggcaggagtg  54780
tcatcatccc catgtttcaa atgaagaatt gcagttcaga gagggcaagt gactggccca  54840
gcctcaacag ctagccagtg gaccccacca gggcttctga ctccagtccg ggttcccttt  54900
ccacccaaat ccatggaggg agctgagccg agaacaggtg tccttcagga agacgtgaag  54960
ccaaagcctc cacctccaaa ctcaggggcc cagggagtcc aggcacccat ccactcacaa  55020
ggctggatat ggtgcattcc aggagagggg ttgggggcga gtggcctctc tgtgtacccg  55080
tggggataga tgcgcaagtg gcatcgccac atcgtgagtc ctggcttcat gggtgagctc  55140
caggtccaac gagaagccaa gcaggggccc cttcaagctc agctttgggc ccgggtcggg  55200
gtacagggta gagcgggcct ccccagcccc tgccatgagg ccaaggcagt gcatcgttcg  55260
cagcgtacat tcagaaacca aagcctagga gctggttatc attccggttt acagctgatg  55320
gaagagcagg tgcttccgag aacccacagt gctctttggc cagtgaccca agggtgcctc  55380
tgagaggcct cgcagcaccc ggaggtgctg ctgaggcaac gccctgactg taagaaggac  55440
cattcatcct cagagagtgg ccgtgatgct gctgcgacag tcccaccatc cctcccgact  55500
ctcactccca acagacttcc cactgtaaag ctgaactctc cagcaaatca cctctcgcca  55560
gactctctcc tcactctctc tgggtccact agaggttcct cagcctctct ttgccttggt  55620
tttcccagct gtaaaatgga gcaaagaggg cctatgtacc cacaaaggtg tggttggagc  55680
gactcctcct acattagggc ctcgagtggg gcttcatgat tggttggtgg aggtctccaa  55740
acccacccag tgccaccgaa ggctgagact gcagatgcaa tgccacaggt gtccttcctc  55800
agcctgggca gctgaacatc atgtgtaaaa cggggataat aagataataa cagccccttg  55860
cacctatgtg gctgtgagga ttaaacaaga taaatgtgta acagtgcctg gctatagaaa  55920
tatttactct tgttattaag ggaagaatat gtgtggctaa aaagggatcg aagatgtaaa  55980
agccaatccc tccccctcta gcatatttaa gggtaatgtt gagttggttt gtggaccatt  56040
tgctgcctgt tagagctgga aggtagggac cccctctcaa cagcgatgct acaaattata  56100
cccattggag gtcaaccaaa agacaaagct tattggctgg acatggtggc tcacacctgt  56160
aatcctagca ctttgggagg ccaaggcagg cggatcactt gagatcagga gttcgagacc  56220
agcctggcca acatggtgaa accccatccc tactaaaaat acaaaaatta gctgggcgtg  56280
gtggtgcaca cctgtaatcc cagctactca ggaggctgag gcaggagaat cactagaacc  56340
caggaggtga aggttgcagt gagccgagat cgcaccactg tactcaaacc gaggcaacag  56400
agggagacgc aatctcaaaa aaaagaaaaa aagacaaagc ttgttaatac cagcatattg  56460
ttaagggaat aaagtaggct gcagaacaac tggtgtaata tggtgccatg tagggaaaat  56520
tacatgtgtg cataggagag gggtctgcaa ggttgtgccc taagatgtta gagtggttcc  56580
tttgcttttc tcttttataa ttttgtattt gacttttaaa taaggaccat aaatcacttt  56640
tataaaatac attctctcca gcccctacta ctcctttaaa gaataagagt ggtttgccca  56700
```

```
agaaagacag ttttttttgc tctggttttc ttgattctga catcagagga aactccttct  56760
catccacttg gggctctggg ttcaggggat tcatttcagg cagattaaag tggtgaccag  56820
gggcattcgt ggacacaggg agggacagga gcaccatcag tttgtctcac acaaccactg  56880
tcatcctcac tgaaggctgt tgcctgatca aaaacagtat tgggccaggc acggtggctc  56940
acacctgtaa taccaccact ttgggaggct gaggtgagtg gatcacttga ggtcaggagt  57000
tcgagatcaa cctggccaac atggtgaaac cttgtctcta ctaaaagttc aaaaattagc  57060
caggcgtggt gggtgcctgt agtcccagct acttgggagg ctgaggcagg agaattgctt  57120
gaacccgaga ggtagaggtt gcagtgagcc gagatggcac caccacactc cagcctgggc  57180
gaccgagggg gactctgtct taaaaaaaaa aaaaaaaaaa aaaaatatat atatatatat  57240
atgtcaaaaa tggggtagtt tttagatcta tagtagttct aaaaacaaag gccatccaag  57300
catgacagat ttacaagcac tattggctat tccagtagtt acaatggagg agagaagctt  57360
ttagttaaaa caaacaaaca acacaacaaa cccagaaacc ttaggtcaaa accaaaattg  57420
tcctctcaga cacaatctgg gaattttctc atgacagtgg gcattagcca actgacatca  57480
gcagcaacca tccgtgtgca cacagtggca ccacctcctc ccaaaaagca gccttcatct  57540
atgccctcat acaatcgttg attattctct ttggattgag gcccggaatt atttaagttt  57600
cttcttgcca gcatgagtct ttcctttctg tatgctcctt atcttctctc tttaatttgg  57660
cagttctgct tgaaatctgg gtctttcatt agtagtagtt caatttggtt ccagaacatt  57720
ctgtggtgtg atgcaatgtg accagagctc acacttcaga gctcttcaag ggccagtctt  57780
actgagcacc tcccagtggc tgcctgtgtg ctgggcgcca cttgtggtgg gcaggagaga  57840
ggaggggaca caaaaggaga cacagctcct tcttagaagc tcaaagttgg ggaccagctg  57900
ccacagaaga gtatgtttag catctgagac accaagatcc agcgtcacaa gggtgtttat  57960
taagcctcct catctctttc tttttctttt tttttttttt tttcctcagg cagtcttact  58020
ctgtcaccca ggctggagtg cagtggcatg atctcggctc actgcatgca accaccacct  58080
cccgggttta agcaattctc ctgcctcagc ctccccagta gctgggatta caggtgccca  58140
ccaccacacc cagctaattt ttgtgttttt agtagagaca gggtttcacc atgttggtca  58200
ggctggtctc gaactcctga cctcagatga ttcacccacc tcggcctccc agtgtgctgg  58260
gattacaggt gtgagccacc gcgcctggcc ttgctgttga ttcatctata gtatgtttga  58320
cttgatgacc tccagttacc ttagacagag gttctcatct aagctccaac tttccatttc  58380
ctttgtcctc gtctttcccc ttaacccctc cacatttctc tcaaaatcac cccacttcta  58440
aaaaatactg tttattttc ttttaaattt caaattatct atactcattg aaataaatca  58500
aaatagcatg gaataagcga aaaaaatgga tcccaccctt ccccactccc attccctagg  58560
gctaaccata gttaaccatt taatgactag gtttttttgt tgttgttatt ttttatttat  58620
ttattttgag acagagtctt actctgtcac ccaggctgga gtgcagtggt gtgatctcgg  58680
ctcactgcaa cctctgcctc ccaggttcaa gcattctcct gcctctgcct cctgagtagc  58740
tgggattaca ggtgcctgcc accacacctg gctaattttt gtacttttgg tagagacagg  58800
gtttctcaat gttagccagg ctggtctcga actcctggcc tcaagtgatc tgcccacctt  58860
ggccttccaa aatactggga ttaaggtatg agccaccgca cccagccctc ctgggctctt  58920
ttcctttagt tgcactcgct ccccgctcct ggagtagagg gatttccgag agactgtggg  58980
ctccagcctt cacctaggcc caggactagg atgcctgccc taacatttat ctttatacct  59040
```

-continued

```
taaagcaaaa cagctggacc ataagcattc aagaacaaac tgtgaataag gagaaagttc  59100
tcccaggaaa caagagcttt agttatgttg ggccagccct tatattcctt agctgttacc  59160
agtcactgct tgatttaatc tcggctatca cttggcctga caggtctgct gctggtgcca  59220
ggatgtctgg gttttgaagc ctggctccat tacatacttc ctgtgtgacc ttgggcaact  59280
tactcaacct gtctgttcct cagtttcccc agctgtatta tgtcagcata atagtttgtt  59340
gtgtgaatta aatgaggtaa taactggaaa tgcttcaaac atggttccta tcatgagaaa  59400
tcctgctttc cgcctaaatg tgctggaaaa ttcctggtgg tgcagaacag gagaccagag  59460
caaaggaaag acagggtgca gaagccaaaa attaccttgg agaacaaagc gcatgttaag  59520
gttatttttg gattctaggt ttatctctgc ttggtcttca gttacctaca agagatccat  59580
ttaggggatt tttgtttgtt tttaacgata gctttattga gatataattc atatgccata  59640
aaagtcactc ttttaaaatg tttccggtat attcacaagg ctgtgcagcc ttccctgtcc  59700
ttgattccag tctgagtttt taactgaagg gataaggagg accacgcttt ccccagacca  59760
gaaccgcggg ccagggggcg attccgctga gtcaccgcgg gcgcctggtg cgcggcggcg  59820
gagcccggga ccttccttgg ctgcccccta gcgagggccg cagcgcagcc tgagacaccc  59880
gccggggccg ctccacggcc gtcggattta gactggaagc tcggtccagg tccccagctt  59940
gatgcgcccg cggtgtagga gaccagcccg actcgagctt cccctgagcc cctggactct  60000
tgactccagc agggcctggg taatgaacgt cagctcccct ttcccaaagg ggttgctctg  60060
ttgggaaggc acccgtttga tacagtagca tagagatggg ttttagcatc aaaatatcag  60120
aattcaagcc ttgctctctg cttactagct gtgtgaccct aaaaaggttt ctgaacgtct  60180
ctgagcttca gtttcctcat cattccttct cacggggtgg ttgtgagcat tacagagatc  60240
ctctctgtga agcccctgtg agtggctcat cctgagggct gaaataaaca tgttattaat  60300
aatccaaaac tggcaaggga tgttgactgg tccccctccc ttgcccaagg agctttctag  60360
aacctgagtt atcattacca aactgtactg ccttgagtaa gaaagttaga aggaatggga  60420
aggatggtgg caggtggagg aaggcggatt ggtcatcacc tccttgcagc aagaaacagc  60480
cccagatcgt gggaaaccta cagacctgct agacagacta ggagcaaaag ctggggcttt  60540
aagaatcccc agggaggttc tcctgagaga gtagccagtt ggattttgta agcagagatt  60600
tgtttgggga ggaggtgaca acgtagggag cagaggggca aagctgtcgg gaatcctgcc  60660
ttgagggcag ggatgtgtgt tggggggagt tgggtcactg gggctcggtg gccttgggca  60720
agtttctacc tctcaggtcc tttacccacc tagggtcgcc atcctgccca cctcacaggt  60780
tacagtgagc ctggatgcac tgtcatgggc aggtgcccag gaaaatggca gacatgttcc  60840
aaacagcacg cagcattccc cagtgatgcc cagggtcacc ttggaggtgg gcgagatgcc  60900
tggggtttct cgtccacccc acaacacctc aggggacagc caaagctgtc ccttcaggta  60960
agctgcacag aagatgtgaa ctctgctgca aagactctat tctttgggag caaaagggac  61020
ccagggtctc acctgcacat ccctgtccct gagggcctag ggttcttgg aggccccagc  61080
cttggcaaaa tgaggaagaa ggtgaaggtt gtctgggccc ctgccaggct ccttcctcgg  61140
ccacgcactc cccttcctgc acacacaccc ttctccctcc accccatctc cattgttgtc  61200
agaaaagtca caataaaaag gtccatattg tctagttccc atacttttaa tttttaaaat  61260
tttatttatt tatttattta tgtatttttt gagacagagt cttaacccag gctggagttc  61320
agtggcatga tctaggctca ctgcaacctc tccctcctgg gttcaagtga ttctcatgcc  61380
tcagcctccc gagtagctga gattacagat atgtgccact atgcccagct aatttttgta  61440
```

```
tttttagtag agacggggtt tcaccatgtt ggccaggctg gtctcgaact cctggcctca  61500
agtgatctgc ctgcctgagc ctccggaagt gctgggattt caggtgtgag ccaccgcact  61560
cggctccaca cttttcactt attaaaagac tgtggtgtcc atcaatggat gaatgaataa  61620
accaatgtgg actatccctc ccattaccca aggaatgaag cacggagccg tgccaagatc  61680
tggattcaca gtgaaagaag ccagtcacca aaagccacgt gctgtgtgac ttcccttata  61740
cgaaatatcc agaagagata catccatggt gacagaaagt agatgagcag ctggggactg  61800
gcgaagggga gaagggggag cagctgtcta tgaggtccag cctttcttct gggtttggtg  61860
agaatgtttt ggaactagat agaggtgata gttgtacaac attgtgaatg tactaaatgc  61920
cactgaatca ttcattttaa atcgttcttt acgttgcatg aattttaagt caatcaaaaa  61980
cagttgtttg aaaagagaaa agcctatggg tagcggcagc agtgattgga tttatgattc  62040
gattccatgg ctcatccctc ccctgcctca ccccctcgcc ctccgacgtc ttcttctttt  62100
actctgaact gttatctttg ttctcatctc tctctctctc tctcaaccct gcagacactt  62160
ttccctttct ttgtctgccc ccaccctcca gatttccgtg tctccagtgt ctccctacga  62220
ggcatgaatt gagactggga gggtgtgatt ctgaagaagg caccaacagt gactcagcta  62280
gcccctttccc ccaccccgcc ccccgggcct caatttagct aaaaaaccac agggacggac  62340
tcaggaggca ataccctttcc aagggtccct aaaaaatgtc ccattttagt gtccaggttt  62400
cactcaactt tagtgcctcc cctaaaatgt gttccttacc tcccacccca ctgcatctaa  62460
gtcactgcct gagaaaacag gattgaggaa aggagaaagg aagagagaga gagaggagga  62520
gagagagaga gagggaggaa ggctgatgga tttagaaaag aagaaaacaa gtggtctgag  62580
gaaaacagcc ttggtgtgtt tattttcctg tctgtgtatc gcttctcggc cttttggcta  62640
agatcaagtg tattttcctg tctgtgtgtc tcgcttagat tacagggatc tgtgggtgat  62700
gacacgtctg gtccaggctg cgtagtcacc tcaagggcat gcttattgat gtgtttttca  62760
attcactatc tttgcatggg agtcccaggc caagaggcac agctgcgcca tttgtctgtt  62820
ggtttagata tcctttatcc agttcttcca gagaaatcat cctgcccttc tggaggaggt  62880
gggcagcagg ggtcagagat gggagggaaa ggaaggagcc aggtccttgg ctaggatgcc  62940
agggtcccct gcctctcacc tggcctgggc tggaggcctc ctgctgtcct gtcactgatc  63000
actaccccgc cccagcctcc tgagttagaa gacacaggct aaagtagagt atttcttcat  63060
tgaaaaaccc atacaaaata aaggttcata aaaaataaaa atttagactg ggtgctgtgg  63120
ctcacacctg tgatcccagc actttgggag gccaaggcag gtggatcgct tgagccctgg  63180
ggttcatgac cagcctgggc aacatagtga aaccccatct ctacaaaaaa tacaaaaaat  63240
tagccaggca tggtggtgca tacctgtggt cccagcttct cagcctatgg acccacatag  63300
aatacaatgt cagcataaga agggagccct ggggtcacca aatggtttgg gcggcaaaga  63360
acctgaaggt tgagagaagt ggcttggtta cccagctgtt ggatgtgaga cctggccact  63420
gcttcttcca taccctagac ctgcaccctg acatctcaag taaaaagttg ggggatgttt  63480
tatggtccag gatgaaggaa gggcagtgag gggcagcgga gcatcacttt gcatttctgt  63540
ctgcctctta ctggctgtgt gacctggggc aggtaacttc ccagactcct gggaatcata  63600
acacctatga tgatgatgat gatgatgatg atgatgatga tgacacctac ctcaaggatt  63660
gccctgaagg gtcacagaga tgcctgcaag gcacctgcat ggagcaagcg cccccttctct  63720
ggcaggtgct gggtgagcac tacctgctgc caggccctgg ggctatggca ctgcgtgacc  63780
```

```
ctgcaagtcc tacctggcga agctgtcgtt cttgtgctca gtcagtgttg gttgtaagac  63840
tgagaagagt cacttcattt tgctctccag ggacatcttt ctgggtccta ttttctgcct  63900
atgtcaagta gcgcctcaag gatgctcctg aaaatgggct tgtctttctt aacatggcag  63960
gtaggtccca aagcattagc atggggcagc tgacctagcc cagccaatgc agtgcagtga  64020
ctcttgcaac cgagtctaat cagaaggtcc atgaacctac gagcatttcc tgtcccagga  64080
tcagggtgga ggctgagcct ccctgcttag agattcttcc catgcattcc actttttcc  64140
ccaaaagaaa atattgaccc ttgagaggca cacagtttat ttattttgca tagtaaatag  64200
tagcctgtat tttaaggatg agttgatttc tgcatcagcc cctgtaggtc atcagccttc  64260
tattggtgca tctgactctc tctagccctg cagggatggt ggagggggag gggaaggagg  64320
gatctttatt ggaaaccagg acagtgagac tcattgccct gtcatctgct ctgtggtgct  64380
gaatgaggca gcccaacaga gaaataccct gagcgagcat ccccagcctc caaaacagtg  64440
gcgcattgcc ctgagtcctg ggaatgacct ttgattctcc tgctcctgac ttggaaccca  64500
tggaaacctc tagaagcagc tgaggaaaac ccaacatgaa aagcagaact ccacactgag  64560
aatataggag gtgatcggaa catacaatga ttcttgctaa gaccgattca cagtttttct  64620
tttttttcga tcgaagaaat actggagaag cctaaagaag gagtctaaaa actctggcac  64680
gtgggccaaa actgtccttg agctaagaat gattttcaca tttttaagtg gttgaaaaat  64740
gaaataaaat aagatgatgt tttgtgacac atgaaagcta tgggaaattc aaattctaat  64800
atctataaat agtgttttat cagaacacag tcatgctcat ttatttatgc tcgatggctg  64860
ctttcccgct acaattacgt tgagcagtta caacagagac cacgtggccc acaaagcctt  64920
acaatattta ctatctggcc ctttccagaa aaaaatgtgc cgactcttga ccttaacctc  64980
agcaatttgg gaggccgagg caggcggatc gcttgagctc tggagttcat gaccagcctg  65040
ggcaacatag taagactcca tctctacaaa aaatacaaaa cattagccag gcatggtggt  65100
gcacacctgt ggtcctagcc actcgggaga ctgaggtggg aggatcgcct gagcccagga  65160
agtcgaggct gcagtgagct gtgatggcac cactgcacct cagcctgggc gacagagcaa  65220
gaccttgtct ccaaataaat aaataatgca aagtaaaata aataaaacca tataaaaagg  65280
aatcaattta aaattataat gaaagctggc cgggcatggt ggctcacgcc tgtaatccca  65340
gcactttggg aggctgaggt gggtggatca cgaggccagg agatcgagac catcttggct  65400
aacacggtga aaccccgtct ctactaaaaa tacaaaaaaa aaattagccg ggcacagtgg  65460
cgggcgcctg tagtcccagc tactcgggag gctgaggcag gagaatgtct tgaacccggg  65520
aggtggagct tgcagtgagc cgagatcgtg ccacttgcag tccagcctgg gcgaaagagc  65580
gagactccgt ctcaaaaaca aaaacaaaaa caaaaacaaa aaaaaattat aatgaaagcc  65640
aaggggcata gtagaacaaa ttttctagag ctcattaagt caaatgagtc accagttagt  65700
aaaacgcagt cacggggaag agagggcagg attctttgaa gcagcggctc tcctaaaaac  65760
aacccaccct tgtccagctg ccttccctcc tgagggtgtt ccctttgact gtgtgacccc  65820
catcccctat ttcccaaccg tccaagccca cctctagcat aatacgagct tttaatccct  65880
ctccctgacc ccaacccgat tttgaagccc agtctagtat tttctcaaat acacttcttg  65940
gctccattcc ttcctttcca tcacctctgc cttttcactg catgcttgga ccactgcagt  66000
cagctcccta tgaacagttg ctctctaccc atccaatcgg ccccgcctgc tgctgccaaa  66060
ttcaccgagg gcacctctgt ggtgctgcct gtggacaaag tccaagccag ccacctcacc  66120
cacctacagg tgagtgggga gcagccagcg tgtccagtgg tttaccccat cgccacagac  66180
```

ttggtgatgt gtcgatgtgc agagaagggg tgttggcagc cacaacacaa gcaaccccgc 66240
cccatgtgag atctaagatg ggcgtgctgg gagccacctc tgagaatcca acagaaggca 66300
gaggggagaa cggctcacac ggcacaaaca ctccttcctt tttttttttt ctttttcctt 66360
tttgaaagga gtctcactct attgcccagg caggagtgca gtggtgcaat ctcagctcac 66420
tgcaacctcc gcctcctagg ttcaagcgat tctccagcct cagcttccca agtagctggg 66480
attacaggta cactccacca tgcccggcta atttttgtgt ttttagtaga gacggggttt 66540
ccctatgttg gccaggctgg tcttgagctc ctgacctcag gtgatctgcc tgccttggcc 66600
tcccaaagtg ctgggattac aggtgtgagc catggggcct agcctccttc catttaaatg 66660
tatgcctaat ttgcccattg agaacggctg agacgcattt taagtggcca gggtctactt 66720
agagttagtg ctcatgacca ggcccaggtc aagcctggct ggccagatgg tgcctttgac 66780
ctgctctgtc tctgtgcaaa ggaatgagct gaaggatggg ggtgcagtgt gtgggcagtg 66840
ggctggggct ggcaggactc agtgactaag ggaagagaac tttcctcact accagcctgt 66900
cttttcaggg caccgcgggg ggctttggga cttggtgatg aacacagcac agagagctgt 66960
ccagcatgcg ggtccctggc ttctcacact tcccaggctc cttcagaggc tctctccaaa 67020
gggagctgct ctctctagaa cccatgaatt tggaatatag gcaaccactg cattggggac 67080
cactgacctc aaacatagag accagagcaa atggggctca tcacgtgaaa ctcatctgga 67140
actctagcag gttcttttat atatatatat atatatatat attttttatt attatacttt 67200
aagttctagg gtacatgtgc acaacatgca ggtttgttac atatgtatac atgtgccatg 67260
ttggtgtgct gcacccatta attcatcatt tacattaggt atatctccta atgctatccc 67320
tccccactcc ccccacccca caacaggccc cagtgtgtga tgttcccctt cctgtgtcca 67380
agtgttctca ttgttcaatt cccacctacg agtgagaaca tgctgtgttt ggttttttttg 67440 tccttgcgat agtttgctga gaatgatggt ttccagcttc atccatgtcc ctacaaagga 67500
catgaactca tcattttttta tggctgcata gtattccatg gtgtatatgt gccacatttt 67560
cttaatccag tctatcattg ttggacattt gggttggttc caagtctttg ctattgtgaa 67620
tagtgccgca ataaacatac gtgtgcatgt gtctttataa cagcatgatt tatattcctt 67680
tggttatata cccagtaatg agatggctgg gtcaaatggt atttctagtt ctagatccct 67740
gaggaatcgc cacactgtct tccacaatgg ttgaactagt ttacagtcct accaacagtg 67800
taaaagtgtt cctatttctc cacatcctct ccagcagctg ttgtttcctg actttttaat 67860
gatcgccatt ctaactggtg tgagatgtta tctcatggtg gttttgattt gcatttctct 67920
gatggccagt gatgatgagc attttttcac atgtctgttg gcgaactcta gcagcttctt 67980
ttcacaagtt catggagaga ggtttcccac tgagggaatc acatctgtct gatcaaaaga 68040
ggcttgggaa atggctctcc tgttcattcc ctgaaaacct ctgatggaac cactgccact 68100
gtggcagccc cagcactggc accccagcca tgattggtgc ccagccaca tctctgctgt 68160 gagccccaga gccctggtta attaatcatc cacgtgttga tggggagagg cccattcaca 68220
aaagcgacat aaagcccagg gagacgtggc cgtggcaaga agggtgtggg actacattcc 68280
gcccccaact gagagattca gaaaccagaa aaaaatggaa aaacatactg tgctcttggg 68340
tgggaaaact aaatatcatg aagggagcaa tttttatagt tttggcctat aatacaattc 68400
cagccgaaat cccagtggaa ctttgagaat ttgcaggaaa aaaaaaaatg tctaaagtac 68460
atctggaaga caaacttaca agaaggtcaa ataattttga aaaagaaaat gatatctaag 68520
cccacctaga gaataagact tgagatccaa agctaaatca ggaggctcta gcaaaattga 68580
cagataagca ggacagagtg catggtgcat tcacctgggg aagagggcag attggtctac 68640
aaataggcct gggtccactg actttagctg ttatatttgg ggagaaactt ttcaacctca 68700
ctccatctta aacctaaaaa tattccagat gaattaataa atataaaaaa ttagaccact 68760
aaaaatgtag aagaaaatgg atgatctttc tataccatag agcaatggaa taaatcacaa 68820
aggaaaacag atttgactat ataaaactta aaccctgccc atcaaaaacc atcagaaacc 68880
aaaataaaag gcaaccaact ggagaagata gttgccacaa atatgatcaa gggttaatgt 68940
tattcataaa ttaagagccc acacaagtca ttagaataag cactgagacc tgaacagaca 69000
agcaaaaaga atgagagtgg gtcggcgcgg cggctcatgc ctgtaatccc agcactttgg 69060
aaggctgaag caggcggatc acttgatccc aggagttcca acaccagcct gagcaacatg 69120
gtgaaaccct gcctctacaa aagtcataaa tattagccgg gtgtgatggc acacgcctgt 69180
agtcccagct actcaggagg ctgaggtggg tggatcactt gagcccggga ggtagagtct 69240
gcagtgagcc aagatcacac cgctgcactc cagctggagc aacagagtga gaccctgact 69300
taaaagaaaa aaaaaaaaaa agaggagaaa aatgctgatc tcactagtaa ttaaaacatc 69360
aggccaggcg cagtggctca cacctttaat cccagcactc tgggaggctg aggcaggcag 69420
atcacttgag atcaggagtt ctagaccagc ttggccaaca tggtgaaatc ccgtctctac 69480
aaaaaataca aaaattcgcc aagcgtggtg gcacatgcct gtgatcccag ctactcggga 69540
ggctgagaca ggagaattgc ttgaacacgg gaggcagagg ttgcagtaag ctgagatcgt 69600
accattccag tccagcctgg gctacagagc gagactctgt cccagaaaaa attaaaacat 69660
cacatattta aacaactcta ggatatcatt taaaaaaaca ttaatagact gttttttaga 69720
gcacttttag gttcacagtg aaactgagtg gaaggtacag agacttcccg tatgttccct 69780
gccctccacg tacagcctcc cccactgcca acgtcctgca ccagagtggt acacttgtta 69840
caaccaatga atcctcatta acatatcatt atcacccaag ttcatagttt acattagtaa 69900
aacatcatct ttcatctata agcacaaaaa ttttttggca tttatttagg tgtatgatta 69960
actcagtgtt gacaagactc acacttcata cccacttgca ctgcatctga gaagcaattg 70020
gtgtctacag ccgctacacc ctcaacaagc ccgatcttgt ttgaaaagca attggtgatg 70080
cttctcaaaa ttctatggac aaagtcagcc gggcatggtg gctcatgcct gtaatcccta 70140
aactttggga ggccgaggca ggcagatcac ctgaggtctg gtgaaaccct gtctctacta 70200
aaaatgcaaa aattacccag gcatggtggc tggggcctgt aatcccagct actcgggagg 70260
ctgaggcagg agaatcgctt gaagcaagga ggcggaggtt tcagtgagcc aagattgcac 70320
cactgcactc cagcctgggt gacaagagtg aaactccatc taaaaaaaaa aaattatgga 70380
caaagttttt caaaaagata tttaatgcaa ctttatttgt aatattggaa catctgaggc 70440
catttcagtg ctaactatta ggggatggtt aggaaaatat ggtacatatg tggaaaggaa 70500
catttggtag ttagtgcccc tgatgtttac aaaggctttt agtgaccaac aaatgctcat 70560
gctataatct tatgtgaaaa aagcaagtag cataattgca actatatttt taatgcatag 70620
aataaaaggc tagaaggaaa tatcacagat ccttgacata cattcccaaa cctttgtaaa 70680
tccgcggatt catgaaaaca gacacatttg cacaagtgcc tgatcttttc tgttatacat 70740
tcattagaag tcaagccctg gtgccacaaa gtatctgcct tttcaaatgt gatcagaatg 70800
ttctcttttg cttcaaggcc atttttcacg aagcagtggc atttttgcct cttcatcaga 70860
gtcaccgtgt gccctggagg actgagaaca gcagagccgt tttaggatgg gacagggcag 70920
ccaggaggat tgggctcact ccctactgag tgcctcactc ccgtacagcc cccatagagg 70980
aagaggggtt caaatttatt cctcagccag atggcatgtg ccgcctgtcc tggaatttca 71040
catcacttat gatggaccaa aattccaaaa gctgaatcca tgattgtcaa agtctggtat 71100
ggcaggatgt caacagtaat cgtttctggg cagagggatg attttctctt cccatcttgc 71160
tttgtataaa tacattttct ataataaggt tgtattactt ttctcatcaa gaaatagcaa 71220
agtactgttt tactcaaaat atgaatagag ccaggcatgg tggcagctta tgcctgtaat 71280
cccaacactt tgagaggcgg atatgggagg atcactttag cccaggagtt tgagaccagc 71340
ctgggcaaca tagtgagacc cccgtcccca ctcccccaaa gaaaacccac aaagcattta 71400
tcctggatta ttcacagggg ccaaaaaaaa aaaaaaattc aggcctccta tagccatgag 71460
ctacgaatat gaaaatatgc aaatgtgtaa gaaaagccag cacatccgat ttttactttt 71520
actttcacac ctctgtccac catgttccaa gagaagaaac ttggtcattg aaaggaatag 71580
atcaaatcca aagaacaaaa ccactgtgct cattaaactt cttagtgttc acaaagcttt 71640
agctgcaggt tgaatggggc aacccgaatt ggctggctca cctgggctgc agggagcaga 71700
gatcgcgaca ctgcactcca gcctgggcaa caaagcgaga ctctatctca aaaaaaaaaa 71760
agttcataaa ttcaaagtta tgaattattt ttaaaataat aataatttac aataaagatg 71820
aggacaaagt gtgagtaaat ggtggtttct atccagctct gttgagctga agtggcatct 71880
ccctgctggg gcttttgggg aagaagggtg tgtgttgctc ttcagatccc aagcctcatg 71940
cccctactgg gccctgtggg gtgcttctca gcccaccagg agagccaccg ttggaacaca 72000
cacgtggggg acctggtggg tgccggtgtg gtgaatgggg gccacagcct gactccagga 72060
agccagcaaa ctcggagctg gaggagtcag gacacccccg atgagtcaag agttggtttt 72120
gctgccagtt gacatctgat tgaaccatct cttcacttct ccgtgcctca ctttccttac 72180
cagacaggct ctgctgatgc tgtccctctc ctgttcagtc gtgccctcac cgttaaagag 72240
aaagagcaaa ctgctgggca gcagcattga ttttttttaat gaagtggaaa gagagctggg 72300
aataacaagt cgggcccacc tcacctgcct cacctggtgg gtttatttgt tttgtttttt 72360 ttttttgtt ttgagacaga gtttcaccct gtcacccagg ctggagtgca gtggtgtaat 72420
ctcagctcac tgcaacctcc acctgccagg ttcaattgat tctcctgcct cagcctcccc 72480
agtagctggg attacaggca cctgccacat gcctggctaa ttattgtatt tttagtagag 72540
atggggtttt accatgttgg ccaggctggt ctcgatctcc tgacctcagg tgatccaccc 72600
acctcggcct cccaaagtgc tgagatcaca ggcgtgagcc accatgcctg gccgtcacct 72660
ggtggtgttg aatatgaact gctgcggtgt tggtaaatta agcaagcaga tagatgtaaa 72720
taacgcttgg gcaggaatat ggagcacggg atgaggatgg gcggccaact gttagagagg 72780
gtagcaggga ggctgagatc tgcctgccat gaactgggag gagaggctcc tctctctctt 72840
cacccccact ctgcccccca acactcctca gaacttatcc tctcctcttc tttccccagg 72900
tgaactttga accaggatgg ctgagccccg ccaggagttc gaagtgatgg aagatcacgc 72960
tgggacgtac gggttggggg acaggaaaga tcagggggc tacaccatgc accaagacca 73020
agagggtgac acggacgctg gcctgaaagg ttagtggaca gccatgcaca gcaggcccag 73080
atcactgcaa gccaaggggt ggcgggaaca gtttgcatcc agaattgcaa agaaatttta 73140
aatacattat tgtcttagac tgtcagtaaa gtaaagcctc attaatttga gtgggccaag 73200
ataactcaag cagtgagata atggccagac acggtggctc acgcctgtaa tcccagcact 73260

```
ttggaaggcc caggcaggag gatcccttga ggccaggaat ttgagaccgg cctgggcaac  73320
atagcaagac cccgtctcta aaataattta aaaattagcc aggtgttgtg gtgcatgtct  73380
atagtcctag ctactcagga tgctgaggca gaaggatcac ttgagcccag gagttcaagg  73440
ttgcagtaag ctgtgattat aaaactgcac tccagcctga gcaacagagc aagaccctgt  73500
caaaaaaaaa agaaaagaaa aaagaaagaa agaaatttac cttgagttac ccacatgagt  73560
gaatgtaggg acagagattt tagggcctta acaatctctc aaatacaggg tactttttga  73620
ggcattagcc acacctgtta gcttataaat cagtggtatt gattagcatg taaaatatgt  73680
gactttaaac attgcttttt atctcttact tagatcaggc ctgagtggcc tctctttagc  73740
aagagttggt tagccctggg attcttactg tagccacatt aataaacaac atcgacttct  73800
aaacattcta taataccatc ttttggccaa attgacttcg cctcttcctc tctctttcca  73860
aatgaaatgt gtttcatttc actgtcagac cacatggttg gggaccccac agagcacaca  73920
gccctccctc tgccttccca tgctggccct tcacccactg ctggagtgcc aggttggtcc  73980
aagggttgga ccaagttgtc tgaggttgtc tcaaggttgg tcgaggctgt ctccgcgctg  74040
ggttgtgcta caaggagccc ttctttccat gggtgtggct ggcagtgagt gctcacagca  74100
acagcccaca gtgcagcccg agggcaggat ggactcagtc cctgcctcca tacccatttc  74160
taaggaggca aaatggcaaa cactctactt ttctctttta atgctaaaaa taagaaaaca  74220
ccttgcagcc cagggtatgg gtagtgcatg gaagccgtgg agttgtgagg tgggaagtga  74280
cctctgctgg atatgtctat tcaggaagat tgctggagtg ggtggggtct ctgggaggtc  74340
ccctgagtgt gggaagctgg gaccaccagc tttctcgcac agggagtggc catcccagct  74400
tggagaggtt ccaggactgg ttgggaggca cgtttcagat ttctatctgt tgaatcagcg  74460
aagatattgg attatgagga atttgggaat taggaaagtg ggtgcaggtg ggttgggggt  74520
aggtgaagga agacatgggc gtattggggg agcaggggct gctcagaggt gttccagaag  74580
ctctgggtga ggaggtgaga gggaccgggg aatgcagctc ggcccagcct ccctgcctga  74640
ggtcagccat cacgtggtga tggcaagatg gaaatgtgct ttctgactgc tccagccagt  74700
gctgccagat tcagctcccc agggagggca cctgagaggc tccaagccag gagatctgtt  74760
ttctcctttg ttttgttttt ttttgttttg ttttgtttta ttatacttta agttctaggg  74820
tacatgtgca caacgtgcag gtttgttaca tatgtataca tgtgccatgt tggtgtgctg  74880
cacccatcaa cttgtcattt acattaggta tatctcctaa tgctatccct ccccccctccc  74940
cccacccccct gttttctcct ttgaatcctt cttagaggcc gggtgcggtg gctcacgcct  75000
gtaatcccag cactttggga ggctgcggca ggaggattgc ttgagcccag gagttccaga  75060
ccagcctggg caacatagtg agacctcgtc tctacagata ataattttaa aaattatccg  75120
ggcatagtgg catgcaccta tagtcccagc tactcaagag gcagaggcag gaggatcact  75180
tgagcccagg aggcggaggt tgccgtgagc caagatccca ccactgcact ccagcctggg  75240
cgacagagac cccccatgtca aataataata ataataaata aatccttctc agtcccttcc  75300
tcactgtgtc cccctccact gaatttttcc acctcctctc ccacttcccc cactcccgct  75360
ttccctctcc ttctctcccc actccatctt tttctttctc tgctgtttct cgtccctccc  75420
tcctctccat cccacaacac tgcctaccct gtccctgccc caccctggtg ctcaggatgt  75480
gtgaagtgag gggtggtagc ccccaagacc tcaaccccga aggttagcct gttgaaacca  75540
ctttctccca gctgcccccc tggcagttgg tgctgctggg ggaaactggg attgggggcc  75600
agattttgcc tcttttcctg acaaagagag atgaagagtt ctctcaccag gtgcctggga  75660
```

ctggggtgtg ggtgtcccag cctatcccag cgcatctgtt ctgcatcatg attaatagtg 75720
ctgctttcag ccgggcgcgg tggctcacac ctgtaatccc agcactttgg gaggctaagg 75780
tgggcagatc acaaggtcag gagttcgaga ccagcctggc caacatggtg aaacctcgtc 75840
tctactaaaa atacaaaaat taaccaggtg tggtggtggg tgcctgtagt cccagctact 75900
tgggaggctg aggcaggaga atcacttgaa tctgggaagc agaggttgca gtgagccaag 75960
atcgtgccac tgcactccag cctgggtgac agagcgagac tccgtcctaa aaaaaaagga 76020
gttttgctct gtcgcccagg ctggagtgta gtggcgccat ctcggctcac cgcaacctgc 76080
gcctcccggg tgcaagcgat tctcctgcct cagcctccca agtagctagg attacaggcg 76140
cctaccacca cgcccggcca gttcttgtat ttttagaaga gacggggttt caccctgttg 76200
gccaggctcg tctgggactc ctgacctcag gtaatccgcc cacctcagcc tcccaaagtg 76260
ctgggattgc aggcatgagc caccgtgccc agtcaactcc ttctcaaaaa aaaaaaaata 76320
gtgctgcttt ctctttcaag tgtcctgatt tgggtgatag taaatgccac tctacttata 76380
agggatctac ctcagaatgc taattgggac atttttgtag cactctactg ttggcagcag 76440
gtgatgctca caacagcccg tgagggtgga tgacgtccgc ttcacagatg acaaaggagc 76500
ctcatgctca gaccgtgggc tgccagagca ggtccatggc tgcagcccca catggaccat 76560 atttcccccct tgtcactctt tccaccaagc tcccttggaa cttcagttat taagctctct 76620
tgggtggaat ccaagttaga atcacaacat gtgcctcata tggattgtgc cagtgaaaaa 76680
tgacattcta tttagaggca gggcagcctg gcttagagtc agtttaaaat atgtattatg 76740
ctgcaacaaa tgtaccatga tcctgtaaga tgttcacaac aagggaactg gatgtggggt 76800
atactgtctg tactaacttc acaagttttc tgtaaatcta aaactgttcc aaaataacaa 76860
gttcgtttaa aattaactcc aggagaccag gtacggtagc taatgcctat aatcccagca 76920
cttcggaagg ctgaggcagg tggattgctt gagcccagga gtttgagaca agcctgggca 76980
acatggtgaa atcctgtctc taaaaaaaat cacaaaaatt agccaggtgt ggtggcgcat 77040
tcctgtagtc ccagctactt gcggggctga ggtgggagaa tcatctgagc ccaggagttt 77100
gaggctgcag tgagctgtga ttgtaccact gcactccaac ctgggcaaca gagcaagacc 77160
ctgtctcaaa aaacaaaaat gaaataaagt ccaggaaaga agtaggtttt accactctta 77220
ttttctgaag agaaaactaa atttaatgtg taaagtgagg acaagttcac caagttagtg 77280
tttgagttgc ctaaaatatg tttgctaaaa ctattcaaag ctttcacata aaacatgatc 77340
agaagttcta tgccaaaaca tatgtgtgtg tatatatata tgcactatat atactgtata 77400
taaaaatgca aaatctaaat tgccaacctt ttagaaattg ctctgaaagg aaagcatttc 77460
aagataattt gcttacccaa agaatatact ttccaagaaa gcaagtaata cttaaggtgt 77520
tcataatcct catcaaatta attcttgcta ctgaaagctt acaaggagct gttttgatgt 77580
cgggtgtgac aggtttgact tggcagaagg tgtcacttta ctaacaacat tttaaataag 77640
tgacagaaga caagaaacta cacgttaaat gccagaacaa agagtgtcta agtggatgct 77700
aagagttgaa atatggctgg atacctgccc aagagagctg aaaagtagat gaaagttggt 77760
tacctataaa ctagtgcacc ctaatgaatt aaaaggtgtt gatgagttaa cttgttatgc 77820
cttccagata agacatgcaa atggggcttc ttcctccttc actacttcca agggatttaa 77880
caaggagacc aatgcaaatg ataaggactg tagggctcaa gctggggaca gattggggaa 77940
agggggacca tcatgcccat atagatgtcc ctgtgccctg gcagtcaagg ctgctgaaaa 78000

```
ataacaaaac ccagaagtct gcgtgatgct gcctctccat ttgtccaaag ccttcttgcg  78060
gcagtttgca ggcttttgca aaagctccag gaccaaggag ctatgttcat gctggaagct  78120
tgttcaggat tagctgttct ttgtgggatg ggtgcagcca gggccaggtg tccagggaca  78180
gtgttttaac aaagggcatg aggtgtctga tctcacagtg gaactccact tgcctttttt  78240
tcatcttctc attctgcttc atgcacagaa ccagccccat cctgaaactg actctaaatt  78300
actcccgccc caggtggagt gcctttctcg gagttcaaca gagccttcct gtcgcccaag  78360
ggacaactcc actgaatgcc caagccacac ccaaaaccta acaagtaaaa accaaattct  78420
gtgctccccc atcctgggcc attcctggtt tctctactgc tgttggtgat accaccatca  78480
gcttgtccat catgaccctg gccagttcct cccacaaccc tccacagcac ccagggacct  78540
cacctccatt ccatccgaca cagatctcct caccacaaac cttggttttg caacagcagc  78600
catgagacct ttacaccctc cgcccttcat cctgtccccc actgaggccc cagagccatt  78660
ccttaaagca gcgcgccaca aactataacc cacaagccaa ttctggtacc cagcctgttt  78720
tgcacagcca gtgaactgac aatgatcttt tcatacagcc agaaaaacaa aacaaaacaa  78780
aaaacaacaa aaaaaaaccc caccattctg agcatgtgac ttccatgttc aagatgtctc  78840
atgttcagaa aggcccctgg aaaaggagga aggggagctg ggcacaaagg gagaccctct  78900
cagctgagct cctcccatcc agacattttc ctggacttcc tatccaatga cttcccttag  78960
cttcttatca gccacccctg tctgcccagg aggctggaag atgtggcctt ttaactgggc  79020
acagctctgt cctctatcat atcagggctc tgttcccaag gagggtagag agaatggaca  79080
ccaggtggac cctcagcagt ctgtgccaca gagggagtgt ttgcaatttc cagactaaaa  79140
gtccccatgt gcttgacggg gtatgtgact acaacgtgat gcttgacttt tcctcatatg  79200
accagagcca ctttgtccat ctggtacaat gtcagctatc tgctaggggc cctccaggat  79260
tcccagtcaa ttccatatct gcatcaccac cattggcact aaataaaata aaatactcaa  79320
gttcctgctg gtgagcatga gcagtgctac actgggccct tcaaccaagg tgacatgata  79380
atgactgaaa ataatcactg ccacttattg gggacgtctc atctgccagg catggtacaa  79440
agtgctttaa ataagcattc aacaatttca tgctgacaga agccctgtga gccagtggag  79500
ctactactat gcccattata caggggagaa aactgaggca gagagaggtt aggtaattcg  79560
ctcagcctca cacaaccaat aggtggtgga gccaggattt gggccccatc tgcctgactc  79620
tctagaggct ctatcttcca gtcttccaga gttgagtcta agccatgaat aggacaatta  79680
gacagcagag gaaacccatt cagccaccat gtgcatgaag agtaaggaat ttctgtcata  79740
cagaggggag tgaattcact gagctgagag ctgaggaacc attgatctga tggctgagac  79800
accactggga agactggaga ggcttttctg ggcatgcagt gccaggcaca ggaggagctg  79860
agggaagatg actaagaggt actggcaaag aattcagaaa ttctgatgga agctttacat  79920
gttaccatca catccatcca tctatccacc catccatcca cccatatctt cctccctcca  79980
cccaatcatg catacatcca gtcatctata caccacccac ccacccatcc atccatccat  80040
ccatcccttc atccatccca tcatccatcc aattatacat acatccaatc atatatctgt  80100
acataatcca ttcttccctc ggttcatcca tccatccatt catccatcca tccacccatc  80160
ccttccttca tccttcctat catccatcca atcatatatc tgtacataat ccattcttcc  80220
ctcggttcat ccatccatcc attcatccat ccatccaccc atcccttcct tcatccttcc  80280
tatcatccat ccaatcatac atatatccaa tcatacatct gcacatcacc agctcatcca  80340
tctatccatt tatccatcca tccttccttc catccatcat tcatccatca tacatacatc  80400
```

```
taaccataca tctctacatc attcattctt ccatcgattc atccaattat ccatcattcc  80460
ttcctccatc catcccatta tccatttgat catacatata tcatctatac atcatccatt  80520
catccatcca tccatccatc cacccatatc ttcatccaat caatcataca tacatcgaat  80580
catctacaca tcacccatcc atccatccat ccattcatct atccacccat ccatccatcc  80640
atccatccat tcatctatcc acccatccat ccatccatcc atccatccat ccatgtaacc  80700
atccagtcat atatccaatt acacatccat ccagttatac attcatacat gcatctaatc  80760
attcaattat acatacacac atccatataa ttctacatcc aattatacct ccatccaatt  80820
acacattcat acacccacct aataaattat taattcatat atccatccat ataattatac  80880
atcaattata catccatcta atcattcagt aattcaccca ccatccagtc atctatccaa  80940
taatacattc atccaatcat ccatccatcc atccacccat tcatccatcc atccgtccgt  81000
ccacccatca tggtatgagc catgatttac cacgatggtc ccctgtggac agcccaggtg  81060
gggcagaact gaagggaagc ccagggctgc ccccataaac atttgcctcc tttacatgga  81120
tgagaactag atccacatgt ataaatcctc atgatttgaa ggtgctttta ccaacattca  81180
ctcatgggat tctcccagga gctctaggag gaggcaggta gagttgaggt catctcacgc  81240
attttacaga tgaggaaacg gaggccctga gaggcaggtc caaggccacc tgaccagaaa  81300
gaagtggaac tgggacttga acccagccat cttgcccctt ggtcccatgc tctctagcct  81360
gtaactcctg cttcctggtg gggcatctcc aggaggaccc tatcggctgg ccatgggcct  81420
gccctggagt cttttgctct gtgtggccat ccttcctccc tcaggagagt gtgtgctccc  81480
agagcacagg ctgtatcttc tgagcatttt gtcccttccc agtacctagc actcagctct  81540
gtatacattg ggctctcaag aattctcaac cttccagagt gtaaggcctt gacctgctca  81600
gccctggata ctgcatgatg cattgataag cccataaaat aaccagggca gattgactcc  81660
cagtggccaa agtgccacag ggaagggaca attcagccct tctaggagga ggaggaggta  81720
gttttctcat ttctattaag gcaacaaaag ctgccttact aaggacattc ttggtggagg  81780
gcgtgactgt caaccactgt gatcatttgg gcctctcttg cccaggcttc ccattctgaa  81840
aggacagttt tattgtaggt acacatggct gccatttcaa atgtaactca cagcttgtcc  81900
atcagtcctt ggaggtcttt ctatgaaagg agcttggtgg cgtccaaaca ccacccaatg  81960
tccacttaga agtaagcacc gtgtctgccc tgagctgact ccttttccaa ggaaggggtt  82020
ggatcgctga gtgtttttcc aggtgtctac ttgttgttaa ttaatagcaa tgacaaagca  82080
gaaggttcat gcgtagctcg gctttctggt atttgctgcc cgttgaccaa tggaagataa  82140
acctttgcct caggtggcac cactagctgg ttaagaggca ctttgtcctt tcacccagga  82200
gcaaacgcac atcacctgtg tcctcatctg atggccctgg tgtggggcac agtcgtgttg  82260
gcagggaggg aggtggggtt ggtccccttt gtgggtttgt tgcgaggccg tgttccagct  82320
gtttccacag ggagcgattt tcagctccac aggacactgc tccccagttc ctcctgagaa  82380
caaaaggggg cgctggggag aggccaccgt tctgagggct cactgtatgt gttccagaat  82440
ctcccctgca gacccccact gaggacggat ctgaggaacc gggctctgaa acctctgatg  82500
ctaagagcac tccaacagcg gaaggtgggc ccccccttcag acgccccctc catgcctcca  82560
gcctgtgctt agccgtgctt tgagcctccc tcctggctgc atctgctgct ccccctggct  82620
gagagatgtg ctcactcctt cggtgctttg caggacagcg tggtgggagc tgagccttgc  82680
gtcgatgcct tgcttgctgg tgctgagtgt gggcaccttc atcccgtgtg tgctctggag  82740
```

```
gcagccaccc ttggacagtc ccgcgcacag ctccacaaag ccccgctcca tacgattgtc  82800
ctcccacacc cccttcaaaa gccccctcct ctctctttct tcaggggcca gtaggtccca  82860
gagcagccat ttggctgagg gaaggggcag gtcagtggac atctgatctt ggtttagtat  82920
ccttcatttt gggggctctg ggtgtggcct gggcctctgg actttggcca cggtgtttgt  82980
tccagccctt ctcctaacct gtcctttcca gacactcggc atctaggtta ttagcacctc  83040
gcatactttc tgacatgctc ctcagtcctg attttgacca tcttctcttg cttcccatct  83100
gtgtcagtca agactgcatt tggctgtaag aaacagaaac cccaactaac tgtggcattt  83160
acatgaagag gtttactttt ctcacataat cagatgtcta gacttggcca gcacctcaag  83220
ggtcattgat gctctcctgt ctttattttc tgtcatcttt agtggttgga ttgttgcctc  83280
atggttacaa agtggctgct gcacttccag gcatcacatc tgcctttgaa gcaggaacaa  83340
gttgcaaagt aaagtggcca aaagggccct gaaactaaat gtgtcccctt aggaaagcag  83400
gagttttctt gcaagtggca atcttctgct tatgtctcat tggccagagc tgggtcttac  83460
ggccacccct tgctgcgagc aaggctggga cattgagcat tttgccgtcc aacctcttta  83520
gcagaataaa ccaaggggga agaacgttaa tagtggcttt tgagtcacta gttggcagta  83580
tctgcccctc tatctttcca tcctccccat ggagtttcaa ggttcctttc tcagtacttc  83640
ttcaggctct gcacgttcat ttggatcttg tgtcttgggg tgaaaaactg gcccaagtgt  83700
ctccccaagc atccaccttt ggattaattt ggaaaatggc tgtcaagtgc ccgcctcttg  83760
cttggtataa tgctacagct ttagaggacg cagcaggcat gggccttgcc gctgaggttc  83820
ttagcctcat gagaatatcc agatcagatt ctcttggctc cttcttagag ccagtgatgc  83880
aagacacttc ctgctcatct tgtcgggacg gttttacaag ttgcctgcca tcctgagaaa  83940
gtctacaaaa cgatgccaga cctcatgcca gcttcccaag ccttgactct cagtgctccc  84000
tcaacaggat tctggaagaa tctcccaaac aagtcgcaat cccctctgga ccctgtgcag  84060
gcatgagact caagagcatt ggctcccacc cctggtggag ggaacactgc tggggctggg  84120
atcttgcctg gttgctccgc ctgcacccaa gacaaccata attaaaatgt ccttcattga  84180
acttggaaag ccttcaaagc tgacaactcc ttatgtgtac ccggaaaggc ctgggagtgt  84240
gccagggcat tgctcgggag ggacgctgat ttggaagcat ttacctgatg agagactgac  84300
agcagctcct ggtagccgag ctttccctcc tgcctctgct gtgaaggtgg acccatccaa  84360
cagtcaaatg cctgactctg gacaggagcg gacctattta ttgccatgca agggactctg  84420
cacttttgaa ttgtgggtca tgggcttgga tttaggggtt agagctggga gaagtcttgg  84480
aagtcaccta gagatgacac tgccattttg cagatgagga aaccgtccaa tcaaaatgga  84540
ccaaggactt gcccaaagcc tcacagcaaa accataggcc cccgcactaa ccccagagtc  84600
cctgtgctgt cttaagaatc aaatagttgt aagcaatcat ctggttttca gtatttcttc  84660
ttttaaaatg cctggggcca tgcccagcag tctgtttcac tgcagcgttt acacagggct  84720
gccgggcttt cctggtggat gagctgggcg gttcatgagc cagaaccact cagcagcatg  84780
tcagtgtgct tcctggggag ctggtagcag gggctccggg ccctacttca gggctgcttt  84840
ctggcatatg gctgatcccc tcctcactcc tcctccctgc attgctcctg cgcaagaagc  84900
aaaggtgagg ggctgggtat ggctcgtcct ggcccctcta aggtggatct cggtggtttc  84960
tagatgtgac agcaccctta gtggatgagg gagctcccgg caagcaggct gccgcgcagc  85020
cccacacgga gatcccagaa ggaaccacag gtgagggtaa gccccagaga cccccaggca  85080
gtcaaggccc tgctgggtgc cccagctgac ctgtgacaga agtgagggag ctttgcgtgt  85140
```

```
ttatcctcct gtggggcagg aacatgggtg gattctggct cctgggaatc ttgggttgtg  85200
agtagctcga tgccttggtg ctcagttacc tccctggctg cctgccagcc tctcagagca  85260
tttagggcct tctggacttc tagatgctcc tcatcttgcc tcagtcagcg cgtcagttcc  85320
agagacttct ctgcagggtt ttctggggca ggtggtggca gacccgtgcc ttcttgacac  85380
ctgaggtcag tccaccctcc tgctcagact gcccagcaca gggtcacctc ccaaggggtg  85440
gaccccaaga tcacctgagc gcacagaggg tgcagatgac tggaccacac cttttggtga  85500
tcttaatgag gtggtcccag aggagctcag acatgcaatc tagcatccag ttctgggact  85560
ctgtctcctt ttcaaacgta ttcatgtaga acaggcatga cgagaatgcc ttgtcaacat  85620
gggtgatggg gaatcaatca gacagggcgc cgggctcaag gctgcagtca cccaagagtg  85680
gctcagccca ccaggcccta ggaaacgcct gcacagcctg gagctcctgg agtcatttcc  85740
ttcatgtctt cttcactgca cttacgtaaa gatgccagcc attggtttgg tgatttggag  85800
ggtgcccagt tgcccaacaa gaaatgcaga agaggcctag ccaggatttc accagcagtg  85860
gagagtagag aagatgtggc cagaaaagag tttcctttcc ctcctaaaga tggtactccc  85920
tgcagctact ggggaagcct gcagcattct ctagggctct gtgtgttgag agcagcccca  85980
ccctggcccc ttctgagtgc atttctgctt tgtgacttga tccgtgaagt cccctgagat  86040
gggcagaggg gatgtcctcg aagctggggc agagcctcat ccttgaacgt gaaggacgtt  86100
tgaagactgt ggcatgatca caggatgaga tcacagggaa cttgagtttc tctcctcctc  86160
tcccttcaca gttatttcac tgagggaaat ccctcccctg cccagaatga aaactctagc  86220
caactcttga cttttccatc actccaaagt agttgaaagt acattagtct ccacagtggc  86280
aaaacagtgt gcaaaagcta aataattaga acagccagtc ccatgtgaca gtcaaagctt  86340
ctaactccat tcaaagttgc agccattccc ctcgagggct ggcagggagg ggaggggtaa  86400
gagaaacagg aaggttctta ctgagttggt cctggtgtga gctgcgtcac actccctgca  86460
gaggtttcaa ggagactctc tctctctctg tctccatggg gaccttattt gaattcttct  86520
actcttaccc cagcctgcca tctccagcta tcctcccctg aagagccctt ctgctgcgct  86580
ggattctggt ggccatgtca tctcctcggc cccgtgggag tctgaagatc tggctgcagc  86640
ctcacctctg aggtcctgct agttgccacc tcttaaacat gatctgaggc tcccatgcac  86700
tctgacctgt gcccacatgg ggcccacggg aaacacgctg gcaagcaaac tgtgggtgtg  86760
cagacggttc tcagggctgc agcacctgtc ctttgctctg cccccaaagc aaggccagcc  86820
catcttccat cctctagtgt tccttggtgg ggccctgacc acagtccacc aggtccctaa  86880
ccagagggga cacacaccag gtgtcctcaa tgtattgcct tgaaacagtt gtgctgggac  86940
tgtgatgggg ggtggccatg tagccacccc caccaccccc aagccactct ctccaaggaa  87000
atcctcctaa agatcccttt acatcctcca tgtggtgggg aggttctaga gttgggtgca  87060
tgtgtcttca gctactgaca atgcagacct tagttggcac ctcgctctgg cctatcctgt  87120
ttgctgttct tggcgctcca gtgaaactcc ccatgggcca tccagttggg gtgcagtgtg  87180
gccacccccct tgcaggttcc tgccttgctg gagagcacag ggccctcctg gctcttgtaa  87240
aacactcccc atggtacaga gaggccagca gtgatgtgag gcccaacctc cctccatggt  87300
gttcccaagc agctcccttt ctggggtcaa ggggtggcaa agacagtgca gcgtccaatt  87360
tctgactcaa gccgggcctg gctatcgcag ctctgcactg tgtgtgacag caaggcaact  87420
cacccagtgc cgtggcagtg accgtgtccg aggaagcctc ctcacaccct ctgtctcaag  87480
```

gactctggca tttagctgga cttgctgtag ctctgagcct ttctgccatt gccatcacct 87540
tgtcagaaac tcaggccgaa tctgcactca gagttgtgcc caggcagttg agccaacact 87600
tgctcagcga tattgtcaca tgacaaggca ctgtcaccac tgggcgtcgt gggtagcgca 87660
gtgtcggctg gatggacccg gagggtgtct gtgtcatgct agtgctagtg atgggagccc 87720
cgtgagccca ttgcccgccc tcccatgccc tcagcagctg cctggggaca gccaatggcc 87780
tgggtgtttc tgaggctacc acatggcttc caggaaactc gagaaccttt ctctcccttg 87840
cctacactct tcacacaggc ctgtgctggc cagcggtggg gatccggcat tcctatctta 87900
ggtgcagaaa gtgactgact cattgcaggc ctgggagata agactgatgg cccagccagc 87960
aagatgtatg gatttctcag aggcagtggc ctctgtcatt gtcctcagga aatgctggtg 88020
attctggtgg cctgaggtca atgcatgtca acgtggccaa cttgccttat aaactttttt 88080
tctggacaat tgcgtgcact gtcctgtaac agtgtcctgt tgtttatgat gcagaaatag 88140
gtgtttttaa agcctattga ttttggtact attaatgtgg tcaggaactt tctcagtctt 88200
tcttgtttgg ggtgagctgt ggcttcctaa acaggaaccc aagacacccc caaaagctgc 88260
tcaccagcac tgccagcctc cctcttacca agtagcaccc gttcaggaca ttctgcgaaa 88320
ggcatttgcc cagaagttgg gaggaaggaa atgtaacatt ttggggcacc taccatatgc 88380
caggcaccag gctaaacgtg ttcacacaaa ttctcttact aaccctcacc atccttctac 88440
aagacaaact agtatcttca tcttggggtt caagatgagg aaatggaggc tcagagaggt 88500
tgaatgaatg ccggtgcctg gatatgaacc ccatctgcct gactccgcaa cccaggcaaa 88560
gtctttcctt gaacttccca gcagccactg cttagacaca gcctccacaa ccatggctca 88620
gcagcaaatt gcttctctga cctcactcag cctgtgtgtc cttgttgagt gaggcattca 88680
ggaccctggt cccaaagtgg agaaagtctt tcctactagg tcatagctac acctgcatgt 88740
gggtgctgtg ccttttgttt agtgaacttt tatcaccagc atcctcagca atgacatttg 88800
cagagaagcc agagctgagg caccttggta ttcttgggat gtgactttcc tgaatgttta 88860
agggaaaatg cccgaaggta cagagagctt ggtttctagt aaacaataac tgtcttgctt 88920
ttaccccccct tcatttgctg acacatacac cagctgaaga agcaggcatt ggagacaccc 88980
ccagcctgga agacgaagct gctggtcacg tgacccaagg tcagtgaact ggaattgcct 89040
gccatgactt gggggttggg gggagggaca tggggtgggc tctgccctga aaagatcatt 89100
tggacctgag ctctaattca caagtccagg agattttagg gagttggttc ttatcaaagg 89160
ttggctactc agatatagaa agagccctag tggttttttt ctaataccat ttctgggtaa 89220
ttcctaaggc atttagtgtt ctgaaagatg ctagccttgt ccagcctggg agttgagaat 89280
gaatgtctaa cagaaactct aggccgggcg tggtggctca cgcctctaat cccagcacta 89340
tgggagaccc aggtgggcag atcacctgag gtcaggagtt tgagaccagc ctggccaaca 89400
tgtgaaatcc tgtctcacta caaataaaaa aattagccgg gtgtggtggt aggtgcctat 89460
aatcccagct actcaggagg ctgaggcagg acaatcgctc gaacccagga ggtggacgtt 89520
gcagtgagcc gagatcgcat cattgcactc cagcctgggc aacaaaagca aaactccgtc 89580
tcaaaaaaaa aaaagaaact caaatatgtg tgacaggcga ttctcactgc aggctgccct 89640
gtggctgatc caggagcaag gccttaacca tgtcatcccc aagcgattgc ttgtaaactt 89700
tcttctgtgc agccttcaac ccttattatg attttcttct caggaaccaa actgctgtat 89760
tcaagaaagg cagctttgtg taatcattta tcataaatat cttaagaaaa atcctagaga 89820
ttcctaattt taggaaatgg gagacctatg gtactgatat aatgtgggct gggcttgttt 89880
tctgtcattt gctagataaa tgaacttgag agcctactgt aaaatgtgga agcttctaga 89940
ttgcagaagg gctggaaaga cactgttctt ttctcccgag tgatgggatc tgtccagtat 90000
ttagagctgc ctctgaggcc atctgattct aggagactct gcctcgttga ggatattttg 90060
aggcctaact acacattcct gcccccagag aggtcacagc ctatagcagg ctgatgtttc 90120
tcatgtcaca tggcacagaa aggcacattt tcgttctcag gctaacaaag agcttcaaaa 90180
actattagaa gggacagtgg ctataagaga agaacctcag tcaatgtgtg aaattaacta 90240
ggaacctggc tcctgtttct tttaggtcat gtttttcagc ttaggtaaaa ctagaggctt 90300
tgataaagca tgacctctag aaatcattgc ttttcataaa tggaagtggg tttgagtttt 90360
ttctactgat tgttagtgca ggtgatgtct acatgccccc agaacatatt ccatgcaaca 90420
aaaaaagccc aggtcaccgt ctttgctggg aacttgactt ttgtgctcac tgaattttaa 90480
gctttctgac agcagcctgg aatcatggag ggataaagta cctattagta agatggaaaa 90540
aggtgtttca ggttggagct gcagtctgtt gagagtaagc tatgggaagg cctgtatacg 90600
aggggtggac ttttcttctg taagtgtcca gagaccaggc ctcctgaaga gggcatgggg 90660
gcttaactta cctggactac tgtgtttaca atactcattt atcttgaact cctcctaacc 90720
cctgagaatt gctacattta gtatttgctg agtacttcct agcatcctag ggaatcaata 90780
gaacattctc ccaaccaggc tgggtgcggt ggctcatgtc tgtaatccca gcactttggg 90840
aggccaaggt aggcagatcc cttgaggcca ggagtgcaag actagcctgg ctgacatggt 90900
gaaaccccgt ctttactaaa aatacaaaag ttagccaggc atggtggtac acacctgtaa 90960
tcccagctac atgggaggag taggaggcag gagaattgct tgaacctggg aggtggaggt 91020
tgctgtgagc cgagatcatg ccactgcact ccagcctggg cgacagagtg agtgagactc 91080
tgtttaaaaa aaaaaaaaaa aaagaacatt ctcctaacct ggcttcttcc tccaggggtg 91140
taattaatca tgtcagtttc ctcattgata cacacacaca cacactacaa tcctgtatcc 91200
attactttc aaggtacatt tactatttac gtttggggtc cttgtctctt ttttaatagt 91260
gtttcttaaa gtcttgtatt atatcagagt acagtaacat cccagtcaag agcactctag 91320
taagctctag gaggaaagcg acttccggaa ggcagtggag acctgtcctg ttggggcagc 91380
ataggggcag cccctgcctc tggtcagttc tggcgctcag gctcagggtt gcctctgggc 91440
tgttcttccc agagactgac aaagggctcc cataaggcac ctgcagagcc tgtgagaagc 91500
tgaagtcaat gttttcctga caccagttga tctgtgcagg atccattgat ttaaccacct 91560
gctgtgtggc atgcactgtg gtcgatgcca ggaacaggaa ttggaggggc ccatgagcat 91620
ggccagtatc acaggctgga ggtgctgctg cgctctgacc gggcctcttg gggatgagcc 91680
catgtcaacc accttgcctc cgatggggtc gggcccacag gttacctttg tgtgtccatg 91740
accacacctt cctccccgac ctcatccaaa tctctttctt ttccaagccc ctgaatcctt 91800
cagggctgca ggttttgttt aaagcagagc tggtgagttg cataggttgt tgcgttggga 91860
ctagatgggg tgttcaaaga gttgggagtt aaaaaacata aagggtattt attaggagaa 91920
ccaaggagtg taattctcct gttcttaata tgcggccagg ttaatgaatg tcacgtgaat 91980
gaaccagaaa aaaatgaagt gtgcccttga tcagctgggt tggtgtgcag caagctgtgt 92040
gaccagggga cagcagtggt cctgagggcc gtcactgtct gccgtgcaga gcccttcctc 92100
ccacgggggc ctacctcacc tgtgccaagg gcttgtctgt ggtcagtgac ctggatagat 92160
ctgaatgggg cttctttttc gaggagtctt atggcaggtc tctcagtaaa gactccattc 92220
ttgatgatca cacattttgg attttccaaa tctgtcagag aatgggcttg aggcggggtt 92280
tgtgggcact agtttcactg gtttcattta ccaaaaaggg gagcagaagt caagtatggt 92340
ggctcatccc tgtaatccca gaggcaagag aattgcttga gcccaggagt tcgagaccag 92400
cctgagcaac ataaggagac cccgtctcca caaaaatgaa aaataacatt ttagtcagac 92460
gtggtggcat gcatctgtgg tcccagctgc ttgggagggt gagatgggag ggttgtttga 92520
gccctggagt taaagttgca atgagctgtg attgcaccac tgcactctag cctgggtgac 92580
agaacgagac cctgtctcaa aaaaaaaaaa aaagaaagaa aaaaaggaaa aaaaaaactc 92640
atgcctgtaa tcccagcact ttggggaccg gggtgggcag atcacgaggt caggagatca 92700
agactatcct agccaacatg gtgaaacccc gtttctacta aaaatacaaa aattagccag 92760
gtgtggtggc acgtgcctgt aatcccagtt actcgggagg ctgaggcagg agaatcgctt 92820
gaaccaggga gtcagaggtt gcagtgagct gagatcgtgc cactgtactc cagcctgggc 92880
gacagagtga gactctgtct caaaccaaaa aaaaggggtg gggggcgggg gcaggagaac 92940
agtgagaggt agggagagga aaggggattc tcgctacacc caaaccagat accatctaga 93000
ggctagaatc tttgggaggc tcaaattccc tagaaagcag gagaagcttc tgtagccctc 93060
ccgctttccc agtagattaa gcccagggcg gctccagatg tgtgacatgc tctgtgccca 93120
accagagccc atcataggca gaggaataac acccacacca gaagggccct cggaggtcac 93180
cacgtccaag aaccctcttt acagatgagg aaactgaggc ccagagaggg gagagccacc 93240
tagcgagctg gtggcggcta gaccaggaga gctgtcattc caagcaagca aaggcaacga 93300
gacgagccca gagctgtgct cccatctctt tgttaggggg cctgggatgc cctctcagtg 93360
tcattttgtc caggatgatg ctccctctct taagcgatta atgcgccctt gctaaccttt 93420
tgctatcgct gcctcttcaa accagaggag ttgagagttc cgggccggca gaggaaggcg 93480
cctgaaaggc ccctggccaa tgagattagc gcccacgtcc agcctggacc ctgcggagag 93540
gcctctgggg tctctgggcc gtgcctcggg gagaaagagc cagaagctcc cgtcccgctg 93600
accgcgagcc ttcctcagca ccgtcccgtt tgcccagcgc ctcctccaac aggaggccct 93660
caggagccct ccctggagtg gggacaaaaa ggcggggact gggccgagaa gggtccggcc 93720
tttccgaagc ccgccaccac tgcgtatctc cacacagagc ctgaaagtgg taaggtggtc 93780
caggaaggct tcctccgaga gccaggcccc ccaggtctga gccaccagct catgtccggc 93840
atgcctgggg ctcccctcct gcctgagggc cccagagagg ccacacgcca accttcgggg 93900
acaggacctg aggacacaga gggcggccgc cacgcccctg agctgctcaa gcaccagctt 93960
ctaggagacc tgcaccagga ggggccgccg ctgaaggggg cagggggcaa agagaggccg 94020
gggagcaagg aggaggtgga tgaagaccgc gacgtcgatg agtcctcccc ccaagactcc 94080
cctccctcca aggcctcccc agcccaagat gggcggcctc cccagacagc cgccagagaa 94140
gccaccagca tcccaggctt cccagcggag ggtgccatcc ccctccctgt ggatttcctc 94200
tccaaagttt ccacagagat cccagcctca gagcccgacg ggcccagtgt agggcgggcc 94260
aaagggcagg atgcccccct ggagttcacg tttcacgtgg aaatcacacc caacgtgcag 94320
aaggagcagg cgcactcgga ggagcatttg ggaagggctg catttccagg ggcccctgga 94380
gaggggccag aggcccgggg cccctctttg ggagaggaca caaaagaggc tgaccttcca 94440
gagccctctg aaaagcagcc tgctgctgct ccgcggggga agcccgtcag ccgggtccct 94500
caactcaaag gtctgtgtct tgagcttctt cgctccttcc ctggggacct cccaggcctc 94560
ccaggctgcg ggcactgcca ctgagcttcc aggcctcccg actcctgctg cttctgacgt 94620

```
tcctaggacg ccactaaatc gacacctggg tgcagctgct ccactccctc ggcctcctcc  94680
cgtgctcagg ctgtggccgc acgcgcccct cacgcttgcc cgccactctg catgtcacca  94740
gcacccccgc tccgtgctcc ccaccttgtt tgactctctg gccacttgat ttgtccacaa  94800
cggcccatca gcccacagga ggtttggtgg gtgccttcca ccgacaggat gacgggtgcc  94860
ctcatggtgt ctagaactct ccaaccctcc catgtaggca taagcagccc cactttgcag  94920
atgaggaaac ggaggctcag agaagtacag taacttgccg aaggccaatg agtagtaagt  94980
gacagagcca ggtttgggat ccaggtaggt tgtctctgaa agacacgcct gtcctgcatc  95040
ccacaacgcc tcccaggagg tgctggagtg tggacgccta acacagagat gtgcagggca  95100
cacacagcag gtgacacaca cagcatccag aggtggccca gagctcatgc tgtgcctttg  95160
gcccagtgcc ctgcccccac ccactctgcc ttgtggcagg aagacaagga gcagacacaa  95220
gatctccctg gtccacatgc caccacctcc ctctgcagag gacaagggga tcctcatgct  95280
ggcattggag gggggttgagc agggcccacc ttgagccctc aggagcacga ccacagcagc  95340
cctgcaggga gggattggtg ggaggagagt cccaagtatc agggagagga gagttggtgt  95400
cccacaggag acctcagagc cacaaggcga gcttgttcat aaatttggga cccttagcat  95460
ttcacagtta tttgcagagc ccagaaatgg atgttactga agctcacagt tgcaagcatc  95520
tgttaaattt ttattagatt ttacttttag ggaaaacttt gaaatgctat aaagaagcct  95580
gtgtttaaaa gttaagacag aggctggggg cgatggctca cgcctgtaat ctcagcactt  95640
tgggaggcca aggcaggtgg atcatttgag gttaggagtt cgagaccagc ctggccaaca  95700
tggtgagacc ctgtctctac taaaattaca aaaaattagc tgggcgtggt ggcgggcacc  95760
tgtagtccca gctactgggg aggctgaagc aggataagtg cttgaaccca ggaggcggag  95820
gttacagtga gccaagatca caccactgta ccctaagcct gggcgacaga gtgagactct  95880
gtctcaaaaa ataaaataaa ataaagttaa gagagaaaaa aatatatcct atatcctttg  95940
ttaaattcca aaacagtagg ggacaaataa ctgacttgac aggttactac aatatttcct  96000
gaaatgatgt tttcttgaat actggcctac tagaggttca taggtgtgtt tggattaaaa  96060
aagagttcca tggcccagtg actgggggaa aaaaataaaa gactaaagta agttaaacag  96120
gcttttctgc tgcaggactt gtcagagcct ttaatgtact aatggccatt gtgaccctct  96180
gagaaggtca cagagtgggt ttcccaaact tacttgattc tacctgctaa catttcctgg  96240
aggaagtttg ggaaatgccg atttagcaga ttcttttgtt gtgccgtgga tggtgctggt  96300
tgatgtgggc aaaacaaaga acacgtgagt cagatccgcc tggggctctt actaaagtgc  96360
aggttcccag gtgccacttt aggcttacag acccagttgt ggggtaagcc tgggagtctt  96420
ttagcaggtg attctgccac atagtatagt tggaaaacct ctgggcatac tcattgctgg  96480
tccctctaga aatccaggtg acaatagcca atgagaagct ccaagagacc cagttgtcca  96540
tggggtagag ggaatgtgat attgaaacca aagaagaaaa tctatgatca gttttcagca  96600
gtgactgtca agagaaggag aagggtgagt tagcgctgat gctggctgac aggtcagcgg  96660
gttggtttca ccaaggagtg tgatgaaggc tgatgttgtc tgtgggaatg tatgatggta  96720
actggtttgt agctaatttg ggggaagcagt gagaattcgt gccctttgaa gaccagtaag  96780
tggcaagaaa cccaccaggc ctggctcagg gctgggctgg gcttggctcg tctcagagca  96840
gctggggctg gtggccaaag ccaccattag tgaggggcag gccctggggg tacaaccagc  96900
aactagggga caaagacaac cctgccagcc tctcctattc tggaggcgtg tgaccagaaa  96960
```

-continued

```
tggagatggg ttggtcagca taagatggcc aggaaggtgg aaatcaggac tgctggcaat  97020
ctagccacat gggcagggga gccgggtggt tccaggcagt ttccaaggcc aagagggtga  97080
gcaggcacct cacagggaat cagggccaag cctggctgca gtgtggagac aatgcaccca  97140
cccccatcct tggatcttgc aggaggctgg gtcctcactg agctaccaac atccatggcc  97200
ctgaggcttt taaaacaccc atccatggag tggggctggt cccagtgggg tgaggctgac  97260
cctggcagaa acagggcagg agcctgtggg ttagggagac tgcaccttcc ttagatagcc  97320
tccatgccat catgtccccg tgacagtttc tgctgcgtcc cctctgcatg gtcccaccct  97380
cggccagcct gctgcccccct cttgccaggt tgcgctaatc agtgacccca gtgtgctgtg  97440
ttgatactaa caatgcgagg cctagcagat tcaagggaaa agagaaccaa ctgggtttcc  97500
accagaccca actaaacaaa catggaccta tcccagagaa atccagcttc accacagctg  97560
gctttctgtg aacagtgaaa atggagtgtg acaagcattc ttattttata ttttatcagc  97620
tcgcatggtc agtaaaagca aagacgggac tggaagcgat gacaaaaaag ccaaggtaag  97680
ctgacgatgc cacggagctc tgcagctggt caagtttaca gagaagctgt gctttatgtc  97740
tgattcattc tcatatataa tgtggggagt atttgtcact aaagtacagc tgtcatttaa  97800
agtgctttgt attttggggc aggcttttaa aaagtccagc atttattagt tttgatactt  97860
accccaggga agagcagttg gcaggttcat gaagtcatgc tcctaattcc agctttctta  97920
gtgtactttc agtgagaccc tgacagtaaa tgaaggtgtg tttgaaaacc aaacccagga  97980
cagtaaatga aggtgtgttt gaaaaccagc cctaggacag taaatgaagc catcttctca  98040
ctgcataaac tgcacccaga tctttgccca tccttctcag tatttcactt cacccattgt  98100
ttactgtctc aatgactggg gaaatgtctg gggaaatgct cccgtaattg cacagtggcg  98160
tttttcctgg aaaatcccac catggctcta gataagacct atttttctta aaggtatcta  98220
aaatttccag cataaattct gtctgaaaca cctgaatttt aatcagtact ggagcccgga  98280
gggcatctcc agttgccaca tagctctgag cattcagtgg tgtgttgagg gctgctcccg  98340
gaagtgcctg cagagtcagg gctccccagc ctcatctagt gaggcagtgg aagggcctgt  98400
ggggatttgg agagctggcc tgggtctctg aagtgatagt gacagctgct tgtcaatcac  98460
ggtgcacatt tagtgccggg ggcagggggc agggaatacc agcctcatgc atgcatgcat  98520
tcatttgttc cttccttcat tcattcattc agtacacatg ggtacaacat ccctgccctg  98580
gagttgccca gagtctaggg aggggaaaga tctattaccc tgggcctcgg ccagctgggg  98640
agtgctgctg gtggagaggg gccgtgtgca gcgagggaag gaggagtcgt caataccccc  98700
accccagctt tgctttcttg tcatcagccc cagggcccca gcctgtgtcc ctcctctccc  98760
attgctactt catctcctgg gtcctcctta ccaagcctga ccacacagag ggccttggcc  98820
gcttccatgg ggaattggaa agcaataaga tagcatcccc tagaagccca gtgaagtctg  98880
ggacaggacc cttctctgag ctctgacttg ctcttggaaa cacttcgagg cttagcctcc  98940
ccactttgtt tcccaagagt gtgacctgtt cccctccaaa cacccccttc tcctccaggg  99000
ccatgcccac ccgtcaaaat cccccacggg caggacgaac tgtgggtgtc agtcaccatc  99060
tatcctgcat cctggttcca gggccccccc cagccccgcc tccataggga caggcgtgca  99120
gacacccgtc cctggctgct tcctcttgtg gaatgggttc aaaagtaagc agtgttgttt  99180
acactgacaa actgaaaaaa aaagaaaaag agataacatt ggaggcttgg cacagtggct  99240
catgcctgta atcccagcac tttgggaggc taaggtggga ggatgtcccc agcccaagag  99300
ttctagacca gcctgggcaa catagcaaga ccccatctca aaaaaaaaat ttaattggcc  99360
```

```
aggcagaggt gggaggatca cttgaaccca aagggtggag gctgcagtga gccgtgatgg  99420
caccactgca ctccagccag ggcaacagag ggagaccctg tctctaaaac aaacaaacaa  99480
acaaacaaac aaaagagtta acattggcca gattaggatt caccagatag tgttaatatt  99540
agtttgattt gagactttaa tcagaaagca catgtgtggt gggggtgggt gtaacctaag  99600
tcaggtagaa tctttccaac ttgggggggg cacactcctg attgtagcca tatgagtctg  99660
tcagtgtggt ggaagagacc atgggttaat gggcaggtaa aaaagcacct tgcctggaat  99720
tgagtagaaa gtaaggccct tcagaccccg tgacacactt ggggacattt tcttgagtaa  99780
catcctaaga ttcatgtacc ttgatgatct ccatcaactt actcatgtga agcaccttta  99840
aaccagtcgt ctccaaattc aggggcacag taacatccaa caggctggag aaagaacgta  99900
ctagaacttc cattcctttt tcatgtcctc ttctaaaagc tttgtcaggg ccaggcgcgg  99960
tggctcacgc ctgtaatccc agcactttgg gaggccgaga cgggtggatc acgaggtcag 100020
gagatcgaga ccatcctggc taacacagtg aaaccccatc tctactaaaa atacaaaaaa 100080
acgagccggg cgtggtggtg ggcgcctgta gtcccagcta ctcgggaggc tgaggcagga 100140
gaatggcgtg aacccaggag gcagagcttg cagtgagccg agattgcacc actgcagtcc 100200
agcctgggcg acagagcgag actccgtctc aaaaaagaaa aagaaaaaga aaaagaactg 100260
tgattgggga ggacggtcac tttcctgttc ttactgatca gaagggatat taagggtacc 100320
tgattcaaac agcctggaga tcactgcttt caaccattac ctgccttatt tatttttagt 100380
tactgtcctt ttttcagttt gtttccctcc tccatgtgct gacttttatt ttgattttat 100440
ttatgtttat gtttaagaca tccacacgtt cctctgctaa aaccttgaaa aataggcctt 100500
gccttagccc caaacacccc actcctggta gctcagaccc tctgatccaa ccctccagcc 100560
ctgctgtgtg cccagagcca ccttcctctc ctaaacacgt ctcttctgtc acttcccgaa 100620
ctggcagttc tggagcaaag gagatgaaac tcaaggtaag gaaaccacct ttgaaaagaa 100680
ccaggctgct ctgctgtggt ttgcaaatgt ggggtttgtt tatttgtttt ttagcctcaa 100740
agacctttct tcaaatgagt tctggcatag aagcaccgtg taaaatagtt agaattctgg 100800
gcaaagggga aaagagagct gggggccatc cctctcagca ccccacaggc tctcatagca 100860
gcagctccta agacacctgg tgggaccttg gtttcgaaat cgctactcta aggctgggca 100920
cggtggctca cacctgtaat cccagctctt taggaggccg aggagggtgg atcacctgag 100980
atcaggagtt cgagaccagc ctggctaaca tggcaaaacc ctgtctctac taaaaataca 101040
aaaattagcc gggcgtggtg ttatgcgtgg tggtaatcgc agctactcgg gaggctgagg 101100
cacaaggatt gcttgaaccc cagaggcaga ggttgtagtt agctccagct tgggcgacag 101160
agcaagaccc tgtcgcaaaa attgtttaaa aaacaaaccc aaaattgcta ctctcattgg 101220
gttcctttgc ccattcctga ttttggcaag agaaatgctt ccagattgcc ctgatctggg 101280
taggacagca tcacgccata gcaacactgc cccgtgagct cactgccccc tcaactagct 101340
tgtggtcctt ggttaatgtc agtttctttt ttgagtttgt gttatgtcta agggtcatct 101400
gctgggtaac ggaacccagg gactgcccta gtccctagac tgtgccatgc ccgactctgc 101460
cagctttgtc agtgatgctg gtgctcgcct cctcgggtgc tcgcctggtc tgagcacacc 101520
caaggagttc ttgaggcctt agggttgttt gcgagagaat gaaagaacac gacctagctc 101580
tctttagcat ccttggtcag gttcaacact gcccccaggg gcctctggtg gagccaacca 101640
ccatcagcca aataaatcca taattagagt cagaaaatgg atgtctgcat atgtgtagtg 101700
```

cactaatgtc ctgccgatga ttgacatgga gtggagagtg acctgatcat tgctgtgagc 101760
tctgctggcc ttggcacaac tcatgctgat aactaatgca cacagttcct ctgggaggaa 101820
atgtcctcag ggaacttgga gtttgggtgg ggatgtgggt ttgtgtgccc agcaagccct 101880
tgtggttgta gcagacacta gtggcatcta ggaggcaaag ggtcacccca gtcttagcca 101940
cgttttgagt caaggtggcg gagtggggct ggtgttgact cttggtggca gtaacttttc 102000
ccaatggtga aaaacccctc tatcatgttt catttacagg gggctgatgg taaaacgaag 102060
atcgccacac cgcggggagc agcccctcca ggccagaagg gccaggccaa cgccaccagg 102120
attccagcaa aaaccccgcc cgctccaaag acaccaccca gctctggtaa gaagaacgtt 102180
ctcttgaatc ttagaggaag ctgaagctct cagaggtaca gccttcattt taggaggcct 102240
taggccactg agaatgaata acccctggca gctggtcagc agcttgcagt ttactaagca 102300
ctggagtctt cattgccttc tcagtccttt tgatttctga ggcaaatgtt gaatccctac 102360
cttttttttt tttttctttt tgagacagag tttcgctttt gttatccagg ccggagtgca 102420
gtggtgtgat ctcagctcac tgcatcctcc acctcccagg ttcaagcgat tctcctacct 102480
cagcctccct agtagctggg attacaggca cctgccacta tgcccggcta atttttttgta 102540 tttttagtag agacagggtt tcaccatgtt ggccaggctg gtctcgaacg cctgacctca 102600
ggtgatccac ctgcctcggc ctcccaaagt gctgggatta caggcatgag ccaccactcc 102660
cagcctgaat cctcactttt tatcaatgaa gaaattgagg ctgattctgc agcatgataa 102720
aaaaaaatac agaaaaagga aaaaaaagaa agaaatcgag cctctgagag tttgcttgac 102780
tgagtctaac cagctcattt taaacccgag gaaaatgcag tcacatgact actaagtggc 102840
agctctcgga gcctctctgg ccccaagtcc agggttccat agaggcagcc ccagcatggc 102900
atgttttcag tccccaaatg agactctgga gacaaatgtc tctggagaca gagcagcagc 102960
ctggataagt cacaatgggt gacgtcactc agggctcaac ccctgggcag cttaacttgc 103020
tagggacgtt aggagtctgc tgcaaaacct gagggtctta gctgagcagt cacaggctgg 103080
gcccgttgcc ctgggctcct gtgagtaaaa cccagtcaat tttgagtacc cagtaaggca 103140
tccattgagt tattttgcag ccaggagtgc tattaagaac agtcgcggct gggcgtggtg 103200
gctcatgcct gtaatcccag cactttggga ggccaaggtg ggcggatcac ctgaggtcag 103260
gagttcgaga ccagcttggc caacatggca aaaccccgtc tctaataaaa atacaaaata 103320
attagctggg cgtggtggcg ggcgcctgta atcccagctt ctcaggaggg tgaggaagga 103380
gaatcacttg aacccaggag gcagaggttg cagtgagctg agatcgcacc attgcactcc 103440
agcctggatg acaaaagtga gattccttct caaaaaaaaa aaaaaaaaaa cagtcgtcct 103500
ctttggggat tagggacagc ctgcctgcct gcccgagcac ttctctcttc cattgcccca 103560
gtgaagtatt ccaggcccct gggtttagac tctgcaccat gtaggggtgt ctgacctgca 103620
cttgctcctt ggtggcacgg gcagcctatg gcacttgctg cgggctgtga ccaaagcctg 103680
gcctggatct tggatcttgg tgactctgct tctccctggc ctgagggagc tgcccagagc 103740
ctgcccacca cctgctgcgt gtctttgcgg tggcatttct cgcacacatg ccgtgcggtg 103800
gcacccccaa ggatggccat tcactaaggc ccattgtttt tgtcttttcg cttcgtgttt 103860
tctggcctgg tgtttttctc atatacatgt gatccaggga taattcccag aattttgaca 103920
ggattttaag tagcgtttgg atcctgctgt tttttttttca cttaacatcg ggccagttga 103980
ctcacactct gtttttttgtt gttgtttttt tgagacggag tctcactgtg tcacccaggc 104040
tgaagtgcag tggcacaatc ttggcatact gcaacctctg cttcccaaat tcaagcagtt 104100
ttcctgcctc agcctcctga gtagctggga ctacaggcac aggccaccac gccctgctaa 104160
tttttgtatt tttagtaaag acagggtttc accattttgg ccagcctagt ctcgaactcc 104220
tgacctcaag tgatccgccc acctcggcct cccaaagtgc tgggattaca ggggactcac 104280
actttgtaac aacctgaaac aacgtgatgc atttcccttt gggtcttacc tgctcttcgg 104340
tggctgcctg caggtggaga gaccctcccc cttgggcccc tcgaccttgt ttcagaatgg 104400
ggcccctgct gggccagctg tgggtgcctg ccacgtgaag gactcattaa ggccctgttt 104460
aagcctgatg ataataaggc tttcgtggat ttttctcttt aagcgactaa gcaagtccag 104520
agaagaccac cccctgcagg gcccagatct gagagaggta ctcgggagcc tacttcgctg 104580
ggagcagcct ccctttgcgt gtgtggccat tcactggctt gtgtttctag agccgggagg 104640
acccttttct gcaatgcagg gttcacacag ggttcgcagc ctgaagatgg agcagtccga 104700
attctcttcc ctgtgcagtt tgcgcagctg tgtttgtctg atgggctttc taatcctgtg 104760
tgctctcctt gacttcaggg acaatggcat tacaggcatg agccaccatg cctggctgtc 104820
tccctatgtt tcagatgaag acataggctt aaggaggtca ggtgacttgc ccacgaccac 104880
tctgtaaata agaggcatga aaagtatttg gagccaccac caccaagccc actggtcacc 104940
ctgggtctct gaagtcaggg aggcaggagg atgggaggtc tgaggaggca gagaggctga 105000
gcctggaggc cctggaggcc gaggccccat ctgttgtttc cttatgtgga aaataagagg 105060
cttcatttgt cctattgcca cagagcgtac tacttcagga acatccaaga catggaaatc 105120
cgcagggcac ggtggctcac gtctataatc ccggcacttt gggaggttga ggtgggagaa 105180
tcgcttgagg ccagaagttc aagaccagcc tgagcaacat agtcagaccc cgtctctata 105240
aaaaacatta tttttaaaaa agacatggaa gtcaaattct aaaaactggt gctggctggg 105300
tgcggtggct catgcctata atcccagcac tttgggaggc cgaggcgggt ggatcacctg 105360
aggtcaggag ttcaagacca gcctggccaa catggtaaaa cctctactaa agaaatcttt 105420
actgaaaata caaaaatcca gtctctacta aaataagtct ctactaaaaa tacaaaaatt 105480
agccaggcgt ggtgctgcac acctgtaata tcagctactc gggaggctga ggcaggagac 105540
tcgcttgatc ccatgcagcg gaggttgcag tgagccgaga tcacgccatt gcactccagc 105600
ctgggcatca gaataagact ccgtctcaaa aaaaaaacca caaaaaaaca aaacaacaac 105660
aaaagaaaac tagtgcttat tcgtcactgg ccaagctgcc cattggctac atgggtgctt 105720
caaagagctg cccttctcca ggtctggcca gcaggtatgt gttacagcaa atgcctgggg 105780
cagcggcagg ggcattgctg cgggaagctt ctggacttgc aggaaagcta agttctcaga 105840
ctgcagggga gctaagcaca cctcggcaca gggtgaggcc tgcggttctc agacttcagt 105900
ctttgtggag cttgagaaaa atgaggcttt gcaggtccca cccctagaga ttctgctcta 105960
tccactcttg aaggggatcg agaaatttgc attttgcaac tcccactttc ctccttgaaa 106020
gctccggaga ttctgacgca gggttccgtg ggccacactt tggaaaatac agacccatga 106080
gatagaatac cagactgttg aagtgtaacg gggacctggg aagtgcagta acagaagcaa 106140
gtttgagggt aaaggacacc cagaggaggg agggacagca tctgcatgga gaggagaaga 106200 gacccccag cagcttccag ggtgttggaa gggtgcgcta gtaactgcta tgcatggcag 106260
gtggggaact gtacgtcagg gcacagcagc atgaagcggt atggctcgtg tggacagcta 106320
gggacaggca ggcgtggagc aggcatcctg ttctgaaggc caaatcccac agaggagcca 106380
gggtgctggc aggagccctg aactagccga acagctgaac agctgaacat tcaccctgtg 106440
gggaaagggt cagaagcgtc caggcttgag ggcacagctg ggtctcgtca ctgcatcacc 106500
cttatttagg ataaaggccc tgaagaattg tattagaggt tggcaaagca tatctaccac 106560
ctcctggagc cacgctggcc gcagggatta taattatttc cattttcaaa ttaaggcctc 106620
tgagctcaga gaggggaagt tacttgtctg aggccacaca gcttgttgga gcccatctct 106680
tgacccaaag actgtggagc cgagttggcc acctctctgg gagcgggtat tggatggtgg 106740
ttgatggttt tccattgctt tcctgggaaa ggggtgtctc tgtccctaag caaaaaggca 106800
gggaggaaga gatgcttccc cagggcagcc gtctgctgta gctgcgcttc caacctggct 106860
tccacctgcc taacccagtg gtgagcctgg gaatggaccc acgggacagg cagcccccag 106920 ggcctttttct gaccccaccc actcgagtcc tggcttcact cccttccttc cttcccaggt 106980
gaacctccaa aatcagggga tcgcagcggc tacagcagcc ccggctcccc aggcactccc 107040
ggcagccgct cccgcacccc gtcccttcca accccaccca cccgggagcc caagaaggtg 107100
gcagtggtcc gtactccacc caagtcgccg tcttccgcca agagccgcct gcagacagcc 107160
cccgtgccca tgccagacct gaagaatgtc aagtccaaga tcggctccac tgagaacctg 107220
aagcaccagc cgggaggcgg gaaggtgaga gtggctggct gcgcgtggag gtgtgggggg 107280
ctgcgcctgg aggggtaggg ctgtgcctgg aagggtaggg ctgcgcctgg aggtgcgcgg 107340
ttgagcgtgg agtcgtggga ctgtgcatgg aggtgtgggg ctccccgcac ctgagcaccc 107400
ccgcataaca ccccagtccc ctctggaccc tcttcaagga agttcagttc tttattgggc 107460
tctccactac actgtgagtg ccctcctcag gcgagagaac gttctggctc ttctcttgcc 107520
ccttcagccc ctgttaatcg gacagagatg gcagggctgt gtctccacgg ccggaggctc 107580
tcatagtcag ggcacccaca gcggttcccc acctgccttc tgggcagaat acactgccac 107640
ccataggtca gcatctccac tcgtgggcca tctgcttagg ttgggttcct ctggattctg 107700
gggagattgg gggttctgtt ttgatcagct gattcttctg ggagcaagtg ggtgctcgcg 107760
agctctccag cttcctaaag gtggagaagc acagacttcg ggggcctggc ctggatccct 107820
ttccccattc ctgtccctgt gcccctcgtc tgggtgcgtt agggctgaca tacaaagcac 107880
cacagtgaaa gaacagcagt atgcctcctc actagccagg tgtgggcggg tgggtttctt 107940
ccaaggcctc tctgtggccg tgggtagcca cctctgtcct gcaccgctgc agtcttccct 108000
ctgtgtgtgc tcctggtagc tctgcgcatg ctcatcttct tataagaaca ccatggcagc 108060
tgggcgtagt ggctcacgcc tataatccca gcactttggg aggctgaggc aggcagatca 108120
cgaggtcagg agttcgagac caacctgacc aacagggtga aacctcgtct ctactaaaaa 108180
tacaaaaata cctgggcgtg gtggtggtgc gcgcctataa tcccagctac tcaggaggct 108240
gaggcaggag aatcgcttga acccaggagg cagaggttgc agtgagccga gatagtgcca 108300
ctgcactcca gtttgagcaa cagagcgaga ctctgtctca aaacaaaata aaacaaacca 108360
aaaaaaccca ccatggctta gggcccagcc tgatgacctc atttttcact tagtcacctc 108420
tctaaaggcc ctgtctccaa atagagtcac attctaaggt acgggggtgt tggggagggg 108480
ggttagggct tcaacatgtg aatttgcggg gaccacaatt cagcccagga ccccgctccc 108540
gccacccagc actggggagc tggggaaggg tgaagaggag gctgggggtg agaaggacca 108600
cagctcactc tgaggctgca gatgtgctgg gccttctggg cactgggcct cggggagcta 108660
gggggctttc tggaaccctg ggcctgcgtg tcagcttgcc tcccccacgc aggcgctctc 108720
cacaccattg aagttcttat cacttgggtc tgagcctggg gcatttggac ggagggtggc 108780
caccagtgca catgggcacc ttgcctcaaa ccctgccacc tccccccacc caggatcccc 108840
cctgcccccg aacaagcttg tgagtgcagt gtcacatccc atcgggatgg aaatggacgg 108900
tcgggttaaa agggacgcat gtgtagaccc tgcctctgtg catcaggcct cttttgagag 108960
tccctgcgtg ccaggcggtg cacagaggtg gagaagactc ggctgtgccc cagagcacct 109020
cctctcatcg aggaaaggac agacagtggc tcccctgtgg ctgtggggac aagggcagag 109080
ctccctggaa cacaggaggg agggaaggaa gagaacatct cagaatctcc ctcctgatgg 109140
caaacgatcc gggttaaatt aaggtccggc cttttcctgc tcaggcatgt ggagcttgta 109200
gtggaagagg ctctctggac cctcatccac cacagtggcc tggttagaga ccttggggaa 109260
ataactcaca ggtgacccag ggcctctgtc ctgtaccgca gctgagggaa actgtcctgc 109320
gcttccactg gggacaatgc gctccctcgt ctccagactt tccagtcctc attcggttct 109380
cgaaagtcgc ctccagaagc cccatcttgg gaccaccgtg actttcattc tccagggtgc 109440
ctggccttgg tgctgcccaa gaccccagag gggccctcac tggcctttcc tgccttttct 109500
cccattgccc acccatgcac ccccatcctg ctccagcacc cagactgcca tccaggatct 109560
cctcaagtca cataacaagc agcacccaca aggtgctccc ttccccctag cctgaatctg 109620
ctgctccccg tctggggttc cccgcccatg cacctctggg ggcccctggg ttctgccata 109680
ccctgccctg tgtcccatgg tggggaatgt ccttctctcc ttatctcttc ccttccctta 109740
aatccaagtt cagttgccat ctcctccagg aagtcttcct ggattcccct ctctcttctt 109800
aaagcccctg taaactctga ccacactgag catgtgtctg ctgctcccta gtctgggcca 109860
tgagtgaggg tggaggccaa gtctcatgca tttttgcagc cccacaaga ctgtgcaggt 109920 ggccggccct cattgaatgc ggggttaatt taactcagcc tctgtgtgag tggatgattc 109980
aggttgccag agacagaacc ctcagcttag catgggaagt agcttccctg ttgaccctga 110040
gttcatctga ggttggcttg gaaggtgtgg gcaccatttg gcccagttct tacagctctg 110100
aagagagcag caggaatggg gctgagcagg gaagacaact ttccattgaa ggcccctttc 110160
agggccagaa ctgtccctcc caccctgcag ctgccctgcc tctgcccatg aggggtgaga 110220
gtcaggcgac ctcatgccaa gtgtagaaag gggcagacgg gagccccagg ttatgacgtc 110280
accatgctgg gtggaggcag cacgtccaaa tctactaaag ggttaaagga gaaagggtga 110340
cttgactttt cttgagatat tttgggggac gaagtgtgga aaagtggcag aggacacagt 110400
cacagcctcc cttaaatgcc aggaaagcct agaaaaattg tctgaaacta aacctcagcc 110460
ataacaaaga ccaacacatg aatctccagg aaaaaagaaa aagaaaaatg tcatacaggg 110520
tccatgcaca agagccttta aaatgacccg ctgaagggtg tcaggcctcc tcctcctgga 110580
ctggcctgaa ggctccacga gcttttgctg agacctttgg gtccctgtgg cctcatgtag 110640
tacccagtat gcagtaagtg ctcaataaat gtttggctac aaaagaggca aagctggcgg 110700
agtctgaaga atccctcaac cgtgccggaa cagatgctaa caccaaaggg aaaagagcag 110760
gagccaagtc acgtttggga acctgcagag gctgaaaact gccgcagatt gctgcaaatc 110820
attgggggaa aaacggaaaa cgtctgtttt cccctttgtg cttttctctg ttttcttctt 110880
tgtgcttttc tctgttttca ggatttgcta cagtgaacat agattgcttt ggggccccaa 110940
atggaattat tttgaaagga aaatgcagat aatcaggtgg ccgcactgga gcaccagctg 111000
ggtaggggta gagattgcag gcaaggagga ggagctgggt ggggtgccag gcaggaagag 111060
cccgtaggcc ccgccgatct tgtgggagtc gtgggtggca gtgttccctc cagactgtaa 111120
aagggagcac ctggcgggaa gagggaattc ttttaaacat cattccagtg cccgagcctc 111180

```
ctggacctgt tgtcatcttg aggtgggcct cccctgggtg actctagtgt gcagcctggc 111240
tgagactcag tggccctggg ttcttactgc tgacacctac cctcaacctc aaccactgcg 111300
gcctcctgtg caccctgatc cagtggctca ttttccactt tcagtcccag ctctatccct 111360
atttgcagtt tccaagtgcc tggtcctcag tcagctcaga cccagccagg ccagcccctg 111420
gttcccacat cccctttgcc aagctcatcc ccgccctgtt tggcctgcgg gagtgggagt 111480
gtgtccagac acagagacaa aggaccagct tttaaaacat tttgttgggg ccaggtgtgg 111540
tggctcacac ctaatcccaa cacctgggga ggccaaggca gaaggatcac ttgagtccag 111600
gagttcaaga ccagcctggg caacataggg agaccctgtc tctacaattt ttttttaat 111660
tagctgggcc tgttggcact ctcctgtagt tccagctact ctagaggctg aggtgggagg 111720
actgcttgag cctgggaggt cagggctgca atgagccatg ttcacaccac tgaacgccag 111780
cctgggcgag accctgtatc aaaaaagtaa agtaaaatga atcctgtacg ttatattaag 111840
gtgccccaaa ttgtacttag aaggatttca tagttttaaa tacttttgtt atttaaaaaa 111900
ttaaatgact gcagcatata aattaggttc ttaatggagg ggaaaaagag tacaagaaaa 111960
gaaataagaa tctagaaaca aagataagag cagaaataaa ccagaaaaca caaccttgca 112020
ctcctaactt aaaaaaaaaa atgaagaaaa cacaaccagt aaaacaacat ataacagcat 112080
taagagctgg ctcctggctg ggcgcggtgg cgcatgcctg taatcccaac actttgggag 112140
gccgatgctg gaggatcact tgagaccagg agttcaaggt tgcagtgagc tatgatcata 112200
ccactacacc ctagcctggg caacacagtg agactgagac tctattaaaa aaaaaatgct 112260
ggttccttcc ttatttcatt cctttattca ttcattcaga caacatttat ggggcacttc 112320
tgagcaccag gctctgtgct aagagctttt gcccccaggg tccaggccag ggacaggggg 112380
caggtgagca gagaaacagg gccagtcaca gcagcaggag gaatgtagga tggagagctt 112440
ggccaggcaa ggacatgcag gggagcagc ctgcacaagt cagcaagcca gagaagacag 112500
gcagaccctt gtttgggacc tgttcagtgg cctttgaaag gacagccccc acccggagtg 112560
ctgggtgcag gagctgaagg aggatagtgg aacactgcaa cgtggagctc ttcagagcaa 112620
aagcaaaata aacaactgga ggcagctggg gcagcagagg gtgtgtgttc agcactaagg 112680
ggtgtgaagc ttgagcgcta ggagagttca cactggcaga agagaggttg gggcagctgc 112740
aagcctctgg acatcgcccg acaggacaga gggtggtgga cggtggccct gaagagaggc 112800
tcagttcagc tggcagtggc cgtgggagtg ctgaagcagg caggctgtcg gcatctgctg 112860
gggacggtta agcaggggtg agggcccagc ctcagcagcc cttcttgggg ggtcgctggg 112920
aaacatagag gagaactgaa gaagcaggga gtcccagggt ccatgcaggg cgagagagaa 112980
gttgctcatg tggggcccag gctgcaggat caggagaact ggggaccctg tgactgccag 113040
cggggagaag gggtgtgca ggatcatgcc cagggaaggg cccaggggcc caagcatggg 113100
ggggcctggt tggctctgag aagatggagc taaagtcact ttctcggagg atgtccaggc 113160
caatagttgg gatgtgaaga cgtgaagcag cacagagcct ggaagcccag gatggacaga 113220
aacctacctg agcagtgggg ctttgaaagc cttggggcgg ggggtgcaat attcaagatg 113280
gccacaagat ggcaatagaa tgctgtaact ttcttggttc tgggccgcag cctgggtggc 113340
tgcttccttc cctgtgtgta ttgatttgtt tctcttttt gagacagagt cttgctgggt 113400
tgcccaggct ggagtgcagt ggtgcgatca tagctcactg cagccttgaa gtcctgagct 113460
caagagatcc ttccacctca gcctcctgag tagttgggac cacaggcttg caccacagtg 113520
cccaactaat ttcttatatt ttttgtagag atggggtttc actgtgtcgc ccaggatggt 113580
```

cttgaactcc tgggctcaag tgatcctcct gcctcagcct cgcaaattgc tgggattaca 113640
ggtgtgagcc accatgcccg accttctctt tttaagggcg tgtgtgtgtg tgtgtgtgtg 113700
tgggcgcact ctcgtcttca ccttccccca gccttgctct gtctctaccc agtcacctct 113760
gcccatctct ccgatctgtt tctctctcct tttacccctc tttcctccct cctcatacac 113820
cactgaccat tatagagaac tgagtattct aaaaatacat tttatttatt tattttgaga 113880
cagagtctca ctctgtcacc caggctggag tgcagtggtg caatctcggc tcactgcaac 113940
ctccgcctcc caggttgaag caactctcct gcctcagcct ccctagtagc tgggattaca 114000
agcacacacc accatgccta gcaaattttt atatttttag tagaggagga gtgtcaccat 114060
gtttgccaag ctggtctcaa actcctggcc tcaggtgatc tgcctacctt ggtctcccaa 114120
agtgctggga ttacaggtgt gagccaccac gcctgccctt aaaaatacat tatatttaat 114180
agcaaagccc cagttgtcac tttaaaaagc atctatgtag aacatttatg tggaataaat 114240
acagtgaatt tgtacgtgga atcgtttgcc tctcctcaat cagggccagg gatgcaggtg 114300
agcttgggct gagatgtcag accccacagt aagtgggggg cagagccagg ctgggaccct 114360
cctctaggac agctctgtaa ctctgagacc ctccaggcat cttttcctgt acctcagtgc 114420
ttctgaaaaa tctgtgtgaa tcaaatcatt ttaaaggagc ttgggttcat cactgtttaa 114480
aggacagtgt aaataattct gaaggtgact ctaccctgtt atttgatctc ttctttggcc 114540
agctgactta acaggacata gacaggtttt cctgtgtcag ttcctaagct gatcaccttg 114600
gacttgaaga ggaggcttgt gtgggcatcc agtgcccacc ccgggttaaa ctcccagcag 114660
agtattgcac tgggcttgct gagcctggtg aggcaaagca cagcacagcg agcaccaggc 114720
agtgctggag acaggccaag tctgggccag cctgggagcc aactgtgagg cacggacggg 114780
gctgtggggc tgtggggctg caggcttggg gccagggagg gagggctggg ctctttggaa 114840
cagccttgag agaactgaac ccaaacaaaa ccagatcaag gtctagtgag agcttagggc 114900
tgctttgggt gctccaggaa attgattaaa ccaagtggac acacaccccc agccccacct 114960
caccacagcc tctccttcag ggtcaaactc tgaccacaga catttctccc ctgactagga 115020
gttccctgga tcaaaattgg gagcttgcaa cacatcgttc tctcccttga tggtttttgt 115080
cagtgtctat ccagagctga agtgtaatat atatgttact gtagctgaga aattaaattt 115140
caggattctg atttcataat gacaaccatt cctcttttct ctcccttctg taaatctaag 115200
attctataaa cggtgttgac ttaatgtgac aattggcagt agttcaggtc tgctttgtaa 115260
atacccttgt gtctattgta aaatctcaca aaggcttgtt gccttttttg tggggttaga 115320
acaagaaaaa gccacatgga aaaaaaattt cttttttgtt tttttgtttg cttgtttttt 115380
tgagacagag tttcactctg tcgcccaggc tggagtgcag tggtgcgatc tccgcccact 115440
gcaagctcca cctcccgggt tcatgctatt ctcctgtctc agcctcccaa gtagctggga 115500
ctgcaggtgc ccgccaccac acctggctaa ttttttttgta tttttagtag agacggggtt 115560
tcaccgtgtt agccaggatg gtctcaatct cctgacctcg tcatctgcct gcctcggcct 115620
cccaaagtgc tgagattaca ggcgtgagcc accgtgcccg gccagaaaaa aacatttcta 115680
agtatgtggc agatactgaa ttattgctta atgtcctttg attcatttgt ttaatttctt 115740
taatggatta gtacagaaaa caaagttctc ttccttgaaa aactggtaag ttttctttgt 115800
cagataagga gagttaaata acccatgaca tttccctttt tgcctcggct tccaggaagc 115860
tcaaagttaa atgtaatgat cactcttgta attatcagtg ttgatgccct tcccttcttc 115920

```
taatgttact ctttacattt tcctgcttta ttattgtgtg tgttttctaa ttctaagctg 115980
ttcccactcc tttctgaaag caggcaaatc ttctaagcct tatccactga aaagttatga 116040
ataaaaaatg atcgtcaagc ctacaggtgc tgaggctact ccagaggctg aggccagagg 116100
accacttgag cccaggaatt tgagacctgg gctgggcagc atagcaagac tctatctcca 116160
ttaaaactat tttttttat ttaaaaaata atccgcaaag aaggagttta tgtgggattc 116220
cttaaaatcg gagggtggca tgaattgatt caaagacttg tgcagagggc gacagtgact 116280
ccttgagaag cagtgtgaga aagcctgtcc cacctccttc cgcagctcca gcctgggctg 116340
aggcactgtc acagtgtctc cttgctggca ggagagaatt tcaacattca ccaaaaagta 116400
gtattgtttt tattaggttt atgaggctgt agccttgagg acagcccagg acaactttgt 116460
tgtcacatag atagcctgtg gctacaaact ctgagatcta gattcttctg cggctgcttc 116520
tgacctgaga aagttgcgga acctcagcga gcctcacatg gcctccttgt ccttaacgtg 116580
gggacggtgg gcaagaaagg tgatgtggca ctagagattt atccatctct aaaggaggag 116640
tggattgtac attgaaacac cagagaagga attacaaagg aagaatttga gtatctaaaa 116700
atgtaggtca ggcgctcctg tgttgattgc agggctattc acaatagcca agatttggaa 116760
gcaacccaag tgtccatcaa cagacaaatg gataaagaaa atgtggtgca tatacacaat 116820
ggaatactat tcagccatga aaaagaatga gaatctgtca tttgaaacaa catggatgga 116880
actggaggac attatgttaa gtgaaataag ccagacagaa ggacagactt cacatgttct 116940
cacacatttg tgggagctaa aaattaaact catggagata gagagtagaa ggatggttac 117000
cagaggctga ggagggtgga ggggagcagg gagaaagtag ggatggttaa tgggtacaaa 117060
aacgtagtta gcatgcatag atctagtatt ggatagcaca gcagggtgac gacagccaac 117120
agtaatttat agtacattta aaaacaacta aaagagtgta actggactgg ctaacatggt 117180
gaaaccccgt ctctactaaa aatacaaaaa ttagctgggc acggtggctc acgcctgtaa 117240
tcccagcact ttgggaggcc gaggcgggcc gatcacgagg tcaggagatc gagaccatcc 117300
tagctaacat ggtgaaaccc cgtctctact acaaatacaa aaaaaagaaa aaattagccg 117360
ggcatggtgg tgggcgcctg tagtcccagc tactcgggag gctgaggcag gagaatggcg 117420
tgaacccggg aggcggagct tgcagtgagc cgagatcgcg ccactgcact ccagcctggg 117480
cgacaaggca agattctatc tcaaaaaaat aaaaataaaa taaaataaaa taataaaata 117540
aaataaaata aaataaaata aaataaataa aataaaatgt ataattggaa tgtttataac 117600
acaagaaatg ataaatgctt gaggtgatag ataccccatt caccgtgatg tgattattgc 117660
acaatgtatg tctgtatcta aatatctcat gtaccccaca agtatataca cctactatgt 117720
acccatataa atttaaaatt aaaaaattat aaaacaaaaa taaataagta aattaaaatg 117780
taggctggac accgtggttc acgcctgtaa tcccagtgct ttgtgaggct gaggtgagag 117840
aatcacttga gcccaggagt ttgagaccgg cctgggtgac atagcgagac cccatcatca 117900
caaagaattt ttaaaaatta gctgggcgtg gtagcacata ccggtagttc cagctacttg 117960
ggagaccgag gcaggaggat tgcttgagcc caggagttta aggctgcagt gagctacgat 118020
ggcgccactg cattccagcc tgggtgacag agtgagagct tgtctctatt ttaaaaataa 118080
taaaaagaat aaataaaaat aaattaaaat gtaaatatgt gcatgttaga aaaaatacac 118140
ccatcagcaa aaagggggta aaggagcgat ttcagtcata attggagaga tgcagaataa 118200
gccagcaatg cagtttcttt tattttggtc aaaaaaaata agcaaaacaa tgttgtaaac 118260
acccagtgct ggcagcaatg tggtgaggct ggctctctca ccagggctca cagggaaaac 118320
```

tcatgcaacc cttttagaaa gccatgtgga gagttgtacc gagaggtttt agaatattta 118380
taactttgac ccagaaattc tattctagga ctctgtgtta tgaaaataac ccatcatatg 118440
gaaaaagctc ctttcagaaa gaggttcatg ggaggctgtt tgtatttttt ttttctttgc 118500
atcaaatcca gctcctgcag gactgtttgt attattgaag tacaaagtgg aatcaataca 118560
aatgttggat agcaggggaa caatattcac aaaatggaat gggacatagt attaaacata 118620
gtgcttctga tgaccgtaga ccatagacaa tgcttaggat atgatatcac ttcttttgtt 118680
gtttttgta ttttgagacg aagtctcatt ctgtcaccca ggctggagtt cagtggcgcc 118740
atctcagctc actgcaacct ccatctcccg ggttcaagct attctccttc ctcaacctcc 118800
cgagtagctg ggttgcgcac caccatgcct ggctaacttt tgtattttta gtacagacgg 118860
ggtttcacca cgttggccag gctgctcttg aactcctgac gtcaggtgat ccaccagcct 118920
tgacctccca aagtgctagg attacaggag ccactgtacc cagcctagga tatgatatca 118980
cttcttagag caagatacaa aattgcatgt gcacaataat tctaccaagt ataggtatac 119040
aggggtagtt atatataaat gagacttcaa ggaaatacaa caaaatgcaa tcgtgattgt 119100
gttagggtgg taagaaaacg gtttttgctt tgatgagctc tgttttttaa aatcgttata 119160
ttttctaata aaaatacata gtcttttgaa ggaacataaa agattatgaa gaaatgagtt 119220
agatattgat tcctattgaa gattcagaca agtaaaatta aggggaaaaa aaacgggatg 119280
aaccagaagt caggctggag ttccaacccc agatccgaca gcccaggctg atggggcctc 119340
cagggcagtg gtttccaccc agcattctca aaagagccac tgaggtctca gtgccatttt 119400
caagatttcg gaagcggcct gggcacggct ggtccttcac tgggatcacc acttggcaat 119460
tatttacacc tgagacgaat gaaaaccaga gtgctgagat tacaggcatg gtggcttacg 119520
cttgtaatcg gctttgggaa gccgaggtgg gctgattgct tgagcccagg agtttcaaac 119580
tatcctggac aacatagcat gacctcgtct ctacaaaaaa tacaaaaaat ttgccaggtg 119640
tggtggcatg tgcctgtggt cccagctact tgggaggctg aagtaggaga atcccctgag 119700
ccctgggaag tcgaggctgc actgagccgt gatggtgtca ctgcactcca gcctgggtga 119760
caaagtgaga ccctatctca caaagaaaaa aaacaaaaca aaaaacccaa agcacactgt 119820
ttccactgtt tccagagttc ctgagaggaa aggtcaccgg gtgaggaaga cgttctcact 119880
gatctggcag agaaaatgtc cagtttttcc aactccctaa accatggttt tctatttcat 119940
agttcttagg caaattggta aaaatcattt ctcatcaaaa cgctgatatt ttcacacctc 120000
cctggtgtct gcagaaagaa ccttccagaa atgcagtcgt gggagaccca tccaggccac 120060
ccctgcttat ggaagagctg agaaaaagcc ccacgggagc atttgctcag cttccgttac 120120
gcacctagtg gcattgtggg tgggagaggg ctggtgggtg gatggaagga gaaggcacag 120180
cccccccttg cagggacaga gccctcgtac agaagggaca ccccacattt gtcttcccca 120240
caaagcggcc tgtgtcctgc ctacggggtc agggcttctc aaacctggct gtgtgtcaga 120300
atcaccaggg gaacttttca aaactagaga gactgaagcc agactcctag attctaattc 120360
taggtcaggg ctaggggctg agattgtaaa aatccacagg tgattctgat gcccggcagg 120420
cttgagaaca gccgcaggga gttctctggg aatgtgccgg tgggtctagc caggtgtgag 120480
tggagatgcc ggggaacttc ctattactca ctcgtcagtg tggccgaaca catttttcac 120540
ttgacctcag gctggtgaac gctcccctct ggggttcagg cctcacgatg ccatcctttt 120600
gtgaagtgag gacctgcaat cccagcttcg taaagcccgc tggaaatcac tcacacttct 120660
gggatgcctt cagagcagcc ctctatccct tcagctcccc tgggatgtga ctcgacctcc 120720
cgtcactccc cagactgcct ctgccaagtc cgaaagtgga ggcatccttg cgagcaagta 120780
ggcgggtcca gggtggcgca tgtcactcat cgaaagtgga ggcgtccttg cgagcaagca 120840
ggcgggtcca gggtggcgtg tcactcatcc ttttttctgg ctaccaaagg tgcagataat 120900
taataagaag ctggatctta gcaacgtcca gtccaagtgt ggctcaaagg ataatatcaa 120960
acacgtcccg ggaggcggca gtgtgagtac cttcacacgt cccatgcgcc gtgctgtggc 121020
ttgaattatt aggaagtggt gtgagtgcgt acacttgcga gacactgcat agaataaatc 121080
cttcttgggc tctcaggatc tggctgcgac ctctgggtga atgtagcccg gctccccaca 121140
ttcccccaca cggtccactg ttcccagaag cccctcctc atattctagg agggggtgtc 121200
ccagcatttc tgggtccccc agcctgcgca ggctgtgtgg acagaatagg gcagatgacg 121260
gaccctctct ccggaccctg cctgggaagc tgagaatacc catcaaagtc tccttccact 121320
catgcccagc cctgtcccca ggagccccat agcccattgg aagttgggct gaaggtggtg 121380
gcacctgaga ctgggctgcc gcctcctccc ccgacacctg ggcaggttga cgttgagtgg 121440
ctccactgtg gacaggtgac ccgtttgttc tgatgagcgg acaccaaggt cttactgtcc 121500
tgctcagctg ctgctcctac acgttcaagg caggagccga ttcctaagcc tccagcttat 121560
gcttagcctg cgccaccctc tggcagagac tccagatgca aagagccaaa ccaaagtgcg 121620
acaggtccct ctgcccagcg ttgaggtgtg gcagagaaat gctgcttttg gcccttttag 121680
atttggctgc ctcttgccag gagtggtggc tcgtgcctgt aattccagca ctttgggaga 121740
ctaaggcggg aggttcgctt gagcccagga gttcaagacc agcctgggca acaatgagac 121800
ccctgtgtct acaaaaagaa ttaaaattag ccaggtgtgg tggcacgcac ctgtagtccc 121860
agctacttgg gaggctgagg tgggaggatt gcctgagtcc gggaggcgga agttgcaagg 121920
agccatgatc gcgccactgc acttcaacct aggcaacaga gtgagacttt gtctcaaaaa 121980
acaatcatat aataatttta aaataaatag atttggcttc ctctaaatgt ccccggggac 122040
tccgtgcatc ttctgtggag tgtctccgtg agattcggga ctcagatcct caagtgcaac 122100
tgacccaccc gataagctga ggcttcatca tcccctggcc ggtctatgtc gactgggcac 122160
ccgaggctcc tctcccacca gctctcttgg tcagctgaaa gcaaactgtt aacaccctgg 122220
ggagctggac gtatgagacc cttggggtgg gaggcgttga tttttgagag caatcacctg 122280
gccctggctg gcagtaccgg gacactgctg tggctccggg gtgggctgtc tccagaaaat 122340
gcctggcctg aggcagccac ccgcatccag cccagagggt ttattcttgc aatgtgctgc 122400
tgcttcctgc cctgagcacc tggatcccgg cttctgccct gaggcccctt gagtcccaca 122460
ggtagcaagc gcttgccctg cggctgctgc atggggctaa ctaacgcttc ctcaccagtg 122520
tctgctaagt gtctcctctg tctcccacgc cctgctctcc tgtcccccca gtttgtctgc 122580
tgtgagggga cagaagaggt gtgtgccgcc cccacccctg cccgggccct tgttcctggg 122640
attgctgttt tcagctgttt gagctttgat cctggttctc tggcttcctc aaagtgagct 122700
cggccagagg aggaaggcca tgtgctttct ggttgaagtc aagtctggtg ccctggtgga 122760
ggctgtgctg ctgaggcgga gctggggaga gagtgcacac gggctgcgtg gccaacccct 122820
ctgggtagct gatgcccaaa gacgctgcag tgcccaggac atctgggacc tccctggggc 122880
ccgcccgtgt gtcccgcgct gtgttcatct gcgggctagc ctgtgacccg cgctgtgctc 122940
gtctgcgggc tagcctgtgt cccgcgctct gcttgtctgc ggtctagcct gtgacctggc 123000
agagagccac cagatgtccc gggctgagca ctgccctctg agcaccttca caggaagccc 123060

```
ttctcctggt gagaagagat gccagcccct ggcatctggg ggcactggat ccctggcctg 123120
agccctagcc tctccccagc ctgggggccc cttcccagca ggctggccct gctccttctc 123180
tacctgggac ccttctgcct cctggctgga ccctggaagc tctgcagggc ctgctgtccc 123240
cctccctgcc ctccaggtat cctgaccacc ggccctggct cccactgcca tccactcctc 123300
tcctttctgg ccgttccctg gtccctgtcc cagcccccct ccccctctca cgagttacct 123360
cacccaggcc agagggaaga gggaaggagg ccctggtcat accagcacgt cctcccacct 123420
ccctcggccc tggtccaccc cctcagtgct ggcctcagag cacagctctc tccaagccag 123480
gccgcgcgcc atccatcctc cctgtccccc aacgtccttg ccacagatca tgtccgccct 123540
gacacacatg ggtctcagcc atctctgccc cagttaactc cccatccata aagagcacat 123600
gccagccgac accaaaataa ttcgggatgg ttccagttta gacctaagtg gaaggagaaa 123660
ccaccacctg ccctgcacct tgttttttgg tgaccttgat aaaccatctt cagccatgaa 123720
gccagctgtc tcccaggaag ctccagggcg gtgcttcctc gggagctgac tgataggtgg 123780
gaggtggctg ccccccttgca ccctcaggtg accccacaca aggccactgc tggaggccct 123840
ggggactcca ggaatgtcaa tcagtgacct gccccccagg ccccacacag ccatggctgc 123900
atagaggcct gcctccaagg gacctgtctg tctgccactg tggagtccct acagcgtgcc 123960
ccccacaggg gagctggttc tttgactgag atcagctggc agctcagggt catcattccc 124020
agagggagcg gtgccctgga ggccacaggc ctcctcatgt gtgtctgcgt ccgctcgagc 124080
ttactgagac actaaatctg ttggtttctg ctgtgccacc tacccaccct gttggtgttg 124140
ctttgttcct attgctaaag acaggaatgt ccaggacact gagtgtgcag gtgcctgctg 124200
gttctcacgt ccgagctgct gaactccgct gggtcctgct tactgatggt ctttgctcta 124260
gtgctttcca gggtccgtgg aagcttttcc tggaataaag cccacgcatc gaccctcaca 124320
gcgcctcccc tctttgaggc ccagcagata ccccactcct gcctttccag caagattttt 124380
cagatgctgt gcatactcat catattgatc acttttttct tcatgcctga ttgtgatctg 124440
tcaatttcat gtcaggaaag ggagtgacat ttttacactt aagcgtttgc tgagcaaatg 124500
tctgggtctt gcacaatgac aatgggtccc tgtttttccc agaggctctt ttgttctgca 124560
gggattgaag acactccagt cccacagtcc ccagctcccc tggggcaggg ttggcagaat 124620
ttcgacaaca catttttcca ccctgactag gatgtgctcc tcatggcagc tgggaaccac 124680
tgtccaataa gggcctgggc ttacacagct gcttctcatt gagttacacc cttaataaaa 124740
taatcccatt ttatcctttt tgtctctctg tcttcctctc tctctgcctt tcctcttctc 124800
tctcctcctc tctcatctcc aggtgcaaat agtctacaaa ccagttgacc tgagcaaggt 124860
gacctccaag tgtggctcat taggcaacat ccatcataaa ccaggtagcc ctgtggaagg 124920
tgagggttgg gacgggaggg tgcagggggt ggaggagtcc tggtgaggct ggaactgctc 124980
cagacttcag aaggggctgg aaaggatatt ttaggtagac ctacatcaag gaaagtgttg 125040
agtgtgaaac ttgcgggagc ccaggaggcg tggtggctcc agctcgctcc tgcccaggcc 125100
atgctgccca agacaaggtg aggcgggagt gaagtgaaat aaggcaggca cagaaagaaa 125160
gcacatattc tcggccgggc gctgtggctc acgcctgtaa ttccagcact ttgggaggcc 125220
aaggtgggtg gatcatgagg tcaggagatt gagaccatcc tggctaacac agtgaaaccc 125280
cgtctctact aaaaatacaa aaaattagcc gggcgtggtg gtgggcgcct gtagtcccag 125340
ctactccgga ggctgaggca ggaaaatggc gtgaacccgg aaggcggagc ttgcagtgag 125400
```

```
cggagtgagc agagatcgcg ccactgcact ccagcctggg cgacagagcg agactccgtc 125460
tcaaaaaaaa aaagcacatg ttctcgcttc tttgtgggat ccaggagata gagaatagaa 125520
ggatggttac cagaggctgg gaagggtagt gaggggatgg tggggggatg gtcaatgggt 125580
acaaaaaaaa tagaataaga cctagtattt gatagtgcaa cagggtgact atagtcaata 125640
ataatttaat tgtacattta aaaataacta aaagatagcc gggtgcagtg gcttacgtct 125700
gtaatcccag tactttggga ggctgaggtg ggcgtttgag accagcctgg ccaacatggt 125760
gaaaccccat ctctactaaa aatacaaaaa ttagccaggc atggtggcgg gcgcctgtaa 125820
tcccagctac tcgggaggct gaggcaggag aatcacttga acctgggagg cagaggttgc 125880
agtgagccga gatcttgcca ctgcactcca gcctgggtga cagtgaaact ccgtctcaaa 125940
aataaaaata aaaatacagc tgggcacggt ggctcacgcc tgtaatccca gcactttggg 126000
aggccgaggc gagcggatca caaggtcagg agatatagac catcctggct aacacggtga 126060
aacccggtct ctactaaaaa tacaaaaaat tagccaggcg tggtggcagg tgcctatagt 126120
cccagctact cacaaggctg aggcaggaga atggcatgaa cctgggaggc ggagcttgca 126180
gtgagccgag attgtgccac tgcactccag cctgggcgag agagtgagac tccgtctcaa 126240
aacaaaaaca aaaacaaaaa caaaaacaaa cacacaacaa aaacctaaaa gaatataaat 126300
ggattgtttg taacacaaag gacaaatgtt tgaggggatg gataccccat tttccatgat 126360
gtgattatta tacattgtgt gtctgtatca aaacatctca tgagccccat aaatatatac 126420
acctaactat gtacccacaa aaattaaaaa aatatatttt ttaaggtgaa gagggaggcg 126480
agatgctggc cttaacccct aacccgttgt tctccctgca agctgtccac agggcctctc 126540
agactcgagg ttcagctata tggatgcatg agcttggtcc ccagccaaca tgggagacac 126600
ttcaccatcg gcagcagcta cagcacagga accctgggtc actgccatgt cccctctgtg 126660
actttgttta aacagaaaat gatgctctgg gccggctgtg gtggcccaca cctataatcc 126720
cagcaccttg ggaggcgggg gtgggcagat tgcctgaggt caggagttgg agatcagcct 126780
ggccgacatg gcgaaacccc atgtctacta aaaatacaaa aactagccag gcatggtggc 126840
acatgcctgt aatcccagct acttgggagg ctgaagcagg agaatcactt gaacccagga 126900
ggcagaggct gagtgagcca agatcgtgcc aatgcactcc agcttgggtg agggagtgag 126960
actccgtctc aaaaaaaaaa aaaaagaaag aaaaagaaaa gaaagtgatc ctactggaac 127020
catgcttact cccctcccca cctcacactg tgtagaaatt agtgctgtcg gccaggcgcg 127080
gtggctcatg cctgtaatcg cagcactttg ggaggccaag gcaggcggat cacgaggtca 127140
ggagatcaag accatcctgg ctaacacagt gaaaccctgt ctctactaaa aatacaaaaa 127200
attagccggg catggtggca ggcacctgta gtcccaacta cttgggaggc tgaggcagga 127260
gaatggcatg aacctgggag gcggagcttg cagtgagcca agatcgcgcc actgcatacc 127320
agcctaggtg acagagtgag actcagcaaa aaaagaaaga aagaaagaaa gaaatcagtg 127380
ctgtctatac ttctttctgc agtgatggaa atattctgta tctgtgctgt ccagtatagt 127440
agccactagc tacatgtggc acttgaaaca tggctggtac agttgaggaa gagtggctgc 127500
catatcggac gacacagcta tagattctgt caccccaccc cgagagtcca gagcggggac 127560
ttctgcctta ggccctattc agggctgatt tttacttgaa cccttactgt gggaagagaa 127620
ggccatgaga agttcagtct agaatgtgac tccttatttt ctggctccct tggacacttt 127680
gtgggattta gtctccctgt ggaaagtatt ccacaagtgg tgccactacc ccagctgtga 127740
gagcagctgg gagctgcttt tgtcatcttt ccctggaaag tcctgtgggc tgtctcttcc 127800
```

```
tcatgccttg tcccatgctt gggcatggtg tcaagcgtca ggagggagaa agggtcctta 127860
tttatttatt tagagaggga cccttcttct gttcccaggc tggagtgcag tggtgcgatc 127920
tcggctcact gcaacctccg cctcctgggt tcaagtgatt ctcctgcctc agcctcctga 127980
gtagctgaga ttacaggcac atgccaacat gcccggctaa ttttttttt ttttttttt 128040
ttttttttt ttttttttt gagatggagt tgtactctca ttgcccaggc tggaatgtaa 128100
tggcacaatc tcggctcact gcaacctcca cctcctggat tcaagcaatt ctcctgtctc 128160
agcttcccaa gtagctggga ttacaggtgc ccgccaccat gctcaactaa tttttgtatt 128220
tttttttag tagagacgag gtttcaccat gttggtcaga ctggtctcaa actcctgacc 128280
tcaggtgatc cacctgcctc ggcctcccaa agtgctagga ttacaggcat gagccaccac 128340
gcccggcctg aaagggttct tatttagtgt gcattttgac attcaattta attccaaggt 128400
cttgtggggt catggtttac aggatgttga tatagaaaag acttcactta atgggccggg 128460
cgcagtggct catgcctgta atcccagcac tttgggaggc cgaggcaggc agatcaggag 128520
gtcaggagat tgagaccatc ctggctaaca cagtgaaacc ccatctctac tgaaaataca 128580
aaaaattagc tgggcgtggt ggcaggcacc tgtagtccca gccactcggt tggctgaggc 128640
aggagaatgg catgaacccg ggaggcggag cttgcagtga gcagagacca tgccactgca 128700
ctccagcctg ggcgacagag caagactctg tctcaagaaa aaaaaaaaaa aacagacttt 128760
acttactgga agccaaccaa tgtatattta gagtaatttt tcctgggctg agctgtcatt 128820
tacttttgca gtatctcaag aagaagagtt tacagtgtaa atatttgatg cacactttga 128880
ttatatagat gaagcaaact attttcaaga gctttgcaag gacttacttg tatccaaaca 128940
ccattctaaa aggagtctta cctacttcta aaggctggtc tctacttgga accacttgct 129000
tggccctggt tcaagtcctg ctgcaaacct ggaagtcctg tcattgtctt cttccctcca 129060
gagcagtggc acccaatcta atttttgctg tgccccagca gcccctggca ctttgccctg 129120
tagactgcag acctcatgta atgtatgtta agtccacaga accacagaag atgatggcaa 129180
gatgctcttg tgtgtgttgt gttctaggag gtggccaggt ggaagtaaaa tctgagaagc 129240
ttgacttcaa ggacagagtc cagtcgaaga ttgggtccct ggacaatatc acccacgtcc 129300
ctggcggagg aaataaaaag gtaaaggggg tagggtgggt tggatgctgc ccttgggtat 129360
atgggcatta atcaagttga gtggacaaag gctggtccag ttcccagagg aggaaaacag 129420
aggcttctgt gttgactggc tggatgtggg ccctcagcag catccagtgg gtctccactg 129480
cctgtctcaa tcacctggag ctttagcacg tttcacacct gggccccaac ctggagaggc 129540
tgaccaatgg gtctcagggg cagctcggtt gctggagttt ttgtttttat ttatttttat 129600
gtatttaagg cagggtctct gtattagtcc attctcacac tgctaataaa gacataccca 129660
agactgggta atttataaag gaaagaggtt taatggactc acagttccac atggctgggg 129720
aggcctcaaa atcatggcgg aaggcaaagg agaagcaaag gcatttctta catggcgaca 129780
ggcaagagag cgtgtgcagg ggaactccca tttataaaac catcagacct catgagattt 129840
attcactatc atgagaacag catgggaaag acccgccccc atgattcagt tacctcccac 129900
tgggtccctc ccatgacaca tggaattatg ggagctacaa ttcaagatga gatttgggtg 129960
gggacacagc caaaccatat cagtctccct ctgtcatcca ggctggagtg cactggcatg 130020
atctcggctc actgcagcct ctacctccct gggtcaggtg atcttcccac ctcagcctcc 130080
caggtagctg gaactacagg tacctgccac tatgcctggc taaatatttt gtatttcctg 130140
```

```
tggagacgag gttttgccac gttgcccagg ctggtcttga actcctgagg tcaagcaata 130200
tgcccacctc ggcctcccaa ggtgctggga ttacaggtgt gagccacagt gctcggccta 130260
agtcactgca gtttttaaag ctcccaggtg attcttcagt gcagtcaaaa gtgagaactg 130320
gctgggtgcg gtggctcatg cctgtaatcc cagcaccttg ggaggcgaag gtgggcagat 130380
ggcttgaggt caggagttca agaccagcct ggccaacatg gtaaaacccc atctctacta 130440
aaaatacaaa agttagctgg gtgtggtggt gcgtgcctgt aatcccagct acttgggagg 130500
ctgaggcatg agaattgctt gaacccaggg gacagaggtt gtagtgagcc gagatcgtgc 130560
cactgcactc cagcctgggc aacagagtga gattccatct cacaaaaaaa aaaaaaagcg 130620
agaaccactg tcctaggccc tgatgtttgc aggcaactaa aaaaggaagt ggacatcccc 130680
agtcagctgt ggcgcaccaa gaacaagtca tgggaacata acctaatttt ctaaatgggt 130740
tactaggcac ttagagcaaa acaatgatgc cgaaatcctg atttcagcaa agcctctgcc 130800
tgcctgtctt ggaagtatcc acatgaggct gctggggcct tggtgtcccc agcagtttct 130860
agtctctagg tcttgctgtg ggtgtctgtg cagtgagggt gtgtgtggcg ctgggtgagc 130920
tctgtctagg cctggcacag gatgcggtct ggtagctgct gcttctcttc tgcagaagcg 130980
cagccaagca ccctctgggg tttcaggccc acacccagcc tgaagttctg ggagtggctc 131040
actttccaac cttcagggtc tcccagcagc tgactgggga gtggtggagg gaaaagggat 131100
tgtattagtc cgttttcacg ccgctgatga agacataccc gatactgggc agtctaaaag 131160
atagaggtct gatggactca cagttccacg tgactgggga ggcctgacaa tcatggtgga 131220
aggtgaaagg cttgtctcac acggtggcag acaagagaaa agagcttgtg caggggaact 131280
ccccttata aaaccatcag atctcgggag acttattcac tatcatgaga acagcacggg 131340
aaagaccctc ctctatgatt caattacctc ccaccaggtc cctcccacaa catgtaggaa 131400
ttgtgggaac tacaattcaa gatgacattt gggtggggac acagccaaac catatcaggg 131460
cgtcccagaa agggtatagg gtctgagacc caagtcagca tgagaaagta tgcttctcat 131520
ggtggcccag ttgggtggaa gtggcagccg ggccgtcttt ccaccaggcc actcaagtag 131580
cagctgagag acccctgccc tggccagtcc ccgccctccc ctcttgccac tgcctctggt 131640
tctgaacaga tgggcaccct catcttgtat ttgtgattaa tgtctaacaa tgtagttttg 131700
tgagaagggt ttgctgatac agccttgctg cagatgctgc gaactgtggc ctggggcaga 131760
ccttacctcc agacacgccc tgaggcaggg gagggcactg gcccgtagct ggccgagagc 131820
tctcgggttg cgcgacaggg atacttttca gcggctgggt cgctatccaa agtgagaaaa 131880
cgaggaggga ccaggaggct gtccgcctca agagatgtgg gggccaggtc cagttatctg 131940
gggaagcagt aagcttctct gctgtttcta accccaggcc tcccctggtc taaggcaggg 132000
cctcccagcc tcggggcact ttaaagatat ctgggcctgg ccccatcccc acagtctgac 132060
tgagtgggtc tggatagggc ctgagcattg gtgatttcct gggtgaaagg aggcccctca 132120
cagtctctgg aagcttctct gtgttaggaa aagctctggg cttgactctg ctttgaaagt 132180
caagatccgc aaatcctctc agcctcagtt tctccttcag caagatgaaa tggaaatgct 132240
gtacctacgt cccggggtgg ttgtgagacc caaaaaagac aatgttctgg aaggttcctg 132300
gtgcgttgca gtcctctaag aacctgagtt agagccacgc tgagtctcag cttcttggct 132360
ccttctgttt caaactcgtc catgtgatag ctcaggaagg gtaggcaggg ccctgccccc 132420
tactcagaaa acaccatcct ggtcctgggg atccccgcag cattagtccc ctgttttccc 132480
agtgtattga gaaaaattgc taacaagcag tggggcacac caccagcctc ctgggttcct 132540
```

ttcagtttgg ggatttttgg acattcccag gaatgtctta aaaaacactt caaaaaacat 132600
taacataaat atttttatca aagcctgtat taaatggtct ttcaagaaaa tacagtaaca 132660
ggtcaggcat ggtggctcat gcctgtaacc ccagcacttt gggaggccaa ggcaggcaga 132720
tcacctgaaa tcaggagttc aagaccaacc tggccaacac agccaaatcc catctctaca 132780
aaaaatacaa aaattagctg ggtgtggtgg cacacacctg tagtcccagc tacttgggag 132840
gccgaggcag gagaattgct tgatcccgga ggcggaggtt gcagtgagcc gagatcgtgc 132900
cactgcactc cagcgtgggt gacaaggtga atctttgtct caaaaaaaaa aaaaaaaaaa 132960
agataaaata cagtatacag taatagagaa caatcctttt ttcaaagtag tgaccccaaa 133020
tgaacaaaat atgcatctag cttaaatgcg aacctggttt tctctacgcc cattcaagcc 133080
cctgcaatag gggcccttca ccccgcatcc atggactcct aaaattatat ggaaaatggc 133140
tgtgtgtgag tgtggatgga catgtgcaca catatttttg gctttaccag atgctcaaag 133200
agcctaggac ccaaaaaggg ctgagaatga ccgtgtcggc cacttcaggg tcatcaggaa 133260
ttgctgtgca ctgctcactt ctccagtgaa cactttctgc ttctgtgttt cctggtatcc 133320
tttgggactc ctggctaggt catgtgtttc tctactttca aaagggcttc agccaggcac 133380
gatggcatga gcctgtagtc ccagttgctc tggaggttaa ggtgggaaga ttgcttgagc 133440
ccaggaattt gaggccagcc tgggcaagta gataggtaga tgattgatag atagatagat 133500
agataaatag atggatagat aagtcgctag acagtcatcc atccacccat ccacacataa 133560
aaaggccttt gtcatgtcat gttttgtggc ccacctgcca gtgttgccca cagttgctgc 133620
ccctccaaac tcatcagtca ctggcaaaca ggaggaatgt gtggctcatg tctgggcatc 133680
agtggctgtg ggagacatcc ttgatcttct ccagcttctc cttccacatt ttcctttgca 133740
atctggcaat atctattaaa ataaaatgtg catgcctttt gacctaagag cttcacttct 133800
aggacccact tacacgtgtg tgacatgatg ttcatacggg tttatttatc tgaggttgtt 133860
catacacacc attgcctgta atcactaaag gcgggagcag cctacacatc catccacaga 133920
ggagtagatg ccttttggta catccgtggc gacggaatac taagcagcct gtgtatctat 133980
acactcacac gtgtttgttt atgtgtggaa tatctctgga gggtacacaa gaaacttaaa 134040
atgatcactg tctctgggga gggtacctgg gtgcctggga ggcaggtcag ggaaggagtg 134100
ggcacaggta ttaccaattg gaagacaata aaaacaacag ctcctggcca ggcgcagtgg 134160
ctcacgcctg taatggcagc actctgagag gctgaggcgg gcagattgct tgcgtccagg 134220
agttcaagac cagcctgggc aacatagcaa aaccccgttt ctattaaaaa tacaaaaaat 134280
tagccaggtg tggtggcatg cacctgtaat cccagctact cgggaggctg aggtgggaga 134340
atcacctgag cctgggaggt caaggctgca gtgaggtgag attgtgccac cgcactctag 134400
cctgggcgat agagcaagac cctgtctcaa aaacaaacaa aaaacagtcc ctggcactct 134460
gggccaggcc tggcagggca gttggcaggg ctggtctttc tctggcactt catctcaccc 134520
tccctccctt cctcttcttg cagattgaaa cccacaagct gaccttccgc gagaacgcca 134580
aagccaagac agaccacggg gcggagatcg tgtacaagtc gccagtggtg tctggggaca 134640
cgtctccacg gcatctcagc aatgtctcct ccaccggcag catcgacatg gtagactcgc 134700
cccagctcgc cacgctagct gacgaggtgt ctgcctccct ggccaagcag ggtttgtgat 134760
caggcccctg gggcggtcaa taattgtgga gaggagagaa tgagagagtg tggaaaaaaa 134820
aagaataatg acccggcccc cgccctctgc ccccagctgc tcctcgcagt tcggttaatt 134880
ggttaatcac ttaacctgct tttgtcactc ggctttggct cgggacttca aaatcagtga 134940
tgggagtaag agcaaatttc atctttccaa attgatgggt gggctagtaa taaaatattt 135000
aaaaaaaaac attcaaaaac atggccacat ccaacatttc ctcaggcaat tccttttgat 135060 tctttttct tcccctcca tgtagaagag ggagaaggag aggctctgaa agctgcttct 135120
gggggatttc aagggactgg gggtgccaac cacctctggc cctgttgtgg gggtgtcaca 135180
gaggcagtgg cagcaacaaa ggatttgaaa cttggtgtgt tcgtggagcc acaggcagac 135240
gatgtcaacc ttgtgtgagt gtgacggggg ttggggtggg gcgggaggcc acgggggagg 135300
ccgaggcagg ggctgggcag aggggagagg aagcacaaga agtgggagtg ggagaggaag 135360
ccacgtgctg gagagtagac atccccctcc ttgccgctgg gagagccaag gcctatgcca 135420
cctgcagcgt ctgagcggcc gcctgtcctt ggtggccggg ggtgggggcc tgctgtgggt 135480
cagtgtgcca ccctctgcag ggcagcctgt gggagaaggg acagcgggta aaaagagaag 135540
gcaagctggc aggagggtgg cacttcgtgg atgacctcct tagaaaagac tgaccttgat 135600
gtcttgagag cgctggcctc ttcctccctc cctgcagggt agggggcctg agttgagggg 135660
cttccctctg ctccacagaa accctgtttt attgagttct gaaggttgga actgctgcca 135720
tgattttggc cactttgcag acctgggact ttagggctaa ccagttctct ttgtaaggac 135780
ttgtgcctct tgggagacgt ccacccgttt ccaagcctgg gccactggca tctctggagt 135840
gtgtgggggt ctgggaggca ggtcccgagc cccctgtcct tcccacggcc actgcagtca 135900
cccctgtctg cgccgctgtg ctgttgtctg ccgtgagagc ccaatcactg cctatacccc 135960
tcatcacacg tcacaatgtc ccgaattccc agcctcacca ccccttctca gtaatgaccc 136020
tggttggttg caggaggtac ctactccata ctgagggtga aattaaggga aggcaaagtc 136080
caggcacaag agtgggaccc cagcctctca ctctcagttc cactcatcca actgggaccc 136140
tcaccacgaa tctcatgatc tgattcggtt ccctgtctcc tcctcccgtc acagatgtga 136200
gccagggcac tgctcagctg tgaccctagg tgtttctgcc ttgttgacat ggagagagcc 136260
ctttcccctg agaaggcctg gccccttcct gtgctgagcc cacagcagca ggctgggtgt 136320
cttggttgtc agtggtggca ccaggatgga agggcaaggc acccagggca ggcccacagt 136380
cccgctgtcc cccacttgca ccctagcttg tagctgccaa cctcccagac agcccagccc 136440
gctgctcagc tccacatgca tagtatcagc cctccacacc cgacaaaggg gaacacaccc 136500
ccttggaaat ggttcttttc ccccagtccc agctggaagc catgctgtct gttctgctgg 136560
agcagctgaa catatacata gatgttgccc tgccctcccc atctgcaccc tgttgagttg 136620
tagttggatt tgtctgttta tgcttggatt caccagagtg actatgatag tgaaaagaaa 136680
aaaaaaaaaa aaaaaggacg catgtatctt gaaatgcttg taaagaggtt tctaacccac 136740
cctcacgagg tgtctctcac ccccacactg ggactcgtgt ggcctgtgtg gtgccaccct 136800
gctggggcct cccaagtttt gaaaggcttt cctcagcacc tgggacccaa cagagaccag 136860
cttctagcag ctaaggaggc cgttcagctg tgacgaaggc ctgaagcaca ggattaggac 136920
tgaagcgatg atgtcccctt ccctacttcc ccttggggct ccctgtgtca gggcacagac 136980
taggtcttgt ggctggtctg gcttgcggcg cgaggatggt tctctctggt catagcccga 137040
agtctcatgg cagtcccaaa ggaggcttac aactcctgca tcacaagaaa aaggaagcca 137100
ctgccagctg gggggatctg cagctcccag aagctccgtg agcctcagcc acccctcaga 137160
ctgggttcct ctccaagctc gccctctgga ggggcagcgc agcctcccac caagggccct 137220
gcgaccacag cagggattgg gatgaattgc ctgtcctgga tctgctctag aggcccaagc 137280
tgcctgcctg aggaaggatg acttgacaag tcaggagaca ctgttcccaa agccttgacc 137340
agagcacctc agcccgctga ccttgcacaa actccatctg ctgccatgag aaaagggaag 137400
ccgcctttgc aaaacattgc tgcctaaaga aactcagcag cctcaggccc aattctgcca 137460
cttctggttt gggtacagtt aaaggcaacc ctgagggact tggcagtaga aatccagggc 137520
ctcccctggg gctggcagct tcgtgtgcag ctagagcttt acctgaaagg aagtctctgg 137580
gcccagaact ctccaccaag agcctccctg ccgttcgctg agtcccagca attctcctaa 137640
gttgaaggga tctgagaagg agaaggaaat gtggggtaga tttggtggtg gttagagata 137700 tgccccccctc attactgcca acagtttcgg ctgcatttct tcacgcacct cggttcctct 137760
tcctgaagtt cttgtgccct gctcttcagc accatgggcc ttcttatacg gaaggctctg 137820
ggatctcccc cttgtggggg caggctcttg gggccagcct aagatcatgg tttagggtga 137880
tcagtgctgg cagataaatt gaaaaggcac gctggcttgt gatcttaaat gaggacaatc 137940
cccccagggc tgggcactcc tcccctcccc tcacttctcc cacctgcaga gccagtgtcc 138000
ttgggtgggc tagataggat atactgtatg ccggctcctt caagctgctg actcacttta 138060
tcaatagttc catttaaatt gacttcagtg gtgagactgt atcctgtttg ctattgcttg 138120
ttgtgctatg gggggagggg ggaggaatgt gtaagatagt taacatgggc aaagggagat 138180
cttggggtgc agcacttaaa ctgcctcgta accctttttca tgatttcaac cacatttgct 138240
agagggaggg agcagccacg gagttagagg cccttggggt ttctcttttc cactgacagg 138300
ctttcccagg cagctggcta gttcattccc tccccagcca ggtgcaggcg taggaatatg 138360
gacatctggt tgctttggcc tgctgccctc tttcaggggt cctaagccca caatcatgcc 138420
tccctaagac cttggcatcc ttccctctaa gccgttggca cctctgtgcc acctctcaca 138480
ctggctccag acacacagcc tgtgcttttg gagctgagat cactcgcttc accctcctca 138540
tctttgttct ccaagtaaag ccacgaggtc ggggcgaggg cagaggtgat cacctgcgtg 138600
tcccatctac agacctgcgg cttcataaaa cttctgattt ctcttcagct ttgaaaaggg 138660
ttaccctggg cactggccta gagcctcacc tcctaataga cttagcccca tgagtttgcc 138720
atgttgagca ggactatttc tggcacttgc aagtcccatg atttcttcgg taattctgag 138780
ggtgggggga gggacatgaa atcatcttag cttagctttc tgtctgtgaa tgtctatata 138840
gtgtattgtg tgttttaaca aatgatttac actgactgtt gctgtaaaag tgaatttgga 138900
aataaagtta ttactctgat taaataaggt ctccattcat ggattccaag gacaagaaag 138960
tcatatagaa tgtctatttt ttaagttctt tcccacgcac ccttagataa tttagctcag 139020
aacaggaaat gatagtatta ataaaagctg gacatcagga ttaacagctc tctctggggc 139080
cctgaaggtg agagttctca gacttgctca tttgcagttg cttctttgtg atgctggcaa 139140
accatcctag tcccattcaa agggcaatac aaagccttgt ggctgacctc acgatgcagc 139200
actcagtttg caagaccggc accagtgtat gcaaacctga gaaggttggg gatgaggata 139260
tgggatcttt catccctgga aatttagtcc agaggcctgg ggctggagca gaacaccaag 139320
ccaatcagct taatgaatgg cttagattcc tgctaggttt gcagagctgc cttctttcct 139380
ttggtacctt attatagatt gaggagtatt tctgctaaac caagataggg ataaccagat 139440
agcatcttca tagcaatgcc acaaaggaaa acaaaaacaa aacagtaatc catcatatta 139500
ttccttagta actatgccaa ggtcatgata ctgaatcctt agattgtttc aaaatactac 139560
ttttctttgc tcttcctgat gtgtttgcca ccgcaggcag atgtttaagt aaaacagatt 139620
ttaactgcag ctacaaaagc agcaacaggc cagcaaaaga gaagtgctat ctcagagagc 139680
atggctttca gagccacaag agacagcctc actggctgtt tcagcttgac tgccatgcaa 139740
agaagagagc agagggagaa ccagccccac ccacttattc atcttgtaca aaaaaaaagc 139800
acctaccagc ctaggctaca tagtgagaca ctatctccac aaaaaaccca cgaaaactag 139860
ctgggtatgg tggcacatgc ctacagtccc agctactggt aaggctgtgg tgggaggatc 139920
tcttgaggcc aggaaggaga tccaggctgc agtgagccaa gattgcacca ctgcactcca 139980
gtctggacaa tcgagcaaga tcccatctca aacaataaaa aaaaaaagcg tgtaacctcc 140040
tcagaagaaa gatgttataa tctcaggcag caggcaagaa ccaatccagg ctctaagcaa 140100
attatgtatc tcactgaccc caccaaacct cagaaaaatt taacagtgag aagcaaaatc 140160
tcctttaaag agcaacttag aacagataga aaatatcata cagctgactt cactagagag 140220
aaagtgcatc aactgctttc actcaacaaa aagaaaaaag agatgatcaa tgcagatccc 140280
ctctcctcct ggcagccctt accctcagtg aaaagccacc accattctct ctctggtggc 140340
catcagatca acctgcggcg ttcccacaag acagaatgga gattttccaa ggtatagagc 140400
aagtcagagt accccaaaga acggcggcag agagccagct ccgaaactgc caacactacc 140460
atgcatacac agttcagtaa gtcaagaaag gcctggtaca cagcattctg taactttttt 140520
ttttattttt ttcaattttt ccttcttttt tttttttaag cactagtctg tgctttgcga 140580
acagaatcaa gacattaaca aagatcagct tctctgaaga aaagcatttc tatagaacaa 140640
agacagctac atgtttcgct gccattacac agctccaaag caggaaaaga aaatatttac 140700
aaaatacaag gttttttttt tccatttttt gtttttgttt tttttttcaa tgctaaaagg 140760
gttattcaga attttcaacc ttataaatag aagaagcact ttatgcatag ggatatggtg 140820
cattattgta ttttttttta aagaaacaat gacaaaccct ttaacttgca aacagaaaaa 140880
aaaatcacta atgttgaaaa ttgtgaaaaa accccaacca ttaa 140924

<210> SEQ ID NO 3
<211> LENGTH: 16
<212> TYPE: DNA
<213> ORGANISM: Artificial Sequence
<220> FEATURE:
<223> OTHER INFORMATION: Miscellaneous sequence

<400> SEQUENCE: 3
atgcatgcat gcatgc 16

<210> SEQ ID NO 4
<211> LENGTH: 20
<212> TYPE: DNA
<213> ORGANISM: Artificial Sequence
<220> FEATURE:
<223> OTHER INFORMATION: ASO-001167

<400> SEQUENCE: 4
aaagatgaaa tttgctctta 20

<210> SEQ ID NO 5
<211> LENGTH: 20
<212> TYPE: DNA
<213> ORGANISM: Artificial Sequence
<220> FEATURE:
<223> OTHER INFORMATION: ASO-001168

<400> SEQUENCE: 5
gaaagatgaa atttgctctt 20

<210> SEQ ID NO 6
<211> LENGTH: 20
<212> TYPE: DNA
<213> ORGANISM: Artificial Sequence
<220> FEATURE:
<223> OTHER INFORMATION: ASO-001169

<400> SEQUENCE: 6
ggaaagatga aatttgctct 20

<210> SEQ ID NO 7
<211> LENGTH: 16
<212> TYPE: DNA
<213> ORGANISM: Artificial Sequence
<220> FEATURE:
<223> OTHER INFORMATION: ASO-000829

<400> SEQUENCE: 7
aagatgaaat ttgctc 16

<210> SEQ ID NO 8
<211> LENGTH: 20
<212> TYPE: DNA
<213> ORGANISM: Artificial Sequence
<220> FEATURE:
<223> OTHER INFORMATION: ASO-001170

<400> SEQUENCE: 8
tggaaagatg aaatttgctc 20

<210> SEQ ID NO 9
<211> LENGTH: 20
<212> TYPE: DNA
<213> ORGANISM: Artificial Sequence
<220> FEATURE:
<223> OTHER INFORMATION: ASO-001171

<400> SEQUENCE: 9
ttggaaagat gaaatttgct 20

<210> SEQ ID NO 10
<211> LENGTH: 20
<212> TYPE: DNA
<213> ORGANISM: Artificial Sequence
<220> FEATURE:
<223> OTHER INFORMATION: ASO-001172

<400> SEQUENCE: 10
tttggaaaga tgaaatttgc 20

<210> SEQ ID NO 11
<211> LENGTH: 20
<212> TYPE: DNA
<213> ORGANISM: Artificial Sequence
<220> FEATURE:
<223> OTHER INFORMATION: ASO-001173

<400> SEQUENCE: 11
atttggaaag atgaaatttg 20

<210> SEQ ID NO 12
<211> LENGTH: 20
<212> TYPE: DNA
<213> ORGANISM: Artificial Sequence
<220> FEATURE:

<223> OTHER INFORMATION: ASO-001174

<400> SEQUENCE: 12
aatttggaaa gatgaaattt 20

<210> SEQ ID NO 13
<211> LENGTH: 20
<212> TYPE: DNA
<213> ORGANISM: Artificial Sequence
<220> FEATURE:
<223> OTHER INFORMATION: ASO-001175

<400> SEQUENCE: 13
caatttggaa agatgaaatt 20

<210> SEQ ID NO 14
<211> LENGTH: 20
<212> TYPE: DNA
<213> ORGANISM: Artificial Sequence
<220> FEATURE:
<223> OTHER INFORMATION: ASO-001176

<400> SEQUENCE: 14
tcaatttgga aagatgaaat 20

<210> SEQ ID NO 15
<211> LENGTH: 20
<212> TYPE: DNA
<213> ORGANISM: Artificial Sequence
<220> FEATURE:
<223> OTHER INFORMATION: ASO-001177

<400> SEQUENCE: 15
atcaatttgg aaagatgaaa 20

<210> SEQ ID NO 16
<211> LENGTH: 20
<212> TYPE: DNA
<213> ORGANISM: Artificial Sequence
<220> FEATURE:
<223> OTHER INFORMATION: ASO-001178

<400> SEQUENCE: 16
catcaatttg gaaagatgaa 20

<210> SEQ ID NO 17
<211> LENGTH: 20
<212> TYPE: DNA
<213> ORGANISM: Artificial Sequence
<220> FEATURE:
<223> OTHER INFORMATION: ASO-001179

<400> SEQUENCE: 17
acccatcaat ttggaaagat 20

<210> SEQ ID NO 18
<211> LENGTH: 20
<212> TYPE: DNA
<213> ORGANISM: Artificial Sequence
<220> FEATURE:
<223> OTHER INFORMATION: ASO-001180

<400> SEQUENCE: 18
ccatcaattt ggaaagatga 20

<210> SEQ ID NO 19
<211> LENGTH: 20
<212> TYPE: DNA
<213> ORGANISM: Artificial Sequence
<220> FEATURE:
<223> OTHER INFORMATION: ASO-001181

<400> SEQUENCE: 19
cccatcaatt tggaaagatg 20

<210> SEQ ID NO 20
<211> LENGTH: 20
<212> TYPE: DNA
<213> ORGANISM: Artificial Sequence
<220> FEATURE:
<223> OTHER INFORMATION: ASO-001182

<400> SEQUENCE: 20
cacccatcaa tttggaaaga 20

<210> SEQ ID NO 21
<211> LENGTH: 20
<212> TYPE: DNA
<213> ORGANISM: Artificial Sequence
<220> FEATURE:
<223> OTHER INFORMATION: ASO-001183

<400> SEQUENCE: 21
ccacccatca atttggaaag 20

<210> SEQ ID NO 22
<211> LENGTH: 20
<212> TYPE: DNA
<213> ORGANISM: Artificial Sequence
<220> FEATURE:
<223> OTHER INFORMATION: ASO-001184

<400> SEQUENCE: 22
cccacccatc aatttggaaa 20

<210> SEQ ID NO 23
<211> LENGTH: 20
<212> TYPE: DNA
<213> ORGANISM: Artificial Sequence
<220> FEATURE:
<223> OTHER INFORMATION: ASO-001062

<400> SEQUENCE: 23
gcccacccat caatttggaa 20

<210> SEQ ID NO 24
<211> LENGTH: 20
<212> TYPE: DNA
<213> ORGANISM: Artificial Sequence
<220> FEATURE:
<223> OTHER INFORMATION: ASO-001063

<400> SEQUENCE: 24
tagcccaccc atcaatttgg 20

<210> SEQ ID NO 25
<211> LENGTH: 20
<212> TYPE: DNA
<213> ORGANISM: Artificial Sequence
<220> FEATURE:
<223> OTHER INFORMATION: ASO-001064

<400> SEQUENCE: 25
ctagcccacc catcaatttg 20

<210> SEQ ID NO 26
<211> LENGTH: 20
<212> TYPE: DNA
<213> ORGANISM: Artificial Sequence
<220> FEATURE:
<223> OTHER INFORMATION: ASO-001065

<400> SEQUENCE: 26
actagcccac ccatcaattt 20

<210> SEQ ID NO 27
<211> LENGTH: 20
<212> TYPE: DNA
<213> ORGANISM: Artificial Sequence
<220> FEATURE:
<223> OTHER INFORMATION: ASO-001066

<400> SEQUENCE: 27
tactagccca cccatcaatt 20

<210> SEQ ID NO 28
<211> LENGTH: 16
<212> TYPE: DNA
<213> ORGANISM: Artificial Sequence
<220> FEATURE:
<223> OTHER INFORMATION: ASO-000830

<400> SEQUENCE: 28
tactagccca cccatc 16

<210> SEQ ID NO 29
<211> LENGTH: 16
<212> TYPE: DNA
<213> ORGANISM: Artificial Sequence
<220> FEATURE:
<223> OTHER INFORMATION: ASO-000260

<400> SEQUENCE: 29
ccctcttcta catgga 16

<210> SEQ ID NO 30
<211> LENGTH: 16
<212> TYPE: DNA
<213> ORGANISM: Artificial Sequence
<220> FEATURE:
<223> OTHER INFORMATION: ASO-000305

<400> SEQUENCE: 30
tgcctctgtg acaccc 16

<210> SEQ ID NO 31
<211> LENGTH: 16
<212> TYPE: DNA
<213> ORGANISM: Artificial Sequence
<220> FEATURE:
<223> OTHER INFORMATION: ASO-000304

<400> SEQUENCE: 31
ttcaaatcct ttgttg 16

<210> SEQ ID NO 32
<211> LENGTH: 16

<212> TYPE: DNA
<213> ORGANISM: Artificial Sequence
<220> FEATURE:
<223> OTHER INFORMATION: ASO-000324

<400> SEQUENCE: 32
cacacaaggt tgacat 16

<210> SEQ ID NO 33
<211> LENGTH: 16
<212> TYPE: DNA
<213> ORGANISM: Artificial Sequence
<220> FEATURE:
<223> OTHER INFORMATION: ASO-000268

<400> SEQUENCE: 33
cgtcacactc acacaa 16

<210> SEQ ID NO 34
<211> LENGTH: 16
<212> TYPE: DNA
<213> ORGANISM: Artificial Sequence
<220> FEATURE:
<223> OTHER INFORMATION: ASO-000223

<400> SEQUENCE: 34
gccaccaagg acaggc 16

<210> SEQ ID NO 35
<211> LENGTH: 16
<212> TYPE: DNA
<213> ORGANISM: Artificial Sequence
<220> FEATURE:
<223> OTHER INFORMATION: ASO-000224

<400> SEQUENCE: 35
cagcttgcct tctctt 16

<210> SEQ ID NO 36
<211> LENGTH: 16
<212> TYPE: DNA
<213> ORGANISM: Artificial Sequence
<220> FEATURE:
<223> OTHER INFORMATION: ASO-000319

<400> SEQUENCE: 36
atcaaggtca gtcttt 16

<210> SEQ ID NO 37
<211> LENGTH: 16
<212> TYPE: DNA
<213> ORGANISM: Artificial Sequence
<220> FEATURE:
<223> OTHER INFORMATION: ASO-000208

<400> SEQUENCE: 37
ccttcagaac tcaata 16

<210> SEQ ID NO 38
<211> LENGTH: 16
<212> TYPE: DNA
<213> ORGANISM: Artificial Sequence
<220> FEATURE:
<223> OTHER INFORMATION: ASO-000689

<400> SEQUENCE: 38
aaagtcccag gtctgc 16

<210> SEQ ID NO 39
<211> LENGTH: 16
<212> TYPE: DNA
<213> ORGANISM: Artificial Sequence
<220> FEATURE:
<223> OTHER INFORMATION: ASO-000434

<400> SEQUENCE: 39
ctaaagtccc aggtct 16

<210> SEQ ID NO 40
<211> LENGTH: 15
<212> TYPE: DNA
<213> ORGANISM: Artificial Sequence
<220> FEATURE:
<223> OTHER INFORMATION: ASO-000409

<400> SEQUENCE: 40
taaagtccca ggtct 15

<210> SEQ ID NO 41
<211> LENGTH: 16
<212> TYPE: DNA
<213> ORGANISM: Artificial Sequence
<220> FEATURE:
<223> OTHER INFORMATION: ASO-000432

<400> SEQUENCE: 41
cctaaagtcc caggtc 16

<210> SEQ ID NO 42
<211> LENGTH: 14
<212> TYPE: DNA
<213> ORGANISM: Artificial Sequence
<220> FEATURE:
<223> OTHER INFORMATION: ASO-000391

<400> SEQUENCE: 42
taaagtccca ggtc 14

<210> SEQ ID NO 43
<211> LENGTH: 20
<212> TYPE: DNA
<213> ORGANISM: Artificial Sequence
<220> FEATURE:
<223> OTHER INFORMATION: ASO-001779

<400> SEQUENCE: 43
tagccctaaa gtcccaggtc 20

<210> SEQ ID NO 44
<211> LENGTH: 15
<212> TYPE: DNA
<213> ORGANISM: Artificial Sequence
<220> FEATURE:
<223> OTHER INFORMATION: ASO-000899

<400> SEQUENCE: 44
ctaaagtccc aggtc 15

<210> SEQ ID NO 45
<211> LENGTH: 16
<212> TYPE: DNA
<213> ORGANISM: Artificial Sequence

<220> FEATURE:
<223> OTHER INFORMATION: ASO-000398

<400> SEQUENCE: 45
ccctaaagtc ccaggt 16

<210> SEQ ID NO 46
<211> LENGTH: 20
<212> TYPE: DNA
<213> ORGANISM: Artificial Sequence
<220> FEATURE:
<223> OTHER INFORMATION: ASO-001778

<400> SEQUENCE: 46
ttagccctaa agtcccaggt 20

<210> SEQ ID NO 47
<211> LENGTH: 16
<212> TYPE: DNA
<213> ORGANISM: Artificial Sequence
<220> FEATURE:
<223> OTHER INFORMATION: ASO-000414

<400> SEQUENCE: 47
gccctaaagt cccagg 16

<210> SEQ ID NO 48
<211> LENGTH: 15
<212> TYPE: DNA
<213> ORGANISM: Artificial Sequence
<220> FEATURE:
<223> OTHER INFORMATION: ASO-000403

<400> SEQUENCE: 48
ccctaaagtc ccagg 15

<210> SEQ ID NO 49
<211> LENGTH: 20
<212> TYPE: DNA
<213> ORGANISM: Artificial Sequence
<220> FEATURE:
<223> OTHER INFORMATION: ASO-001780

<400> SEQUENCE: 49
gttagcccta aagtcccagg 20

<210> SEQ ID NO 50
<211> LENGTH: 15
<212> TYPE: DNA
<213> ORGANISM: Artificial Sequence
<220> FEATURE:
<223> OTHER INFORMATION: ASO-000433

<400> SEQUENCE: 50
gccctaaagt cccag 15

<210> SEQ ID NO 51
<211> LENGTH: 14
<212> TYPE: DNA
<213> ORGANISM: Artificial Sequence
<220> FEATURE:
<223> OTHER INFORMATION: ASO-000411

<400> SEQUENCE: 51
ccctaaagtc ccag 14

<210> SEQ ID NO 52
<211> LENGTH: 20
<212> TYPE: DNA
<213> ORGANISM: Artificial Sequence
<220> FEATURE:
<223> OTHER INFORMATION: ASO-001781

<400> SEQUENCE: 52
ggttagccct aaagtcccag 20

<210> SEQ ID NO 53
<211> LENGTH: 16
<212> TYPE: DNA
<213> ORGANISM: Artificial Sequence
<220> FEATURE:
<223> OTHER INFORMATION: ASO-000389

<400> SEQUENCE: 53
tagccctaaa gtccca 16

<210> SEQ ID NO 54
<211> LENGTH: 16
<212> TYPE: DNA
<213> ORGANISM: Artificial Sequence
<220> FEATURE:
<223> OTHER INFORMATION: ASO-001939

<400> SEQUENCE: 54
tagccctaaa gtccca 16

<210> SEQ ID NO 55
<211> LENGTH: 16
<212> TYPE: DNA
<213> ORGANISM: Artificial Sequence
<220> FEATURE:
<223> OTHER INFORMATION: ASO-001932

<400> SEQUENCE: 55
tagccctaaa gtccca 16

<210> SEQ ID NO 56
<211> LENGTH: 16
<212> TYPE: DNA
<213> ORGANISM: Artificial Sequence
<220> FEATURE:
<223> OTHER INFORMATION: ASO-001925

<400> SEQUENCE: 56
tagccctaaa gtccca 16

<210> SEQ ID NO 57
<211> LENGTH: 16
<212> TYPE: DNA
<213> ORGANISM: Artificial Sequence
<220> FEATURE:
<223> OTHER INFORMATION: ASO-001924

<400> SEQUENCE: 57
tagccctaaa gtccca 16

<210> SEQ ID NO 58
<211> LENGTH: 16
<212> TYPE: DNA
<213> ORGANISM: Artificial Sequence
<220> FEATURE:
<223> OTHER INFORMATION: ASO-001952

<400> SEQUENCE: 58
tagccctaaa gtccca 16

<210> SEQ ID NO 59
<211> LENGTH: 16
<212> TYPE: DNA
<213> ORGANISM: Artificial Sequence
<220> FEATURE:
<223> OTHER INFORMATION: ASO-001931

<400> SEQUENCE: 59
tagccctaaa gtccca 16

<210> SEQ ID NO 60
<211> LENGTH: 16
<212> TYPE: DNA
<213> ORGANISM: Artificial Sequence
<220> FEATURE:
<223> OTHER INFORMATION: ASO-001953

<400> SEQUENCE: 60
tagccctaaa gtccca 16

<210> SEQ ID NO 61
<211> LENGTH: 16
<212> TYPE: DNA
<213> ORGANISM: Artificial Sequence
<220> FEATURE:
<223> OTHER INFORMATION: ASO-001945

<400> SEQUENCE: 61
tagccctaaa gtccca 16

<210> SEQ ID NO 62
<211> LENGTH: 16
<212> TYPE: DNA
<213> ORGANISM: Artificial Sequence
<220> FEATURE:
<223> OTHER INFORMATION: ASO-001946

<400> SEQUENCE: 62
tagccctaaa gtccca 16

<210> SEQ ID NO 63
<211> LENGTH: 16
<212> TYPE: DNA
<213> ORGANISM: Artificial Sequence
<220> FEATURE:
<223> OTHER INFORMATION: ASO-001971

<400> SEQUENCE: 63
tagccctaaa gtccca 16

<210> SEQ ID NO 64
<211> LENGTH: 16
<212> TYPE: DNA
<213> ORGANISM: Artificial Sequence
<220> FEATURE:
<223> OTHER INFORMATION: ASO-001938

<400> SEQUENCE: 64
tagccctaaa gtccca 16

<210> SEQ ID NO 65

<211> LENGTH: 16
<212> TYPE: DNA
<213> ORGANISM: Artificial Sequence
<220> FEATURE:
<223> OTHER INFORMATION: ASO-001959

<400> SEQUENCE: 65
tagccctaaa gtccca 16

<210> SEQ ID NO 66
<211> LENGTH: 16
<212> TYPE: DNA
<213> ORGANISM: Artificial Sequence
<220> FEATURE:
<223> OTHER INFORMATION: ASO-001965

<400> SEQUENCE: 66
tagccctaaa gtccca 16

<210> SEQ ID NO 67
<211> LENGTH: 20
<212> TYPE: DNA
<213> ORGANISM: Artificial Sequence
<220> FEATURE:
<223> OTHER INFORMATION: ASO-001782

<400> SEQUENCE: 67
tggttagccc taaagtccca 20

<210> SEQ ID NO 68
<211> LENGTH: 16
<212> TYPE: DNA
<213> ORGANISM: Artificial Sequence
<220> FEATURE:
<223> OTHER INFORMATION: ASO-000900

<400> SEQUENCE: 68
tagccctaaa gtccca 16

<210> SEQ ID NO 69
<211> LENGTH: 16
<212> TYPE: DNA
<213> ORGANISM: Artificial Sequence
<220> FEATURE:
<223> OTHER INFORMATION: ASO-000435

<400> SEQUENCE: 69
ttagccctaa agtccc 16

<210> SEQ ID NO 70
<211> LENGTH: 16
<212> TYPE: DNA
<213> ORGANISM: Artificial Sequence
<220> FEATURE:
<223> OTHER INFORMATION: ASO-000423

<400> SEQUENCE: 70
gttagcccta aagtcc 16

<210> SEQ ID NO 71
<211> LENGTH: 14
<212> TYPE: DNA
<213> ORGANISM: Artificial Sequence
<220> FEATURE:
<223> OTHER INFORMATION: ASO-000442

<400> SEQUENCE: 71
tagccctaaa gtcc 14

<210> SEQ ID NO 72
<211> LENGTH: 16
<212> TYPE: DNA
<213> ORGANISM: Artificial Sequence
<220> FEATURE:
<223> OTHER INFORMATION: ASO-000416

<400> SEQUENCE: 72
ggttagccct aaagtc 16

<210> SEQ ID NO 73
<211> LENGTH: 14
<212> TYPE: DNA
<213> ORGANISM: Artificial Sequence
<220> FEATURE:
<223> OTHER INFORMATION: ASO-000438

<400> SEQUENCE: 73
gttagcccta aagt 14

<210> SEQ ID NO 74
<211> LENGTH: 16
<212> TYPE: DNA
<213> ORGANISM: Artificial Sequence
<220> FEATURE:
<223> OTHER INFORMATION: ASO-000581

<400> SEQUENCE: 74
actggttagc cctaaa 16

<210> SEQ ID NO 75
<211> LENGTH: 16
<212> TYPE: DNA
<213> ORGANISM: Artificial Sequence
<220> FEATURE:
<223> OTHER INFORMATION: ASO-000639

<400> SEQUENCE: 75
aactggttag ccctaa 16

<210> SEQ ID NO 76
<211> LENGTH: 16
<212> TYPE: DNA
<213> ORGANISM: Artificial Sequence
<220> FEATURE:
<223> OTHER INFORMATION: ASO-000558

<400> SEQUENCE: 76
gaactggtta gcccta 16

<210> SEQ ID NO 77
<211> LENGTH: 16
<212> TYPE: DNA
<213> ORGANISM: Artificial Sequence
<220> FEATURE:
<223> OTHER INFORMATION: ASO-000597

<400> SEQUENCE: 77
gagaactggt tagccc 16

<210> SEQ ID NO 78
<211> LENGTH: 16
<212> TYPE: DNA

<213> ORGANISM: Artificial Sequence
<220> FEATURE:
<223> OTHER INFORMATION: ASO-000245

<400> SEQUENCE: 78
tacaaagaga actggt 16

<210> SEQ ID NO 79
<211> LENGTH: 16
<212> TYPE: DNA
<213> ORGANISM: Artificial Sequence
<220> FEATURE:
<223> OTHER INFORMATION: ASO-000897

<400> SEQUENCE: 79
cacaagtcct tacaaa 16

<210> SEQ ID NO 80
<211> LENGTH: 16
<212> TYPE: DNA
<213> ORGANISM: Artificial Sequence
<220> FEATURE:
<223> OTHER INFORMATION: ASO-000185

<400> SEQUENCE: 80
ggcacaagtc cttaca 16

<210> SEQ ID NO 81
<211> LENGTH: 15
<212> TYPE: DNA
<213> ORGANISM: Artificial Sequence
<220> FEATURE:
<223> OTHER INFORMATION: ASO-000426

<400> SEQUENCE: 81
aggcacaagt cctta 15

<210> SEQ ID NO 82
<211> LENGTH: 16
<212> TYPE: DNA
<213> ORGANISM: Artificial Sequence
<220> FEATURE:
<223> OTHER INFORMATION: ASO-000417

<400> SEQUENCE: 82
gaggcacaag tcctta 16

<210> SEQ ID NO 83
<211> LENGTH: 16
<212> TYPE: DNA
<213> ORGANISM: Artificial Sequence
<220> FEATURE:
<223> OTHER INFORMATION: ASO-000393

<400> SEQUENCE: 83
agaggcacaa gtcctt 16

<210> SEQ ID NO 84
<211> LENGTH: 16
<212> TYPE: DNA
<213> ORGANISM: Artificial Sequence
<220> FEATURE:
<223> OTHER INFORMATION: ASO-000449

<400> SEQUENCE: 84
aagaggcaca agtcct 16

<210> SEQ ID NO 85
<211> LENGTH: 15
<212> TYPE: DNA
<213> ORGANISM: Artificial Sequence
<220> FEATURE:
<223> OTHER INFORMATION: ASO-000406

<400> SEQUENCE: 85
agaggcacaa gtcct 15

<210> SEQ ID NO 86
<211> LENGTH: 16
<212> TYPE: DNA
<213> ORGANISM: Artificial Sequence
<220> FEATURE:
<223> OTHER INFORMATION: ASO-000392

<400> SEQUENCE: 86
ccaagaggca caagtc 16

<210> SEQ ID NO 87
<211> LENGTH: 15
<212> TYPE: DNA
<213> ORGANISM: Artificial Sequence
<220> FEATURE:
<223> OTHER INFORMATION: ASO-000444

<400> SEQUENCE: 87
caagaggcac aagtc 15

<210> SEQ ID NO 88
<211> LENGTH: 16
<212> TYPE: DNA
<213> ORGANISM: Artificial Sequence
<220> FEATURE:
<223> OTHER INFORMATION: ASO-000443

<400> SEQUENCE: 88
cccaagaggc acaagt 16

<210> SEQ ID NO 89
<211> LENGTH: 14
<212> TYPE: DNA
<213> ORGANISM: Artificial Sequence
<220> FEATURE:
<223> OTHER INFORMATION: ASO-000450

<400> SEQUENCE: 89
caagaggcac aagt 14

<210> SEQ ID NO 90
<211> LENGTH: 16
<212> TYPE: DNA
<213> ORGANISM: Artificial Sequence
<220> FEATURE:
<223> OTHER INFORMATION: ASO-000258

<400> SEQUENCE: 90
ctcccaagag gcacaa 16

<210> SEQ ID NO 91
<211> LENGTH: 16
<212> TYPE: DNA
<213> ORGANISM: Artificial Sequence
<220> FEATURE:

<223> OTHER INFORMATION: ASO-000205

<400> SEQUENCE: 91
tggccgtggg aaggac 16

<210> SEQ ID NO 92
<211> LENGTH: 16
<212> TYPE: DNA
<213> ORGANISM: Artificial Sequence
<220> FEATURE:
<223> OTHER INFORMATION: ASO-000213

<400> SEQUENCE: 92
ggtgaggctg ggaatt 16

<210> SEQ ID NO 93
<211> LENGTH: 15
<212> TYPE: DNA
<213> ORGANISM: Artificial Sequence
<220> FEATURE:
<223> OTHER INFORMATION: ASO-000293

<400> SEQUENCE: 93
gtgaggctgg gaatt 15

<210> SEQ ID NO 94
<211> LENGTH: 16
<212> TYPE: DNA
<213> ORGANISM: Artificial Sequence
<220> FEATURE:
<223> OTHER INFORMATION: ASO-000321

<400> SEQUENCE: 94
tggtgaggct gggaat 16

<210> SEQ ID NO 95
<211> LENGTH: 16
<212> TYPE: DNA
<213> ORGANISM: Artificial Sequence
<220> FEATURE:
<223> OTHER INFORMATION: ASO-000226

<400> SEQUENCE: 95
ctcagtatgg agtagg 16

<210> SEQ ID NO 96
<211> LENGTH: 16
<212> TYPE: DNA
<213> ORGANISM: Artificial Sequence
<220> FEATURE:
<223> OTHER INFORMATION: ASO-000682

<400> SEQUENCE: 96
aatttcaccc tcagta 16

<210> SEQ ID NO 97
<211> LENGTH: 16
<212> TYPE: DNA
<213> ORGANISM: Artificial Sequence
<220> FEATURE:
<223> OTHER INFORMATION: ASO-000673

<400> SEQUENCE: 97
ttaatttcac cctcag 16

<210> SEQ ID NO 98
<211> LENGTH: 16
<212> TYPE: DNA
<213> ORGANISM: Artificial Sequence
<220> FEATURE:
<223> OTHER INFORMATION: ASO-000578

<400> SEQUENCE: 98
cttaatttca ccctca 16

<210> SEQ ID NO 99
<211> LENGTH: 17
<212> TYPE: DNA
<213> ORGANISM: Artificial Sequence
<220> FEATURE:
<223> OTHER INFORMATION: ASO-000540-21

<400> SEQUENCE: 99
ccttaatttc accctca 17

<210> SEQ ID NO 100
<211> LENGTH: 17
<212> TYPE: DNA
<213> ORGANISM: Artificial Sequence
<220> FEATURE:
<223> OTHER INFORMATION: ASO-000540-22

<400> SEQUENCE: 100
ccttaatttc accctca 17

<210> SEQ ID NO 101
<211> LENGTH: 17
<212> TYPE: DNA
<213> ORGANISM: Artificial Sequence
<220> FEATURE:
<223> OTHER INFORMATION: ASO-000540-23

<400> SEQUENCE: 101
ccttaatttc accctca 17

<210> SEQ ID NO 102
<211> LENGTH: 17
<212> TYPE: DNA
<213> ORGANISM: Artificial Sequence
<220> FEATURE:
<223> OTHER INFORMATION: ASO-000540-24

<400> SEQUENCE: 102
tcccttaatt tcaccct 17

<210> SEQ ID NO 103
<211> LENGTH: 17
<212> TYPE: DNA
<213> ORGANISM: Artificial Sequence
<220> FEATURE:
<223> OTHER INFORMATION: ASO-000540-25

<400> SEQUENCE: 103
tcccttaatt tcaccct 17

<210> SEQ ID NO 104
<211> LENGTH: 17
<212> TYPE: DNA
<213> ORGANISM: Artificial Sequence
<220> FEATURE:
<223> OTHER INFORMATION: ASO-000540-26

<400> SEQUENCE: 104
tcccttaatt tcaccct 17

<210> SEQ ID NO 105
<211> LENGTH: 17
<212> TYPE: DNA
<213> ORGANISM: Artificial Sequence
<220> FEATURE:
<223> OTHER INFORMATION: ASO-000540-27

<400> SEQUENCE: 105
tcccttaatt tcaccct 17

<210> SEQ ID NO 106
<211> LENGTH: 17
<212> TYPE: DNA
<213> ORGANISM: Artificial Sequence
<220> FEATURE:
<223> OTHER INFORMATION: ASO-000540-28

<400> SEQUENCE: 106
tcccttaatt tcaccct 17

<210> SEQ ID NO 107
<211> LENGTH: 17
<212> TYPE: DNA
<213> ORGANISM: Artificial Sequence
<220> FEATURE:
<223> OTHER INFORMATION: ASO-000540-29

<400> SEQUENCE: 107
tcccttaatt tcaccct 17

<210> SEQ ID NO 108
<211> LENGTH: 17
<212> TYPE: DNA
<213> ORGANISM: Artificial Sequence
<220> FEATURE:
<223> OTHER INFORMATION: ASO-000540-3

<400> SEQUENCE: 108
cccttaattt caccctc 17

<210> SEQ ID NO 109
<211> LENGTH: 18
<212> TYPE: DNA
<213> ORGANISM: Artificial Sequence
<220> FEATURE:
<223> OTHER INFORMATION: ASO-000540-42

<400> SEQUENCE: 109
cccttaattt caccctca 18

<210> SEQ ID NO 110
<211> LENGTH: 18
<212> TYPE: DNA
<213> ORGANISM: Artificial Sequence
<220> FEATURE:
<223> OTHER INFORMATION: ASO-000540-43

<400> SEQUENCE: 110
cccttaattt caccctca 18

<210> SEQ ID NO 111
<211> LENGTH: 18

<212> TYPE: DNA
<213> ORGANISM: Artificial Sequence
<220> FEATURE:
<223> OTHER INFORMATION: ASO-000540-44

<400> SEQUENCE: 111
cccttaattt caccctca 18

<210> SEQ ID NO 112
<211> LENGTH: 18
<212> TYPE: DNA
<213> ORGANISM: Artificial Sequence
<220> FEATURE:
<223> OTHER INFORMATION: ASO-000540-45

<400> SEQUENCE: 112
cccttaattt caccctca 18

<210> SEQ ID NO 113
<211> LENGTH: 18
<212> TYPE: DNA
<213> ORGANISM: Artificial Sequence
<220> FEATURE:
<223> OTHER INFORMATION: ASO-000540-46

<400> SEQUENCE: 113
cccttaattt caccctca 18

<210> SEQ ID NO 114
<211> LENGTH: 18
<212> TYPE: DNA
<213> ORGANISM: Artificial Sequence
<220> FEATURE:
<223> OTHER INFORMATION: ASO-000540-47

<400> SEQUENCE: 114
cccttaattt caccctca 18

<210> SEQ ID NO 115
<211> LENGTH: 18
<212> TYPE: DNA
<213> ORGANISM: Artificial Sequence
<220> FEATURE:
<223> OTHER INFORMATION: ASO-000540-48

<400> SEQUENCE: 115
cccttaattt caccctca 18

<210> SEQ ID NO 116
<211> LENGTH: 18
<212> TYPE: DNA
<213> ORGANISM: Artificial Sequence
<220> FEATURE:
<223> OTHER INFORMATION: ASO-000540-49

<400> SEQUENCE: 116
cccttaattt caccctca 18

<210> SEQ ID NO 117
<211> LENGTH: 17
<212> TYPE: DNA
<213> ORGANISM: Artificial Sequence
<220> FEATURE:
<223> OTHER INFORMATION: ASO-000540-5

<400> SEQUENCE: 117
cccttaattt caccctc 17

<210> SEQ ID NO 118
<211> LENGTH: 18
<212> TYPE: DNA
<213> ORGANISM: Artificial Sequence
<220> FEATURE:
<223> OTHER INFORMATION: ASO-000540-50

<400> SEQUENCE: 118
cccttaattt caccctca 18

<210> SEQ ID NO 119
<211> LENGTH: 18
<212> TYPE: DNA
<213> ORGANISM: Artificial Sequence
<220> FEATURE:
<223> OTHER INFORMATION: ASO-000540-51

<400> SEQUENCE: 119
cccttaattt caccctca 18

<210> SEQ ID NO 120
<211> LENGTH: 18
<212> TYPE: DNA
<213> ORGANISM: Artificial Sequence
<220> FEATURE:
<223> OTHER INFORMATION: ASO-000540-52

<400> SEQUENCE: 120
tcccttaatt tcaccctc 18

<210> SEQ ID NO 121
<211> LENGTH: 18
<212> TYPE: DNA
<213> ORGANISM: Artificial Sequence
<220> FEATURE:
<223> OTHER INFORMATION: ASO-000540-53

<400> SEQUENCE: 121
tcccttaatt tcaccctc 18

<210> SEQ ID NO 122
<211> LENGTH: 18
<212> TYPE: DNA
<213> ORGANISM: Artificial Sequence
<220> FEATURE:
<223> OTHER INFORMATION: ASO-000540-54

<400> SEQUENCE: 122
tcccttaatt tcaccctc 18

<210> SEQ ID NO 123
<211> LENGTH: 18
<212> TYPE: DNA
<213> ORGANISM: Artificial Sequence
<220> FEATURE:
<223> OTHER INFORMATION: ASO-000540-55

<400> SEQUENCE: 123
tcccttaatt tcaccctc 18

<210> SEQ ID NO 124
<211> LENGTH: 19
<212> TYPE: DNA
<213> ORGANISM: Artificial Sequence

<220> FEATURE:
<223> OTHER INFORMATION: ASO-000540-69

<400> SEQUENCE: 124
tcccttaatt tcaccctca 19

<210> SEQ ID NO 125
<211> LENGTH: 19
<212> TYPE: DNA
<213> ORGANISM: Artificial Sequence
<220> FEATURE:
<223> OTHER INFORMATION: ASO-000540-70

<400> SEQUENCE: 125
tcccttaatt tcaccctca 19

<210> SEQ ID NO 126
<211> LENGTH: 19
<212> TYPE: DNA
<213> ORGANISM: Artificial Sequence
<220> FEATURE:
<223> OTHER INFORMATION: ASO-000540-71

<400> SEQUENCE: 126
tcccttaatt tcaccctca 19

<210> SEQ ID NO 127
<211> LENGTH: 19
<212> TYPE: DNA
<213> ORGANISM: Artificial Sequence
<220> FEATURE:
<223> OTHER INFORMATION: ASO-000540-72

<400> SEQUENCE: 127
tcccttaatt tcaccctca 19

<210> SEQ ID NO 128
<211> LENGTH: 19
<212> TYPE: DNA
<213> ORGANISM: Artificial Sequence
<220> FEATURE:
<223> OTHER INFORMATION: ASO-000540-73

<400> SEQUENCE: 128
tcccttaatt tcaccctca 19

<210> SEQ ID NO 129
<211> LENGTH: 19
<212> TYPE: DNA
<213> ORGANISM: Artificial Sequence
<220> FEATURE:
<223> OTHER INFORMATION: ASO-000540-74

<400> SEQUENCE: 129
tcccttaatt tcaccctca 19

<210> SEQ ID NO 130
<211> LENGTH: 19
<212> TYPE: DNA
<213> ORGANISM: Artificial Sequence
<220> FEATURE:
<223> OTHER INFORMATION: ASO-000540-75

<400> SEQUENCE: 130
tcccttaatt tcaccctca 19

<210> SEQ ID NO 131
<211> LENGTH: 19
<212> TYPE: DNA
<213> ORGANISM: Artificial Sequence
<220> FEATURE:
<223> OTHER INFORMATION: ASO-000540-76

<400> SEQUENCE: 131
tcccttaatt tcaccctca 19

<210> SEQ ID NO 132
<211> LENGTH: 19
<212> TYPE: DNA
<213> ORGANISM: Artificial Sequence
<220> FEATURE:
<223> OTHER INFORMATION: ASO-000540-77

<400> SEQUENCE: 132
tcccttaatt tcaccctca 19

<210> SEQ ID NO 133
<211> LENGTH: 17
<212> TYPE: DNA
<213> ORGANISM: Artificial Sequence
<220> FEATURE:
<223> OTHER INFORMATION: ASO-000540-8

<400> SEQUENCE: 133
cccttaattt caccctc 17

<210> SEQ ID NO 134
<211> LENGTH: 17
<212> TYPE: DNA
<213> ORGANISM: Artificial Sequence
<220> FEATURE:
<223> OTHER INFORMATION: ASO-000540-9

<400> SEQUENCE: 134
cccttaattt caccctc 17

<210> SEQ ID NO 135
<211> LENGTH: 17
<212> TYPE: DNA
<213> ORGANISM: Artificial Sequence
<220> FEATURE:
<223> OTHER INFORMATION: TBD-mm10

<400> SEQUENCE: 135
ccttgatttc gccctca 17

<210> SEQ ID NO 136
<211> LENGTH: 17
<212> TYPE: DNA
<213> ORGANISM: Artificial Sequence
<220> FEATURE:
<223> OTHER INFORMATION: TBD-mm11

<400> SEQUENCE: 136
ccttgatttc accctct 17

<210> SEQ ID NO 137
<211> LENGTH: 17
<212> TYPE: DNA
<213> ORGANISM: Artificial Sequence
<220> FEATURE:
<223> OTHER INFORMATION: TBD-mm12

<400> SEQUENCE: 137
ccttagtttc accctcg 17

<210> SEQ ID NO 138
<211> LENGTH: 18
<212> TYPE: DNA
<213> ORGANISM: Artificial Sequence
<220> FEATURE:
<223> OTHER INFORMATION: TBD-mm19

<400> SEQUENCE: 138
cccttgattt caccctca 18

<210> SEQ ID NO 139
<211> LENGTH: 18
<212> TYPE: DNA
<213> ORGANISM: Artificial Sequence
<220> FEATURE:
<223> OTHER INFORMATION: TBD-mm20

<400> SEQUENCE: 139
cccttaattt caccctcg 18

<210> SEQ ID NO 140
<211> LENGTH: 18
<212> TYPE: DNA
<213> ORGANISM: Artificial Sequence
<220> FEATURE:
<223> OTHER INFORMATION: TBD-mm21

<400> SEQUENCE: 140
cccttagttt caccctca 18

<210> SEQ ID NO 141
<211> LENGTH: 18
<212> TYPE: DNA
<213> ORGANISM: Artificial Sequence
<220> FEATURE:
<223> OTHER INFORMATION: TBD-mm22

<400> SEQUENCE: 141
cccttgattt cgccctca 18

<210> SEQ ID NO 142
<211> LENGTH: 18
<212> TYPE: DNA
<213> ORGANISM: Artificial Sequence
<220> FEATURE:
<223> OTHER INFORMATION: TBD-mm23

<400> SEQUENCE: 142
cccttgattt caccctcg 18

<210> SEQ ID NO 143
<211> LENGTH: 18
<212> TYPE: DNA
<213> ORGANISM: Artificial Sequence
<220> FEATURE:
<223> OTHER INFORMATION: TBD-mm24

<400> SEQUENCE: 143
cccttgattt caccctct 18

<210> SEQ ID NO 144

<211> LENGTH: 19
<212> TYPE: DNA
<213> ORGANISM: Artificial Sequence
<220> FEATURE:
<223> OTHER INFORMATION: TBD-mm31

<400> SEQUENCE: 144
tcccttgatt tcaccctca 19

<210> SEQ ID NO 145
<211> LENGTH: 19
<212> TYPE: DNA
<213> ORGANISM: Artificial Sequence
<220> FEATURE:
<223> OTHER INFORMATION: TBD-mm32

<400> SEQUENCE: 145
tcccttaatt tcaccctcg 19

<210> SEQ ID NO 146
<211> LENGTH: 19
<212> TYPE: DNA
<213> ORGANISM: Artificial Sequence
<220> FEATURE:
<223> OTHER INFORMATION: TBD-mm33

<400> SEQUENCE: 146
acccttaatt tcaccctca 19

<210> SEQ ID NO 147
<211> LENGTH: 19
<212> TYPE: DNA
<213> ORGANISM: Artificial Sequence
<220> FEATURE:
<223> OTHER INFORMATION: TBD-mm34

<400> SEQUENCE: 147
tcccttgatt tcgccctca 19

<210> SEQ ID NO 148
<211> LENGTH: 19
<212> TYPE: DNA
<213> ORGANISM: Artificial Sequence
<220> FEATURE:
<223> OTHER INFORMATION: TBD-mm35

<400> SEQUENCE: 148
tcccttagtt tcaccctcg 19

<210> SEQ ID NO 149
<211> LENGTH: 19
<212> TYPE: DNA
<213> ORGANISM: Artificial Sequence
<220> FEATURE:
<223> OTHER INFORMATION: TBD-mm36

<400> SEQUENCE: 149
acccttgatt tcaccctca 19

<210> SEQ ID NO 150
<211> LENGTH: 17
<212> TYPE: DNA
<213> ORGANISM: Artificial Sequence
<220> FEATURE:
<223> OTHER INFORMATION: TBD-mm7

<400> SEQUENCE: 150
ccttgatttc accctca 17

<210> SEQ ID NO 151
<211> LENGTH: 17
<212> TYPE: DNA
<213> ORGANISM: Artificial Sequence
<220> FEATURE:
<223> OTHER INFORMATION: TBD-mm8

<400> SEQUENCE: 151
ccttagtttc accctca 17

<210> SEQ ID NO 152
<211> LENGTH: 17
<212> TYPE: DNA
<213> ORGANISM: Artificial Sequence
<220> FEATURE:
<223> OTHER INFORMATION: TBD-mm9

<400> SEQUENCE: 152
ccttaatttc accctcg 17

<210> SEQ ID NO 153
<211> LENGTH: 16
<212> TYPE: DNA
<213> ORGANISM: Artificial Sequence
<220> FEATURE:
<223> OTHER INFORMATION: ASO-000540

<400> SEQUENCE: 153
ccttaatttc accctc 16

<210> SEQ ID NO 154
<211> LENGTH: 15
<212> TYPE: DNA
<213> ORGANISM: Artificial Sequence
<220> FEATURE:
<223> OTHER INFORMATION: ASO-000555

<400> SEQUENCE: 154
cttaatttca ccctc 15

<210> SEQ ID NO 155
<211> LENGTH: 14
<212> TYPE: DNA
<213> ORGANISM: Artificial Sequence
<220> FEATURE:
<223> OTHER INFORMATION: ASO-000579

<400> SEQUENCE: 155
ttaatttcac cctc 14

<210> SEQ ID NO 156
<211> LENGTH: 17
<212> TYPE: DNA
<213> ORGANISM: Artificial Sequence
<220> FEATURE:
<223> OTHER INFORMATION: ASO-000540-1

<400> SEQUENCE: 156
cccttaattt caccctc 17

<210> SEQ ID NO 157
<211> LENGTH: 17
<212> TYPE: DNA

<213> ORGANISM: Artificial Sequence
<220> FEATURE:
<223> OTHER INFORMATION: ASO-000540-10

<400> SEQUENCE: 157
cccttaattt caccctc 17

<210> SEQ ID NO 158
<211> LENGTH: 17
<212> TYPE: DNA
<213> ORGANISM: Artificial Sequence
<220> FEATURE:
<223> OTHER INFORMATION: ASO-000540-11

<400> SEQUENCE: 158
cccttaattt caccctc 17

<210> SEQ ID NO 159
<211> LENGTH: 17
<212> TYPE: DNA
<213> ORGANISM: Artificial Sequence
<220> FEATURE:
<223> OTHER INFORMATION: ASO-000540-12

<400> SEQUENCE: 159
cccttaattt caccctc 17

<210> SEQ ID NO 160
<211> LENGTH: 17
<212> TYPE: DNA
<213> ORGANISM: Artificial Sequence
<220> FEATURE:
<223> OTHER INFORMATION: ASO-000540-13

<400> SEQUENCE: 160
cccttaattt caccctc 17

<210> SEQ ID NO 161
<211> LENGTH: 17
<212> TYPE: DNA
<213> ORGANISM: Artificial Sequence
<220> FEATURE:
<223> OTHER INFORMATION: ASO-000540-14

<400> SEQUENCE: 161
ccttaatttc accctca 17

<210> SEQ ID NO 162
<211> LENGTH: 17
<212> TYPE: DNA
<213> ORGANISM: Artificial Sequence
<220> FEATURE:
<223> OTHER INFORMATION: ASO-000540-15

<400> SEQUENCE: 162
ccttaatttc accctca 17

<210> SEQ ID NO 163
<211> LENGTH: 17
<212> TYPE: DNA
<213> ORGANISM: Artificial Sequence
<220> FEATURE:
<223> OTHER INFORMATION: ASO-000540-16

<400> SEQUENCE: 163
ccttaatttc accctca 17

<210> SEQ ID NO 164
<211> LENGTH: 17
<212> TYPE: DNA
<213> ORGANISM: Artificial Sequence
<220> FEATURE:
<223> OTHER INFORMATION: ASO-000540-17

<400> SEQUENCE: 164
ccttaatttc accctca 17

<210> SEQ ID NO 165
<211> LENGTH: 17
<212> TYPE: DNA
<213> ORGANISM: Artificial Sequence
<220> FEATURE:
<223> OTHER INFORMATION: ASO-000540-18

<400> SEQUENCE: 165
ccttaatttc accctca 17

<210> SEQ ID NO 166
<211> LENGTH: 17
<212> TYPE: DNA
<213> ORGANISM: Artificial Sequence
<220> FEATURE:
<223> OTHER INFORMATION: ASO-000540-19

<400> SEQUENCE: 166
ccttaatttc accctca 17

<210> SEQ ID NO 167
<211> LENGTH: 17
<212> TYPE: DNA
<213> ORGANISM: Artificial Sequence
<220> FEATURE:
<223> OTHER INFORMATION: ASO-000540-2

<400> SEQUENCE: 167
cccttaattt caccctc 17

<210> SEQ ID NO 168
<211> LENGTH: 17
<212> TYPE: DNA
<213> ORGANISM: Artificial Sequence
<220> FEATURE:
<223> OTHER INFORMATION: ASO-000540-20

<400> SEQUENCE: 168
ccttaatttc accctca 17

<210> SEQ ID NO 169
<211> LENGTH: 18
<212> TYPE: DNA
<213> ORGANISM: Artificial Sequence
<220> FEATURE:
<223> OTHER INFORMATION: ASO-000540-56

<400> SEQUENCE: 169
tcccttaatt tcaccctc 18

<210> SEQ ID NO 170
<211> LENGTH: 18
<212> TYPE: DNA
<213> ORGANISM: Artificial Sequence
<220> FEATURE:

<223> OTHER INFORMATION: ASO-000540-57

<400> SEQUENCE: 170
tcccttaatt tcaccctc 18

<210> SEQ ID NO 171
<211> LENGTH: 18
<212> TYPE: DNA
<213> ORGANISM: Artificial Sequence
<220> FEATURE:
<223> OTHER INFORMATION: ASO-000540-58

<400> SEQUENCE: 171
tcccttaatt tcaccctc 18

<210> SEQ ID NO 172
<211> LENGTH: 18
<212> TYPE: DNA
<213> ORGANISM: Artificial Sequence
<220> FEATURE:
<223> OTHER INFORMATION: ASO-000540-59

<400> SEQUENCE: 172
tcccttaatt tcaccctc 18

<210> SEQ ID NO 173
<211> LENGTH: 17
<212> TYPE: DNA
<213> ORGANISM: Artificial Sequence
<220> FEATURE:
<223> OTHER INFORMATION: ASO-000540-6

<400> SEQUENCE: 173
cccttaattt caccctc 17

<210> SEQ ID NO 174
<211> LENGTH: 18
<212> TYPE: DNA
<213> ORGANISM: Artificial Sequence
<220> FEATURE:
<223> OTHER INFORMATION: ASO-000540-60

<400> SEQUENCE: 174
tcccttaatt tcaccctc 18

<210> SEQ ID NO 175
<211> LENGTH: 18
<212> TYPE: DNA
<213> ORGANISM: Artificial Sequence
<220> FEATURE:
<223> OTHER INFORMATION: ASO-000540-61

<400> SEQUENCE: 175
tcccttaatt tcaccctc 18

<210> SEQ ID NO 176
<211> LENGTH: 18
<212> TYPE: DNA
<213> ORGANISM: Artificial Sequence
<220> FEATURE:
<223> OTHER INFORMATION: ASO-000540-62

<400> SEQUENCE: 176
tcccttaatt tcaccctc 18

<210> SEQ ID NO 177
<211> LENGTH: 18
<212> TYPE: DNA
<213> ORGANISM: Artificial Sequence
<220> FEATURE:
<223> OTHER INFORMATION: ASO-000540-63

<400> SEQUENCE: 177
tcccttaatt tcaccctc 18

<210> SEQ ID NO 178
<211> LENGTH: 18
<212> TYPE: DNA
<213> ORGANISM: Artificial Sequence
<220> FEATURE:
<223> OTHER INFORMATION: ASO-000540-64

<400> SEQUENCE: 178
tcccttaatt tcaccctc 18

<210> SEQ ID NO 179
<211> LENGTH: 18
<212> TYPE: DNA
<213> ORGANISM: Artificial Sequence
<220> FEATURE:
<223> OTHER INFORMATION: ASO-000540-65

<400> SEQUENCE: 179
tcccttaatt tcaccctc 18

<210> SEQ ID NO 180
<211> LENGTH: 19
<212> TYPE: DNA
<213> ORGANISM: Artificial Sequence
<220> FEATURE:
<223> OTHER INFORMATION: ASO-000540-66

<400> SEQUENCE: 180
tcccttaatt tcaccctca 19

<210> SEQ ID NO 181
<211> LENGTH: 19
<212> TYPE: DNA
<213> ORGANISM: Artificial Sequence
<220> FEATURE:
<223> OTHER INFORMATION: ASO-000540-67

<400> SEQUENCE: 181
tcccttaatt tcaccctca 19

<210> SEQ ID NO 182
<211> LENGTH: 19
<212> TYPE: DNA
<213> ORGANISM: Artificial Sequence
<220> FEATURE:
<223> OTHER INFORMATION: ASO-000540-68

<400> SEQUENCE: 182
tcccttaatt tcaccctca 19

<210> SEQ ID NO 183
<211> LENGTH: 16
<212> TYPE: DNA
<213> ORGANISM: Artificial Sequence
<220> FEATURE:
<223> OTHER INFORMATION: ASO-000540-mm1

<400> SEQUENCE: 183
ccttgatttc accctc 16

<210> SEQ ID NO 184
<211> LENGTH: 16
<212> TYPE: DNA
<213> ORGANISM: Artificial Sequence
<220> FEATURE:
<223> OTHER INFORMATION: ASO-000540-mm2

<400> SEQUENCE: 184
ccttaatttc gccctc 16

<210> SEQ ID NO 185
<211> LENGTH: 16
<212> TYPE: DNA
<213> ORGANISM: Artificial Sequence
<220> FEATURE:
<223> OTHER INFORMATION: ASO-000540-mm3

<400> SEQUENCE: 185
ccttagtttc accctc 16

<210> SEQ ID NO 186
<211> LENGTH: 16
<212> TYPE: DNA
<213> ORGANISM: Artificial Sequence
<220> FEATURE:
<223> OTHER INFORMATION: ASO-000540-mm4

<400> SEQUENCE: 186
ccttgatttc gccctc 16

<210> SEQ ID NO 187
<211> LENGTH: 16
<212> TYPE: DNA
<213> ORGANISM: Artificial Sequence
<220> FEATURE:
<223> OTHER INFORMATION: ASO-000540-mm5

<400> SEQUENCE: 187
ccttggtttc accctc 16

<210> SEQ ID NO 188
<211> LENGTH: 16
<212> TYPE: DNA
<213> ORGANISM: Artificial Sequence
<220> FEATURE:
<223> OTHER INFORMATION: ASO-000540-mm6

<400> SEQUENCE: 188
ccttagtttc gccctc 16

<210> SEQ ID NO 189
<211> LENGTH: 17
<212> TYPE: DNA
<213> ORGANISM: Artificial Sequence
<220> FEATURE:
<223> OTHER INFORMATION: TBD-mm1

<400> SEQUENCE: 189
cccttgattt caccctc 17

<210> SEQ ID NO 190
<211> LENGTH: 17

<212> TYPE: DNA
<213> ORGANISM: Artificial Sequence
<220> FEATURE:
<223> OTHER INFORMATION: TBD-mm2

<400> SEQUENCE: 190
cccttagttt caccctc 17

<210> SEQ ID NO 191
<211> LENGTH: 18
<212> TYPE: DNA
<213> ORGANISM: Artificial Sequence
<220> FEATURE:
<223> OTHER INFORMATION: TBD-mm25

<400> SEQUENCE: 191
tcccttgatt tcaccctc 18

<210> SEQ ID NO 192
<211> LENGTH: 18
<212> TYPE: DNA
<213> ORGANISM: Artificial Sequence
<220> FEATURE:
<223> OTHER INFORMATION: TBD-mm26

<400> SEQUENCE: 192
tcccttaatt tcgccctc 18

<210> SEQ ID NO 193
<211> LENGTH: 18
<212> TYPE: DNA
<213> ORGANISM: Artificial Sequence
<220> FEATURE:
<223> OTHER INFORMATION: TBD-mm27

<400> SEQUENCE: 193
tcccttagtt tcaccctc 18

<210> SEQ ID NO 194
<211> LENGTH: 18
<212> TYPE: DNA
<213> ORGANISM: Artificial Sequence
<220> FEATURE:
<223> OTHER INFORMATION: TBD-mm28

<400> SEQUENCE: 194
tcccttgatt tcgccctc 18

<210> SEQ ID NO 195
<211> LENGTH: 18
<212> TYPE: DNA
<213> ORGANISM: Artificial Sequence
<220> FEATURE:
<223> OTHER INFORMATION: TBD-mm29

<400> SEQUENCE: 195
tcccttagtt tcgccctc 18

<210> SEQ ID NO 196
<211> LENGTH: 17
<212> TYPE: DNA
<213> ORGANISM: Artificial Sequence
<220> FEATURE:
<223> OTHER INFORMATION: TBD-mm3

<400> SEQUENCE: 196
cccttaattt cgccctc 17

<210> SEQ ID NO 197
<211> LENGTH: 18
<212> TYPE: DNA
<213> ORGANISM: Artificial Sequence
<220> FEATURE:
<223> OTHER INFORMATION: TBD-mm30

<400> SEQUENCE: 197
acccttgatt tcaccctc 18

<210> SEQ ID NO 198
<211> LENGTH: 17
<212> TYPE: DNA
<213> ORGANISM: Artificial Sequence
<220> FEATURE:
<223> OTHER INFORMATION: TBD-mm4

<400> SEQUENCE: 198
cccttgattt cgccctc 17

<210> SEQ ID NO 199
<211> LENGTH: 17
<212> TYPE: DNA
<213> ORGANISM: Artificial Sequence
<220> FEATURE:
<223> OTHER INFORMATION: TBD-mm5

<400> SEQUENCE: 199
cccttggttt caccctc 17

<210> SEQ ID NO 200
<211> LENGTH: 17
<212> TYPE: DNA
<213> ORGANISM: Artificial Sequence
<220> FEATURE:
<223> OTHER INFORMATION: TBD-mm6

<400> SEQUENCE: 200
cccttagttt cgccctc 17

<210> SEQ ID NO 201
<211> LENGTH: 16
<212> TYPE: DNA
<213> ORGANISM: Artificial Sequence
<220> FEATURE:
<223> OTHER INFORMATION: ASO-000662

<400> SEQUENCE: 201
cccttaattt caccct 16

<210> SEQ ID NO 202
<211> LENGTH: 15
<212> TYPE: DNA
<213> ORGANISM: Artificial Sequence
<220> FEATURE:
<223> OTHER INFORMATION: ASO-000566

<400> SEQUENCE: 202
ccttaatttc accct 15

<210> SEQ ID NO 203
<211> LENGTH: 17
<212> TYPE: DNA
<213> ORGANISM: Artificial Sequence

<220> FEATURE:
<223> OTHER INFORMATION: ASO-000540-30

<400> SEQUENCE: 203
tcccttaatt tcaccct 17

<210> SEQ ID NO 204
<211> LENGTH: 17
<212> TYPE: DNA
<213> ORGANISM: Artificial Sequence
<220> FEATURE:
<223> OTHER INFORMATION: ASO-000540-31

<400> SEQUENCE: 204
tcccttaatt tcaccct 17

<210> SEQ ID NO 205
<211> LENGTH: 17
<212> TYPE: DNA
<213> ORGANISM: Artificial Sequence
<220> FEATURE:
<223> OTHER INFORMATION: ASO-000540-32

<400> SEQUENCE: 205
tcccttaatt tcaccct 17

<210> SEQ ID NO 206
<211> LENGTH: 17
<212> TYPE: DNA
<213> ORGANISM: Artificial Sequence
<220> FEATURE:
<223> OTHER INFORMATION: ASO-000540-33

<400> SEQUENCE: 206
tcccttaatt tcaccct 17

<210> SEQ ID NO 207
<211> LENGTH: 17
<212> TYPE: DNA
<213> ORGANISM: Artificial Sequence
<220> FEATURE:
<223> OTHER INFORMATION: ASO-000540-34

<400> SEQUENCE: 207
tcccttaatt tcaccct 17

<210> SEQ ID NO 208
<211> LENGTH: 17
<212> TYPE: DNA
<213> ORGANISM: Artificial Sequence
<220> FEATURE:
<223> OTHER INFORMATION: ASO-000540-35

<400> SEQUENCE: 208
tcccttaatt tcaccct 17

<210> SEQ ID NO 209
<211> LENGTH: 17
<212> TYPE: DNA
<213> ORGANISM: Artificial Sequence
<220> FEATURE:
<223> OTHER INFORMATION: ASO-000540-36

<400> SEQUENCE: 209
tcccttaatt tcaccct 17

<210> SEQ ID NO 210
<211> LENGTH: 18
<212> TYPE: DNA
<213> ORGANISM: Artificial Sequence
<220> FEATURE:
<223> OTHER INFORMATION: ASO-000540-37

<400> SEQUENCE: 210
cccttaattt caccctca 18

<210> SEQ ID NO 211
<211> LENGTH: 18
<212> TYPE: DNA
<213> ORGANISM: Artificial Sequence
<220> FEATURE:
<223> OTHER INFORMATION: ASO-000540-38

<400> SEQUENCE: 211
cccttaattt caccctca 18

<210> SEQ ID NO 212
<211> LENGTH: 18
<212> TYPE: DNA
<213> ORGANISM: Artificial Sequence
<220> FEATURE:
<223> OTHER INFORMATION: ASO-000540-39

<400> SEQUENCE: 212
cccttaattt caccctca 18

<210> SEQ ID NO 213
<211> LENGTH: 17
<212> TYPE: DNA
<213> ORGANISM: Artificial Sequence
<220> FEATURE:
<223> OTHER INFORMATION: ASO-000540-4

<400> SEQUENCE: 213
cccttaattt caccctc 17

<210> SEQ ID NO 214
<211> LENGTH: 18
<212> TYPE: DNA
<213> ORGANISM: Artificial Sequence
<220> FEATURE:
<223> OTHER INFORMATION: ASO-000540-40

<400> SEQUENCE: 214
cccttaattt caccctca 18

<210> SEQ ID NO 215
<211> LENGTH: 18
<212> TYPE: DNA
<213> ORGANISM: Artificial Sequence
<220> FEATURE:
<223> OTHER INFORMATION: ASO-000540-41

<400> SEQUENCE: 215
cccttaattt caccctca 18

<210> SEQ ID NO 216
<211> LENGTH: 17
<212> TYPE: DNA
<213> ORGANISM: Artificial Sequence
<220> FEATURE:
<223> OTHER INFORMATION: TBD-mm13

<400> SEQUENCE: 216
tcccttgatt tcaccct 17

<210> SEQ ID NO 217
<211> LENGTH: 17
<212> TYPE: DNA
<213> ORGANISM: Artificial Sequence
<220> FEATURE:
<223> OTHER INFORMATION: TBD-mm14

<400> SEQUENCE: 217
tcccttaatt tcaccca 17

<210> SEQ ID NO 218
<211> LENGTH: 17
<212> TYPE: DNA
<213> ORGANISM: Artificial Sequence
<220> FEATURE:
<223> OTHER INFORMATION: TBD-mm15

<400> SEQUENCE: 218
tcccttaatt tcgccct 17

<210> SEQ ID NO 219
<211> LENGTH: 17
<212> TYPE: DNA
<213> ORGANISM: Artificial Sequence
<220> FEATURE:
<223> OTHER INFORMATION: TBD-mm16

<400> SEQUENCE: 219
tcccttgatt tcaccca 17

<210> SEQ ID NO 220
<211> LENGTH: 17
<212> TYPE: DNA
<213> ORGANISM: Artificial Sequence
<220> FEATURE:
<223> OTHER INFORMATION: TBD-mm17

<400> SEQUENCE: 220
tcccttgatt tcacccg 17

<210> SEQ ID NO 221
<211> LENGTH: 17
<212> TYPE: DNA
<213> ORGANISM: Artificial Sequence
<220> FEATURE:
<223> OTHER INFORMATION: TBD-mm18

<400> SEQUENCE: 221
tcccttagtt tcgccct 17

<210> SEQ ID NO 222
<211> LENGTH: 14
<212> TYPE: DNA
<213> ORGANISM: Artificial Sequence
<220> FEATURE:
<223> OTHER INFORMATION: ASO-000628

<400> SEQUENCE: 222
ccttaatttc accc 14

<210> SEQ ID NO 223

<211> LENGTH: 15
<212> TYPE: DNA
<213> ORGANISM: Artificial Sequence
<220> FEATURE:
<223> OTHER INFORMATION: ASO-000642

<400> SEQUENCE: 223
cccttaattt caccc 15

<210> SEQ ID NO 224
<211> LENGTH: 16
<212> TYPE: DNA
<213> ORGANISM: Artificial Sequence
<220> FEATURE:
<223> OTHER INFORMATION: ASO-000274

<400> SEQUENCE: 224
tcccttaatt tcaccc 16

<210> SEQ ID NO 225
<211> LENGTH: 14
<212> TYPE: DNA
<213> ORGANISM: Artificial Sequence
<220> FEATURE:
<223> OTHER INFORMATION: ASO-000339

<400> SEQUENCE: 225
ccttaatttc accc 14

<210> SEQ ID NO 226
<211> LENGTH: 16
<212> TYPE: DNA
<213> ORGANISM: Artificial Sequence
<220> FEATURE:
<223> OTHER INFORMATION: ASO-000536

<400> SEQUENCE: 226
ttcccttaat ttcacc 16

<210> SEQ ID NO 227
<211> LENGTH: 15
<212> TYPE: DNA
<213> ORGANISM: Artificial Sequence
<220> FEATURE:
<223> OTHER INFORMATION: ASO-000603

<400> SEQUENCE: 227
tcccttaatt tcacc 15

<210> SEQ ID NO 228
<211> LENGTH: 14
<212> TYPE: DNA
<213> ORGANISM: Artificial Sequence
<220> FEATURE:
<223> OTHER INFORMATION: ASO-000666

<400> SEQUENCE: 228
tcccttaatt tcac 14

<210> SEQ ID NO 229
<211> LENGTH: 16
<212> TYPE: DNA
<213> ORGANISM: Artificial Sequence
<220> FEATURE:
<223> OTHER INFORMATION: ASO-000272

<400> SEQUENCE: 229
agagtgagag gctggg 16

<210> SEQ ID NO 230
<211> LENGTH: 16
<212> TYPE: DNA
<213> ORGANISM: Artificial Sequence
<220> FEATURE:
<223> OTHER INFORMATION: ASO-000255

<400> SEQUENCE: 230
tggatgagtg gaactg 16

<210> SEQ ID NO 231
<211> LENGTH: 14
<212> TYPE: DNA
<213> ORGANISM: Artificial Sequence
<220> FEATURE:
<223> OTHER INFORMATION: ASO-000336

<400> SEQUENCE: 231
ggatgagtgg aact 14

<210> SEQ ID NO 232
<211> LENGTH: 15
<212> TYPE: DNA
<213> ORGANISM: Artificial Sequence
<220> FEATURE:
<223> OTHER INFORMATION: ASO-000206

<400> SEQUENCE: 232
gttggatgag tggaa 15

<210> SEQ ID NO 233
<211> LENGTH: 15
<212> TYPE: DNA
<213> ORGANISM: Artificial Sequence
<220> FEATURE:
<223> OTHER INFORMATION: ASO-000271

<400> SEQUENCE: 233
agttggatga gtgga 15

<210> SEQ ID NO 234
<211> LENGTH: 14
<212> TYPE: DNA
<213> ORGANISM: Artificial Sequence
<220> FEATURE:
<223> OTHER INFORMATION: ASO-000340

<400> SEQUENCE: 234
gttggatgag tgga 14

<210> SEQ ID NO 235
<211> LENGTH: 16
<212> TYPE: DNA
<213> ORGANISM: Artificial Sequence
<220> FEATURE:
<223> OTHER INFORMATION: ASO-000229

<400> SEQUENCE: 235
cagggaaccg aatcag 16

<210> SEQ ID NO 236
<211> LENGTH: 16
<212> TYPE: DNA

<213> ORGANISM: Artificial Sequence
<220> FEATURE:
<223> OTHER INFORMATION: ASO-000273

<400> SEQUENCE: 236
gccctggctc acatct 16

<210> SEQ ID NO 237
<211> LENGTH: 16
<212> TYPE: DNA
<213> ORGANISM: Artificial Sequence
<220> FEATURE:
<223> OTHER INFORMATION: ASO-000264

<400> SEQUENCE: 237
acaaggcaga aacacc 16

<210> SEQ ID NO 238
<211> LENGTH: 14
<212> TYPE: DNA
<213> ORGANISM: Artificial Sequence
<220> FEATURE:
<223> OTHER INFORMATION: ASO-000341

<400> SEQUENCE: 238
tgtcaacaag gcag 14

<210> SEQ ID NO 239
<211> LENGTH: 16
<212> TYPE: DNA
<213> ORGANISM: Artificial Sequence
<220> FEATURE:
<223> OTHER INFORMATION: ASO-000198

<400> SEQUENCE: 239
tgccctgggt gccttg 16

<210> SEQ ID NO 240
<211> LENGTH: 16
<212> TYPE: DNA
<213> ORGANISM: Artificial Sequence
<220> FEATURE:
<223> OTHER INFORMATION: ASO-000210

<400> SEQUENCE: 240
agcgggactg tgggcc 16

<210> SEQ ID NO 241
<211> LENGTH: 14
<212> TYPE: DNA
<213> ORGANISM: Artificial Sequence
<220> FEATURE:
<223> OTHER INFORMATION: ASO-000342

<400> SEQUENCE: 241
gggacagcgg gact 14

<210> SEQ ID NO 242
<211> LENGTH: 16
<212> TYPE: DNA
<213> ORGANISM: Artificial Sequence
<220> FEATURE:
<223> OTHER INFORMATION: ASO-000333

<400> SEQUENCE: 242
gcgggctggg ctgtct 16

<210> SEQ ID NO 243
<211> LENGTH: 16
<212> TYPE: DNA
<213> ORGANISM: Artificial Sequence
<220> FEATURE:
<223> OTHER INFORMATION: ASO-000199

<400> SEQUENCE: 243
cagaacagac agcatg 16

<210> SEQ ID NO 244
<211> LENGTH: 16
<212> TYPE: DNA
<213> ORGANISM: Artificial Sequence
<220> FEATURE:
<223> OTHER INFORMATION: ASO-000280

<400> SEQUENCE: 244
tctatgtata tgttca 16

<210> SEQ ID NO 245
<211> LENGTH: 16
<212> TYPE: DNA
<213> ORGANISM: Artificial Sequence
<220> FEATURE:
<223> OTHER INFORMATION: ASO-000211

<400> SEQUENCE: 245
atctatgtat atgttc 16

<210> SEQ ID NO 246
<211> LENGTH: 15
<212> TYPE: DNA
<213> ORGANISM: Artificial Sequence
<220> FEATURE:
<223> OTHER INFORMATION: ASO-000347

<400> SEQUENCE: 246
catctatgta tatgt 15

<210> SEQ ID NO 247
<211> LENGTH: 16
<212> TYPE: DNA
<213> ORGANISM: Artificial Sequence
<220> FEATURE:
<223> OTHER INFORMATION: ASO-000352

<400> SEQUENCE: 247
acatctatgt atatgt 16

<210> SEQ ID NO 248
<211> LENGTH: 16
<212> TYPE: DNA
<213> ORGANISM: Artificial Sequence
<220> FEATURE:
<223> OTHER INFORMATION: ASO-000232

<400> SEQUENCE: 248
caacagggtg cagatg 16

<210> SEQ ID NO 249
<211> LENGTH: 16
<212> TYPE: DNA
<213> ORGANISM: Artificial Sequence
<220> FEATURE:

<223> OTHER INFORMATION: ASO-000257

<400> SEQUENCE: 249
agcataaaca gacaaa 16

<210> SEQ ID NO 250
<211> LENGTH: 16
<212> TYPE: DNA
<213> ORGANISM: Artificial Sequence
<220> FEATURE:
<223> OTHER INFORMATION: ASO-000388

<400> SEQUENCE: 250
atagtcactc tggtga 16

<210> SEQ ID NO 251
<211> LENGTH: 15
<212> TYPE: DNA
<213> ORGANISM: Artificial Sequence
<220> FEATURE:
<223> OTHER INFORMATION: ASO-000390

<400> SEQUENCE: 251
tagtcactct ggtga 15

<210> SEQ ID NO 252
<211> LENGTH: 14
<212> TYPE: DNA
<213> ORGANISM: Artificial Sequence
<220> FEATURE:
<223> OTHER INFORMATION: ASO-000413

<400> SEQUENCE: 252
agtcactctg gtga 14

<210> SEQ ID NO 253
<211> LENGTH: 16
<212> TYPE: DNA
<213> ORGANISM: Artificial Sequence
<220> FEATURE:
<223> OTHER INFORMATION: ASO-000405

<400> SEQUENCE: 253
catagtcact ctggtg 16

<210> SEQ ID NO 254
<211> LENGTH: 14
<212> TYPE: DNA
<213> ORGANISM: Artificial Sequence
<220> FEATURE:
<223> OTHER INFORMATION: ASO-000430

<400> SEQUENCE: 254
tagtcactct ggtg 14

<210> SEQ ID NO 255
<211> LENGTH: 16
<212> TYPE: DNA
<213> ORGANISM: Artificial Sequence
<220> FEATURE:
<223> OTHER INFORMATION: ASO-000447

<400> SEQUENCE: 255
tcatagtcac tctggt 16

<210> SEQ ID NO 256
<211> LENGTH: 14
<212> TYPE: DNA
<213> ORGANISM: Artificial Sequence
<220> FEATURE:
<223> OTHER INFORMATION: ASO-000396

<400> SEQUENCE: 256
tacatgcgtc cttt 14

<210> SEQ ID NO 257
<211> LENGTH: 16
<212> TYPE: DNA
<213> ORGANISM: Artificial Sequence
<220> FEATURE:
<223> OTHER INFORMATION: ASO-000395

<400> SEQUENCE: 257
gatacatgcg tccttt 16

<210> SEQ ID NO 258
<211> LENGTH: 16
<212> TYPE: DNA
<213> ORGANISM: Artificial Sequence
<220> FEATURE:
<223> OTHER INFORMATION: ASO-000394

<400> SEQUENCE: 258
aagatacatg cgtcct 16

<210> SEQ ID NO 259
<211> LENGTH: 16
<212> TYPE: DNA
<213> ORGANISM: Artificial Sequence
<220> FEATURE:
<223> OTHER INFORMATION: ASO-000421

<400> SEQUENCE: 259
ttcaagatac atgcgt 16

<210> SEQ ID NO 260
<211> LENGTH: 16
<212> TYPE: DNA
<213> ORGANISM: Artificial Sequence
<220> FEATURE:
<223> OTHER INFORMATION: ASO-000400

<400> SEQUENCE: 260
atttcaagat acatgc 16

<210> SEQ ID NO 261
<211> LENGTH: 16
<212> TYPE: DNA
<213> ORGANISM: Artificial Sequence
<220> FEATURE:
<223> OTHER INFORMATION: ASO-000248

<400> SEQUENCE: 261
gcatttcaag atacat 16

<210> SEQ ID NO 262
<211> LENGTH: 16
<212> TYPE: DNA
<213> ORGANISM: Artificial Sequence
<220> FEATURE:
<223> OTHER INFORMATION: ASO-000451

<400> SEQUENCE: 262
aagcatttca agatac 16

<210> SEQ ID NO 263
<211> LENGTH: 16
<212> TYPE: DNA
<213> ORGANISM: Artificial Sequence
<220> FEATURE:
<223> OTHER INFORMATION: ASO-000707

<400> SEQUENCE: 263
acaagcattt caagat 16

<210> SEQ ID NO 264
<211> LENGTH: 16
<212> TYPE: DNA
<213> ORGANISM: Artificial Sequence
<220> FEATURE:
<223> OTHER INFORMATION: ASO-000619

<400> SEQUENCE: 264
ttacaagcat ttcaag 16

<210> SEQ ID NO 265
<211> LENGTH: 16
<212> TYPE: DNA
<213> ORGANISM: Artificial Sequence
<220> FEATURE:
<223> OTHER INFORMATION: ASO-000671

<400> SEQUENCE: 265
aacctcttta caagca 16

<210> SEQ ID NO 266
<211> LENGTH: 16
<212> TYPE: DNA
<213> ORGANISM: Artificial Sequence
<220> FEATURE:
<223> OTHER INFORMATION: ASO-000221

<400> SEQUENCE: 266
gttagaaacc tcttta 16

<210> SEQ ID NO 267
<211> LENGTH: 16
<212> TYPE: DNA
<213> ORGANISM: Artificial Sequence
<220> FEATURE:
<223> OTHER INFORMATION: ASO-000298

<400> SEQUENCE: 267
ccacacaggc cacacg 16

<210> SEQ ID NO 268
<211> LENGTH: 16
<212> TYPE: DNA
<213> ORGANISM: Artificial Sequence
<220> FEATURE:
<223> OTHER INFORMATION: ASO-000311

<400> SEQUENCE: 268
gtctctgttg ggtccc 16

<210> SEQ ID NO 269
<211> LENGTH: 16

<212> TYPE: DNA
<213> ORGANISM: Artificial Sequence
<220> FEATURE:
<223> OTHER INFORMATION: ASO-000290

<400> SEQUENCE: 269
tgaacggcct ccttag 16

<210> SEQ ID NO 270
<211> LENGTH: 16
<212> TYPE: DNA
<213> ORGANISM: Artificial Sequence
<220> FEATURE:
<223> OTHER INFORMATION: ASO-000437

<400> SEQUENCE: 270
ctgtgcttca ggcctt 16

<210> SEQ ID NO 271
<211> LENGTH: 16
<212> TYPE: DNA
<213> ORGANISM: Artificial Sequence
<220> FEATURE:
<223> OTHER INFORMATION: ASO-000446

<400> SEQUENCE: 271
tcctgtgctt caggcc 16

<210> SEQ ID NO 272
<211> LENGTH: 16
<212> TYPE: DNA
<213> ORGANISM: Artificial Sequence
<220> FEATURE:
<223> OTHER INFORMATION: ASO-000685

<400> SEQUENCE: 272
aatcctgtgc ttcagg 16

<210> SEQ ID NO 273
<211> LENGTH: 14
<212> TYPE: DNA
<213> ORGANISM: Artificial Sequence
<220> FEATURE:
<223> OTHER INFORMATION: ASO-000410

<400> SEQUENCE: 273
tcctgtgctt cagg 14

<210> SEQ ID NO 274
<211> LENGTH: 15
<212> TYPE: DNA
<213> ORGANISM: Artificial Sequence
<220> FEATURE:
<223> OTHER INFORMATION: ASO-000604

<400> SEQUENCE: 274
aatcctgtgc ttcag 15

<210> SEQ ID NO 275
<211> LENGTH: 16
<212> TYPE: DNA
<213> ORGANISM: Artificial Sequence
<220> FEATURE:
<223> OTHER INFORMATION: ASO-000490

<400> SEQUENCE: 275
taatcctgtg cttcag 16

<210> SEQ ID NO 276
<211> LENGTH: 14
<212> TYPE: DNA
<213> ORGANISM: Artificial Sequence
<220> FEATURE:
<223> OTHER INFORMATION: ASO-000529

<400> SEQUENCE: 276
aatcctgtgc ttca 14

<210> SEQ ID NO 277
<211> LENGTH: 16
<212> TYPE: DNA
<213> ORGANISM: Artificial Sequence
<220> FEATURE:
<223> OTHER INFORMATION: ASO-000532

<400> SEQUENCE: 277
ctaatcctgt gcttca 16

<210> SEQ ID NO 278
<211> LENGTH: 15
<212> TYPE: DNA
<213> ORGANISM: Artificial Sequence
<220> FEATURE:
<223> OTHER INFORMATION: ASO-000508

<400> SEQUENCE: 278
taatcctgtg cttca 15

<210> SEQ ID NO 279
<211> LENGTH: 16
<212> TYPE: DNA
<213> ORGANISM: Artificial Sequence
<220> FEATURE:
<223> OTHER INFORMATION: ASO-000219

<400> SEQUENCE: 279
cctaatcctg tgcttc 16

<210> SEQ ID NO 280
<211> LENGTH: 14
<212> TYPE: DNA
<213> ORGANISM: Artificial Sequence
<220> FEATURE:
<223> OTHER INFORMATION: ASO-000656

<400> SEQUENCE: 280
taatcctgtg cttc 14

<210> SEQ ID NO 281
<211> LENGTH: 15
<212> TYPE: DNA
<213> ORGANISM: Artificial Sequence
<220> FEATURE:
<223> OTHER INFORMATION: ASO-000522

<400> SEQUENCE: 281
ctaatcctgt gcttc 15

<210> SEQ ID NO 282
<211> LENGTH: 15
<212> TYPE: DNA
<213> ORGANISM: Artificial Sequence

<220> FEATURE:
<223> OTHER INFORMATION: ASO-000513

<400> SEQUENCE: 282
cctaatcctg tgctt 15

<210> SEQ ID NO 283
<211> LENGTH: 16
<212> TYPE: DNA
<213> ORGANISM: Artificial Sequence
<220> FEATURE:
<223> OTHER INFORMATION: ASO-000640

<400> SEQUENCE: 283
tcctaatcct gtgctt 16

<210> SEQ ID NO 284
<211> LENGTH: 14
<212> TYPE: DNA
<213> ORGANISM: Artificial Sequence
<220> FEATURE:
<223> OTHER INFORMATION: ASO-000661

<400> SEQUENCE: 284
ctaatcctgt gctt 14

<210> SEQ ID NO 285
<211> LENGTH: 16
<212> TYPE: DNA
<213> ORGANISM: Artificial Sequence
<220> FEATURE:
<223> OTHER INFORMATION: ASO-000478

<400> SEQUENCE: 285
gtcctaatcc tgtgct 16

<210> SEQ ID NO 286
<211> LENGTH: 15
<212> TYPE: DNA
<213> ORGANISM: Artificial Sequence
<220> FEATURE:
<223> OTHER INFORMATION: ASO-000500

<400> SEQUENCE: 286
tcctaatcct gtgct 15

<210> SEQ ID NO 287
<211> LENGTH: 14
<212> TYPE: DNA
<213> ORGANISM: Artificial Sequence
<220> FEATURE:
<223> OTHER INFORMATION: ASO-000601

<400> SEQUENCE: 287
cctaatcctg tgct 14

<210> SEQ ID NO 288
<211> LENGTH: 16
<212> TYPE: DNA
<213> ORGANISM: Artificial Sequence
<220> FEATURE:
<223> OTHER INFORMATION: ASO-000643

<400> SEQUENCE: 288
agtcctaatc ctgtgc 16

<210> SEQ ID NO 289
<211> LENGTH: 15
<212> TYPE: DNA
<213> ORGANISM: Artificial Sequence
<220> FEATURE:
<223> OTHER INFORMATION: ASO-000600

<400> SEQUENCE: 289
gtcctaatcc tgtgc 15

<210> SEQ ID NO 290
<211> LENGTH: 14
<212> TYPE: DNA
<213> ORGANISM: Artificial Sequence
<220> FEATURE:
<223> OTHER INFORMATION: ASO-000525

<400> SEQUENCE: 290
tcctaatcct gtgc 14

<210> SEQ ID NO 291
<211> LENGTH: 16
<212> TYPE: DNA
<213> ORGANISM: Artificial Sequence
<220> FEATURE:
<223> OTHER INFORMATION: ASO-000453

<400> SEQUENCE: 291
tcagtcctaa tcctgt 16

<210> SEQ ID NO 292
<211> LENGTH: 16
<212> TYPE: DNA
<213> ORGANISM: Artificial Sequence
<220> FEATURE:
<223> OTHER INFORMATION: ASO-000553

<400> SEQUENCE: 292
cttcagtcct aatcct 16

<210> SEQ ID NO 293
<211> LENGTH: 15
<212> TYPE: DNA
<213> ORGANISM: Artificial Sequence
<220> FEATURE:
<223> OTHER INFORMATION: ASO-000622

<400> SEQUENCE: 293
gcttcagtcc taatc 15

<210> SEQ ID NO 294
<211> LENGTH: 16
<212> TYPE: DNA
<213> ORGANISM: Artificial Sequence
<220> FEATURE:
<223> OTHER INFORMATION: ASO-000325

<400> SEQUENCE: 294
ctgacacagg gagccc 16

<210> SEQ ID NO 295
<211> LENGTH: 16
<212> TYPE: DNA
<213> ORGANISM: Artificial Sequence
<220> FEATURE:
<223> OTHER INFORMATION: ASO-000215

<400> SEQUENCE: 295
gccagaccag ccacaa 16

<210> SEQ ID NO 296
<211> LENGTH: 14
<212> TYPE: DNA
<213> ORGANISM: Artificial Sequence
<220> FEATURE:
<223> OTHER INFORMATION: ASO-000482

<400> SEQUENCE: 296
caggagttgt aagc 14

<210> SEQ ID NO 297
<211> LENGTH: 16
<212> TYPE: DNA
<213> ORGANISM: Artificial Sequence
<220> FEATURE:
<223> OTHER INFORMATION: ASO-000337

<400> SEQUENCE: 297
tgcaggagtt gtaagc 16

<210> SEQ ID NO 298
<211> LENGTH: 16
<212> TYPE: DNA
<213> ORGANISM: Artificial Sequence
<220> FEATURE:
<223> OTHER INFORMATION: ASO-000480

<400> SEQUENCE: 298
atgcaggagt tgtaag 16

<210> SEQ ID NO 299
<211> LENGTH: 16
<212> TYPE: DNA
<213> ORGANISM: Artificial Sequence
<220> FEATURE:
<223> OTHER INFORMATION: ASO-000644

<400> SEQUENCE: 299
gatgcaggag ttgtaa 16

<210> SEQ ID NO 300
<211> LENGTH: 14
<212> TYPE: DNA
<213> ORGANISM: Artificial Sequence
<220> FEATURE:
<223> OTHER INFORMATION: ASO-000695

<400> SEQUENCE: 300
tgcaggagtt gtaa 14

<210> SEQ ID NO 301
<211> LENGTH: 16
<212> TYPE: DNA
<213> ORGANISM: Artificial Sequence
<220> FEATURE:
<223> OTHER INFORMATION: ASO-000455

<400> SEQUENCE: 301
tgatgcagga gttgta 16

<210> SEQ ID NO 302

<211> LENGTH: 16
<212> TYPE: DNA
<213> ORGANISM: Artificial Sequence
<220> FEATURE:
<223> OTHER INFORMATION: ASO-000531

<400> SEQUENCE: 302
gtgatgcagg agttgt 16

<210> SEQ ID NO 303
<211> LENGTH: 16
<212> TYPE: DNA
<213> ORGANISM: Artificial Sequence
<220> FEATURE:
<223> OTHER INFORMATION: ASO-000651

<400> SEQUENCE: 303
tgtgatgcag gagttg 16

<210> SEQ ID NO 304
<211> LENGTH: 15
<212> TYPE: DNA
<213> ORGANISM: Artificial Sequence
<220> FEATURE:
<223> OTHER INFORMATION: ASO-00007

<400> SEQUENCE: 304
tgtgatgcag gagtt 15

<210> SEQ ID NO 305
<211> LENGTH: 14
<212> TYPE: DNA
<213> ORGANISM: Artificial Sequence
<220> FEATURE:
<223> OTHER INFORMATION: ASO-000419

<400> SEQUENCE: 305
gtgatgcagg agtt 14

<210> SEQ ID NO 306
<211> LENGTH: 15
<212> TYPE: DNA
<213> ORGANISM: Artificial Sequence
<220> FEATURE:
<223> OTHER INFORMATION: ASO-000730

<400> SEQUENCE: 306
tgtgatgcag gagtt 15

<210> SEQ ID NO 307
<211> LENGTH: 15
<212> TYPE: DNA
<213> ORGANISM: Artificial Sequence
<220> FEATURE:
<223> OTHER INFORMATION: ASO-000728

<400> SEQUENCE: 307
tgtgatgcag gagtt 15

<210> SEQ ID NO 308
<211> LENGTH: 15
<212> TYPE: DNA
<213> ORGANISM: Artificial Sequence
<220> FEATURE:
<223> OTHER INFORMATION: ASO-000729

<400> SEQUENCE: 308
tgtgatgcag gagtt 15

<210> SEQ ID NO 309
<211> LENGTH: 15
<212> TYPE: DNA
<213> ORGANISM: Artificial Sequence
<220> FEATURE:
<223> OTHER INFORMATION: ASO-000727

<400> SEQUENCE: 309
tgtgatgcag gagtt 15

<210> SEQ ID NO 310
<211> LENGTH: 15
<212> TYPE: DNA
<213> ORGANISM: Artificial Sequence
<220> FEATURE:
<223> OTHER INFORMATION: ASO-000715

<400> SEQUENCE: 310
tgtgatgcag gagtt 15

<210> SEQ ID NO 311
<211> LENGTH: 12
<212> TYPE: DNA
<213> ORGANISM: Artificial Sequence
<220> FEATURE:
<223> OTHER INFORMATION: ASO-000716

<400> SEQUENCE: 311
gatgcaggag tt 12

<210> SEQ ID NO 312
<211> LENGTH: 15
<212> TYPE: DNA
<213> ORGANISM: Artificial Sequence
<220> FEATURE:
<223> OTHER INFORMATION: ASO-000721

<400> SEQUENCE: 312
tgtgatgcag gagtt 15

<210> SEQ ID NO 313
<211> LENGTH: 15
<212> TYPE: DNA
<213> ORGANISM: Artificial Sequence
<220> FEATURE:
<223> OTHER INFORMATION: ASO-000722

<400> SEQUENCE: 313
tgtgatgcag gagtt 15

<210> SEQ ID NO 314
<211> LENGTH: 15
<212> TYPE: DNA
<213> ORGANISM: Artificial Sequence
<220> FEATURE:
<223> OTHER INFORMATION: ASO-000723

<400> SEQUENCE: 314
tgtgatgcag gagtt 15

<210> SEQ ID NO 315
<211> LENGTH: 15
<212> TYPE: DNA

```
<213> ORGANISM: Artificial Sequence
<220> FEATURE:
<223> OTHER INFORMATION: ASO-000724

<400> SEQUENCE: 315

tgtgatgcag gagtt                                                        15


<210> SEQ ID NO 316
<211> LENGTH: 15
<212> TYPE: DNA
<213> ORGANISM: Artificial Sequence
<220> FEATURE:
<223> OTHER INFORMATION: ASO-000725

<400> SEQUENCE: 316

tgtgatgcag gagtt                                                        15


<210> SEQ ID NO 317
<211> LENGTH: 15
<212> TYPE: DNA
<213> ORGANISM: Artificial Sequence
<220> FEATURE:
<223> OTHER INFORMATION: ASO-000726

<400> SEQUENCE: 317

tgtgatgcag gagtt                                                        15


<210> SEQ ID NO 318
<211> LENGTH: 15
<212> TYPE: DNA
<213> ORGANISM: Artificial Sequence
<220> FEATURE:
<223> OTHER INFORMATION: ASO-000731

<400> SEQUENCE: 318

tgtgatgcag gagtt                                                        15


<210> SEQ ID NO 319
<211> LENGTH: 12
<212> TYPE: DNA
<213> ORGANISM: Artificial Sequence
<220> FEATURE:
<223> OTHER INFORMATION: ASO-000718

<400> SEQUENCE: 319

tgatgcagga gt                                                           12


<210> SEQ ID NO 320
<211> LENGTH: 14
<212> TYPE: DNA
<213> ORGANISM: Artificial Sequence
<220> FEATURE:
<223> OTHER INFORMATION: ASO-000445

<400> SEQUENCE: 320

ttgtgatgca ggag                                                         14


<210> SEQ ID NO 321
<211> LENGTH: 15
<212> TYPE: DNA
<213> ORGANISM: Artificial Sequence
<220> FEATURE:
<223> OTHER INFORMATION: ASO-000436

<400> SEQUENCE: 321

cttgtgatgc aggag                                                        15
```

<210> SEQ ID NO 322
<211> LENGTH: 12
<212> TYPE: DNA
<213> ORGANISM: Artificial Sequence
<220> FEATURE:
<223> OTHER INFORMATION: ASO-000717

<400> SEQUENCE: 322
gtgatgcagg ag 12

<210> SEQ ID NO 323
<211> LENGTH: 16
<212> TYPE: DNA
<213> ORGANISM: Artificial Sequence
<220> FEATURE:
<223> OTHER INFORMATION: ASO-000570

<400> SEQUENCE: 323
ttcttgtgat gcagga 16

<210> SEQ ID NO 324
<211> LENGTH: 15
<212> TYPE: DNA
<213> ORGANISM: Artificial Sequence
<220> FEATURE:
<223> OTHER INFORMATION: ASO-000408

<400> SEQUENCE: 324
tcttgtgatg cagga 15

<210> SEQ ID NO 325
<211> LENGTH: 14
<212> TYPE: DNA
<213> ORGANISM: Artificial Sequence
<220> FEATURE:
<223> OTHER INFORMATION: ASO-000401

<400> SEQUENCE: 325
cttgtgatgc agga 14

<210> SEQ ID NO 326
<211> LENGTH: 12
<212> TYPE: DNA
<213> ORGANISM: Artificial Sequence
<220> FEATURE:
<223> OTHER INFORMATION: ASO-000719

<400> SEQUENCE: 326
tgtgatgcag ga 12

<210> SEQ ID NO 327
<211> LENGTH: 16
<212> TYPE: DNA
<213> ORGANISM: Artificial Sequence
<220> FEATURE:
<223> OTHER INFORMATION: ASO-000313

<400> SEQUENCE: 327
cagagggcga gcttgg 16

<210> SEQ ID NO 328
<211> LENGTH: 16
<212> TYPE: DNA
<213> ORGANISM: Artificial Sequence
<220> FEATURE:

<223> OTHER INFORMATION: ASO-000331

<400> SEQUENCE: 328
aatccctgct gtggtc 16

<210> SEQ ID NO 329
<211> LENGTH: 14
<212> TYPE: DNA
<213> ORGANISM: Artificial Sequence
<220> FEATURE:
<223> OTHER INFORMATION: ASO-000251

<400> SEQUENCE: 329
aggcaattca tccc 14

<210> SEQ ID NO 330
<211> LENGTH: 16
<212> TYPE: DNA
<213> ORGANISM: Artificial Sequence
<220> FEATURE:
<223> OTHER INFORMATION: ASO-000574

<400> SEQUENCE: 330
tggtcaaggc tttggg 16

<210> SEQ ID NO 331
<211> LENGTH: 16
<212> TYPE: DNA
<213> ORGANISM: Artificial Sequence
<220> FEATURE:
<223> OTHER INFORMATION: ASO-000218

<400> SEQUENCE: 331
tctggtcaag gctttg 16

<210> SEQ ID NO 332
<211> LENGTH: 16
<212> TYPE: DNA
<213> ORGANISM: Artificial Sequence
<220> FEATURE:
<223> OTHER INFORMATION: ASO-000634

<400> SEQUENCE: 332
ctctggtcaa ggcttt 16

<210> SEQ ID NO 333
<211> LENGTH: 16
<212> TYPE: DNA
<213> ORGANISM: Artificial Sequence
<220> FEATURE:
<223> OTHER INFORMATION: ASO-000497

<400> SEQUENCE: 333
ggtgctctgg tcaagg 16

<210> SEQ ID NO 334
<211> LENGTH: 14
<212> TYPE: DNA
<213> ORGANISM: Artificial Sequence
<220> FEATURE:
<223> OTHER INFORMATION: ASO-000569

<400> SEQUENCE: 334
ggtgctctgg tcaa 14

<210> SEQ ID NO 335
<211> LENGTH: 16
<212> TYPE: DNA
<213> ORGANISM: Artificial Sequence
<220> FEATURE:
<223> OTHER INFORMATION: ASO-000565

<400> SEQUENCE: 335
gctgaggtgc tctggt 16

<210> SEQ ID NO 336
<211> LENGTH: 16
<212> TYPE: DNA
<213> ORGANISM: Artificial Sequence
<220> FEATURE:
<223> OTHER INFORMATION: ASO-000296

<400> SEQUENCE: 336
agtttgtgca aggtca 16

<210> SEQ ID NO 337
<211> LENGTH: 16
<212> TYPE: DNA
<213> ORGANISM: Artificial Sequence
<220> FEATURE:
<223> OTHER INFORMATION: ASO-000663

<400> SEQUENCE: 337
gagtttgtgc aaggtc 16

<210> SEQ ID NO 338
<211> LENGTH: 15
<212> TYPE: DNA
<213> ORGANISM: Artificial Sequence
<220> FEATURE:
<223> OTHER INFORMATION: ASO-000670

<400> SEQUENCE: 338
agtttgtgca aggtc 15

<210> SEQ ID NO 339
<211> LENGTH: 16
<212> TYPE: DNA
<213> ORGANISM: Artificial Sequence
<220> FEATURE:
<223> OTHER INFORMATION: ASO-000261

<400> SEQUENCE: 339
ggagtttgtg caaggt 16

<210> SEQ ID NO 340
<211> LENGTH: 15
<212> TYPE: DNA
<213> ORGANISM: Artificial Sequence
<220> FEATURE:
<223> OTHER INFORMATION: ASO-000262

<400> SEQUENCE: 340
ggagtttgtg caagg 15

<210> SEQ ID NO 341
<211> LENGTH: 16
<212> TYPE: DNA
<213> ORGANISM: Artificial Sequence
<220> FEATURE:
<223> OTHER INFORMATION: ASO-000275

<400> SEQUENCE: 341
tggagtttgt gcaagg 16

<210> SEQ ID NO 342
<211> LENGTH: 16
<212> TYPE: DNA
<213> ORGANISM: Artificial Sequence
<220> FEATURE:
<223> OTHER INFORMATION: ASO-000247

<400> SEQUENCE: 342
atggagtttg tgcaag 16

<210> SEQ ID NO 343
<211> LENGTH: 15
<212> TYPE: DNA
<213> ORGANISM: Artificial Sequence
<220> FEATURE:
<223> OTHER INFORMATION: ASO-000303

<400> SEQUENCE: 343
tggagtttgt gcaag 15

<210> SEQ ID NO 344
<211> LENGTH: 15
<212> TYPE: DNA
<213> ORGANISM: Artificial Sequence
<220> FEATURE:
<223> OTHER INFORMATION: ASO-000299

<400> SEQUENCE: 344
atggagtttg tgcaa 15

<210> SEQ ID NO 345
<211> LENGTH: 16
<212> TYPE: DNA
<213> ORGANISM: Artificial Sequence
<220> FEATURE:
<223> OTHER INFORMATION: ASO-000270

<400> SEQUENCE: 345
agatggagtt tgtgca 16

<210> SEQ ID NO 346
<211> LENGTH: 16
<212> TYPE: DNA
<213> ORGANISM: Artificial Sequence
<220> FEATURE:
<223> OTHER INFORMATION: ASO-000297

<400> SEQUENCE: 346
agcagatgga gtttgt 16

<210> SEQ ID NO 347
<211> LENGTH: 16
<212> TYPE: DNA
<213> ORGANISM: Artificial Sequence
<220> FEATURE:
<223> OTHER INFORMATION: ASO-000259

<400> SEQUENCE: 347
ttctttaggc agcaat 16

<210> SEQ ID NO 348
<211> LENGTH: 16

```
<212> TYPE: DNA
<213> ORGANISM: Artificial Sequence
<220> FEATURE:
<223> OTHER INFORMATION: ASO-000220

<400> SEQUENCE: 348

tgtacccaaa ccagaa                                                    16


<210> SEQ ID NO 349
<211> LENGTH: 15
<212> TYPE: DNA
<213> ORGANISM: Artificial Sequence
<220> FEATURE:
<223> OTHER INFORMATION: ASO-000278

<400> SEQUENCE: 349

gttgccttta actgt                                                     15


<210> SEQ ID NO 350
<211> LENGTH: 16
<212> TYPE: DNA
<213> ORGANISM: Artificial Sequence
<220> FEATURE:
<223> OTHER INFORMATION: ASO-000334

<400> SEQUENCE: 350

gccctggatt tctact                                                    16


<210> SEQ ID NO 351
<211> LENGTH: 16
<212> TYPE: DNA
<213> ORGANISM: Artificial Sequence
<220> FEATURE:
<223> OTHER INFORMATION: ASO-000241

<400> SEQUENCE: 351

tggtggagag ttctgg                                                    16


<210> SEQ ID NO 352
<211> LENGTH: 16
<212> TYPE: DNA
<213> ORGANISM: Artificial Sequence
<220> FEATURE:
<223> OTHER INFORMATION: ASO-000289

<400> SEQUENCE: 352

ttctcagatc ccttca                                                    16


<210> SEQ ID NO 353
<211> LENGTH: 16
<212> TYPE: DNA
<213> ORGANISM: Artificial Sequence
<220> FEATURE:
<223> OTHER INFORMATION: ASO-000233

<400> SEQUENCE: 353

ctctaaccac caccaa                                                    16


<210> SEQ ID NO 354
<211> LENGTH: 16
<212> TYPE: DNA
<213> ORGANISM: Artificial Sequence
<220> FEATURE:
<223> OTHER INFORMATION: ASO-000201

<400> SEQUENCE: 354
```

agggcacaag aacttc 16

<210> SEQ ID NO 355
<211> LENGTH: 15
<212> TYPE: DNA
<213> ORGANISM: Artificial Sequence
<220> FEATURE:
<223> OTHER INFORMATION: ASO-000645

<400> SEQUENCE: 355
atcttaggct ggccc 15

<210> SEQ ID NO 356
<211> LENGTH: 16
<212> TYPE: DNA
<213> ORGANISM: Artificial Sequence
<220> FEATURE:
<223> OTHER INFORMATION: ASO-000546

<400> SEQUENCE: 356
gatcttaggc tggccc 16

<210> SEQ ID NO 357
<211> LENGTH: 16
<212> TYPE: DNA
<213> ORGANISM: Artificial Sequence
<220> FEATURE:
<223> OTHER INFORMATION: ASO-000692

<400> SEQUENCE: 357
tgatcttagg ctggcc 16

<210> SEQ ID NO 358
<211> LENGTH: 15
<212> TYPE: DNA
<213> ORGANISM: Artificial Sequence
<220> FEATURE:
<223> OTHER INFORMATION: ASO-000511

<400> SEQUENCE: 358
gatcttaggc tggcc 15

<210> SEQ ID NO 359
<211> LENGTH: 15
<212> TYPE: DNA
<213> ORGANISM: Artificial Sequence
<220> FEATURE:
<223> OTHER INFORMATION: ASO-000538

<400> SEQUENCE: 359
tgatcttagg ctggc 15

<210> SEQ ID NO 360
<211> LENGTH: 16
<212> TYPE: DNA
<213> ORGANISM: Artificial Sequence
<220> FEATURE:
<223> OTHER INFORMATION: ASO-000214

<400> SEQUENCE: 360
atgatcttag gctggc 16

<210> SEQ ID NO 361
<211> LENGTH: 14
<212> TYPE: DNA
<213> ORGANISM: Artificial Sequence

<220> FEATURE:
<223> OTHER INFORMATION: ASO-000653

<400> SEQUENCE: 361
gatcttaggc tggc 14

<210> SEQ ID NO 362
<211> LENGTH: 16
<212> TYPE: DNA
<213> ORGANISM: Artificial Sequence
<220> FEATURE:
<223> OTHER INFORMATION: ASO-000615

<400> SEQUENCE: 362
catgatctta ggctgg 16

<210> SEQ ID NO 363
<211> LENGTH: 16
<212> TYPE: DNA
<213> ORGANISM: Artificial Sequence
<220> FEATURE:
<223> OTHER INFORMATION: ASO-000524

<400> SEQUENCE: 363
ccatgatctt aggctg 16

<210> SEQ ID NO 364
<211> LENGTH: 15
<212> TYPE: DNA
<213> ORGANISM: Artificial Sequence
<220> FEATURE:
<223> OTHER INFORMATION: ASO-000492

<400> SEQUENCE: 364
catgatctta ggctg 15

<210> SEQ ID NO 365
<211> LENGTH: 16
<212> TYPE: DNA
<213> ORGANISM: Artificial Sequence
<220> FEATURE:
<223> OTHER INFORMATION: ASO-000468

<400> SEQUENCE: 365
accatgatct taggct 16

<210> SEQ ID NO 366
<211> LENGTH: 15
<212> TYPE: DNA
<213> ORGANISM: Artificial Sequence
<220> FEATURE:
<223> OTHER INFORMATION: ASO-000698

<400> SEQUENCE: 366
ccatgatctt aggct 15

<210> SEQ ID NO 367
<211> LENGTH: 14
<212> TYPE: DNA
<213> ORGANISM: Artificial Sequence
<220> FEATURE:
<223> OTHER INFORMATION: ASO-000593

<400> SEQUENCE: 367
catgatctta ggct 14

<210> SEQ ID NO 368
<211> LENGTH: 16
<212> TYPE: DNA
<213> ORGANISM: Artificial Sequence
<220> FEATURE:
<223> OTHER INFORMATION: ASO-000519

<400> SEQUENCE: 368
aaaccatgat cttagg 16

<210> SEQ ID NO 369
<211> LENGTH: 16
<212> TYPE: DNA
<213> ORGANISM: Artificial Sequence
<220> FEATURE:
<223> OTHER INFORMATION: ASO-000582

<400> SEQUENCE: 369
ctaaaccatg atctta 16

<210> SEQ ID NO 370
<211> LENGTH: 16
<212> TYPE: DNA
<213> ORGANISM: Artificial Sequence
<220> FEATURE:
<223> OTHER INFORMATION: ASO-000635

<400> SEQUENCE: 370
ccctaaacca tgatct 16

<210> SEQ ID NO 371
<211> LENGTH: 16
<212> TYPE: DNA
<213> ORGANISM: Artificial Sequence
<220> FEATURE:
<223> OTHER INFORMATION: ASO-000471

<400> SEQUENCE: 371
caccctaaac catgat 16

<210> SEQ ID NO 372
<211> LENGTH: 16
<212> TYPE: DNA
<213> ORGANISM: Artificial Sequence
<220> FEATURE:
<223> OTHER INFORMATION: ASO-000701

<400> SEQUENCE: 372
atcaccctaa accatg 16

<210> SEQ ID NO 373
<211> LENGTH: 16
<212> TYPE: DNA
<213> ORGANISM: Artificial Sequence
<220> FEATURE:
<223> OTHER INFORMATION: ASO-000533

<400> SEQUENCE: 373
tgatcaccct aaacca 16

<210> SEQ ID NO 374
<211> LENGTH: 16
<212> TYPE: DNA
<213> ORGANISM: Artificial Sequence
<220> FEATURE:
<223> OTHER INFORMATION: ASO-000323

<400> SEQUENCE: 374
gaggagtgcc cagccc 16

<210> SEQ ID NO 375
<211> LENGTH: 16
<212> TYPE: DNA
<213> ORGANISM: Artificial Sequence
<220> FEATURE:
<223> OTHER INFORMATION: ASO-000329

<400> SEQUENCE: 375
tgcaggtggg agaagt 16

<210> SEQ ID NO 376
<211> LENGTH: 14
<212> TYPE: DNA
<213> ORGANISM: Artificial Sequence
<220> FEATURE:
<223> OTHER INFORMATION: ASO-000194

<400> SEQUENCE: 376
tatctagccc accc 14

<210> SEQ ID NO 377
<211> LENGTH: 15
<212> TYPE: DNA
<213> ORGANISM: Artificial Sequence
<220> FEATURE:
<223> OTHER INFORMATION: ASO-000192

<400> SEQUENCE: 377
ctatctagcc caccc 15

<210> SEQ ID NO 378
<211> LENGTH: 14
<212> TYPE: DNA
<213> ORGANISM: Artificial Sequence
<220> FEATURE:
<223> OTHER INFORMATION: ASO-000343

<400> SEQUENCE: 378
tatcctatct agcc 14

<210> SEQ ID NO 379
<211> LENGTH: 15
<212> TYPE: DNA
<213> ORGANISM: Artificial Sequence
<220> FEATURE:
<223> OTHER INFORMATION: ASO-000212

<400> SEQUENCE: 379
ttgataaagt gagtc 15

<210> SEQ ID NO 380
<211> LENGTH: 15
<212> TYPE: DNA
<213> ORGANISM: Artificial Sequence
<220> FEATURE:
<223> OTHER INFORMATION: ASO-000230

<400> SEQUENCE: 380
attgataaag tgagt 15

<210> SEQ ID NO 381

<211> LENGTH: 15
<212> TYPE: DNA
<213> ORGANISM: Artificial Sequence
<220> FEATURE:
<223> OTHER INFORMATION: ASO-000188

<400> SEQUENCE: 381
aactattgat aaagt 15

<210> SEQ ID NO 382
<211> LENGTH: 14
<212> TYPE: DNA
<213> ORGANISM: Artificial Sequence
<220> FEATURE:
<223> OTHER INFORMATION: ASO-000415

<400> SEQUENCE: 382
gaactattga taaa 14

<210> SEQ ID NO 383
<211> LENGTH: 14
<212> TYPE: DNA
<213> ORGANISM: Artificial Sequence
<220> FEATURE:
<223> OTHER INFORMATION: ASO-000448

<400> SEQUENCE: 383
ggaactattg ataa 14

<210> SEQ ID NO 384
<211> LENGTH: 16
<212> TYPE: DNA
<213> ORGANISM: Artificial Sequence
<220> FEATURE:
<223> OTHER INFORMATION: ASO-000190

<400> SEQUENCE: 384
aaatggaact attgat 16

<210> SEQ ID NO 385
<211> LENGTH: 14
<212> TYPE: DNA
<213> ORGANISM: Artificial Sequence
<220> FEATURE:
<223> OTHER INFORMATION: ASO-000191

<400> SEQUENCE: 385
aatggaacta ttga 14

<210> SEQ ID NO 386
<211> LENGTH: 15
<212> TYPE: DNA
<213> ORGANISM: Artificial Sequence
<220> FEATURE:
<223> OTHER INFORMATION: ASO-000348

<400> SEQUENCE: 386
tcaatttaaa tggaa 15

<210> SEQ ID NO 387
<211> LENGTH: 15
<212> TYPE: DNA
<213> ORGANISM: Artificial Sequence
<220> FEATURE:
<223> OTHER INFORMATION: ASO-000349

<400> SEQUENCE: 387
gtcaatttaa atgga 15

<210> SEQ ID NO 388
<211> LENGTH: 16
<212> TYPE: DNA
<213> ORGANISM: Artificial Sequence
<220> FEATURE:
<223> OTHER INFORMATION: ASO-000200

<400> SEQUENCE: 388
ggatacagtc tcacca 16

<210> SEQ ID NO 389
<211> LENGTH: 16
<212> TYPE: DNA
<213> ORGANISM: Artificial Sequence
<220> FEATURE:
<223> OTHER INFORMATION: ASO-000630

<400> SEQUENCE: 389
gcaaacagga tacagt 16

<210> SEQ ID NO 390
<211> LENGTH: 15
<212> TYPE: DNA
<213> ORGANISM: Artificial Sequence
<220> FEATURE:
<223> OTHER INFORMATION: ASO-000614

<400> SEQUENCE: 390
caaacaggat acagt 15

<210> SEQ ID NO 391
<211> LENGTH: 14
<212> TYPE: DNA
<213> ORGANISM: Artificial Sequence
<220> FEATURE:
<223> OTHER INFORMATION: ASO-000563

<400> SEQUENCE: 391
aaacaggata cagt 14

<210> SEQ ID NO 392
<211> LENGTH: 16
<212> TYPE: DNA
<213> ORGANISM: Artificial Sequence
<220> FEATURE:
<223> OTHER INFORMATION: ASO-000527

<400> SEQUENCE: 392
tagcaaacag gataca 16

<210> SEQ ID NO 393
<211> LENGTH: 16
<212> TYPE: DNA
<213> ORGANISM: Artificial Sequence
<220> FEATURE:
<223> OTHER INFORMATION: ASO-000617

<400> SEQUENCE: 393
atagcaaaca ggatac 16

<210> SEQ ID NO 394
<211> LENGTH: 16
<212> TYPE: DNA

<213> ORGANISM: Artificial Sequence
<220> FEATURE:
<223> OTHER INFORMATION: ASO-000539

<400> SEQUENCE: 394
aatagcaaac aggata 16

<210> SEQ ID NO 395
<211> LENGTH: 16
<212> TYPE: DNA
<213> ORGANISM: Artificial Sequence
<220> FEATURE:
<223> OTHER INFORMATION: ASO-000691

<400> SEQUENCE: 395
caatagcaaa caggat 16

<210> SEQ ID NO 396
<211> LENGTH: 15
<212> TYPE: DNA
<213> ORGANISM: Artificial Sequence
<220> FEATURE:
<223> OTHER INFORMATION: ASO-000589

<400> SEQUENCE: 396
aatagcaaac aggat 15

<210> SEQ ID NO 397
<211> LENGTH: 16
<212> TYPE: DNA
<213> ORGANISM: Artificial Sequence
<220> FEATURE:
<223> OTHER INFORMATION: ASO-000509

<400> SEQUENCE: 397
gcaatagcaa acagga 16

<210> SEQ ID NO 398
<211> LENGTH: 15
<212> TYPE: DNA
<213> ORGANISM: Artificial Sequence
<220> FEATURE:
<223> OTHER INFORMATION: ASO-000674

<400> SEQUENCE: 398
caatagcaaa cagga 15

<210> SEQ ID NO 399
<211> LENGTH: 15
<212> TYPE: DNA
<213> ORGANISM: Artificial Sequence
<220> FEATURE:
<223> OTHER INFORMATION: ASO-000488

<400> SEQUENCE: 399
gcaatagcaa acagg 15

<210> SEQ ID NO 400
<211> LENGTH: 16
<212> TYPE: DNA
<213> ORGANISM: Artificial Sequence
<220> FEATURE:
<223> OTHER INFORMATION: ASO-000507

<400> SEQUENCE: 400
agcaatagca aacagg 16

<210> SEQ ID NO 401
<211> LENGTH: 15
<212> TYPE: DNA
<213> ORGANISM: Artificial Sequence
<220> FEATURE:
<223> OTHER INFORMATION: ASO-000521

<400> SEQUENCE: 401
agcaatagca aacag 15

<210> SEQ ID NO 402
<211> LENGTH: 16
<212> TYPE: DNA
<213> ORGANISM: Artificial Sequence
<220> FEATURE:
<223> OTHER INFORMATION: ASO-000288

<400> SEQUENCE: 402
aagcaatagc aaacag 16

<210> SEQ ID NO 403
<211> LENGTH: 15
<212> TYPE: DNA
<213> ORGANISM: Artificial Sequence
<220> FEATURE:
<223> OTHER INFORMATION: ASO-000552

<400> SEQUENCE: 403
aagcaatagc aaaca 15

<210> SEQ ID NO 404
<211> LENGTH: 16
<212> TYPE: DNA
<213> ORGANISM: Artificial Sequence
<220> FEATURE:
<223> OTHER INFORMATION: ASO-000250

<400> SEQUENCE: 404
caaatgtggt tgaaat 16

<210> SEQ ID NO 405
<211> LENGTH: 16
<212> TYPE: DNA
<213> ORGANISM: Artificial Sequence
<220> FEATURE:
<223> OTHER INFORMATION: ASO-000294

<400> SEQUENCE: 405
gcaaatgtgg ttgaaa 16

<210> SEQ ID NO 406
<211> LENGTH: 16
<212> TYPE: DNA
<213> ORGANISM: Artificial Sequence
<220> FEATURE:
<223> OTHER INFORMATION: ASO-000318

<400> SEQUENCE: 406
tagcaaatgt ggttga 16

<210> SEQ ID NO 407
<211> LENGTH: 16
<212> TYPE: DNA
<213> ORGANISM: Artificial Sequence
<220> FEATURE:

<223> OTHER INFORMATION: ASO-000308

<400> SEQUENCE: 407
cccaagggcc tctaac 16

<210> SEQ ID NO 408
<211> LENGTH: 16
<212> TYPE: DNA
<213> ORGANISM: Artificial Sequence
<220> FEATURE:
<223> OTHER INFORMATION: ASO-000254

<400> SEQUENCE: 408
aaagcaacca gatgtc 16

<210> SEQ ID NO 409
<211> LENGTH: 16
<212> TYPE: DNA
<213> ORGANISM: Artificial Sequence
<220> FEATURE:
<223> OTHER INFORMATION: ASO-000545

<400> SEQUENCE: 409
aagagggcag caggcc 16

<210> SEQ ID NO 410
<211> LENGTH: 16
<212> TYPE: DNA
<213> ORGANISM: Artificial Sequence
<220> FEATURE:
<223> OTHER INFORMATION: ASO-000476

<400> SEQUENCE: 410
gaaagagggc agcagg 16

<210> SEQ ID NO 411
<211> LENGTH: 16
<212> TYPE: DNA
<213> ORGANISM: Artificial Sequence
<220> FEATURE:
<223> OTHER INFORMATION: ASO-000620

<400> SEQUENCE: 411
ctgaaagagg gcagca 16

<210> SEQ ID NO 412
<211> LENGTH: 16
<212> TYPE: DNA
<213> ORGANISM: Artificial Sequence
<220> FEATURE:
<223> OTHER INFORMATION: ASO-000477

<400> SEQUENCE: 412
ccctgaaaga gggcag 16

<210> SEQ ID NO 413
<211> LENGTH: 16
<212> TYPE: DNA
<213> ORGANISM: Artificial Sequence
<220> FEATURE:
<223> OTHER INFORMATION: ASO-000562

<400> SEQUENCE: 413
tgattgtggg cttagg 16

<210> SEQ ID NO 414
<211> LENGTH: 16
<212> TYPE: DNA
<213> ORGANISM: Artificial Sequence
<220> FEATURE:
<223> OTHER INFORMATION: ASO-000547

<400> SEQUENCE: 414
atgattgtgg gcttag 16

<210> SEQ ID NO 415
<211> LENGTH: 15
<212> TYPE: DNA
<213> ORGANISM: Artificial Sequence
<220> FEATURE:
<223> OTHER INFORMATION: ASO-000696

<400> SEQUENCE: 415
tgattgtggg cttag 15

<210> SEQ ID NO 416
<211> LENGTH: 14
<212> TYPE: DNA
<213> ORGANISM: Artificial Sequence
<220> FEATURE:
<223> OTHER INFORMATION: ASO-000279

<400> SEQUENCE: 416
gattgtgggc ttag 14

<210> SEQ ID NO 417
<211> LENGTH: 16
<212> TYPE: DNA
<213> ORGANISM: Artificial Sequence
<220> FEATURE:
<223> OTHER INFORMATION: ASO-000543

<400> SEQUENCE: 417
catgattgtg ggctta 16

<210> SEQ ID NO 418
<211> LENGTH: 14
<212> TYPE: DNA
<213> ORGANISM: Artificial Sequence
<220> FEATURE:
<223> OTHER INFORMATION: ASO-000626

<400> SEQUENCE: 418
tgattgtggg ctta 14

<210> SEQ ID NO 419
<211> LENGTH: 15
<212> TYPE: DNA
<213> ORGANISM: Artificial Sequence
<220> FEATURE:
<223> OTHER INFORMATION: ASO-000650

<400> SEQUENCE: 419
atgattgtgg gctta 15

<210> SEQ ID NO 420
<211> LENGTH: 15
<212> TYPE: DNA
<213> ORGANISM: Artificial Sequence
<220> FEATURE:
<223> OTHER INFORMATION: ASO-000599

<400> SEQUENCE: 420
catgattgtg ggctt 15

<210> SEQ ID NO 421
<211> LENGTH: 16
<212> TYPE: DNA
<213> ORGANISM: Artificial Sequence
<220> FEATURE:
<223> OTHER INFORMATION: ASO-000542

<400> SEQUENCE: 421
gcatgattgt gggctt 16

<210> SEQ ID NO 422
<211> LENGTH: 16
<212> TYPE: DNA
<213> ORGANISM: Artificial Sequence
<220> FEATURE:
<223> OTHER INFORMATION: ASO-000463

<400> SEQUENCE: 422
ggcatgattg tgggct 16

<210> SEQ ID NO 423
<211> LENGTH: 15
<212> TYPE: DNA
<213> ORGANISM: Artificial Sequence
<220> FEATURE:
<223> OTHER INFORMATION: ASO-000605

<400> SEQUENCE: 423
gcatgattgt gggct 15

<210> SEQ ID NO 424
<211> LENGTH: 14
<212> TYPE: DNA
<213> ORGANISM: Artificial Sequence
<220> FEATURE:
<223> OTHER INFORMATION: ASO-000479

<400> SEQUENCE: 424
catgattgtg ggct 14

<210> SEQ ID NO 425
<211> LENGTH: 14
<212> TYPE: DNA
<213> ORGANISM: Artificial Sequence
<220> FEATURE:
<223> OTHER INFORMATION: ASO-000474

<400> SEQUENCE: 425
gcatgattgt gggc 14

<210> SEQ ID NO 426
<211> LENGTH: 15
<212> TYPE: DNA
<213> ORGANISM: Artificial Sequence
<220> FEATURE:
<223> OTHER INFORMATION: ASO-000675

<400> SEQUENCE: 426
ggcatgattg tgggc 15

<210> SEQ ID NO 427
<211> LENGTH: 16

<212> TYPE: DNA
<213> ORGANISM: Artificial Sequence
<220> FEATURE:
<223> OTHER INFORMATION: ASO-000537

<400> SEQUENCE: 427
aggcatgatt gtgggc 16

<210> SEQ ID NO 428
<211> LENGTH: 16
<212> TYPE: DNA
<213> ORGANISM: Artificial Sequence
<220> FEATURE:
<223> OTHER INFORMATION: ASO-000287

<400> SEQUENCE: 428
agggaggcat gattgt 16

<210> SEQ ID NO 429
<211> LENGTH: 15
<212> TYPE: DNA
<213> ORGANISM: Artificial Sequence
<220> FEATURE:
<223> OTHER INFORMATION: ASO-000292

<400> SEQUENCE: 429
gggaggcatg attgt 15

<210> SEQ ID NO 430
<211> LENGTH: 16
<212> TYPE: DNA
<213> ORGANISM: Artificial Sequence
<220> FEATURE:
<223> OTHER INFORMATION: ASO-000216

<400> SEQUENCE: 430
ttagggaggc atgatt 16

<210> SEQ ID NO 431
<211> LENGTH: 15
<212> TYPE: DNA
<213> ORGANISM: Artificial Sequence
<220> FEATURE:
<223> OTHER INFORMATION: ASO-000266

<400> SEQUENCE: 431
ttagggaggc atgat 15

<210> SEQ ID NO 432
<211> LENGTH: 16
<212> TYPE: DNA
<213> ORGANISM: Artificial Sequence
<220> FEATURE:
<223> OTHER INFORMATION: ASO-000256

<400> SEQUENCE: 432
tcttagggag gcatga 16

<210> SEQ ID NO 433
<211> LENGTH: 16
<212> TYPE: DNA
<213> ORGANISM: Artificial Sequence
<220> FEATURE:
<223> OTHER INFORMATION: ASO-000269

<400> SEQUENCE: 433
gaggtggcac agaggt 16

<210> SEQ ID NO 434
<211> LENGTH: 15
<212> TYPE: DNA
<213> ORGANISM: Artificial Sequence
<220> FEATURE:
<223> OTHER INFORMATION: ASO-000350

<400> SEQUENCE: 434
cagtgtgaga ggtgg 15

<210> SEQ ID NO 435
<211> LENGTH: 14
<212> TYPE: DNA
<213> ORGANISM: Artificial Sequence
<220> FEATURE:
<223> OTHER INFORMATION: ASO-000353

<400> SEQUENCE: 435
cagtgtgaga ggtg 14

<210> SEQ ID NO 436
<211> LENGTH: 16
<212> TYPE: DNA
<213> ORGANISM: Artificial Sequence
<220> FEATURE:
<223> OTHER INFORMATION: ASO-000310

<400> SEQUENCE: 436
acaaagatga ggaggg 16

<210> SEQ ID NO 437
<211> LENGTH: 16
<212> TYPE: DNA
<213> ORGANISM: Artificial Sequence
<220> FEATURE:
<223> OTHER INFORMATION: ASO-000309

<400> SEQUENCE: 437
aacaaagatg aggagg 16

<210> SEQ ID NO 438
<211> LENGTH: 16
<212> TYPE: DNA
<213> ORGANISM: Artificial Sequence
<220> FEATURE:
<223> OTHER INFORMATION: ASO-000263

<400> SEQUENCE: 438
gaagagaaat cagaag 16

<210> SEQ ID NO 439
<211> LENGTH: 16
<212> TYPE: DNA
<213> ORGANISM: Artificial Sequence
<220> FEATURE:
<223> OTHER INFORMATION: ASO-000197

<400> SEQUENCE: 439
tctaggccag tgccca 16

<210> SEQ ID NO 440
<211> LENGTH: 14
<212> TYPE: DNA
<213> ORGANISM: Artificial Sequence

<220> FEATURE:
<223> OTHER INFORMATION: ASO-000239

<400> SEQUENCE: 440
agtctattag gagg 14

<210> SEQ ID NO 441
<211> LENGTH: 16
<212> TYPE: DNA
<213> ORGANISM: Artificial Sequence
<220> FEATURE:
<223> OTHER INFORMATION: ASO-000267

<400> SEQUENCE: 441
gctcaacatg gcaaac 16

<210> SEQ ID NO 442
<211> LENGTH: 15
<212> TYPE: DNA
<213> ORGANISM: Artificial Sequence
<220> FEATURE:
<223> OTHER INFORMATION: ASO-000306

<400> SEQUENCE: 442
tgcaagtgcc agaaa 15

<210> SEQ ID NO 443
<211> LENGTH: 14
<212> TYPE: DNA
<213> ORGANISM: Artificial Sequence
<220> FEATURE:
<223> OTHER INFORMATION: ASO-000345

<400> SEQUENCE: 443
gcaagtgcca gaaa 14

<210> SEQ ID NO 444
<211> LENGTH: 16
<212> TYPE: DNA
<213> ORGANISM: Artificial Sequence
<220> FEATURE:
<223> OTHER INFORMATION: ASO-000193

<400> SEQUENCE: 444
aatcatggga cttgca 16

<210> SEQ ID NO 445
<211> LENGTH: 16
<212> TYPE: DNA
<213> ORGANISM: Artificial Sequence
<220> FEATURE:
<223> OTHER INFORMATION: ASO-000284

<400> SEQUENCE: 445
gatttcatgt ccctcc 16

<210> SEQ ID NO 446
<211> LENGTH: 15
<212> TYPE: DNA
<213> ORGANISM: Artificial Sequence
<220> FEATURE:
<223> OTHER INFORMATION: ASO-000209

<400> SEQUENCE: 446
gctaagctaa gatga 15

<210> SEQ ID NO 447
<211> LENGTH: 14
<212> TYPE: DNA
<213> ORGANISM: Artificial Sequence
<220> FEATURE:
<223> OTHER INFORMATION: ASO-000207

<400> SEQUENCE: 447
ctaagctaag atga 14

<210> SEQ ID NO 448
<211> LENGTH: 15
<212> TYPE: DNA
<213> ORGANISM: Artificial Sequence
<220> FEATURE:
<223> OTHER INFORMATION: ASO-000301

<400> SEQUENCE: 448
tagacattca cagac 15

<210> SEQ ID NO 449
<211> LENGTH: 15
<212> TYPE: DNA
<213> ORGANISM: Artificial Sequence
<220> FEATURE:
<223> OTHER INFORMATION: ASO-000234

<400> SEQUENCE: 449
tatagacatt cacag 15

<210> SEQ ID NO 450
<211> LENGTH: 16
<212> TYPE: DNA
<213> ORGANISM: Artificial Sequence
<220> FEATURE:
<223> OTHER INFORMATION: ASO-000332

<400> SEQUENCE: 450
aaacacacaa tacact 16

<210> SEQ ID NO 451
<211> LENGTH: 16
<212> TYPE: DNA
<213> ORGANISM: Artificial Sequence
<220> FEATURE:
<223> OTHER INFORMATION: SPC-15693-01

<400> SEQUENCE: 451
cagcaacagt cagtgt 16

<210> SEQ ID NO 452
<211> LENGTH: 16
<212> TYPE: DNA
<213> ORGANISM: Artificial Sequence
<220> FEATURE:
<223> OTHER INFORMATION: SPC-15692-01

<400> SEQUENCE: 452
acagcaacag tcagtg 16

<210> SEQ ID NO 453
<211> LENGTH: 16
<212> TYPE: DNA
<213> ORGANISM: Artificial Sequence
<220> FEATURE:
<223> OTHER INFORMATION: SPC-15691-01

<400> SEQUENCE: 453
tacagcaaca gtcagt 16

<210> SEQ ID NO 454
<211> LENGTH: 16
<212> TYPE: DNA
<213> ORGANISM: Artificial Sequence
<220> FEATURE:
<223> OTHER INFORMATION: SPC-15690-01

<400> SEQUENCE: 454
ttacagcaac agtcag 16

<210> SEQ ID NO 455
<211> LENGTH: 16
<212> TYPE: DNA
<213> ORGANISM: Artificial Sequence
<220> FEATURE:
<223> OTHER INFORMATION: SPC-15689-01

<400> SEQUENCE: 455
tttacagcaa cagtca 16

<210> SEQ ID NO 456
<211> LENGTH: 16
<212> TYPE: DNA
<213> ORGANISM: Artificial Sequence
<220> FEATURE:
<223> OTHER INFORMATION: SPC-15688-01

<400> SEQUENCE: 456
ttttacagca acagtc 16

<210> SEQ ID NO 457
<211> LENGTH: 16
<212> TYPE: DNA
<213> ORGANISM: Artificial Sequence
<220> FEATURE:
<223> OTHER INFORMATION: SPC-15687-01

<400> SEQUENCE: 457
cttttacagc aacagt 16

<210> SEQ ID NO 458
<211> LENGTH: 16
<212> TYPE: DNA
<213> ORGANISM: Artificial Sequence
<220> FEATURE:
<223> OTHER INFORMATION: SPC-15686-01

<400> SEQUENCE: 458
acttttacag caacag 16

<210> SEQ ID NO 459
<211> LENGTH: 16
<212> TYPE: DNA
<213> ORGANISM: Artificial Sequence
<220> FEATURE:
<223> OTHER INFORMATION: SPC-15685-01

<400> SEQUENCE: 459
cacttttaca gcaaca 16

<210> SEQ ID NO 460

<211> LENGTH: 16
<212> TYPE: DNA
<213> ORGANISM: Artificial Sequence
<220> FEATURE:
<223> OTHER INFORMATION: SPC-15684-01

<400> SEQUENCE: 460
tcacttttac agcaac 16

<210> SEQ ID NO 461
<211> LENGTH: 16
<212> TYPE: DNA
<213> ORGANISM: Artificial Sequence
<220> FEATURE:
<223> OTHER INFORMATION: SPC-15683-01

<400> SEQUENCE: 461
ttcactttta cagcaa 16

<210> SEQ ID NO 462
<211> LENGTH: 16
<212> TYPE: DNA
<213> ORGANISM: Artificial Sequence
<220> FEATURE:
<223> OTHER INFORMATION: SPC-15682-01

<400> SEQUENCE: 462
attcactttt acagca 16

<210> SEQ ID NO 463
<211> LENGTH: 16
<212> TYPE: DNA
<213> ORGANISM: Artificial Sequence
<220> FEATURE:
<223> OTHER INFORMATION: SPC-15681-01

<400> SEQUENCE: 463
aattcacttt tacagc 16

<210> SEQ ID NO 464
<211> LENGTH: 16
<212> TYPE: DNA
<213> ORGANISM: Artificial Sequence
<220> FEATURE:
<223> OTHER INFORMATION: SPC-15680-01

<400> SEQUENCE: 464
aaattcactt ttacag 16

<210> SEQ ID NO 465
<211> LENGTH: 16
<212> TYPE: DNA
<213> ORGANISM: Artificial Sequence
<220> FEATURE:
<223> OTHER INFORMATION: SPC-15679-01

<400> SEQUENCE: 465
caaattcact tttaca 16

<210> SEQ ID NO 466
<211> LENGTH: 20
<212> TYPE: DNA
<213> ORGANISM: Artificial Sequence
<220> FEATURE:
<223> OTHER INFORMATION: ASO-002090

<400> SEQUENCE: 466
atttccaaat tcacttttac 20

<210> SEQ ID NO 467
<211> LENGTH: 20
<212> TYPE: DNA
<213> ORGANISM: Artificial Sequence
<220> FEATURE:
<223> OTHER INFORMATION: ASO-002043

<400> SEQUENCE: 467
atttccaaat tcacttttac 20

<210> SEQ ID NO 468
<211> LENGTH: 20
<212> TYPE: DNA
<213> ORGANISM: Artificial Sequence
<220> FEATURE:
<223> OTHER INFORMATION: ASO-002076

<400> SEQUENCE: 468
atttccaaat tcacttttac 20

<210> SEQ ID NO 469
<211> LENGTH: 20
<212> TYPE: DNA
<213> ORGANISM: Artificial Sequence
<220> FEATURE:
<223> OTHER INFORMATION: ASO-002062

<400> SEQUENCE: 469
atttccaaat tcacttttac 20

<210> SEQ ID NO 470
<211> LENGTH: 20
<212> TYPE: DNA
<213> ORGANISM: Artificial Sequence
<220> FEATURE:
<223> OTHER INFORMATION: ASO-002082

<400> SEQUENCE: 470
atttccaaat tcacttttac 20

<210> SEQ ID NO 471
<211> LENGTH: 20
<212> TYPE: DNA
<213> ORGANISM: Artificial Sequence
<220> FEATURE:
<223> OTHER INFORMATION: ASO-000753

<400> SEQUENCE: 471
atttccaaat tcacttttac 20

<210> SEQ ID NO 472
<211> LENGTH: 20
<212> TYPE: DNA
<213> ORGANISM: Artificial Sequence
<220> FEATURE:
<223> OTHER INFORMATION: ASO-001940

<400> SEQUENCE: 472
atttccaaat tcacttttac 20

<210> SEQ ID NO 473
<211> LENGTH: 20
<212> TYPE: DNA

<213> ORGANISM: Artificial Sequence
<220> FEATURE:
<223> OTHER INFORMATION: ASO-001933

<400> SEQUENCE: 473
atttccaaat tcacttttac 20

<210> SEQ ID NO 474
<211> LENGTH: 20
<212> TYPE: DNA
<213> ORGANISM: Artificial Sequence
<220> FEATURE:
<223> OTHER INFORMATION: ASO-001919

<400> SEQUENCE: 474
atttccaaat tcacttttac 20

<210> SEQ ID NO 475
<211> LENGTH: 20
<212> TYPE: DNA
<213> ORGANISM: Artificial Sequence
<220> FEATURE:
<223> OTHER INFORMATION: ASO-002094

<400> SEQUENCE: 475
atttccaaat tcacttttac 20

<210> SEQ ID NO 476
<211> LENGTH: 20
<212> TYPE: DNA
<213> ORGANISM: Artificial Sequence
<220> FEATURE:
<223> OTHER INFORMATION: ASO-002034

<400> SEQUENCE: 476
atttccaaat tcacttttac 20

<210> SEQ ID NO 477
<211> LENGTH: 20
<212> TYPE: DNA
<213> ORGANISM: Artificial Sequence
<220> FEATURE:
<223> OTHER INFORMATION: ASO-002036

<400> SEQUENCE: 477
atttccaaat tcacttttac 20

<210> SEQ ID NO 478
<211> LENGTH: 20
<212> TYPE: DNA
<213> ORGANISM: Artificial Sequence
<220> FEATURE:
<223> OTHER INFORMATION: ASO-002084

<400> SEQUENCE: 478
atttccaaat tcacttttac 20

<210> SEQ ID NO 479
<211> LENGTH: 20
<212> TYPE: DNA
<213> ORGANISM: Artificial Sequence
<220> FEATURE:
<223> OTHER INFORMATION: ASO-002037

<400> SEQUENCE: 479
atttccaaat tcacttttac 20

<210> SEQ ID NO 480
<211> LENGTH: 20
<212> TYPE: DNA
<213> ORGANISM: Artificial Sequence
<220> FEATURE:
<223> OTHER INFORMATION: ASO-002058

<400> SEQUENCE: 480
atttccaaat tcacttttac 20

<210> SEQ ID NO 481
<211> LENGTH: 20
<212> TYPE: DNA
<213> ORGANISM: Artificial Sequence
<220> FEATURE:
<223> OTHER INFORMATION: ASO-002057

<400> SEQUENCE: 481
atttccaaat tcacttttac 20

<210> SEQ ID NO 482
<211> LENGTH: 20
<212> TYPE: DNA
<213> ORGANISM: Artificial Sequence
<220> FEATURE:
<223> OTHER INFORMATION: ASO-001926

<400> SEQUENCE: 482
atttccaaat tcacttttac 20

<210> SEQ ID NO 483
<211> LENGTH: 20
<212> TYPE: DNA
<213> ORGANISM: Artificial Sequence
<220> FEATURE:
<223> OTHER INFORMATION: ASO-002092

<400> SEQUENCE: 483
atttccaaat tcacttttac 20

<210> SEQ ID NO 484
<211> LENGTH: 20
<212> TYPE: DNA
<213> ORGANISM: Artificial Sequence
<220> FEATURE:
<223> OTHER INFORMATION: ASO-002023

<400> SEQUENCE: 484
atttccaaat tcacttttac 20

<210> SEQ ID NO 485
<211> LENGTH: 20
<212> TYPE: DNA
<213> ORGANISM: Artificial Sequence
<220> FEATURE:
<223> OTHER INFORMATION: ASO-000758

<400> SEQUENCE: 485
atttccaaat tcacttttac 20

<210> SEQ ID NO 486
<211> LENGTH: 20
<212> TYPE: DNA
<213> ORGANISM: Artificial Sequence
<220> FEATURE:

<223> OTHER INFORMATION: ASO-002065

<400> SEQUENCE: 486
atttccaaat tcacttttac 20

<210> SEQ ID NO 487
<211> LENGTH: 20
<212> TYPE: DNA
<213> ORGANISM: Artificial Sequence
<220> FEATURE:
<223> OTHER INFORMATION: ASO-002038

<400> SEQUENCE: 487
atttccaaat tcacttttac 20

<210> SEQ ID NO 488
<211> LENGTH: 20
<212> TYPE: DNA
<213> ORGANISM: Artificial Sequence
<220> FEATURE:
<223> OTHER INFORMATION: ASO-002039

<400> SEQUENCE: 488
atttccaaat tcacttttac 20

<210> SEQ ID NO 489
<211> LENGTH: 20
<212> TYPE: DNA
<213> ORGANISM: Artificial Sequence
<220> FEATURE:
<223> OTHER INFORMATION: ASO-000763

<400> SEQUENCE: 489
atttccaaat tcacttttac 20

<210> SEQ ID NO 490
<211> LENGTH: 20
<212> TYPE: DNA
<213> ORGANISM: Artificial Sequence
<220> FEATURE:
<223> OTHER INFORMATION: ASO-000768

<400> SEQUENCE: 490
atttccaaat tcacttttac 20

<210> SEQ ID NO 491
<211> LENGTH: 17
<212> TYPE: DNA
<213> ORGANISM: Artificial Sequence
<220> FEATURE:
<223> OTHER INFORMATION: 17-18-19mer-1

<400> SEQUENCE: 491
tccaaattca cttttac 17

<210> SEQ ID NO 492
<211> LENGTH: 17
<212> TYPE: DNA
<213> ORGANISM: Artificial Sequence
<220> FEATURE:
<223> OTHER INFORMATION: 17-18-19mer-10

<400> SEQUENCE: 492
tccaaattca cttttac 17

<210> SEQ ID NO 493
<211> LENGTH: 17
<212> TYPE: DNA
<213> ORGANISM: Artificial Sequence
<220> FEATURE:
<223> OTHER INFORMATION: 17-18-19mer-13

<400> SEQUENCE: 493
tccaaattca cttttac 17

<210> SEQ ID NO 494
<211> LENGTH: 18
<212> TYPE: DNA
<213> ORGANISM: Artificial Sequence
<220> FEATURE:
<223> OTHER INFORMATION: 17-18-19mer-16

<400> SEQUENCE: 494
ttccaaattc acttttac 18

<210> SEQ ID NO 495
<211> LENGTH: 18
<212> TYPE: DNA
<213> ORGANISM: Artificial Sequence
<220> FEATURE:
<223> OTHER INFORMATION: 17-18-19mer-22

<400> SEQUENCE: 495
ttccaaattc acttttac 18

<210> SEQ ID NO 496
<211> LENGTH: 18
<212> TYPE: DNA
<213> ORGANISM: Artificial Sequence
<220> FEATURE:
<223> OTHER INFORMATION: 17-18-19mer-28

<400> SEQUENCE: 496
ttccaaattc acttttac 18

<210> SEQ ID NO 497
<211> LENGTH: 18
<212> TYPE: DNA
<213> ORGANISM: Artificial Sequence
<220> FEATURE:
<223> OTHER INFORMATION: 17-18-19mer-34

<400> SEQUENCE: 497
ttccaaattc acttttac 18

<210> SEQ ID NO 498
<211> LENGTH: 17
<212> TYPE: DNA
<213> ORGANISM: Artificial Sequence
<220> FEATURE:
<223> OTHER INFORMATION: 17-18-19mer-4

<400> SEQUENCE: 498
tccaaattca cttttac 17

<210> SEQ ID NO 499
<211> LENGTH: 18
<212> TYPE: DNA
<213> ORGANISM: Artificial Sequence
<220> FEATURE:
<223> OTHER INFORMATION: 17-18-19mer-40

<400> SEQUENCE: 499
ttccaaattc acttttac 18

<210> SEQ ID NO 500
<211> LENGTH: 19
<212> TYPE: DNA
<213> ORGANISM: Artificial Sequence
<220> FEATURE:
<223> OTHER INFORMATION: 17-18-19mer-46

<400> SEQUENCE: 500
tttccaaatt cacttttac 19

<210> SEQ ID NO 501
<211> LENGTH: 19
<212> TYPE: DNA
<213> ORGANISM: Artificial Sequence
<220> FEATURE:
<223> OTHER INFORMATION: 17-18-19mer-52

<400> SEQUENCE: 501
tttccaaatt cacttttac 19

<210> SEQ ID NO 502
<211> LENGTH: 19
<212> TYPE: DNA
<213> ORGANISM: Artificial Sequence
<220> FEATURE:
<223> OTHER INFORMATION: 17-18-19mer-58

<400> SEQUENCE: 502
tttccaaatt cacttttac 19

<210> SEQ ID NO 503
<211> LENGTH: 19
<212> TYPE: DNA
<213> ORGANISM: Artificial Sequence
<220> FEATURE:
<223> OTHER INFORMATION: 17-18-19mer-64

<400> SEQUENCE: 503
tttccaaatt cacttttac 19

<210> SEQ ID NO 504
<211> LENGTH: 17
<212> TYPE: DNA
<213> ORGANISM: Artificial Sequence
<220> FEATURE:
<223> OTHER INFORMATION: 17-18-19mer-7

<400> SEQUENCE: 504
tccaaattca cttttac 17

<210> SEQ ID NO 505
<211> LENGTH: 19
<212> TYPE: DNA
<213> ORGANISM: Artificial Sequence
<220> FEATURE:
<223> OTHER INFORMATION: 17-18-19mer-70

<400> SEQUENCE: 505
tttccaaatt cacttttac 19

<210> SEQ ID NO 506
<211> LENGTH: 20

```
<212> TYPE: DNA
<213> ORGANISM: Artificial Sequence
<220> FEATURE:
<223> OTHER INFORMATION: ASO-001933-mm1

<400> SEQUENCE: 506

gtttccaaat tcacttttac                                                    20


<210> SEQ ID NO 507
<211> LENGTH: 20
<212> TYPE: DNA
<213> ORGANISM: Artificial Sequence
<220> FEATURE:
<223> OTHER INFORMATION: ASO-001933-mm2

<400> SEQUENCE: 507

atttccagat tcacttttac                                                    20


<210> SEQ ID NO 508
<211> LENGTH: 20
<212> TYPE: DNA
<213> ORGANISM: Artificial Sequence
<220> FEATURE:
<223> OTHER INFORMATION: ASO-001933-mm3

<400> SEQUENCE: 508

ttttccaaat tcacttttac                                                    20


<210> SEQ ID NO 509
<211> LENGTH: 20
<212> TYPE: DNA
<213> ORGANISM: Artificial Sequence
<220> FEATURE:
<223> OTHER INFORMATION: ASO-001933-mm4

<400> SEQUENCE: 509

gtttccagat tcacttttac                                                    20


<210> SEQ ID NO 510
<211> LENGTH: 20
<212> TYPE: DNA
<213> ORGANISM: Artificial Sequence
<220> FEATURE:
<223> OTHER INFORMATION: ASO-001933-mm5

<400> SEQUENCE: 510

atttccaagt tcacttttgc                                                    20


<210> SEQ ID NO 511
<211> LENGTH: 20
<212> TYPE: DNA
<213> ORGANISM: Artificial Sequence
<220> FEATURE:
<223> OTHER INFORMATION: ASO-001933-mm6

<400> SEQUENCE: 511

atttccagat tcgcttttac                                                    20


<210> SEQ ID NO 512
<211> LENGTH: 16
<212> TYPE: DNA
<213> ORGANISM: Artificial Sequence
<220> FEATURE:
<223> OTHER INFORMATION: SPC-15678-01

<400> SEQUENCE: 512
```

ccaaattcac ttttac 16

<210> SEQ ID NO 513
<211> LENGTH: 20
<212> TYPE: DNA
<213> ORGANISM: Artificial Sequence
<220> FEATURE:
<223> OTHER INFORMATION: SPC-15857-01

<400> SEQUENCE: 513
atttccaaat tcacttttac 20

<210> SEQ ID NO 514
<211> LENGTH: 20
<212> TYPE: DNA
<213> ORGANISM: Artificial Sequence
<220> FEATURE:
<223> OTHER INFORMATION: SPC-15858-01

<400> SEQUENCE: 514
atttccaaat tcacttttac 20

<210> SEQ ID NO 515
<211> LENGTH: 20
<212> TYPE: DNA
<213> ORGANISM: Artificial Sequence
<220> FEATURE:
<223> OTHER INFORMATION: SPC-15860-01

<400> SEQUENCE: 515
atttccaaat tcacttttac 20

<210> SEQ ID NO 516
<211> LENGTH: 20
<212> TYPE: DNA
<213> ORGANISM: Artificial Sequence
<220> FEATURE:
<223> OTHER INFORMATION: SPC-15864-01

<400> SEQUENCE: 516
atttccaaat tcacttttac 20

<210> SEQ ID NO 517
<211> LENGTH: 20
<212> TYPE: DNA
<213> ORGANISM: Artificial Sequence
<220> FEATURE:
<223> OTHER INFORMATION: SPC-15868-01

<400> SEQUENCE: 517
atttccaaat tcacttttac 20

<210> SEQ ID NO 518
<211> LENGTH: 20
<212> TYPE: DNA
<213> ORGANISM: Artificial Sequence
<220> FEATURE:
<223> OTHER INFORMATION: SPC-15872-01

<400> SEQUENCE: 518
atttccaaat tcacttttac 20

<210> SEQ ID NO 519
<211> LENGTH: 20
<212> TYPE: DNA
<213> ORGANISM: Artificial Sequence

<220> FEATURE:
<223> OTHER INFORMATION: SPC-15873-01

<400> SEQUENCE: 519
atttccaaat tcacttttac 20

<210> SEQ ID NO 520
<211> LENGTH: 20
<212> TYPE: DNA
<213> ORGANISM: Artificial Sequence
<220> FEATURE:
<223> OTHER INFORMATION: SPC-15874-01

<400> SEQUENCE: 520
atttccaaat tcacttttac 20

<210> SEQ ID NO 521
<211> LENGTH: 20
<212> TYPE: DNA
<213> ORGANISM: Artificial Sequence
<220> FEATURE:
<223> OTHER INFORMATION: SPC-15878-01

<400> SEQUENCE: 521
atttccaaat tcacttttac 20

<210> SEQ ID NO 522
<211> LENGTH: 20
<212> TYPE: DNA
<213> ORGANISM: Artificial Sequence
<220> FEATURE:
<223> OTHER INFORMATION: SPC-15879-01

<400> SEQUENCE: 522
atttccaaat tcacttttac 20

<210> SEQ ID NO 523
<211> LENGTH: 20
<212> TYPE: DNA
<213> ORGANISM: Artificial Sequence
<220> FEATURE:
<223> OTHER INFORMATION: SPC-15880-01

<400> SEQUENCE: 523
atttccaaat tcacttttac 20

<210> SEQ ID NO 524
<211> LENGTH: 20
<212> TYPE: DNA
<213> ORGANISM: Artificial Sequence
<220> FEATURE:
<223> OTHER INFORMATION: SPC-15883-01

<400> SEQUENCE: 524
atttccaaat tcacttttac 20

<210> SEQ ID NO 525
<211> LENGTH: 20
<212> TYPE: DNA
<213> ORGANISM: Artificial Sequence
<220> FEATURE:
<223> OTHER INFORMATION: SPC-15888-01

<400> SEQUENCE: 525
atttccaaat tcacttttac 20

<210> SEQ ID NO 526
<211> LENGTH: 20
<212> TYPE: DNA
<213> ORGANISM: Artificial Sequence
<220> FEATURE:
<223> OTHER INFORMATION: ASO-000754

<400> SEQUENCE: 526
tatttccaaa ttcactttta 20

<210> SEQ ID NO 527
<211> LENGTH: 20
<212> TYPE: DNA
<213> ORGANISM: Artificial Sequence
<220> FEATURE:
<223> OTHER INFORMATION: ASO-002055

<400> SEQUENCE: 527
tatttccaaa ttcactttta 20

<210> SEQ ID NO 528
<211> LENGTH: 20
<212> TYPE: DNA
<213> ORGANISM: Artificial Sequence
<220> FEATURE:
<223> OTHER INFORMATION: ASO-002035

<400> SEQUENCE: 528
tatttccaaa ttcactttta 20

<210> SEQ ID NO 529
<211> LENGTH: 20
<212> TYPE: DNA
<213> ORGANISM: Artificial Sequence
<220> FEATURE:
<223> OTHER INFORMATION: ASO-002048

<400> SEQUENCE: 529
tatttccaaa ttcactttta 20

<210> SEQ ID NO 530
<211> LENGTH: 20
<212> TYPE: DNA
<213> ORGANISM: Artificial Sequence
<220> FEATURE:
<223> OTHER INFORMATION: ASO-002053

<400> SEQUENCE: 530
tatttccaaa ttcactttta 20

<210> SEQ ID NO 531
<211> LENGTH: 20
<212> TYPE: DNA
<213> ORGANISM: Artificial Sequence
<220> FEATURE:
<223> OTHER INFORMATION: ASO-002067

<400> SEQUENCE: 531
tatttccaaa ttcactttta 20

<210> SEQ ID NO 532
<211> LENGTH: 20
<212> TYPE: DNA
<213> ORGANISM: Artificial Sequence
<220> FEATURE:
<223> OTHER INFORMATION: ASO-001954

<400> SEQUENCE: 532
tatttccaaa ttcactttta 20

<210> SEQ ID NO 533
<211> LENGTH: 20
<212> TYPE: DNA
<213> ORGANISM: Artificial Sequence
<220> FEATURE:
<223> OTHER INFORMATION: ASO-001947

<400> SEQUENCE: 533
tatttccaaa ttcactttta 20

<210> SEQ ID NO 534
<211> LENGTH: 20
<212> TYPE: DNA
<213> ORGANISM: Artificial Sequence
<220> FEATURE:
<223> OTHER INFORMATION: ASO-002081

<400> SEQUENCE: 534
tatttccaaa ttcactttta 20

<210> SEQ ID NO 535
<211> LENGTH: 20
<212> TYPE: DNA
<213> ORGANISM: Artificial Sequence
<220> FEATURE:
<223> OTHER INFORMATION: ASO-001966

<400> SEQUENCE: 535
tatttccaaa ttcactttta 20

<210> SEQ ID NO 536
<211> LENGTH: 20
<212> TYPE: DNA
<213> ORGANISM: Artificial Sequence
<220> FEATURE:
<223> OTHER INFORMATION: ASO-002025

<400> SEQUENCE: 536
tatttccaaa ttcactttta 20

<210> SEQ ID NO 537
<211> LENGTH: 20
<212> TYPE: DNA
<213> ORGANISM: Artificial Sequence
<220> FEATURE:
<223> OTHER INFORMATION: ASO-002033

<400> SEQUENCE: 537
tatttccaaa ttcactttta 20

<210> SEQ ID NO 538
<211> LENGTH: 20
<212> TYPE: DNA
<213> ORGANISM: Artificial Sequence
<220> FEATURE:
<223> OTHER INFORMATION: ASO-001960

<400> SEQUENCE: 538
tatttccaaa ttcactttta 20

<210> SEQ ID NO 539

<211> LENGTH: 20
<212> TYPE: DNA
<213> ORGANISM: Artificial Sequence
<220> FEATURE:
<223> OTHER INFORMATION: ASO-002056

<400> SEQUENCE: 539
tatttccaaa ttcactttta 20

<210> SEQ ID NO 540
<211> LENGTH: 20
<212> TYPE: DNA
<213> ORGANISM: Artificial Sequence
<220> FEATURE:
<223> OTHER INFORMATION: ASO-002063

<400> SEQUENCE: 540
tatttccaaa ttcactttta 20

<210> SEQ ID NO 541
<211> LENGTH: 20
<212> TYPE: DNA
<213> ORGANISM: Artificial Sequence
<220> FEATURE:
<223> OTHER INFORMATION: ASO-002089

<400> SEQUENCE: 541
tatttccaaa ttcactttta 20

<210> SEQ ID NO 542
<211> LENGTH: 20
<212> TYPE: DNA
<213> ORGANISM: Artificial Sequence
<220> FEATURE:
<223> OTHER INFORMATION: ASO-002073

<400> SEQUENCE: 542
tatttccaaa ttcactttta 20

<210> SEQ ID NO 543
<211> LENGTH: 20
<212> TYPE: DNA
<213> ORGANISM: Artificial Sequence
<220> FEATURE:
<223> OTHER INFORMATION: ASO-002027

<400> SEQUENCE: 543
tatttccaaa ttcactttta 20

<210> SEQ ID NO 544
<211> LENGTH: 20
<212> TYPE: DNA
<213> ORGANISM: Artificial Sequence
<220> FEATURE:
<223> OTHER INFORMATION: ASO-002075

<400> SEQUENCE: 544
tatttccaaa ttcactttta 20

<210> SEQ ID NO 545
<211> LENGTH: 20
<212> TYPE: DNA
<213> ORGANISM: Artificial Sequence
<220> FEATURE:
<223> OTHER INFORMATION: ASO-002028

<400> SEQUENCE: 545
tatttccaaa ttcactttta 20

<210> SEQ ID NO 546
<211> LENGTH: 20
<212> TYPE: DNA
<213> ORGANISM: Artificial Sequence
<220> FEATURE:
<223> OTHER INFORMATION: ASO-002085

<400> SEQUENCE: 546
tatttccaaa ttcactttta 20

<210> SEQ ID NO 547
<211> LENGTH: 20
<212> TYPE: DNA
<213> ORGANISM: Artificial Sequence
<220> FEATURE:
<223> OTHER INFORMATION: ASO-002083

<400> SEQUENCE: 547
tatttccaaa ttcactttta 20

<210> SEQ ID NO 548
<211> LENGTH: 20
<212> TYPE: DNA
<213> ORGANISM: Artificial Sequence
<220> FEATURE:
<223> OTHER INFORMATION: ASO-000759

<400> SEQUENCE: 548
tatttccaaa ttcactttta 20

<210> SEQ ID NO 549
<211> LENGTH: 20
<212> TYPE: DNA
<213> ORGANISM: Artificial Sequence
<220> FEATURE:
<223> OTHER INFORMATION: ASO-000769

<400> SEQUENCE: 549
tatttccaaa ttcactttta 20

<210> SEQ ID NO 550
<211> LENGTH: 20
<212> TYPE: DNA
<213> ORGANISM: Artificial Sequence
<220> FEATURE:
<223> OTHER INFORMATION: ASO-000764

<400> SEQUENCE: 550
tatttccaaa ttcactttta 20

<210> SEQ ID NO 551
<211> LENGTH: 17
<212> TYPE: DNA
<213> ORGANISM: Artificial Sequence
<220> FEATURE:
<223> OTHER INFORMATION: 17-18-19mer-11

<400> SEQUENCE: 551
ttccaaattc actttta 17

<210> SEQ ID NO 552
<211> LENGTH: 17
<212> TYPE: DNA

<213> ORGANISM: Artificial Sequence
<220> FEATURE:
<223> OTHER INFORMATION: 17-18-19mer-14

<400> SEQUENCE: 552
ttccaaattc actttta 17

<210> SEQ ID NO 553
<211> LENGTH: 18
<212> TYPE: DNA
<213> ORGANISM: Artificial Sequence
<220> FEATURE:
<223> OTHER INFORMATION: 17-18-19mer-17

<400> SEQUENCE: 553
tttccaaatt cactttta 18

<210> SEQ ID NO 554
<211> LENGTH: 17
<212> TYPE: DNA
<213> ORGANISM: Artificial Sequence
<220> FEATURE:
<223> OTHER INFORMATION: 17-18-19mer-2

<400> SEQUENCE: 554
ttccaaattc actttta 17

<210> SEQ ID NO 555
<211> LENGTH: 18
<212> TYPE: DNA
<213> ORGANISM: Artificial Sequence
<220> FEATURE:
<223> OTHER INFORMATION: 17-18-19mer-23

<400> SEQUENCE: 555
tttccaaatt cactttta 18

<210> SEQ ID NO 556
<211> LENGTH: 18
<212> TYPE: DNA
<213> ORGANISM: Artificial Sequence
<220> FEATURE:
<223> OTHER INFORMATION: 17-18-19mer-29

<400> SEQUENCE: 556
tttccaaatt cactttta 18

<210> SEQ ID NO 557
<211> LENGTH: 18
<212> TYPE: DNA
<213> ORGANISM: Artificial Sequence
<220> FEATURE:
<223> OTHER INFORMATION: 17-18-19mer-35

<400> SEQUENCE: 557
tttccaaatt cactttta 18

<210> SEQ ID NO 558
<211> LENGTH: 18
<212> TYPE: DNA
<213> ORGANISM: Artificial Sequence
<220> FEATURE:
<223> OTHER INFORMATION: 17-18-19mer-41

<400> SEQUENCE: 558
tttccaaatt cactttta 18

<210> SEQ ID NO 559
<211> LENGTH: 19
<212> TYPE: DNA
<213> ORGANISM: Artificial Sequence
<220> FEATURE:
<223> OTHER INFORMATION: 17-18-19mer-47

<400> SEQUENCE: 559
atttccaaat tcactttta 19

<210> SEQ ID NO 560
<211> LENGTH: 17
<212> TYPE: DNA
<213> ORGANISM: Artificial Sequence
<220> FEATURE:
<223> OTHER INFORMATION: 17-18-19mer-5

<400> SEQUENCE: 560
ttccaaattc actttta 17

<210> SEQ ID NO 561
<211> LENGTH: 19
<212> TYPE: DNA
<213> ORGANISM: Artificial Sequence
<220> FEATURE:
<223> OTHER INFORMATION: 17-18-19mer-53

<400> SEQUENCE: 561
atttccaaat tcactttta 19

<210> SEQ ID NO 562
<211> LENGTH: 19
<212> TYPE: DNA
<213> ORGANISM: Artificial Sequence
<220> FEATURE:
<223> OTHER INFORMATION: 17-18-19mer-59

<400> SEQUENCE: 562
atttccaaat tcactttta 19

<210> SEQ ID NO 563
<211> LENGTH: 19
<212> TYPE: DNA
<213> ORGANISM: Artificial Sequence
<220> FEATURE:
<223> OTHER INFORMATION: 17-18-19mer-65

<400> SEQUENCE: 563
atttccaaat tcactttta 19

<210> SEQ ID NO 564
<211> LENGTH: 19
<212> TYPE: DNA
<213> ORGANISM: Artificial Sequence
<220> FEATURE:
<223> OTHER INFORMATION: 17-18-19mer-71

<400> SEQUENCE: 564
atttccaaat tcactttta 19

<210> SEQ ID NO 565
<211> LENGTH: 17
<212> TYPE: DNA
<213> ORGANISM: Artificial Sequence
<220> FEATURE:

```
<223> OTHER INFORMATION: 17-18-19mer-8

<400> SEQUENCE: 565

ttccaaattc actttta                                                17


<210> SEQ ID NO 566
<211> LENGTH: 20
<212> TYPE: DNA
<213> ORGANISM: Artificial Sequence
<220> FEATURE:
<223> OTHER INFORMATION: ASO-001954-mm1

<400> SEQUENCE: 566

tatttccaga ttcactttta                                             20


<210> SEQ ID NO 567
<211> LENGTH: 20
<212> TYPE: DNA
<213> ORGANISM: Artificial Sequence
<220> FEATURE:
<223> OTHER INFORMATION: ASO-001954-mm2

<400> SEQUENCE: 567

tatttccgaa ttcactttta                                             20


<210> SEQ ID NO 568
<211> LENGTH: 20
<212> TYPE: DNA
<213> ORGANISM: Artificial Sequence
<220> FEATURE:
<223> OTHER INFORMATION: ASO-001954-mm3

<400> SEQUENCE: 568

gatttccaaa ttcactttta                                             20


<210> SEQ ID NO 569
<211> LENGTH: 20
<212> TYPE: DNA
<213> ORGANISM: Artificial Sequence
<220> FEATURE:
<223> OTHER INFORMATION: ASO-001954-mm4

<400> SEQUENCE: 569

ggtttccaaa ttcactttta                                             20


<210> SEQ ID NO 570
<211> LENGTH: 20
<212> TYPE: DNA
<213> ORGANISM: Artificial Sequence
<220> FEATURE:
<223> OTHER INFORMATION: ASO-001954-mm5

<400> SEQUENCE: 570

aatttccaga ttcactttta                                             20


<210> SEQ ID NO 571
<211> LENGTH: 20
<212> TYPE: DNA
<213> ORGANISM: Artificial Sequence
<220> FEATURE:
<223> OTHER INFORMATION: ASO-001954-mm6

<400> SEQUENCE: 571

tatttccaag ttcgctttta                                             20
```

<210> SEQ ID NO 572
<211> LENGTH: 16
<212> TYPE: DNA
<213> ORGANISM: Artificial Sequence
<220> FEATURE:
<223> OTHER INFORMATION: SPC-15677-01

<400> SEQUENCE: 572
tccaaattca ctttta 16

<210> SEQ ID NO 573
<211> LENGTH: 20
<212> TYPE: DNA
<213> ORGANISM: Artificial Sequence
<220> FEATURE:
<223> OTHER INFORMATION: SPC-15859-01

<400> SEQUENCE: 573
tatttccaaa ttcactttta 20

<210> SEQ ID NO 574
<211> LENGTH: 20
<212> TYPE: DNA
<213> ORGANISM: Artificial Sequence
<220> FEATURE:
<223> OTHER INFORMATION: SPC-15861-01

<400> SEQUENCE: 574
tatttccaaa ttcactttta 20

<210> SEQ ID NO 575
<211> LENGTH: 20
<212> TYPE: DNA
<213> ORGANISM: Artificial Sequence
<220> FEATURE:
<223> OTHER INFORMATION: SPC-15862-01

<400> SEQUENCE: 575
tatttccaaa ttcactttta 20

<210> SEQ ID NO 576
<211> LENGTH: 20
<212> TYPE: DNA
<213> ORGANISM: Artificial Sequence
<220> FEATURE:
<223> OTHER INFORMATION: SPC-15863-01

<400> SEQUENCE: 576
tatttccaaa ttcactttta 20

<210> SEQ ID NO 577
<211> LENGTH: 20
<212> TYPE: DNA
<213> ORGANISM: Artificial Sequence
<220> FEATURE:
<223> OTHER INFORMATION: SPC-15865-01

<400> SEQUENCE: 577
tatttccaaa ttcactttta 20

<210> SEQ ID NO 578
<211> LENGTH: 20
<212> TYPE: DNA
<213> ORGANISM: Artificial Sequence
<220> FEATURE:
<223> OTHER INFORMATION: SPC-15867-01

<400> SEQUENCE: 578
tatttccaaa ttcactttta 20

<210> SEQ ID NO 579
<211> LENGTH: 20
<212> TYPE: DNA
<213> ORGANISM: Artificial Sequence
<220> FEATURE:
<223> OTHER INFORMATION: SPC-15869-01

<400> SEQUENCE: 579
tatttccaaa ttcactttta 20

<210> SEQ ID NO 580
<211> LENGTH: 20
<212> TYPE: DNA
<213> ORGANISM: Artificial Sequence
<220> FEATURE:
<223> OTHER INFORMATION: SPC-15871-01

<400> SEQUENCE: 580
tatttccaaa ttcactttta 20

<210> SEQ ID NO 581
<211> LENGTH: 20
<212> TYPE: DNA
<213> ORGANISM: Artificial Sequence
<220> FEATURE:
<223> OTHER INFORMATION: SPC-15882-01

<400> SEQUENCE: 581
tatttccaaa ttcactttta 20

<210> SEQ ID NO 582
<211> LENGTH: 20
<212> TYPE: DNA
<213> ORGANISM: Artificial Sequence
<220> FEATURE:
<223> OTHER INFORMATION: SPC-15886-01

<400> SEQUENCE: 582
tatttccaaa ttcactttta 20

<210> SEQ ID NO 583
<211> LENGTH: 20
<212> TYPE: DNA
<213> ORGANISM: Artificial Sequence
<220> FEATURE:
<223> OTHER INFORMATION: SPC-15887-01

<400> SEQUENCE: 583
tatttccaaa ttcactttta 20

<210> SEQ ID NO 584
<211> LENGTH: 20
<212> TYPE: DNA
<213> ORGANISM: Artificial Sequence
<220> FEATURE:
<223> OTHER INFORMATION: SPC-15890-01

<400> SEQUENCE: 584
tatttccaaa ttcactttta 20

<210> SEQ ID NO 585
<211> LENGTH: 20

<212> TYPE: DNA
<213> ORGANISM: Artificial Sequence
<220> FEATURE:
<223> OTHER INFORMATION: SPC-15893-01

<400> SEQUENCE: 585
tatttccaaa ttcactttta 20

<210> SEQ ID NO 586
<211> LENGTH: 20
<212> TYPE: DNA
<213> ORGANISM: Artificial Sequence
<220> FEATURE:
<223> OTHER INFORMATION: ASO-002072

<400> SEQUENCE: 586
ttatttccaa attcactttt 20

<210> SEQ ID NO 587
<211> LENGTH: 20
<212> TYPE: DNA
<213> ORGANISM: Artificial Sequence
<220> FEATURE:
<223> OTHER INFORMATION: ASO-000755

<400> SEQUENCE: 587
ttatttccaa attcactttt 20

<210> SEQ ID NO 588
<211> LENGTH: 20
<212> TYPE: DNA
<213> ORGANISM: Artificial Sequence
<220> FEATURE:
<223> OTHER INFORMATION: ASO-002071

<400> SEQUENCE: 588
ttatttccaa attcactttt 20

<210> SEQ ID NO 589
<211> LENGTH: 20
<212> TYPE: DNA
<213> ORGANISM: Artificial Sequence
<220> FEATURE:
<223> OTHER INFORMATION: ASO-000760

<400> SEQUENCE: 589
ttatttccaa attcactttt 20

<210> SEQ ID NO 590
<211> LENGTH: 20
<212> TYPE: DNA
<213> ORGANISM: Artificial Sequence
<220> FEATURE:
<223> OTHER INFORMATION: ASO-001920

<400> SEQUENCE: 590
ttatttccaa attcactttt 20

<210> SEQ ID NO 591
<211> LENGTH: 20
<212> TYPE: DNA
<213> ORGANISM: Artificial Sequence
<220> FEATURE:
<223> OTHER INFORMATION: ASO-002080

<400> SEQUENCE: 591
ttatttccaa attcactttt 20

<210> SEQ ID NO 592
<211> LENGTH: 20
<212> TYPE: DNA
<213> ORGANISM: Artificial Sequence
<220> FEATURE:
<223> OTHER INFORMATION: ASO-001927

<400> SEQUENCE: 592
ttatttccaa attcactttt 20

<210> SEQ ID NO 593
<211> LENGTH: 20
<212> TYPE: DNA
<213> ORGANISM: Artificial Sequence
<220> FEATURE:
<223> OTHER INFORMATION: ASO-001941

<400> SEQUENCE: 593
ttatttccaa attcactttt 20

<210> SEQ ID NO 594
<211> LENGTH: 20
<212> TYPE: DNA
<213> ORGANISM: Artificial Sequence
<220> FEATURE:
<223> OTHER INFORMATION: ASO-002045

<400> SEQUENCE: 594
ttatttccaa attcactttt 20

<210> SEQ ID NO 595
<211> LENGTH: 20
<212> TYPE: DNA
<213> ORGANISM: Artificial Sequence
<220> FEATURE:
<223> OTHER INFORMATION: ASO-001934

<400> SEQUENCE: 595
ttatttccaa attcactttt 20

<210> SEQ ID NO 596
<211> LENGTH: 20
<212> TYPE: DNA
<213> ORGANISM: Artificial Sequence
<220> FEATURE:
<223> OTHER INFORMATION: ASO-002074

<400> SEQUENCE: 596
ttatttccaa attcactttt 20

<210> SEQ ID NO 597
<211> LENGTH: 20
<212> TYPE: DNA
<213> ORGANISM: Artificial Sequence
<220> FEATURE:
<223> OTHER INFORMATION: ASO-002093

<400> SEQUENCE: 597
ttatttccaa attcactttt 20

<210> SEQ ID NO 598
<211> LENGTH: 20
<212> TYPE: DNA
<213> ORGANISM: Artificial Sequence

<220> FEATURE:
<223> OTHER INFORMATION: ASO-002054

<400> SEQUENCE: 598
ttatttccaa attcactttt 20

<210> SEQ ID NO 599
<211> LENGTH: 20
<212> TYPE: DNA
<213> ORGANISM: Artificial Sequence
<220> FEATURE:
<223> OTHER INFORMATION: ASO-002091

<400> SEQUENCE: 599
ttatttccaa attcactttt 20

<210> SEQ ID NO 600
<211> LENGTH: 20
<212> TYPE: DNA
<213> ORGANISM: Artificial Sequence
<220> FEATURE:
<223> OTHER INFORMATION: ASO-002064

<400> SEQUENCE: 600
ttatttccaa attcactttt 20

<210> SEQ ID NO 601
<211> LENGTH: 20
<212> TYPE: DNA
<213> ORGANISM: Artificial Sequence
<220> FEATURE:
<223> OTHER INFORMATION: ASO-002066

<400> SEQUENCE: 601
ttatttccaa attcactttt 20

<210> SEQ ID NO 602
<211> LENGTH: 20
<212> TYPE: DNA
<213> ORGANISM: Artificial Sequence
<220> FEATURE:
<223> OTHER INFORMATION: ASO-002044

<400> SEQUENCE: 602
ttatttccaa attcactttt 20

<210> SEQ ID NO 603
<211> LENGTH: 20
<212> TYPE: DNA
<213> ORGANISM: Artificial Sequence
<220> FEATURE:
<223> OTHER INFORMATION: ASO-002047

<400> SEQUENCE: 603
ttatttccaa attcactttt 20

<210> SEQ ID NO 604
<211> LENGTH: 20
<212> TYPE: DNA
<213> ORGANISM: Artificial Sequence
<220> FEATURE:
<223> OTHER INFORMATION: ASO-002046

<400> SEQUENCE: 604
ttatttccaa attcactttt 20

<210> SEQ ID NO 605
<211> LENGTH: 20
<212> TYPE: DNA
<213> ORGANISM: Artificial Sequence
<220> FEATURE:
<223> OTHER INFORMATION: ASO-000765

<400> SEQUENCE: 605
ttatttccaa attcactttt 20

<210> SEQ ID NO 606
<211> LENGTH: 20
<212> TYPE: DNA
<213> ORGANISM: Artificial Sequence
<220> FEATURE:
<223> OTHER INFORMATION: ASO-000770

<400> SEQUENCE: 606
ttatttccaa attcactttt 20

<210> SEQ ID NO 607
<211> LENGTH: 17
<212> TYPE: DNA
<213> ORGANISM: Artificial Sequence
<220> FEATURE:
<223> OTHER INFORMATION: 17-18-19mer-12

<400> SEQUENCE: 607
tttccaaatt cactttt 17

<210> SEQ ID NO 608
<211> LENGTH: 17
<212> TYPE: DNA
<213> ORGANISM: Artificial Sequence
<220> FEATURE:
<223> OTHER INFORMATION: 17-18-19mer-15

<400> SEQUENCE: 608
tttccaaatt cactttt 17

<210> SEQ ID NO 609
<211> LENGTH: 18
<212> TYPE: DNA
<213> ORGANISM: Artificial Sequence
<220> FEATURE:
<223> OTHER INFORMATION: 17-18-19mer-18

<400> SEQUENCE: 609
atttccaaat tcactttt 18

<210> SEQ ID NO 610
<211> LENGTH: 18
<212> TYPE: DNA
<213> ORGANISM: Artificial Sequence
<220> FEATURE:
<223> OTHER INFORMATION: 17-18-19mer-24

<400> SEQUENCE: 610
atttccaaat tcactttt 18

<210> SEQ ID NO 611
<211> LENGTH: 17
<212> TYPE: DNA
<213> ORGANISM: Artificial Sequence
<220> FEATURE:
<223> OTHER INFORMATION: 17-18-19mer-3

<400> SEQUENCE: 611
tttccaaatt cactttt 17

<210> SEQ ID NO 612
<211> LENGTH: 18
<212> TYPE: DNA
<213> ORGANISM: Artificial Sequence
<220> FEATURE:
<223> OTHER INFORMATION: 17-18-19mer-30

<400> SEQUENCE: 612
atttccaaat tcactttt 18

<210> SEQ ID NO 613
<211> LENGTH: 18
<212> TYPE: DNA
<213> ORGANISM: Artificial Sequence
<220> FEATURE:
<223> OTHER INFORMATION: 17-18-19mer-36

<400> SEQUENCE: 613
atttccaaat tcactttt 18

<210> SEQ ID NO 614
<211> LENGTH: 18
<212> TYPE: DNA
<213> ORGANISM: Artificial Sequence
<220> FEATURE:
<223> OTHER INFORMATION: 17-18-19mer-42

<400> SEQUENCE: 614
atttccaaat tcactttt 18

<210> SEQ ID NO 615
<211> LENGTH: 19
<212> TYPE: DNA
<213> ORGANISM: Artificial Sequence
<220> FEATURE:
<223> OTHER INFORMATION: 17-18-19mer-48

<400> SEQUENCE: 615
tatttccaaa ttcactttt 19

<210> SEQ ID NO 616
<211> LENGTH: 19
<212> TYPE: DNA
<213> ORGANISM: Artificial Sequence
<220> FEATURE:
<223> OTHER INFORMATION: 17-18-19mer-54

<400> SEQUENCE: 616
tatttccaaa ttcactttt 19

<210> SEQ ID NO 617
<211> LENGTH: 17
<212> TYPE: DNA
<213> ORGANISM: Artificial Sequence
<220> FEATURE:
<223> OTHER INFORMATION: 17-18-19mer-6

<400> SEQUENCE: 617
tttccaaatt cactttt 17

<210> SEQ ID NO 618

<211> LENGTH: 19
<212> TYPE: DNA
<213> ORGANISM: Artificial Sequence
<220> FEATURE:
<223> OTHER INFORMATION: 17-18-19mer-60

<400> SEQUENCE: 618
tatttccaaa ttcactttt 19

<210> SEQ ID NO 619
<211> LENGTH: 19
<212> TYPE: DNA
<213> ORGANISM: Artificial Sequence
<220> FEATURE:
<223> OTHER INFORMATION: 17-18-19mer-66

<400> SEQUENCE: 619
tatttccaaa ttcactttt 19

<210> SEQ ID NO 620
<211> LENGTH: 19
<212> TYPE: DNA
<213> ORGANISM: Artificial Sequence
<220> FEATURE:
<223> OTHER INFORMATION: 17-18-19mer-72

<400> SEQUENCE: 620
tatttccaaa ttcactttt 19

<210> SEQ ID NO 621
<211> LENGTH: 17
<212> TYPE: DNA
<213> ORGANISM: Artificial Sequence
<220> FEATURE:
<223> OTHER INFORMATION: 17-18-19mer-9

<400> SEQUENCE: 621
tttccaaatt cactttt 17

<210> SEQ ID NO 622
<211> LENGTH: 20
<212> TYPE: DNA
<213> ORGANISM: Artificial Sequence
<220> FEATURE:
<223> OTHER INFORMATION: ASO-001941-mm1

<400> SEQUENCE: 622
atatttccaa attcactttt 20

<210> SEQ ID NO 623
<211> LENGTH: 20
<212> TYPE: DNA
<213> ORGANISM: Artificial Sequence
<220> FEATURE:
<223> OTHER INFORMATION: ASO-001941-mm2

<400> SEQUENCE: 623
ttatttccaa attcacttta 20

<210> SEQ ID NO 624
<211> LENGTH: 20
<212> TYPE: DNA
<213> ORGANISM: Artificial Sequence
<220> FEATURE:
<223> OTHER INFORMATION: ASO-001941-mm3

<400> SEQUENCE: 624
ttatttccaa attcactttg 20

<210> SEQ ID NO 625
<211> LENGTH: 20
<212> TYPE: DNA
<213> ORGANISM: Artificial Sequence
<220> FEATURE:
<223> OTHER INFORMATION: ASO-001941-mm4

<400> SEQUENCE: 625
atatttccag attcactttt 20

<210> SEQ ID NO 626
<211> LENGTH: 20
<212> TYPE: DNA
<213> ORGANISM: Artificial Sequence
<220> FEATURE:
<223> OTHER INFORMATION: ASO-001941-mm5

<400> SEQUENCE: 626
ttatttccaa gttcactttc 20

<210> SEQ ID NO 627
<211> LENGTH: 20
<212> TYPE: DNA
<213> ORGANISM: Artificial Sequence
<220> FEATURE:
<223> OTHER INFORMATION: ASO-001941-mm6

<400> SEQUENCE: 627
ttatttccag attcgctttt 20

<210> SEQ ID NO 628
<211> LENGTH: 16
<212> TYPE: DNA
<213> ORGANISM: Artificial Sequence
<220> FEATURE:
<223> OTHER INFORMATION: SPC-15676-01

<400> SEQUENCE: 628
ttccaaattc actttt 16

<210> SEQ ID NO 629
<211> LENGTH: 20
<212> TYPE: DNA
<213> ORGANISM: Artificial Sequence
<220> FEATURE:
<223> OTHER INFORMATION: SPC-15866-01

<400> SEQUENCE: 629
ttatttccaa attcactttt 20

<210> SEQ ID NO 630
<211> LENGTH: 20
<212> TYPE: DNA
<213> ORGANISM: Artificial Sequence
<220> FEATURE:
<223> OTHER INFORMATION: SPC-15870-01

<400> SEQUENCE: 630
ttatttccaa attcactttt 20

<210> SEQ ID NO 631
<211> LENGTH: 20
<212> TYPE: DNA

<213> ORGANISM: Artificial Sequence
<220> FEATURE:
<223> OTHER INFORMATION: SPC-15875-01

<400> SEQUENCE: 631
ttatttccaa attcactttt 20

<210> SEQ ID NO 632
<211> LENGTH: 20
<212> TYPE: DNA
<213> ORGANISM: Artificial Sequence
<220> FEATURE:
<223> OTHER INFORMATION: SPC-15876-01

<400> SEQUENCE: 632
ttatttccaa attcactttt 20

<210> SEQ ID NO 633
<211> LENGTH: 20
<212> TYPE: DNA
<213> ORGANISM: Artificial Sequence
<220> FEATURE:
<223> OTHER INFORMATION: SPC-15877-01

<400> SEQUENCE: 633
ttatttccaa attcactttt 20

<210> SEQ ID NO 634
<211> LENGTH: 20
<212> TYPE: DNA
<213> ORGANISM: Artificial Sequence
<220> FEATURE:
<223> OTHER INFORMATION: SPC-15881-01

<400> SEQUENCE: 634
ttatttccaa attcactttt 20

<210> SEQ ID NO 635
<211> LENGTH: 20
<212> TYPE: DNA
<213> ORGANISM: Artificial Sequence
<220> FEATURE:
<223> OTHER INFORMATION: SPC-15884-01

<400> SEQUENCE: 635
ttatttccaa attcactttt 20

<210> SEQ ID NO 636
<211> LENGTH: 20
<212> TYPE: DNA
<213> ORGANISM: Artificial Sequence
<220> FEATURE:
<223> OTHER INFORMATION: SPC-15885-01

<400> SEQUENCE: 636
ttatttccaa attcactttt 20

<210> SEQ ID NO 637
<211> LENGTH: 20
<212> TYPE: DNA
<213> ORGANISM: Artificial Sequence
<220> FEATURE:
<223> OTHER INFORMATION: SPC-15889-01

<400> SEQUENCE: 637
ttatttccaa attcactttt 20

<210> SEQ ID NO 638
<211> LENGTH: 20
<212> TYPE: DNA
<213> ORGANISM: Artificial Sequence
<220> FEATURE:
<223> OTHER INFORMATION: SPC-15891-01

<400> SEQUENCE: 638
ttatttccaa attcactttt 20

<210> SEQ ID NO 639
<211> LENGTH: 20
<212> TYPE: DNA
<213> ORGANISM: Artificial Sequence
<220> FEATURE:
<223> OTHER INFORMATION: SPC-15892-01

<400> SEQUENCE: 639
ttatttccaa attcactttt 20

<210> SEQ ID NO 640
<211> LENGTH: 20
<212> TYPE: DNA
<213> ORGANISM: Artificial Sequence
<220> FEATURE:
<223> OTHER INFORMATION: SPC-15894-01

<400> SEQUENCE: 640
ttatttccaa attcactttt 20

<210> SEQ ID NO 641
<211> LENGTH: 20
<212> TYPE: DNA
<213> ORGANISM: Artificial Sequence
<220> FEATURE:
<223> OTHER INFORMATION: SPC-15895-01

<400> SEQUENCE: 641
ttatttccaa attcactttt 20

<210> SEQ ID NO 642
<211> LENGTH: 20
<212> TYPE: DNA
<213> ORGANISM: Artificial Sequence
<220> FEATURE:
<223> OTHER INFORMATION: SPC-15896-01

<400> SEQUENCE: 642
ttatttccaa attcactttt 20

<210> SEQ ID NO 643
<211> LENGTH: 25
<212> TYPE: DNA
<213> ORGANISM: Artificial Sequence
<220> FEATURE:
<223> OTHER INFORMATION: ASO-002020

<400> SEQUENCE: 643
actttatttc caaattcact tttac 25

<210> SEQ ID NO 644
<211> LENGTH: 20
<212> TYPE: DNA
<213> ORGANISM: Artificial Sequence
<220> FEATURE:

<223> OTHER INFORMATION: ASO-000756

<400> SEQUENCE: 644
tttatttcca aattcacttt 20

<210> SEQ ID NO 645
<211> LENGTH: 20
<212> TYPE: DNA
<213> ORGANISM: Artificial Sequence
<220> FEATURE:
<223> OTHER INFORMATION: ASO-001967

<400> SEQUENCE: 645
tttatttcca aattcacttt 20

<210> SEQ ID NO 646
<211> LENGTH: 20
<212> TYPE: DNA
<213> ORGANISM: Artificial Sequence
<220> FEATURE:
<223> OTHER INFORMATION: ASO-001955

<400> SEQUENCE: 646
tttatttcca aattcacttt 20

<210> SEQ ID NO 647
<211> LENGTH: 20
<212> TYPE: DNA
<213> ORGANISM: Artificial Sequence
<220> FEATURE:
<223> OTHER INFORMATION: ASO-001948

<400> SEQUENCE: 647
tttatttcca aattcacttt 20

<210> SEQ ID NO 648
<211> LENGTH: 25
<212> TYPE: DNA
<213> ORGANISM: Artificial Sequence
<220> FEATURE:
<223> OTHER INFORMATION: ASO-002086

<400> SEQUENCE: 648
actttatttc caaattcact tttac 25

<210> SEQ ID NO 649
<211> LENGTH: 25
<212> TYPE: DNA
<213> ORGANISM: Artificial Sequence
<220> FEATURE:
<223> OTHER INFORMATION: ASO-002029

<400> SEQUENCE: 649
actttatttc caaattcact tttac 25

<210> SEQ ID NO 650
<211> LENGTH: 20
<212> TYPE: DNA
<213> ORGANISM: Artificial Sequence
<220> FEATURE:
<223> OTHER INFORMATION: ASO-001961

<400> SEQUENCE: 650
tttatttcca aattcacttt 20

<210> SEQ ID NO 651
<211> LENGTH: 25
<212> TYPE: DNA
<213> ORGANISM: Artificial Sequence
<220> FEATURE:
<223> OTHER INFORMATION: ASO-002095

<400> SEQUENCE: 651
actttatttc caaattcact tttac 25

<210> SEQ ID NO 652
<211> LENGTH: 25
<212> TYPE: DNA
<213> ORGANISM: Artificial Sequence
<220> FEATURE:
<223> OTHER INFORMATION: ASO-002059

<400> SEQUENCE: 652
actttatttc caaattcact tttac 25

<210> SEQ ID NO 653
<211> LENGTH: 25
<212> TYPE: DNA
<213> ORGANISM: Artificial Sequence
<220> FEATURE:
<223> OTHER INFORMATION: ASO-002077

<400> SEQUENCE: 653
actttatttc caaattcact tttac 25

<210> SEQ ID NO 654
<211> LENGTH: 25
<212> TYPE: DNA
<213> ORGANISM: Artificial Sequence
<220> FEATURE:
<223> OTHER INFORMATION: ASO-002021

<400> SEQUENCE: 654
actttatttc caaattcact tttac 25

<210> SEQ ID NO 655
<211> LENGTH: 20
<212> TYPE: DNA
<213> ORGANISM: Artificial Sequence
<220> FEATURE:
<223> OTHER INFORMATION: ASO-000761

<400> SEQUENCE: 655
tttatttcca aattcacttt 20

<210> SEQ ID NO 656
<211> LENGTH: 25
<212> TYPE: DNA
<213> ORGANISM: Artificial Sequence
<220> FEATURE:
<223> OTHER INFORMATION: ASO-002068

<400> SEQUENCE: 656
actttatttc caaattcact tttac 25

<210> SEQ ID NO 657
<211> LENGTH: 20
<212> TYPE: DNA
<213> ORGANISM: Artificial Sequence
<220> FEATURE:
<223> OTHER INFORMATION: ASO-000766

<400> SEQUENCE: 657
tttatttcca aattcacttt 20

<210> SEQ ID NO 658
<211> LENGTH: 20
<212> TYPE: DNA
<213> ORGANISM: Artificial Sequence
<220> FEATURE:
<223> OTHER INFORMATION: ASO-000771

<400> SEQUENCE: 658
tttatttcca aattcacttt 20

<210> SEQ ID NO 659
<211> LENGTH: 18
<212> TYPE: DNA
<213> ORGANISM: Artificial Sequence
<220> FEATURE:
<223> OTHER INFORMATION: 17-18-19mer-19

<400> SEQUENCE: 659
tatttccaaa ttcacttt 18

<210> SEQ ID NO 660
<211> LENGTH: 18
<212> TYPE: DNA
<213> ORGANISM: Artificial Sequence
<220> FEATURE:
<223> OTHER INFORMATION: 17-18-19mer-25

<400> SEQUENCE: 660
tatttccaaa ttcacttt 18

<210> SEQ ID NO 661
<211> LENGTH: 18
<212> TYPE: DNA
<213> ORGANISM: Artificial Sequence
<220> FEATURE:
<223> OTHER INFORMATION: 17-18-19mer-31

<400> SEQUENCE: 661
tatttccaaa ttcacttt 18

<210> SEQ ID NO 662
<211> LENGTH: 18
<212> TYPE: DNA
<213> ORGANISM: Artificial Sequence
<220> FEATURE:
<223> OTHER INFORMATION: 17-18-19mer-37

<400> SEQUENCE: 662
tatttccaaa ttcacttt 18

<210> SEQ ID NO 663
<211> LENGTH: 18
<212> TYPE: DNA
<213> ORGANISM: Artificial Sequence
<220> FEATURE:
<223> OTHER INFORMATION: 17-18-19mer-43

<400> SEQUENCE: 663
tatttccaaa ttcacttt 18

<210> SEQ ID NO 664
<211> LENGTH: 19

<212> TYPE: DNA
<213> ORGANISM: Artificial Sequence
<220> FEATURE:
<223> OTHER INFORMATION: 17-18-19mer-49

<400> SEQUENCE: 664
ttatttccaa attcacttt 19

<210> SEQ ID NO 665
<211> LENGTH: 19
<212> TYPE: DNA
<213> ORGANISM: Artificial Sequence
<220> FEATURE:
<223> OTHER INFORMATION: 17-18-19mer-55

<400> SEQUENCE: 665
ttatttccaa attcacttt 19

<210> SEQ ID NO 666
<211> LENGTH: 19
<212> TYPE: DNA
<213> ORGANISM: Artificial Sequence
<220> FEATURE:
<223> OTHER INFORMATION: 17-18-19mer-61

<400> SEQUENCE: 666
ttatttccaa attcacttt 19

<210> SEQ ID NO 667
<211> LENGTH: 19
<212> TYPE: DNA
<213> ORGANISM: Artificial Sequence
<220> FEATURE:
<223> OTHER INFORMATION: 17-18-19mer-67

<400> SEQUENCE: 667
ttatttccaa attcacttt 19

<210> SEQ ID NO 668
<211> LENGTH: 19
<212> TYPE: DNA
<213> ORGANISM: Artificial Sequence
<220> FEATURE:
<223> OTHER INFORMATION: 17-18-19mer-73

<400> SEQUENCE: 668
ttatttccaa attcacttt 19

<210> SEQ ID NO 669
<211> LENGTH: 20
<212> TYPE: DNA
<213> ORGANISM: Artificial Sequence
<220> FEATURE:
<223> OTHER INFORMATION: ASO-001967-mm1

<400> SEQUENCE: 669
attatttcca aattcacttt 20

<210> SEQ ID NO 670
<211> LENGTH: 20
<212> TYPE: DNA
<213> ORGANISM: Artificial Sequence
<220> FEATURE:
<223> OTHER INFORMATION: ASO-001967-mm2

<400> SEQUENCE: 670
tttatttcca agttcacttt 20

<210> SEQ ID NO 671
<211> LENGTH: 20
<212> TYPE: DNA
<213> ORGANISM: Artificial Sequence
<220> FEATURE:
<223> OTHER INFORMATION: ASO-001967-mm3

<400> SEQUENCE: 671
gttatttcca aattcacttt 20

<210> SEQ ID NO 672
<211> LENGTH: 20
<212> TYPE: DNA
<213> ORGANISM: Artificial Sequence
<220> FEATURE:
<223> OTHER INFORMATION: ASO-001967-mm4

<400> SEQUENCE: 672
attatttcca gattcacttt 20

<210> SEQ ID NO 673
<211> LENGTH: 20
<212> TYPE: DNA
<213> ORGANISM: Artificial Sequence
<220> FEATURE:
<223> OTHER INFORMATION: ASO-001967-mm5

<400> SEQUENCE: 673
tttatttcca ggttcacttt 20

<210> SEQ ID NO 674
<211> LENGTH: 20
<212> TYPE: DNA
<213> ORGANISM: Artificial Sequence
<220> FEATURE:
<223> OTHER INFORMATION: ASO-001967-mm6

<400> SEQUENCE: 674
cttatttcca agttcacttt 20

<210> SEQ ID NO 675
<211> LENGTH: 16
<212> TYPE: DNA
<213> ORGANISM: Artificial Sequence
<220> FEATURE:
<223> OTHER INFORMATION: SPC-15675-01

<400> SEQUENCE: 675
tttccaaatt cacttt 16

<210> SEQ ID NO 676
<211> LENGTH: 20
<212> TYPE: DNA
<213> ORGANISM: Artificial Sequence
<220> FEATURE:
<223> OTHER INFORMATION: ASO-002006

<400> SEQUENCE: 676
ctttatttcc aaattcactt 20

<210> SEQ ID NO 677
<211> LENGTH: 20
<212> TYPE: DNA
<213> ORGANISM: Artificial Sequence

<220> FEATURE:
<223> OTHER INFORMATION: ASO-000757

<400> SEQUENCE: 677
ctttatttcc aaattcactt 20

<210> SEQ ID NO 678
<211> LENGTH: 20
<212> TYPE: DNA
<213> ORGANISM: Artificial Sequence
<220> FEATURE:
<223> OTHER INFORMATION: ASO-002017

<400> SEQUENCE: 678
ctttatttcc aaattcactt 20

<210> SEQ ID NO 679
<211> LENGTH: 20
<212> TYPE: DNA
<213> ORGANISM: Artificial Sequence
<220> FEATURE:
<223> OTHER INFORMATION: ASO-001928

<400> SEQUENCE: 679
ctttatttcc aaattcactt 20

<210> SEQ ID NO 680
<211> LENGTH: 21
<212> TYPE: DNA
<213> ORGANISM: Artificial Sequence
<220> FEATURE:
<223> OTHER INFORMATION: ASO-001968

<400> SEQUENCE: 680
actttatttc caaattcact t 21

<210> SEQ ID NO 681
<211> LENGTH: 20
<212> TYPE: DNA
<213> ORGANISM: Artificial Sequence
<220> FEATURE:
<223> OTHER INFORMATION: ASO-001921

<400> SEQUENCE: 681
ctttatttcc aaattcactt 20

<210> SEQ ID NO 682
<211> LENGTH: 20
<212> TYPE: DNA
<213> ORGANISM: Artificial Sequence
<220> FEATURE:
<223> OTHER INFORMATION: ASO-001989

<400> SEQUENCE: 682
ctttatttcc aaattcactt 20

<210> SEQ ID NO 683
<211> LENGTH: 20
<212> TYPE: DNA
<213> ORGANISM: Artificial Sequence
<220> FEATURE:
<223> OTHER INFORMATION: ASO-001942

<400> SEQUENCE: 683
ctttatttcc aaattcactt 20

<210> SEQ ID NO 684
<211> LENGTH: 15
<212> TYPE: DNA
<213> ORGANISM: Artificial Sequence
<220> FEATURE:
<223> OTHER INFORMATION: ASO-000128

<400> SEQUENCE: 684
tttccaaatt cactt 15

<210> SEQ ID NO 685
<211> LENGTH: 20
<212> TYPE: DNA
<213> ORGANISM: Artificial Sequence
<220> FEATURE:
<223> OTHER INFORMATION: ASO-001935

<400> SEQUENCE: 685
ctttatttcc aaattcactt 20

<210> SEQ ID NO 686
<211> LENGTH: 16
<212> TYPE: DNA
<213> ORGANISM: Artificial Sequence
<220> FEATURE:
<223> OTHER INFORMATION: ASO-000013

<400> SEQUENCE: 686
atttccaaat tcactt 16

<210> SEQ ID NO 687
<211> LENGTH: 20
<212> TYPE: DNA
<213> ORGANISM: Artificial Sequence
<220> FEATURE:
<223> OTHER INFORMATION: ASO-002002

<400> SEQUENCE: 687
ctttatttcc aaattcactt 20

<210> SEQ ID NO 688
<211> LENGTH: 20
<212> TYPE: DNA
<213> ORGANISM: Artificial Sequence
<220> FEATURE:
<223> OTHER INFORMATION: ASO-000762

<400> SEQUENCE: 688
ctttatttcc aaattcactt 20

<210> SEQ ID NO 689
<211> LENGTH: 20
<212> TYPE: DNA
<213> ORGANISM: Artificial Sequence
<220> FEATURE:
<223> OTHER INFORMATION: ASO-002010

<400> SEQUENCE: 689
ctttatttcc aaattcactt 20

<210> SEQ ID NO 690
<211> LENGTH: 20
<212> TYPE: DNA
<213> ORGANISM: Artificial Sequence
<220> FEATURE:
<223> OTHER INFORMATION: ASO-002005

<400> SEQUENCE: 690
ctttatttcc aaattcactt 20

<210> SEQ ID NO 691
<211> LENGTH: 20
<212> TYPE: DNA
<213> ORGANISM: Artificial Sequence
<220> FEATURE:
<223> OTHER INFORMATION: ASO-001998

<400> SEQUENCE: 691
ctttatttcc aaattcactt 20

<210> SEQ ID NO 692
<211> LENGTH: 20
<212> TYPE: DNA
<213> ORGANISM: Artificial Sequence
<220> FEATURE:
<223> OTHER INFORMATION: ASO-002001

<400> SEQUENCE: 692
ctttatttcc aaattcactt 20

<210> SEQ ID NO 693
<211> LENGTH: 20
<212> TYPE: DNA
<213> ORGANISM: Artificial Sequence
<220> FEATURE:
<223> OTHER INFORMATION: ASO-001994

<400> SEQUENCE: 693
ctttatttcc aaattcactt 20

<210> SEQ ID NO 694
<211> LENGTH: 20
<212> TYPE: DNA
<213> ORGANISM: Artificial Sequence
<220> FEATURE:
<223> OTHER INFORMATION: ASO-002013

<400> SEQUENCE: 694
ctttatttcc aaattcactt 20

<210> SEQ ID NO 695
<211> LENGTH: 20
<212> TYPE: DNA
<213> ORGANISM: Artificial Sequence
<220> FEATURE:
<223> OTHER INFORMATION: ASO-002009

<400> SEQUENCE: 695
ctttatttcc aaattcactt 20

<210> SEQ ID NO 696
<211> LENGTH: 20
<212> TYPE: DNA
<213> ORGANISM: Artificial Sequence
<220> FEATURE:
<223> OTHER INFORMATION: ASO-000767

<400> SEQUENCE: 696
ctttatttcc aaattcactt 20

<210> SEQ ID NO 697

<211> LENGTH: 20
<212> TYPE: DNA
<213> ORGANISM: Artificial Sequence
<220> FEATURE:
<223> OTHER INFORMATION: ASO-000772

<400> SEQUENCE: 697
ctttatttcc aaattcactt 20

<210> SEQ ID NO 698
<211> LENGTH: 20
<212> TYPE: DNA
<213> ORGANISM: Artificial Sequence
<220> FEATURE:
<223> OTHER INFORMATION: BMT-214296

<400> SEQUENCE: 698
ctttacttcc aaattcactt 20

<210> SEQ ID NO 699
<211> LENGTH: 16
<212> TYPE: DNA
<213> ORGANISM: Artificial Sequence
<220> FEATURE:
<223> OTHER INFORMATION: ASO-000013-mm1

<400> SEQUENCE: 699
gtttccaaat tcactt 16

<210> SEQ ID NO 700
<211> LENGTH: 16
<212> TYPE: DNA
<213> ORGANISM: Artificial Sequence
<220> FEATURE:
<223> OTHER INFORMATION: ASO-000013-mm2

<400> SEQUENCE: 700
atttccaagt tcactt 16

<210> SEQ ID NO 701
<211> LENGTH: 16
<212> TYPE: DNA
<213> ORGANISM: Artificial Sequence
<220> FEATURE:
<223> OTHER INFORMATION: ASO-000013-mm3

<400> SEQUENCE: 701
atttccgaat tcactt 16

<210> SEQ ID NO 702
<211> LENGTH: 16
<212> TYPE: DNA
<213> ORGANISM: Artificial Sequence
<220> FEATURE:
<223> OTHER INFORMATION: ASO-000013-mm4

<400> SEQUENCE: 702
gtttccagat tcactt 16

<210> SEQ ID NO 703
<211> LENGTH: 16
<212> TYPE: DNA
<213> ORGANISM: Artificial Sequence
<220> FEATURE:
<223> OTHER INFORMATION: ASO-000013-mm5

<400> SEQUENCE: 703
gtttccaaat tcacta 16

<210> SEQ ID NO 704
<211> LENGTH: 16
<212> TYPE: DNA
<213> ORGANISM: Artificial Sequence
<220> FEATURE:
<223> OTHER INFORMATION: ASO-000013-mm6

<400> SEQUENCE: 704
atttccagat tcactc 16

<210> SEQ ID NO 705
<211> LENGTH: 16
<212> TYPE: DNA
<213> ORGANISM: Artificial Sequence
<220> FEATURE:
<223> OTHER INFORMATION: ASO-000898

<400> SEQUENCE: 705
atttccaaat tcactt 16

<210> SEQ ID NO 706
<211> LENGTH: 20
<212> TYPE: DNA
<213> ORGANISM: Artificial Sequence
<220> FEATURE:
<223> OTHER INFORMATION: ASO-001942-mm1

<400> SEQUENCE: 706
ctttatttcc agattcactt 20

<210> SEQ ID NO 707
<211> LENGTH: 20
<212> TYPE: DNA
<213> ORGANISM: Artificial Sequence
<220> FEATURE:
<223> OTHER INFORMATION: ASO-001942-mm2

<400> SEQUENCE: 707
ctttatttcc aaattcactg 20

<210> SEQ ID NO 708
<211> LENGTH: 20
<212> TYPE: DNA
<213> ORGANISM: Artificial Sequence
<220> FEATURE:
<223> OTHER INFORMATION: ASO-001942-mm3

<400> SEQUENCE: 708
ctttatttcc aaattcgctt 20

<210> SEQ ID NO 709
<211> LENGTH: 20
<212> TYPE: DNA
<213> ORGANISM: Artificial Sequence
<220> FEATURE:
<223> OTHER INFORMATION: ASO-001942-mm4

<400> SEQUENCE: 709
ctttatttcc agattcacta 20

<210> SEQ ID NO 710
<211> LENGTH: 20
<212> TYPE: DNA

<213> ORGANISM: Artificial Sequence
<220> FEATURE:
<223> OTHER INFORMATION: ASO-001942-mm5

<400> SEQUENCE: 710
ctttatttcc aggttcactt 20

<210> SEQ ID NO 711
<211> LENGTH: 20
<212> TYPE: DNA
<213> ORGANISM: Artificial Sequence
<220> FEATURE:
<223> OTHER INFORMATION: ASO-001942-mm6

<400> SEQUENCE: 711
ctttatttcc gagttcactt 20

<210> SEQ ID NO 712
<211> LENGTH: 16
<212> TYPE: DNA
<213> ORGANISM: Artificial Sequence
<220> FEATURE:
<223> OTHER INFORMATION: SPC-15674-01

<400> SEQUENCE: 712
atttccaaat tcactt 16

<210> SEQ ID NO 713
<211> LENGTH: 19
<212> TYPE: DNA
<213> ORGANISM: Artificial Sequence
<220> FEATURE:
<223> OTHER INFORMATION: ASO-002004

<400> SEQUENCE: 713
ctttatttcc aaattcact 19

<210> SEQ ID NO 714
<211> LENGTH: 19
<212> TYPE: DNA
<213> ORGANISM: Artificial Sequence
<220> FEATURE:
<223> OTHER INFORMATION: ASO-002012

<400> SEQUENCE: 714
ctttatttcc aaattcact 19

<210> SEQ ID NO 715
<211> LENGTH: 20
<212> TYPE: DNA
<213> ORGANISM: Artificial Sequence
<220> FEATURE:
<223> OTHER INFORMATION: ASO-001962

<400> SEQUENCE: 715
actttatttc caaattcact 20

<210> SEQ ID NO 716
<211> LENGTH: 20
<212> TYPE: DNA
<213> ORGANISM: Artificial Sequence
<220> FEATURE:
<223> OTHER INFORMATION: ASO-001956

<400> SEQUENCE: 716
actttatttc caaattcact 20

<210> SEQ ID NO 717
<211> LENGTH: 20
<212> TYPE: DNA
<213> ORGANISM: Artificial Sequence
<220> FEATURE:
<223> OTHER INFORMATION: ASO-001949

<400> SEQUENCE: 717
actttatttc caaattcact 20

<210> SEQ ID NO 718
<211> LENGTH: 19
<212> TYPE: DNA
<213> ORGANISM: Artificial Sequence
<220> FEATURE:
<223> OTHER INFORMATION: ASO-001987

<400> SEQUENCE: 718
ctttatttcc aaattcact 19

<210> SEQ ID NO 719
<211> LENGTH: 19
<212> TYPE: DNA
<213> ORGANISM: Artificial Sequence
<220> FEATURE:
<223> OTHER INFORMATION: ASO-001991

<400> SEQUENCE: 719
ctttatttcc aaattcact 19

<210> SEQ ID NO 720
<211> LENGTH: 19
<212> TYPE: DNA
<213> ORGANISM: Artificial Sequence
<220> FEATURE:
<223> OTHER INFORMATION: ASO-001995

<400> SEQUENCE: 720
ctttatttcc aaattcact 19

<210> SEQ ID NO 721
<211> LENGTH: 19
<212> TYPE: DNA
<213> ORGANISM: Artificial Sequence
<220> FEATURE:
<223> OTHER INFORMATION: ASO-001992

<400> SEQUENCE: 721
ctttatttcc aaattcact 19

<210> SEQ ID NO 722
<211> LENGTH: 19
<212> TYPE: DNA
<213> ORGANISM: Artificial Sequence
<220> FEATURE:
<223> OTHER INFORMATION: ASO-002000

<400> SEQUENCE: 722
ctttatttcc aaattcact 19

<210> SEQ ID NO 723
<211> LENGTH: 19
<212> TYPE: DNA
<213> ORGANISM: Artificial Sequence
<220> FEATURE:

<223> OTHER INFORMATION: ASO-001996

<400> SEQUENCE: 723
ctttatttcc aaattcact 19

<210> SEQ ID NO 724
<211> LENGTH: 19
<212> TYPE: DNA
<213> ORGANISM: Artificial Sequence
<220> FEATURE:
<223> OTHER INFORMATION: ASO-002008

<400> SEQUENCE: 724
ctttatttcc aaattcact 19

<210> SEQ ID NO 725
<211> LENGTH: 19
<212> TYPE: DNA
<213> ORGANISM: Artificial Sequence
<220> FEATURE:
<223> OTHER INFORMATION: ASO-002015

<400> SEQUENCE: 725
ctttatttcc aaattcact 19

<210> SEQ ID NO 726
<211> LENGTH: 19
<212> TYPE: DNA
<213> ORGANISM: Artificial Sequence
<220> FEATURE:
<223> OTHER INFORMATION: ASO-002016

<400> SEQUENCE: 726
ctttatttcc aaattcact 19

<210> SEQ ID NO 727
<211> LENGTH: 19
<212> TYPE: DNA
<213> ORGANISM: Artificial Sequence
<220> FEATURE:
<223> OTHER INFORMATION: ASO-001986

<400> SEQUENCE: 727
ctttatttcc aaattcact 19

<210> SEQ ID NO 728
<211> LENGTH: 19
<212> TYPE: DNA
<213> ORGANISM: Artificial Sequence
<220> FEATURE:
<223> OTHER INFORMATION: 17-18-19mer-50

<400> SEQUENCE: 728
ctttatttcc aaattcact 19

<210> SEQ ID NO 729
<211> LENGTH: 19
<212> TYPE: DNA
<213> ORGANISM: Artificial Sequence
<220> FEATURE:
<223> OTHER INFORMATION: 17-18-19mer-62

<400> SEQUENCE: 729
ctttatttcc aaattcact 19

<210> SEQ ID NO 730
<211> LENGTH: 19
<212> TYPE: DNA
<213> ORGANISM: Artificial Sequence
<220> FEATURE:
<223> OTHER INFORMATION: 17-18-19mer-68

<400> SEQUENCE: 730
ctttatttcc aaattcact 19

<210> SEQ ID NO 731
<211> LENGTH: 19
<212> TYPE: DNA
<213> ORGANISM: Artificial Sequence
<220> FEATURE:
<223> OTHER INFORMATION: 17-18-19mer-74

<400> SEQUENCE: 731
ctttatttcc aaattcact 19

<210> SEQ ID NO 732
<211> LENGTH: 19
<212> TYPE: DNA
<213> ORGANISM: Artificial Sequence
<220> FEATURE:
<223> OTHER INFORMATION: ASO-001995-mm1

<400> SEQUENCE: 732
ctttatttcc agattcact 19

<210> SEQ ID NO 733
<211> LENGTH: 19
<212> TYPE: DNA
<213> ORGANISM: Artificial Sequence
<220> FEATURE:
<223> OTHER INFORMATION: ASO-001995-mm2

<400> SEQUENCE: 733
ctttgtttcc aaattcact 19

<210> SEQ ID NO 734
<211> LENGTH: 19
<212> TYPE: DNA
<213> ORGANISM: Artificial Sequence
<220> FEATURE:
<223> OTHER INFORMATION: ASO-001995-mm3

<400> SEQUENCE: 734
ctttatttcc aaattcacg 19

<210> SEQ ID NO 735
<211> LENGTH: 19
<212> TYPE: DNA
<213> ORGANISM: Artificial Sequence
<220> FEATURE:
<223> OTHER INFORMATION: ASO-001995-mm4

<400> SEQUENCE: 735
ctttgtttcc agattcact 19

<210> SEQ ID NO 736
<211> LENGTH: 19
<212> TYPE: DNA
<213> ORGANISM: Artificial Sequence
<220> FEATURE:
<223> OTHER INFORMATION: ASO-001995-mm5

<400> SEQUENCE: 736
ctttgtttcc aagttcact 19

<210> SEQ ID NO 737
<211> LENGTH: 19
<212> TYPE: DNA
<213> ORGANISM: Artificial Sequence
<220> FEATURE:
<223> OTHER INFORMATION: ASO-001995-mm6

<400> SEQUENCE: 737
ctttatttcc gagttcact 19

<210> SEQ ID NO 738
<211> LENGTH: 16
<212> TYPE: DNA
<213> ORGANISM: Artificial Sequence
<220> FEATURE:
<223> OTHER INFORMATION: SPC-15673-01

<400> SEQUENCE: 738
tatttccaaa ttcact 16

<210> SEQ ID NO 739
<211> LENGTH: 18
<212> TYPE: DNA
<213> ORGANISM: Artificial Sequence
<220> FEATURE:
<223> OTHER INFORMATION: ASO-002003

<400> SEQUENCE: 739
ctttatttcc aaattcac 18

<210> SEQ ID NO 740
<211> LENGTH: 18
<212> TYPE: DNA
<213> ORGANISM: Artificial Sequence
<220> FEATURE:
<223> OTHER INFORMATION: ASO-002007

<400> SEQUENCE: 740
ctttatttcc aaattcac 18

<210> SEQ ID NO 741
<211> LENGTH: 18
<212> TYPE: DNA
<213> ORGANISM: Artificial Sequence
<220> FEATURE:
<223> OTHER INFORMATION: ASO-002011

<400> SEQUENCE: 741
ctttatttcc aaattcac 18

<210> SEQ ID NO 742
<211> LENGTH: 18
<212> TYPE: DNA
<213> ORGANISM: Artificial Sequence
<220> FEATURE:
<223> OTHER INFORMATION: ASO-001988

<400> SEQUENCE: 742
ctttatttcc aaattcac 18

<210> SEQ ID NO 743
<211> LENGTH: 18

<212> TYPE: DNA
<213> ORGANISM: Artificial Sequence
<220> FEATURE:
<223> OTHER INFORMATION: ASO-001999

<400> SEQUENCE: 743
ctttatttcc aaattcac 18

<210> SEQ ID NO 744
<211> LENGTH: 18
<212> TYPE: DNA
<213> ORGANISM: Artificial Sequence
<220> FEATURE:
<223> OTHER INFORMATION: ASO-001993

<400> SEQUENCE: 744
ctttatttcc aaattcac 18

<210> SEQ ID NO 745
<211> LENGTH: 18
<212> TYPE: DNA
<213> ORGANISM: Artificial Sequence
<220> FEATURE:
<223> OTHER INFORMATION: ASO-001997

<400> SEQUENCE: 745
ctttatttcc aaattcac 18

<210> SEQ ID NO 746
<211> LENGTH: 18
<212> TYPE: DNA
<213> ORGANISM: Artificial Sequence
<220> FEATURE:
<223> OTHER INFORMATION: 17-18-19mer-26

<400> SEQUENCE: 746
ctttatttcc aaattcac 18

<210> SEQ ID NO 747
<211> LENGTH: 18
<212> TYPE: DNA
<213> ORGANISM: Artificial Sequence
<220> FEATURE:
<223> OTHER INFORMATION: 17-18-19mer-32

<400> SEQUENCE: 747
ctttatttcc aaattcac 18

<210> SEQ ID NO 748
<211> LENGTH: 18
<212> TYPE: DNA
<213> ORGANISM: Artificial Sequence
<220> FEATURE:
<223> OTHER INFORMATION: 17-18-19mer-44

<400> SEQUENCE: 748
ctttatttcc aaattcac 18

<210> SEQ ID NO 749
<211> LENGTH: 19
<212> TYPE: DNA
<213> ORGANISM: Artificial Sequence
<220> FEATURE:
<223> OTHER INFORMATION: 17-18-19mer-51

<400> SEQUENCE: 749
actttatttc caaattcac 19

<210> SEQ ID NO 750
<211> LENGTH: 19
<212> TYPE: DNA
<213> ORGANISM: Artificial Sequence
<220> FEATURE:
<223> OTHER INFORMATION: 17-18-19mer-57

<400> SEQUENCE: 750
actttatttc caaattcac 19

<210> SEQ ID NO 751
<211> LENGTH: 19
<212> TYPE: DNA
<213> ORGANISM: Artificial Sequence
<220> FEATURE:
<223> OTHER INFORMATION: 17-18-19mer-63

<400> SEQUENCE: 751
actttatttc caaattcac 19

<210> SEQ ID NO 752
<211> LENGTH: 19
<212> TYPE: DNA
<213> ORGANISM: Artificial Sequence
<220> FEATURE:
<223> OTHER INFORMATION: 17-18-19mer-69

<400> SEQUENCE: 752
actttatttc caaattcac 19

<210> SEQ ID NO 753
<211> LENGTH: 19
<212> TYPE: DNA
<213> ORGANISM: Artificial Sequence
<220> FEATURE:
<223> OTHER INFORMATION: 17-18-19mer-75

<400> SEQUENCE: 753
actttatttc caaattcac 19

<210> SEQ ID NO 754
<211> LENGTH: 18
<212> TYPE: DNA
<213> ORGANISM: Artificial Sequence
<220> FEATURE:
<223> OTHER INFORMATION: ASO-001997-mm1

<400> SEQUENCE: 754
ctttatttcc agattcac 18

<210> SEQ ID NO 755
<211> LENGTH: 18
<212> TYPE: DNA
<213> ORGANISM: Artificial Sequence
<220> FEATURE:
<223> OTHER INFORMATION: ASO-001997-mm2

<400> SEQUENCE: 755
ctttatttcc gaattcac 18

<210> SEQ ID NO 756
<211> LENGTH: 18
<212> TYPE: DNA
<213> ORGANISM: Artificial Sequence
<220> FEATURE:
<223> OTHER INFORMATION: ASO-001997-mm3

<400> SEQUENCE: 756
ctttgtttcc aaattcac 18

<210> SEQ ID NO 757
<211> LENGTH: 18
<212> TYPE: DNA
<213> ORGANISM: Artificial Sequence
<220> FEATURE:
<223> OTHER INFORMATION: ASO-001997-mm4

<400> SEQUENCE: 757
ctttgtttcc agattcac 18

<210> SEQ ID NO 758
<211> LENGTH: 18
<212> TYPE: DNA
<213> ORGANISM: Artificial Sequence
<220> FEATURE:
<223> OTHER INFORMATION: ASO-001997-mm5

<400> SEQUENCE: 758
ctttatttcc aggttcac 18

<210> SEQ ID NO 759
<211> LENGTH: 18
<212> TYPE: DNA
<213> ORGANISM: Artificial Sequence
<220> FEATURE:
<223> OTHER INFORMATION: ASO-001997-mm6

<400> SEQUENCE: 759
ctttgtttcc aagttcac 18

<210> SEQ ID NO 760
<211> LENGTH: 16
<212> TYPE: DNA
<213> ORGANISM: Artificial Sequence
<220> FEATURE:
<223> OTHER INFORMATION: SPC-15672-01

<400> SEQUENCE: 760
ttatttccaa attcac 16

<210> SEQ ID NO 761
<211> LENGTH: 18
<212> TYPE: DNA
<213> ORGANISM: Artificial Sequence
<220> FEATURE:
<223> OTHER INFORMATION: 17-18-19mer-21

<400> SEQUENCE: 761
actttatttc caaattca 18

<210> SEQ ID NO 762
<211> LENGTH: 18
<212> TYPE: DNA
<213> ORGANISM: Artificial Sequence
<220> FEATURE:
<223> OTHER INFORMATION: 17-18-19mer-27

<400> SEQUENCE: 762
actttatttc caaattca 18

<210> SEQ ID NO 763
<211> LENGTH: 18
<212> TYPE: DNA
<213> ORGANISM: Artificial Sequence
<220> FEATURE:
<223> OTHER INFORMATION: 17-18-19mer-33

<400> SEQUENCE: 763
actttatttc caaattca 18

<210> SEQ ID NO 764
<211> LENGTH: 18
<212> TYPE: DNA
<213> ORGANISM: Artificial Sequence
<220> FEATURE:
<223> OTHER INFORMATION: 17-18-19mer-39

<400> SEQUENCE: 764
actttatttc caaattca 18

<210> SEQ ID NO 765
<211> LENGTH: 18
<212> TYPE: DNA
<213> ORGANISM: Artificial Sequence
<220> FEATURE:
<223> OTHER INFORMATION: 17-18-19mer-45

<400> SEQUENCE: 765
actttatttc caaattca 18

<210> SEQ ID NO 766
<211> LENGTH: 16
<212> TYPE: DNA
<213> ORGANISM: Artificial Sequence
<220> FEATURE:
<223> OTHER INFORMATION: SPC-15671-01

<400> SEQUENCE: 766
tttatttcca aattca 16

<210> SEQ ID NO 767
<211> LENGTH: 16
<212> TYPE: DNA
<213> ORGANISM: Artificial Sequence
<220> FEATURE:
<223> OTHER INFORMATION: SPC-15670-01

<400> SEQUENCE: 767
ctttatttcc aaattc 16

<210> SEQ ID NO 768
<211> LENGTH: 16
<212> TYPE: DNA
<213> ORGANISM: Artificial Sequence
<220> FEATURE:
<223> OTHER INFORMATION: SPC-15669-01

<400> SEQUENCE: 768
actttatttc caaatt 16

<210> SEQ ID NO 769
<211> LENGTH: 16
<212> TYPE: DNA
<213> ORGANISM: Artificial Sequence
<220> FEATURE:
<223> OTHER INFORMATION: ASO-000139

<400> SEQUENCE: 769
aactttattt ccaaat 16

<210> SEQ ID NO 770
<211> LENGTH: 16
<212> TYPE: DNA
<213> ORGANISM: Artificial Sequence
<220> FEATURE:
<223> OTHER INFORMATION: SPC-15668-01

<400> SEQUENCE: 770
aactttattt ccaaat 16

<210> SEQ ID NO 771
<211> LENGTH: 16
<212> TYPE: DNA
<213> ORGANISM: Artificial Sequence
<220> FEATURE:
<223> OTHER INFORMATION: SPC-15667-01

<400> SEQUENCE: 771
taactttatt tccaaa 16

<210> SEQ ID NO 772
<211> LENGTH: 16
<212> TYPE: DNA
<213> ORGANISM: Artificial Sequence
<220> FEATURE:
<223> OTHER INFORMATION: SPC-15666-01

<400> SEQUENCE: 772
ataactttat ttccaa 16

<210> SEQ ID NO 773
<211> LENGTH: 16
<212> TYPE: DNA
<213> ORGANISM: Artificial Sequence
<220> FEATURE:
<223> OTHER INFORMATION: ASO-000118

<400> SEQUENCE: 773
aataacttta tttcca 16

<210> SEQ ID NO 774
<211> LENGTH: 16
<212> TYPE: DNA
<213> ORGANISM: Artificial Sequence
<220> FEATURE:
<223> OTHER INFORMATION: SPC-15665-01

<400> SEQUENCE: 774
aataacttta tttcca 16

<210> SEQ ID NO 775
<211> LENGTH: 16
<212> TYPE: DNA
<213> ORGANISM: Artificial Sequence
<220> FEATURE:
<223> OTHER INFORMATION: ASO-000101

<400> SEQUENCE: 775
taataacttt atttcc 16

<210> SEQ ID NO 776

<211> LENGTH: 16
<212> TYPE: DNA
<213> ORGANISM: Artificial Sequence
<220> FEATURE:
<223> OTHER INFORMATION: SPC-15664-01

<400> SEQUENCE: 776
taataacttt atttcc 16

<210> SEQ ID NO 777
<211> LENGTH: 16
<212> TYPE: DNA
<213> ORGANISM: Artificial Sequence
<220> FEATURE:
<223> OTHER INFORMATION: ASO-000148

<400> SEQUENCE: 777
gtaataactt tatttc 16

<210> SEQ ID NO 778
<211> LENGTH: 15
<212> TYPE: DNA
<213> ORGANISM: Artificial Sequence
<220> FEATURE:
<223> OTHER INFORMATION: ASO-000184

<400> SEQUENCE: 778
taataacttt atttc 15

<210> SEQ ID NO 779
<211> LENGTH: 15
<212> TYPE: DNA
<213> ORGANISM: Artificial Sequence
<220> FEATURE:
<223> OTHER INFORMATION: ASO-000112

<400> SEQUENCE: 779
gtaataactt tattt 15

<210> SEQ ID NO 780
<211> LENGTH: 16
<212> TYPE: DNA
<213> ORGANISM: Artificial Sequence
<220> FEATURE:
<223> OTHER INFORMATION: ASO-000170

<400> SEQUENCE: 780
agtaataact ttattt 16

<210> SEQ ID NO 781
<211> LENGTH: 16
<212> TYPE: DNA
<213> ORGANISM: Artificial Sequence
<220> FEATURE:
<223> OTHER INFORMATION: ASO-000154

<400> SEQUENCE: 781
gagtaataac tttatt 16

<210> SEQ ID NO 782
<211> LENGTH: 15
<212> TYPE: DNA
<213> ORGANISM: Artificial Sequence
<220> FEATURE:
<223> OTHER INFORMATION: ASO-000125

<400> SEQUENCE: 782
agtaataact ttatt 15

<210> SEQ ID NO 783
<211> LENGTH: 15
<212> TYPE: DNA
<213> ORGANISM: Artificial Sequence
<220> FEATURE:
<223> OTHER INFORMATION: ASO-000167

<400> SEQUENCE: 783
gagtaataac tttat 15

<210> SEQ ID NO 784
<211> LENGTH: 16
<212> TYPE: DNA
<213> ORGANISM: Artificial Sequence
<220> FEATURE:
<223> OTHER INFORMATION: ASO-000134

<400> SEQUENCE: 784
agagtaataa ctttat 16

<210> SEQ ID NO 785
<211> LENGTH: 16
<212> TYPE: DNA
<213> ORGANISM: Artificial Sequence
<220> FEATURE:
<223> OTHER INFORMATION: ASO-000175

<400> SEQUENCE: 785
cagagtaata acttta 16

<210> SEQ ID NO 786
<211> LENGTH: 15
<212> TYPE: DNA
<213> ORGANISM: Artificial Sequence
<220> FEATURE:
<223> OTHER INFORMATION: ASO-000178

<400> SEQUENCE: 786
agagtaataa cttta 15

<210> SEQ ID NO 787
<211> LENGTH: 15
<212> TYPE: DNA
<213> ORGANISM: Artificial Sequence
<220> FEATURE:
<223> OTHER INFORMATION: ASO-000138

<400> SEQUENCE: 787
cagagtaata acttt 15

<210> SEQ ID NO 788
<211> LENGTH: 16
<212> TYPE: DNA
<213> ORGANISM: Artificial Sequence
<220> FEATURE:
<223> OTHER INFORMATION: ASO-000171

<400> SEQUENCE: 788
tcagagtaat aacttt 16

<210> SEQ ID NO 789
<211> LENGTH: 16
<212> TYPE: DNA

<213> ORGANISM: Artificial Sequence
<220> FEATURE:
<223> OTHER INFORMATION: ASO-000236

<400> SEQUENCE: 789
atcagagtaa taactt 16

<210> SEQ ID NO 790
<211> LENGTH: 15
<212> TYPE: DNA
<213> ORGANISM: Artificial Sequence
<220> FEATURE:
<223> OTHER INFORMATION: ASO-000127

<400> SEQUENCE: 790
tcagagtaat aactt 15

<210> SEQ ID NO 791
<211> LENGTH: 14
<212> TYPE: DNA
<213> ORGANISM: Artificial Sequence
<220> FEATURE:
<223> OTHER INFORMATION: ASO-000177

<400> SEQUENCE: 791
cagagtaata actt 14

<210> SEQ ID NO 792
<211> LENGTH: 16
<212> TYPE: DNA
<213> ORGANISM: Artificial Sequence
<220> FEATURE:
<223> OTHER INFORMATION: ASO-000238

<400> SEQUENCE: 792
aatcagagta ataact 16

<210> SEQ ID NO 793
<211> LENGTH: 16
<212> TYPE: DNA
<213> ORGANISM: Artificial Sequence
<220> FEATURE:
<223> OTHER INFORMATION: ASO-000222

<400> SEQUENCE: 793
taatcagagt aataac 16

<210> SEQ ID NO 794
<211> LENGTH: 15
<212> TYPE: DNA
<213> ORGANISM: Artificial Sequence
<220> FEATURE:
<223> OTHER INFORMATION: ASO-000307

<400> SEQUENCE: 794
aatcagagta ataac 15

<210> SEQ ID NO 795
<211> LENGTH: 16
<212> TYPE: DNA
<213> ORGANISM: Artificial Sequence
<220> FEATURE:
<223> OTHER INFORMATION: ASO-000204

<400> SEQUENCE: 795
ttaatcagag taataa 16

<210> SEQ ID NO 796
<211> LENGTH: 15
<212> TYPE: DNA
<213> ORGANISM: Artificial Sequence
<220> FEATURE:
<223> OTHER INFORMATION: ASO-000330

<400> SEQUENCE: 796
taatcagagt aataa 15

<210> SEQ ID NO 797
<211> LENGTH: 16
<212> TYPE: DNA
<213> ORGANISM: Artificial Sequence
<220> FEATURE:
<223> OTHER INFORMATION: ASO-000326

<400> SEQUENCE: 797
tttaatcaga gtaata 16

<210> SEQ ID NO 798
<211> LENGTH: 15
<212> TYPE: DNA
<213> ORGANISM: Artificial Sequence
<220> FEATURE:
<223> OTHER INFORMATION: ASO-000249

<400> SEQUENCE: 798
tttaatcaga gtaat 15

<210> SEQ ID NO 799
<211> LENGTH: 20
<212> TYPE: DNA
<213> ORGANISM: Artificial Sequence
<220> FEATURE:
<223> OTHER INFORMATION: ASO-002022

<400> SEQUENCE: 799
ttatttccaa attcactttt 20

<210> SEQ ID NO 800
<211> LENGTH: 20
<212> TYPE: DNA
<213> ORGANISM: Artificial Sequence
<220> FEATURE:
<223> OTHER INFORMATION: ASO-002026

<400> SEQUENCE: 800
ttatttccaa attcactttt 20

<210> SEQ ID NO 801
<211> LENGTH: 20
<212> TYPE: DNA
<213> ORGANISM: Artificial Sequence
<220> FEATURE:
<223> OTHER INFORMATION: ASO-002024

<400> SEQUENCE: 801
ttatttccaa attcactttt 20

<210> SEQ ID NO 802
<211> LENGTH: 25
<212> TYPE: DNA
<213> ORGANISM: Artificial Sequence
<220> FEATURE:

-continued

```
<223> OTHER INFORMATION: ASO-002049

<400> SEQUENCE: 802

actttatttc caaattcact tttac                                          25


<210> SEQ ID NO 803
<211> LENGTH: 25
<212> TYPE: DNA
<213> ORGANISM: Artificial Sequence
<220> FEATURE:
<223> OTHER INFORMATION: ASO-002019

<400> SEQUENCE: 803

actttatttc caaattcact tttac                                          25


<210> SEQ ID NO 804
<211> LENGTH: 16
<212> TYPE: DNA
<213> ORGANISM: Artificial Sequence
<220> FEATURE:
<223> OTHER INFORMATION: Miscellaneous sequence

<400> SEQUENCE: 804

gtgcgtgcgt gcgtgc                                                    16


<210> SEQ ID NO 805
<211> LENGTH: 16
<212> TYPE: DNA
<213> ORGANISM: Artificial Sequence
<220> FEATURE:
<223> OTHER INFORMATION: Miscellaneous sequence

<400> SEQUENCE: 805

ctgcctgcct gcctgc                                                    16
```

METHODS OF SELECTING THERAPEUTIC MOLECULES

REFERENCE TO EARLIER FILED APPLICATIONS

This application is a PCT application claiming the benefit of U.S. Provisional Application No. 62/112,058, filed Feb. 4, 2015, U.S. Provisional Application No. 62/156,684, filed May 4, 2015, and U.S. Provisional Application No. 62/279,610, filed Jan. 15, 2016, all of which are incorporated herein by reference in its entirety.

REFERENCE TO SEQUENCE LISTING SUBMITTED ELECTRONICALLY VIA EFS-WEB

The content of the electronically submitted sequence listing (Name: 3338.0350003_SequenceListing_ST25.txt; Size: 339,764 bytes; and Date of Creation: Dec. 18, 2017) submitted in this application is incorporated herein by reference in its entirety.

FIELD OF INVENTION

The present invention relates to methods for selecting therapeutic molecules that have reduced toxic side effects. The methods can be used in vitro or in silico to screen molecules before administration to laboratory animals or the methods can be used in vivo in laboratory animals.

BACKGROUND

In the field of specifically-targeted therapeutics, some therapeutic molecules cause toxic side effects, such as by non-specifically interacting with proteins, stimulating an unwanted immune response or accumulating in tissues. One central concern when administering therapeutic molecules to a subject is the potential neurotoxicity of the molecules. Exposure to neurotoxic molecules can lead to damage to the brain and peripheral nervous system, causing long term physiological problems. As such, it is important that therapeutic molecules not only be effective at treating a desired disease or disorder, but also have acceptable toxicity, for example neurotoxicity, when administered.

Determination of the most effective therapeutic molecules usually involves synthesizing a large number of molecules designed to target a factor in a cell and testing that large number of molecules for activity and toxicity. While animal studies can be performed to determine toxicity, it is neither ethically nor economically desirable to perform animal studies where a large number of animals die due to a large number of the molecules being tested having toxic properties. Thus, improved ways of determining the toxicity, such as the neurotoxicity, of a therapeutic molecule without requiring animal testing are needed.

SUMMARY OF INVENTION

The present disclosure provides a method of testing or determining in vivo acute neurotoxicity of a molecule comprising measuring oscillations in intracellular free calcium concentration ("calcium oscillations") in vitro in neuronal cells which are in contact with the molecule.

The present disclosure also provides a method for selecting a molecule having tolerable in vivo acute neurotoxicity comprising measuring calcium oscillations in vitro in neuronal cells in vitro which are in contact with the molecule, wherein the molecule exhibits a calcium oscillation level comparable to a control.

The above methods of the present disclosure that involve measuring calcium oscillations can further comprise calculating a sequence score of the molecule, e.g., a polynucleotide comprising a nucleotide sequence, wherein the sequence score is calculated by formula (I):

(number of C nucleotides or analogs thereof in the nucleotide sequence−number of G nucleotides or analogs thereof in the nucleotide sequence)/total nucleotide length of the nucleotide sequence (I).

The present invention also provides a method of determining in vivo acute neurotoxicity of a molecule comprising a nucleotide sequence, the method comprising calculating a sequence score, wherein the sequence score is calculated by formula (I):

(number of C nucleotides or analogs thereof in the nucleotide sequence−number of G nucleotides or analogs thereof in the nucleotide sequence)/total nucleotide length of the nucleotide sequence (I).

The present invention also provides a method of selecting a molecule comprising a nucleotide sequence having tolerable in vivo acute neurotoxicity comprising calculating a sequence score using formula (I):

(number of C nucleotides or analogs thereof in the nucleotide sequence−number of G nucleotides or analogs thereof in the nucleotide sequence)/total nucleotide length of the nucleotide sequence (I), wherein the nucleotide sequence has a sequence score of greater than or equal to 0.2.

In other embodiments, the present disclosure provides a method of selecting a molecule having tolerable in vivo acute neurotoxicity comprising measuring in vivo tolerability. The present invention provides methods where the in vivo tolerability is graded into one of five tolerability categories. The present invention also provides that the tolerability categories can be 1) hyperactivity; 2) decreased activity and arousal; 3) motor dysfunction and/or ataxia; 4) abnormal posture and breathing; and 5) tremor and/or convulsions. In one embodiment, the in vivo tolerability can be measured by injecting a molecule into a brain of a mammal and grading the mammal's tolerability in a tolerability category on a scale of 0 to 20.

The above methods of the present invention can further comprise measuring tubulin intensity in a culture of neuronal cells, expression of a target protein, or behavioral performance of the molecule.

The present invention also provides methods for administering a molecule that has been tested according to the above methods to a subject in need of treatment of a disease or condition.

In certain embodiments, the molecule comprises a protein, a peptide, a small molecule, a polynucleotide (e.g., an antisense oligonucleotide), or any combination thereof.

EMBODIMENTS

E1. A method of testing or determining in vivo acute neurotoxicity of a molecule comprising measuring calcium oscillations in vitro in neuronal cells which are in contact with the molecule.

E2. The method of embodiment 1, wherein the calcium oscillations of the molecule are compared to the calcium oscillations in neuronal cells that are not exposed to the molecule ("control cells").

E3. The method of embodiment 2, wherein the control cells are vehicle control cells.

E4. The method of embodiment 3, wherein the calcium oscillations in the neuronal cells that are in contact with the molecule are about 70% or higher, about 75% or higher, about 80% or higher, about 85% or higher, about 90% or higher, about 95% or higher, about 96% or higher, about 97% or higher, about 98% or higher, about 99% or higher, about 100% or higher, about 120% or higher, about 140% or higher, about 160% or higher, about 180% or higher, about 200% or higher, about 220% or higher, about 240% or higher, or about 250% or higher compared to the calcium oscillations in the vehicle control cells.

E5. A method of selecting or identifying a molecule having tolerable in vivo acute neurotoxicity comprising measuring calcium oscillations in vitro in neuronal cells which are in contact with the molecule, wherein the neuronal cells in contact with the molecule exhibit calcium oscillations at a level comparable to or higher than that of vehicle control cells.

E6. The method of embodiment 5, wherein the calcium oscillations in the neuronal cells that have been in contact with the molecule are about 70% or higher, about 75% or higher, about 80% or higher, about 85% or higher, about 90% or higher, about 95% or higher, about 96% or higher, about 97% or higher, about 98% or higher, about 99% or higher, about 100% or higher, about 120% or higher, about 140% or higher, about 160% or higher, about 180% or higher, about 200% or higher, about 220% or higher, about 240% or higher, or about 250% or higher compared to the calcium oscillations in the vehicle control cells.

E7. The method of any one of embodiments 1 to 6, wherein the neuronal cells are prepared from mammal primary cortical neurons.

E8. The method of any one of embodiments 1 to 7, wherein the molecule comprises a small molecule, a polynucleotide, a protein, a peptide, or any combination thereof.

E9. The method of embodiment 8, wherein the protein comprises an antibody or antigen-binding fragment thereof, a fusion protein, a cytokine, a cell surface receptor, a hormone, a growth factor, or any combination thereof.

E10. The method of any one of embodiments 1 to 9, wherein the calcium oscillations are AMPA receptor-dependent calcium oscillations.

E11. The method of any one of embodiments 1 to 10, wherein the calcium oscillations are measured in the presence of $Mg^{2+}$ ions.

E12. The method of embodiment 11, wherein the concentration of $Mg^{2+}$ ion is at least about 0.5 mM, at least about 0.6 mM, at least about 0.7 mM, at least about 0.8 mM, at least about 0.9 mM, at least about 1 mM, at least about 1.5 mM, at least about 2.0 mM, at least about 2.5 mM, at least about 3.0 mM, at least about 4 mM, at least about 5 mM, or at least about 10 mM.

E13. The method of one of embodiments 1 to 12, wherein the calcium oscillations are determined by measuring fluorescence of a calcium dye.

E14. The method of one of embodiments 1 to 13, further comprising administering the molecule to a subject in need of treatment of a disease or condition.

E15. The method of embodiment 14, wherein the disease or condition is selected from the group consisting of a viral infection, a neurological disorder (e.g., Alzheimer's disease, progressive supranuclear palsy, Down syndrome, dementia pugilistica (chronic traumatic encephalopathy and other traumatic brain injury), frontotemporal dementia with parkinsonism linked to chromosome 17 (FTDP-17), Lytico-Bodig disease (Parkinson-dementia complex of Guam), Tangle-predominant dementia, ganglioglioma, gangliocytoma, meningioangiomatosis, subacute sclerosing panencephalitis, lead encephalopathy, Hemimegalencephaly, tuberous sclerosis, Hallervorden-Spatz disease, Pick's disease, corticobasal ganglionic degeneration, argyrophilic grain disease, corticobasal degeneration, lipofuscinosis, frontotemporal dementia, supranuclear palsy, and frontotemporal lobar degeneration, a disease of brain network dysfunction (e.g., all forms of epilepsy and depression), a spinal cord disorder, a peripheral neuropathy, a cranial nerve disorder (e.g., Trigeminal neuralgia), an autonomic nervous system disorder (e.g., dysautonomia or multiple system atrophy), a movement disorder of a central and peripheral nervous system (e.g., Parkinson's disease, essential tremor, amyotrophic lateral sclerosis, Tourette's Syndrome, multiple sclerosis or various types of peripheral neuropathy), a sleep disorder (e.g., Narcolepsy), migraine or other types of headache (e.g., cluster headache and tension headache), lower back and neck pain, central neuropathy, a neuropsychiatric illness, attention deficit hyperactivity disorder, autism, Huntington's disease, Rett Syndrome, Angelman Syndrome, organic psychosis, an infection of the brain or spinal cord (including meningitis), or a prion disease), anemia, cancer, leukemia, an inflammatory condition or an autoimmune disease (e.g. arthritis, psoriasis, lupus erythematosus, multiple sclerosis), a bacterial infection, frontotemporal dementia-tau (FTD-tau), frontotemporal dementia and parkinsonism linked to chromosome 17 (FTDP-17), corticobasal degeneration (CBD), traumatic brain injury, chronic traumatic encephalopathy, HIV associated neurocognitive disorders, Argyrophilic grain disease, Down syndrome-Alzheimer's disease, Amnestic mild cognitive impairment-Alzheimer's disease, Parkinson's disease dementia, Hallervorden-Spatz disease (Pantothenate kinase-associated neurodegeneration), Niemann Pick disease type C, Myotonic dystrophy, Amyotrophic lateral sclerosis, Hemimegalencephaly, Tuberous sclerosis complex, Focal cortical dysplasia type 2b, Ganglion cell tumors, Dravet Syndrome (severe myoclonic epilepsy of infancy), Temporal lobe epilepsy, Ohtahara syndrome (early infantile epileptic encephalopathy with suppression bursts), Lafora body disease, Generalized epilepsy with febrile seizures, Infantile spasms (West syndrome), Lennox Gastaut syndrome, Angelman Syndrome, Rett Syndrome, Landau Kleffner syndrome, focal seizures, simple focal seizures (no loss of consciousness), focal dyscognitive seizures (impairment of consciousness), focal seizure evolving to generalised tonic-clonic (GTC) convulsions, generalised seizures (convulsive or non-convulsive with bilateral discharges involving subcortical structures), absence seizures, myoclonic seizures, clonic seizures, tonic seizures, tonic-clonic seizures and atonic seizures, an autistic disorder, an autism spectrum disorder, an Asperger's disorder, a pervasive developmental disorder, and any combination thereof.

E16. The method of any one of embodiments 1 to 15, wherein the molecule comprises a polynucleotide.

E17. The method of embodiment 16, further comprising calculating a sequence score, wherein the sequence score is calculated by formula (I):

(number of C nucleotides or analogs thereof in the polynucleotide–number of G nucleotides or analogs thereof in the polynucleotide)/total nucleotide length (number) of the polynucleotide (I).

E18. A method of determining in vivo acute neurotoxicity of a molecule comprising a polynucleotide, the method comprising calculating a sequence score, wherein the sequence score is calculated by formula (I):

(number of C nucleotides or analogs thereof in the polynucleotide−number of G nucleotides or analogs thereof in the polynucleotide)/total nucleotide length (number) of the polynucleotide (I), E19. A method of selecting a molecule comprising a polynucleotide having tolerable in vivo acute neurotoxicity comprising calculating a sequence score using formula (I):

(number of C nucleotides or analogs thereof in the polynucleotide−number of G nucleotides or analogs thereof in the polynucleotide)/total nucleotide length (number) of the polynucleotide (I), wherein the polynucleotide has a sequence score of greater than or equal to 0.2.

E20. The method of any one of embodiments 17 to 19, wherein the sequence score is greater than or equal to 0.2, greater than or equal to 0.25, greater than or equal to 0.3, greater than or equal to 0.35, greater than or equal to 0.4, greater than or equal to 0.45, greater than or equal to 0.5, greater than or equal to 0.55, greater than or equal to 0.6, greater than or equal to 0.65, greater than or equal to 0.7, greater than or equal to 0.75, greater than or equal to 0.8, greater than or equal to 0.85, greater than or equal to 0.9, greater than or equal to 0.95, greater than or equal to 1.0, greater than or equal to 1.5, greater than or equal to 2.0, greater than or equal to 3.0, or greater than or equal to 4.0.

E21. The method of any one of embodiments 16 to 20, wherein the polynucleotide comprises DNA or RNA.

E22. The method of any one of embodiments 16 to 21, wherein the polynucleotide is single stranded.

E23. The method of any one of embodiments 16 to 22, wherein the polynucleotide is an antisense oligonucleotide (i.e., oligomer) of about 10 to about 50 nucleotides in length.

E24. The method of embodiment 23, wherein the antisense oligonucleotide modulates an expression of a target protein.

E25. The method of embodiment 23, wherein the antisense oligonucleotide targets an mRNA of the target protein.

E26. The method of embodiment 25, wherein the mRNA is pre-mRNA or mature mRNA.

E27. The method of any one of embodiments 25 to 26, wherein the mRNA is expressed in a cell.

E28. The method of embodiment 27, wherein the mRNA is expressed in a neuronal cell.

E29. The method of any one of embodiments 23 to 28, wherein the antisense oligonucleotide modulates mRNA expression of the target gene in the culture of neuronal cells.

E30. The method of any one of embodiments 23 to 29, wherein the antisense oligonucleotide modulates protein expression encoded by the target protein in the culture of the neuronal cells.

E31. The method of any one of embodiments 23 to 30, wherein the antisense oligonucleotide is complementary to an mRNA or a pre-mRNA of the target gene.

E32. The method of any one of embodiments 1 to 31, further measuring reduction of in vitro expression of a target protein of the molecule.

E33. The method of any one of embodiments 1 to 32, further comprising measuring an in vivo tolerability of the molecule.

E34. The method of embodiment 33, wherein the in vivo tolerability is measured by administering the molecule to a mammal and grading the mammal's tolerability in a tolerability category.

E35. The method of embodiment 33, wherein the molecule is administered to the brain of the mammal.

E36. A method of testing or determining in vivo tolerability of a molecule comprising administering the molecule to a mammal and grading the mammal's tolerability in a tolerability category.

E37. The method of any one of embodiments 34 to 36, wherein the tolerability category comprises at least one, at least two, at least three, at least four, or at least five tolerability categories.

E38. The method of embodiment 37, wherein the tolerability category is selected from the group consisting of: 1) hyperactivity; 2) decreased activity and arousal; 3) motor dysfunction and/or ataxia; 4) abnormal posture and breathing; 5) tremor and/or convulsions, and two or more combinations thereof.

E39. The method of embodiment 38, wherein the molecule exhibits an in vivo tolerability score of 0 to 4 in each of the tolerability category.

E40. The method of embodiment 39, wherein the molecule exhibits a sum of the in vivo tolerability scores between 0 and 8.

E41. The method embodiment 39 or 40, wherein the molecule exhibits a sum of the in vivo tolerability scores is between 0 and 6, between 0 and 5, between 0 and 4, between 0 and 3, between 0 and 2, or between 0 and 1.

E42. The method of any one of embodiments 1 to 41, further comprising measuring a behavioral test score of the molecule.

E43. The method of embodiment 42, wherein the behavioral test score is measured by administering the molecule to a mammal and grading the mammal's' behavioral performance.

E44. The method of any one of embodiments 41 to 43, wherein the behavioral test is a short term memory test, a spatial learning and memory test, a gait analysis test, or any combination thereof.

E45. The method of any one of embodiments 1 to 44, further comprising measuring tubulin intensity of the molecule in a culture of neuronal cells.

E46. The method of embodiment 45, wherein the tubulin intensity of the molecule is compared to the tubulin intensity in neuronal cells not exposed to the molecule.

E47. The method of embodiment 46, wherein the molecule reduces less than about 25%, less than about 20%, less than about 15%, less than about 10%, less than about 5%, or less than about 1% of the tubulin intensity in the culture of neuronal cells.

E48. The method of any one of embodiments 1 to 47, further comprising administering the molecule to a subject in need of treatment for a disease or condition.

E49. The method of embodiment 48, wherein the disease or a condition is selected from the group consisting of a viral infection, a neurological disorder (e.g., Alzheimer's disease, progressive supranuclear palsy, Down syndrome, dementia pugilistica (chronic traumatic encephalopathy and other traumatic brain injury), frontotemporal dementia with parkinsonism linked to chromosome 17 (FTDP-17), Huntington's disease, Rett Syndrome, Angelman Syndrome, Lytico-Bodig disease (Parkinson-dementia complex of Guam), Tangle-predominant dementia, ganglioglioma, gangliocytoma, meningioangiomatosis, subacute sclerosing panencephalitis, lead encephalopathy, Hemimegalencephaly, tuberous sclerosis, Hallervorden-Spatz disease, Pick's disease, corticobasal ganglionic degeneration, argyrophilic grain disease, corticobasal degeneration, lipofuscinosis, frontotemporal dementia, supranuclear palsy, and frontotemporal lobar degeneration, a disease of brain network dysfunction (e.g., all forms of epilepsy and depression), a spinal cord disorder, a peripheral neuropathy, a cranial nerve disorder (e.g., Trigeminal neuralgia), an autonomic nervous system disorder (e.g., dysautonomia or multiple system atrophy), a movement disorder of a central and peripheral nervous system (e.g., Parkinson's disease, essential tremor, amyotrophic lateral sclerosis, Tourette's Syndrome, multiple sclerosis or various types of peripheral neuropathy), a sleep disorder (e.g., Narcolepsy), migraine or other types of headache (e.g., cluster headache and tension headache), lower back and neck pain, central neuropathy, a neuropsychiatric illness, attention deficit hyperactivity disorder, autism, Huntington's disease, organic psychosis, an infection of the brain or spinal cord (including meningitis), or a prion disease), anemia, cancer, leukemia, an inflammatory condition or an autoimmune disease (e.g. arthritis, psoriasis, lupus erythematosus, multiple sclerosis), a bacterial infection, frontotemporal dementia-tau (FTD-tau), frontotemporal dementia and parkinsonism linked to chromosome 17 (FTDP-17), corticobasal degeneration (CBD), traumatic brain injury, chronic traumatic encephalopathy, HIV associated neurocognitive disorders, Argyrophilic grain disease, Down syndrome-Alzheimer's disease, Amnestic mild cognitive impairment-Alzheimer's disease, Parkinson's disease dementia, Hallervorden-Spatz disease (Pantothenate kinase-associated neurodegeneration), Niemann Pick disease type C, Myotonic dystrophy, Amyotrophic lateral sclerosis, Hemimegalencephaly, Tuberous sclerosis complex, Focal cortical dysplasia type 2b, Ganglion cell tumors, Dravet Syndrome (severe myoclonic epilepsy of infancy), Temporal lobe epilepsy, Ohtahara syndrome (early infantile epileptic encephalopathy with suppression bursts), Lafora body disease, Generalized epilepsy with febrile seizures, Infantile spasms (West syndrome), Lennox Gastaut syndrome, Angelman Syndrome, Rett Syndrome, Landau Kleffner syndrome, focal seizures, simple focal seizures (no loss of consciousness), focal dyscognitive seizures (impairment of consciousness), focal seizure evolving to generalised tonic-clonic (GTC) convulsions, generalised seizures (convulsive or non-convulsive with bilateral discharges involving subcortical structures), absence seizures, myoclonic seizures, clonic seizures, tonic seizures, tonic-clonic seizures and atonic seizures, an autistic disorder, an autism spectrum disorder, an Asperger's disorder, a pervasive developmental disorder, and any combination thereof.

E50. The method of embodiment 49, wherein the molecule treats or prevents a disease or condition.

E51. The method of any one of embodiments 16 to 50, wherein the polynucleotide is an antisense oligonucleotide.

E52. The method of any one of embodiments 16 to 51, wherein the polynucleotide comprises at least one nucleotide analog.

E53. The method of any one of embodiments 16 to 52, wherein the polynucleotide comprises at least two, at least three, at least four, at least five, at least six, at least seven, at least eight, at least nine, or at least ten nucleotide analogs.

E54. The method of embodiment 52 or 53, wherein the nucleotide analog or analogs are Locked Nucleic Acid (LNA); 2'-O-alkyl-RNA; 2'-amino-DNA; 2'-fluoro-DNA; arabino nucleic acid (ANA); 2'-fluoro-ANA, hexitol nucleic acid (HNA), intercalating nucleic acid (INA), constrained ethyl nucleoside (cEt), 2'-O-methyl nucleic acid (2'-OMe), 2'-O-methoxyethyl nucleic acid (2'-MOE), or any combination thereof.

E55. The method of any one of embodiments 23 to 54, wherein the antisense oligonucleotide comprises an internucleoside linkage selected from: a phosphodiester linkage, a phosphotriester linkage, a methylphosphonate linkage, a phosphoramidate linkage, a phosphorothioate linkage, and combinations thereof.

E56. The method of any one of embodiments 23 to 55, wherein the antisense oligonucleotide is a gapmer, a blockmer, a mixmer, or a wingmer.

E57. The method of any one of embodiments 1 to 56, wherein when the molecule is administered to laboratory animals, more than 20% of the animals survive.

E58. The method of any one of embodiments 1 to 57, wherein when the molecule is administered to laboratory animals, more than 50% of the animals survive.

E59. The method of any one of embodiments 1 to 58, wherein when the molecule is administered to laboratory animals, more than 85% of the animals survive.

E60. A molecule selected from the method of any one of embodiments 1 to 59.

E61. A method of treating a disease or condition comprising administering the molecule of embodiment 60.

E62. The method of embodiment 61, wherein the disease or condition associated with a neuronal cell.

E63. A method of testing or determining in vivo acute neurotoxicity of a molecule comprising the steps of 1) adding the molecule to a culture of neuronal cells and 2) measuring calcium oscillations in vitro in the neuronal cells.

E64. The method of Embodiment 63, further comprising comparing the calcium oscillations in the neuronal cells with the calcium oscillations in neuronal cells that are not exposed to the molecule ("control cells").

E65. The method of Embodiment 63 or 64, wherein the neuronal cells are prepared from mammalian cortical neurons.

E66. The method of any one of Embodiments 63 to 65, wherein the calcium oscillations are AMPA receptor dependent.

E67. The method of any one of Embodiments 63 to 66, wherein the calcium oscillations are measured in the presence of $Mg^{2+}$ ions.

E68. The method of Embodiment 67, wherein the concentration of $Mg^{2+}$ ion is at least about 0.5 mM, at least about 0.6 mM, at least about 0.7 mM, at least about 0.8 mM, at least about 0.9 mM, at least about 1 mM, at least about 1.5 mM, at least about 2.0 mM, at least about 2.5 mM, at least about 3.0 mM, at least about 4 mM, at least about 5 mM, or at least about 10 mM.

E69. The method of any one of Embodiments 63 to 68, wherein the molecule comprises a small molecule, a polynucleotide, a protein, a peptide, or any combination thereof.

E70. The method of Embodiment 69, further comprising a step of calculating a sequence score, wherein the sequence score is calculated by formula (I):

(number of C nucleotides or analogs thereof in the polynucleotide−number of G nucleotides or analogs thereof in the polynucleotide)/total nucleotide number in the polynucleotide (I).

E71. A method of determining in vivo acute neurotoxicity of a molecule comprising a nucleotide sequence, the method comprising calculating a sequence score, wherein the sequence score is calculated by formula (I):

(number of C nucleotides or analogs thereof in the nucleotide sequence−number of G nucleotides or analogs thereof in the nucleotide sequence)/total nucleotide number in the nucleotide sequence (I), wherein the nucleotide sequence has a sequence score of greater than or equal to 0.2.

E72. The method of any one of Embodiments 63 to 71, further comprising measuring in vivo tolerability of the molecule.

E73. The method of any one of Embodiments 63 to 72, further comprising measuring tublin intensity in a culture of neuronal cells.

E74. The method of any one of Embodiments 63 to 73, wherein the molecule is an antisense oligonucleotide.

E75. The method of any one of Embodiments 63 to 74, wherein when the molecule is administered to laboratory animals, more than 50% of the animals survive.

E76. The method of any one of Embodiments 63 to 74, wherein when the molecule is administered to laboratory animals, more than 85% of the animals survive.

E77. A molecule for use in treating a disease or condition, wherein the molecule is determined or identified to have tolerable in vivo acute neurotoxicity by the method of Embodiments 63 to 76.

E78. The molecule of Embodiment 77, wherein the disease or condition is associated with a neuronal cell.

E79. An antisense oligonucleotide for use in treating a neurological disease or condition in a subject in need thereof, wherein calcium oscillations in neuronal cells that are in contact with the antisense oligonucleotide are about 70% or higher, about 75% or higher, about 80% or higher, about 85% or higher, about 90% or higher, about 95% or higher, about 96% or higher, about 97% or higher, about 98% or higher, about 99% or higher, about 100% or higher, about 120% or higher, about 140% or higher, about 160% or higher, about 180% or higher, about 200% or higher, about 220% or higher, about 240% or higher, or about 250% or higher compared to the calcium oscillations in vehicle control cells.

E80. An antisense oligonucleotide for use in treating a neurological disease or condition having the sequence score greater than or equal to 0.2, greater than or equal to 0.25, greater than or equal to 0.3, greater than or equal to 0.35, greater than or equal to 0.4, greater than or equal to 0.45, greater than or equal to 0.5, greater than or equal to 0.55, greater than or equal to 0.6, greater than or equal to 0.65, greater than or equal to 0.7, greater than or equal to 0.75, greater than or equal to 0.8, greater than or equal to 0.85, greater than or equal to 0.9, greater than or equal to 0.95, greater than or equal to 1.0, greater than or equal to 1.5, greater than or equal to 2.0, greater than or equal to 3.0, or greater than or equal to 4.0.

E81. In a method of testing or determining in vivo neurotoxicity of a molecule, the improvement comprising measuring calcium oscillations in vitro in neuronal cells which are in contact with the molecule.

E82. In a method of selecting or identifying a molecule having tolerable in vivo neurotoxicity, the improvement comprising measuring calcium oscillations in vitro in neuronal cells which are in contact with the molecule, wherein the neuronal cells in contact with the molecule exhibit calcium oscillations at a level comparable to or higher than that of vehicle control cells.

E83. In the method of Embodiments 81 or 82, the improvement further comprising calculating a sequence score, wherein the molecule comprises a polynucleotide and wherein the sequence score of the polynucleotide is calculated by formula (I):

(number of C nucleotides or analogs thereof in the polynucleotide−number of G nucleotides or analogs thereof in the polynucleotide)/total nucleotide number in the polynucleotide (I).

E84. In the method of determining in vivo acute neurotoxicity of a molecule comprising a polynucleotide, the improvement comprising calculating a sequence score of the polynucleotide, wherein the sequence score is calculated by formula (I):

(number of C nucleotides or analogs thereof in the polynucleotide−number of G nucleotides or analogs thereof in the polynucleotide)/total nucleotide number in the polynucleotide (I).

E85. In a method of selecting a molecule comprising a polynucleotide having tolerable in vivo acute neurotoxicity, the improvement comprising calculating a sequence score using formula (I):

(number of C nucleotides or analogs thereof in the polynucleotide−number of G nucleotides or analogs thereof in the polynucleotide)/total nucleotide number in the polynucleotide (I), wherein the polynucleotide has a sequence score of greater than or equal to 0.2.

E86. In the methods of Embodiments 81 to 85, the improvement further comprising measuring reduction of in vitro expression of a target protein of the molecule.

E87. In the method of any one of Embodiments 81 to 85, the improvement further comprising measuring an in vivo tolerability of the molecule.

E88. In the method of Embodiment 87, wherein the in vivo tolerability is measured by administering the molecule to a mammal and grading the mammal's tolerability in a tolerability category.

BRIEF DESCRIPTION OF FIGURES

FIG. 4: shows the impact of Tau antisense oligonucleotide on spontaneous calcium oscillations in primary neurons. FIG. 4 lists the oligomer name, ASO identification number, ASO sequence, SEQ ID Number, target start and end positions on the MAPT pre-mRNA sequence, and calcium oscillation data as a percent of control (as discussed in Example 2 below). Examples of oligomers with mismatched bases are provided in FIG. 4 as "mm." The specific mismatched base-pairs are bolded, underlined, italicized, and highlighted.

FIG. 5: shows in vivo tolerability of exemplary antisense oligonucleotides. FIG. 5 lists the ASO identification number, ASO sequence, SEQ ID Number, target start and end positions on the MAPT pre-mRNA sequence, in vivo acute tolerability score (as discussed in Example 6 below) and the percent of brain MAPT mRNA remaining after administration (as also discussed in Example 6 below).

FIG. 6: shows Tau protein reduction by exemplary antisense oligonucleotides. FIG. 6 lists the SEQ ID number, oligomer name, ASO identification number, ASO sequence, target start and end positions on the MAPT pre-mRNA sequence, target start on the mature mRNA sequence and normalized Tau/Tuj-1 and Tuj-1 immunocytochemistry values (as discussed in Example 7 below). Examples of oligomers with mismatched bases are provided in FIG. 7 as "mm." The specific mismatched base-pairs are bolded, underlined, italicized, and highlighted.

DETAILED DESCRIPTION OF INVENTION

I. Definitions

Figure 1:
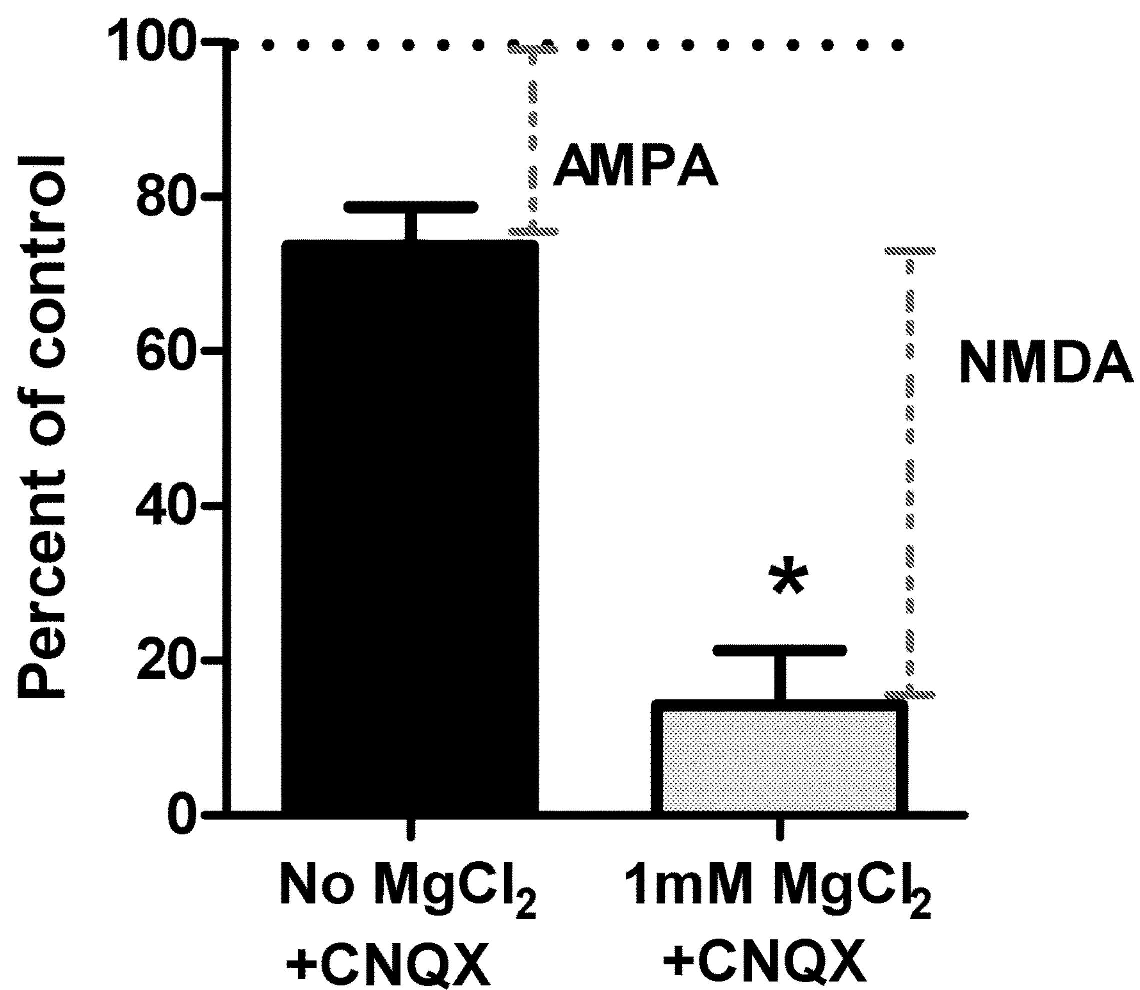
FIG. 1: Graph demonstrating primary neuronal spontaneous calcium oscillations. Primary neuronal spontaneous calcium oscillations were measured as described previously (Murphy et. al., 1992, J. Neurosci. 12:4834-4845). Addition of the α-amino-3-hydroxy-5-methyl-4-isoxazolepropionic acid (AMPA) receptor antagonist, 6-Cyano-7-nitroquinoxaline-2,3-dione (CNQX; 3 μM), reduced calcium oscillations by 20% representing the total AMPA response in the assay (AMPA labeled bar shown). Calcium oscillations were reduced further, by about 80%, when N-methyl-D-aspartate (NMDA) receptor function was blocked by 1 mM $MgCl_2$ (NMDA labeled bar shown).

It is to be noted that the term "a" or "an" entity refers to one or more of that entity; for example, "a molecule," is understood to represent one or more molecules. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. Unless otherwise indicated, nucleotide sequences are written left to right in 5' to 3' orientation. Amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

The term "about" is used herein to mean approximately, roughly, around, or in the regions of. When the term "about" is used in conjunction with a numerical range, it modifies that range by extending the boundaries above and below the numerical values set forth. In general, the term "about" can modify a numerical value above and below the stated value by a variance of, e.g., 10 percent, up or down (higher or lower). For example, about 70% can include 70%-7% to 70%+7%, i.e., 63% to 77%.

The term "therapeutic molecule" refers to any compound having a therapeutic effect in vivo for treatment of a disease or condition. Non-limiting examples of the therapeutic molecules include oligomers, one or more nucleotides, one or more nucleosides, one or more amino acids, polynucleotides, peptides, proteins, polypeptides, or small molecule compounds that are naturally occurring, modified, recombinantly produced, or chemically synthesized. Proteins that are therapeutic molecules include, but are not limited to, antibodies or antigen-binding fragments thereof, fusion proteins, cytokines, cell surface receptors, hormones, growth factors, or any combination thereof.

The term "oligomer" in the context of the present invention, refers to a molecule formed by covalent linkage of two or more nucleotides (i.e., an oligonucleotide). The oligomer comprises a contiguous nucleotide sequence of from about 10 to about 50, such as 10-20, 16-20, 10-30, 10-35, 10-40, or 10-45 nucleotides in length. The terms "antisense oligomer," "antisense oligonucleotide," and "ASO" as used herein are interchangeable with the term "oligomer." In various embodiments, the oligomer of the invention does not comprise RNA (units). In some embodiments, the oligomer comprises one or more DNA units. In one embodiment, the oligomer according to the invention is a linear molecule or is synthesized as a linear molecule. In some embodiments, the oligomer is a single stranded molecule, and does not comprise short regions of, for example, at least 3, 4 or 5 contiguous nucleotides, which are complementary to equivalent regions within the same oligomer (i.e. duplexes)—in this regard, the oligomer is not (essentially) double stranded. In some embodiments, the oligomer is essentially not double stranded. In some embodiments, the oligomer is not a siRNA. In various embodiments, the oligomer of the invention consists entirely of the contiguous nucleotide region. Thus, in some embodiments the oligomer is not substantially self-complementary.

The term "nucleic acids," "nucleotides," "nucleotide sequence," or "nucleic acid sequence" is intended to encompass plural nucleic acids (e.g., two or more, three or more, etc.). The term "nucleic acid" or "nucleoside" refers to a single nucleic acid segment, e.g., a DNA, an RNA, or an analog thereof, present in a polynucleotide. In some embodiments, the terms "nucleotide", "unit" and "monomer" are used interchangeably. It will be recognized that when referring to a sequence of nucleotides or monomers, what is referred to is the sequence of bases, such as A, T, G, C or U, and analogs thereof. The term "nucleotide sequence" refers to a molecule comprising at least two nucleotides connected to each other.

The term "nucleotide" as used herein, refers to a glycoside comprising a sugar moiety, a base moiety and a covalently linked group (linkage group), such as a phosphate or phosphorothioate internucleotide linkage group, and covers both naturally occurring nucleotides, such as DNA or RNA, and non-naturally occurring nucleotides comprising modified sugar and/or base moieties, which are also referred to as "nucleotide analogs" herein. Herein, a single nucleotide (unit) can also be referred to as a monomer or nucleic acid unit. In certain embodiments, the term "nucleotide analogs" refers to nucleotides having modified sugar moieties. Non-limiting examples of the nucleotides having modified sugar moieties (e.g., LNA) are disclosed elsewhere herein, e.g., 2'-O-methyl, 2'-fluoro (2'-F), 2'-O-methoxyethyl (2'-MOE), and 2',4'-constrained 2'-O-ethyl (cEt). In other embodiments, the term "nucleotide analogs" refers to nucleotides having modified base moieties. The nucleotides having modified base moieties include, but are not limited to, 5-methylcytosine, isocytosine, pseudoisocytosine, 5-bromouracil, 5-propynyluracil, 6-aminopurine, 2-aminopurine, inosine, diaminopurine, or 2-chloro-6-aminopurine. In certain embodiments when referring to the sequence score formula disclosed herein, the nucleotide analog of cytosine is 5-methyl cytosine.

The term "polynucleotide" as used herein refers to two or more nucleotides linked in sequence. Exemplary polynucleotides can comprise a nucleotide sequence having two nucleotides, three nucleotides, four nucleotides, five nucleotides, six nucleotides, seven nucleotides, eight nucleotides, nine nucleotides, ten nucleotides, oligonucleotides, 50 nucleotides, 51 nucleotides, or more. In some embodiments, polynucleotides comprise a nucleotide sequence longer than 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, 20 nucleotides, 21 nucleotides, 22 nucleotides, 23 nucleotides, 24 nucleotides 26 nucleotides, 27 nucleotides, 28 nucleotides, 29 nucleotides, 30 nucleotides. In other embodiments, polynucleotides comprise an oligomer (e.g., antisense oligonucleotide). In yet other embodiments, polynucleotides comprise a nucleotide sequence encoding a protein or polypeptide. In still other embodiments, polynucleotides comprise a nucleotide sequence longer than 100 nucleotides, longer than 200 nucleotides, longer than 300 nucleotides, longer than 400 nucleotides, longer than 500 nucleotides, longer than 1000 nucleotides, longer than 1500 nucleotides, longer than 2000 nucleotides, longer than 3000 nucleotides, longer than 4000 nucleotides, or longer than 5000 nucleotides.

The term "nucleoside" as used herein is used to refer to a glycoside comprising a sugar moiety and a base moiety, and can therefore be used when referring to the nucleotide units, which are covalently linked by the internucleotide linkages between the nucleotides of the oligomer. In the field of biotechnology, the term "nucleotide" is often used to refer to a nucleic acid monomer or unit, and as such in the context of an oligonucleotide can refer to the base—such as the "nucleotide sequence," typically refer to the nucleobase sequence (i.e., the presence of the sugar backbone and internucleoside linkages are implicit). Likewise, particularly in the case of oligonucleotides where one or more of the internucleoside linkage groups are modified, the term "nucleotide" can refer to a "nucleoside" for example the term "nucleotide" can be used, even when specifying the presence or nature of the linkages between the nucleosides.

The term "nucleotide length" as used herein means the total number of the nucleotides (monomers) in a given sequence. For example, the sequence of AAAgatgaaatttgctcTTA (SEQ ID NO: 4) has 20 nucleotides; thus the nucleotide length of the sequence is 20. The term "nucleotide length" is used herein interchangeably with "nucleotide number."

The term "transcript" as used herein can refer to a primary transcript that is synthesized by transcription of DNA and becomes a messenger RNA (mRNA) after processing, i.e., a precursor messenger RNA (pre-mRNA), and the processed mRNA itself. The term "transcript" can be interchangeably used with "pre-mRNA" and "mRNA." After DNA strands are transcribed to primary transcripts, the newly synthesized primary transcripts are modified in several ways to be converted to their mature, functional forms to produce different proteins and RNAs such as mRNA, tRNA, rRNA, lncRNA, miRNA and others. Thus, the term "transcript" can include exons, introns, 5' UTRs, and 3' UTRs.

The term "expression" as used herein refers to a process by which a polynucleotide produces a gene product, for example, a RNA or a polypeptide. It includes, without limitation, transcription of the polynucleotide into messenger RNA (mRNA) and the translation of an mRNA into a polypeptide. Expression produces a "gene product." As used herein, a gene product can be either a nucleic acid, e.g., a messenger RNA produced by transcription of a gene, or a polypeptide which is translated from a transcript. Gene products described herein further include nucleic acids with post transcriptional modifications, e.g., polyadenylation or splicing, or polypeptides with post translational modifications, e.g., methylation, glycosylation, the addition of lipids, association with other protein subunits, or proteolytic cleavage.

In determining the degree of "complementarity" between oligomers of the invention (or regions thereof) and the target region of the nucleic acid which encodes the mammalian gene, such as those disclosed herein, the degree of "complementarity" (also, "homology" or "identity") is expressed as the percentage identity (or percentage homology) between the sequence of the oligomer (or region thereof) and the sequence of the target region (or the reverse complement of the target region) that best aligns therewith. The percentage is calculated by counting the number of aligned bases that are identical between the two sequences, dividing by the total number of contiguous monomers in the oligomer, and multiplying by 100. In such a comparison, if gaps exist, it is preferable that such gaps are merely mismatches rather than areas where the number of monomers within the gap differs between the oligomer of the invention and the target region.

The term "complement" as used herein indicates a sequence that is complementary to a reference sequence. It is well known that complementarity is the base principle of DNA replication and transcription as it is a property shared between two DNA or RNA sequences, such that when they are aligned antiparallel to each other, the nucleotide bases at each position in the sequences will be complementary, much like looking in the mirror and seeing the reverse of things. Therefore, for example, the complement of a sequence of 5' "ATGC"3' can be written as 3' "TACG"5' or 5' "GCAT"3'. The terms "reverse complement", "reverse complementary" and "reverse complementarity" as used herein are interchangeable with the terms "complement", "complementary" and "complementarity."

The term “comparable to” is used herein to mean a value that is as much as 30% less than or more than the reference value to which it is being compared. As an example, if a value is as much as 30% less than the reference value, then the value is considered “comparable to” the reference value: e.g., 70 is comparable to 100, 80 is comparable to 100, 90 is comparable to 100, 100 is comparable to 100, 110 is comparable to 100, 120 is comparable to 100, and 130 is comparable to 100. A calcium oscillation level of a molecule that is comparable to the calcium oscillation level of a control means that the calcium oscillation level of the molecule is ±30%, ±20%, ±10%, or ±5% of the calcium oscillation level of the control.

The term “design” or “oligomer design” or “ASO Sequence” as used herein refers to a pattern of nucleotides (e.g., DNA) and nucleotide analogs (e.g., LNA) in a given sequence. As used herein, the design of an oligomer is shown by a combination of upper case letters and lower case letters. For example, an oligomer sequence of tatttccaaattcactttta (SEQ ID NO: 573) can have oligomer designs of ASO-002350 (TAtTTccaaattcactTTTA), ASO-002374 (TAtTTccaaattcacTtTTA), ASO-002386 (TATTtccaaattcaCTttTA), ASO-002227 (TATtTccaaattcactTTTA), ASO-002245 (TAttTCcaaattcactTTTA), ASO-002261 (TATtTccaaattcacTTtTA), ASO-002276 (ATttCcaaattcactTTTA), ASO-002228 (TATTtccaaattcaCtTtTA), ASO-002255 (TATTtccaaattcactTTTA), ASO-002285 (TATTtccaaattcacTTtTA), ASO-002230 (TATTtccaaattcacTtTTA), ASO-002256 (TATTtccaaattcAcTttTA), or ASO-002279 (TATTtccaaattcActTtTA), wherein the upper case letter indicates a nucleotide analog (e.g., LNA) and the lower case letter indicates a nucleotide (e.g., DNA)

Figure 2:
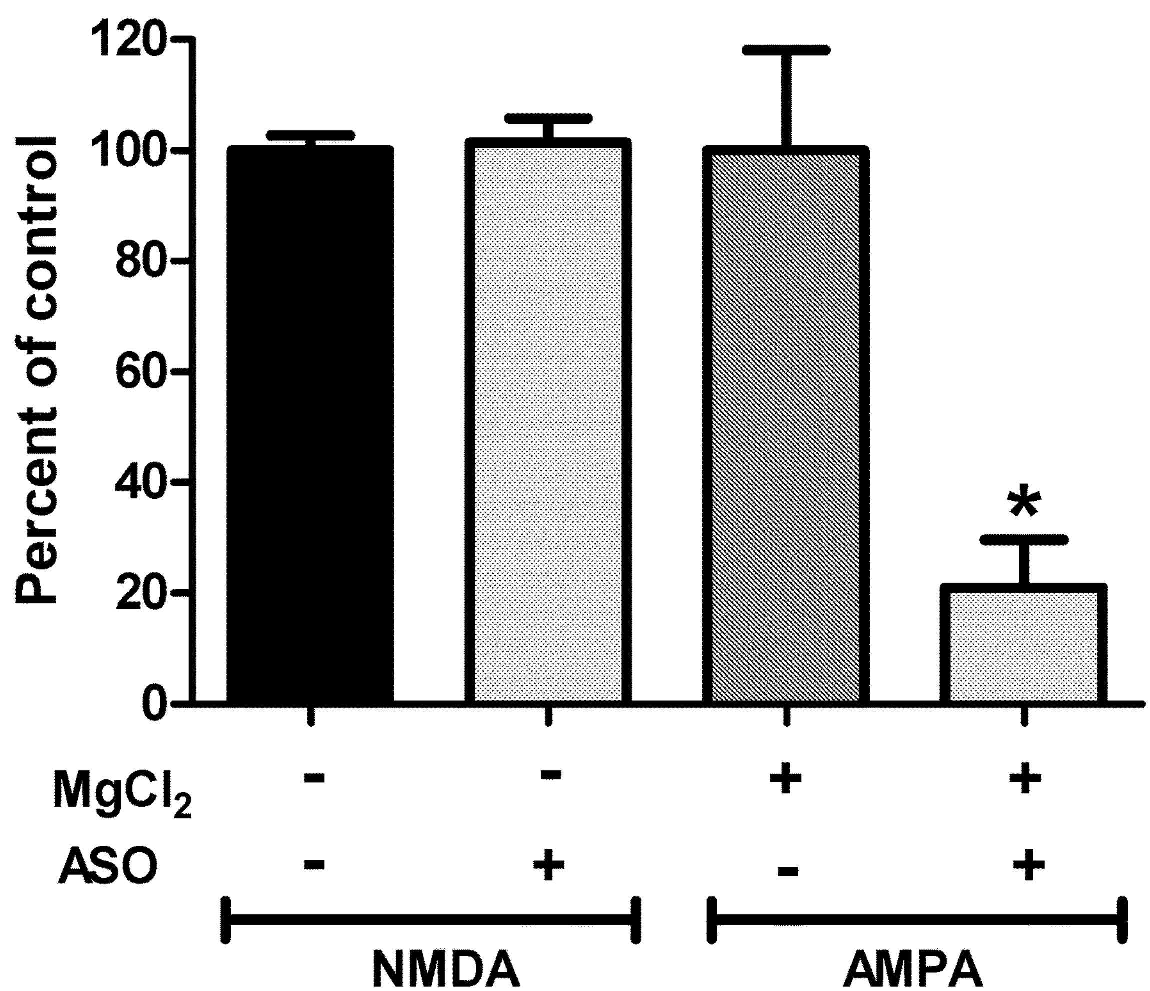
FIG. 2: Graph showing inhibition of AMPA mediated calcium oscillations by antisense oligomers as an indication of neuronal network activity disruption. Antisense oligomer inhibition of spontaneous calcium oscillations mediated by either NMDA or AMPA was assessed in the presence or absence of 1 mM $MgCl_2$ (representing 100% control in each case). Addition of 25 μM antisense oligomers (TGTgatgcaggaGTT) (SEQ ID NO: 304) (ASO-00007) inhibited AMPA receptor but not NMDA receptor mediated oscillations. The ASO and other oligomerss that behaved similarly, were shown to negatively impact central nervous system (CNS) network activity in vivo and electrophysiologic spontaneous neuronal activity in vitro (data not shown).

The term “chemical structure” of an oligomer as used herein refers to a detailed description of the components of the oligomers, e.g., nucleotides (e.g., DNA), nucleotide analogs (e.g., beta-D-oxy-LNA), nucleotide base (e.g., A, T, G, C, U, or MC), and backbone structure (e.g., phosphorothioate or phosphorodiester). For example, a chemical structure of ASO-002350 can be OxyTs OxyAs DNAts OxyTs OxyTs DNAcs DNAcs DNAas DNAas DNAas DNAts DNAts DNAcs DNAas DNAcs DNAts OxyTs OxyTs OxyTs OxyAs. FIGS. 2, 16B, and 20B lists non-limiting examples of chemical structures that can be applied to any one of the oligomers disclosed herein.

“Potency” is normally expressed as an IC50 or EC50 value, in nM or pM unless otherwise stated. IC50 is the median inhibitory concentration of a therapeutic molecule. EC50 is the median effective concentration of a therapeutic molecule relative to a vehicle or saline control. In functional assays, IC50 is the concentration that reduces a biological response, e.g., transcription of mRNA or protein expression, by 50% of the biological response that is achieved without the therapeutic molecule. In functional assays, EC50 is the concentration of a therapeutic molecule that produces 50% of the biological response, e.g., transcription of mRNA or protein expression. IC50 or EC50 can be calculated by any number of means known in the art.

By “toxic side effect” is meant an effect that causes debilitation of a living subject, including, but not limited to, death, pain, tremors, convulsions, seizures, an inhibition of movement, or loss of memory. A “toxic” compound can cause toxic side effects when a subject is exposed to the toxic compound, such as by injection, ingestion, inhalation or other routes, and is not suitable for administration in mammal, e.g., rodent. In one embodiment, the toxic side effect includes neurotoxicity in vivo. In another embodiment, the toxic side effect is in vivo acute neurotoxicity. A “neurotoxic” compound can alter the normal activity of the nervous system in such a way as to cause damage to nervous tissue, including brain tissue, such as neurons, and peripheral nervous tissue.

By “tolerable” is meant a molecule that is well tolerated by a live subject, e.g., a molecule that, when administered, causes no harmful effects that are either visible or can be tested for using general quality of life tests or by measuring in vivo tolerability scores as described herein.

By “subject” or “individual” or “animal” or “patient” or “mammal,” is meant any subject, particularly a mammalian subject, for whom diagnosis, prognosis, or therapy is desired. Mammalian subjects include humans, domestic animals, farm animals, sports animals, and zoo animals including, e.g., humans, non-human primates, dogs, cats, guinea pigs, rabbits, rats, mice, horses, cattle, bears, and so on.

An “effective amount” of a therapeutic molecule as disclosed herein is an amount sufficient to carry out a specifically stated purpose. An “effective amount” can be determined empirically and in a routine manner, in relation to the stated purpose.

Terms such as “treating” or “treatment” or “to treat” or “alleviating” or “to alleviate” refer to both (1) therapeutic measures that cure, slow down, lessen symptoms of, and/or halt progression of a diagnosed pathologic condition or disorder and (2) prophylactic or preventative measures that prevent and/or slow the development of a targeted pathologic condition or disorder. Thus, those in need of treatment include those already with the disorder; those prone to have the disorder; and those in whom the disorder is to be prevented. In certain embodiments, a subject is successfully “treated” for a disease or condition disclosed elsewhere herein according to the methods provided herein if the patient shows, e.g., total, partial, or transient alleviation or elimination of symptoms associated with the disease or disorder.

II. Methods of Using Calcium Oscillation Assays to Determine In Vivo Neurotoxicity The present disclosure provides methods for testing or determining the toxicity (e.g., in vivo acute neurotoxicity) of a molecule by measuring certain characteristics of the molecule. The present disclosure also provides methods for selecting a molecule having reduced toxic side effects. Such methods are helpful to reduce unnecessary killing of animals during testing of the molecule’s toxicity and/or enhance the possibilities that the molecules will be safe for in vivo administration. The present methods can also improve efficiency (i.e., shorten) the evaluation period of candidate molecules by reducing the screening time period for selection of molecules that do not exhibit in vivo acute neurotoxicity. The present methods comprise identifying molecules that have lower or reduced toxicity. For example, molecules can be assayed to determine if they have low toxicity (e.g., in vivo acute neurotoxicity), and if they are found to have low toxicity, the molecules are selected for use in further testing or administration to a subject such as a mammal. In some embodiments, if the molecule is found to have low toxicity, it is administered to a laboratory animal for further testing of the molecule.

Not being bound by any theory, the present disclosure identifies (i) a correlation between calcium oscillations of a molecule in vitro in neuronal cells and the sequence score of the molecule (e.g., polynucleotide comprising a sequence), (ii) a correlation between calcium oscillations of a molecule and the in vivo neurotoxicity of the molecule; (iii) a correlation between the sequence score of a molecule (e.g., polynucleotide comprising a sequence) and the in vivo neurotoxicity of the molecule, or (iv) any combination thereof. In one embodiment, the disclosure shows that a molecule exhibiting calcium oscillations in neuronal cells comparable to (i.e., less than 30% or higher than) the calcium oscillations in neuronal cells not exposed to the molecule shows less in vivo neurotoxicity when administered to a mammal in vivo. In another embodiment, the disclosure shows that a molecule exhibiting calcium oscillations in neuronal cells comparable to (i.e., less than 30% or higher than) the calcium oscillations in neuronal cells not exposed to the molecule has a sequence score equal to or greater than 0.2. In other embodiments, the disclosure shows that a molecule having a sequence score equal to or greater than 0.2 exhibits less in vivo neurotoxicity when the molecule is administered to a mammal in vivo. Therefore, identification of the correlations among the calcium oscillation assay, sequence score, and in vivo neurotoxicity allows one to predict the in vivo neurotoxicity based on the calcium oscillation in vitro assay and the sequence score. In a further embodiment, the present invention allows one to predict the in vivo neurotoxicity based on the calcium oscillation in vitro assay, the sequence score and the change in tubulin intensity in a cell as discussed further supra.

In one aspect, the disclosure sets forth a calcium oscillation assay as one way of measuring or predicting toxicity of a molecule. In another aspect, the disclosure provides a sequence score method to measure or predict toxicity of a molecule. In other aspects, the disclosure provides a combined method of using a calcium oscillation assay and a sequence score method. The disclosure also provides an in vivo tolerability assay that can be used separately or combined with the calcium oscillation assay and/or the sequence score method. Any other methods disclosed in this application and/or known in the art can further be combined with the calcium oscillation assay and/or the sequence score method.

II.A. Calcium Oscillation Assays

In one embodiment, the toxicity, e.g., in vivo acute neurotoxicity, of the molecule is tested by measuring intracellular free calcium oscillations (calcium oscillations) in vitro in neuronal cells which are in contact or have been in contact with the molecule. Examples of assays measuring calcium oscillations are discussed in further detail below. In some embodiments, the molecule is considered to have an acceptable toxicity (e.g., in vivo acute neurotoxicity) if the molecule does not significantly reduce calcium oscillations in a cell exposed to the molecule compared to the calcium oscillations in a control cell. In some embodiments, the control cell is a cell that has not been exposed to the test molecule, but otherwise is under the same condition as the cells exposed to the test molecule. In some embodiments, the calcium oscillation assay can include a positive control cell (i.e., a cell exposed to a molecule that is known to reduce calcium oscillations to an untolerable level) or a negative control cell (i.e., a cell exposed to a molecule that is known not to affect calcium oscillations in the cell). In another embodiment, the control cell is exposed to a medium that carries the tested molecule to the culture of neuronal cells, e.g., water, buffer, or saline, without the test molecule (i.e., vehicle control).

In one embodiment, the disclosure provides a method of testing, identifying, or determining in vivo acute neurotoxicity of a molecule comprising measuring calcium oscillations in vitro in neuronal cells which are in contact or have been in contact with the molecule. In another embodiment, the disclosure includes a method of testing, identifying, or determining in vivo acute neurotoxicity of a molecule comprising (1) adding the molecule to a culture of neuronal cells and (2) measuring calcium oscillations in vitro in the neuronal cells. In another embodiment, the disclosure provides a method of predicting in vivo acute neurotoxicity of a molecule comprising a step of (1) adding the molecule to a culture of neuronal cells and (2) measuring calcium oscillations in vitro in the neuronal cells.

In certain embodiments, the disclosure provides a method of testing, identifying, or determining in vivo acute neurotoxicity of a molecule or selecting or identifying a molecule having tolerable in vivo acute neurotoxicity comprising (i) measuring calcium oscillations in vitro in neuronal cells after adding the molecule in a culture of the neuronal cells, wherein the calcium oscillations in the neuronal cells are comparable to or higher than the calcium oscillations of vehicle controls and (ii) administering the molecule to a human in need thereof.

In other embodiments, the disclosure includes a method of selecting or identifying a molecule having tolerable in vivo acute neurotoxicity comprising measuring calcium oscillations in vitro in neuronal cells which are in contact with the molecule, wherein the contacted neuronal cells exhibit calcium oscillations at a level comparable to or higher than that of control cells. In some embodiments, the disclosure provides a method of selecting or identifying a molecule having tolerable in vivo acute neurotoxicity comprising a step of (i) adding a molecule to a culture of neuronal cells and (ii) measuring calcium oscillations in the neuronal cells in vitro, wherein the neuronal cells with the molecule exhibit calcium oscillations at a level comparable to or higher than that of control cells.

Calcium oscillations are important for the proper functions of neuronal cells. Networks of cortical neurons have been shown to undergo spontaneous calcium oscillations resulting in the release of the neurotransmitter glutamate. Calcium oscillations can also regulate interactions of neurons with associate glia, in addition to other associated neurons in the network, to release other neurotransmitters in addition to glutamate. Regulated calcium oscillations are required for homeostasis of neuronal networks for normal brain function. (See, Shashank et al., *Brain Research,* 1006 (1): 8-17 (2004); Rose et al., Nature Neurosci., 4:773-774 (2001); Zonta et al., *J. Physiol Paris.,* 96(3-4):193-8 (2002); Pasti et al., *J. Neurosci.,* 21(2): 477-484 (2001).) Glutamate also activates two distinct ion channels, α-amino-3-hydroxy-5-methyl-4-isoxazolepropionic acid (AMPA) receptors and N-methyl-D-aspartate (NMDA) receptors.

In some embodiments, the calcium oscillations measured in the present methods are AMPA-dependent calcium oscillations. In some embodiments, the calcium oscillations are NMDA-dependent calcium oscillations. In some embodiments, the calcium oscillations are gamma-aminobutyric acid (GABA)-dependent calcium oscillations. In some embodiments, the calcium oscillations can be a combination of two or more of AMPA-dependent, NMDA-dependent or GABA-dependent calcium oscillations.

In certain embodiments, the calcium oscillations measured in the present methods are AMPA-dependent calcium oscillations. In order to measure AMPA-dependent calcium oscillations, the calcium oscillations can be measured in the presence of $Mg^{2+}$ ions (e.g., $MgCl_2$). In certain embodiments, the method further comprises adding $Mg^{2+}$ ions (e.g., $MgCl_2$) at an amount that allows for detection of AMPA-dependent calcium oscillations. In some embodiments, the effective ion concentration allowing for detection of AMPA-dependent calcium oscillations is at least about 0.5 mM. In other embodiments, the effective ion concentration of $Mg^{2+}$ ions (e.g., $MgCl_2$) to induce AMPA-dependent calcium oscillations is at least about 0.6 mM, at least about 0.7 mM, at least about 0.8 mM, at least about 0.9 mM, at least about 1 mM, at least about 1.5 mM, at least about 2.0 mM, at least about 2.5 mM, at least about 3.0 mM, at least about 4 mM, at least about 5 mM, at least about 6 mM, at least about 7 mM, at least about 8 mM, at least about 9 mM, or at least about 10 mM. In a particular embodiment, the concentration of $Mg^{2+}$ ions useful for the methods is 1 mM. In certain embodiments, the concentration of $Mg^{2+}$ ions (e.g., $MgCl_2$) useful for the present methods is about 1 mM to about 10 mM, about 1 mM to about 15 mM, about 1 mM to about 20 mM, or about 1 mM to about 25 mM. $Mg^{2+}$ ions may be added by the addition of magnesium salts, such as magnesium carbonate, magnesium chloride, magnesium citrate, magnesium hydroxide, magnesium oxide, magnesium sulfate, and magnesium sulfate heptahydrate.

In some embodiments, calcium oscillations are measured in the present method through the use of fluorescent probes which detect the fluctuations of intracellular calcium levels. For example, detection of intracellular calcium flux can be achieved by staining the cells with fluorescent dyes which bind to calcium ions (known as fluorescent calcium indicators) with a resultant, detectable change in fluorescence (e.g., Fluo-4 AM and Fura Red AM dyes available from Molecular Probes. Eugene, Oreg., United States of America).

Fluorescent dyes useful for the calcium oscillation assay often provide for ratiometric detection on intracellular calcium flux by calibrating fluorescence intensities measured a wavelength. In some embodiments, fluorescence of the stained cells (including stained individual cells) can be measured by confocal, or standard, fluorescence microscopy, optionally at a number of time points or continuously (e.g., real-time) to provide, for example, time lapse measurements. Those skilled in the art will appreciate that there can be other suitable methods for measuring intracellular calcium flux, for example, by viral transduction of genetically encoded calcium indicators, etc.

In one embodiment, the calcium oscillations measured in the present methods are the cumulative increase in calcium oscillations within a culture of neuronal cells, whereby the time to reach the maximum fluorescence signal constitutes the magnitude of the calcium response. The fluorescent measurements can be analyzed to identify oscillations in intracellular calcium flux and/or a "threshold" representing a point at which the intracellular calcium flux of a given oscillation is progressing either to a maximum or minimum. In another embodiment, the calcium oscillations measured in the present methods are the frequency of calcium oscillations. The term "oscillation frequency" refers to the time between oscillations. In an embodiment, the oscillation frequency can be determined by a time interval from commencement of a first oscillation in intracellular calcium flux to a commencement of a second oscillation in intracellular calcium flux. In other embodiments, the calcium oscillations measured in the present methods are the combination of the oscillation frequency and magnitude.

In some embodiments, the calcium oscillations were measured by using any methods known in the art. In certain embodiments, the calcium oscillations can be measured by a fluorescent plate reader, e.g., Flexstation 2 and 3 plate reader or FLIPR™ (Fluorescence Imaging Plate Reader). In other embodiments, the calcium oscillations can be measured as shown in Murphy et al., *J. Neurosci.* 12, 4834-4845 (1992).

Neuronal cells useful for the invention can be isolated from mammalian neuronal cells, e.g., mouse neuronal cells, rat neuronal cells, human neuronal cells, or other neuronal cells. In certain embodiments, the neuronal cells do not express an endogenous transcript encoding a protein, for example, if a human protein is targeted in a mouse cell, the mouse cell has the endogenous version of the transcript deleted from its genome. In certain embodiments, primary neurons can be generated by papain digestion according to manufacturer's protocol (Worthington Biochemical Corporation, LK0031050). In one embodiment, forebrains are prepared by the following example. Forebrains can be dissected from hTau mouse E18 BAC-Tg embryos expressing the entire target gene on a murine MAPT-null background and can be incubated at 37° C. for 30-45 minutes in papain/DNase/Earle's balanced salt solution (EBSS) solution. After trituration and centrifugation of cell pellet, the reaction is stopped by incubation with EBSS containing protease inhibitors, bovine serum albumin (BSA) and DNase. The cells can be triturated and washed with Neurobasal (NB, Invitrogen) supplemented with 2% B-27, 100 μg/ml penicillin, 85 μg/ml streptomycin, 0.5 mM glutamine. The cells are plated in supplemented NB media onto poly-D-lysine-coated 96-well optical imaging plates (BD Biosciences) at 15,000 cells/well.

In some embodiments, the calcium oscillations for a molecule having tolerable in vivo acute neurotoxicity are compared with the calcium oscillations in a cell not exposed to the molecule. In some embodiments, calcium oscillations for a molecule with tolerable in vivo acute toxicity are greater than or equal to about 250%, greater than or equal to about 240%, greater than or equal to about 230%, greater than or equal to about 220%, greater than or equal to about 210%, greater than or equal to about 200% greater than or equal to about 190%, greater than or equal to about 180%, greater than or equal to about 170%, greater than or equal to about 160%, greater than or equal to about 150%, greater than or equal to about 140%, greater than or equal to about 130%, greater than or equal to about 120%, greater than or equal to about 110%, greater than or equal to about 100%, greater than or equal to about 99%, greater than or equal to about 98%, greater than or equal to about 97%, greater than or equal to about 96%, greater than or equal to about 95%, greater than or equal to about 90%, greater than or equal to about 85%, greater than or equal to about 80%, greater than or equal to about 75%, or greater than or equal to about 70% of calcium oscillations in a vehicle control cell (e.g., water or saline). As used herein, the term "greater than or equal to" can be interchangeably used with "at least." In other embodiments, the calcium oscillations with tolerable in vivo acute toxicity are greater than or equal to 100% of the calcium oscillations in the vehicle control cells. In certain embodiments, the calcium oscillations with tolerable in vivo acute toxicity are greater than or equal to about 70% of the calcium oscillations in the vehicle control cells. In certain embodiments, the calcium oscillations with tolerable in vivo acute toxicity are greater than or equal to about 75% of the calcium oscillations in the vehicle control cells. In other embodiments, the calcium oscillations with tolerable in vivo acute toxicity are about 70% to about 250%, about 70% to about 200%, about 75% to about 200%, about 70% to about 180%, about 75% to about 150%, about 80% to about 200%, about 90% to about 200%, about 100% to about 200%, or about 80% to about 250% of the calcium oscillations in the vehicle control cells.

In some embodiments, the calcium oscillations in a cell exposed to a molecule having a tolerable in vivo acute neurotoxicity exhibits less than about 25%, less than about 20%, less than about 15%, less than about 10%, less than about 5%, or less than about 1% reduction compared to the calcium oscillations in a vehicle control cell. In other embodiments, the calcium oscillations in a cell exposed to a molecule having tolerable in vivo acute neurotoxicity are less than about 30%, less than about 25%, about 20%, about 15%, about 10%, about 5%, about 4%, about 3%, about 2%, or about 1% reduced compared to the calcium oscillations in a vehicle control cell.

In certain embodiments, molecules that cause greater than desired reductions in calcium oscillations are considered to be molecules that have unacceptable neurotoxicity. In these embodiments, molecules that cause a greater than desired reduction in calcium oscillations are considered as having a risk of toxic side effects if administered to a subject. In certain embodiments, the present disclosure provides a method of identifying or determining a molecule having intolerable in vivo neurotoxicity comprising measuring calcium oscillations in vitro in neuronal cells after being in contact with the molecule in the neuronal cells. In some embodiments, the calcium oscillations of a molecule having intolerable in vivo neurotoxicity are less than 70%, 60%, 50%, 40%, 30%, 20%, 10%, 5%, or 1% of the calcium oscillations in a vehicle control cell. In certain embodiments, the present disclosure incudes a method of identifying or determining a molecule having intolerable in vivo neurotoxicity comprising measuring calcium oscillations in vitro in neuronal cells after being in contact with the molecule in the neuronal cells, wherein the calcium oscillations of the molecule is equal to or less than 50% of the calcium oscillations in a vehicle control cell.

In some embodiments, the molecule is a therapeutic molecule. In other embodiments, the molecule comprises a small molecule, a polynucleotide, a protein, a peptide, or any combination thereof. Non-limiting examples of the molecules are described elsewhere herein.

II.B. Sequence Score Methods

The present disclosure is also directed to a method of testing or determining in vivo neurotoxicity of a molecule (e.g., polynucleotide) comprising a nucleotide sequence. In some embodiments, the method comprises measuring a sequence score calculated by formula (I):

$$\frac{\#\text{ of } C \text{ nucleotides and analogs thereof} - \#\text{ of } G \text{ nucleotides and analogs thereof}}{\text{Total nucleotide length (number)}}. \tag{I}$$

In other embodiments, the oligomer of the invention has a sequence score greater than or equal to 0.2.

In some embodiments, the method comprises measuring a sequence calculated by formula (IA):

$$\frac{\#\text{ of } C \text{ nucleotides and 5-methylcytosine nucleotides} - \#\text{ of } G \text{ nucleotides}}{\text{Total nucleotide length}}. \tag{IA}$$

In other embodiments, the oligomer of the invention has a sequence score greater than or equal to 0.2.

In these embodiments, a sequence score of greater than or equal to a cut off value corresponds to a reduced neurotoxicity of the oligomer.

For example, a nucleotide sequence of ATGCATGCATGCATGC (SEQ ID NO: 3) has a sequence score of 0 ((4Cs-4Gs)/16). The sequence of GTGCGTGCGTGCGTGC (SEQ ID NO: 732) has a sequence score of −0.25 ((4Cs-8Gs)/16). The sequence of CTGCCTGCCTGCCTGC (SEQ ID NO: 733) has a sequence score of 0.25 ((8Cs-4Gs)/16). In certain embodiments, a polynucleotide comprising a nucleotide sequence (e.g., an oligomer) is considered to have an acceptable neurotoxicity if it has a sequence score greater than or equal to about 0.2, greater than or equal to about 0.25, greater than or equal to about 0.3, greater than or equal to about 0.35, greater than or equal to about 0.4, greater than or equal to about 0.45, greater than or equal to about 0.5, greater than or equal to about 0.55, greater than or equal to about 0.6, greater than or equal to about 0.65, greater than or equal to about 0.7, greater than or equal to about 0.75, greater than or equal to about 0.8, greater than or equal to about 0.85, greater than or equal to about 0.9, greater than or equal to about 0.95, greater than or equal to about 1.0, greater than or equal to about 1.5, greater than or equal to about 2.0, greater than or equal to about 3.0 or greater than or equal to about 4.0. In certain embodiments, a polynucleotide is considered to have an acceptable neurotoxicity if it has a sequence score greater than or equal to 0.2, greater than or equal to 0.25, greater than or equal to 0.3, greater than or equal to 0.35, greater than or equal to 0.4, greater than or equal to 0.45, greater than or equal to 0.5, greater than or equal to 0.55, greater than or equal to 0.6, greater than or equal to 0.65, greater than or equal to 0.7, greater than or equal to 0.75, greater than or equal to 0.8, greater than or equal to 0.85, greater than or equal to 0.9, greater than or equal to 0.95, greater than or equal to 1.0, greater than or equal to 1.5, greater than or equal to 2.0, greater than or equal to 3.0 or greater than or equal to 4.0. In some embodiments, the sequence score of a polynucleotide with acceptable neurotoxicity is equal to or greater than 0.2.

In certain embodiments, molecules comprising nucleotide sequences that have a sequence score below the set thresholds are considered to be molecules that have unacceptable neurotoxicity. In these embodiments, molecules having a sequence score below the set thresholds are considered as having a risk of toxic side effects if administered to a subject.

In certain embodiments, any of the above methods for selecting a molecule can be used in combination. When used in combination, if the molecule is selected as a molecule with acceptable neurotoxicity for more than one method, then the molecule is considered to have a greater chance of having acceptable neurotoxicity when administered to a test subject or patient.

In certain embodiments, the present disclosure includes a method of selecting a polynucleotide having tolerable in vivo acute neurotoxicity comprising (i) performing a calcium oscillation assay disclosed herein and (ii) calculating a sequence score disclosed herein, wherein the calcium oscillations of the polynucleotide are equal to or greater than 75% of the calcium oscillations in a vehicle cell and the sequence score of the polynucleotide is greater than or equal to 0.25. In some embodiments, the calcium oscillation assay and/or the sequence score method are sufficient to predict, identify, or determine in vivo acute neurotoxicity of a molecule and do not require additional in vivo tolerability studies. The calcium oscillation assay and/or the sequence score method can be especially useful for screening numerous candidate molecules to determine their in vivo neurotoxicities.

II.C. In Vivo Tolerability Assays

In other embodiments, the present invention is also directed to a method of selecting or identifying a molecule having tolerable in vivo neurotoxicity by performing in vivo tolerability studies. When the number of candidate molecules are small, an in vivo tolerability study can provide a direct indication of in vivo neurotoxicity. In other embodiments, an in vivo tolerability study can be used in combination with the calcium oscillation assay and/or the sequence score method. The in vivo tolerability study can also be used after selecting a small number of candidate molecules after performing the calcium oscillation assay and/or sequence score calculation. In some embodiments, the in vivo tolerability score is measured by administering the molecule to a mammal, e.g., to the brain of the mammal, e.g., via intracerebroventricular (ICV) administration or intrathecal (IT) administration.

For example, molecules can be injected into a laboratory animal by ICV or IT. The laboratory animal can be a rodent, such as a mouse, rat, guinea pig or hamster, but can also be another animal typically used in laboratory testing. In certain embodiments, the animals are observed at 0.5 hour, 1 hour, 1.5 hours, 2 hours, 2.5 hours, 3 hours, 3.5 hours, 4 hours, 4.5 hours or 5 hours following the injection of a molecule. Animals are observed for behavioral side effects and scored for the severity of side effects on a scale of zero (no side effects) to 20 (convulsions resulting in euthanasia). The tolerability scale can be divided into at least one of the following neurobehavioral categories: 1) hyperactivity 2) decreased activity and arousal 3) motor dysfunction/ataxia 4) abnormal posture and breathing and 5) tremor/convulsions. In some embodiments, the tolerability scale comprises at least two, at least three, at least four, or at least five neurobehavioral categories. Each category is scored on a scale of 0-4, with the worst possible total score of 20 and the best possible total score of 0. Animals are observed for changes in behavior, for example in the home cage, but they can be observed in other environments. In some embodiments, animals are removed from the home cage for more detailed observations which included measurement of grip strength and righting reflex.

Figure 3:
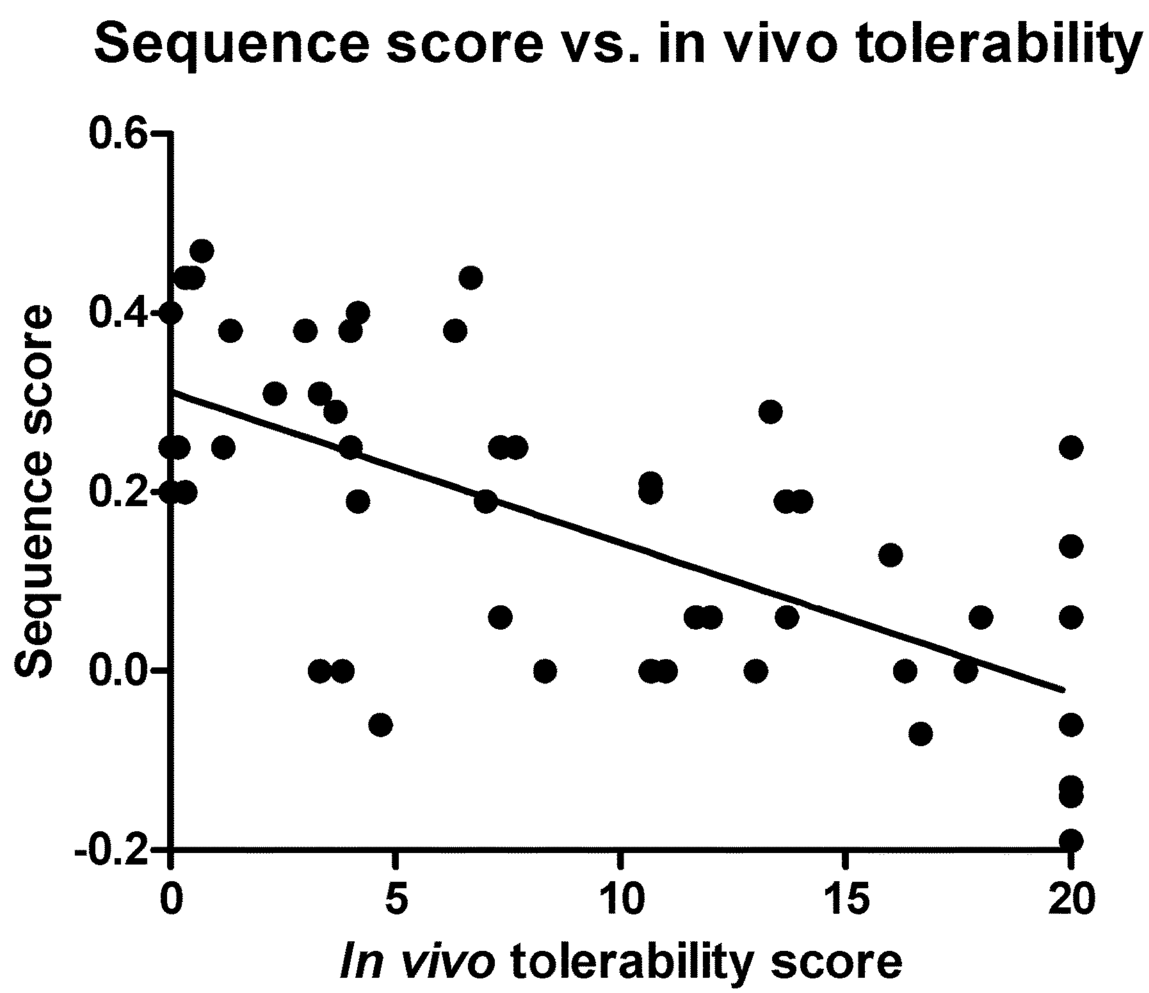
FIG. 3: Correlation analysis of sequence score vs. in vivo tolerability score. Sequence score for each oligomer was calculated by inserting appropriate numbers in the formula: ((number of C nucleotides or the analogs−number of G nucleotides)/nucleotide length (number) in the oligomer). In vivo tolerability scores were calculated based upon observations following a single intra-cerebroventricular (i.c.v.) administration of 100 μg oligomers in mice or intra-thecal (i.t.) administration of 900 μg oligomers or up to 1500 μg in rats. The rodents were observed under five categories: 1) hyperactivity; 2) decreased activity and arousal; 3) motor dysfunction and/or ataxia; 4) abnormal posture and breathing; and 5) tremor and/or convulsions. The total in vivo tolerability score is the sum of five unit scores; each of the unit scores is measured on a scale of 0-4. Therefore, the total score of in vivo tolerability can range from 0 to 20. The sequence score calculated by the formula is on the X-axis, and the in vivo tolerability score is on the Y-axis.

In certain embodiments, an in vivo cumulative tolerability threshold following an injection of a molecule is set at 4. For example, the correlation analysis in FIG. 3 shows that the molecules having in vivo tolerability lower than 4 tend to have a sequence score equal to or higher than 0.2.

In other embodiments, the disclosure includes a method of identifying or selecting a molecule having tolerable in vivo neurotoxicity comprising (i) performing a calcium oscillation assay, (ii) calculating sequence score, (iii) performing an in vivo tolerability study, and (iv) administering the molecule to a mammal in need of treatment of a disease or condition.

II.D. Tubulin Intensity Assays

In certain embodiments, the methods of the disclosure further comprise measuring long term in vivo toxicities of a molecule. For example, long term toxicities can be determined by measuring the change in tubulin intensity in a cell by the molecule when the cell comes in contact with a molecule. In certain embodiments, the change in tubulin intensity is measured along with one or both of the change in calcium oscillation, sequence score, and/or in vivo tolerability assay. Examples of assays measuring the change in tubulin intensity in a cell are provided below. In some embodiments, the molecule exhibits tubulin intensity in a cell greater than or equal to 99%, greater than or equal to 98%, greater than or equal to 97%, greater than or equal to 96%, greater than or equal to 95%, greater than or equal to 90%, greater than or equal to 85%, greater than or equal to 80%, greater than or equal to 75%, or greater than or equal to 70% of tubulin intensity in a cell that is not exposed to the molecule, i.e., a control cell, as defined above. In some embodiments, the tubulin intensity in a cell that is not exposed to the tested molecule is referred to as the tubulin intensity in a control cell. In some embodiments, the molecule reduces less than about 30%, less than about 25%, less than about 20%, less than about 15%, less than about 10%, less than about 5%, or less than about 1% of the tubulin intensity in a vehicle control cell.

II.E. Behavioral Test

The present methods can further comprise measuring a behavioral performance of an animal by a molecule. In one embodiment, the method comprises a behavioral test score, which can be measured by administering the molecule to a mammal and grading the mammal's behavioral performance. In certain embodiments, the behavioral test is a short term memory test, a spatial learning and memory test, a gait analysis test, or any combination thereof. In one embodiment, the behavioral performance is measured by injecting the molecule to a mammal, e.g., a brain of a mammal, e.g., intracerebroventricular (ICV) or intrathecal (IT) administration, and grading the mammal's behavioral performance on a scale of 0 to 4. In certain embodiments, the behavioral score is less than or equal to the total score of 3, the total score of 2, the total score of 1, or the total score of 0. In some embodiments, the behavioral score is determined as described in Example 5 below.

In some embodiments, the behavioral score is measured by the following methods, including a novel object rejection test, a water maze test, a gait analysis test, and/or any combination thereof. Therapeutic molecules are injected into a laboratory animal by ICV or IT. The laboratory animal can be a mammal, e.g., a rodent, such as a mouse, rat, guinea pig or hamster, but can also be another animal typically used in laboratory testing. In certain embodiments, the animals are observed at about 0.5 hour, about 1 hour, about 1.5 hours, about 2 hours, about 2.5 hours, about 3 hours, about 3.5 hours, about 4 hours, about 4.5 hours or about 5 hours following the injection of the molecule.

In one embodiment, a behavioral score is obtained with a novel object recognition test. Short term recognition memory can be measured using the novel object recognition (NOR) task. NOR testing is based on the spontaneous behavior of rodents to explore a novel object more than a familiar one (Dodart et. al., Neuroreport (1997) 8(5): 1173-8; Ennaceur and Delacour, Behay. Brain Res. (1988) 31 (1):47-59). The NOR testing can be used similar to the test shown in Example 5, or can be modified as necessary.

In one embodiment, a behavioral score is obtained with a water maze test, such as the Morris Water Maze. Spatial learning and memory can be assessed based on a Morris Water Maze test as shown in Morris J. Neurosci. (1984) 11(1):47-60) or the test shown in Example 5 herein. In another embodiment, a spatial learning and memory test can be assessed by a modified Morris Water Maze test as necessary.

In one embodiment, a behavioral score is obtained with a gait analysis test, such as the Catwalk. The Catwalk (Noldus, The Netherlands) is an automated and computerized gait-analysis technique that allows objective quantification of multiple static and dynamic gait parameters. The gait analysis test can be measured by the Catwalk assay shown in Example 5 or a modified Catwalk test as necessary.

Statistical analysis of behavioral test data can be analyzed using statistical analysis methods known to those of skill in the art. In some embodiments, statistical analyses for behavioral tests are conducted using GraphPad Prism (GraphPad Software, Inc., La Jolla, Calif.). For NOR, data are analyzed using either a paired t-test for within-group analyses or by an ANOVA followed by a Dunnett's post-hoc test for between group analyses. For Morris Water Maze (MWM), a repeated MWM ANOVA is used to analyze the acquisition phase and a one-way ANOVA followed by Dunnett's post-hoc for probe trial analyses.

Not being bound by any theory, the molecule with less reduction (70% or higher) in calcium oscillations compared to a control (e.g., saline) has a higher sequence score (e.g., higher than 0.2). Also not being bound by any theory, the molecule with less reduction (70% or higher) in calcium oscillations compared to a control and a higher sequence score (higher than 0.2) has a lower in vivo behavioral score (e.g., less than 4). In other embodiments, the molecule with less reduction (70% or higher) in calcium oscillations compared to a control and a higher sequence score (higher than 0.2) has tolerable in vivo acute neurotoxicity.

II.F. Diagnostic or Therapeutic Methods

The molecules selected according to the present methods can be utilized as research reagents for, for example, diagnostics, therapeutics and prophylaxis. In certain embodiments, the invention provides a method for both selecting a molecule and then utilizing the molecule.

In other embodiments, the molecules selected according to the present methods are therapeutic molecules. In still other embodiments, the method comprising a calcium oscillation assay, a sequence score method, and/or in vivo tolerability test can further comprise administering the selected molecule to a subject in need thereof.

Therefore, for therapeutics, an animal or a human, suspected of having a disease or disorder can be treated by administering molecules in accordance with this disclosure. Further provided are methods of treating a mammal, such as treating a human, suspected of having or being prone to a disease or condition by administering a therapeutically or prophylactically effective amount of one or more of the molecules of the disclosure. In some embodiments, the disclosure provides a method of treating a mammal, e.g., a human, comprising (1) selecting a molecule having tolerable in vivo acute neurotoxicity as described elsewhere herein (e.g., calcium oscillation assay, sequence score calculation, and/or in vivo tolerability study) and (2) administering the molecule to the mammal. The molecules, a conjugate or a pharmaceutical composition according to the invention is typically administered in an effective amount. In some embodiments, the molecules or conjugate of the invention is used in therapy.

The disclosure also provides a method of administering a molecule to a subject for the treatment of a neurological disease or condition. In certain embodiments, the neurological disorder is a neurodegenerative disorder, an epileptic disorder, an idiopathic adult epileptic disorder, or any combination thereof. In other embodiments, the disease or condition is a neurodegenerative disorder with tauopathy (i.e., (a neurodegenerative disease which involves accumulation of tau protein in the brain), an epileptic disorder with tauopathy (an epileptic disorder which involves accumulation of tau protein in the brain), an epileptic disorder without tauopathy (an epileptic disorder which does not involve accumulation of tau protein in the brain), an idiopathic adult epileptic disorder without tauopathy (an idiopathic adult epileptic disorder which does not involve accumulation of tau protein in the brain), or any combination thereof. In certain other embodiments, the disease or condition for treatment or prophylaxis is a neurodegenerative disease with tauopathy.

In certain embodiments, the disease or condition is progressive supranuclear palsy, Down syndrome, dementia pugilistica (chronic traumatic encephalopathy and other traumatic brain injury), frontotempotal dementia with parkinsonism linked to chromosome 17 (FTDP-17), Lytico-Bodig disease (Parkinson-dementia complex of Guam), Tangle-predominant dementia, ganglioglioma, gangliocytoma, meningioangiomatosis, subacute sclerosing panencephalitis, lead encephalopathy, Hemimegalencephaly, tuberous sclerosis, Hallervorden-Spatz disease, Pick's disease, corticobasal ganglionic degeneration, argyrophilic grain disease, corticobasal degeneration, lipofuscinosis, frontotemporal dementia, supranuclear palsy, and frontotemporal lobar degeneration, a disease of brain network dysfunction (e.g., all forms of epilepsy and depression), dravet syndrome, a spinal cord disorder, a peripheral neuropathy, a cranial nerve disorder (e.g., Trigeminal neuralgia), an autonomic nervous system disorder (e.g., dysautonomia or multiple system atrophy), a movement disorder of a central and peripheral nervous system (e.g., Parkinson's disease, essential tremor, amyotrophic lateral sclerosis, Tourette's Syndrome, multiple sclerosis or various types of peripheral neuropathy), a sleep disorder (e.g., Narcolepsy), migraine or other types of headache (e.g., cluster headache and tension headache), lower back and neck pain, central neuropathy, a neuropsychiatric illness, attention deficit hyperactivity disorder, autism, Huntington's disease, Rett Syndrome, Angelman syndrome, organic psychosis, an infection of the brain or spinal cord (including meningitis), or a prion disease), anemia, cancer, leukemia, an inflammatory condition or an autoimmune disease (e.g. arthritis, psoriasis, lupus erythematosus, multiple sclerosis), a bacterial infection, and any combination thereof.

In certain other embodiments, the disease or condition is a neurodegenerative disease with tauopathy, e.g., progressive supranuclear palsy, frontotemporal dementia-tau (FTD-tau), frontotemporal dementia and parkinsonism linked to chromosome 17 (FTDP-17), corticobasal degeneration (CBD), traumatic brain injury, chronic traumatic encephalopathy, HIV associated neurocognitive disorders, Argyrophilic grain disease, Down syndrome-Alzheimer's disease, Amnestic mild cognitive impairment-Alzheimer's disease, Parkinson's disease dementia, Hallervorden-Spatz disease (Pantothenate kinase-associated neurodegeneration), Niemann Pick disease type C, Myotonic dystrophy, Amyotrophic lateral sclerosis, Parkinson's disease or Huntington's disease. In certain embodiments, the disease or condition is an epileptic disorder with tauopathy, e.g., Hemimegalencephaly, Tuberous sclerosis complex, Focal cortical dysplasia type 2b, or Ganglion cell tumors. In certain embodiments, the disease or condition is an epileptic disorder without tauopathy, e.g., Dravet Syndrome (severe myoclonic epilepsy of infancy), Temporal lobe epilepsy, Ohtahara syndrome (early infantile epileptic encephalopathy with suppression bursts), Lafora body disease, Generalized epilepsy with febrile seizures, Infantile spasms (West syndrome), Lennox Gastaut syndrome, Angelman Syndrome, Rett Syndrome, Landau Kleffner syndrome. In certain embodiments, the disease or condition is an idiopathic adult epileptic disorder without tauopathy, e.g., focal seizures, simple focal seizures (no loss of consciousness), focal dyscognitive seizures (impairment of consciousness), focal seizure evolving to generalised tonic-clonic (GTC) convulsions, generalised seizures (convulsive or non-convulsive with bilateral discharges involving subcortical structures), absence seizures, myoclonic seizures, clonic seizures, tonic seizures, tonic-clonic seizures or atonic seizures. In certain embodiments, the disease or condition is an autistic disorder, an autism spectrum disorder (e.g., as defined in the Diagnostic and Statistical Manual of Mental Disorders V (DSM-V)), an Asperger's disorder or a pervasive developmental disorder.

The invention further provides for a molecule according to the invention, for use for the treatment of one or more of the diseases associated with neuronal cells or referred to herein, such as a disease selected from Alzheimer's disease, progressive supranuclear palsy, Down syndrome, dementia pugilistica (chronic traumatic encephalopathy and other traumatic brain injury), frontotemporal dementia with parkinsonism linked to chromosome 17 (FTDP-17), Lytico-Bodig disease (Parkinson-dementia complex of Guam), Tangle-predominant dementia, ganglioglioma, gangliocytoma, meningioangiomatosis, subacute sclerosing panencephalitis, lead encephalopathy, Hemimegalencephaly, tuberous sclerosis, Hallervorden-Spatz disease, Pick's disease, corticobasal ganglionic degeneration, argyrophilic grain disease, corticobasal degeneration, lipofuscinosis, frontotemporal dementia, supranuclear palsy, and frontotemporal lobar degeneration (reviewed in Frost et. al., Trends Cell Biol (2015) 25: 216-53; Dyment et. al., Neurobiol. Aging (2014) Sep. 6: S0197-4580; Moussaud et. al., Mol. Neurodeg (2014) 29:43 Ross et. al., South Med. J. (2014) 107: 715-21), Huntington's disease, Rett Syndrome, and Angelman syndrome. In addition, the invention provides for therapeutic molecule use for the treatment diseases of brain network dysfunction including all forms of epilepsy and depression (Inoue et. al., Epilepsy (2012) 102: 8-12; Xi et. al., Med Hypotheses (2011) 76: 897-900; Hou et. al., Can. J. Psychiatry (2004) 3: 164-71).

The disclosure also provides for the use of the molecules or conjugates of the invention as described for the manufacture of a medicament for the treatment of a disease or disorder as referred to herein, or for a method of the treatment of as a disorder as referred to herein. Also provided is a composition for use in treating a disease or disorder as referred to herein.

III. Molecules (e.g., Therapeutic Molecules)

The molecules to be screened or selected according to the present invention include therapeutic molecules. In one embodiment, a therapeutic molecule comprises a protein, a peptide, a polynucleotide (e.g., an oligomer), a saccharide, a lipid, a liposome and a particulate, a biomaterial, a pharmaceutical, a vitamin, a nucleic acid, an amino acid, a polypeptide, an enzyme cofactor, a steroid, a carbohydrate, heparin, a metal containing agent, a receptor antagonist, a receptor agonist, a receptor or a portion of a receptor, an extracellular matrix protein, a cell surface molecule, an antigen, a hapten, a small molecule, or any combination thereof.

In certain embodiments, a therapeutic molecule is a protein comprising cytokines, enzymes, growth factors, monoclonal antibody, antibody fragments, single-chain antibodies, albumin, immunoglobulins, clotting factors, somatropin, amylase, lipase, protease, cellulose, urokinase, galactosidase, staphylokinase, hyaluronidase, tissue plasminogen activator, or any combination thereof.

In one embodiment, a molecule of the invention comprises at least one of a therapeutic molecule that is an antigen binding site (e.g., an antigen binding site of an antibody, antibody variant, or antibody fragment), a receptor binding portion of ligand, or a ligand binding portion of a receptor.

In another embodiment, a molecule of the invention targets one or more endogenously produced proteins or peptides in vivo, one or more mRNAs or pre-mRNAs encoding the proteins or peptides, or one or more genes encoding the proteins or peptides. In some embodiments, the molecule comprises a polynucleotide (e.g., oligomer), a nucleotide, or a small molecule.

A molecule also can comprise any therapeutic small molecule or drug as the therapeutic molecule useful for the methods disclosed herein. Small molecules can comprise any therapeutic molecules that is not a peptide, a polypeptide, a protein, and a polynucleotide. Small molecule can include a single nucleotide or nucleoside, e.g., RNA or DNA.

In one embodiment, the therapeutic molecule modulates cellular activation or inhibition (e.g., by binding to a cell surface receptor and resulting in transmission of an activating or inhibitory signal). In one embodiment, the therapeutic molecule is capable of initiating transduction of a signal which results in death of the cell (e.g., by a cell signal induced pathway, by complement fixation or exposure to a payload (e.g., a toxic payload) present on the binding molecule), or which modulates a disease or disorder in a subject (e.g., by mediating or promoting cell killing, or by modulating the amount of a substance which is bioavailable (e.g., by enhancing or reducing the amount of a ligand such as TNFα in the subject)). In another embodiment, the molecules of the invention have at least one binding site specific for an antigen targeted for reduction or elimination, e.g., a cell surface antigen or a soluble antigen.

In another embodiment, binding of a therapeutic molecule of the invention to a target molecule (e.g. antigen) results in the reduction or elimination of the target molecule or a cell expressing the target molecule, e.g., from a tissue or from circulation. In another embodiment, the therapeutic molecule has at least one binding site specific for a target molecule that can be used to detect the presence of the target molecule (e.g., to detect a contaminant or diagnose a condition or disorder). Exemplary therapeutic molecules are discussed further below.

III.A. Antigen Binding Portions

In certain embodiments, a molecule useful for the disclosure comprises at least one therapeutic molecule which is a binding site, e.g., an antigen binding portion of an antibody. In one embodiment, the molecule for the methods disclosed herein is a polypeptide.

In other embodiments, a binding site of a molecule of the invention comprises an antigen binding portion of an antibody. The term "antigen-binding portion" refers to a polypeptide fragment of an immunoglobulin, antibody, or antibody variant which binds antigen or competes with intact antibody (i.e., with the intact antibody from which they were derived) for antigen binding (i.e., specific binding). For example, the antigen binding portions can be derived from any of the antibodies or antibody variants known in the art. Antigen binding portions can be produced by recombinant or biochemical methods that are well known in the art. Exemplary antigen-binding fragments include VH and VL regions, Fv, Fab, Fab', and (Fab')2.

In other embodiments, a therapeutic molecule of the invention comprises a binding site from a single chain binding molecule (e.g., a single chain variable region or scFv). Techniques described for the production of single chain antibodies (U.S. Pat. No. 4,694,778; Bird, Science 242:423-442 (1988); Huston et al., Proc. Natl. Acad. Sci. USA 85:5879-5883 (1988); and Ward et al., Nature 334: 544-554 (1989)) can be adapted to produce single chain molecules. Single chain antibodies are formed by linking the heavy and light chain fragments of the Fv region via an amino acid bridge, resulting in a single chain antibody. Techniques for the assembly of functional Fv fragments in *E. coli* may also be used (Skerra et al., Science 242:1038-1041 (1988)).

Polypeptides useful for the disclosure can comprise a variable region or portion thereof (e.g. a VL and/or VH domain) derived from an antibody using art recognized protocols or may be obtained from an art-recognized antibody using standard molecular biology techniques.

In one embodiment, a molecule useful for the invention binds to a molecule which is useful in treating cancer.

In still other embodiments, a molecule useful for the invention binds to a molecule which is useful in treating an autoimmune or inflammatory disease or disorder.

For example, a molecule, e.g., a polypeptide, can bind to an antigen present on an immune cell (e.g., a B or T cell) or an autoantigen responsible for an autoimmune disease or disorder. Examples of autoimmune diseases that can be diagnosed, prevented or treated by the methods and compositions of the present invention include, but are not limited to, Crohn's disease; Inflammatory bowel disease (IBD); systemic lupus erythematosus; ulcerative colitis; rheumatoid arthritis; Goodpasture's syndrome; Grave's disease; Hashimoto's thyroiditis; pemphigus vulgaris; myasthenia gravis; scleroderma; autoimmune hemolytic anemia; autoimmune thrombocytopenic purpura; polymyositis and dermatomyositis; pernicious anemia; Sjögren's syndrome; ankylosing spondylitis; vasculitis; type I diabetes mellitus; neurological disorders, multiple sclerosis, and secondary diseases caused as a result of autoimmune diseases.

In other embodiments, a therapeutic molecule of the invention that binds to a target molecule associated with an inflammatory disease or disorder. As used herein the term "inflammatory disease or disorder" includes diseases or disorders which are caused, at least in part, or exacerbated by inflammation, e.g., increased blood flow, edema, activation of immune cells (e.g., proliferation, cytokine production, or enhanced phagocytosis). For example, a molecule of the invention can bind to an inflammatory factor (e.g., a matrix metalloproteinase (MMP), TNFα, an interleukin, a plasma protein, a cytokine, a lipid metabolite, a protease, a toxic radical, a mitochondrial protein, an apoptotic protein, an adhesion molecule, etc.) involved or present in an area in aberrant amounts, e.g., in amounts which may be advantageous to alter, e.g., to benefit the subject. The inflammatory process is the response of living tissue to damage. The cause of inflammation may be due to physical damage, chemical substances, micro-organisms, tissue necrosis, cancer or other agents. Acute inflammation is short-lasting, e.g., lasting only a few days. If it is longer-lasting however, then it may be referred to as chronic inflammation.

Inflammatory disorders include acute inflammatory disorders, chronic inflammatory disorders, and recurrent inflammatory disorders. Acute inflammatory disorders are generally of relatively short duration, and last for from about a few minutes to about one to two days, although they may last several weeks. The main characteristics of acute inflammatory disorders include increased blood flow, exudation of fluid and plasma proteins (edema) and emigration of leukocytes, such as neutrophils. Chronic inflammatory disorders, generally, are of longer duration, e.g., weeks to months to years or even longer, and are associated histologically with the presence of lymphocytes and macrophages and with proliferation of blood vessels and connective tissue. Recurrent inflammatory disorders include disorders which recur after a period of time or which have periodic episodes. Examples of recurrent inflammatory disorders include asthma and multiple sclerosis. Some disorders may fall within one or more categories. Inflammatory disorders are generally characterized by heat, redness, swelling, pain and loss of function. Examples of causes of inflammatory disorders include, but are not limited to, microbial infections (e.g., bacterial, viral and fungal infections), physical agents (e.g., burns, radiation, and trauma), chemical agents (e.g., toxins and caustic substances), tissue necrosis and various types of immunologic reactions. Examples of inflammatory disorders include, but are not limited to, osteoarthritis, rheumatoid arthritis, acute and chronic infections (bacterial, viral and fungal); acute and chronic bronchitis, sinusitis, and other respiratory infections, including the common cold; acute and chronic gastroenteritis and colitis; acute and chronic cystitis and urethritis; acute respiratory distress syndrome; cystic fibrosis; acute and chronic dermatitis; acute and chronic conjunctivitis; acute and chronic serositis (pericarditis, peritonitis, synovitis, pleuritis and tendinitis); uremic pericarditis; acute and chronic cholecystis; acute and chronic vaginitis; acute and chronic uveitis; drug reactions; and burns (thermal, chemical, and electrical).

In yet other embodiments, a therapeutic molecule of the invention binds to a molecule which is useful in treating a neurological disease or disorder. For example, a polypeptide may bind to an antigen present on a neural cell (e.g., a neuron or a glial cell). In certain embodiments, the antigen associated with a neurological disorder may be an autoimmune or inflammatory disorder described supra. As used herein, the term "neurological disease or disorder" includes disorders or conditions in a subject wherein the nervous system either degenerates (e.g., neurodegenerative disorders, as well as disorders where the nervous system fails to develop properly or fails to regenerate following injury, e.g., spinal cord injury. Examples of neurological disorders that can be diagnosed, prevented or treated by the methods and compositions of the present invention include, but are not limited to, Multiple Sclerosis, Huntington's Disease, Rett Syndrome, Angelman Syndrome, Alzheimer's Disease, Parkinson's Disease, progressive supranuclear palsy, epilepsy, dravet syndrome, neuropathic pain, traumatic brain injury, Guillain-Barré syndrome and chronic inflammatory demyelinating polyneuropathy (CIDP).

In other aspects, the therapeutic molecule of the invention comprises antigen binding sites, or portions thereof, derived from modified forms of antibodies. Exemplary such forms include, e.g., minibodies, diabodies, triabodies, nanobodies, camelids, Dabs, tetravalent antibodies, intradiabodies (e.g., Jendreyko et al. 2003. J. Biol. Chem. 278:47813), fusion proteins (e.g., antibody cytokine fusion proteins, proteins fused to at least a portion of an Fc receptor), and bispecific antibodies.

III.B Non-Immunoglobulin Binding Molecules

In certain other embodiments, a therapeutic molecule of the invention comprises one or more binding sites derived from a non-immunoglobulin binding molecule. As used herein, the term "non-immunoglobulin binding molecules" are binding molecules whose binding sites comprise a portion (e.g., a scaffold or framework) which is derived from a polypeptide other than an immunoglobulin, but which can be engineered (e.g., mutagenized) to confer a desired binding specificity.

Other examples of therapeutic molecules not derived from antibody molecules include receptor binding sites and ligand binding sites which are discussed in more detail infra.

Non-immunoglobulin therapeutic moieties can comprise binding site portions that are derived from a member of the immunoglobulin superfamily that is not an immunoglobulin (e.g. a T-cell receptor or a cell-adhesion protein (e.g., CTLA-4, N-CAM, telokin)). Such binding molecules comprise a binding site portion which retains the conformation of an immunoglobulin fold and is capable of specifically binding an IGF1-R epitope. In other embodiments, non-immunoglobulin binding molecules of the invention also comprise a binding site with a protein topology that is not based on the immunoglobulin fold (e.g., such as ankyrin repeat proteins or fibronectins) but which nonetheless are capable of specifically binding to a target (e.g. an IGF-1R epitope).

In one embodiment, a therapeutic moiety is derived from a fibronectin binding molecule. Fibronectin binding molecules (e.g., molecules comprising the Fibronectin type I, II, or III domains) display CDR-like loops which, in contrast to immunoglobulins, do not rely on intra-chain disulfide bonds. In one exemplary embodiment, the fibronectin polypeptide is as AdNectin® (Adnexus Therpaeutics, Waltham, Mass.).

In another embodiment, a therapeutic molecule of the invention comprises a binding site from an Affibody® (Abcam, Cambridge, Mass.). In another embodiment, a therapeutic molecule of the invention comprises a binding site from an Anticalin® (Pieris AG, Friesing, Germany). In another embodiment, a therapeutic molecule of the invention comprises a binding site from a cysteine-rich polypeptide. In other embodiments, a therapeutic molecule of the invention comprises a binding site from a repeat protein. Other non-immunoglobulin binding sites which may be employed in molecules of the invention include binding sites derived from Src homology domains (e.g. SH2 or SH3 domains), PDZ domains, beta-lactamase, high affinity protease inhibitors, or small disulfide binding protein scaffolds such as scorpion toxins.

III.C. Binding Portions of Receptors or Ligands

In other aspects, a molecule of the invention comprises a ligand binding site of a receptor and/or a receptor binding portion of a ligand. Exemplary binding portions of receptors or ligands that can be present in a molecule of the invention are set forth below:

III. C.1. Cytokines and Cytokine Receptors

Cytokines have pleiotropic effects on the proliferation, differentiation, and functional activation of lymphocytes. Various cytokines, or receptor binding portions thereof, can be utilized in the fusion proteins of the invention as therapeutic molecules, binding sites and/or domains. Exemplary cytokines include the interleukins (e.g. IL-1, IL-2, IL-3, IL-4, IL-5, IL-6, IL-7, IL-8, IL-10, IL-11, IL-12, IL-13, and IL-18), the colony stimulating factors (CSFs) (e.g. granulocyte CSF (G-CSF), granulocyte-macrophage CSF (GM-CSF), and monocyte macrophage CSF (M-CSF)), tumor necrosis factor (TNF) alpha and beta, cytotoxic T lymphocyte antigen 4 (CTLA-4), and interferons such as interferon-α, β, or γ (U.S. Pat. Nos. 4,925,793 and 4,929,554).

Cytokine receptors typically consist of a ligand-specific alpha chain and a common beta chain. Exemplary cytokine receptors include those for GM-CSF, (U.S. Pat. No. 5,639,605), IL-4 (U.S. Pat. No. 5,599,905), IL-5 (U.S. Pat. No. 5,453,491), IL10 receptor, IFNγ (EP0240975), and the TNF family of receptors (e.g., TNFα (e.g. TNFR-1 (EP 417, 563), TNFR-2 (EP 417,014) lymphotoxin beta receptor).

III.C.2. Adhesion Proteins

Adhesion molecules are membrane-bound proteins that allow cells to interact with one another. Various adhesion proteins, including leukocyte homing receptors and cellular adhesion molecules, or receptor binding portions thereof, can be incorporated in a fusion protein of the invention as therapeutic molecules, binding sites and/or domains. Leukocyte homing receptors are expressed on leukocyte cell surfaces during inflammation and include the β-1 integrins (e.g. VLA-1, 2, 3, 4, 5, and 6) which mediate binding to extracellular matrix components, and the β2-integrins (e.g. LFA-1, LPAM-1, CR3, and CR4) which bind cellular adhesion molecules (CAMs) on vascular endothelium. Exemplary CAMs include ICAM-1, ICAM-2, VCAM-1, and MAdCAM-1. Other CAMs include those of the selectin family including E-selectin, L-selectin, and P-selectin.

III.C.3. Chemokines

Chemokines, chemotactic proteins which stimulate the migration of leucocytes towards a site of infection, can also be incorporated into a fusion protein of the invention. Exemplary chemokines include Macrophage inflammatory proteins (MIP-1-α and MIP-1-(3), neutrophil chemotactic factor, and RANTES (regulated on activation normally T-cell expressed and secreted).

III.C.4. Hormones

Exemplary growth hormones for use as therapeutic moieties in the fusion proteins of the invention include renin, human growth hormone (HGH; U.S. Pat. No. 5,834,598), N-methionyl human growth hormone; bovine growth hormone; growth hormone releasing factor; parathyroid hormone (PTH); thyroid stimulating hormone (TSH); thyroxine; proinsulin and insulin (U.S. Pat. Nos. 5,157,021 and 6,576,608); follicle stimulating hormone (FSH); calcitonin, luteinizing hormone (LH), leptin, glucagons; bombesin; somatropin; mullerian-inhibiting substance; relaxin and prorelaxin; gonadotropin-associated peptide; prolactin; placental lactogen; OB protein; or mullerian-inhibiting substance.

III.C.5. Receptors and Ligands

In one embodiment, a polypeptide of the invention combines the binding site(s) of the ligand or receptor (e.g. the extracellular domain (ECD) of a receptor) with at least one genetically-fused Fc region (i.e., scFc region). In certain embodiments, the ligand binding portion of a receptor is derived from a receptor selected from a receptor of the Immunoglobulin (Ig) superfamily (e.g., a soluble T-cell receptor, e.g., mTCR® (Medigene AG, Munich, Germany), a receptor of the TNF receptor superfamily described supra (e.g., a soluble TNFα receptor of an immunoadhesin), a receptor of the Glial Cell-Derived Neurotrophic Factor (GDNF) receptor family (e.g., GFRα3), a receptor of the G-protein coupled receptor (GPCR) superfamily, a receptor of the Tyrosine Kinase (TK) receptor superfamily, a receptor of the Ligand-Gated (LG) superfamily, a receptor of the chemokine receptor superfamily, IL-1/Toll-like Receptor (TLR) superfamily, and a cytokine receptor superfamily.

In other embodiments, the binding site or domain of the receptor-binding portion of a ligand is derived from a ligand bound by an antibody or antibody variant described supra. For example, the ligand can bind a receptor selected from the group consisting of a receptor of the Immunoglobulin (Ig) superfamily, a receptor of the TNF receptor superfamily, a receptor of the G-protein coupled receptor (GPCR) superfamily, a receptor of the Tyrosine Kinase (TK) receptor superfamily, a receptor of the Ligand-Gated (LG) superfamily, a receptor of the chemokine receptor superfamily, IL-1/Toll-like Receptor (TLR) superfamily, and a cytokine receptor superfamily. In one exemplary embodiment, the binding site of the receptor-binding portion of a ligand is derived from a ligand belonging to the TNF ligand superfamily described supra (e.g., CD40L).

Growth factors or their receptors (or receptor binding or ligand binding portions thereof) may be incorporated in the fusion proteins of the invention. Exemplary growth factors include Vascular Endothelial Growth Factor (VEGF) and its isoforms (U.S. Pat. No. 5,194,596); Fibroblastic Growth Factors (FGF), including aFGF and bFGF; atrial natriuretic factor (ANF); hepatic growth factors (HGFs; U.S. Pat. Nos. 5,227,158 and 6,099,841), neurotrophic factors such as bone-derived neurotrophic factor (BDNF), glial cell derived neurotrophic factor ligands (e.g., GDNF, neuturin, artemin, and persephin), neurotrophin-3, -4, -5, or -6 (NT-3, NT-4, NT-5, or NT-6), or a nerve growth factor such as NGF-β platelet-derived growth factor (PDGF) (U.S. Pat. Nos. 4,889,919, 4,845,075, 5,910,574, and 5,877,016); transforming growth factors (TGF) such as TGF-alpha and TGF-beta (WO 90/14359), osteoinductive factors including bone morphogenetic protein (BMP); insulin-like growth factors-I and -II (IGF-I and IGF-II; U.S. Pat. Nos. 6,403,764 and 6,506,874); Erythropoietin (EPO); Thrombopoeitin (TPO; stem-cell factor (SCF), thrombopoietin (TPO, c-Mpl ligand), and the Wnt polypeptides (U.S. Pat. No. 6,159,462).

Exemplary growth factor receptors which may be used as therapeutic moieties of the invention include EGF receptors; VEGF receptors (e.g. Flt1 or Flk1/KDR), PDGF receptors (WO 90/14425); HGF receptors (U.S. Pat. Nos. 5,648,273, and 5,686,292), and neurotrophic receptors including the low affinity receptor (LNGFR), also termed as p75NTR or p'75, which binds NGF, BDNF, and NT-3, and high affinity receptors that are members of the trk family of the receptor tyrosine kinases (e.g. trkA, trkB (EP 455,460), trkC (EP 522,530)).

III.C.6. Heterodimeric Receptors

In one embodiment, antagonists to cytokines that utilize an β specificity determining component which, when combined with the cytokine, binds to a first β signal transducing component to form a nonfunctional intermediate which then binds to a second β signal transducing component causing β-receptor dimerization and consequent signal transduction can be made using the methods of the invention. Such molecules are described in the art (see e.g., U.S. Pat. No. 6,927,044). In one example, a soluble specificity determining component of the receptor and the extracellular domain of the first β signal transducing component of the cytokine receptor are combined to form a heterodimer that binds the cytokine to form a nonfunctional complex. Exemplary cytokines that can be inhibited using such heterodimeric receptors include: ILL IL-2, IL-3, IL-4, IL-5, IL-3, IL-4, IL-5, IL-11, IL-15, GMCSF, LIF, INFα, and TGFβ.

III.D. Molecule Comprising a Polynucleotide

A molecule for the disclosure can also comprise a polynucleotide (e.g., oligomers). In some embodiments, the nucleotide sequence encodes any polypeptide disclosed above in Sections III.A, III.B, and III.C.1-III.C.5. In certain embodiments, the nucleotide sequence binds or hybridizes to a nucleic acid sequence (DNA or RNA, e.g., pre-mRNA or mRNA) encoding one or more polypeptides disclosed above in Sections III.A., III.B., and III.C.1-III.C.5. The term "nucleotide sequence" herein means the molecule in which more than two nucleotides are connected to each other as a sequence. In one embodiment, the nucleotide sequence for the present disclosure is DNA. In another embodiment, the nucleotide sequence for the present disclosure is RNA. In other embodiments, the nucleotide sequence for the present disclosure is a combination of DNA and RNA. In still other embodiments, the nucleotide sequence for the disclosure comprises one or more chemically modified nucleotides. In yet other embodiments, the nucleotide sequence comprises at least two nucleotides, at least three nucleotides, at least four nucleotides, at least five nucleotides, at least six nucleotides, at least seven nucleotides, at least eight nucleotides, at least nine nucleotides, at least 10 nucleotides, or at least 11 nucleotides in length. In other embodiments, the nucleotide sequence comprises at least 15 nucleotides, at least 20 nucleotides, at least 25 nucleotides, at least 30 nucleotides, at least 35 nucleotides, at least 40 nucleotides, at least 45 nucleotides, at least 50 nucleotides, at least 55 nucleotides, at least 60 nucleotides, at least 65 nucleotides, at least 70 nucleotides, at least 80 nucleotides, at least 90 nucleotides, at least 100 nucleotides, at least 150 nucleotides, at least 200 nucleotides, at least 300 nucleotides, at least 400 nucleotides, at least 500 nucleotides, at least 600 nucleotides, at least 700 nucleotides, at least 800 nucleotides, at least 900 nucleotides, at least 1000 nucleotides, at least 2000 nucleotides, at least 3000 nucleotides, or at least 4000 nucleotides. In this regard, the nucleotide sequence of the invention can affect indirect inhibition of the protein through a reduction in mRNA levels, typically in a mammalian cell, such as a human cell, such as a neuronal cell. Nucleotide sequences of any type can be analyzed using the methods of the current invention. In certain embodiments, nucleotide sequences targeting pre-mRNA or mRNAs that are primarily expressed in neuronal cells as proteins are analyzed for selected characteristics as discussed elsewhere herein. Examples of genes that can be targeted by nucleotide sequences selected by the methods of the present invention include, but are not limited to, microtubule-associated protein tau (encoded by the MAPT gene), brain acid soluble protein 1 (encoded by the BASP1 gene), or amyloid precursor protein (encoded by the APP gene). In some embodiments, the nucleotide sequence for the present methods is an oligomer.

III.D.1. Oligomers (Antisense Oligonucleotide)

In certain embodiments, the therapeutic molecule useful for the invention is an oligomer. Oligomers have a nucleotide sequence from 10-50, such as 10-30 nucleotides in length which comprises a contiguous nucleotide sequence of a total of from 10-30 nucleotides.

In certain embodiments, the oligomers target microtubule-associated protein tau (MAPT). In a pathologic state associated with disease, MAPT is also known as neurofibrillary tangle protein or paired helical filament-tau (PHF-tau). The sequence for the MAPT gene can be found under publicly available Accession Number NC_000017.11 and the sequence for the MAPT pre-mRNA transcript can be found under publicly available Accession Number NG_007398. The sequence for Tau protein can be found under publicly available Accession Numbers: P10636, P18518, Q14799, Q15549, Q15550, Q15551, Q1RMF6, Q53YB1, Q5CZI7, QSXWFO, Q6QT54, Q9UDJ3, Q9UMH0, Q9UQ96, each of which is incorporated by reference herein in its entirety. Natural variants of the MAPT gene product are known. For example, natural variants of Tau protein can contain one or more amino acid substitutions selected from: RSH, RSL, D285N, V289A, K574T, L583V, G589V, N596K, N613H, P618L, P618S, G620V, S622N, K634M, S637F, V654M, E659V, K6861, G706R, R723W, or any combinations thereof. Therefore, the oligomers of the present invention can be designed to reduce or inhibit expression of the natural variants of the Tau protein. The Tau protein sequence is provided as SEQ ID NO: 1, and a nucleotide sequence is provided as SEQ ID NO: 2.

In certain embodiments, the oligomers target a pre-mRNA or mRNA encoding brain acid soluble protein 1

(BASP1). BASP1 is also known as 22 kDa neuronal tissue-enriched acidic protein, neuronal axonal membrane protein NAP-22, NAP22, CAP-23, NAP-22, CAP23, or Neuronal Tissue-Enriched Acidic Protein. The BASP1 gene encodes a membrane bound protein with several transient phosphorylation sites and PEST motifs. Conservation of proteins with PEST sequences among different species supports their functional significance. PEST sequences typically occur in proteins with high turnover rates. Immunological characteristics of this protein are species specific. This protein also undergoes N-terminal myristoylation.

Another example of a target nucleic acid sequence of the oligomers is BASP1 pre-mRNA or BASP1 mRNA. BASP1 cDNA which corresponds to BASP1 mRNA is known as GenBank Accession No. NM_006317.4.

In certain embodiments, the therapeutic molecules (e.g., oligomers) target a pre-mRNA encoding an amyloid precursor protein. Amyloid precursor protein (APP) is an integral membrane protein expressed in many tissues and concentrated in the synapses of neurons. Its function has been implicated as a regulator of synapse formation, neural plasticity and iron export. APP is best known as the precursor molecule whose proteolysis generates beta amyloid (Aβ), a 37 to 49 amino acid peptide whose amyloid fibrillar form is the primary component of amyloid plaques found in the brains of Alzheimer's disease patients.

In humans, the gene for APP is located on chromosome 21 and contains 18 exons spaning 290 kilobases. Several alternative splicing isoforms of APP have been observed in humans, ranging in length from 365 to 770 amino acids, with certain isoforms preferentially expressed in neurons; changes in the neuronal ratio of these isoforms have been associated with Alzheimer's disease. Mutations in critical regions of Amyloid Precursor Protein, including the region that generates amyloid beta (Aβ), cause familial susceptibility to Alzheimer's disease. For example, several mutations outside the AP region associated with familial Alzheimer's have been found to dramatically increase production of Aβ.

A further example of a target nucleic acid sequence of the oligomers is APP pre-mRNA or APP mRNA. APP cDNA which corresponds to APP mRNA is known as GenBank Accession No. Y00264.

In some embodiments, the present method is utilized to select any therapeutic molecules comprising a nucleotide sequence (e.g., oligomers) that hybridize to a region within a MAPT transcript, e.g., SEQ ID NO: 2 (SEQ ID NO: 2 can be mRNA if "t" is replaced with "u"), a BASP1 transcript or an APP transcript.

In one embodiment, random therapeutic molecules comprising nucleotide sequences (e.g., oligomers) targeting certain regions of pre-mRNA or mRNA encoding MAPT, BASP1, or APP are prepared to test their toxicities. The therapeutic molecules comprising nucleotide sequences can then be subject to the methods of the present invention described elsewhere herein. In certain embodiments, examples of the oligomers (i.e., antisense oligonucleotides) include, but are not limited to, the oligomers listed in FIGS. 4 and 5.

The oligomers can include any oligomer design, e.g., a pattern of nucleoside sugar modifications. In an embodiment, the oligomer comprises at least 1 modified nucleoside, such as at least 2, at least 3, at least 4, at least 5, at least 6, at least 7, at least 8, at least 9, at least 10, at least 11, at least 12, at least 13, at least 14, at least 15 or at least 16 modified nucleosides.

In an embodiment, the oligomer of the invention comprises modifications, which are independently selected from these three types of modifications (modified sugar, modified nucleobase and modified internucleoside linkage) or a combination thereof.

In a further embodiment the oligonucleotide comprises at least one modified internucleoside linkage. In other embodiments, the internucleoside linkages within the contiguous nucleotide sequence are phosphorothioate or boranophosphate internucleoside linkages.

In some embodiments, the oligomer of the invention comprises at least one LNA unit or at least one 2' substituted modified nucleoside.

The oligomer of the invention can comprise a nucleotide sequence which comprises both nucleotides and nucleotide analogs, and can be in the form of a gapmer, blockmer, mixmer, headmer, tailmer, or totalmer. Examples of configurations of a gapmer, blockmer, mixmer, headmer, tailmer, or totalmer that can be used with the oligomer of the invention are described in U.S. Patent Appl. Publ. No. 2012/0322851.

The nucleotides of the oligomer of the invention or contiguous nucleotides sequence thereof can be coupled together via linkage groups. Suitably each nucleotide is linked to the 3' adjacent nucleotide via a linkage group. Suitable internucleotide linkages include those listed within WO2007/031091, for example the internucleotide linkages listed on the first paragraph of page 34 of WO2007/031091.

US Publication No. 2011/0130441, which was published Jun. 2, 2011, refers to oligomeric compounds having at least one bicyclic nucleoside attached to the 3' or 5' termini by a neutral internucleoside linkage. The oligomers of the invention can therefore have at least one bicyclic nucleoside attached to the 3' or 5' termini by a neutral internucleoside linkage, such as one or more phosphotriester, methylphosphonate, MMI, amide-3, formacetal or thioformacetal. The remaining linkages can be phosphorothioate.

In the context the term "conjugate" is intended to indicate a heterogeneous molecule formed by the covalent or non-covalent attachment ("conjugation") of the oligomer as described herein to one or more non-nucleotide, or non-polynucleotide moieties. Examples of non-nucleotide or non-polynucleotide moieties include macromolecular agents such as proteins, fatty acid chains, sugar residues, glycoproteins, polymers, or combinations thereof. Typically proteins can be antibodies for a target protein. In some embodiments, typical polymers are polyethylene glycol.

Therefore, in various embodiments, the oligomer of the invention comprises both a polynucleotide region which typically consists of a contiguous sequence of nucleotides, and a further non-nucleotide region. When referring to the oligomer of the invention comprising a contiguous nucleotide sequence, the compound can comprise non-nucleotide components, such as a conjugate component.

The invention also provides for a conjugate comprising the oligomer according to the invention as herein described, and at least one non-nucleotide or non-polynucleotide moiety covalently attached to said oligomer. Therefore, in various embodiments where the oligomer of the invention comprises a specified nucleic acid or nucleotide sequence, as herein disclosed, the compound can also comprise at least one non-nucleotide or non-polynucleotide moiety (e.g., not comprising one or more nucleotides or nucleotide analogs) covalently attached to said oligomer.

Conjugation (to a conjugate moiety) can enhance the activity, cellular distribution or cellular uptake of the oligomer of the invention. Such moieties include, but are not limited to, antibodies, polypeptides, lipid moieties such as a cholesterol moiety, cholic acid, a thioether.

The oligomers of the invention can also be conjugated to active drug substances, for example, aspirin, ibuprofen, a sulfa drug, an antidiabetic, an antibacterial or an antibiotic.

In certain embodiments the conjugated moiety is a sterol, such as cholesterol.

IV. Pharmaceutical Composition and Administration Routes

The therapeutic molecules of the invention can be used in pharmaceutical formulations and compositions. Suitably, such compositions comprise a pharmaceutically acceptable diluent, carrier, salt or adjuvant.

The therapeutic molecules of the invention can be included in a unit formulation such as in a pharmaceutically acceptable carrier or diluent in an amount sufficient to deliver to a patient a therapeutically effective amount without causing serious side effects in the treated patient. However, in some forms of therapy, serious side effects may be acceptable in terms of ensuring a positive outcome to the therapeutic treatment.

The formulated drug may comprise pharmaceutically acceptable binding agents and adjuvants. Capsules, tablets, or pills can contain for example the following compounds: microcrystalline cellulose, gum or gelatin as binders; starch or lactose as excipients; stearates as lubricants; various sweetening or flavoring agents. For capsules the dosage unit may contain a liquid carrier like fatty oils. Likewise coatings of sugar or enteric agents may be part of the dosage unit. The therapeutic molecule formulations can also be emulsions of the active pharmaceutical ingredients and a lipid forming a micellular emulsion.

The pharmaceutical compositions of the present invention can be administered in a number of ways depending upon whether local or systemic treatment is desired and upon the area to be treated. Administration can be (a) oral (b) pulmonary, e.g., by inhalation or insufflation of powders or aerosols, including by nebulizer; intratracheal, intranasal, (c) topical including epidermal, transdermal, ophthalmic and to mucous membranes including vaginal and rectal delivery; or (d) parenteral including intravenous, intraarterial, subcutaneous, intraperitoneal or intramuscular injection or infusion; or intracranial, e.g., intrathecal, intra-cerebroventricular, or intraventricular, administration. In one embodiment the therapeutic molecule is administered IV, IP, orally, topically or as a bolus injection or administered directly in to the target organ. In another embodiment, the therapeutic molecule is administered intrathecal or intra-cerebroventricular as a bolus injection.

Pharmaceutical compositions and formulations for topical administration can include transdermal patches, ointments, lotions, creams, gels, drops, sprays, suppositories, liquids and powders. Conventional pharmaceutical carriers, aqueous, powder or oily bases, thickeners and the like may be necessary or desirable. Examples of topical formulations include those in which the oligomer of the invention are in admixture with a topical delivery agent such as lipids, liposomes, fatty acids, fatty acid esters, steroids, chelating agents and surfactants. Compositions and formulations for oral administration include but are not limited to powders or granules, microparticulates, nanoparticulates, suspensions or solutions in water or non-aqueous media, capsules, gel capsules, sachets, tablets or minitablets. Compositions and formulations for parenteral, intrathecal, intra-cerebroventricular, or intraventricular administration can include sterile aqueous solutions which can also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids. Delivery of drug to the target tissue can be enhanced by carrier-mediated delivery including, but not limited to, cationic liposomes, cyclodextrins, porphyrin derivatives, branched chain dendrimers, polyethylenimine polymers, nanoparticles and microspheres (Dass C R. J Pharm Pharmacol 2002; 54(1):3-27).

The pharmaceutical formulations of the present invention, which can conveniently be presented in unit dosage form, can be prepared according to conventional techniques well known in the pharmaceutical industry. Such techniques include the step of bringing into association the active ingredients with the pharmaceutical carrier(s) or excipient (s). In general the formulations are prepared by uniformly and intimately bringing into association the active ingredients with liquid carriers or finely divided solid carriers or both, and then, if necessary, shaping the product.

For parenteral, subcutaneous, intradermal or topical administration the formulation can include a sterile diluent, buffers, regulators of tonicity and antibacterials. The therapeutic molecules can be prepared with carriers that protect against degradation or immediate elimination from the body, including implants or microcapsules with controlled release properties. For intravenous administration the carriers can be physiological saline or phosphate buffered saline. International Publication No. WO2007/031091 (A2), published Mar. 22, 2007, further provides suitable pharmaceutically acceptable diluent, carrier and adjuvants.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986);); Crooks, Antisense drug Technology: Principles, strategies and applications, $2^{nd}$ Ed. CRC Press (2007) and in Ausubel et al. (1989) Current Protocols in Molecular Biology (John Wiley and Sons, Baltimore, Md.).

All of the references cited above, as well as all references cited herein, are incorporated herein by reference in their entireties.

The following examples are offered by way of illustration and not by way of limitation.

Examples

Example 1: Construction of Molecules

A number of molecules (e.g., oligomers) are designed to target the 3' UTR of MAPT pre-mRNA. For example, the oligomers were constructed to target nucleotides 134,821-138,940 and 72,802-73,072 of SEQ ID NO: 2. The exemplary sequences of the oligomers are described in FIGS. 4, 5, and 6. In some embodiments, the oligomers were designed to be gapmers or mixmers. The same methods can be applied to any other sequences disclosed herein. The gapmers were constructed to contain LNAs (upper case letters), for example, Beta-deoxy LNA at the 5' end and the 3' end and contain a phosphorothioate backbone, but the LNAs can be substituted with any other nucleotide analogs and the backbone can be other types of backbones (e.g., a phosphodiester linkage, a phosphotriester linkage, a methylphosphonate linkage, a phosphoramidate linkage, or combinations thereof).

The oligomers were synthesized using methods well known in the art. Exemplary methods of preparing such oligomers are described in Barciszewski et al., Chapter 10-"Locked Nucleic Acid Aptamers" in Nucleic Acid and Peptide Aptamers: Methods and Protocols, vol. 535, Gunter Mayer (ed.) (2009).

Example 2: Spontaneous Calcium Oscillation Measurement of Antisense Oligonucleotides To measure primary cortical neuron spontaneous calcium oscillation, rat primary cortical neurons were prepared from Sprague-Dawley rat embryos (E19). Cells were plated 25,000 cells/well onto 384 well poly-D-lysine coated FLIPR plates (Greiner Bio-One) in 25 μl/well Neurobasal media containing B27 supplement and 2 mM glutamine (day 1 in vitro, DIV1). Cells were grown for 11 days at 37° C. in 5% $CO_2$ and fed with 25 μl of additional media on day 4 in vitro ("DIV04") and day 8 in vitro ("DIV08") for use on day 11 in vitro ("DIV11"). On the day of the experiment, media was removed from the plate and the cells were washed once with 50 μl/well of 37° C. assay buffer (Hank's Balanced Salt Solution with 2 mM $CaCl_2$ and 10 mM Hopes pH 7.4). Oscillations were tested in the presence and absence of 1 mM $MgCl_2$ (FIG. 1). Cells were loaded with a cell permanent fluorescent calcium dye, fluo-4 AM (Life Technologies). Fluo-4 AM was prepared at 2.5 mm in DMSO containing 20% plutonic F-127 then diluted 1:1000 in assay buffer. Cells were incubated 1 hr with 20 μl of 2.5 μM fluo-4 AM at 37° C. in 5% $CO_2$. After 1 hr 20 μl of room temperature assay buffer was added and the cells were allowed to equilibrate to room temperature for 10 additional minutes and placed in the fluorescent imaging plate reader (FLIPR). Baseline signal (measurement of intracellular calcium) was read for 100 seconds (1 reading/second) before the addition of anti-sense oligomers. Oligomers were added with a 384 well head in the FLIPR in 20 μl of assay buffer at 75 μM for a final concentration of 25 μM. FLIPR signal was read for an additional 200 seconds (1 reading/second) after the addition of oligomer. A second 5 minute post addition plate read (300 one second points) on the FLIPR was conducted to allow for additional data capture. Raw data from the 5 minute read was exported and, using Excel, spike amplitude and frequency was calculated. Calculations were performed by measuring the average FLIPR signal over the 300 second read for control (non-treated) wells. For treated wells, a scoring system was developed where a score of 1 was given for each 1 second read where signal increase greater than 50% of the average control value (calculated above). A score of 0 was given for each 1 second read that increase less than 50% of average control value. For each treatment a total score was calculated and converted to percent control for graphical purposes. If the antisense oligomer produced a calcium oscillation response greater than that of the untreated cell, percent of control is expressed as greater than 100% (FIG. 4).

Effect of oligomers on primary neuronal spontaneous calcium oscillations was measured under two conditions, in the presence and absence of 1 mM MgCl2 as described previously (Murphy et. al., 1992, 1 Neurosci. 12:4834-4845). This was done to isolated N-methyl-D-aspartate (NMDA)- and α-amino-3-hydroxy-5-methyl-4-isoxazole-propionic acid (AMPA)-receptor mediated calcium oscillations. Data presented in FIG. 1 show that, addition of the AMPA receptor antagonist, 6-Cyano-7-nitroquinoxaline-2,3-dione (CNQX; 3 μM), reduced calcium oscillations by 20% representing the total AMPA response in the assay (FIG. 1AMPA labeled bar shown). Calcium oscillations were reduced further, by about 80%, when (NMDA) receptor function was blocked by 1 mM $MgCl_2$ (FIG. 1 NMDA labeled bar shown).

Antisense oligomer inhibition of spontaneous calcium oscillations mediated by either NMDA or AMPA was assessed in the presence or absence of 1 mM $MgCl_2$ (representing 100% control in each case; FIG. 2). Addition of 25 μM antisense oligomers (ASO) inhibited AMPA receptor but not NMDA receptor mediated oscillations (FIG. 2). ASOs, and other oligomers that behaved similarly, were shown to negatively impact central nervous system (CNS) network activity in vivo and electrophysiologic spontaneous neuronal activity in vitro (data not shown). Tau antisense oligonucleotide impact on spontaneous calcium oscillations in primary neurons is summarized in FIG. 4. See Murphy et al., *J. Neurosci.* 12, 4834-4845 (1992).

Calcium oscillation reduction in the neuronal cells was measured for the oligomers of the invention and compared with that of the control cells (i.e., the calcium oscillations in the neuronal cells that are not treated with the oligomers). Tau antisense oligonucleotide impact on spontaneous calcium oscillations in primary neurons is shown in FIG. 4. The oligomers in neuronal cells showing AMPA-mediated oscillations that are equal to or greater than 75% of the calcium oscillations in the untreated control cells were selected for further analysis.

Example 3: Calcium Oscillation Measurement Using Small Molecules

The effect of small molecules on calcium oscillations will be measured using substantially the same method provided in Example 2. To measure primary cortical neuron spontaneous calcium oscillation, rat primary cortical neurons will be prepared. Cells will be plated and be grown for use on the appropriate date. As discussed in Example 2, the effect of small molecules on primary neuronal spontaneous calcium oscillations will be measured under two conditions, in the presence and absence of 1 mM MgCl2 as described previously (Murphy et. al., 1992, J. Neurosci. 12:4834-4845).

Cells will be loaded with a cell permanent fluorescent calcium dye. Cells will be incubated and allowed to equilibrate to room temperature to measure the fluorescent intensity. Raw data will be exported, and spike amplitude and frequency will be calculated.

Small molecule inhibition of spontaneous calcium oscillations mediated by either NMDA or AMPA will be assessed. Addition of small molecule will inhibit AMPA receptor mediated oscillations. Small molecules that reduce calcium oscillations to levels below 70% of control will be expected to negatively impact CNS network activity in vivo and electrophysiologic spontaneous neuronal activity in vitro.

Example 4: Calcium Oscillation Measurement Using Therapeutic Proteins

The effect of therapeutic proteins, such as antibodies or antigen-binding fragments thereof, fusion proteins, cytokines, cell surface receptors, hormones or growth factors, on calcium oscillations will be measured using substantially the same method provided in Example 2. To measure primary cortical neuron spontaneous calcium oscillation, rat primary cortical neurons will be prepared. Cells will be plated and be grown for use on the appropriate date. As discussed in Example 2, the effect of therapeutic proteins on primary neuronal spontaneous calcium oscillations will be measured under two conditions, in the presence and absence of 1 mM $MgCl_2$ as described previously (Murphy et. al., 1992, J. Neurosci. 12:4834-4845). Cells will be loaded with a cell permanent fluorescent calcium dye. Cells will be incubated and allowed to equilibrate to room temperature to measure the fluorescent intensity. Raw data will be exported, and spike amplitude and frequency will be calculated.

Therapeutic protein inhibition of spontaneous calcium oscillations mediated by either NMDA or AMPA will be assessed. Addition of therapeutic protein will inhibit AMPA receptor mediated oscillations. Therapeutic proteins that reduce calcium oscillations to levels below 70% of control will be expected to negatively impact CNS network activity in vivo and electrophysiologic spontaneous neuronal activity in vitro.

Example 5: Sequence Score Calculation

The Sequence score of each oligomer was calculated to predict the suitability of the oligomers. Sequence score is a mathematical calculation determined for all oligomers and is based on the percent of G and C nucleotides, or analogs thereof, within a given oligomer sequence. The following formula was applied to all oligomers in order to calculate sequence score:

$$\frac{\text{number of } C \text{ nucleotides or analogs thereof} - \text{number of } G \text{ nucleotides or analogs thereof}}{\text{nucleotide length}} \quad \text{(I)}$$

An example calculation is given for oligomer ASO-000013 (SEQ ID NO: 686; sequence score 0.25): ATTtccaaattcaCTT: 4-0/16=sequence score of 0.25.

The sequence score of the selected oligomers were calculated for further studies. To determine the cut off value for the sequence score, an in vivo tolerability study was performed as shown in Example 6.

Example 6: In Vivo Tolerability

The in vivo tolerability of the oligomers was tested to see how the oligomer was tolerated when injected into an animal.

Subject

In vivo tolerability of the oligomers were tested in mice and rats. Animals for Tau qPCR and behavioral studies were adult, C57B1/6J female mice (20-30 g; Jackson Laboratories, Bar Harbor, Me.) housed 3-4 per cage. Animals were held in colony rooms maintained at constant temperature (21±2° C.) and humidity (50±10%) and illuminated for 12 hours per day (lights on at 0600 hours). In some cases, male and female transgenic mice (30-40 g) expressing a tau transgene derived from a human PAC, H1 haplotype driven by the tau promoter (Polydoro et. al., J. Neurosci. (2009) 29(34): 10741-9), and in which the native mouse Tau gene was deleted, were used to assess pharmacodynamic endpoints and tissue drug concentrations. For intrathecal infusion studies, female Sprague-Dawley rats (180-225 g at testing; Harlan) were singly housed in colony rooms maintained at a constant temperature (21±2° C.) and humidity (50±10%) and illuminated for 12 hours per day (lights on at 0600 h). All animals had ad libitum access to food and water throughout the studies. Behavioral studies were conducted between 0700 and 1500 hours. Animals were maintained in accordance with the guidelines of the Animal Care and Use Committee of the Bristol-Myers Squibb Company, and the "Guide for Care and Use of Laboratory Animals" published by the National Institutes of Health. Research protocols were approved by the Bristol-Myers Squibb Company Animal Care and Use Committee.

Administration Routes-Intra-Cerebroventricular or Intrathecal Injections.

The oligomers were administered to mice by either intracerebroventricular (i.c.v.) injection or intrathecal injection. Intracerebroventricular injections were performed using a Hamilton micro syringe fitted with a 27 or 30-gauge needle, according to the method of Haley and McCormick. The needle was equipped with a polyethylene guard at 2.5 mm from the tip in order to limit its penetration into the brain. Mice were anesthetized using isoflurane anesthetic (1.5-4%). The mouse to be injected, weighing 20-30 g, was held by the loose skin at the back of the neck with the thumb and first fingers of one hand. Applying gentle but firm pressure, the head of the animal was then immobilized by pressing against a firm flat level surface. The needle tip was then inserted through the scalp and the skull, about 1 mm lateral and 1 mm caudal to bregma. Once the needle was positioned, antisense oligonucleotide was given in a volume of 5 microliters in saline vehicle and injected into the right (or left) lateral ventricle over 20-30 seconds. The needle was left in place for 10 seconds before removal. This procedure required no surgery or incision. Animals were warmed on heating pads until they recovered from the procedure. Brain tissue (right, frontal cortical region) was collected on dry ice or RNAlater for drug concentration analysis and Tau qPCR respectively at multiple time points following dosing, e.g., 1 week through 16 weeks post-dosing.

For intrathecal (IT) injections of mice, animals were maintained under light isoflurane anesthesia (1.5-5%). The mouse was held securely in one hand by the pelvic girdle and inserting a 30G ½ inch needle connected to a Hamilton syringe into the tissue between the dorsal aspects of L5 and L6, perpendicular to the vertebral column. When the needle enters the subarachnoid space, a sudden lateral movement of the tail was observed. This reflex was used as an indicator of successful placement of the needle for IT administration. A 5-10 μL volume of antisense oligonucleotide was injected slowly (over approximately 60 seconds) into the subarachnoid space.

For intrathecal injections in rats, intrathecal catheters were surgically implanted using methods described by Yaksh and Rudy, Physiol. Behay. (1976) 17(6): 1031-6. The rat was mounted to a stereotaxic frame with isoflurane anesthesia maintained through a nose cone. A skin incision was made beginning approximately at the line joining the ears and extending caudally about 3 cm along the midline. The muscle where it attached to the occipital crest of the skull was cut about 3 mm lateral on both sides of the muscle midline. Using retractors or forceps, the muscle was peeled caudally to expose the cisternal membrane at the base of the skull. The fascia and tissue were carefully removed from the membrane. The bent beveled end of a 16-22 gauge needle was used to make a 1-2 mm lateral incision in the cisternal membrane. A sterilized IT catheter, made of polyethylene tubing (PE10 tubing stretched to approximately 1.3 mm outer diameter), was inserted through the incision and carefully advanced caudally through the subarachnoid space while it was rotated between thumb and forefinger and while the base of the tail was gently pulled to align the spinal cord using the other hand. If any resistance was encountered, the catheter was retracted slightly, and slowly advanced again. Once the catheter had been advanced to the desired area, it was flushed with 20 μL sterile saline and the cranial end was passed through the skin using a 19 gauge needle about 1 cm from the incision. The catheter was plugged with a pin. Rats were given oral antibiotics for 5 days following the surgery. At least five days after surgery, a single antisense oligonucleotide injection was diluted in water and delivered via a programmable infusion pump (Knopf) at a rate of 10 μl/minute in a volume of 10 to 50 μl. A brief saline flush of 5 ul was given just prior to the antisense oligonucleotide delivery and a 10 μl saline flush was given just following the oligonucleotide delivery at a rate of 10 μl/minute to cover the dead volume of the catheter (6-7 μl). A saline flush of 20 ul was also given to animals 1-2×/week until used for an experiment.

Acute Tolerability Behavioral Assessments

For one hour following the single injection of antisense oligonucleotide ICV or IT, animals were observed for behavioral side effects and scored for the severity of side effects on a scale of zero (no side effects) to 20 (convulsions resulting in euthanasia). The tolerability scale was divided into 5 neurobehavioral categories: 1) hyperactivity 2) decreased activity and arousal 3) motor dysfunction/ataxia 4) abnormal posture and breathing and 5) tremor/convulsions. Each category was scored on a scale of 0-4, with the worst possible total score of 20. Animals were observed for changes in behavior in the home cage, and then they were removed from the home cage for more detailed observations which included measurement of grip strength and righting reflex.

Novel Object Recognition

Short term recognition memory was measured using the novel object recognition (NOR) task. NOR testing was based on the spontaneous behavior of rodents to explore a novel object more than a familiar one (Dodart et. al., Neuroreport (1997) 8(5): 1173-8; Ennaceur and Delacour, Behay. Brain Res. (1988) 31 (1):47-59). After a one hour retention interval between training (T1) and testing (T2) sessions, mice remembering the objects from the training session will show a preference for the novel object on the test session. For these experiments, animals were handled for 3 days and habituated to the chamber (48 cm×38 cm×20 cm) on the day prior to the test session. The chamber was made of polyethylene and lined with vinyl flooring. On the test day, animals were placed in the rectangular test chamber and allowed to explore two identical objects (7.6 cm high×5.1 cm wide) for a 15 minute training period. One hour later, mice were placed back into the test chamber for a 10 minute test session, this time with one object they had observed during training and one novel object. Objects were cleaned thoroughly with 25% ethanol between training and testing sessions and between subjects, and were cleaned again at the end of the day with mild detergent. Object exploration was only considered when the animal's nose was pointed at the object. Exploration was recorded using ObjectScan tracking software (Cleversys, Reston, Va.). Data are reported as percent of time spent exploring objects (i.e., novel time/novel+familiar time*100).

Morris Water Maze

Spatial learning and memory was assessed based on Morris Water Maze assay (Morris J. Neurosci. (1984) 11(1): 47-60). Water maze represents a pool with the diameter of 120 cm. Water was made opaque using white, non-toxic tempura paint (20° C.±1). The pool was surrounded with distinct extra-maze cues.

Prior to hidden platform training, all mice were exposed to the water maze pool by allowing them to swim down the rectangular channel during 2 pre-training trials. The escape platform was placed in the middle of the channel. If a mouse was not able to find and mount the platform during 60 sec trial, it was guided to it and allowed to sit for up to 10 sec. After pre-training, mice underwent hidden platform training, during which a 10×10 cm platform was submerged 1.5 cm below the surface. The platform location remained the same throughout training whereas the drop location varied randomly between the four daily trials as well as across the 4 days of training. Mice received 2 sessions per day for 4 consecutive days. Each session consisted of 2 trials with a 10-min inter-trial interval. The maximum time allowed per trial was 60 sec. If a mouse did not find or mount the platform, it was guided to the platform by the experimenter. All mice were allowed to sit on the platform for 10 sec after each training trial.

For probe trials, the platform was removed and each mouse was allowed to swim for 60 sec. The drop location for the probe trials was 180° from the platform location used during hidden platform training. After 60 sec, mice were guided to the platform location before retrieval from the pool. For early memory retrieval mice were probed 2 h after the last hidden platform training; long term memory recall was assessed 16 h following the last hidden platform training. 2 h following the 16 h probe trial, all mice underwent the visible platform training, where a local cue (pole built using legos) was placed above the hidden platform. Mice were given 2 training trials. All behavior was recorded with a video tracking system (Cleversys Inc). Escape latencies, distance traveled, swim paths, swim speeds, and platform crossings were recorded automatically for subsequent analysis.

Catwalk

The Catwalk (Noldus, The Netherlands) is an automated and computerized gait-analysis technique that allows objective quantification of multiple static and dynamic gait parameters. Mice were placed on one end of the catwalk and allowed free exploration for 3 min or until they have 5 compliant trials, whichever comes first. Data were exported and classified using the Catwalk software. An average of classified trials was used for data analysis. Measures of interest include but are not limited to: print position or the distance between the position of the hind paw and previous placement of the ipsilateral front paw, initial and terminal dual stances, paw swing speed, and paw stand or the duration of paw contact with the glass plate in a step cycle.

Behavioral Statistics

Statistical analyses for all behavioral tests were conducted using GraphPad Prism (GraphPad Software, Inc., La Jolla, Calif.). For NOR, data were analyzed using either a paired t-test for within-group analyses or by an ANOVA followed by a Dunnett's post-hoc test for between group analyses. For MWM, a repeated MWM ANOVA was used to analyze the acquisition phase and a one-way ANOVA followed by Dunnett's post-hoc for probe trial analyses.

Results

In vivo acute tolerability for the oligomers determined based on the above assays is shown in FIG. 5. In vivo cumulative tolerability threshold following an ICV injection of 100 μg of an oligomer was set at 4.

Furthermore, the correlation between the sequence score of each oligomer and the in vivo acute tolerability of the oligomer was studied. The correlation analysis shows that the oligomers having in vivo tolerability lower than 4 tend to have a sequence score equal to or higher than 0.2. See FIG. 3. Therefore, FIG. 3 indicates that the sequence score of oligomers can be used to predict in vivo tolerability of the oligomers.

Example 7: In Vitro Reduction in Tau Protein

Each of the oligomers targeting the 3' UTR of an MAPT transcript was tested for its ability to decrease Tau protein in mouse primary neurons expressing the entire human MAPT gene as a bacmid containing transgene (C57-b16 BAC-Tg hTau; Polydoro et. al., I Neurosci. (2009) 29 (34): 10747-9). Primary hTau mouse embryonic forebrain neuronal cultures do not express endogenous mouse tau as mouse tau was knocked out. Primary neurons were generated by papain digestion according to manufacturer's protocol (Worthington Biochemical Corporation, LK0031050). Briefly, forebrains were dissected from hTau mouse E18 BAC-Tg embryos expressing the entire human microtubule-associated protein Tau (MAPT) gene on a murine MAPT-null background and were incubated at 37° C. for 30-45 minutes in papain/DNase/Earle's balanced salt solution (EBSS) solution. After trituration and centrifugation of cell pellet, the reaction was stopped by incubation with EBSS containing protease inhibitors, bovine serum albumin (BSA) and DNase. The cells were triturated and washed with Neurobasal (NB, Invitrogen) supplemented with 2% B-27, 100 μg/ml penicillin, 85 μg/ml streptomycin, and 0.5 mM glutamine. The cells were plated in supplemented NB media onto poly-D-lysine-coated 96-well optical imaging plates (BD Biosciences) at 15,000 cells/well.

After obtaining the primary hTau mouse embryonic forebrain neuronal cultures expressing a human MAPT gene, the cultures were treated with oligomers to inhibit the Tau mRNA and protein expression. The cultures were then subject to immunocytochemistry and imaging to measure the inhibition. One day post plating (DIV 1), half of the supplemented neurobasal (NB) media on the primary hTau mouse embryonic forebrain neuronal cultures was removed and replaced with supplemented NB media containing various concentrations of LNA oligomers. Primary hTau neuronal cultures were cultured with LNA oligomers until 13 days post plating (DIV 13). On DIV 13, the cultures were rinsed with Dulbecco's phosphate-buffered saline lacking calcium and magnesium (DPBS, Invitrogen) and fixed in 4% paraformaldehyde/4% sucrose/DPBS for 15 min. Cultures were rinsed and then blocked and permeabilized in DPBS plus 0.1% Triton X-100 (TX-100) and 3% BSA for one hour at room temperature. Cultures were rinsed and then incubated for two hours at room temperature with primary antibody 1:500, Tau5 antibody to measure Tau protein, Invitrogen AHB0042; and 1:500, β-III tubulin (TuJ-1) antibody to measure neurite area, Abcam ab41489) in DPBS plus 3% BSA and 0.1% TX-100. Cultures were rinsed and incubated with Hoeschst 33342 nuclear dye (1:800, Invitrogen) and AlexaFluor fluorescence-conjugated secondary antibodies (Invitrogen, 1:500) in DPBS plus 3% BSA and 0.1% TX-100 for one hour at room temperature. Cultures were rinsed abundantly and stored in DPBS until imaging. Imaging was conducted using the Cellomics VTi automated immunofluorescence imaging system. In brief, using untreated wells, saturation levels for each fluorophore channel were set to 70%. Then 12 sequential images were acquired from each well, and total fluorescence intensity and total fluorescence area were calculated for both Tau and TuJ-1 proteins using the Cellomics VTi SpotDetector (version 4) image analysis software. To evaluate Tau protein reduction resulting from oligomer treatment, a Tau5 total fluorescence intensity-to-Tuj-1 total fluorescence area ratio (Tau/TuJ-1) was created for each well and then all data were normalized to the average Tau/Tuj-1 ratio of the untreated wells. TuJ-1 intensity acts as an internal standard for each sample. To evaluate neurite/neuronal toxicity from oligomer treatment, the Tuj-1 total fluorescence area from each well was normalized to the average Tuj-1 total fluorescence area of the untreated wells. Nuclei counts from each well were also acquired as an alternative measure of toxicity associated with LNA oligomer treatment. Data are expressed as mean±S.D. For immunocytochemistry, data points represent the mean±S.D. from wells treated in triplicate. Potency values were generated using wells treated with a broad concentration range of LNA oligomer, from which the resulting normalized Tau/Tuj-1 and Tuj-1 values were analyzed compared to normalized values from saline control samples. Analysis was done using non-linear regression with top and bottom values set at fixed values of 100% and 0%, respectively, where 100% inhibition represents a complete reduction of signal compared to the control sample (FIG. 3). For qPCR, data were analyzed using a one-way ANOVA with a Dunnett's multiple comparison test to compare saline- and LNA oligomer-treated groups. Statistical significance was set at a value of $p<0.05$.

The reduction of Tau protein by each oligomer was compared with saline. The results of the Tau protein reduction compared to Saline are shown in FIG. 6. If the Tau protein level in antisense oligonucleotide treated neurons was equal to or higher than in control cells, percent inhibition is expressed as zero inhibition. If present, If 'N.D.' indicates 'not determined' and 'TBD' indicates 'to be determined'.

Example 8: Oligomer Prioritization

Properties of selected oligomers can be described as shown in Table 1. Based on these criteria, certain oligomers were selected for additional dose-response testing in vitro and in vivo.

TABLE 1

Summary of criteria used to prioritize oligomers for additional testing.

| Assay | Prioritization Criteria |
|---|---|
| Tau protein reduction | >70% reduction in Tau protein (5 μM oligomer) |
| Calcium oscillations | <25% reduction in calcium oscillations |
| Sequence score | Sequence score ≥ 0.20 |

In other embodiment, oligomers can be selected based on the following characteristics: (1) Tau protein reduction >30% reduction in Tau protein (5 μM oligomer); (2) calcium oscillations <25% reduction in calcium oscillations; and (3) sequence score equal to or higher than 0.2.

The invention claimed is:

1. A method of identifying a molecule having tolerable in vivo acute neurotoxicity before administering the molecule to a laboratory animal, comprising:

(a) selecting a molecule comprising a polynucleotide having a sequence score of greater than or equal to 0.2, comprising calculating the sequence score of the polynucleotide by formula (I):

(number of C nucleotides or analogs thereof in the polynucleotide−number of G nucleotides or analogs thereof in the polynucleotide)/total nucleotide length (number) of the polynucleotide (I), wherein the polynucleotide is single-stranded or one strand of a double-stranded molecule, (b) adding the molecule to a culture of neuronal cells, (c) measuring calcium oscillations in vitro in the neuronal cells which are in contact with the molecule, (d) identifying the molecule as having tolerable in vivo acute neurotoxicity when the neuronal cells in contact with the molecule exhibit calcium oscillations at a level between about 30% less than and the same as that of vehicle control cells, or at a level higher than that of vehicle control cells, (e) administering the molecule identified as having tolerable in vivo acute neurotoxicity to a laboratory animal, and (f) measuring an in vivo tolerability of the molecule in the laboratory animal.

2. The method of claim 1, wherein the calcium oscillations in the neuronal cells in contact with the molecule are about 70% or higher compared to the calcium oscillations in the vehicle control cells.

3. The method of claim 1, wherein the calcium oscillations are AMPA receptor-dependent calcium oscillations.

4. The method of claim 1, wherein the calcium oscillations are measured in the presence of $Mg^{2+}$ ions.

5. The method of claim 1, wherein the in vivo tolerability is a tolerability category selected from the group consisting of: 1) hyperactivity; 2) decreased activity and arousal; 3) motor dysfunction and/or ataxia; 4) abnormal posture and breathing; 5) tremor and/or convulsions, and two or more combinations thereof.

6. The method of claim 5, wherein the molecule exhibits a sum of in vivo tolerability scores between 0 and 8.

7. The method of claim 1, wherein the method further comprises measuring a behavioral test score of the laboratory animal.

8. The method of claim 7, wherein the behavioral test is a short term memory test, a spatial learning and memory test, a gait analysis test, or any combination thereof.

9. The method of claim 1, further comprising measuring tubulin intensity of the molecule in a culture of neuronal cells.

10. The method of claim 9, wherein the molecule reduces less than about 25% of the tubulin intensity in the culture of neuronal cells.

11. The method of claim 1, wherein the polynucleotide comprises DNA.

12. The method of claim 1, wherein the polynucleotide comprises RNA.

13. The method of claim 1, wherein the polynucleotide is single-stranded.

14. The method of claim 1, wherein the polynucleotide comprises an antisense oligonucleotide.

15. The method of claim 14, wherein the antisense oligonucleotide comprises at least one nucleotide analog.

16. The method of claim 15, wherein the at least one nucleotide analog is a Locked Nucleic Acid (LNA), 2'-O-alkyl-RNA, 2'-amino-DNA, 2'-fluoroDNA, arabino nucleic acid (ANA), 2'-fluoro-ANA, hexitol nucleic acid (HNA), intercalating nucleic acid (INA), constrained ethyl nucleoside (cEt), 2'-O-methyl nucleic acid (2'-OMe), 2'-O-methoxyethyl nucleic acid (2'-MOE), or any combination thereof.

17. The method of claim 14, wherein the antisense oligonucleotide comprises an internucleoside linkage that is a phosphodiester linkage, a phosphotriester linkage, a methylphosphonate linkage, a phosphoramidate linkage, a phosphorothioate linkage, or any combination thereof.

18. The method of claim 14, wherein the antisense oligonucleotide is a gapmer, blockmer, mixmer, or a wingmer.

19. The method of claim 14, wherein the antisense oligonucleotide is a headmer, tailmer, or totalmer.

* * * * *